United States Patent
Roemer et al.

(10) Patent No.: US 6,783,985 B1
(45) Date of Patent: Aug. 31, 2004

(54) GENE DISRUPTION METHODOLOGIES FOR DRUG TARGET DISCOVERY

(75) Inventors: Terry Roemer, Montréal (CA); Bo Jiang, Montreal (CA); Charles Boone, Toronto (CA); Howard Bussey, Westmount (CA)

(73) Assignee: Elitra Pharmaceuticals Inc., San Diego, CA (US)

( * ) Notice: Subject to any disclaimer, the term of this patent is extended or adjusted under 35 U.S.C. 154(b) by 0 days.

(21) Appl. No.: 09/792,024

(22) Filed: Feb. 20, 2001

Related U.S. Application Data

(60) Provisional application No. 60/183,534, filed on Feb. 18, 2000.

(51) Int. Cl.[7] .......................... C12N 15/01; C12N 15/04

(52) U.S. Cl. ........................... 435/440; 435/471; 435/4; 435/6; 435/29; 435/34; 435/243; 435/254.1; 435/254.11; 435/254.22; 435/255.1

(58) Field of Search .......................... 435/4, 6, 29, 34, 435/440, 471, 243, 254.1, 254.11, 254.22, 254.3, 254.7, 254.8, 254.9, 255.1, 255.3, 255.4, 256.1, 256.2, 256.6

(56) References Cited

U.S. PATENT DOCUMENTS

| | | |
|---|---|---|
| 5,464,758 A | 11/1995 | Gossen et al. |
| 5,569,588 A | 10/1996 | Ashby et al. |
| 5,604,097 A | 2/1997 | Brenner |
| 5,614,377 A | 3/1997 | Bulawa |
| 5,635,400 A | 6/1997 | Brenner |
| 5,654,413 A | 8/1997 | Brenner |
| 5,770,358 A | 6/1998 | Dower et al. |
| 5,801,015 A | 9/1998 | Cottarel et al. |
| 5,807,522 A | 9/1998 | Brown et al. |
| 5,821,038 A | 10/1998 | Fleer et al. |
| 5,821,353 A | 10/1998 | Douglas et al. |
| 5,846,719 A | 12/1998 | Brenner et al. |
| 5,876,931 A | 3/1999 | Holden |
| 5,939,306 A | 8/1999 | Alex et al. |
| 5,972,708 A | 10/1999 | Sherratt et al. |
| 5,976,866 A | 11/1999 | Heidler et al. |
| 6,004,779 A | 12/1999 | Bradley et al. |
| 6,015,689 A | 1/2000 | Okado et al. |
| 6,022,949 A | 2/2000 | Okado et al. |
| 6,046,000 A | 4/2000 | McCarthy et al. |
| 6,046,002 A | 4/2000 | Davis et al. |
| 6,096,511 A | 8/2000 | Nielsen-Kahn et al. |
| 6,117,641 A | 9/2000 | Berlin et al. |
| 6,138,077 A | 10/2000 | Brenner |
| 6,140,489 A | 10/2000 | Brenner |
| 6,150,516 A | 11/2000 | Brenner et al. |
| 6,194,166 B1 | 2/2001 | Okado et al. |
| 6,228,579 B1 | 5/2001 | Zyskind et al. |
| 6,232,074 B1 | 5/2001 | Dawson et al. |
| 6,248,525 B1 | 6/2001 | Nilsen |

(List continued on next page.)

FOREIGN PATENT DOCUMENTS

| | | |
|---|---|---|
| EP | 799 897 | 10/1997 |
| EP | 816 511 | 1/1998 |
| EP | 982 401 | 3/2000 |
| WO | WO 95/06132 | 3/1995 |
| WO | WO 97/16540 | 5/1997 |
| WO | WO 97/48822 | 12/1997 |
| WO | WO 98/21366 | 5/1998 |
| WO | WO 98/44135 | 10/1998 |
| WO | WO 98/45426 | 10/1998 |
| WO | WO 99/10474 | 3/1999 |
| WO | WO 99/23244 | 5/1999 |
| WO | WO 99/31269 | 6/1999 |
| WO | WO99/52926 | 10/1999 |
| WO | WO 00/09695 | 2/2000 |
| WO | WO 00/15838 | 3/2000 |
| WO | WO 00/34481 | 6/2000 |
| WO | WO 00/36082 | 6/2000 |
| WO | WO 00/39287 | 7/2000 |
| WO | WO 00/44906 | 8/2000 |
| WO | WO 00/53781 | 9/2000 |
| WO | WO 00/68420 | 11/2000 |
| WO | WO 00/75305 | 12/2000 |
| WO | WO 01/02550 | 1/2001 |
| WO | WO 01/14533 | 3/2001 |
| WO | WO 01/77295 | 10/2001 |

OTHER PUBLICATIONS

Mazhari–Tabrizi et al. Chromosomal promoter replacement in *Saccharomyces cerevisiae*: construction of conditional lethal strains for the cloning of glycosyltransferases from various organisms. Nov. 1999. Glycoconjugates Journal 16(11): 673–679.*

(List continued on next page.)

*Primary Examiner*—James Ketter
*Assistant Examiner*—David Lambertson
(74) *Attorney, Agent, or Firm*—Jones Day

(57) ABSTRACT

The present invention provides methods and compositions that enable the experimental determination as to whether any gene in the genome of a diploid pathogenic organism is essential, and whether it is required for virulence or pathogenicity. The methods involve the construction of genetic mutants in which one allele of a specific gene is inactivated while the other allele of the gene is placed under conditional expression. The identification of essential genes and those genes critical to the development of virulent infections, provides a basis for the development of screens for new drugs against such pathogenic organisms. The present invention further provides *Candida albicans* genes that are demonstrated to be essential and are potential targets for drug screening. The nucleotide sequence of the target genes can be used for various drug discovery purposes, such as expression of the recombinant protein, hybridization assay and construction of nucleic acid arrays. The uses of proteins encoded by the essential genes, and genetically engineered cells comprising modified alleles of essential genes in various screening methods are also encompassed by the invention.

29 Claims, 7 Drawing Sheets

U.S. PATENT DOCUMENTS

| | | |
|---|---|---|
| 6,277,564 B1 | 8/2001 | Berlin et al. |
| 6,280,963 B1 | 8/2001 | Koltin et al. |
| 6,294,651 B1 | 9/2001 | Okado et al. |
| 6,303,115 B1 | 10/2001 | Natsoulis |
| 6,320,033 B1 | 11/2001 | Bourbonnais et al. |
| 2001/0031724 A1 | 10/2001 | Roemer et al. |

OTHER PUBLICATIONS

Rosenbluh et al. Isolation of genes from Candida albicans by complementation in *Saccharomyces cerevisiae*. 1985. Molecular and General Genetics 200(3): 500–502.*

U.S. patent application Ser. No. 60/123,807, Berlin et al., filed Mar. 11, 1999.

Aaron et al. The *Candida albicans* ERG26 gene encoding the C–3 sterol dehydrogenase (C–4 decarboxylase) is essential for growth. FEMS Yeast Research 2001, 1411:1–9.

Brown et al. Signature–tagged and directed mutagenesis identify PABA synthetase as essential for Aspergillus fumigatus pathogenicity. Mol. Microbiol. Jun. 2000:36(6):1371–80.

Brown JL and Bussey H. The yeast KRE9 gene encodes an O glycoprotein involved in cell surface beta–glucan assembly. Mol Cell Biol. Oct. 1993;13(10):6346–56.

Enloe et al. A single–transformation gene function test in diploid Candida albicans. J. Bacteriol. Oct. 2000;182(20):5730–6.

Fonzi et al. Isogenic strain construction and gene mapping in Candida albicans. Genetics. Jul. 1993;134(3):717–28.

Gari et al. A set of vectors with a tetracycline–regulatable promoter system for modulated gene expression in *Saccharomyces cerevisiae*. Yeast Jul. 1997;13(9):837–48.

Goldstein et al Three new dominant drug resistance cassettes for gene disruption in *Saccharomyces cerevisiae*. Yeast. Oct. 1999;15(14):1541–53.

Gow et al. Genes associated with dimorphism and virulence of *Candida albicans*. Can. J. Bot. 1995, 73(suppl.1):S335–S342.

Hirt RP et al. Microsporidia are related to Fungi: evidence from the largest subunit of RNA polymerase II and other proteins. Proc. Natl. Acad Sci U S A. Jan. 19, 1999;96(2):580–5.

Hull et al. Evidence for mating of the "asexual" yeast *Candida albicans* in a mammalian host. Science. Jul. 14, 2000;289(5477):307–10.

Katinka MD et al. Genome sequence and gene compaction of the eukaryote parasite Encephaliozoon cuniculi. Nature Nov. 22, 2001;414(6862):450–3.

Kwon–Chung K. Gene disruption to evaluate the role of fungal candidate virulence genes. Curr Opin Microbiol. Aug. 1998;1(4):381–9. Review.

Magee and Scherer, Genome mapping and gene discovery in *Candida albicans*. ASM News. Nov. 1998;64:505–11.

Magee BB and Magee PT, Induction of mating in *Candida albicans* by construction of MTLa and MTLalpha strains. Science. Jul. 14, 2000;289(5477):310–3.

Mao et al. Overexpression of a dominant–negative allele of SEC4 inhibits growth and protein secretion in *Candida albicans*. J. Bacteriol. Dec. 1999;181(23):7235–42.

Mendoza et al. Translation elongation factor 2 is encoded by a single essential gene in *Candida albicans*. Gene. Mar. 18, 1999;229(1–2):183–91.

Mio et al. Isolation of the *Candida albicans* homologs of *Saccharomyces cerevisiae* KRE6 and SKNI: expression and physiological function. J. Bacteriol. Apr. 1997;179(7):2363–72.

Mio et al. Cloning of the *Candida albicans* homolog of *Saccharomyces cerevisiae* GSCI/FKSI and its involvement in beta–1,3–glucan synthesis. J. Bacteriol. Jul. 1997;179(13):4096–105.

Munro et al. Chs1 of *Candida albicans* is an essential chitin synthase required for synthesis of the septum and for cell integrity, Mol Microbiol. Mar. 2001;39(5):1414–26.

Nakayama et al. Tetracycline–regulatable system to tightly control gene expression in the pathogenic fungus *Candida albicans* Infect. Immun. Dec. 2000;68(12):6712–9.

Pla et al. Understanding *Candida albicans* at the molecular level. Yeast. Dec. 1996;12(16):1677–702.

Shoemaker et al., Quantitative phenotypic analysis of yeast deletion mutants using a highly parallel molecular bar–coding strategy. Nat Genet. Dec. 1996;14(4):450–6.

van den Brink et al. Increased resistance to 14 alpha–demethylase inhibitors (DMIs) in Aspergillus niger by coexpression of the Penicillium italicum eburicol 14 alpha–demethylase (cyp51) and the A. niger cytochrome P450 reductase (cprA) genes. J Biotechnol. Aug. 20, 1996;49(1–3):13–8.

Venkateswarlu et al. NADPH cytochrome P–450 oxidoreductase and susceptibility to ketoconazole. Antimicrob Agents Chemother. Jul. 1998;42(7):1756–61.

* cited by examiner

• STEP 1: GENE REPLACEMENT

• STEP 2: CONDITIONAL EXPRESSION
        BY PROMOTER REPLACEMENT

GENE DISRUPTION METHODOLOGIES FOR DRUG TARGET DISCOVERY

This application claims priority to the U.S. provisional application serial No. 60/183,534, filed Feb. 18, 2000, which is incorporated herein by reference in its entirety.

1. INTRODUCTION

The present invention is directed toward (1) methods for constructing strains useful for identification and validation of gene products as effective targets for therapeutic intervention, (2) methods for identifying and validating gene products as effective targets for therapeutic intervention, (3) a collection of identified essential genes, and (4) screening methods and assay procedures for the discovery of new drugs.

2. BACKGROUND OF THE INVENTION

Validation of a cellular target for drug screening purposes generally involves an experimental demonstration that inactivation of that gene product leaves the cell inviable. Accordingly, a drug active against the same essential gene product expressed, for example, by a pathogenic fungus, would be predicted to be an effective therapeutic agent. Similarly, a gene product required for fungal pathogenicity and virulence is also expected to provide a suitable target for drug screening programs. Target validation in this instance is based upon a demonstration that inactivation of the gene encoding the virulence factor creates a fungal strain that is shown to be either less pathogenic or, ideally, avirulent, in animal model studies. Identification and validation of drug targets are critical issues for detection and discovery of new drugs because these targets form the basis for high through-put screens within the pharmaceutical industry.

Target discovery has traditionally been a costly, time-consuming process, in which newly-identified genes and gene products have been individually analyzed as potentially-suitable drug targets. DNA sequence analysis of entire genomes has markedly accelerated the gene discovery process. Consequently, new methods and tools are required to analyze this information, first to identify all of the genes of the organism, and then, to discern which genes encode products that will be suitable targets for the discovery of effective, non-toxic drugs. Gene discovery through sequence analysis alone does not validate either known or novel genes as drug targets. Elucidation of the function of a gene from the underlying and a determination of whether or not that gene is essential still present substantial obstacles to the identification of appropriate drug targets. These obstacles are especially pronounced in diploid organisms.

C. albicans is a major fungal pathogen of humans. An absence of identified specific, sensitive, and unique drug targets in this organism has hampered the development of effective, non-toxic compounds for clinical use. The recent completion of the DNA sequence analysis of the entire C. albicans genome has rejuvenated efforts to identify new antifungal drug targets. Nevertheless, two primary obstacles to the exploitation of this information for the development of useful drug targets remain: the paucity of suitable markers for genetic manipulations in C. albicans and the inherent difficulty in establishing, in this diploid organism, whether a specific gene encodes an essential product. Co-pending provisional patent application No. 60/183,462, filed Feb. 18, 2000, was filed as U.S. nonprovisional application Ser. No. 09/785,669, on Feb. 16, 2001, which has issued as U.S. Pat. No. 6,562,595 on May 13, 2003, discloses the identification of dominant selectable markers, and the construction of two genes encoding those markers, which are suitable for transformation and gene disruption in C. albicans.

Current methods for gene disruption in C. albicans (FIG. 1) typically involve a multistep process employing a "URA blaster" gene cassette which is recombined into the genome, displacing the target gene of interest. The URA blaster cassette comprises the CaURA3 marker which is selectable in the corresponding auxotrophic host and which is flanked by direct repeats of the *Salmonella typhimurium* HisG gene. The URA blaster cassette also carries flanking sequences corresponding to the gene to be replaced, which facilitate precise replacement of that gene by homologous recombination. Putative heterozygous transformants, which have had one allele of the target gene deleted, are selected as uracil prototrophs, and their identity and chromosomal structure confirmed by Southern blot and PCR analyses. Isolates within which intrachromosomal recombination events have occurred between HisG repeats, leading to excision of the CaURA3 gene and loss of the integrated cassette, are selected on 5-fluoroorotic acid (5-FOA) containing media. This allows a repetition of the entire process, including reuse of the Ura-blaster cassette, for disruption of the second allele of the target gene. In those instances in which the target gene is nonessential, homozygous gene disruptions are produced in the second round gene replacement and identified by Southern blot and PCR analyses.

However, homozygous deletion strains, which lack both alleles of a gene that is essential will not be viable. Accordingly, the Ura blaster method will not provide an unequivocal result, establishing the essential nature of the target gene since alternative explanations, including poor growth of a viable mutant strain, may be equally likely for the negative results obtained. More recent approaches for identification of essential genes, including those disclosed by Wilson, R. B., Davis, D., Mitchell, A. P. (1999) J. Bacteriol. 181:1868–74, employ multiple auxotrophic markers and a PCR-based gene disruption strategy. Although such methods effectively overcome the need to use the Ura Blaster cassette, determination of whether a given gene is essential, and therefore, a potentially useful target, remains labor-intensive and unsuitable for genome-wide analyses. Substantial effort is required to support a statistically valid conclusion that a given gene is essential when using either the Ura blaster cassette or multiple auxotrophic marker-based methods for gene disruption in Candida albicans. Typically, between 30 and 40 second round transformants must all be confirmed as reconstructed heterozygous strains (using PCR or Southern blot analysis) resulting from homologous recombination between the disruption fragment and previously constructed disruption allele, before statistical support to the claim that the gene is essential can be made. Moreover, since secondary mutations may be selected in either the transformation step or 5-FOA counterselection (if the Ura blaster cassette is reused), two independently constructed heterozygous strains are preferably examined during the attempted disruption of the second allele. In addition, demonstration that a particular phenotype is linked to the homozygous mutation of the target gene (and not a secondary mutation) requires complementation of the defect by transforming a wild type copy of the gene back into the disruption strain.

Finally, the Ura blaster method precludes direct demonstration of gene essentiality. Therefore, one is unable to critically evaluate the terminal phenotype characteristic of essential target genes. Consequently, establishing whether inactivation of a validated drug target gene results in cell death (i.e., a cidal terminal phenotype) versus growth inhibition (i.e., a static terminal phenotype) is not possible with current approaches, despite the value such information would provide in prioritizing drug targets for suitability in drug development.

Clearly, since current gene disruption methods are labor intensive and largely refractile to a high throughput strategy for target validation, there is a need for effective methods and tools for unambiguous, rapid, and accurate identification of essential genes in diploid, pathogenic fungi, and particularly, in *Candida albicans*. The present invention overcomes these limitations in current drug discovery approaches by enabling high throughput strategies that provide rapid identification, validation, and prioritization of drug targets, and consequently, accelerate drug screening.

3. SUMMARY OF THE INVENTION

The present invention provides effective and efficient methods that enable, for each gene in the genome of an organism, the experimental determination as to whether that gene is essential, and for a pathogenic organism, in addition, whether it is required for virulence or pathogenicity. The identification and validation of essential genes and those genes critical to the development of virulent infections, provides a basis for the development of high-throughput screens for new drugs against the pathogenic organism.

The present invention can be practiced with any organism independent of ploidy, and in particular, pathogenic fungi. Preferably, the pathogenic fungi are diploid pathogenic fungi, including but not limited to *Candida albicans, Aspergillus fumigatus, Cryptococcus neoformans* and the like.

In one embodiment, the present invention is directed toward a method for constructing a diploid fungal strain in which one allele of a gene is modified by insertion of or replacement by a cassette comprising an expressible dominant selectable marker. This cassette is introduced into the chromosome by recombination, thereby providing a heterozygous strain in which the first allele of the gene is inactivated.

The other allele of the gene is modified by the introduction, by recombination, of a promoter replacement fragment comprising a heterologous promoter, such that the expression of the second allele of the gene is regulated by the heterologous promoter. Expression from the heterologous promoter can be regulated by the presence of a transactivator protein comprising a DNA-binding domain and transcription activation domain. The DNA-binding domain of this transactivator protein recognizes and binds to a sequence in the heterologous promoter and increases transcription of that promoter. The transactivator protein can be produced in the cell by expressing a nucleotide sequence encoding the protein.

This method for the construction of a diploid fungus having both alleles of a gene modified, is carried out, in parallel, with each and every gene of the organism, thereby allowing the assembly a collection of diploid fungal cells each of which comprises the modified alleles of a gene. This collection, therefore, comprises modified alleles of substantially all of the genes of the diploid organism. As used herein, the term "substantially all" includes at least 60%, 70%, 80%, 90%, 95% or 99% of the total. Preferably, every gene in the genome of the diploid organism is represented in the collection.

The present invention also encompasses diploid organisms, such as diploid pathogenic fungal strains, comprising modified alleles of a gene, where the first allele of a gene is inactivated by insertion of or replacement by a nucleotide sequence encoding an expressible dominant selectable marker; and where the second allele of the gene has also been modified so that expression of the second allele is regulated by a heterologous promoter. In one aspect of the present invention, the alleles modified in the mutant diploid pathogenic fungal strain correspond to an essential gene, which is required for growth, viability and survival of the strain. In another aspect of the present invention, the modified alleles correspond to a gene required for the virulence and pathogenicity of the diploid pathogenic fungal strain against a host organism. In both cases, the essential gene and the virulence/pathogenicity gene are potential drug targets.

Accordingly, the present invention encompasses collections of mutant diploid fungal strains wherein each collection comprises a plurality of strains, each strain containing the modified alleles of a different gene. The collections of strains of the invention include modified alleles for substantially all the different essential genes in the genome of a fungus or substantially all the different virulence genes in the genome of a pathogenic fungus.

In another embodiment, the present invention is also directed to nucleic acid microarrays which comprise a plurality of defined nucleotide sequences disposed at identifiable positions in an array on a substrate. The defined nucleotide sequences can comprise oligonucleotides complementary to, and capable of hybridizing with, the nucleotide sequences of the essential genes of the diploid pathogenic organism that are required for the growth and survival of the diploid pathogenic organism, the nucleotide sequences of genes contributing to the pathogenicity or virulence of the organism, and/or the unique molecular tags employed to mark each of the mutant strains.

The present invention is also directed to methods for the identification of genes essential to the survival of a diploid organism, and of genes that contribute to the virulence and/or pathogenicity of the diploid pathogenic organism. First, the invention provides mutants of diploid organisms, such as mutant fungal cells, having one allele of a gene inactivated by insertion of or replacement with a disruption cassette, and the other allele modified by a nucleic acid molecule comprising a heterologous regulated promoter, such that expression of that second allele is under the control of the heterologous promoter. Second, such mutant cells are cultured under conditions where the second allele of the modified gene is substantially not expressed. The viability or pathogenicity of the cells are then determined. The resulting loss of viability or exhibition of a severe growth defect indicates that the gene that is modified in the mutant cells is essential to the survival of a pathogenic fungus. Similarly, the resulting loss of virulence and/or pathogenicity of the mutant cells indicates that the gene that is modified contributes to the virulence and/or pathogenicity of the pathogenic fungus.

In yet another embodiment of the present invention, the mutant pathogenic fungal strains constructed according to the methods disclosed are used for the detection of antifungal agents effective against pathogenic fungi. Mutant cells of the invention are cultured under differential growth conditions in the presence or absence of a test compound. The growth rates are then compared to indicate whether or not the compound is active against a target gene product. The second allele of the target gene may be substantially underexpressed to provide cells with enhanced sensitivity to compounds active against the gene product expressed by the modified allele. Alternatively, the second allele may be substantially overexpressed to provide cells with increased resistance to compounds active against the gene product expressed by the modified allele of the target gene.

In yet another embodiment of the present invention, the strains constructed according to the methods disclosed are used for the screening of therapeutic agents effective for the treatment of non-infectious diseases in a plant or an animal, such as a human. As a consequence of the similarity of a target's amino acid sequence with a plant or animal counterpart, or the lack of sequence similarity, active compounds so identified may have therapeutic applications for the treatment of diseases in the plant or animal, in particular, human diseases, such as cancers and immune disorders.

The present invention, in other embodiments, further encompasses the use of transcriptional profiling and proteomics techniques to analyze the expression of essential and/or virulence genes under a variety of conditions, including in the presence of known drugs. The information yielded from such studies can be used to uncover the target and mechanism of known drugs, to discover new drugs that act in a similar fashion to known drugs, and to delineate the interactions between gene products that are essential to growth and survival of the organism and that are instrumental to virulence and pathogenicity of the organism.

In a further embodiment of the present invention, a set of genes of a pathogenic organism are identified as potential targets for drug screening. Such genes comprise, genes that have been determined, using the methods and criteria disclosed herein, to be essential for survival of a pathogenic fungus and/or for the virulence and/or pathogenicity of the pathogenic fungus. The polynucleotides of the essential genes or virulence genes of a pathogenic organism (i.e., the target genes) provided by the present invention can be used by various drug discovery purposes. Without limitation, the polynucleotides can be used to express recombinant protein for characterization, screening or therapeutic use; as markers for host tissues in which the pathogenic organisms invade or reside (either permanently or at a particular stage of development or in a disease states); to compare with DNA sequences of other related or distant pathogenic organisms to identify potential orthologous essential or virulence genes; for selecting and making oligomers for attachment to a nucleic acid array for examination of expression patterns; to raise anti-protein antibodies using DNA immunization techniques; as an antigen to raise anti-DNA antibodies or elicit another immune response; and as a therapeutic agent (e.g antisense). Where the polynucleotide encodes a protein which binds or potentially binds to another protein (such as, for example, in a receptor-ligand interaction), the polynucleotide can also be used in assays to identify polynucleotides encoding the other protein with which binding occurs or to identify inhibitors of the binding interaction.

The polypeptides or proteins encoded by the essential genes and virulence genes (i.e. the target gene products) provided by the present invention can also be used in assays to determine biological activity, including its uses as a member in a panel or an array of multiple proteins for high-throughput screening; to raise antibodies or to elicit immune response; as a reagent (including the labeled reagent) in assays designed to quantitatively determine levels of the protein (or its receptor) in biological fluids; as a marker for host tissues in which the pathogenic organisms invade or reside (either permanently or at a particular stage of development or in a disease states); and, of course, to isolate correlative receptors or ligands (also referred to as binding partners) especially in the case of virulence factors. Where the protein binds or potentially binds to another protein (such as, for example, in a receptor-ligand interaction), the protein can be used to identify the other protein with which binding occurs or to identify inhibitors of the binding interaction. Proteins involved in these binding interactions can also be used to screen for peptide or small molecule inhibitors or agonists of the binding interaction, such as those involved in invasiveness, and pathogenicity of the pathogenic organism.

Any or all of these drug discovery utilities are capable of being developed into a kit for commercialization as research products. The kits may comprise polynucleotides and/or polypeptides corresponding to a plurality of essential genes and virulence genes of the invention, antibodies, and/or other reagents.

4. BRIEF DESCRIPTION OF THE DRAWINGS

Figure 1:
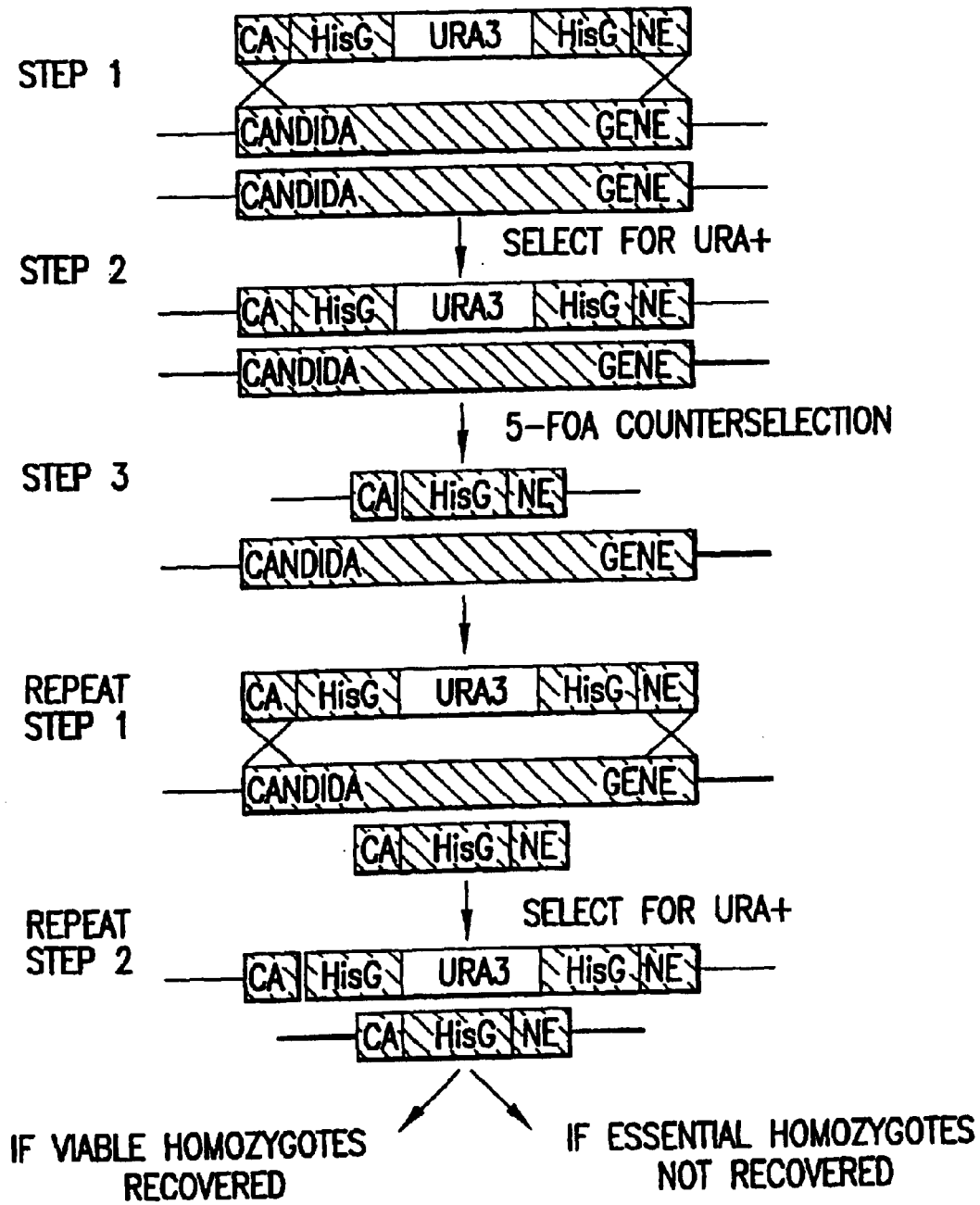
FIG. 1 depicts the URA blaster method for gene disruption in *Candida albicans*.
Figure 2A:
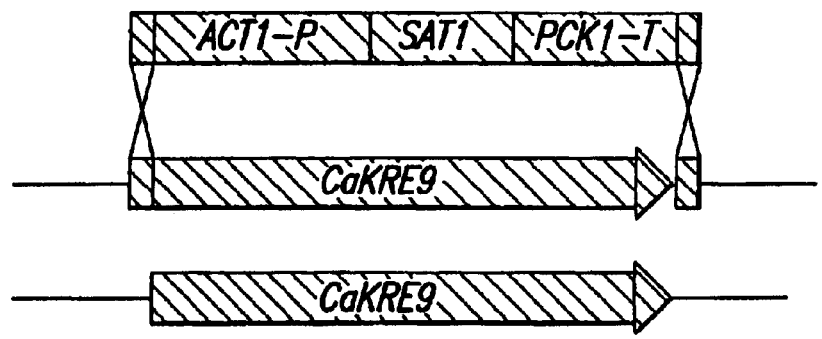
FIG. 2 depicts the GRACE method for constructing a gene disruption of one allele of a gene (CaKRE9), and promoter replacement of the second allele of the target gene, placing the second allele under conditional, regulated control by a heterologous promoter.

FIG. 2A presents two steps of the Grace method, in which one allele of a target gene is replaced with a first selectable marker, while the promoter of a second allele of a target gene is replaced with a promoter replacement fragment comprising a second expressible selectable marker and a heterologous promoter.

Figure 2A:
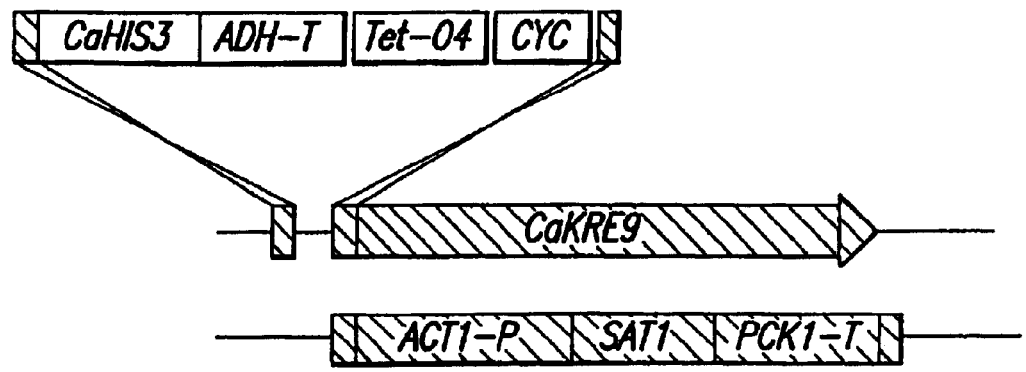
Figure 2B:
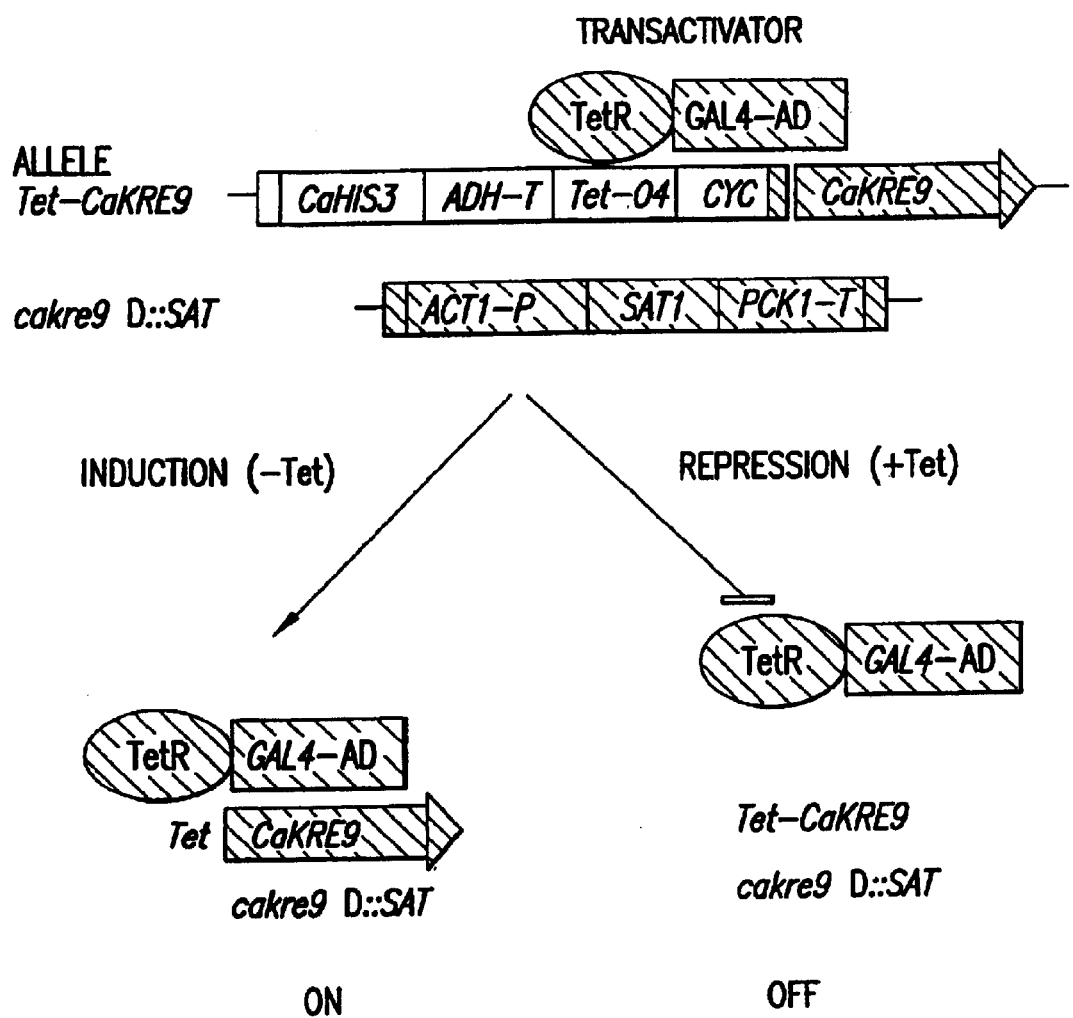

FIG. 2B presents tetracycline-regulated, conditional expression of a target gene in strain constructed according to the Grace method.

Figure 3:
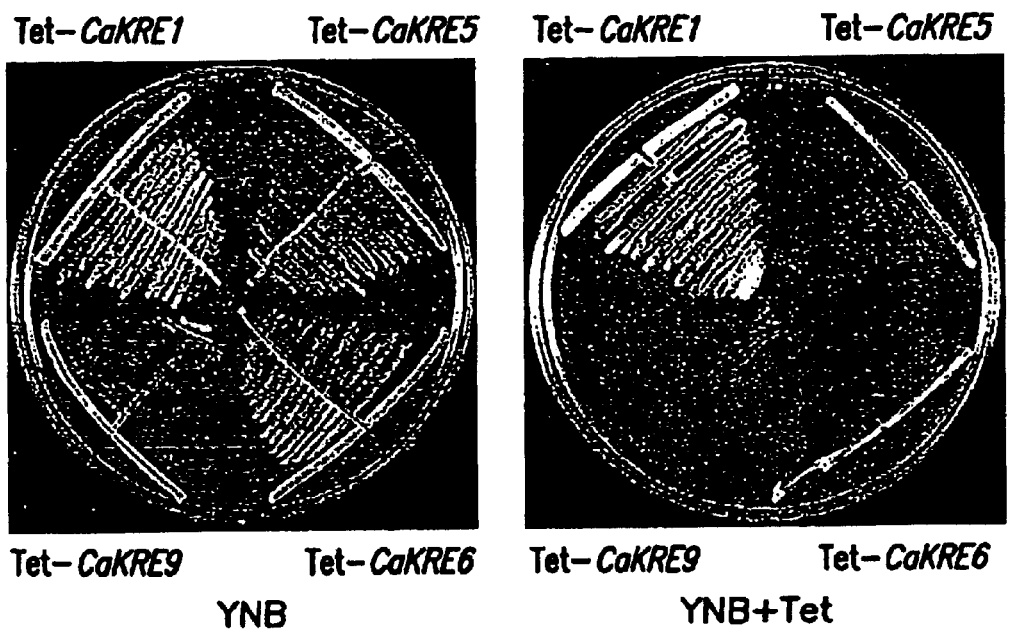

FIG. 3 presents conditional gene expression, using GRACE technology, with KRE1, KRE5, KRE6 and KRE9.

Figure 4:
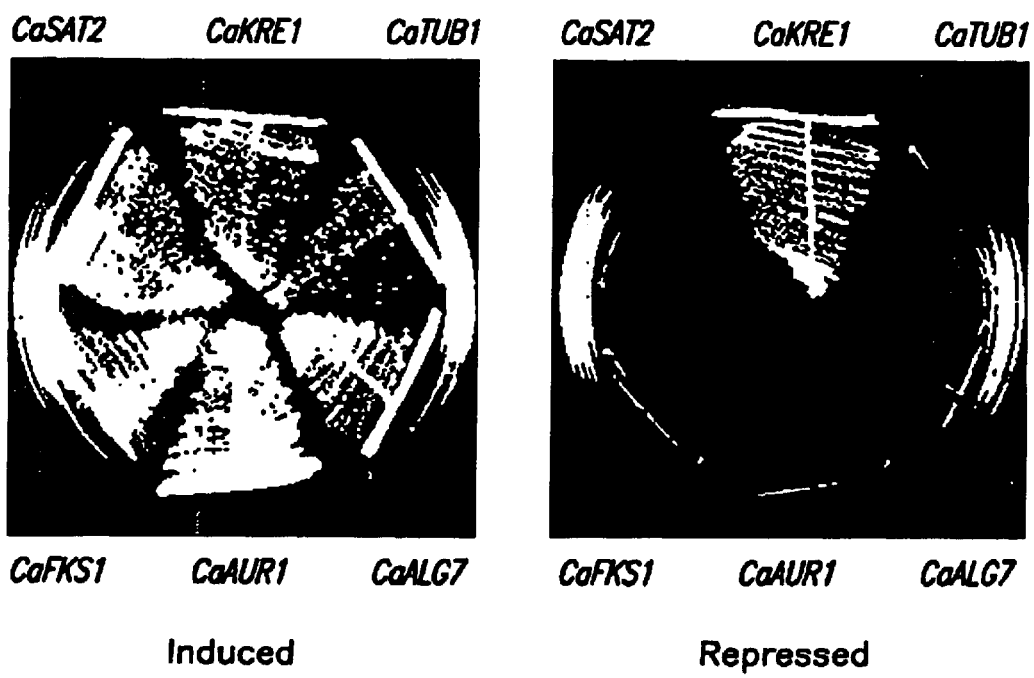

FIG. 4 presents conditional gene expression using GRACE technology with CaKRE1, CaTUB1, CaALG7, CaAUR1, CaFKS1 and CaSAT2.

Figure 5:
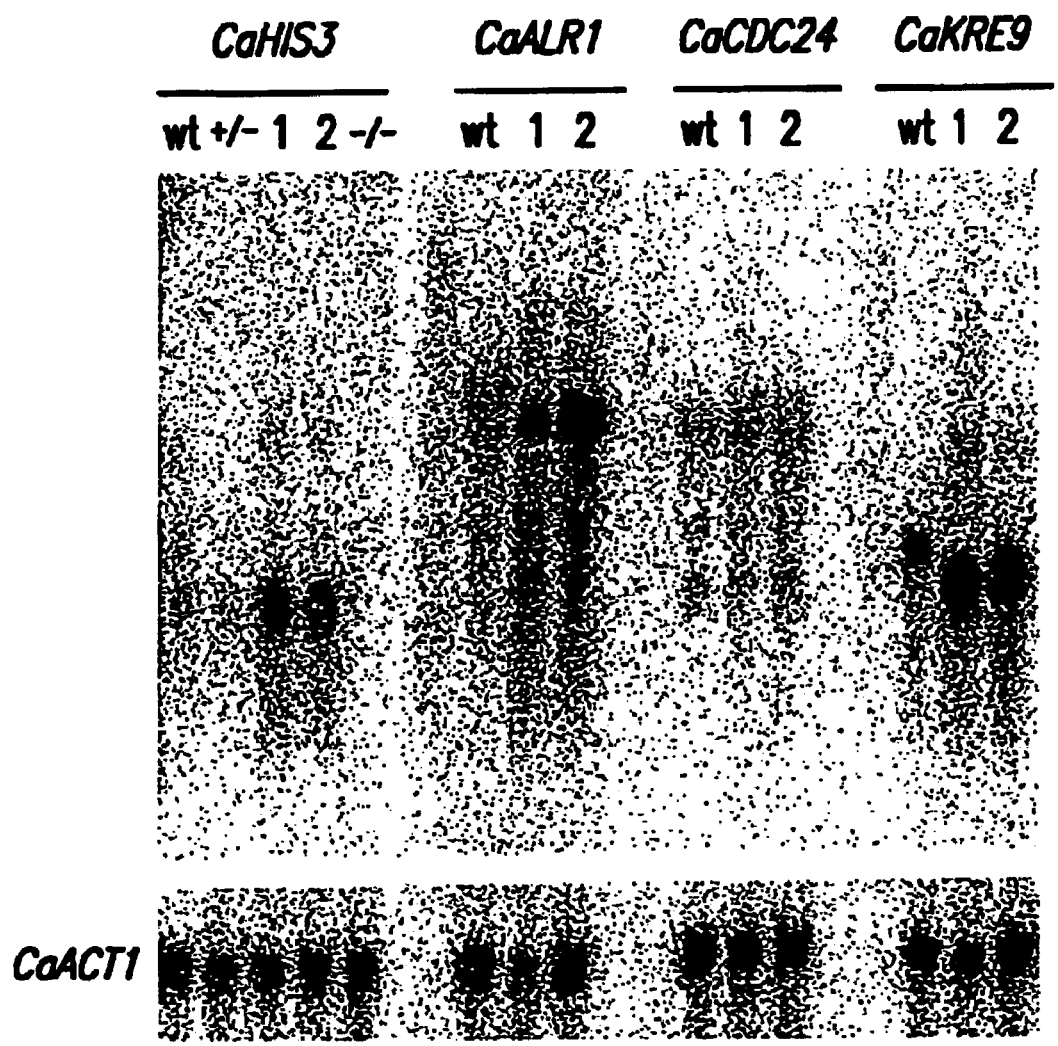

FIG. 5 presents a Northern Blot Analysis of CaHIS3, CaALR1, CaCDC24 and CaKRE9 mRNA isolated from GRACE strains to illustrate elevated expression under non-repressing conditions.

FIG. 6 presents growth of a CaHIS3 heterozygote strain and a tetracycline promoter-regulated CaHIS3 GRACE strain compared to growth of a wild-type diploid CaHIS3 strain in the presence and absence of 3-aminotriazole (3-AT).

Figure 6A:
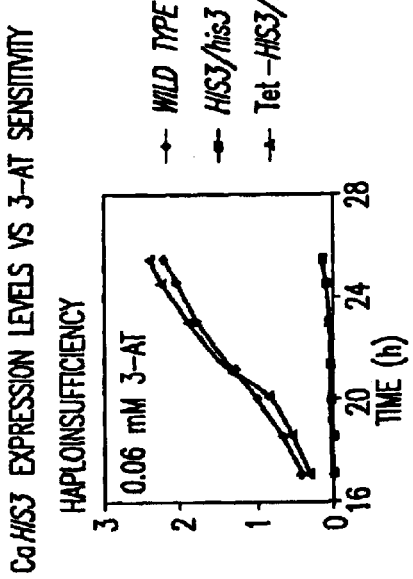

FIG. 6A depicts growth of a wild-type strain and a CaHIS3 heterozygote strain as compared with a CaHIS3 GRACE strain constitutively expressing the tetracycline promoter-regulated imidazoleglycerol phosphate dehydratase, in the presence of inhibitory levels of 3-aminotriazole.

Figure 6C:
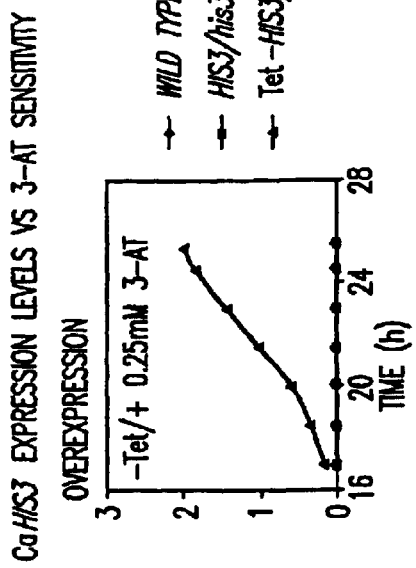
Figure 6B:
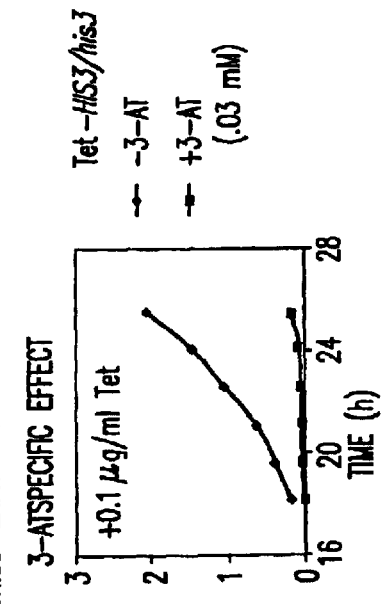

FIG. 6B depicts growth of a wild-type strain, a haploinsufficient CaHIS3 heterozygote strain, and a CaHIS3 GRACE strain constitutively expressing the tetracycline promoter-regulated imidazoleglycerol phosphate dehydratase, in the presence of an intermediate level of 3-aminotriazole.

FIG. 6C depicts growth of a wild-type strain, a haploinsufficient CaHIS3 heterozygote strain, and a CaHIS3 GRACE strain minimally expressing the tetracycline promoter-regulated imidazoleglycerol phosphate dehydratase, in the presence of an intermediate level of 3-aminotriazole.

Figure 6D:
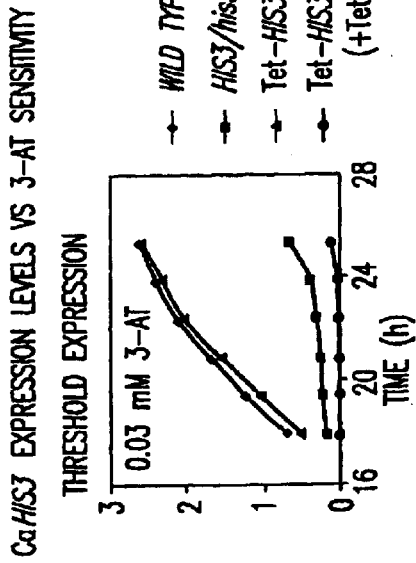

FIG. 6D demonstrates the hypersensitivity of the CaHIS3 GRACE strain minimally expressing the tetracycline promoter-regulated imidazoleglycerol phosphate dehydratase, in the presence of an intermediate level of 3-aminotriazole.

5. DETAILED DESCRIPTION OF THE INVENTION

5.1 Gene Disruption and Drug Target Discovery

The present invention provides a systematic and efficient method for drug target identification and validation. The approach is based on genomics information as well as the biological function of individual genes.

The methods of the invention generates a collection of genetic mutants in which the dosage of specific genes can be modulated, such that their functions in growth, survival, and/or pathogenicity can be investigated. The information accrued from such investigations allows the identification of individual gene products as potential drug targets. The present invention further provides methods of use of the genetic mutants either individually or as a collection in drug screening and for investigating the mechanisms of drug action.

Generally, in gene disruption experiments, the observation that homozygous deletions cannot be generated for both alleles of a gene in a diploid organism, cannot, per se, support the conclusion that the gene is an essential gene. Rather, a direct demonstration of expression of the gene in question that is coupled with viability of the cell carrying that gene, is required for the unambiguous confirmation that the gene in question is essential.

A direct demonstration that a given gene is essential for survival of a cell can be established by disrupting its expression in diploid organisms which have a haploid stage. For example, in *Saccharomyces cerevisiae*, this is achieved by complete removal of the gene product through gene disruption methods in a diploid cell type, followed by sporulation and tetrad dissection of the meiotic progeny to enable direct comparison of haploid yeast strains possessing single mutational differences. However, such an approach is not applicable to asexual yeast strains, which include most diploid pathogenic cell types, and alternative methods are required for eliminating expression of a putative essential gene.

In one embodiment, the invention provides a method for creating a diploid mutant cell of an organism in which the dosage of a specific gene can be modulated. By this method of the invention, one allele of a target gene in a diploid cell of an organism is disrupted while the second allele is modified by having its promoter replaced by a regulated promoter of heterologous origin. A strain constructed in this manner is said to comprise a modified allelic pair, i.e., a gene wherein both alleles are modified as described above. Where the genomic DNA sequence of the organism is available, this process may be repeated with each and every gene of the organism, thereby constructing a collection of mutant organisms each harboring a disrupted allele and an allele which can be conditionally expressed. This gene disruption strategy, therefore, provides a substantially complete set of potential drug target genes for that organism. This collection of mutant organisms, comprising a substantially complete set of modified allelic pairs, forms the basis for the development of high throughput drug screening assays. A collection of such mutant organisms can be made even when the genomic sequences of an organism are not completely sequenced. It is contemplated that a smaller collection of mutant organisms can be made, wherein in each mutant organism, one allele of a desired subset of gene is disrupted, and the other allele of the genes in this subset is placed under conditional expression. The method of the invention employed for the construction of such strains is referred to herein as the GRACE method, where the acronym is derived from the phrase gene replacement and conditional expression.

The GRACE method, which involves disruption of one allele coupled with conditional expression of the other allele, overcomes limitations relying upon repeated cycles of disruption with the URA blaster cassette followed by counterselection for its loss. The GRACE method permits large scale target validation in a diploid pathogenic microorganism, such as a pathogenic fungus.

The GRACE method of the invention, as applied to a diploid cell involves two steps: (i) gene replacement resulting in disruption of the coding and/or non-coding region(s) of one wild type allele by insertion, truncation, and/or deletion, and (ii) conditional expression of the remaining wild type allele via promoter replacement or conditional protein instability (FIG. 2). Detailed descriptions of the method is provided in later sections.

Isolated mutant organisms resulting from the application of the GRACE method are referred to herein as GRACE strains of the organism. Such mutant strains of an organism are encompassed by the invention. In a particular embodiment, a collection of GRACE strains which are generated by subjecting substantially all the different genes in the genome of the organism to modification by the GRACE method is provided. In this collection, each strain comprises the modified alleles of a different gene, and substantially all the genes of the organism are represented in the collection. It is intended that a GRACE strain is generated for every gene in an organism of interest. Alternatively, a smaller collection of GRACE strains of an organism can be generated wherein a desired subset of the genes in the organism are modified by the GRACE method.

A gene is generally considered essential when viability and/or normal growth of the organism is substantially coupled to or dependent on the expression of the gene. An essential function for a cell depends in part on the genotype of the cell and in part the cell's environment. Multiple genes are required for some essential function, for example, energy metabolism, biosynthesis of cell structure, replication and repair of genetic material, etc. Thus, the expression of many genes in an organism are essential for its growth and/or survival. Accordingly, when the viability or normal growth of a GRACE strain under a defined set of conditions is coupled to or dependent on the conditional expression of the remaining functional allele of a modified allelic gene pair, the gene which has been modified in this strain by the GRACE method is referred to as an "essential gene" of the organism.

A gene is generally considered to contribute to the virulence/pathogenicity of an organism when pathogenicity of the organism is associated at least in part to the expression of the gene. Many genes in an organism are expected to contribute to the virulence and/or pathogenicity of the organism. Accordingly, when the virulence and/or pathogenicity of a GRACE strain to a defined host or to defined set of cells from a host is associated with the conditional expression of the remaining functional allele of a modified allelic gene pair, the gene which has been modified in this strain by the GRACE method is referred to as a "virulence gene" of the organism.

The present invention provides a convenient and efficient method to identify essential genes of a pathogenic organism, and to validate their usefulness in drug discovery programs.

The method of the invention can similarly be used to identify virulence genes of a pathogenic organism. The identities of these essential genes and virulence genes of an organism as identified by the GRACE method are encompassed in the present invention. Substantially all of the essential genes and virulence genes of an organism can be identified and validated by the GRACE method of the invention.

Each of the essential genes and virulence genes so identified represent a potential drug target for the organism, and can be used individually or as a collection in various methods of drug screening. Depending on the objective of the drug screening program and the target disease, the essential genes and virulence genes of the invention can be classified and divided into subsets based on the structural features, functional properties, and expression profile of the gene products. The gene products encoded by the essential genes and virulence genes within each subset may share similar biological activity, similar intracellular localization, structural homology, and/or sequence homology. Subsets may also be created based on the homology or similarity in sequence to other organisms in a similar or distant taxonomic group, e.g. homology to *Saccharomyces cerevisiae* genes, or to human genes, or a complete lack of sequence similarity or homology to genes of other organisms, such as *S. cerevisiae* or human. Subsets may also be created based on the display of cidal terminal phenotype or static terminal phenotype by the organism bearing the modified gene. Such subsets, referred to as essential gene sets or virulence gene sets, which can be conveniently investigated as a group in a drug screening program, are provided by the present invention. Accordingly, the present invention provides a plurality of mutant organisms, such as a collection of GRACE strains, each comprising the modified alleles of a different gene, wherein each gene is essential for the growth and/or survival of the cells.

In a specific embodiment, substantially all of the essential genes in the genome of a pathogenic fungus are identified by the GRACE method, and the GRACE strains containing the modified allelic pairs of essential genes are included in a collection of GRACE strains. In another specific embodiment, substantially all of the virulence genes in the genome of a pathogenic fungus are identified by the GRACE method, and the GRACE strains containing the modified allelic pairs of virulence genes are included in a collection of GRACE strains.

For *Candida albicans*, a GRACE strain collection for the entire genome may comprise approximately 7000 modified allelic pairs of genes based on analysis of the *C. albicans* genome sequence. The complete set of essential genes of *C. albicans* is estimated to comprise approximately 1000 genes. The present invention provides the identities of some of these genes in *C. albicans*, and the various uses of these genes and their products as drug targets. In addition, estimates as to the number of genes participating in the virulence of this pathogen range between 100 and 400 genes. Once the identity of an essential gene is known, various types of mutants containing one or more copies of the mutated essential gene created by other methods beside the GRACE method are contemplated and encompassed by the invention.

The invention also provides biological and computational methods, and reagents that allow the isolation and identification of genes that are homologous to the identified essential and virulence genes of *C. albicans*. Information obtained from the GRACE strains of diploid organisms can be used to identify homologous sequences in haploid organisms. The identities and uses of such homologous genes are also encompassed by the present invention.

For clarity of discussion, the invention is described in the subsections below by way of example for the pathogenic fungus, *Candida albicans*. However, the principles may be analogously applied to the essential and virulence genes of other pathogens and parasites, of plants and animals including humans. The GRACE method can be applied to any pathogenic organisms that has a diploid phase in their life cycles. Hence, the term diploid pathogenic organism is not limited to organism that exist exclusively in diploid form, but encompasses also organisms that have both haploid and diploid phases in their life cycle.

For example, the GRACE method for drug target identification and validation can be directly applied to other pathogenic fungi. Deuteromycetous fungi, i.e. those lacking a sexual cycle and classical genetics, (in which *C. albicans* is included), represent the majority of human fungal pathogens. *Aspergillus fumigatus* is another medically-significant member of this phylum, which, more strictly, includes members of the Ascomycota and the Basidiomycota. *A. fumigatus*, an Ascomyte is the predominant air borne infectious fungal agent causing respiratory infection, or invasive aspergillosis (IA), in immunocompromised patients. While relatively unknown 20 years ago, today the number of IA cases is estimated to be several thousand per year. Moreover, IA exhibits a mortality rate exceeding 50% and neither amphothericin B nor fluconazole are highly efficacious. Compounding these problems is that identification of novel drug targets is limited by the current state of target validation in this organism.

The GRACE method demonstrated for *C. albicans* is readily adapted for use with *A. fumigatus*, for the following reasons. Although, *A. fumigatus* possesses a haploid genome, the GRACE method could be simplified to one step-conditional promoter replacement of the wild type promoter. Since *A. fumigatus*, in contrast to *Candida albicans*, adheres to the universal genetic code, extensive site-directed mutagenesis, like that required to engineer the GRACE method for *C. albicans*, would not be required. Moreover, essential molecular biology techniques such as transformation and gene disruption via homologous recombination have been developed for *A. fumigatus*. Selectable markers are available for these techniques in *A. fumigatus*, and include genes conferring antibiotic resistance to hygromycin B and phleomycin, and the auxotrophic marker, ura3. Furthermore, both public and private *A. fumigatus* genome sequencing projects exist. Therefore, sequence information is available both for the identification of putative essential genes as well as for the experimental validation of these drug targets using the GRACE method. Additional pathogenic deuteromycetous fungi to which the GRACE method may be applied include *Aspergillus flavus, Aspergillus niger*, and *Coccidiodes immitis*.

In another aspect of the present invention, the GRACE method for drug target identification and validation is applied to Basidiomycetous pathogenic fungi. One particular, medically-significant member of this phylum is *Cryptococcus neoformans*. This air borne pathogen represents the fourth (7–8%) most commonly recognized cause of life-threatening infections in AIDS patients. Transformation and gene disruption strategies exist for *C. neoformans* and a publically funded genome sequencing project for this organism is in place. *C. neoformans* possesses a sexual cycle, thus enabling the GRACE method to be employed with both haploid and diploid strains. Other medically-significant Basidiomycetes include *Trichosporon beigelii* and *Schizophylum commune*.

In the same way medically relevant fungal pathogens are suitable for a rational drug target discovery using the GRACE method, so too may plant fungal pathogens and animal pathogens be examined to identify novel drug targets for agricultural and veterinary purposes. The quality and yield of many agricultural crops including fruits, nuts, vegetables, rice, soybeans, oats, barley and wheat are significantly reduced by plant fungal pathogens. Examples include the wheat fungal pathogens causing leaf blotch (*Septoria tritici*, glume blotch (*Septoria nodorum*), various wheat rusts (*Puccinia recondita, Puccinia graminis*); powdery mildew (various species), and stem/stock rot (Fusarium spp.) Other particularly destructive examples of plant pathogens include, *Phytophthora infestans*, the causative agent of the Irish potato famine, the Dutch elm disease causing ascomycetous fungus, *Ophiostoma ulmi*, the corn smut causing pathogen, *Ustilago maydis* and the rice-blast-causing pathogen *Magnapurtla grisea*. The emerging appearance of fungicidal-resistant plant pathogens and increasing reliance on monoculture practices, clearly indicate a growing need for novel and improved fungicidal compounds. Accordingly, the present invention encompasses the application of the GRACE method to identify and validate drug targets in pathogens and parasites of plants and livestock. Table I lists exemplary groups of haploid and diploid fungi of medical, agricultural, or commercial value.

TABLE I

Exemplary Haploid and Diploid Fungi

| Animal pathogens: | Plant Pathogens: | General Commercial Significance |
|---|---|---|
| | Ascomycota | |
| *Aspergillus fumigatus* | *Alternaria solanii* | *Aspergillus niger* |
| Alternaria spp | *Gaeumannomyces graminis* | *Schizosaccharomyces pombe* |
| *Blastomyces dermatidis* | *Cercospora zeae-maydis* | *Pichia pastoris* |
| Candida spp including | *Botrytis cinerea* | *Hansenula polymorpha* |
| *Candida dublinensis* | *Claviceps purpurea* | *Ashbya gossipii* |
| *Candida glabrata* | *Corticum rolfsii* | *Aspergillus nidulans* |
| *Candida krusei* | *Endothia parasitica* | *Trichoderma reesei* |
| *Candida lustaniae* | *Sclerotinia sclerotiorum* | *Aureobasidium pullulans* |
| *Candida parapsilopsis* | *Erysiphe gramini* | *Yarrowia lipolytica* |
| *Candida tropicalis* | *Erysiphe triticii* | *Candida utilis* |
| *Coccidioides immitis* | Fusarium spp. | *Kluveromyces lactis* |
| *Exophalia dermatiditis* | *Magnaporthe grisea* | |
| *Fusarium oxysporum* | *Plasmopara viticola* | |
| *Histoplasma capsulatum* | *Penicillium digitatum* | |
| *Pneumocystis carinii* | *Ophiostoma ulmi* | |
| | Rhizoctonia species including *oryzae* | |
| | Septoria species including | |
| | *Septoria avenae* | |
| | *Septoria nodorum* | |
| | *Septoria passerinii* | |
| | *Septoria triticii* | |
| | *Venturia inequalis* | |
| | *Verticillium dahliae* | |
| | *Verticillium albo-atrum* | |
| | Basidiomycota | |
| *Cryptococcus neoformans* | Puccinia spp including | *Agaricus campestris* |
| *Trichosporon beigelii* | *Puccinia coronata* | *Phanerochaete chrysosporium* |
| | *Puccinia graminis* | *Gloeophyllum trabeum* |
| | *Puccinia recondita* | *Trametes versicolor* |
| | *Puccinia striiformis* | |
| | Tilletia spp including | |
| | *Tilletia caries* | |

TABLE I-continued

Exemplary Haploid and Diploid Fungi

| Animal pathogens: | Plant Pathogens: | General Commercial Significance |
|---|---|---|
| | *Tilletia controversa* | |
| | *Tilletia indica* | |
| | *Tilletia tritici* | |
| | *Tilletia foetida* | |
| | *Ustilago maydis* | |
| | *Ustilago hordeii* | |
| | Zygomycota | |
| *Absidia corymbifera* | | |
| *Mucor rouxii* | | |
| *Rhizomucor pusillus* | | |
| *Rhizopus arrhizus* | | |

All Candida species except *Candida glabrata* are obligate diploid species that lack a haploid phase in its life cycle, and are thus subject to the application of the GRACE methods.

5.2 Construction of GRACE Strains

According to the invention, in a GRACE strain of a diploid organism, only one allele of a gene is eliminated, while the second allele is placed under the control of the heterologous promoter, the activity of which is regulatable. Where the gene is essential, elimination of both alleles will be lethal or severely crippling for growth. Therefore, in the present invention, a heterologous promoter is used to provide a range of levels of expression of the second allele. Depending on the conditions, the second allele can be non-expressing, underexpressing, overexpressing, or expressing at a normal level relative to that when the allele is linked to its native promoter. A heterologous promoter is a promoter from a different gene from the same pathogenic organism, or it can be a promoter from a different species.

Precise replacement of a target gene is facilitated by using a gene disruption cassette comprising a selectable marker, preferably a dominant selectable marker, that is expressible in the strain of interest. The availability of two distinct dominant selectable markers allows the gene replacement process to be engineered at both alleles of the target gene, without the required counterselection step inherent in existing methods.

In particular, the present invention encompasses a method for constructing a strain of diploid pathogenic fungal cells, in which both alleles of a gene are modified, the method comprising the steps of (a) modifying a first allele of a gene in diploid pathogenic fungal cells by recombination using a gene disruption cassette comprising a nucleotide sequence encoding a selectable marker that is expressible in the cells, thereby providing heterozygous pathogenic fungal cells in which the first allele of the gene is inactivated; and (b) modifying the second allele of the gene in the heterozygous diploid pathogenic fungal cells by recombination with a promoter replacement fragment comprising a heterologous promoter, such that the expression of the second allele of the gene is regulated by the heterologous promoter.

The process can be repeated for a desired subset of the genes such that a collection of GRACE strains is generated wherein each strain comprises a modified allelic pair of a different gene. By repeating this process for every gene in a pathogenic fungus, a complete set of GRACE strains representing the entire genome of the pathogenic fungus can be obtained. Thus, the present invention provides a method of assembling a collection of diploid pathogenic fungal cells, each of which comprises the modified alleles of a different gene. The method comprises repeating the steps of modifying pairs of alleles a plurality of times, wherein a different pair of gene alleles is modified with each repetition, thereby providing the collection of diploid pathogenic fungal cells each comprising the modified alleles of a different gene.

A preferred embodiment for the construction of GRACE strains, uses the following two-step method. C. albicans is used as an example.

5.2.1 Heterozygote Construction by Gene Disruption

Several art-known methods are available to create a heterozygote mutant. In less preferred embodiments, auxotrophic markers, such as but not limited to CaURA3, CaHIS3, CaLEU2, or CaTRP1, could be used for gene disruption if desired. However, the preferred method of heterozygote construction in diploid fungi employs a genetically modified dominant selectable marker. C. albicans is sensitive to the nucleoside-like antibiotic streptothricin at a concentration of 200 micrograms per milliliter. The presence of the *Escherichia coli* SAT1 gene within C. albicans allows acetylation of the drug rendering it nontoxic and permitting the strain to grow in the presence of streptothricin at a concentration of 200 micrograms per milliliter. Expression of the SAT1 gene in C. albicans is made possible by engineering the gene so that its DNA sequence is altered to conform to the genetic code of this organism and by providing a CaACT1 promoter (Morschhauser et al. (1998) Mol. Gen. Genet. 257:412–420) and a CaPCK1 terminator sequence (Leuker et al. (1997) Gene 192: 235–40). This genetically modified marker is referred to as CaSAT1 which is the subject of a copending United States nonprovisional application, filed Feb. 16, 2001.

C. albicans is also sensitive to a second fungicidal compound, blasticidin, whose cognate resistance gene from *Bacillus cereus*, BSR, has similarly been genetically engineered for expression in C. albicans (CaBSR1), and has been shown to confer a dominant drug resistance phenotype. PCR amplification of either dominant selectable marker so as to include about 65 bp of flanking sequence identical to the sequence 5' and 3' of the C. albicans gene to be disrupted, allows construction of a gene disruption cassette for any given C. albicans gene.

By employing the method of Baudin et al. (1993, Nucleic Acids Research 21:3329–30), a gene disruption event can be obtained following transformation of a C. albicans strain with the PCR-amplified gene disruption cassette and selection for drug resistant transformants that have precisely replaced the wild type gene with the dominant selectable marker. Such mutant strains can be selected for growth in the presence of a drug, such as but not limited to streptothricin. The resulting gene disruptions are generally heterozygous in the diploid C. albicans, with one copy of the allelic pair on one homologous chromosome disrupted, and the other allele on the other homologous chromosome remaining as a wild type allele as found in the initial parental strain. The disrupted allele is non-functional, and expression from this allele of the gene is nil. By repeating this process for all the genes in the genome of an organism, a set of gene disruptions can be obtained for every gene in the organism. The method can also be applied to a desired subset of genes.

5.2.2 Conditional Expression by a Tetracycline-Regulatable Promoter

The conditional expression system used in this embodiment of the invention comprises a regulatable promoter and a means for regulating promoter activity. Conditional expression of the remaining wild type allele in a heterozygote constructed as set forth in Section 5.1.1 is achieved by replacing its promoter with a tetracycline-regulatable promoter system that is developed initially for *S. cerevisiae* but which is modified for use in C. albicans. See Gari et al., 1997, Yeast 13:837–848; and Nagahashi et al., 1997, Mol. Gen. Genet. 255:372–375.

Briefly, conditional expression is achieved by first constructing a transactivation fusion protein comprising the *E. coli* TetR tetracycline repressor domain or DNA binding domain (amino acids 1–207) fused to the transcription activation domain of *S. cerevisiae* GAL4 (amino acids 785–881) or HAP4 (amino acids 424–554). Multiple CTG codon corrections were introduced to comply with the C. albicans genetic code. The nucleotide sequences encoding the transactivation fusion proteins of *E. coli* TetR (amino acids 1–207) plus *S. cerevisiae* GAL4 (amino acids 785–881), and of *E. coli* TetR (amino acids 1–207) plus *S. cerevisiae* HAP4 (amino acids 424–554), both of which have been modified for proper expression in C. albicans are encompassed by the present invention. Accordingly, the invention provides haploid or diploid cells that can comprise a nucleotide sequence encoding a transactivation fusion protein expressible in the cells, wherein the transactivation fusion protein comprises a DNA binding domain and a transcription activation domain.

Constitutive expression of the transactivation fusion protein in C. albicans can be achieved by providing a CaACT1 promoter and CaACT1 terminator sequence. However, it will be appreciated that any regulatory regions, promoters and terminators, that are functional in C. albicans can be used to express the fusion protein. Thus, a nucleic acid molecule comprising a promoter functional in C. albicans, the coding region of a transactivation fusion protein, and a terminator functional in C. albicans, are encompassed by the present invention. Such a nucleic acid molecule can be a plasmid, a cosmid, a transposon, or a mobile genetic element. In a preferred embodiment, the TetR-Gal4 or TetR-Hap4 transactivators can be stably integrated into a C. albicans strain, by using either ura3 and his3 auxotrophic markers.

In this embodiment, the invention farther provides that a promoter replacement fragment comprising a nucleotide sequence encoding heterologous promoter which comprises at least one copy of a nucleotide sequence which is recognized by the DNA binding domain of the transactivation fusion protein, and wherein binding of the transactivation fusion protein increases transcription of the heterologous promoter. The heterologous tetracycline promoter initially developed for *S. cerevisiae* gene expression, contains an ADHI3' terminator sequence, variable number of copies of the tetracycline operator sequence (2, 4, or 7 copies), and the CYC1 basal promoter. The tetracycline promoter has been subcloned adjacent to both CaHIS3 and CaSAT1 selectable markers in the orientation favoring tetracycline promoter-dependent regulation when placed immediately upstream the open reading frame of the gene of interest. PCR amplification of the CaHIS3-Tet promoter cassette incorporates 65 bp of flanking sequence homologous to the promoter sequence around nucleotide positions −200 and −1 (relative to the start codon) of the target gene, thereby producing a conditional promoter replacement fragment for transformation. When transformed into a C. albicans strain made heterozygous as described in Section 5.1.1 using the CaSAT1 disruption cassette, homologous recombination between the promoter replacement fragment and the promoter of the wild type allele generates a strain in which the remaining wild type gene is conditionally regulated gene by the tetracycline promoter. Transformants are selected as His prototrophs and verified by Southern blot and PCR analysis.

In this particular embodiment, the promoter is induced in the absence of tetracycline, and repressed by the presence of tetracycline. Analogs of tetracycline, including but not limited to chlortetracycline, demeclocycline, doxycycline, meclocycline, methocycline, minocycline hydrochloride, anhydrotetracycline, and oxytetracycline, can also be used to repress the expression of the modified gene allele in a GRACE strain.

The present invention also encompasses alternative variants of the tetracycline promoter system, based upon a mutated tetracycline repressor (tetR) molecule, designated tetR', which is activated (i.e. binds to its cognate operator sequence) by binding of the antibiotic effector molecule to promote expression, and is repressed (i.e. does not bind to the operator sequence) in the absence of the antibiotic effectors, when the tetR' is used instead of, or in addition to, the wild-type tetR. For example, the GRACE method could be performed using tetR' instead of tetR in cases where repression is desired under conditions which lack the presence of tetracycline, such as shut off of a gene participating in drug transport (e.g CaCDR1, CaPDR5, or CaMDR1). Also, the GRACE method could be adapted to incorporate both the tetR and tetR' molecules in a dual activator/repressor system where tetR is fused to an activator domain and tetR' is fused to a general repressor (e.g. CaSsr6 or CaTup1) to enhance or further repress expression in the presence of the antibiotic effector molecules (Belli et al., 1998, Nucl Acid Res 26:942–947 which is incorporated herein by reference). These methods of providing conditional expression are also contemplated.

In another embodiment of the invention, the method may also be applied to haploid pathogenic fungi by modifying the single allele of the gene via recombination of the allele with a promoter replacement fragment comprising a nucleotide sequence encoding a heterologous promoter, such that the expression of the gene is conditionally regulated by the heterologous promoter. By repeating this process for a preferred subset of genes in a haploid pathogenic organism, or its entire genome, a collection or a complete set of conditional mutant strains can be obtained. A preferred subset of genes comprises genes that share substantial nucleotide sequence homology with target genes of other organisms, e.g., C. albicans and S. cerevisiae. For example, this variation to the method of the invention may be applied to haploid fungal pathogens including, but not limited to, animal fugal pathogens such as *Aspergillus fumigatus, Aspergillus niger, Aspergillus flavis, Candida glabrata, Cryptococcus neoformans, Coccidioides immitis, Exophalia dermatiditis, Fusarium oxysporum, Histoplasma capsulatum, Phneumocystis carinii, Trichosporon beigelii, Rhizopus arrhizus, Mucor rouxii, Rhizomucor pusillus,* or *Absidia corymbigera*, or the plant fungal pathogens, such as *Botrytis cinerea, Erysiphe graminis, Magnaporthe grisea, Puccinia recodita, Septoria triticii, Tilletia controversa, Ustilago maydis*, or any species falling within the genera of any of the above species.

The means to achieve conditional expression are not restricted to the tetracycline promoter system and can be performed using other conditional promoters. Such conditional promoter may, for example, be regulated by a repressor which repress transcription from the promoter under particular condition or by a transactivator which increases transcription from the promoter, such as, when in the presence of an inducer. For example, the C. albicans CaPCK1 promoter is not transcribed in the presence of glucose but has a high level of expression in cells grown on other carbon sources, such as succinate, and therefore could also be adopted for conditional expression of the modified allele in a GRACE strain. To this end, it has been shown that both CaHIS1 and CaSAT1 are essential for growth on glucose-containing medium using the CaPCK1 promoter as an alternative to the tetracycline promoter in the above description. In this instance, the CaPCK1 promoter is heterologous to the gene expressed and not to the organism, and such heterologous promoters are also encompassed in the invention. Alternative promoters that could functionally replace the tetracycline promoter include but are not limited to other antibiotic-based regulatable promoter systems (e.g., pristinamycin-induced promoter or PIP) as well as *Candida albicans* conditionally-regulated promoters such as MET25, MAL2, PHO5, GAL1,10, STE2, or STE3.

In a preferred embodiment of the GRACE method, performing the gene disruption first enables heterozygous strains to be constructed and separately collected as a heterozygote strain collection during the process of drug target validation. Such a *C. albicans* heterozygote strain collection enables drug screening approaches based on haploinsufficiency for validated targets within the collection. As used herein, the term "haploinsufficiency" refers to the phenomenon whereby heterozygous strains for a given gene express approximately half the normal diploid level of a particular gene product. Consequently, these strains provide constructions having a diminished level of the encoded gene product, and they may be used directly in screens for antifungal compounds. Here differential sensitivity of a diploid parent, as compared with its heterozygous derivative, will indicate that a drug is active against the encoded gene product.

It is clear to those skilled in the art that the order of allele modification followed in this embodiment of the invention is not critical, and that it is feasible to perform these steps in a different order such that the conditional-expressing allele is constructed first and the disruption of the remaining wild type gene allele be performed subsequently. However, where the promoter replacement step is carried out first, care should be taken to delete sequences homologous to those employed in the gene disruption step.

A specific application of the GRACE method, as used to construct modified alleles of the target gene CaKRE9 is provided in Section 6.

5.2.3 Alternative Methods of Conditional Expression

In other embodiments of the invention, conditional expression could be achieved by means other than the reliance of conditional promoters. For example, conditional expression could be achieved by the replacement of the wild type allele in heterozygous strains with temperature sensitive alleles derived in vitro, and their phenotype would then be analyzed at the nonpermissive temperature. In a related approach, insertion of a ubiquitination signal into the remaining wild type allele to destabilize the gene product during activation conditions can be adopted to examine phenotypic effects resulting from gene inactivation. Collectively, these examples demonstrate the manner in which *C. albicans* genes can be disrupted and conditionally regulated using the GRACE method.

In an alternative embodiment of the present invention, a constitutive promoter regulated by an excisable transactivator can be used. The promoter is placed upstream to a target gene to repress expression to the basal level characteristic of the promoter. For example, in a fungal cell, a heterologous promoter containing lexA operator elements may be used in combination with a fusion protein composed of the lexA DNA binding domain and any transcriptional activator domain (e.g. GAL4, HAP4, VP16) to provide constitutive expression of a target gene. Counterselection mediated by 5-FOA can be used to select those cells which have excised the gene encoding the fusion protein. This procedure enables an examination of the phenotype associated with repression of the target gene to the basal level of expression provided by the lexA heterologous promoter in the absence of a functional transcription activator. The GRACE strains generated by this approach can be used for drug target validation as described in detail in the sections below. In this system, the low basal level expression associated with the heterologous promoter is critical. Thus, it is preferable that the basal level of expression of the promoter is low to make this alternative shut-off system more useful for target validation.

Alternatively, conditional expression of a target gene can be achieved without the use of a transactivator containing a DNA binding, transcriptional activator domain. A cassette could be assembled to contain a heterologous constitutive promoter downstream of, for example, the URA3 selectable marker, which is flanked with a direct repeat containing homologous sequences to the 5' portion of the target gene. Additional homologous sequences upstream of the target, when added to this cassette would facilitate homologous recombination and replacement of the native promoter with above-described heterologous promoter cassette immediately upstream of the start codon of the target gene or open reading frame. Conditional expression is achieved by selecting strains, by using 5-FOA containing media, which have excised the heterologous constitutive promoter and URA3 marker (and consequently lack those regulatory sequences upstream of the target gene required for expression of the gene) and examining the growth of the resulting strain versus a wild type strain grown under identical conditions.

5.3 Identification of Essential Genes and Virulence Genes 5.3.1 Essential Genes

The present invention provides methods for determining whether the gene that has been modified in a GRACE strain is an essential gene or a virulence gene in a pathogenic organism of interest. To determine whether a gene is an essential gene in an organism, a GRACE strain containing the modified alleles of the gene is cultured under conditions wherein the second modified allele of the gene which is under conditional expression, is substantially underexpressed or not expressed. The viability and/or growth of the GRACE strain is compared with that of a wild type strain cultured under the same conditions. A loss or reduction of viability or growth indicates that the gene is essential to the survival of a pathogenic fungus. Accordingly, the present invention provides a method for identifying essential genes in a diploid pathogenic organism comprising the steps of culturing a plurality of GRACE strains under culture conditions wherein the second allele of each of the gene modified in the respective GRACE strain is substantially underexpressed or not expressed; determining viability and/ or growth indicator(s) of the cells; and comparing that with the viability and/or growth indicator(s) of wild type cells. The level of expression of the second allele can be less than 50% of the non-modified allele, less than 30%, less than 20%, and preferably less than 10%. Depending on the heterologous promoter used, the level of expression can be controlled by, for example, antibiotics, metal ions, specific chemicals, nutrients, pH, temperature, etc.

Candida albicans is used herein as an example which has been analyzed by the GRACE methodology.

For example, C. albicans conditional gene expression using the GRACE method was performed using CaKRE1, CaKRE5, CaKRE6, and CaKRE9 (FIG. 3). CaKRE5, CaKRE6, and CaKRE9 are predicted to be essential or conditionally essential (CaKRE9 null strains are nonviable on glucose but viable on galactose), in C. albicans as demonstrated by gene disruption using the Ura blaster method. CaKRE1 has been demonstrated as a nonessential gene using the Ura blaster method in C. albicans. Strains heterozygous for the above genes were constructed by PCR-based gene disruption method using the CaSAT1 disruption cassette followed by tetracycline regulated promoter replacement of the native promoter of the wild type allele. Robust growth of each of these strains suggests expression proceeds normally in the absence of tetracycline. When tetracycline is added to the growth medium, expression of these tetracycline promoter-regulated genes is greatly reduced or abolished. In the presence of tetracycline, the GRACE strain cells containing each one of the three essential C. albicans genes cited above stop growing. As expected, only the CaKRE1 GRACE strain demonstrates robust growth despite repression of CaKRE1 expression.

To further examine the utility of the GRACE method in target validation, growth of four additional GRACE strains controlling expression of the known essential genes CaTUB1, CaALG7, CaAUR1, and CaFKS1, as well as the predicted: essential gene CaSAT2, and CaKRE1 were compared under inducing versus repressing conditions (FIG. 4). As expected, GRACE strains of CaTUB1, CaALG7, CaAUR1 and CaFKS1 failed to grow under repressing conditions, unlike the non-essential CaKRE1 GRACE strain. Furthermore, as predicted, the CaSAT2 GRACE strain demonstrates essentiality of this gene in C. albicans. The CaSAT2 gene, which has been engineered as a dominant selectable marker for use in C. albicans, is a C. albicans gene that is homologous to a S. cerevisiae gene but is unrelated to the Sat1 gene of E. coli.

In all cases based on other disruption data that have been generated, this is the expected response if the tetracycline regulated gene is repressed to a level where it is nonfunctional in the presence of tetracycline. Furthermore, in applying the GRACE methodology of conditional gene disruption to two additional C. albicans genes (CaYPD1, and CaYNL194c) whose S. cerevisiae counterpart is known not to be essential, no inhibition of growth was observed when these strains were incubated in the presence of tetracycline. These results establish that the method of conditional gene expression using a GRACE strain is a reliable indicator of gene essentiality.

Furthermore, the utility of the present method, as a rapid and accurate means to identifying the complete set of essential genes in C. albicans, has been demonstrated by an analysis of the null phenotype of a large number of genes using the GRACE two-step method of gene disruption and conditional expression. Target genes were selected as being fungal specific and essential. Such genes are referred to as target essential genes in the screening assays described below.

A literature search identified reports of URA blaster-based gene disruption experiments on a total of 89 genes, of which 13 genes were presumed to be essential, based on the inability to construct homozygous deletion strains. The 13 genes are. CaCCT8 (Rademacher et al., Microbiology, UK 144, 2951–2960 (1998)); CaFKS1 (Mio et al., J. Bacteriol, 179, 4096–105 (1997); and Douglas, et al., Antimicrob Agents Chemother 41, 2471–9 (1997)); CaHSP90 (Swoboda et al., Infect Immun 63, 4506–14 (1995)); CaKRE6 (Mio et al., J. Bacteriol 179, 2363–72 (1997)); CaNMT1 (Weinberg et al., Mol Microbiol 16, 241–50 (1995)); CaPRS1 (Payne et al., J. Med. Vet. Mycol. 35, 305–12 (1997)); CaPSA1 (Care et al., Mol Microbiol 34, 792–798 (1999)); CaRAD6 (Care et al., Mol Microbiol 34, 792–798 (1999)); CaSEC4 (Mao et al., J. Bacteriol 181, 7235–7242 (1999)); CaSEC14 (Monteoliva et al., Yeast 12, 1097–105 (1996)); CaSNF1 (Petter et al., Infect Immun. 65, 4909–17 (1997)); CaTOP2 (Keller, et al., Biochem J., 329–39 (1997)); and CaEFT2 (Mendoza et al., Gene 229, 183–1991 (1999)). These 13 putatively essential genes and CaTUB1, CaALG1, and CaAUR1 of *C. albicans* are not initially identified by the GRACE method. However, GRACE strains containing modified alleles of any one of these 17 genes and their uses are encompassed by the invention, for example, the CaTUB1, CaALG1, and CaAUR1 GRACE strains in FIG. 4 and the CaKRE6 GRACE strain in FIG. 3. Any of these 17 genes may be included as a control for comparisons in the methods of the invention, or as a positive control for essentiality in the collections of essential genes of the invention. The nucleic acid molecules comprising a nucleotide sequence corresponding to any of these 17 genes may be used in the methods of drug discovery of the invention as drug targets, or they may be included individually or in subgroups as controls in a kit or in a nucleic acid microarray of the invention.

In contrast to the use of conventional method, application of the GRACE method has already identified significantly more *C. albicans* essential genes than previously determined by the collective efforts of the entire *C. albicans* research community. The data presented herewith establishes the speed inherent to the approach of the invention and, therefore, the feasibility of extending the GRACE method to the examination of all the genes of the *C. albicans* genome, the identification of the complete set of essential genes of this diploid fungal pathogen, and its application to other species.

An alternative method is available for assessing the essentiality of the modified gene in a GRACE strain. According to the invention, repression of expression of the modified gene allele within a GRACE strain may be achieved by homologous recombination-mediated excision of the gene encoding the transactivator protein. In a preferred embodiment, where conditional expression of a target gene is achieved using the tetracycline-regulated promoter, constitutive expression (under nonrepressing conditions) may be repressed by homologous recombination-mediated excision of the transactivator gene (TetR-GAL4AD). In this way, an absolute achievable repression level is produced independently of that produced by tetracycline-mediated inactivation of the transactivator protein. Excision of the transactivator gene is made possible by virtue of the selectable marker and integration strategy used in GRACE strain construction. Stable integration of the CaURA3-marked plasmid containing the TetR-GAL4AD transactivator gene into the CaLEU2 locus results in a tandem duplication of CaLEU2 flanking the integrated plasmid. Counterselection on 5-FOA-containing medium can then be performed to select for excision of the CaURA3-marked transactivator gene and to directly examine whether this alternative repression strategy reveals the target gene to be essential.

Three examples of genes defined as essential on 5-FOA containing medium but lacking any detectable growth impairment on tetracycline supplemented medium are the genes, CaYCL052c, CaYNL194c and CaYJR046c. Presumably, this is due to the target gene exhibiting a lower basal level of expression under conditions where the transactivator gene has been completely eliminated than its gene product incompletely inactivated by addition of tetracycline. Thus, the GRACE method offers two independent approaches for the determination of whether or not a given gene is essential for viability of the host strain.

5.3.2 Virulence/Pathogenicity Genes

The present invention also provides methods of using the GRACE strains of a diploid pathogenic organism to identify virulence/pathogenicity genes. In addition to uncovering essential genes of a pathogenic organism, the GRACE methodology enables the identification of other genes and gene products potentially relevant to the screening of drugs useful for the treatment of diseases caused by the pathogenic organism. Nonessential genes and their gene products of a pathogen which nevertheless display indispensable roles in the pathogenesis process, may therefore serve as potential drug targets for prophylactic drug development and could be used in combination with existing cidal therapeutics to improve treatment strategies. Thus, genes and their products implicated in virulence and/or pathogenicity represent another important class of potential drug targets. Moreover, some of the genes implicated in virulence and pathogenicity may be species-specific, and unique to a particular strain of pathogen. It has been estimated that approximately 6–7% of the genes identified through the *C. albicans* sequencing project are absent in *S. cerevisiae*. This represents as many as 420 *Candida albicans*-specific genes which potentially participate in the process of pathogenesis or virulence. Such a large scale functional evaluation of this gene set can only be achieved using the GRACE methodology of the invention.

Although essential genes provide preferred targets, value would also be placed on those nonessential *C. albicans* specific genes identified. The potential role of nonessential *C. albicans*-specific genes in pathogenesis may be evaluated and prioritized according to virulence assays (e.g. buccal epithelial cell adhesion assays and macrophage assays) and various *C. albicans* infection studies (e.g. oral, vaginal, systemic) using mouse or other animal models. In the same manner described above for essential genes, it is equally feasible to demonstrate whether nonessential genes comprising the GRACE strain collection are required for pathogenicity in a cellular assay or in a mouse model system. Accordingly, GRACE strains that fail to cause fungal infection in mice under conditions of gene inactivation by tetracycline (or alternative gene inactivation means) define the GRACE virulence/pathogenicity subset of genes. More defined subsets of pathogenicity genes, for example those genes required for particular steps in pathogenesis (e.g. adherence or invasion) can be determined by applying the GRACE pathogenicity subset of strains to in vitro assays which measure the corresponding process. For example, examining GRACE pathogenicity strains in a buccal adhesion or macrophage assay by conditional expression of individual genes would identify those pathogenicity factors required for adherence or cell invasion respectively. Moreover, essential genes that display substantially reduced virulence and growth rate when only partially inactivated represent "multifactorial" drug targets for which even minimally inhibitory high specificity compounds would display therapeutic value.

Accordingly, to determine whether a gene contributes toward the virulence/pathogenicity of a pathogenic organism in a host, a GRACE strain of the pathogen containing the modified alleles of the gene is allowed to infect host cells or animals under conditions wherein the second modified allele of the gene which is under conditional expression, is substantially underexpressed or not expressed. After the host cells and/or animals have been contacted with the GRACE strain for an appropriate period of time, the condition of the cells and/or animals is compared with cells and/or animals infected by a wild type strain under the same conditions.

Various aspects of the infected cell's morphology, physiology, and/or biochemistry can be measured by methods known in the art. When an animal model is used, the progression of the disease, severity of the symptoms, and/or survival of the host can be determined. Any loss or reduction of virulence or pathogenicity displayed by the GRACE strain indicates that the gene modified in the strain contributes to or is critical to the virulence and/or pathogenicity of the virus. Such genes are referred to as target virulence genes in the screening assays described below.

In another aspect of the present invention, GRACE methodology can be used for the identification and delineation of genetic pathways known to be essential to the development of pathogenicity. For example, extensive work in S. cerevisiae has uncovered a number of processes including cell adhesion, signal transduction, cytoskeletal assembly, that play roles in the dimorphic transition between yeast and hyphal morphologies. Deletion of orthologous genes participating in functionally homologous cellular pathways in pathogenic fungi such as C. albicans, A. fumigatis, and C. neoformans, has clearly demonstrated a concomitant loss of virulence. Therefore, the use of GRACE strains of orthologous genes found in C. albicans and other pathogenic fungi could rapidly validate potential antifungal drug target genes whose inactivation impairs hyphal development and pathogenicity.

5.3.3 Validation of Genes Encoding Drug Targets

Target gene validation refers to the process by which a gene product is identified as suitable for use in screening methods or assays in order to find modulators of the function or structure of that gene product. Criteria used for validation of a gene product as a target for drug screening, however, may be varied depending on the desired mode of action that the compounds sought will have, as well as the host to be protected.

In one aspect of the present invention, a set of GRACE strains identified and grouped as having only modified alleles of essential genes can be used directly for drug screening.

In another aspect, the initial set of essential genes is further characterized using, for example, nucleotide sequence comparisons, to identify a subset of essential genes which include only those genes specific to fungi—that is, a subset of genes encoding essential genes products which do not have homologs in a host of the pathogen, such as humans. Modulators, and preferably inhibitors, of such a subset of genes in a fungal pathogen of humans would be predicted to be much less likely to have toxic side effects when used to treat humans.

Similarly, other subsets of the larger essential gene set could be defined to include only those GRACE strains carrying modified allele pairs that do not have a homologous sequence in one or more host (e.g., mammalian) species to allow the detection of compounds expected to be used in veterinary applications. In addition, using other homology criteria, a subset of GRACE strains could be identified that would be used for the detection of anti-fungal compounds active against agricultural pathogens, inhibiting targets that do not have homologs in the crop to be protected.

Current C. albicans gene disruption strategies identify nonessential genes and permit the inference that other genes are essential, based on a failure to generate a homozygous null mutant. The null phenotype of a drug target predicts the absolute efficaciousness of the "perfect" drug acting on this target. For example, the difference between a cidal (cell death) versus static (inhibitory growth) null terminal phenotype for a particular drug target. Gene disruption of CaERG11, the drug target of fluconazole, is presumed to be essential based on the failure to construct a homozygous CaERG11 deletion strain using the URA blaster method. However, direct evaluation of its null phenotype being cidal or static could not be performed in the pathogen, and only after the discovery of fluconazole was it possible to biochemically determine both the drug, and presumably the drug target to be static rather than as cidal. Despite the success fluconazole enjoys in the marketplace, its fungistatic mode of action contributes to its primary limitation, i.e., drug resistance after prolonged treatment. Therefore, for the first time, the ability to identify and evaluate cidal null phenotypes for validated drug targets within the pathogen as provided by the invention, now enables directed strategies to identifying antifungal drugs that specifically display a fungicidal mode of action.

Using a single GRACE strain or a desired collection of GRACE strains comprising essential genes, one or more target genes can be directly evaluated as displaying either a cidal or static null phenotype. This is determined by first incubating GRACE strains under repressing conditions for the conditional expression of the second allele for varying lengths of time in liquid culture, and measuring the percentage of viable cells following plating a defined number of cells onto growth conditions which relieve repression. The percentage of viable cells that remain after return to non-repressing conditions reflects either a cidal (low percent survival) or static (high percent survival) phenotype. Alternatively, vital dyes such as methylene blue or propidium iodide could be used to quantify percent viability of cells for a particular strain under repressing versus inducing conditions. As known fungicidal drug targets are included in the GRACE strain collection (e.g CaAUR1), direct comparisons can be made between this standard fungicidal drug target and novel targets comprising the drug target set. In this way each member of the target set can be immediately ranked and prioritized against an industry standard cidal drug target to select appropriate drug targets and screening assays for the identification of the most rapid-acting cidal compounds.

5.4 Essential Genes and Virulence Genes 5.4.1 Nucleic Acids Encoding Targets, Vectors, and Host Cells By practice of the methods of the invention, the essentiality and the contribution to virulence of substantially all the genes in the genome of an organism can be determined. The identities of essential genes and virulence genes of a diploid pathogenic organism, such as Candida albicans, once revealed by the methods of the invention, allow the inventors to study their functions and evaluate their usefulness as drug targets. Information regarding the structure and function of the gene product of the individual essential gene or virulence gene allows one to design reagents and assays to find compounds that interfere with its expression or function in the pathogenic organism. Accordingly, the present invention provides information on whether a gene or its product(s) is essential to growth, survival, or proliferation of the pathogenic organism, or that a gene or its product(s) contributes to virulence or pathogenicity of the organism with respect to a host. Based on this information, the invention further provides, in various embodiments, novel uses of the nucleotide and/or amino acid sequences of genes that are essential and/or that contributes to virulence or pathogenicity of a pathogenic organism, for purpose of discovering drugs that act against the pathogenic organism. Moreover, the present invention provides specifically the use of this information to identify orthologs of these essential genes in a non-pathogenic yeast, such as *Saccharomyces cerevisiae*, and the use of these orthologs in drug screening methods. Although the nucleotide sequence of the orthologs of these essential genes in *S. cerevisiae* may be known, it was not appreciated that these *S. cerevisiae* genes can be useful for discovering drugs against pathogenic fungi.

As used herein, the terms "gene" and "recombinant gene" refer to nucleic acid molecules comprising a nucleotide sequence encoding a polypeptide or a biologically active ribonucleic acid (RNA). The term can further include nucleic acid molecules comprising upstream, downstream, and/or intron nucleotide sequences. The term "open reading frame (ORF)," means a series of nucleotide triplets coding for amino acids without any termination codons and the triplet sequence is translatable into protein using the codon usage information appropriate for a particular organism.

As used herein, the term "target gene" refers to either an essential gene or a virulence gene useful in the invention, especially in the context of drug screening. The terms "target essential gene" and "target virulence gene" will be used where it is appropriate to refer to the two groups of genes separately. However, it is expected that some genes will contribute to virulence and be essential to the survival of the organism. The target genes of the invention may be partially characterized, fully characterized, or validated as a drug target, by methods known in the art and/or methods taught hereinbelow. As used herein, the term "target organism" refers to a pathogenic organism, the essential and/or virulence genes of which are useful in the invention.

The term "nucleotide sequence" refers to a heteropolymer of nucleotides, including but not limited to ribonucleotides and deoxyribonucleotides, or the sequence of these nucleotides. The terms "nucleic acid" and "polynucleotide" are also used interchangeably herein to refer to a heteropolymer of nucleotides, which may be unmodified or modified DNA or RNA. For example, polynucleotides can be single-stranded or double-stranded DNA, DNA that is a mixture of single-stranded and double-stranded regions, hybrid molecules comprising DNA and RNA with a mixture of single-stranded and double-stranded regions. In addition, the polynucleotide can be composed of triple stranded regions comprising DNA, RNA, or both. A polynucleotide can also contain one or modified bases, or DNA or RNA backbones modified for nuclease resistance or other reasons. Generally, nucleic acid segments provided by this invention can be assembled from fragments of the genome and short oligonucleotides, or from a series of oligonucleotides, or from individual nucleotides, to provide a synthetic nucleic acid.

The term "recombinant," when used herein to refer to a polypeptide or protein, means that a polypeptide or protein is derived from recombinant (e.g., microbial or mammalian) expression systems. "Microbial" refers to recombinant polypeptides or proteins made in bacterial or fungal (e.g., yeast) expression systems. As a product, "recombinant microbial" defines a polypeptide or protein essentially unaccompanied by associated native glycosylation. Polypeptides or proteins expressed in most bacterial cultures, e.g., *E. coli*, will be free of glycosylation modifications; polypeptides or proteins expressed in yeast will be glycosylated.

The term "expression vehicle or vector" refers to a plasmid or phage or virus, for expressing a polypeptide from a nucleotide sequence. An expression vehicle can comprise a transcriptional unit, also referred to as an expression construct, comprising an assembly of (1) a genetic element or elements having a regulatory role in gene expression, for example, promoters or enhancers, (2) a structural or coding sequence which is transcribed into mRNA and translated into protein, and which is operably linked to the elements of (1); and (3) appropriate transcription initiation and termination sequences. "Operably linked" refers to a link in which the regulatory regions and the DNA sequence to be expressed are joined and positioned in such a way as to permit transcription, and ultimately, translation. In the case of *C. albicans*, due to its unusual codon usage, modification of a coding sequence derived from other organisms may be necessary to ensure a polypeptide having the expected amino acid sequence is produced in this organism. Structural units intended for use in yeast or eukaryotic expression systems preferably include a leader sequence enabling extracellular secretion of translated protein by a host cell. Alternatively, where a recombinant protein is expressed without a leader or transport sequence, it may include an N-terminal methionine residue. This residue may or may not be subsequently cleaved from the expressed recombinant protein to provide a final product.

The term "recombinant host cells" means cultured cells which have stably integrated a recombinant transcriptional unit into chromosomal DNA or carry stably the recombinant transcriptional unit extrachromosomally. Recombinant host cells as defined herein will express heterologous polypeptides or proteins, and RNA encoded by the DNA segment or synthetic gene in the recombinant transcriptional unit. This term also means host cells which have stably integrated a recombinant genetic element or elements having a regulatory role in gene expression, for example, promoters or enhancers. Recombinant expression systems as defined herein will express RNA, polypeptides or proteins endogenous to the cell upon induction of the regulatory elements linked to the endogenous DNA segment or gene to be expressed. The cells can be prokaryotic or eukaryotic.

The term "polypeptide" refers to the molecule form by joining amino acids to each other by peptide bonds, and may contain amino acids other than the twenty commonly used gene-encoded amino acids. The term "active polypeptide" refers to those forms of the polypeptide which retain the biologic and/or immunologic activities of any naturally occurring polypeptide. The term "naturally occurring polypeptide" refers to polypeptides produced by cells that have not been genetically engineered and specifically contemplates various polypeptides arising from post-translational modifications of the polypeptide including, but not limited to, proteolytic processing, acetylation, carboxylation, glycosylation, phosphorylation, lipidation and acylation.

The term "isolated" as used herein refers to a nucleic acid or polypeptide separated from at least one macromolecular component (e.g., nucleic acid or polypeptide) present with the nucleic acid or polypeptide in its natural source. In one embodiment, the polynucleotide or polypeptide is purified such that it constitutes at least 95% by weight, more preferably at least 99.8% by weight, of the indicated biological macromolecules present (but water, buffers, and other small molecules, especially molecules having a molecular weight of less than 1000 daltons, can be present).

Table II lists a set of fungal specific genes that are demonstrated to be essential in *C. albicans* when conditionally expressed under the tetracycline repression system in the respective GRACE strains or when the gene encoding the transactivator protein is excised in the respective GRACE strain in a 5-FOA assay.

TABLE II

| Gene designation | DNA SeqID | Protein SeqID | Primer KOup | Primer KOdn | Primer tet up | Primer tet dn | Primer A | Primer B |
|---|---|---|---|---|---|---|---|---|
| CaYBR070C (SAT2) | 1 | 63 | 124 | 185 | 246 | 307 | 368 | 429 |
| CaYBR167C (POP7) | 2 | 64 | 125 | 186 | 247 | 308 | 369 | 430 |
| CaYBR243C (ALG7) | 3 | 65 | 126 | 187 | 248 | 309 | 370 | 431 |
| CaYCL031C (RRP7) | 4 | 66 | 127 | 188 | 249 | 310 | 371 | 432 |
| CaYDL105W | 5 | 67 | 128 | 189 | 250 | 311 | 372 | 433 |
| CaYDL153C (SAS10) | 6 | 68 | 129 | 190 | 251 | 312 | 373 | 434 |
| CaYDR052C (DBF4) | 7 | 69 | 130 | 191 | 252 | 313 | 374 | 435 |
| CaYDR118W (APC4) | 8 | 70 | 131 | 192 | 253 | 314 | 375 | 436 |
| CaYDR361C | 9 | 71 | 132 | 193 | 254 | 315 | 376 | 437 |
| CaYDR412W | 10 | 72 | 133 | 194 | 255 | 316 | 377 | 438 |
| CaYDR498C (SEC20) | 11 | 73 | 134 | 195 | 256 | 317 | 378 | 439 |
| CaYER026C (CHO1) | 12 | 74 | 135 | 196 | 257 | 318 | 379 | 440 |
| CaYGR090W | 13 | 75 | 136 | 197 | 258 | 319 | 380 | 441 |
| CaYGR245C | 14 | 76 | 137 | 198 | 259 | 320 | 381 | 442 |
| CaYHR007C (ERG11) | 15 | 77 | 138 | 199 | 260 | 321 | 382 | 443 |
| CaYHR036W | 16 | 78 | 139 | 200 | 261 | 322 | 383 | 444 |
| CaYHR058C (MED6) | 17 | 79 | 140 | 201 | 262 | 323 | 384 | 445 |
| CaYHR118C (ORC6) | 18 | 80 | 141 | 202 | 263 | 324 | 385 | 446 |
| CaYHR172W (SPC97) | 19 | 81 | 142 | 203 | 264 | 325 | 386 | 447 |
| CaYHR196W | 20 | 82 | 143 | 204 | 265 | 326 | 387 | 448 |
| CaYIR011C (STS1) | 21 | 83 | 144 | 205 | 266 | 327 | 388 | 449 |
| CaYJL069C | 22 | 84 | 145 | 206 | 267 | 328 | 389 | 450 |
| CaYJL090C (DPB11) | 23 | 85 | 146 | 207 | 268 | 329 | 390 | 451 |
| CaYJR041C | 24 | 86 | 147 | 208 | 269 | 330 | 391 | 452 |
| CaYJR112W (NNF1) | 25 | 87 | 148 | 209 | 270 | 331 | 392 | 453 |
| CaYKL004W (AUR1) | 26 | 88 | 149 | 210 | 271 | 332 | 393 | 454 |
| CaYKL033W | 27 | 89 | 150 | 211 | 272 | 333 | 394 | 455 |
| CaYKR025W (RPC37) | 28 | 90 | 151 | 212 | 273 | 334 | 395 | 456 |
| CaYKR063C (LAS1) | 29 | 91 | 152 | 213 | 274 | 335 | 396 | 457 |
| CaYKR071C | 30 | 92 | 153 | 214 | 275 | 336 | 397 | 458 |
| CaYKR081C | 31 | 93 | 154 | 215 | 276 | 337 | 398 | 459 |
| CaYKR083C | 32 | 94 | 155 | 216 | 277 | 338 | 399 | 460 |
| CaYLL003W (SF11) | 33 | 95 | 156 | 217 | 278 | 339 | 400 | 461 |
| CaYLR002C | 34 | 96 | 157 | 218 | 279 | 340 | 401 | 462 |
| CaYLR103C (CDC45) | 35 | 97 | 158 | 219 | 280 | 341 | 402 | 463 |
| CaYLR342W (FKS1) | 36 | 98 | 159 | 220 | 281 | 342 | 403 | 464 |
| CaYLR355C (ILV5) | 37 | 99 | 160 | 221 | 282 | 343 | 404 | 465 |
| CaYML025C (YML6) | 38 | 100 | 161 | 222 | 283 | 344 | 405 | 466 |
| CaYML085C (TUB1) | 39 | 101 | 162 | 223 | 284 | 345 | 406 | 467 |
| CaYMR149W (SWP1) | 40 | 102 | 163 | 224 | 285 | 346 | 407 | 468 |
| CaYMR200W (ROT1) | 41 | 103 | 164 | 225 | 286 | 347 | 408 | 469 |
| CaYMR220W (ERG8) | 42 | 104 | 165 | 226 | 287 | 348 | 409 | 470 |
| CaYMR277W (FCP1) | 43 | 105 | 166 | 227 | 288 | 349 | 410 | 471 |
| CaYNL132W | 44 | 106 | 167 | 228 | 289 | 350 | 411 | 472 |
| CaYNL149C | 45 | 107 | 168 | 229 | 290 | 351 | 412 | 473 |
| CaYNL151C (RPC31) | 46 | 108 | 169 | 230 | 291 | 352 | 413 | 474 |
| CaYNL181W | 47 | 109 | 170 | 231 | 292 | 353 | 414 | 475 |
| CaYNL232W (CSL4) | 48 | 110 | 171 | 232 | 293 | 354 | 415 | 476 |
| CaYNL245C | 49 | 111 | 172 | 233 | 294 | 355 | 416 | 477 |
| CaYNL256W | 50 | 112 | 173 | 234 | 295 | 356 | 417 | 478 |
| CaYNL260C | 51 | 113 | 174 | 235 | 296 | 357 | 418 | 479 |
| CaYOR004W | 52 | 114 | 175 | 236 | 297 | 358 | 419 | 480 |
| CaYOR075W (UFE1) | 53 | 115 | 176 | 237 | 298 | 359 | 420 | 481 |
| CaYOR148C (SPP2) | 54 | 116 | 177 | 238 | 299 | 360 | 421 | 482 |
| CaYOR206W | 55 | 117 | 178 | 239 | 300 | 361 | 422 | 483 |
| CaYOR287C | 56 | 118 | 179 | 240 | 301 | 362 | 423 | 484 |
| CaYPL128C (TBF1) | 57 | 119 | 180 | 241 | 302 | 363 | 424 | 485 |
| CaYPL160W (CDC60) | 58 | 120 | 181 | 242 | 303 | 364 | 425 | 486 |
| CaYPL228W (CET1) | 59 | 121 | 182 | 243 | 304 | 365 | 426 | 487 |
| CaYPR165W (RHO1) | 60 | 122 | 183 | 244 | 305 | 366 | 427 | 488 |
| CaYPR175W (DPB2) | 61 | 123 | 184 | 245 | 306 | 367 | 428 | 489 |
| CaYPL160W (CDC60) | 62 | N/A | 181 | 242 | 303 | 364 | 425 | 486 |

In one embodiment, the present invention provides the identities of 61 essential genes. Although the nucleotide sequence and the reading frame of a number of these genes are known, the fact that these genes are essential to the growth and/or survival of Candida albicans was not known until the inventors' discovery. Thus, the uses of these genes and their gene products are encompassed by the present invention. Also provided in Table II are SEQ ID NOs: that are used herein to identify the open reading frame, the deduced amino acid sequence and related oligonucleotide sequences for each identified essential gene.

Accordingly, SEQ ID NO:1 through to SEQ ID NO:62 each identifies a nucleotide sequence of the opening reading frame (ORF) of an identified essential gene. The nucleotide sequences labeled as SEQ ID NO:1–62 were obtained from a Candida albicans genomic sequence database version 6 assembled by the Candida albicans Sequencing Project and is accessible by internet at the web sites of Stanford University and University of Minnesota (See http://www-sequence.stanford.edu:8080/ and http://alces.med.umn.edu/Candida.html).

The predicted amino acid sequence of the identified essential genes are set forth in SEQ ID NO:63 through to SEQ ID NO:123 which are obtained by conceptual translation of the nucleotide sequences of SEQ ID NO: 1 through to 61 once the reading frame is determined. As it is well known in the art, the codon CTG is translated to a serine residue in C. albicans, instead of the usual leucine in other organisms. Accordingly, the conceptual translation of the ORF is performed using the codon usage of C. albicans.

The DNA sequences were generated by sequencing reactions and may contain minor errors which may exist as misidentified nucleotides, insertions, and/or deletions. However, such minor errors, if present, in the sequence database should not disturb the identification of the ORF as an essential gene of the invention. Since clones containing the ORF are available, one can readily repeat the sequencing and correct the minor error(s). Moreover, minor sequence errors do not affect the construction of GRACE strains and the uses of the GRACE strains, since these methods do not require absolute sequence identity between the chromosomal DNA sequences and the sequences of the gene in the primers or recombinant DNA. In some instances, the correct reading frame of the C. albicans gene can be identified by comparing its overall amino acid sequence with known S. cerevisiae sequences.

Thus, in one embodiment of the invention, conceptual translation of the nucleotide sequence of SEQ ID NO: 62 leads to an apparently premature termination of the opening reading frame when compared to its ortholog in S. cerevisiae. To maintain the reading frame, four nucleotides were added to create SEQ ID NO: 58 which results in the amino acid sequence of SEQ ID NO: 120. In another embodiment, the invention provides the genomic sequence of an identified essential gene, wherein the genomic sequence as set forth in SEQ ID NO: 490 contains an intron. The unpublished nucleotide sequence which does not contain intron sequence and encodes a protein is set forth in SEQ ID NO: 39.

SEQ ID NO:124–486 refers to oligonucleotide primers and probes that were designed for and used in the construction of the GRACE strain for the corresponding identified essential gene. (i.e., SEQ ID NO:124–184 knockout upstream primer (KO-UP); SEQ ID NO:185–245 knockout downstream primer (KO-Down); SEQ ID NO:246–306 tetracycline promoter upstream primer (Tet-Up); SEQ ID NO:307–367 Tetracycline promoter downstream primer (Tet-Down); and SEQ ID NO:368–489 primers for identification of the respective GRACE strains (primers A and B). Therefore, each set of oligonucleotides can be used to identify a unique essential gene and a unique GRACE strain, e.g. by hybridization, or PCR.

The essential genes listed in Table II can be obtained using cloning methods well known to those of skill in the art, and include but are not limited to the use of appropriate probes to detect the genes within an appropriate cDNA or gDNA (genomic DNA) library. (See, for example, Sambrook et al., 1989, Molecular Cloning: A Laboratory Manual, Cold Spring Harbor Laboratories, which is incorporated herein by reference in its entirety.) Probes for the sequences identified herein can be synthesized based on the DNA sequences disclosed herein in SEQ ID NO:1–62.

As used herein, "target gene" (i.e. essential and/or virulence gene) refers to (a) a gene containing at least one of the DNA sequences and/or fragments thereof that are set forth in SEQ ID NO:1 through to SEQ ID NO:62; (b) any DNA sequence or fragment thereof that encodes the amino acid sequence that are set forth in SEQ ID NO:63 through to SEQ ID NO:123 using the universal genetic code or the codon usage of C. albicans; (c) any DNA sequence that hybridizes to the complement of the nucleotide sequences set forth in SEQ ID NO:1 through to SEQ ID NO:62 under stringent conditions, e.g., hybridization to filter-bound DNA in 6×sodium chloride/sodium citrate (SSC) at about 45° C. followed by one or more washes in 0.2×SSC/0.1% SDS at about 50–65° C., or under highly stringent conditions, e.g., hybridization to filter-bound nucleic acid in 6×SSC at about 45° C. followed by one or more washes in 0.1×SSC/0.2% SDS at about 68° C., or under other hybridization conditions which are apparent to those of skill in the art (see, for example, Ausubel, F. M. et al., eds., 1989, Current Protocols in Molecular Biology, Vol. 1, Green Publishing Associates, Inc. and John Wiley & Sons, Inc., New York, at pp. 6.3.1–6.3.6 and 2.10.3). Preferably, the polynucleotides that hybridize to the complements of the DNA sequences disclosed herein encode gene products, e.g., gene products that are functionally equivalent to a gene product encoded by a target gene. As described above, target gene sequences include not only degenerate nucleotide sequences that encode the amino acid sequences of SEQ ID NO:63 to 123 in C. albicans, but also degenerate nucleotide sequences that when translated in organisms other than C. Albicans, would yield a polypeptide comprising one of the amino acid sequences of SEQ ID NO:63 to 123, or a fragment thereof. One of skill in the art would know how to select the appropriate codons or modify the nucleotide sequences of SEQ ID NO: 1 to 62 when using the target gene sequences in C. albicans or in other organisms. Moreover, the term "target gene" encompasses genes that are naturally occurring in Saccharomyces cerevisiae or variants thereof, that share extensive nucleotide sequence homology with C. albicans genes having one of the DNA sequences that are set forth in SEQ ID NO:1 through to SEQ ID NO:62, i.e., the orthologs in S. cerevisiae. It is contemplated that methods for drug screening that can be applied to C. albicans genes can also be applied to orthologs of the same genes in the non-pathogenic S. cerevisiae.

In another embodiment, the invention also encompasses the following polynucleotides, host cells expressing such polynucleotides and the expression products of such nucleotides: (a) polynucleotides that encode portions of target gene product that corresponds to its functional domains, and the polypeptide products encoded by such nucleotide sequences, and in which, in the case of receptor-type gene products, such domains include, but are not limited to signal sequences, extracellular domains (ECD), transmembrane domains (TM) and cytoplasmic domains (CD); (b) polynucleotides that encode mutants of a target gene product, in which all or part of one of its domains is deleted or altered, and which, in the case of receptor-type gene products, such mutants include, but are not limited to, mature proteins in which the signal sequence is cleaved, soluble receptors in which all or a portion of the TM is deleted, and nonfunctional receptors in which all or a portion of CD is deleted; and (d) polynucleotides that encode fusion proteins containing a target gene product or one of its domains fused to another polypeptide.

The invention also includes polynucleotides, preferably DNA molecules, that hybridize to, and are therefore the complements of, the DNA sequences of the target gene sequences. Such hybridization conditions can be highly stringent or less highly stringent, as described above and known in the art. The nucleic acid molecules of the invention that hybridize to the above described DNA sequences include oligodeoxynucleotides ("oligos") which hybridize to the target gene under highly stringent or stringent conditions. In general, for oligos between 14 and 70 nucleotides in length the melting temperature (Tm) is calculated using the formula:

$$Tm(° C.)=81.5+16.6(\log[\text{monovalent cations (molar)}])+0.41(\% G+C)-(500/N)$$

where N is the length of the probe. If the hybridization is carried out in a solution containing formamide, the melting temperature may be calculated using the equation:

$$Tm(° C.)=81.5+16.6(\log[\text{monovalent cations (molar)}])+0.41(\% G+C)-(0.61)(\% \text{ formamide})-(500/N).$$

where N is the length of the probe. In general, hybridization is carried out at about 20–25 degrees below Tm (for DNA-DNA hybrids) or about 10–15 degrees below Tm (for RNA-DNA hybrids). Other exemplary highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). Examples of such oligos are set forth in SEQ ID NO:124–489.

These nucleic acid molecules can encode or act as target gene antisense molecules, useful, for example, in target gene regulation and/or as antisense primers in amplification reactions of target gene nucleotide sequences. Further, such sequences can be used as part of ribozyme and/or triple helix sequences, also useful for target gene regulation. Still further, such molecules can be used as components of diagnostic methods whereby the presence of the pathogen can be detected. The uses of these nucleic acid molecules are discussed in detail below.

Fragments of the target genes of the invention can be at least 10 nucleotides in length. In alternative embodiments, the fragments can be about 20, 30, 40, 50, 60, 70, 80, 90, 100, 200, 300, 400, 500, 1000, 1500, 2000, 2500, 3000, 3500, 4000, 4500, 5000 or more contiguous nucleotides in length. Alternatively, the fragments can comprise nucleotide sequences that encode at least 10, 20, 30, 40, 50, 100, 150, 200, 250, 300, 350, 400, 450 or more contiguous amino acid residues of the target gene products. Fragments of the target genes of the invention can also refer to exons or introns of the above described nucleic acid molecules, as well as portions of the coding regions of such nucleic acid molecules that encode functional domains such as signal sequences, extracellular domains (ECD), transmembrane domains (TM) and cytoplasmic domains (CD).

5.4.2 Homologous Target Genes

In addition to the nucleotide sequences of *Candida albicans* described above, homologs or orthologs of these target gene sequences, as can be present in other species, can be identified and isolated by molecular biological techniques well known in the art, and without undue experimentation, used in the methods of the invention. For example, homologous target genes in *Aspergillus fumigatus, Aspergillus flavus, Aspergillus niger, Coccidiodes immitis, Cryptococcus neoformans, Histoplasma capsulatum, Phytophthora infestans, Puccinia seconditii, Pneumocystis carinii*, or any species falling within the genera of any of the above species. Other yeasts in the genera of Candida, Saccharomyces, Schizosaccharomyces, Sporobolomyces, Torulopsis, Trichosporon, Tricophyton, Dermatophytes, Microsproum, Wickerhamia, Ashbya, Blastomyces, Candida, Citeromyces, Crebrothecium, Cryptococcus, Debaryomyces, Endomycopsis, Geotrichum, Hansenula, Kloeckera, Kluveromyces, Lipomyces, Pichia, Rhodosporidium, Rhodotorula, and Yarrowia are also contemplated. Also included are homologs of these target gene sequences can be identified in and isolated from animal fugal pathogens such as *Aspergillus fumigatus, Aspergillus niger, Aspergillus flavis, Candida tropicalis, Candida parapsilopsis, Candida krusei, Cryptococcus neoformans, Coccidioides immitis, Exophalia dermatiditis, Fusarium oxysporum, Histoplasma capsulatum, Phneumocystis carinii, Trichosporon beigelii, Rhizopus arrhizus, Mucor rouxii, Rhizomucor pusillus*, or *Absidia corymbigera*, or the plant fungal pathogens, such as *Alternaria solanii, Botrytis cinerea, Erysiphe graminis, Magnaporthe grisea, Puccinia recodita, Sclerotinia sclerotiorum, Septoria triticii, Tilletia controversa, Ustilago maydis, Venturia inequalis, Verticullium dahliae* or any species falling within the genera of any of the above species.

Accordingly, the present invention provides nucleotide sequences that are hybridizable to the polynucleotides of the target genes, and that are of a species other than *Saccharomyces cerevisiae* and *Candida albicans*. In one embodiment, the present invention encompasses an isolated nucleic acid comprising a nucleotide sequence that is at least 50% identical to a nucleotide sequence selected from the group consisting of SEQ ID No. 1 through to SEQ ID NO:62. In another embodiment, the present invention encompasses an isolated nucleic acid comprising a nucleotide sequence that hybridizes under medium stringency conditions to a second nucleic acid that consists of a nucleotide sequence selected from the group consisting of SEQ ID NO:1 through to SEQ ID NO:62.

In yet another embodiment, the present invention includes an isolated nucleic acid comprising a nucleotide sequence that encodes a polypeptide the amino acid sequence of which is at least 50% identical to an amino acid sequence selected from the group consisting of SEQ ID No.63 through to 123, wherein the polypeptide is that of a species other than *Saccharomyces cerevisiae* and *Candida albicans*.

Although the nucleotide sequences and amino acid sequences of homologs or orthologs of such genes in *S. cerevisiae* is mostly published, uses of such homologs or orthologs in *S. cerevisiae* in drug screening are not known and are thus specifically provided by the invention. To use such nucleotide and/or amino acid sequences of *S. cerevisiae*, public databases, such as Stanford Genomic Resources (www-genome.stanford.edu), Munich Information Centre for Protein Sequences (www.mips.biochem.mpg.de), or Proteome (www.proteome.com) may be used to identify and retrieve the sequences. In cases where the ortholog or homolog of a *C. albicans* gene in *S. cerevisiae* is known, the name of the *S. cerevisiae* gene is indicated in parenthesis in column 1 of Table I. Orthologs of *S. cerevisiae* can also be identified by hybridization assays using nucleic acid probes consisting of any one of the nucleotide sequences of SEQ ID NO: 1 to 61, and 490.

The nucleotide sequences of the invention still further include nucleotide sequences that have at least 40%, 45%, 55%, 60%, 65%, 70%, 75%, 80%, 85%, 90%, 95%, 98% or more nucleotide sequence identity to the nucleotide sequences set forth in SEQ ID NO:1 through to SEQ ID NO:62. The nucleotide sequences of the invention also include nucleotide sequences that encode polypeptides having at least 25%, 30%, 40%, 50%, 55%, 60%, 65%, 70%, 75%, 80%, 85%, 90%, 95%, 98% or higher amino acid sequence identity or similarity to the amino acid sequences set forth in SEQ ID NO:63 through to 123.

To determine the percent identity of two amino acid sequences or of two nucleotide sequences, the sequences are aligned for optimal comparison purposes (e.g., gaps can be introduced in the sequence of a first amino acid or nucleotide sequence for optimal alignment with a second amino acid or nucleotide sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e. % identity=number of identical overlapping positions/total number of positions×100%). In one embodiment, the two sequences are the same length.

The determination of percent identity between two sequences can also be accomplished using a mathematical algorithm. A preferred, non-limiting example of a mathematical algorithm utilized for the comparison of two sequences is the algorithm of Karlin and Altschul (1990) Proc. Natl. Acad. Sci. U.S.A. 87:2264–2268, modified as in Karlin and Altschul (1993) Proc. Natl. Acad. Sci. U.S.A. 90:5873–5877. Such an algorithm is incorporated into the NBLAST and XBLAST programs of Altschul et al., 1990, J. Mol. Biol. 215:403–0. BLAST nucleotide searches can be performed with the NBLAST nucleotide program parameters set, e.g., for score=100, wordlength=12 to obtain nucleotide sequences homologous to a nucleic acid molecules of the present invention. BLAST protein searches can be performed with the XBLAST program parameters set, e.g., to score-50, wordlength=3 to obtain amino acid sequences homologous to a protein molecule of the present invention. To obtain gapped alignments for comparison purposes, Gapped BLAST can be utilized as described in Altschul et al., 1997, Nucleic Acids Res. 25:3389–3402. Alternatively, PSI-BLAST can be used to perform an iterated search which detects distant relationships between molecules (Id.). When utilizing BLAST, Gapped BL, AST, and PSI-Blast programs, the default parameters of the respective programs (e.g., of XBLAST and NBLAST) can be used (see, e.g., http://www.ncbi.nlm.nih.gov). Another preferred, non-limiting example of a mathematical algorithm utilized for the comparison of sequences is the algorithm of Myers and Miller, (1988) CABIOS 4:11–17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

To isolate homologous target genes, the *C. albicans* target gene sequence described above can be labeled and used to screen a cDNA library constructed from mRNA obtained from the organism of interest. Hybridization conditions should be of a lower stringency when the cDNA library was derived from an organism different from the type of organism from which the labeled sequence was derived. cDNA screening can also identify clones derived from alternatively spliced transcripts in the same or different species. Alternatively, the labeled fragment can be used to screen a genomic library derived from the organism of interest, again, using appropriately stringent conditions. Low stringency conditions will be well known to those of skill in the art, and will vary predictably depending on the specific organisms from which the library and the labeled sequences are derived. For guidance regarding such conditions see, for example, Sambrook et al., 1989, Molecular Cloning, A Laboratory Manual, Cold Spring Harbor Press, N.Y.; and Ausubel et al., 1989, Current Protocols in Molecular Biology, (Green Publishing Associates and Wiley Interscience, N.Y.).

Further, a homologous target gene sequence can be isolated by performing a polymerase chain reaction (PCR) using two degenerate oligonucleotide primer pools designed on the basis of amino acid sequences within the target gene of interest. The template for the reaction can be cDNA obtained by reverse transcription of mRNA prepared from the organism of interest. The PCR product can be subcloned and sequenced to ensure that the amplified sequences represent the sequences of a homologous target gene sequence.

The PCR fragment can then be used to isolate a full length cDNA clone by a variety of methods well known to those of ordinary skill in the art. Alternatively, the labeled fragment can be used to screen a genomic library.

PCR technology can also be utilized to isolate full length cDNA sequences. For example, RNA can be isolated, following standard procedures, from an organism of interest. A reverse transcription reaction can be performed on the RNA using an oligonucleotide primer specific for the most 5' end of the amplified fragment for the priming of first strand synthesis. The resulting RNA/DNA hybrid can then be "tailed" with guanines using a standard terminal transferase reaction, the hybrid can be digested with RNAase H, and second strand synthesis can then be primed with a poly-C primer. Thus, cDNA sequences upstream of the amplified fragment can easily be isolated. For a review of cloning strategies which can be used, see e.g., Sambrook et al., 1989, Molecular Cloning, A Laboratory Manual, Cold Springs Harbor Press, N.Y.; and Ausubel et al., 1989, Current Protocols in Molecular Biology, (Green Publishing Associates and Wiley Interscience, N.Y.).

Additionally, an expression library can be constructed utilizing DNA isolated from or cDNA synthesized from the organism of interest. In this manner, gene products made by the homologous target gene can be expressed and screened using standard antibody screening techniques in conjunction with antibodies raised against the *C. albicans* gene product, as described, below. (For screening techniques, see, for example, Harlow, E. and Lane, eds., 1988, "Antibodies: A Laboratory Manual," Cold Spring Harbor Press, Cold Spring Harbor). Library clones detected via their reaction with such labeled antibodies can be purified and subjected to sequence analysis by well known methods.

Alternatively, homologous target genes or polypeptides may be identified by searching a database to identify sequences having a desired level of homology to a target gene or polypeptide involved in proliferation, virulence or pathogenicity. A variety of such databases are available to those skilled in the art, including GenBank and GenSeq. In various embodiments, the databases are screened to identify nucleic acids with at least 97%, at least 95%, at least 90%, at least 85%, at least 80%, at least 70%, at least 60%, at least 50%, or at least 40% identity to a target nucleotide sequence, or a portion thereof. In other embodiments, the databases are screened to identify polypeptides having at least 99%, at least 95%, at least 90%, at least 85%, at least 80%, at least 70%, at least 60%, at least 50%, at least 40% or at least 25% identity or similarity to a polypeptide involved in proliferation, virulence or pathogenicity or a portion thereof.

Alternatively, functionally homologous target sequences or polypeptides may be identified by creating mutations that have phenotypes by removing or altering the function of a gene. This can be done for one or all genes in a given fungal species including, for example: *Saccharomyces cerevisiae, Candida albicans,* and *Aspergillus fumigatus.* Having mutants in the genes of one fungal species offers a method to identify functionally similar genes (orthologs) or related genes (paralogs) in another species, by use of a functional complementation test.

A library of gene or cDNA copies of messenger RNA of genes can be made from a given species, e.g. *Candida albicans*, and the library cloned into a vector permitting expression (for example, with the *Candida albicans* promoters or a *Saccharomyces cerevisiae* promoter) of the genes in a second species, e.g. *Saccharomyces cerevisiae*. Such a library is referred to as a "heterologous library." Transformation of the *Candida albicans* heterologous library into a defined mutant of *Saccharomyces cerevisiae* that is functionally deficient with respect to the identified gene, and screening or selecting for a gene in the heterologous library that restores phenotypic function in whole or in part of the mutational defect is said to be "heterologous functional complementation" and in this example, permits identification of gene in *Candida albicans* that are functionally related to the mutated gene in *Saccharomyces cerevisiae*. Inherent in this functional-complementation method, is the ability to restore gene function without the requirement for sequence similarity of nucleic acids or polypeptides; that is, this method permits interspecific identification of genes with conserved biological function, even where sequence similarity comparisons fail to reveal or suggest such conservation.

In those instances in which the gene to be tested is an essential gene, a number of possibilities exist regarding performing heterologous functional complementation tests. The mutation in the essential gene can be a conditional allele, including but not limited to, a temperature-sensitive allele, an allele conditionally expressed from a regulatable promoter, or an allele that has been rendered the mRNA transcript or the encoded gene product conditionally unstable. Alternatively, the strain carrying a mutation in an essential gene can be propagated using a copy of the native gene (a wild type copy of the gene mutated from the same species) on a vector comprising a marker that can be selected against, permitting selection for those strains carrying few or no copies of the vector and the included wild type allele. A stain constructed in this manner is transformed with the heterologous library, and those clones in which a heterologous gene can functionally complement the essential gene mutation, are selected on medium non-permissive for maintenance of the plasmid carrying the wild type gene.

In the following example, the identification, by functional complementation, of a *Candida albicans* homolog of a *Saccharomyces cerevisiae* gene, KRE 9, is described. (Lussier et al. 1998, "The *Candida albicans* KRE 9 gene is required for cell wall β-1,6-glucan synthesis and is essential for growth on glucose," *Proc. Natl. Acad. Sci. USA* 95: 9825–30). The host strain was a *Saccharomyces cerevisiae* haploid null mutant in KRE 9, kre 9::HIS3, which has a severe growth defect phenotype. The host strain carried a wild type copy of the native *Saccharomyces cerevisiae* KRE 9 gene on a LYS-2 based pRS317 shuttle vector and was transformed with a *Candida albicans* genomic library. This heterologous library was constructed using, as a vector, the multicopy plasmid YEp352, which carries the URA3 gene as a selectable marker. To screen for plasmids supporting growth of the kre 9::HIS 3 mutant host, approximately 20,000 colonies capable of growth in the absence of histidine, lysine, and uracil, were replica-plated onto minimal medium containing α-amino adipate as a nitrogen source to allow selection for cells that have lost the LYS2 plasmid-based copy of KRE 9 and that possess a copy of a functionally-complementing *Candida albicans* ortholog, CaKRE 9. These cells were tested further for loss of the pRS317-KRE 9 plasmid by their inability to grow in the absence of lysine, and YEp352-based *Candida albicans* genomic DNA was recovered from them. On retransformation of the *Saccharomyces cerevisiae* kre 9::HIS3 mutant, a specific genomic insert of 8 kb of *Candida albicans* was recovered that was able to restore growth partially. Following further subcloning using functional complementation for selection, a 1.6 kb DNA fragment was obtained that contained the functional *Candida albicans* KRE 9 gene.

A heterologous functional complementation test is not restricted to the exchange of genetic information between *Candida albicans* and *Saccharomyces cerevisiae*; functional complementation tests can be performed, as described above, using any pair of fungal species. For example, the CRE1 gene of the fungus *Sclerotininia sclerotiorum* can functionally complement the creAD30 mutant of the CREA gene of *Aspergillus nidulans* (see Vautard et al. 1999, "The glucose repressor gene CRE1 from *Sclerotininia sclerotiorum* is functionally related to CREA from *Aspergillus nidulans* but not to the Mig proteins from *Saccharomyces cerevisiae*," FEBS Lett. 453: 54–58).

In yet another embodiment, where the source of nucleic acid deposited on a gene expression array and the source of the nucleic acid probe being hybridized to the array are from two different species of organisms, the results allow rapid identification of homologous genes in the two species.

In yet another embodiment, the invention also encompasses (a) DNA vectors that contain a nucleotide sequence comprising any of the foregoing coding sequences of the target gene and/or their complements (including antisense); (b) DNA expression vectors that contain a nucleotide sequence comprising any of the foregoing coding sequences operably linked with a regulatory element that directs the expression of the coding sequences; and (c) genetically engineered host cells that contain any of the foregoing coding sequences of the target gene operably linked with a regulatory element that directs the expression of the coding sequences in the host cell. Vectors, expression constructs, expression vectors, and genetically engineered host cells containing the coding sequences of homologous target genes of other species (excluding *S. cerevisiae*) are also contemplated. Also contemplated are genetically engineered host cells containing mutant alleles in homologous target genes of the other species. As used herein, regulatory elements include but are not limited to inducible and non-inducible promoters, enhancers, operators and other elements known to those skilled in the art that drive and regulate expression. Such regulatory elements include but are not limited to the lac system, the trp system, the tet system and other antibiotic-based repression systems (e.g. PIP), the TAC system, the TRC system, the major operator and promoter regions of phage A, the control regions of fd coat protein, and the fungal promoters for 3-phosphoglycerate kinase, acid phosphatase, the yeast mating pheromone responsive promoters (e.g. STE2 and STE3), and promoters isolated from genes involved in carbohydrate metabolism (e.g. GAL promoters), phosphate-responsive promoters (e.g. PHO5), or amino acid metabolism (e.g. MET genes). The invention includes fragments of any of the DNA vector sequences disclosed herein.

A variety of techniques can be utilized to further characterize the identified essential genes and virulence genes. First, the nucleotide sequence of the identified genes can be used to reveal homologies to one or more known sequence motifs which can yield information regarding the biological function of the identified gene product. Computer programs well known in the art can be employed to identify such relationships. Second, the sequences of the identified genes can be used, utilizing standard techniques such as in situ hybridization, to place the genes onto chromosome maps and genetic maps which can be correlated with similar maps constructed for another organism, e.g., *Saccharomyces cerevisiae*. The information obtained through such characterizations can suggest relevant methods for using the polynucleotides and polypeptides for discovery of drugs against *Candida albicans* and other pathogens.

Methods for performing the uses listed above are well known to those skilled in the art. References disclosing such methods include without limitation "Molecular Cloning: A Laboratory Manual," 2d ed., Cold Spring Harbor Laboratory Press, Sambrook, J., E. F. Fritsch and T. Maniatis eds., 1989, and "Methods in Enzymology: Guide to Molecular Cloning Techniques," Academic Press, Berger, S. L. and A. R. Kimmel eds., 1987. Many of the uses of the polynucleotides and polypeptides of the identified essential genes are discussed in details hereinbelow.

5.4.3 Target Gene Products

The target gene products used and encompassed in the methods and compositions of the present invention include those gene products (e.g., RNA or proteins) that are encoded by the target essential gene sequences as described above, such as, the target gene sequences set forth in SEQ ID NO:1 through to 62. In Table II, the amino acid sequences of SEQ ID NO: 63 to 123 are deduced using the codon usage of *C. albicans* from the respective nucleotide sequences of SEQ ID NO: 1 to 61. However, when expressed in an organism other than *C. albicans*, protein products of the target genes having the amino acid sequences of SEQ ID NO: 63 to 123 may be encoded by nucleotide sequences that are translated using the universal genetic code. One of skill in the art would know the modifications that are necessary to accommodate for such a difference in codon usage.

In addition, however, the methods and compositions of the invention also use and encompass proteins and polypeptides that represent functionally equivalent gene products. Such functionally equivalent gene products include, but are not limited to, natural variants of the polypeptides having an amino acid sequence set forth in SEQ ID NO:63 through to 123.

Such equivalent target gene products can contain, e.g., deletions, additions or substitutions of amino acid residues within the amino acid sequences encoded by the target gene sequences described above, but which result in a silent change, thus producing a functionally equivalent target gene product. Amino acid substitutions can be made on the basis of similarity in polarity, charge, solubility, hydrophobicity, hydrophilicity and/or the amphipathic nature of the residues involved. For example, nonpolar (i.e., hydrophobic) amino acid residues can include alanine (Ala or A), leucine (Leu or L), isoleucine (Ile or I), valine (Val or V), proline (Pro or P), phenylalanine (Phe or F), tryptophan (Trp or W) and methionine (Met or M); polar neutral amino acid residues can include glycine (Gly or G), serine (Ser or S), threonine (Thr or T), cysteine (Cys or C), tyrosine (Tyr or Y), asparagine (Asn or N) and glutamine (Gln or Q); positively charged (i.e., basic) amino acid residues can include arginine (Arg or R), lysine (Lys or K) and histidine (His or H); and negatively charged (i.e., acidic) amino acid residues can include aspartic acid (Asp or D) and glutamic acid (Glu or E).

In one particular embodiment, a composition comprising a mixture of natural variants of the polypeptides having one of SEQ ID NO:63 through to 123 is provided. Since it is known in the art that, in *C. albicans*, 99% of the tRNA molecules that recognize the codon CTG is charged with a serine residue, and 1% are charged with a leucine residue, there is a possibility that during biosynthesis, a leucine is incorporated into a growing polypeptide chain Accordingly, when a nucleotide sequence comprising the codon CTG is translated in *C. albicans*, a small percentage of the resulting polypeptides may have a leucine residue in positions where a serine residue encoded by CTG (conforming to the codon usage of *C. albicans*) is expected. The product of translation of such a nucleotide sequence may comprise a mixture of polypeptides with minor leucine/serine variations at positions that correspond to a CTG codon in the nucleotide sequence.

"Functionally equivalent," as the term is utilized herein, refers to a polypeptide capable of exhibiting a substantially similar in vivo activity as the *Candida albicans* target gene product encoded by one or more of the target gene sequences described in Table II. Alternatively, when utilized as part of assays described hereinbelow, the term "functionally equivalent" can refer to peptides or polypeptides that are capable of interacting with other cellular or extracellular molecules in a manner substantially similar to the way in which the corresponding portion of the target gene product would interact with such other molecules. Preferably, the functionally equivalent target gene products of the invention are also the same size or about the same size as a target gene product encoded by one or more of the target gene sequences described in Table II.

In another embodiment of the invention, the use of target gene products that are RNA or proteins of *Saccharomyces cerevisiae* are provided.

Peptides and polypeptides corresponding to one or more domains of the target gene products (e.g., signal sequence, TM, ECD, CD, or ligand-binding domains), truncated or deleted target gene products (e.g., polypeptides in which one or more domains of a target gene product are deleted) and fusion target gene proteins (e.g., proteins in which a full length or truncated or deleted target gene product, or a peptide or polypeptide corresponding to one or more domains of a target gene product is fused to an unrelated protein) are also within the scope of the present invention. Such peptides and polypeptides (also referred to as chimeric protein or polypeptides) can be readily designed by those skilled in the art on the basis of the target gene nucleotide and amino acid sequences listed in Table II. Exemplary fusion proteins can include, but are not limited to, epitope tag-fusion proteins which facilitates isolation of the target gene product by affinity chromatography using reagents that binds the epitope. Other exemplary fusion proteins include fusions to any amino acid sequence that allows, e.g., the fusion protein to be anchored to a cell membrane, thereby allowing target gene polypeptides to be exhibited on a cell surface; or fusions to an enzyme (e.g., β-galactosidase encoded by the LAC4 gene of *Kluyveronmyces lactis* (Leuker et al., 1994, Mol. Gen. Genet., 245:212–217)), to a fluorescent protein (e.g., from *Renilla reniformis* (Srikantha et al., 1996, J. Bacteriol. 178:121–129), or to a luminescent protein which can provide a marker function. Accordingly, the invention provides a fusion protein comprising a fragment of a first polypeptide fused to a second polypeptide, said fragment of the first polypeptide consisting of at least 6 consecutive residues of an amino acid sequence selected from one of SEQ ID NO: 63 to 123.

Other modifications of the target gene product coding sequences described above can be made to generate polypeptides that are better suited, e.g., for expression, for scale up, etc. in a chosen host cell. For example, cysteine residues can be deleted or substituted with another amino acid in order to eliminate disulfide bridges.

The target gene products of the invention preferably comprise at least as many contiguous amino acid residues as are necessary to represent an epitope fragment (that is, for the gene products to be recognized by an antibody directed to the target gene product). For example, such protein fragments or peptides can comprise at least about 8 contiguous amino acid residues from a full length differentially expressed or pathway gene product. In alternative embodiments, the protein fragments and peptides of the invention can comprise about 6, 10, 20, 30, 40, 50, 60, 70, 80, 90, 100, 150, 200, 250, 300, 350, 400, 450 or more contiguous amino acid residues of a target gene product.

The target gene products used and encompassed in the methods and compositions of the present invention also encompass amino acid sequences encoded by one or more of the above-described target gene sequences of the invention wherein domains often encoded by one or more exons of those sequences, or fragments thereof, have been deleted. The target gene products of the invention can still further comprise post translational modifications, including, but not limited to, glycosylations, acetylations and myristylations.

The target gene products of the invention can be readily produced, e.g., by synthetic techniques or by methods of recombinant DNA technology using techniques that are well known in the art. Thus, methods for preparing the target gene products of the invention are discussed herein. First, the polypeptides and peptides of the invention can be synthesized or prepared by techniques well known in the art. See, for example, Creighton, 1983, *Proteins: Structures and Molecular Principles*, W.H. Freeman and Co., N.Y., which is incorporated herein by reference in its entirety. Peptides can, for example, be synthesized on a solid support or in solution.

Alternatively, recombinant DNA methods which are well known to those skilled in the art can be used to construct expression vectors containing target gene protein coding sequences such as those set forth in SEQ ID NO: 1 through to 61, and appropriate transcriptiona/translational control signals. These methods include, for example, in vitro recombinant DNA techniques, synthetic techniques and in vivo recombination/genetic recombination. See, for example, the techniques described in Sambrook et al., 1989, *Molecular Cloning: A Laboratory Manual*, Cold Spring Harbor Press, Cold Spring Harbor, N.Y., Pla et al., Yeast 12:1677–1702 (1996), which are incorporated by reference herein in their entireties, and Ausubel, 1989, supra. Alternatively, RNA capable of encoding target gene protein sequences can be chemically synthesized using, for example, synthesizers. See, for example, the techniques described in *Oligonucleotide Synthesis*, 1984, Gait, M. J. ed., IRL Press, Oxford, which is incorporated by reference herein in its entirety.

A variety of host-expression vector systems can be utilized to express the target gene coding sequences of the invention. Such host-expression systems represent vehicles by which the coding sequences of interest can be produced and subsequently purified, but also represent cells which can, when transformed or transfected with the appropriate nucleotide coding sequences, exhibit the target gene protein of the invention in situ. These include but are not limited to microorganisms such as bacteria (e.g., *E. coli, B. subtilis*) transformed with recombinant bacteriophage DNA, plasmid DNA or cosmid DNA expression vectors containing target gene protein coding sequences; yeast (e.g, Saccharomyces, Schizosaccharomyces, Neurospora, Aspergillus, Candida, Pichia) transformed with recombinant yeast expression vectors containing the target gene protein coding sequences; insect cell systems infected with recombinant virus expression vectors (e.g., baculovirus) containing the target gene protein coding sequences; plant cell systems infected with recombinant virus expression vectors (e.g., cauliflower mosaic virus, CaMV; tobacco mosaic virus, TMV) or transformed with recombinant plasmid expression vectors (e.g, Ti plasmid) containing target gene protein coding sequences; or mammalian cell systems (e.g. COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter). If necessary, the nucleotide sequences of coding regions may be modified according to the codon usage of the host such that the translated product has the correct amino acid sequence.

In bacterial systems, a number of expression vectors can be advantageously selected depending upon the use intended for the target gene protein being expressed. For example, when a large quantity of such a protein is to be produced, for the generation of antibodies or to screen peptide libraries, for example, vectors which direct the expression of high levels of fusion protein products that are readily purified can be desirable. Such vectors include, but are not limited, to the *E. coli* expression vector pUR278 (Ruther et al., 1983, *EMBO J*. 2:1791), in which the target gene protein coding sequence can be ligated individually into the vector in frame with the lacZ coding region so that a fusion protein is produced; pIN vectors (Inouye & Inouye, 1985, *Nucleic Acids Res*. 13:3101–3109; Van Heeke & Schuster, 1989, *J. Biol. Chem*. 264:5503–5509); and the like. pGEX vectors can also be used to express foreign polypeptides as fusion proteins with glutathione 5-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene protein can be released from the GST moiety.

When a target gene is to be expressed in mammalian host cells, a number of viral-based expression systems can be utilized. In cases where an adenovirus is used as an expression vector, the target gene coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non essential region of the viral genome (e.g., region E1 or E3) will result in a recombinant virus that is viable and capable of expressing target gene protein in infected hosts, (e.g., See Logan & Shenk, 1984, *Proc. Natl. Acad Sci USA* 81:3655–3659). Specific initiation signals can also be required for efficient translation of inserted target gene coding sequences. These signals include the ATG initiation codon and adjacent sequences. In cases where an entire target gene, including its own initiation codon and adjacent sequences, is inserted into the appropriate expression vector, no additional translational control signals can be needed. However, in cases where only a portion of the target gene coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see Bittner et al., 1987, *Methods in Enzymol.* 153:516–544).

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used.

For long-term, high-yield production of recombinant proteins, stable expression is preferred. For example, cell lines which stably express the target gene protein can be engineered. Host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells can be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express the target gene protein. Such engineered cell lines can be particularly useful in screening and evaluation of compounds that affect the endogenous activity of the target gene protein.

A number of selection systems can be used, including but not limited to the herpes simplex virus thymidine kinase (Wigler et al., 1977, *Cell* 11:223), hypoxanthine-guanine phosphoribosyltransferase (Szybalska & Szybalski, 1962, *Proc. Natl. Acad. Sci. USA* 48:2026), and adenine phosphoribosyltransferase (Lowy et al., 1980, *Cell* 22:817) genes can be employed in tk$^-$, hgprt$^-$ or aprt$^-$ cells, respectively. Also, antimetabolite resistance can be used as the basis of selection for dhfr, which confers resistance to methotrexate (Wigler et al., 1980, *Proc. Natl. Acad. Sci. USA* 77:3567; O'Hare et al., 1981, *Proc. Natl. Acad. Sci. USA* 78:1527); gpt, which confers resistance to mycophenolic acid (Mulligan & Berg, 1981, *Proc. Natl. Acad. Sci. USA* 78:2072); neo, which confers resistance to the aminoglycoside G-418 (Colberre-Garapin et al., 1981, *J. Mol. Biol.* 150:1); and hygro, which confers resistance to hygromycin (Santerre et al., 1984, *Gene* 30:147) genes.

Alternatively, any fusion protein may be readily purified by utilizing an antibody specific for the fusion protein being expressed. For example, a system described by Janknecht et al. allows for the ready purification of non-denatured fusion proteins expressed in human cells lines (Janknecht et al., 1991, *Proc. Natl. Acad. Sci. USA* 88: 8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto Ni$^{2+}$ nitriloacetic acid-agarose columns and histidine-tagged proteins are selectively eluted with imidazole-containing buffers. Fusions at the carboxy terminal of the target gene product are also contemplated.

When used as a component in assay systems such as those described herein the target gene protein can be labeled, either directly or indirectly, to facilitate detection of a complex formed between the target gene protein and a test substance. Any of a variety of suitable labeling systems can be used including but not limited to radioisotopes such as $^{125}$I; enzyme labeling systems that generate a detectable colorimetric signal or light when exposed to substrate; and fluorescent labels.

Indirect labeling involves the use of a protein, such as a labeled antibody, which specifically binds to either a target gene product. Such antibodies include but are not limited to polyclonal antibodies, monoclonal antibodies (mAbs), human, humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above.

Following expression of the target gene protein encoded by the identified target nucleotide sequence, the protein is purified. Protein purification techniques are well known in the art. Proteins encoded and expressed from identified exogenous nucleotide sequence17 s can be partially purified using precipitation techniques, such as precipitation with polyethylene glycol. Alternatively, epitopetagging of the protein can be used to allow simple one step purification of the protein. In addition, chromatographic methods such as ion-exchange chromatography, gel filtration, use of hydroxyapaptite columns, immobilized reactive dyes, chromatofocusing, and use of high-performance liquid chromatography, may also be used to purify the protein. Electrophoretic methods such as one-dimensional gel electrophoresis, high-resolution two-dimensional polyacrylamide electrophoresis, isoelectric focusing, and others are contemplated as purification methods. Also, affinity chromatographic methods, comprising solid phase bound-antibody, ligand presenting columns and other affinity chromatographic matrices are contemplated as purification methods in the present invention.

In addition, the purified target gene products, fragments thereof, or derivatives thereof may be administered to an individual in a pharmaceutically acceptable carrier to induce an immune response against the protein or polypeptide. Preferably, the immune response is a protective immune response which protects the individual. Methods for determining appropriate dosages of the protein (including use of adjuvants) and pharmaceutically acceptable carriers are familiar to those skilled in the art.

5.4.4 Antibodies Specific for Target Gene Products

Described herein are methods for the production of antibodies capable of specifically recognizing epitopes of one or more of the target gene products described above. Such antibodies can include, but are not limited to, polyclonal antibodies, monoclonal antibodies (mAbs), human, humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above.

For the production of antibodies to a target gene or gene product, various host animals can be immunized by injection with a target gene protein, or a portion thereof. Such host animals can include but are not limited to rabbits, mice, and rats, to name but a few. Various adjuvants can be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. Accordingly, the invention provides a method of eliciting an immune response in an animal, comprising introducing into the animal an immunogenic composition comprising an isolated polypeptide, the amino acid sequence of which comprises at least 6 consecutive residues of one of SEQ ID NO: 63 to 123.

Polyclonal antibodies are heterogeneous populations of antibody molecules derived from the sera of animals immunized with an antigen, such as target gene product, or an antigenic functional derivative thereof. For the production of polyclonal antibodies, host animals such as those described above, can be immunized by injection with differentially expressed or pathway gene product supplemented with adjuvants as also described above. The antibody titer in the immunized animal can be monitored over time by standard techniques, such as with an enzyme linked immunosorbent assay (ELISA) using immobilized polypeptide. If desired, the antibody molecules can be isolated from the animal (e.g., from the blood) and further purified by well-known techniques, such as protein A chromatography to obtain the IgG fraction.

Monoclonal antibodies, which are homogeneous populations of antibodies to a particular antigen, can be obtained by any technique which provides for the production of antibody molecules by continuous cell lines in culture. These include, but are not limited to the hybridoma technique of Kohler and Milstein, (1975, *Nature* 256:495–497; and U.S. Pat. No. 4,376,110), the human B-cell hybridoma technique (Kosbor et al., 1983, *Immunology Today* 4:72; Cole et al., 1983, *Proc. Natl. Acad. Sci. USA* 80:2026–2030), and the EBV-hybridoma technique (Cole et al., 1985, *Monoclonal Antibodies And Cancer Therapy*, Alan R. Liss, Inc., pp. 77–96). Such antibodies can be of any immunoglobulin class including IgG, IgM, IgE, IgA, IgD and any subclass thereof. The hybridoma producing the mAb of this invention can be cultivated in vitro or in viva. Production of high titers of mAbs in vivo makes this the presently preferred method of production.

Alternative to preparing monoclonal antibody-secreting hybridomas, a monoclonal antibody directed against a polypeptide of the invention can be identified and isolated by screening a recombinant combinatorial immunoglobulin library (e.g., an antibody phage display library) with the polypeptide of interest. Kits for generating and screening phage display libraries are commercially available (e.g., the Pharmacia *Recombinant Phage Antibody System*, Catalog No. 27-9400-01; and the Stratagene *SurfZAP*™ *Phage Display Kit*, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J.* 12:725–734.

Additionally, recombinant antibodies, such as chimeric and humanized monoclonal antibodies, comprising both human and non-human portions, which can be made using standard recombinant DNA techniques, are within the scope of the invention. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 4,816,397, which are incorporated herein by reference in their entirety.) Humanized antibodies are antibody molecules from non-human species having one or more complementarily determining regions (CDRs) from the non-human species and a framework region from a human immunoglobulin molecule. (See, e.g., Queen, U.S. Pat. No. 5,585,089, which is incorporated herein by reference in its entirety.) Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison (1985) *Science* 229:1202–1207; Oi et al. (1986) *Bio/Techniques* 4:214; U.S. Pat. No. 5,225,539; Jones et al. (1986) *Nature* 321:552–525; Verhoeyan et al. (1988) *Science* 239:1534; and Beidler et al. (1988) *J. Immunol.* 141:4053–4060.

Completely human antibodies are particularly desirable for therapeutic treatment of human patients. Such antibodies can be produced using transgenic mice which are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA and IgE antibodies. For an overview of this technology for producing human antibodies, see Lonberg and Huszar (1995, *Int. Rev. Immunol.* 13:65–93). For a detailed discussion of this technology for producing human antibodies and human monoclonal antibodies and protocols for producing such antibodies, see, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al. (1994) *Bio/Technology* 12:899–903).

Antibody fragments which recognize specific epitopes can be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries can be constructed (Huse et al., 1989, *Science* 246:1275–1281) to allow rapid and easy identification of monoclonal Fab fragments with the desired specificity.

Antibodies of the present invention may also be described or specified in terms of their binding affinity to a target gene product. Preferred binding affinities include those with a dissociation constant or Kd less than $5\times10^{-6}$M, $10^{-6}$M, $5\times10^{-7}$M, $10^{-7}$M, $5\times10^{-8}$M, $10^{-8}$M, $5\times10^{-9}$M, $10^{-9}$M, $5\times10^{-10}$M, $10^{-10}$M, $5\times10^{-11}$M, $10^{-11}$M, $5\times10^{-12}$M, $10^{-12}$M, $5\times10^{-13}$M, $10^{-13}$M, $5\times10^{-14}$M, $10^{-14}$M, $5\times10^{-15}$M, or $10^{-15}$M.

Antibodies directed against a target gene product or fragment thereof can be used to detect the a target gene product in order to evaluate the abundance and pattern of expression of the polypeptide under various environmental conditions, in different morphological forms (myceliun, yeast, spores) and stages of an organism's life cycle. Antibodies directed against a target gene product or fragment thereof can be used diagnostically to monitor levels of a target gene product in the tissue of an infected host as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Further, antibodies directed against a target gene product or fragment thereof can be used therapeutically to treat an infectious disease by preventing infection, and/or inhibiting growth of the pathogen. Antibodies can also be used to modify a biological activity of a target gene product. Antibodies to gene products related to virulence or pathogenicity can also be used to prevent infection and alleviate one or more symptoms associated with infection by the organism. To facilitate or enhance its therapeutic effect, an antibody (or fragment thereof) may be conjugated to a therapeutic moiety such as a toxin or fungicidal agent. Techniques for conjugating a therapeutic moiety to antibodies are well known, see, e.g., Thorpe et al., "The Preparation And Cytotoxic Properties Of Antibody-Toxin Conjugates", Immunol. Rev., 62:119–58 (1982).

An antibody with or without a therapeutic moiety conjugated to it can be used as a therapeutic that is administered alone or in combination with chemotherapeutic agents.

5.4.5 Antisense Molecules

The use of antisense molecules as inhibitors of gene expression may be a specific, genetically based therapeutic approach (for a review, see Stein, in Ch. 69, Section 5 "Cancer: Principle and Practice of Oncology", 4th ed., ed. by DeVita et al., J.B. Lippincott, Philadelphia 1993). The present invention provides the therapeutic or prophylactic use of nucleic acids of at least six nucleotides that are antisense to a target essential or virulence gene or a portion thereof. An "antisense" target nucleic acid as used herein refers to a nucleic acid capable of hybridizing to a portion of a target gene RNA (preferably mRNA) by virtue of some sequence complementarity. The invention further provides pharmaceutical compositions comprising an effective amount of the antisense nucleic acids of the invention in a pharmaceutically acceptable carrier, as described infra.

In another embodiment, the invention is directed to methods for inhibiting the expression of a target gene in an organism of interest, such as *C. albicans* in vitro or in vivo comprising providing the cell with an effective amount of a composition comprising an antisense nucleic acid of the invention. Multiple antisense polynucleotides hybridizable to different target genes may be used in combinations, sequentially or simultaneously.

In another embodiment, the present invention is directed toward methods for modulating expression of an essential gene which has been identified by the methods described supra, in which an antisense RNA molecule, which inhibits translation of mRNA transcribed from an essential gene, is expressed from a regulatable promoter. In one aspect of this embodiment, the antisense RNA molecule is expressed in a GRACE strain of *Candida albicans* or another GRACE strain constructed from another diploid pathogenic organism. In other aspects of this embodiment, the antisense RNA molecule is expressed in a wild-type or other non-GRACE strain of *Candida albicans* or another diploid pathogenic organism, including animal fugal pathogens such as *Aspergillus fumigatus, Aspergillus niger, Aspergillus flavis, Candida tropicalis, Candida parapsilopsis, Candida krusei, Cryptococcus neoformans, Coccidioides immitis, Exophalia dermatiditis, Fusarium oxysporum, Histoplasma capsulatum, Phneumocystis carinii, Trichosporon beigelii, Rhizopus arrhizus, Mucor rouxii, Rhizomucor pusillus,* or *Absidia corymbigera,* or the plant fungal pathogens, such as *Botrytis cinerea, Erysiphe graminis, Magnaporthe grisea, Puccinia recodita, Septoria triticii, Tilletia controversa, Ustilago maydiss,* or any species falling within the genera of any of the above species.

The nucleic acid molecule comprising an antisense nucleotide sequence of the invention may be complementary to a coding and/or noncoding region of a target gene mRNA. The antisense molecules will bind to the complementary target gene mRNA transcripts and reduce or prevent translation. Absolute complementarity, although preferred, is not required. A sequence "complementary" to a portion of an RNA, as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. One skilled in the art can ascertain a tolerable degree of mismatch by use of standard procedures to determine the melting point of the hybridized complex.

Nucleic acid molecules that are complementary to the 5' end of the message, e.g., the 5' untranslated sequence up to and including the AUG initiation codon, should work most efficiently at inhibiting translation. However, sequences complementary to the 3' untranslated sequences of mRNAs have recently been shown to be effective at inhibiting translation of mRNAs as well. See generally, Wagner, R., 1994, Nature 372:333–335.

Nucleic acid molecules comprising nucleotide sequences complementary to the 5' untranslated region of the mRNA can include the complement of the AUG start codon. Antisense nucleic acid molecules complementary to mRNA coding regions are less efficient inhibitors of translation but could be used in accordance with the invention. Whether designed to hybridize to the 5'-, 3'- or coding region of target gene mRNA, antisense nucleic acids should be at least six nucleotides in length, and are preferably oligonucleotides ranging from 6 to about 50 nucleotides in length. In specific aspects, the oligonucleotide is at least 10 nucleotides, at least 17 nucleotides, at least 25 nucleotides, at least 50 nucleotides, or at least 200 nucleotides.

Regardless of the choice of target gene sequence, it is preferred that in vitro studies are first performed to quantitate the ability of the antisense molecule to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The antisense molecule can be DNA or RNA or chimeric mixtures or derivatives or modified versions thereof, single-stranded or double-stranded. The antisense molecule can be modified at the base moiety, sugar moiety, or phosphate backbone, for example, to improve stability of the molecule, hybridization, etc. The antisense molecule may include other appended groups such as peptides (e.g., for targeting cell receptors in vivo), hybridization-triggered cleavage agents. (See, e.g., Krol et al., 1988, BioTechniques 6:958–976) or intercalating agents. (See, e.g., Zon, 1988, Pharm. Res. 5:539–549). To this end, the antisense molecule may be conjugated to another molecule, e.g., a peptide, hybridization triggered cross-linking agent, transport agent, hybridization-triggered cleavage agent, etc.

The antisense molecule may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense molecule may also comprise at least one modified sugar moiety selected from the group including but not limited to arabinose, 2-fluoroarabinose, xylulose, and hexose.

In yet another embodiment, the antisense molecule comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense molecule is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330).

Antisense molecules of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448–7451), etc.

While antisense nucleotides complementary to the coding region of a target gene could be used, those complementary to the transcribed untranslated region are also preferred.

Pharmaceutical compositions of the invention comprising an effective amount of an antisense nucleic acid in a pharmaceutically acceptable carrier, can be administered to a subject infected with the pathogen of interest.

The amount of antisense nucleic acid which will be effective in the treatment of a particular disease caused by the pathogen will depend on the site of the infection or condition, and can be determined by standard techniques. Where possible, it is desirable to determine the antisense cytotoxicity of the pathogen to be treated in vitro, and then in useful animal model systems prior to testing and use in humans.

A number of methods have been developed for delivering antisense DNA or RNA to cells; e.g., antisense molecules can be injected directly into the tissue site in which the pathogens are residing, or modified antisense molecules, designed to target the desired cells (e.g., antisense molecule linked to peptides or antibodies that specifically bind receptors or antigens expressed on the pathogen's cell surface) can be administered systemically. Antisense molecules can be delivered to the desired cell population via a delivery complex. In a specific embodiment, pharmaceutical compositions comprising antisense nucleic acids of the target genes are administered via biopolymers (e.g., poly-β-1→4-N-acetylglucosamine polysaccharide), liposomes, microparticles, or microcapsules. In various embodiments of the invention, it may be useful to use such compositions to achieve sustained release of the antisense nucleic acids. In a specific embodiment, it may be desirable to utilize liposomes targeted via antibodies to specific identifiable pathogen antigens (Leonetti et al., 1990, Proc. Natl. Acad. Sci. U.S.A. 87:2448–2451; Renneisen et al., 1990, J. Biol. Chem. 265:16337–16342).

5.4.6 Ribozyme Molecules

Ribozymes are enzymatic RNA molecules capable of catalyzing the specific cleavage of RNA (For a review see, for example Rossi, J., 1994, Current Biology 4:469–471). The mechanism of ribozyme action involves sequence specific hybridization of the ribozyme molecule to complementary target RNA, followed by a endonucleolytic cleavage. The composition of ribozyme molecules must include one or more sequences complementary to the target gene mRNA, and must include the well known catalytic sequence responsible for mRNA cleavage. For this sequence, see U.S. Pat. No. 5,093,246, which is incorporated by reference herein in its entirety. As such, within the scope of the invention are engineered hammerhead motif ribozyme molecules that specifically and efficiently catalyze endonucleolytic cleavage of RNA sequences encoding target gene proteins.

Ribozyme molecules designed to catalytically cleave specific target gene mRNA transcripts can also be used to prevent translation of target gene mRNA and expression of target genes. While ribozymes that cleave mRNA at site specific recognition sequences can be used to destroy target gene mRNAs, the use of hammerhead ribozymes is preferred. Hammerhead ribozymes cleave mRNAs at locations dictated by flanking regions that form complementary base pairs with the target gene mRNA. The sole requirement is that the target mRNA have the following sequence of two bases: 5'-UG-3'. The construction and production of hammerhead ribozymes is well known in the art and is described more fully in Haseloff and Gerlach, 1988, Nature, 334:585–591. Preferably the ribozyme is engineered so that the cleavage recognition site is located near the 5' end of the target gene mRNA; i.e., to increase efficiency and minimize the intracellular accumulation of non-functional mRNA scripts.

The ribozymes of the present invention also include RNA endoribonucleases (hereinafter "Cech-type ribozymes") such as the one which occurs naturally in *Tetrahymena thermophila* (known as the IVS, or L-19 IVS RNA) and which has been extensively described by Thomas Cech and collaborators (Zaug, et al., 1984, Science, 224:574–578; Zaug and Cech, 1986, Science, 231:470–475; Zaug, et al., 1986, Nature, 324:429–433; published International patent application No. WO 88/04300 by University Patents Inc.; Been and Cech, 1986, Cell, 47:207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in a target gene.

As in the antisense approach, the ribozymes can be composed of modified oligonucleotides (e.g. for improved stability, targeting, etc.) and should be delivered to cells which express the target gene in vivo. Because ribozymes unlike antisense molecules, are catalytic, a lower intracellular concentration is required for efficiency. Multiple ribozyme molecules directed against different target genes can also be used in combinations, sequentially or simultaneously.

Anti-sense RNA and DNA, ribozyme, and triple helix molecules of the invention can be prepared by any method known in the art for the synthesis of DNA and RNA molecules. These include techniques for chemically synthesizing oligodeoxyribonucleotides and oligoribonucleotides well known in the art such as for example solid phase phosphormidite chemical synthesis. Alternatively, RNA molecules can be generated by in vitro and in vivo transcription of DNA sequences encoding the antisense RNA molecule. Such DNA sequences can be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines. These nucleic acid constructs can be administered selectively to the desired cell population via a delivery complex.

Various well-known modifications to the DNA molecules can be introduced as a means of increasing intracellular stability and half-life. Possible modifications include, but are not limited to, the addition of flanking sequences of ribo- or deoxy-nucleotides to the 5' and/or 3' ends of the molecule or the use of phosphorothioate or 2' O-methyl rather than phosphodiesterase linkages within the oligodeoxyribonucleotide backbone.

5.5 Screening Assays

The following assays are designed to identify compounds that bind to target gene products, bind to other cellular proteins that interact with the target gene product, and to compounds that interfere with the interaction of the target gene product with other cellular proteins. Compounds identified via such methods can include compounds which modulate the activity of a polypeptide encoded by a target gene of the invention (that is, increase or decrease its activity, relative to activity observed in the absence of the compound). Alternatively, compounds identified via such methods can include compounds which modulate the expression of the polynucleotide (that is, increase or decrease expression relative to expression levels observed in the absence of the compound), or increase or decrease the stability of the expressed product encoded by that polynucleotide. Compounds, such as compounds identified via the methods of the invention, can be tested using standard assays well known to those of skill in the art for their ability to modulate activity/expression.

Accordingly, the present invention provides a method for identifying an antimycotic compound comprising screening a plurality of compounds to identify a compound that modulates the activity or level of a gene product, said gene product being encoded by a nucleotide sequence selected from the group consisting of SEQ ID NO: 1 to 61 or a nucleotide sequence that is naturally occurring in *Saccharomyces cerevisiae* and that is the ortholog of a gene having a nucleotide sequence selected from the group consisting of SEQ ID NO: 1 to 61.

5.5.1 In Vitro Screening Assays

In vitro systems are designed to identify compounds capable of binding the target gene products of the invention. Compounds identified in this manner are useful, for example, in modulating the activity of wild type and/or mutant target gene products, are useful in elucidating the biological function of target gene products, are utilized in screens for identifying other compounds that disrupt normal target gene product interactions, or are useful themselves for the disruption of such interactions.

The principle of the assays used to identify compounds that bind to the target gene product involves preparing a reaction mixture comprising the target gene product and the test compound under conditions and for a time sufficient to allow the two components to interact and bind, thus forming a complex which is removed and/or detected within the reaction mixture. These assays are conducted in a variety of ways. For example, one method involves anchoring target gene product or the test substance onto a solid phase and detecting target gene product/test compound complexes anchored, via the intermolecular binding reaction, to the solid phase at the end of the reaction. In one embodiment of such a method, the target gene product is anchored onto a solid surface, and the test compound, which is not anchored, is labeled, either directly or indirectly.

In practice, microtiter plates are conveniently utilized as the solid phase. The anchored component is immobilized by non-covalent or covalent attachments. Non-covalent attachment can be accomplished by simply coating the solid surface with a solution of the protein and drying the coated surface. Alternatively, an immobilized antibody, preferably a monoclonal antibody, specific for the protein to be immobilized is used to anchor the protein to the solid surface. The surfaces are prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface is accomplished in a number of ways. Where the previously nonimmobilized component is pre-labeled, the detection of label immobilized on the surface indicates that complexes were formed. Where the previously nonimmobilized component is not pre-labeled, an indirect label is used to detect complexes anchored on the surface; e.g., using a labeled antibody specific for the previously nonimmobilized component (the antibody, in turn, is directly labeled or indirectly labeled with a labeled anti-Ig antibody).

Alternatively, a reaction is conducted in a liquid phase, the reaction products are separated from unreacted components, and complexes are detected; e.g., using an immobilized antibody specific for the target gene product or for the test compound, to anchor complexes formed in solution, and a second labeled antibody, specific for the other component of the complex to allow detection of anchored complexes.

5.5.1.1 Assays for Proteins that Interact with a Target Gene Product

Any method suitable for detecting protein-protein interactions can be employed for identifying novel target protein-cellular or extracellular protein interactions.

The target gene products of the invention interact, in vivo, with one or more cellular or extracellular macromolecules, such as proteins. Such macromolecules include, but are not limited to, nucleic acid molecules and proteins identified via methods such as those described above. For purposes of this discussion, such cellular and extracellular macromolecules are referred to herein as "binding partners." Compounds that disrupt such interactions can be useful in regulating the activity of the target gene protein, especially mutant target gene proteins. Such compounds include, but are not limited to molecules such as antibodies, peptides, and the like, as described.

The basic principle of the assay systems used to identify compounds that interfere with the interaction between the target gene product and its cellular or extracellular binding partner or partners involves preparing a reaction mixture containing the target gene product and the binding partner under conditions and for a time sufficient to allow the two to interact and bind, thus forming a complex. In order to test a compound for inhibitory activity, the reaction mixture is prepared in the presence and absence of the test compound. The test compound is initially included in the reaction mixture, or added at a time subsequent to the addition of target gene product and its cellular or extracellular binding partner. Control reaction mixtures are incubated without the test compound. The formation of complexes between the target gene protein and the cellular or extracellular binding partner is then detected. The formation of a complex in the control reaction, but not in the reaction mixture containing the test compound, indicates that the compound interferes with the interaction of the target gene protein and the interactive binding partner. Additionally, complex formation within reaction mixtures containing the test compound and normal target gene protein can also be compared to complex formation within reaction mixtures containing the test compound and a mutant target gene protein. This comparison can be important in those cases wherein it is desirable to identify compounds that disrupt intermolecular interactions involving mutant but not normal target gene proteins.

The assay for compounds that interfere with the interaction of the target gene products and binding partners is conducted in either a heterogeneous or a homogeneous format. Heterogeneous assays involve anchoring either the target gene product or the binding partner onto a solid phase and detecting complexes anchored on the solid phase at the end of the reaction. In homogeneous assays, the entire reaction is carried out in a liquid phase. In either approach, the order of addition of reactants is varied to obtain different information about the compounds being tested. For example, test compounds that interfere with the interaction between the target gene products and the binding partners, e.g., by competition, are identified by conducting the reaction in the presence of the test substance; i.e., by adding the test substance to the reaction mixture prior to or simultaneously with the target gene protein and an interacting cellular or extracellular binding partner. Alternatively, test compounds that disrupt preformed complexes, e.g. compounds with higher binding constants that displace one of the components from the complex, are tested by adding the test compound to the reaction mixture after complexes have been formed. The various formats are described briefly below.

In a heterogeneous assay system, either the target gene protein or the interactive cellular or extracellular binding partner, is anchored onto a solid surface, while the non-anchored species is labeled, either directly or indirectly. In practice, microtiter plates are conveniently utilized. The anchored species is immobilized either by non-covalent or covalent attachment. Non-covalent attachment is accomplished simply by coating the solid surface with a solution of the target gene product or binding partner and drying the coated surface. Alternatively, an immobilized antibody specific for the species to be anchored is used to anchor the species to the solid surface. The surfaces can be prepared in advance and stored.

In order to conduct the assay, the partner of the immobilized species is exposed to the coated surface with or without the test compound. After the reaction is complete, unreacted components are removed (e.g, by washing) and any complexes formed will remain immobilized on the solid surface. The detection of complexes anchored on the solid surface is accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, is directly labeled or indirectly labeled with a labeled anti-Ig antibody). Depending upon the order of addition of reaction components, test compounds which inhibit complex formation or which disrupt preformed complexes are detected.

Alternatively, the reaction is conducted in a liquid phase in the presence or absence of the test compound, the reaction products separated from unreacted components, and complexes detected; e.g., using an immobilized antibody specific for one of the binding components to anchor any complexes formed in solution, and a second, labeled antibody specific for the other partner to detect anchored complexes. Again, depending upon the order of addition of reactants to the liquid phase, test compounds which inhibit complex or which disrupt preformed complexes are identified.

In an alternate embodiment of the invention, a homogeneous assay can be used. In this approach, a preformed complex of the target gene protein and the interacting cellular or extracellular binding partner is prepared in which either the target gene product or its binding partner is labeled, but the signal generated by the label is quenched due to complex formation (see, e.g., U.S. Pat. No. 4,109,496 by Rubenstein which utilizes this approach for immunoassays). The addition of a test substance that competes with and displaces one of the species from the preformed complex results in the generation of a signal above background. In this way, test substances which disrupt target gene protein/cellular or extracellular binding partner interaction are identified.

In a particular embodiment, the target gene product is prepared for immobilization using recombinant DNA techniques described above. For example, the target gene coding region is fuse to a glutathione-S-transferase (GST) gene using a fusion vector, such as pGEX-5X-1, in such a manner that its binding activity is maintained in the resulting fusion protein. The interactive cellular or extracellular binding partner is purified and used to raise a monoclonal antibody, using methods routinely practiced in the art and as described above. This antibody is labeled with the radioactive isotope $^{125}$I, for example, by methods routinely practiced in the art. In a heterogeneous assay, e.g., the GST-target gene fusion protein is anchored to glutathione-agarose beads. The interactive cellular or extracellular binding partner is then added in the presence or absence of the test compound in a manner that allows interaction and binding to occur. At the end of the reaction period, unbound material can be washed away, and the labeled monoclonal antibody is added to the system and allowed to bind to the complexed components. The interaction between the target gene protein and the interactive cellular or extracellular binding partner is detected by measuring the amount of radioactivity that remains associated with the glutathione-agarose beads. A successful inhibition of the interaction by the test compound results in a decrease in measured radioactivity.

Alternatively, the GST-target gene fusion protein and the interactive cellular or extracellular binding partner are mixed together in liquid in the absence of the solid glutathione-agarose beads. The test compound is added either during or after the species are allowed to interact. This mixture is added to the glutathione-agarose beads and unbound material is washed away. Again the extent of inhibition of the target gene product/binding partner interaction is detected by adding the labeled antibody and measuring the radioactivity associated with the beads.

In another embodiment of the invention, these same techniques are employed using peptide fragments that correspond to the binding domains of the target gene product and/or the interactive cellular or extracellular binding partner (in cases where the binding partner is a protein), in place of one or both of the full length proteins. Any number of methods routinely practiced in the art are used to identify and isolate the binding sites. These methods include, but are not limited to, mutagenesis of the gene encoding one of the proteins and screening for disruption of binding in a co-immunoprecipitation assay. Compensating mutations in the gene encoding the second species in the complex are then selected. Sequence analysis of the genes encoding the respective proteins reveals the mutations that correspond to the region of the protein involved in interactive binding.

Alternatively, one protein is anchored to a solid surface using methods described above, and allowed to interact with and bind to its labeled binding partner, which has been treated with a proteolytic enzyme, such as trypsin. After washing, a short, labeled peptide comprising the binding domain remains associated with the solid material, and can be isolated and identified by amino acid sequencing. Also, once the gene coding for the cellular or extracellular binding partner is obtained, short gene segments are engineered to express peptide fragments of the protein, which are tested for binding activity and purified or synthesized.

For example, and not by way of limitation, a target gene product is anchored to a solid material as described, above, by making a GST-target gene fusion protein and allowing it to bind to glutathione agarose beads. The interactive cellular or extracellular binding partner is labeled with a radioactive isotope, such as $^{35}$S, and cleaved with a proteolytic enzyme such as trypsin. Cleavage products are added to the anchored GST-target gene fusion protein and allowed to bind. After washing away unbound peptides, labeled bound material, representing the cellular or extracellular binding partner binding domain, is eluted, purified, and analyzed for amino acid sequence by well known methods. Peptides so identified are produced synthetically or fused to appropriate facilitative proteins using well known recombinant DNA technology.

5.5.1.2 Screening a Combinatorial Chemical Library

In one embodiment of the present invention, the proteins encoded by the fungal genes identified using the methods of the present invention are isolated and expressed. These recombinant proteins are then used as targets in assays to screen libraries of compounds for potential drug candidates. The generation of chemical libraries is well known in the art. For example, combinatorial chemistry is used to generate a library of compounds to be screened in the assays described herein. A combinatorial chemical library is a collection of diverse chemical compounds generated by either chemical synthesis or biological synthesis by combining a number of chemical "building block" reagents. For example, a linear combinatorial chemical library such as a polypeptide library is formed by combining amino acids in every possible combination to yield peptides of a given length. Millions of chemical compounds theoretically can be synthesized through such combinatorial mixings of chemical building blocks. For example, one commentator observed that the systematic, combinatorial mixing of 100 interchangeable chemical building blocks results in the theoretical synthesis of 100 million tetrameric compounds or 10 billion pentameric compounds. (Gallop et al., "Applications of Combinatorial Technologies to Drug Discovery, Background and Peptide Combinatorial Libraries," Journal of Medicinal Chemistry, Vol. 37, No. 9, 1233–1250 (1994). Other chemical libraries known to those in the art may also be used, including natural product libraries.

Once generated, combinatorial libraries are screened for compounds that possess desirable biological properties. For example, compounds which may be useful as drugs or to develop drugs would likely have the ability to bind to the target protein identified, expressed and purified as discussed above. Further, if the identified target protein is an enzyme candidate compounds would likely interfere with the enzymatic properties of the target protein. For example, the enzymatic function of a target protein may be to serve as a protean, nuclease, phosphatase, dehydrogenase, transporter protein, transcriptional enzyme, replication component, and any other type of enzyme known or unknown. Thus, the present invention contemplates using the protein products described above to screen combinatorial chemical libraries.

In some embodiments of the present invention, the biochemical activity of the protein, as well as the chemical structure of a substrate on which the protein acts is known. In other embodiments of the present invention, the biochemical activity of the target protein is unknown and the target protein has no known substrates.

In some embodiments of the present invention, libraries of compounds are screened to identify compounds that function as inhibitors of the target gene product. First, a library of small molecules is generated using methods of combinatorial library formation well known in the art. U.S. Pat. Nos. 5,463,564 and 5,574,656, to Agrafiotis, et al., entitled "System and Method of Automatically Generating Chemical Compounds with Desired Properties," the disclosures of which are incorporated herein by reference in their entireties, are two such teachings. Then the library compounds are screened to identify those compounds that possess desired structural and functional properties. U.S. Pat. No. 5,684,711, the disclosure of which is incorporated herein by reference in its entirety, also discusses a method for screening libraries.

To illustrate the screening process, the target gene product, an enzyme, and chemical compounds of the library are combined and permitted to interact with one another. A labeled substrate is added to the incubation. The label on the substrate is such that a detectable signal is emitted from metabolized substrate molecules. The emission of this signal permits one to measure the effect of the combinatorial library compounds on the enzymatic activity of target enzymes by comparing it to the signal emitted in the absence of combinatorial library compounds. The characteristics of each library compound are encoded so that compounds demonstrating activity against the enzyme can be analyzed and features common to the various compounds identified can be isolated and combined into future iterations of libraries.

Once a library of compounds is screened, subsequent libraries are generated using those chemical building blocks that possess the features shown in the first round of screen to have activity against the target enzyme. Using this method, subsequent iterations of candidate compounds will possess more and more of those structural and functional features required to inhibit the function of the target enzyme, until a group of enzyme inhibitors with high specificity for the enzyme can be found. These compounds can then be further tested for their safety and efficacy as antibiotics for use in mammals.

It will be readily appreciated that this particular screening methodology is exemplary only. Other methods are well known to those skilled in the art. For example, a wide variety of screening techniques are known for a large number of naturally-occurring targets when the biochemical function of the target protein is known. For example, some techniques involve the generation and use of small peptides to probe and analyze target proteins both biochemically and genetically in order to identify and develop drug leads. Such techniques include the methods described in PCT publications No. WO9935494, WO9819162, WO9954728, the disclosures of which are incorporated herein by reference in their entireties.

Similar methods may be used to identify compounds which inhibit the activity of proteins from organisms other than *Candida albicans* which are homologous to the *Candida albicans* target proteins described herein. For example, the proteins may be from animal fugal pathogens such as *Aspergillus fumigatus, Aspergillus niger, Aspergillus flavis, Candida tropicalis, Candida parapsilopsis, Candida krusei,* *Cryptococcus neoformans, Coccidioides immitis, Exophalia dermatiditis, Fusarium oxysporum, Histoplasma capsulatum, Phneumocystis carinii, Trichosporon beigelii, Rhizopus arrhizus, Mucor rouxii, Rhizomucor pusillus,* or *Absidia corymbigera*, or the plant fungal pathogens, such as *Botrytis cinerea, Erysiphe graminis, Magnaporthe grisea, Puccinia recodita, Septoria triticii, Tilletia controversa, Ustilago maydis*, or any species falling within the genera of any of the above species. In some embodiments, the proteins are from an organism other than *Saccharomyces cerevisiae*.

5.5.1.3 In vitro Enzyme Assays

GRACE methods and strains are used to develop in vitro assays for biochemical activities that are shown to be essential to cell viability. A number of essential genes identified by the GRACE conditional expression methodologies display statistically significant similarity to biochemically characterized gene products from other organisms. For example, based on amino acid sequence similarity, a number of essential and fungal specific genes listed in Table II are predicted to possess the following biochemical activities:

| | |
|---|---|
| CaRHO1 | GTPase involved in (1,3)-β-glucan synthesis and polarity |
| CaYHR118c (ORC6) | Origin of replication complex subunit |
| CaYPL128c (TBP1) | Telomere binding protein |
| CaYNL256w | Dihydropteroate synthase |
| CaYKL004w (AUR1) | Phosphatidylinositol: ceramide phosphoinositol transferase |
| CaYJL090c (DPB11) | DNA polB subunit |
| CaYOL149w (DCP1) | mRNA decapping enzyme |
| CaYNL151c (RPC31) | RNA polIII subunit |
| CaYOR148c (SPP2) | RNA splicing |
| CaYER026c (CHO1) | Phosphatidylserine synthase |

Therefore, a number of well characterized standard in vitro biochemical assays (e.g., DNA binding, RNA processing, GTP binding and hydrolysis, and phosphorylation) are readily adapted for these validated drug targets. For example the validated target, CaRHO1, is used within a in vitro-based drug screen by adapting standard GTPase assays developed for a wide range of such proteins. Alternatively, novel assays are developed using biochemical information pertaining to validated drug targets within our GRACE strain collection. Any assays known in the art for enzymes with similar biochemical activities (e.g., mechanism of action, class of substrate) are adapted for screening for inhibitors of the enzymes encoded by these essential *C. albicans* genes.

For example, a number of features make the *C. albicans* gene, CaTBF1, a candidate for in vitro assay development. CaTBF1 shares significant homology to its *S. cerevisiae* counterpart, TBF1, a telomere binding factor. In addition, the DNA sequence CaTBF1p recognizes is known and is relatively short Koering et al., Nucleic Acid Res. 28:2519–2526, which is incorporated herein by reference in its entirety), enabling inexpensive synthesis of oligonucleotides corresponding to this element. Moreover since this assay only requires the target protein and a DNA fragment containing the nucleotide sequence it recognizes, only purification of CaTBF1p protein is necessary in order to develop an in vitro binding assay. One preferred embodiment of this in vitro assay involves crosslinking the DNA element to the bottom of a well, incubation of radiolabeled CaTBF1p to facilitate protein-DNA binding, a series of washes to remove unbound material, and determination of the percentage of bound radiolabeled CaTBF1p. Alternatively, purified CaTBF1p is attached to the well and radiolabeled oligonucleotides added. Drug screening, including the use of high throughput screening technique, is performed by searching for compounds that inhibit the protein-DNA binding measured in this assay.

Similarly, a second validated drug target, CaORC6, is used in this type of assay since its *S. cerevisiae* homolog, ORC6, directly binds a DNA element within the origin of replication of yeast chromosomes (Mizushima et al., 2000, Genes & Development 14:1631–1641, which is incorporated herein by reference in its entirety). Biochemical purification of any of these targets could be achieved, for example, by PCR-based construction of *C. albicans* heterozygous strains in which the gene encoding the CaORC6 protein has been modified to include a carboxy-terminal hexahistidine tag enabling purification of the chimeric protein using standard $Ni^{+2}$ affinity column chromatography techniques.

For other targets like CaDPB11, a homolog of which in *S. cerevisiae* encode proteins that physically associate with Sld2p (Kamimura et al., 1998, Cell Biol. 18:6102–6109, which is incorporated herein by reference in its entirety), in vitro assays similar to those described above are developed. In addition, two-hybrid assays based on known physical interactions are developed for any validated targets within the GRACE strain collection.

The present invention also provides cell extracts useful in establishing in vitro assays for suitable biochemical targets. For example, in an embodiment of the present invention, GRACE-derived *C. albicans* strains are grown either under constitutive expression conditions or transcription repression conditions to either overproduce or deplete a particular gene product. Cellular extracts resulting from strains incubated under these two conditions are compared with extracts prepared from identically-grown wild type strains. These extracts are then used for the rapid evaluation of targets using existing in vitro assays or new assays directed toward novel gene products, without having to purify the gene product. Such a whole cell extract approach to in vitro assay development is typically necessary for targets involved in cell wall biosynthetic pathways (e.g. (1,3)-β-glucan synthesis or chitin synthesis) which involve multiple gene products that transit the secretory pathway before receiving essential post-translational modifications required for their functional activity. GRACE-derived strains for conditional expression of target genes involved in these, or other cell wall pathways (e.g. (1,6-β-glucan synthesis) enable in vitro assays to be performed directly in *C. albicans*.

5.5.2 Cell-based Screening Assays

Current cell-based assays used to identify or to characterize compounds for drug discovery and development frequently depend on detecting the ability of a test compound to modulate the activity of a target molecule located within a cell or located on the surface of a cell. Most often such target molecules are proteins such as enzymes, receptors and the like. However, target molecules also include other molecules such as DNAs, lipids, carbohydrates and RNAs including messenger RNAs, ribosomal RNAs, tRNAs and the like. A number of highly sensitive cell-based assay methods are available to those of skill in the art to detect binding and interaction of test compounds with specific target molecules. However, these methods are generally not highly effective when the test compound binds to or otherwise interacts with its target molecule with moderate or low affinity. In addition, the target molecule may not be readily accessible to a test compound in solution, such as when the target molecule is located inside the cell or within a cellular compartment such as the periplasm of a bacterial cell. Thus, current cell-based assay methods are limited in that they are not effective in identifying or characterizing compounds that interact with their targets with moderate to low affinity or compounds that interact with targets that are not readily accessible.

The cell-based assay methods of the present invention have substantial advantages over current cell-based assays. These advantages derive from the use of sensitized cells in which the level or activity of at least one gene product required for fungal proliferation, virulence, or pathogenicity (the target molecule) has been specifically reduced to the point where the presence or absence of its function becomes a rate-determining step for fungal growth, survival, proliferation, virulence, or pathogenicity. Such sensitized cells become much more sensitive to compounds that are active against the affected target molecule. For example, sensitized cells are obtained by growing a GRACE strain in the presence of a concentration of inducer or repressor which provides a level of a gene product required for fungal growth, survival, proliferation, virulence, or pathogenicity such that the presence or absence of its function becomes a rate determining step for fungal growth, survival, proliferation, virulence, or pathogenicity. Thus, cell-based assays of the present invention are capable of detecting compounds exhibiting low or moderate potency against the target molecule of interest because such compounds are substantially more potent on sensitized cells than on non-sensitized cells. The effect may be such that a test compound may be two to several times more potent, at least times more potent, at least 20 times more potent, at least 50 times more potent, at least 100 times more potent, at least 1000 times more potent, or even more than 1000 times more potent when tested on the sensitized cells as compared to the non-sensitized cells.

Due in part to the increased appearance of antibiotic resistance in pathogenic microorganisms and to the significant side-effects associated with some currently used antibiotics, novel antibiotics acting at new targets are highly sought after in the art. Yet, another limitation in the current art related to cell-based assays is the problem of repeatedly identifying hits against the same kinds of target molecules in the same limited set of biological pathways. This may occur when compounds acting at such new targets are discarded, ignored or fail to be detected because compounds acting at the "old" targets are encountered more frequently and are more potent than compounds acting at the new targets. As a result, the majority of antibiotics in use currently interact with a relatively small number of target molecules within an even more limited set of biological pathways.

The use of sensitized cells of the current invention provides a solution to the above problems in two ways. First, desired compounds acting at a target of interest, whether a new target or a previously known but poorly exploited target, can now be detected above the "noise" of compounds acting at the "old" targets due to the specific and substantial increase in potency of such desired compounds when tested on the sensitized cells of the current invention. Second, the methods used to sensitize cells to compounds acting at a target of interest may also sensitize these cells to compounds acting at other target molecules within the same biological pathway. For example, expression of a gene encoding a ribosomal protein at a level such that the function of the ribosomal protein becomes rate limiting for fungal growth, survival, proliferation, virulence, or pathogenicity is expected to sensitize the cell to compounds acting at that ribosomal protein to compounds acting at any of the ribosomal components (proteins or rRNA) or even to compounds acting at any target which is part of the protein synthesis pathway. Thus an important advantage of the present invention is the ability to reveal new targets and pathways that were previously not readily accessible to drug discovery methods.

Sensitized cells of the present invention are prepared by reducing the activity or level of a target molecule. The target molecule may be a gene product, such as an RNA or polypeptide produced from the nucleic acids required for fungal growth, survival, proliferation, virulence, or pathogenicity described herein. In addition, the target may be an RNA or polypeptide in the same biological pathway as the nucleic acids required for fungal growth, survival, proliferation, virulence, or pathogenicity as described herein. Such biological pathways include, but are not limited to, enzymatic, biochemical and metabolic pathways as well as pathways involved in the production of cellular structures such as the cell membrane.

Current methods employed in the arts of medicinal and combinatorial chemistries are able to make use of structure-activity relationship information derived from testing compounds in various biological assays including direct binding assays and cell-based assays. Occasionally compounds are directly identified in such assays that are sufficiently potent to be developed as drugs. More often, initial hit compounds exhibit moderate or low potency. Once a hit compound is identified with low or moderate potency, directed libraries of compounds are synthesized and tested in order to identify more potent leads. Generally these directed libraries are combinatorial chemical libraries consisting of compounds with structures related to the hit compound but containing systematic variations including additions, subtractions and substitutions of various structural features. When tested for activity against the target molecule, structural features are identified that either alone or in combination with other features enhance or reduce activity. This information is used to design subsequent directed libraries containing compounds with enhanced activity against the target molecule. After one or several iterations of this process, compounds with substantially increased activity against the target molecule are identified and may be further developed as drugs. This process is facilitated by use of the sensitized cells of the present invention since compounds acting at the selected targets exhibit increased potency in such cell-based assays, thus; more compounds can now be characterized providing more useful information than would be obtained otherwise.

Thus, it is now possible using cell-based assays of the present invention to identify or characterize compounds that previously would not have been readily identified or characterized including compounds that act at targets that previously were not readily exploited using cell-based assays. The process of evolving potent drug leads from initial hit compounds is also substantially improved by the cell-based assays of the present invention because, for the same number of test compounds, more structure-function relationship information is likely to be revealed.

The method of sensitizing a cell entails selecting a suitable gene. A suitable gene is one whose expression is required for the growth, survival, proliferation, virulence, or pathogenicity of the cell to be sensitized. The next step is to obtain a cell in which the level or activity of the target can be reduced to a level where it is rate limiting for growth, survival, proliferation, virulence or pathogenicity. For example, the cell may be a GRACE strain in which the selected gene is under the control of a regulatable promoter. The amount of RNA transcribed from the selected gene is limited by varying the concentration of an inducer or repressor which acts on the regulatable promoter, thereby varying the activity of the promoter driving transcription of the RNA. Thus, cells are sensitized by exposing them to an inducer or repressor concentration that results in an RNA level such that the function of the selected gene product becomes rate limiting for fungal growth, survival, proliferation, virulence, or pathogenicity.

In one embodiment of the cell-based assays, GRACE strains, in which the sequences required for fungal growth, survival, proliferation, virulence, or pathogenicity of *Candida albicans* described herein are under the control of a regulatable promoter, are grown in the presence of a concentration of inducer or repressor which causes the function of the gene products encoded by these sequences to be rate limiting for fungal growth, survival, proliferation, virulence, or pathogenicity. To achieve that goal, a growth inhibition dose curve of inducer or repressor is calculated by plotting various doses of inducer or repressor against the corresponding growth inhibition caused by the limited levels of the gene product required for fungal proliferation. From this dose-response curve, conditions providing various growth rates, from 1 to 100% as compared to inducer or repressor-free growth, can be determined. For example, if the regulatable promoter is repressed by tetracycline, the GRACE strain may be grown in the presence of varying levels of tetracyline. Similarly, inducible promoters may be used. In this case, the GRACE strains are grown in the presence of varying concentrations of inducer. For example, the highest concentration of the inducer or repressor that does not reduce the growth rate significantly can be estimated from the dose-response curve. Cellular proliferation can be monitored by growth medium turbidity via OD measurements. In another example, the concentration of inducer or repressor that reduces growth by 25% can be predicted from the dose-response curve. In still another example, a concentration of inducer or repressor that reduces growth by 50% can be calculated from the dose-response curve. Additional parameters such as colony forming units (cfu) are also used to measure cellular growth, survival and/or viability.

In another embodiment of the present invention, an individual haploid strain may similarly be used as the basis for detection of an antifungal or therapeutic agent. In this embodiment, the test organism (e.g. *Aspergillus fumigatus, Cryptococcus neoformans, Magnaportha grisea* or any other haploid organisms represented in Table I) is a strain constructed by modifying the single allele of the target gene in one step by recombination with a promoter replacement fragment comprising a heterologous regulatable promoter, such that the expression of the gene is conditionally regulated by the heterologous promoter. Like individual diploid GRACE strains, sensitized haploid cells may similarly be used in whole cell-based assay methods to identify compounds displaying a preferential activity against the affected target.

In various embodiments, the modified strain is grown under a first set of conditions where the heterologous promoter is expressed at a relatively low level (i.e. partially repressed) and the extent of growth determined. This experiment is repeated in the presence of a test compound and a second measurement of growth obtained. The extent of growth in the presence and in the absence of the test compound are then compared to provide a first indicator value. Two further experiments are performed, using non-repressing growth conditions where the target gene is expressed at substantially higher levels than in the first set of conditions. The extent of growth is determined in the presence and absence of the test compound under the second set of conditions to obtain a second indicator value. The first and second indicator values are then compared. If the indicator values are essentially the same, the data suggest that the test compound does not inhibit the test target. However, if the two indicator values are substantially different, the data indicates that the level of expression of the target gene product may determine the degree of inhibition by the test compound and, therefore, it is likely that the gene product is the target of that test compound. Whole-cell assays comprising collections or subsets of multiple sensitized strains may also be screened, for example, in a series of 96-well, 384-well, or even 1586-well microtiter plates, with each well containing individual strains sensitized to identify compounds displaying a preferential activity against each affected target comprising a target set or subset selected from, but not limited to the group consisting of fungal-specific, pathogen-specific, desired biochemical-function, human-homolog, cellular localization, and signal transduction cascade target sets.

Cells to be assayed are exposed to the above-determined concentrations of inducer or repressor. The presence of the inducer or repressor at this sub-lethal concentration reduces the amount of the proliferation-required gene product to the lowest amount in the cell that will support growth. Cells grown in the presence of this concentration of inducer or repressor are therefore specifically more sensitive to inhibitors of the proliferation-required protein or RNA of interest as well as to inhibitors of proteins or RNAs in the same biological pathway as the proliferation-required protein or RNA of interest but not specifically more sensitive to inhibitors of unrelated proteins or RNAs.

Cells pretreated with sub-inhibitory concentrations of inducer or repressor, which therefore contain a reduced amount of proliferation-required target gene product, are used to screen for compounds that reduce cell growth. The sub-lethal concentration of inducer or repressor may be any concentration consistent with the intended use of the assay to identify candidate compounds to which the cells are more sensitive than are control cells in which this gene product is not rate-limiting. For example, the sub-lethal concentration of the inducer or repressor may be such that growth inhibition is at least about 5%, at least about 8%, at least about 10%, at least about 20%, at least about 30%, at least about 40%, at least about 50%, at least about 60% at least about 75%, at least 80%, at least 90%, at least 95% or more than 95%. Cells which are pre-sensitized using the preceding method are more sensitive to inhibitors of the target protein because these cells contain less target protein to inhibit than wild-type cells.

It will be appreciated that similar methods may be used to identify compounds which inhibit virulence or pathogenicity. In such methods, the virulence or pathogenicity of cells exposed to the candidate compound which express rate limiting levels of a gene product involved in virulence or pathogenicity is compared to their virulence or pathogenicity of cells exposed to the candidate compound in which the levels of the gene product are not rate limiting. Virulence or pathogenicity may be measured using the techniques described herein.

In another embodiment of the cell-based assays of the present invention, the level or activity of a gene product required for fungal growth, survival, proliferation, virulence, or pathogenicity is reduced using a mutation, such as a temperature sensitive mutation, in the sequence required for fungal growth, survival, proliferation, virulence, or pathogenicity and an inducer or repressor level which, in conjunction with the temperature sensitive mutation, provides levels of the gene product required for fungal growth, survival, proliferation, virulence, or pathogenicity which are rate limiting for proliferation. Growing the cells at an intermediate temperature between the permissive and restrictive temperatures of the temperature sensitive mutant where the mutation is in a gene required for fungal growth, survival, proliferation, virulence, or pathogenicity produces cells with reduced activity of the gene product required for growth, survival, proliferation, virulence, or pathogenicity. The concentration of inducer or repressor is chosen so as to further reduces the activity of the gene product required for fungal growth, survival, proliferation, virulence, or pathogenicity. Drugs that may not have been found using either the temperature sensitive mutation or the inducer or repressor alone may be identified by determining whether cells in which expression of the nucleic acid encoding the proliferation-required gene product has been reduced and which are grown at a temperature between the permissive temperature and the restrictive temperature are substantially more sensitive to a test compound than cells in which expression of the gene product required for fungal growth, survival, proliferation, virulence, or pathogenicity has not been reduced and which are grown at a permissive temperature. Also drugs found previously from either the use of the inducer or repressor alone or the temperature sensitive mutation alone may have a different sensitivity profile when used in cells combining the two approaches, and that sensitivity profile may indicate a more specific action of the drug in inhibiting one or more activities of the gene product.

Temperature sensitive mutations may be located at different sites within a gene and may lie within different domains of the protein. For example, the dnaB gene of *Escherichia coli* encodes the replication fork DNA helicase. DnaB has several domains, including domains for oligomerization, ATP hydrolysis, DNA binding, interaction with primase, interaction with DnaC, and interaction with DnaA. Temperature sensitive mutations in different domains of DnaB confer different phenotypes at the restrictive temperature, which include either an abrupt stop or a slow stop in DNA replication either with or without DNA breakdown (Wechsler, J. A. and Gross, J. D. 1971 *Escherichia coli* mutants temperature-sensitive for DNA synthesis. Mol. Gen. Genetics 113:273–284) and termination of growth or cell death. Thus, temperature sensitive mutations in different domains of the protein may be used in conjunction with GRACE strains in which expression of the protein is under the control of a regulatable promoter.

It will be appreciated that the above method may be performed with any mutation which reduces but does not eliminate the activity or level of the gene product which is required for fungal growth, survival, proliferation, virulence, or pathogenicity.

When screening for antimicrobial agents against a gene product required for fungal growth, survival, proliferation, virulence, or pathogenicity, growth inhibition, virulence or pathogenicity of cells containing a limiting amount of that gene product can be assayed. Growth inhibition can be measured by directly comparing the amount of growth, measured by the optical density of the culture relative to uninoculated growth medium, between an experimental sample and a control sample. Alternative methods for assaying cell proliferation include measuring green fluorescent protein (GFP) reporter construct emissions, various enzymatic activity assays, and other methods well known in the art. Virulence and pathogenicity may be measured using the techniques described herein.

It will be appreciated that the above method may be performed in solid phase, liquid phase, a combination of the two preceding media, or in vivo. For example, cells grown on nutrient agar containing the inducer or repressor which acts on the regulatable promoter used to express the proliferation required gene product may be exposed to compounds spotted onto the agar surface. A compound's effect may be judged from the diameter of the resulting killing zone, the area around the compound application point in which cells do not grow. Multiple compounds may be transferred to agar plates and simultaneously tested using automated and semi-automated equipment including but not restricted to multi-channel pipettes (for example the Beckman Multimek) and multi-channel spotters (for example the Genomic Solutions Flexys). In this way multiple plates and thousands to millions of compounds may be tested per day.

The compounds are also tested entirely in liquid phase using microtiter plates as described below. Liquid phase screening may be performed in microtiter plates containing 96, 384, 1536 or more wells per microtiter plate to screen multiple plates and thousands to millions of compounds per day. Automated and semi-automated equipment are used for addition of reagents (for example cells and compounds) and for determination of cell density.

The compounds are also tested in vivo using the methods described herein.

It will be appreciated that each of the above cell-based assays may be used to identify compounds which inhibit the activity of gene products from organisms other than *Candida albicans* which are homologous to the *Candida albicans* gene products described herein. For example, the target gene products may be from animal fugal pathogens such as *Aspergillus fumigatus, Aspergillus niger, Aspergillus flavis, Candida tropicalis, Candida parapsilopsis, Candida krusei, Cryptococcus neoformans, Coccidioides immitis, Exophalia dermatiditis, Fusarium oxysporum, Histoplasma capsulatum, Phneumocystis carinii, Trichosporon beigelii, Rhizopus arrhizus, Mucor rouxii, Rhizomucor pusillus*, or *Absidia corymbigera*, or the plant fungal pathogens, such as *Botrytis cinerea, Erysiphe graminis, Magnaporthe grisea, Puccinia recodita, Septoria triticii, Tilletia controversa, Ustilago maydis*, or any species falling within the genera of any of the above species. In some embodiments, the gene products are from an organism other than *Saccharomyces cerevisiae*.

5.5.2.1 Cell-based Assays Using GRACE Strains

GRACE strains in which one allele of a gene required for fungal growth, survival, proliferation, virulence, or pathogenicity is inactivated while the other allele is under the control of a regulatable promoter are constructed using the methods described herein. For the purposes of the present example, the regulatable promoter may be the tetracycline regulated promoter described herein, but it will be appreciated that any regulatable promoter may be used.

In one embodiment of the present invention, an individual GRACE strain is used as the basis for detection of a therapeutic agent active against a diploid pathogenic fungal cell. In this embodiment, the test organism is a GRACE strain having a modified allelic gene pair, where the first allele of the gene has been inactivated by the insertion of, or replacement by, a nucleotide sequence encoding an expressible, dominant selectable marker and the second allele has been modified, by recombination, to place the second allele under the controlled expression of a heterologous promoter. This test GRACE strain is then grown under a first set of conditions where the heterologous promoter is expressed at a relatively low level ("repressing") and the extent of growth determined. This measurement may be carried out using any appropriate standard known to those skilled in the art including optical density, wet weight of pelleted cells, total cell count, viable count, DNA content, and the like. This experiment is repeated in the presence of a test compound and a second measurement of growth obtained. The extent of growth in the presence and in the absence of the test compound, which can conveniently be expressed in terms of indicator values, are then compared. A dissimilarity in the extent of growth or indicator values provides an indication that the test compound may interact with the target essential gene product.

To gain more information, two further experiments are performed, using a second set of "non-repressing" growth conditions where the second allele, under the control of the heterologous promoter, is expressed at a level substantially higher than in the first set of conditions described above. The extent of growth or indicator values is determined in the presence and absence of the test compound under this second set of conditions. The extent of growth or indicator values in the presence and in the absence of the test compound are then compared. A dissimilarity in the extent of growth or indicator values provides an indication that may interact with the target essential gene product.

Furthermore, the extent of growth in the first and in the second set of growth conditions can also be compared. If the extent of growth is essentially the same, the data suggest that the test compound does not inhibit the gene product encoded by the modified allelic gene pair carried by the GRACE strain tested. However, if the extent of growth are substantially different, the data indicate that the level of expression of the subject gene product may determine the degree of inhibition by the test compound and, therefore, it is likely that the subject gene product is the target of that test compound.

Although each GRACE strain can be tested individually, it will be more efficient to screen entire sets or subsets of a GRACE strain collection at one time. Therefore in one aspect of this invention, arrays may be established, for example in a series of 96-well microtiter plates, with each well containing a single GRACE strain. In one representative, but not limiting approach, four microtiter plates are used, comprising two pairs where the growth medium in one pair supports greater expression of the heterologous promoter controlling the remaining active allele in each strain, than the medium in the other pair of plates. One member of each pair is supplemented with a compound to be tested and measurements of growth of each GRACE strain is determined using standard procedures to provide indicator values for each isolate tested. The collection of diploid pathogenic GRACE strains used in such a method for screening for therapeutic agents may comprise, for example, a substantially complete set of all the modified allelic gene pairs of the organism, the substantially complete set of all the modified allelic essential gene pairs of the organism or the collection may be selected from a subset of GRACE strains selected from, but not limited to the group consisting of fungal-specific, pathogen-specific, desired biochemical-function, human-homolog, cellular localization, and signal transduction cascade target sets.

The GRACE strains are grown in medium comprising a range of tetracycline concentrations to obtain the growth inhibitory dose-response curve for each strain. First, seed cultures of the GRACE strains are grown in the appropriate medium. Subsequently, aliquots of the seed cultures are diluted into medium containing varying concentrations of tetracycline. For example, the GRACE strains may be grown in duplicate cultures containing two-fold serial dilutions of tetracycline. Additionally, control cells are grown in duplicate without tetracycline. The control cultures are started from equal amounts of cells derived from the same initial seed culture of a GRACE strain of interest. The cells are grown for an appropriate period of time and the extent of growth is determined using any appropriate technique. For example, the extent of growth may be determined by measuring the optical density of the cultures. When the control culture reaches mid-log phase the percent growth (relative to the control culture) for each of the tetracycline containing cultures is plotted against the log concentrations of tetracycline to produce a growth inhibitory dose response curve for tetracycline. The concentration of tetracycline that inhibits cell growth to 50% ($IC_{50}$) as compared to the 0 mM tetracyline control (0% growth inhibition) is then calculated from the curve. Alternative methods of measuring growth are also contemplated. Examples of these methods include measurements of proteins, the expression of which is engineered into the cells being tested and can readily be measured. Examples of such proteins include green fluorescent protein (GFP) and various enzymes.

Cells are pretreated with the selected concentration of tetracycline and then used to test the sensitivity of cell populations to candidate compounds. For example, the cells may be pretreated with a concentration of tetracycline which inhibits growth by at least about 5%, at least about 8%, at least about 10%, at least about 20%, at least about 30%, at least about 40%, at least about 50%, at least about 60% at least about 75%, at least 80%, at least 90%, at least 95% or more than 95%. The cells are then contacted with the candidate compound and growth of the cells in tetracycline containing medium is compared to growth of the control cells in medium which lacks tetracycline to determine whether the candidate compound inhibits growth of the sensitized cells (i.e. the cells grown in the presence of tetracycline). For example, the growth of the cells in tetracycline containing medium may be compared to the growth of the cells in medium lacking tetracycline to determine whether the candidate compound inhibits the growth of the sensitized cells (i.e. the cells grown in the presence of tetracyline) to a greater extent than the candidate compound inhibits the growth of cells grown in the absence of tetracycline. For example, if a significant difference in growth is observed between the sensitized cells (i.e. the cells grown in the presence of tetracycline) and the non-sensitized cells (i.e. the cells grown in the absence of tetracycline), the candidate compound may be used to inhibit the proliferation of the organism or may be further optimized to identify compounds which have an even greater ability to inhibit the growth, survival, or proliferation of the organism.

Similarly, the virulence or pathogenicity of cells exposed to a candidate compound which express a rate limiting amount of a gene product required for virulence or pathogenicity may be compared to the virulence or pathogenicity of cells exposed to the candidate compound in which the level of expression of the gene product required for virulence or pathogenicity is not rate limiting. In such methods, test animals are challenged with the GRACE strain and fed a diet containing the desired amount of tetracycline and the candidate compound. Thus, the GRACE strain infecting the test animals expresses a rate limiting amount of a gene product required for virulence or pathogenicity (i.e. the GRACE cells in the test animals are sensitized). Control animals are challenged with the GRACE strain and are fed a diet containing the candidate compound but lacking tetracycline. The virulence or pathogenicity of the GRACE strain in the test animals is compared to that in the control animals. For example, the virulence or pathogenicity of the GRACE strain in the test animals may be compared to that in the control animals to determine whether the candidate compound inhibits the virulence or pathogenicity of the sensitized GRACE cells (i.e. the cells in the animals whose diet included tetracyline) to a greater extent than the candidate compound inhibits the growth of the GRACE cells in animals whose diet lacked tetracycline. For example, if a significant difference in growth is observed between the sensitized GRACE cells (i.e. the cells in animals whose diet included tetracycline) and the non-sensitized cells (i.e. the GRACE cells animals whose diet did not include tetracycline), the candidate compound may be used to inhibit the virulence or pathogenicity of the organism or may be further optimized to identify compounds which have an even greater ability to inhibit the virulence or pathogenicity of the organism. Virulence or pathogenicity may be measured using the techniques described therein.

It will be appreciated that the above cell-based assays may be used to identify compounds which inhibit the activity of gene products from organisms other than *Candida albicans* which are homologous to the *Candida albicans* gene products described herein. For example, the gene products may be from animal fugal pathogens such as *Aspergillus fumigatus, Aspergillus niger, Aspergillus flavis, Candida tropicalis, Candida parapsilopsis, Candida krusei, Cryptococcus neoformans, Coccidioides immitis, Exophalia dermatiditis, Fusarium oxysporum, Histoplasma capsulatum, Phneumocystis carinii, Trichosporon beigelii, Rhizopus arrhizus, Mucor rouxii, Rhizomucor pusillus*, or *Absidia corymbigera*, or the plant fungal pathogens, such as *Botrytis cinerea, Erysiphe graminis, Magnaporthe grisea, Puccinia recodita, Septoria triticii, Tilletia controversa, Ustilago maydis*, or any species falling within the genera of any of the above species. In some embodiments, the gene products are from an organism other than *Saccharomyces cerevisae*.

The cell-based assay described above may also be used to identify the biological pathway in which a nucleic acid required for fungal proliferation, virulence or pathogenicity or the gene product of such a nucleic acid lies. In such methods, cells expressing a rate limiting level of a target nucleic acid required for fungal proliferation, virulence or pathogenicity and control cells in which expression of the target nucleic acid is not rate limiting are contacted with a panel of antibiotics known to act in various pathways. If the antibiotic acts in the pathway in which the target nucleic acid or its gene product lies, cells in which expression of target nucleic acid is rate limiting will be more sensitive to the antibiotic than cells in which expression of the target nucleic acid is not rate limiting.

As a control, the results of the assay may be confirmed by contacting a panel of cells in which the levels of many different genes required for proliferation, virulence or pathogenicity, including the target gene, is rate limiting. If the antibiotic is acting specifically, heightened sensitivity to the antibiotic will be observed only in the cells in which the target gene is rate limiting (or cells in which genes in the same pathway as the target gene is rate limiting) but will not be observed generally in which a gene product required for proliferation, virulence or pathogenicity is rate limiting.

It will be appreciated that the above method for identifying the biological pathway in which a nucleic acid required for proliferation, virulence or pathogenicity lies may be applied to nucleic acids from organisms other than *Candida albicans* which are homologous to the *Candida albicans* nucleic acids described herein. For example, the nucleic acids may be from animal fugal pathogens such as

*Aspergillus fumigatus, Aspergillus niger, Aspergillus flavis, Candida tropicalis, Candida parapsilopsis, Candida krusei, Cryptococcus neoformans, Coccidioides immitis, Exophalia dermatiditis, Fusarium oxysporum, Histoplasma capsulatum, Phneumocystis carinii, Trichosporon beigelii, Rhizopus arrhizus, Mucor rouxii, Rhizomucor pusillus,* or *Absidia corymbigera,* or the plant fungal pathogens, such as *Botrytis cinerea, Erysiphe graminis, Magnaporthe grisea, Puccinia recodita, Septoria triticii, Tilletia controversa, Ustilago maydis,* or any species falling within the genera of any of the above species. In some embodiments, the nucleic acids are from an organism other than *Saccharomyces cerevisae.*

Similarly, the above method may be used to determine the pathway on which a test compound, such as a test antibiotic acts. A panel of cells, each of which expresses a rate limiting amount of a gene product required for fungal proliferation, virulence or pathogenicity where the gene product lies in a known pathway, is contacted with a compound for which it is desired to determine the pathway on which it acts. The sensitivity of the panel of cells to the test compound is determined in cells in which expression of the nucleic acid encoding the gene product required for proliferation, virulence or pathogenicity is at a rate limiting level and in control cells in which expression of the gene product required for proliferation, virulence or pathogenicity is not at a rate limiting level. If the test compound acts on the pathway in which a particular gene product required for proliferation, virulence, or pathogenicity lies, cells in which expression of that particular gene product is at a rate limiting level will be more sensitive to the compound than the cells in which gene products in other pathways are at a rate limiting level. In addition, control cells in which expression of the particular gene required for fungal proliferation, virulence or pathogenicity is not rate limiting will not exhibit heightened sensitivity to the compound. In this way, the pathway on which the test compound acts may be determined.

It will be appreciated that the above method for determining the pathway on which a test compound acts may be applied to organisms other than *Candida albicans* by using panels of cells in which the activity or level of gene products which are homologous to the *Candida albicans* gene products described herein is rate limiting. For example, the gene products may be from animal fugal pathogens such as *Aspergillus fumigatus, Aspergillus niger, Aspergillus flavis, Candida tropicalis, Candida parapsilopsis, Candida krusei, Cryptococcus neoformans, Coccidioides immitis, Exophalia dermatiditis, Fusarium oxysporum, Histoplasma capsulatum, Phneumocystis carinii, Trichosporon beigelii, Rhizopus arrhizus, Mucor rouxii, Rhizomucor pusillus,* or *Absidia corymbigera,* or the plant fungal pathogens, such as *Botrytis cinerea, Erysiphe graminis, Magnaporthe grisea, Puccinia recodita, Septoria triticii, Tilletia controversa, Ustilago maydis,* or any species falling within the genera of any of the above species. In some embodiments, the gene products are from an organism other than *Saccharomyces cerevisiae.* Example 6.4, infra, provided below describes one method for performing such assays.

One skilled in the art will appreciate that further optimization of the assay conditions, such as the concentration of inducer or repressor used to produce rate limiting levels of a gene product required for fungal proliferation, virulence or pathogenicity and/or the growth conditions used for the assay (for example incubation temperature and medium components) may further increase the selectivity and/or magnitude of the antibiotic sensitization exhibited.

It will be appreciated that the above methods for identifying the pathway in which a gene required for growth, survival, proliferation, virulence or pathogenicity lies or the pathway on which an antibiotic acts may be performed using organisms other than *Candida albicans* in which gene products homologous to the *Candida albicans* gene products described herein are rate limiting. For example, the gene products may be from animal fugal pathogens such as *Aspergillus fumigatus, Aspergillus niger, Aspergillus flavis, Candida tropicalis, Candida parapsilopsis, Candida krusei, Cryptococcus neoformans, Coccidioides immitis, Exophalia dermatiditis, Fusarium oxysporum, Histoplasma capsulatum, Phneumocystis carinii, Trichosporon beigelii, Rhizopus arrhizus, Mucor rouxii, Rhizomucor pusillus,* or *Absidia corymbigera,* or the plant fungal pathogens, such as *Botrytis cinerea, Erysiphe graminis, Magnaporthe grisea, Puccinia recodita, Septoria triticii, Tilletia controversa, Ustilago maydis,* or any species falling within the genera of any of the above species. In some embodiments, the gene products are from an organism other than *Saccharomyces cerevisae.*

Furthermore, as discussed above, panels of GRACE strains may be used to characterize the point of intervention of any compound affecting an essential biological pathway including antibiotics with no known mechanism of action.

Another embodiment of the present invention is a method for determining the pathway against which a test antibiotic compound is active, in which the activity of proteins or nucleic acids involved in pathways required for fungal growth, survival, proliferation, virulence or pathogenicity is reduced by contacting cells with a sub-lethal concentration of a known antibiotic which acts against the protein or nucleic acid. The method is similar to those described above for determining which pathway a test antibiotic acts against, except that rather than reducing the activity or level of a gene product required for fungal proliferation, virulence or pathogenicity by expressing the gene product at a rate limiting amount in a GRACE strain, the activity or level of the gene product is reduced using a sub-lethal level of a known antibiotic which acts against the gene product.

Growth inhibition resulting from the presence of sub-lethal concentration of the known antibiotic may be at least about 5%, at least about 8%, at least about 10%, at least about 20%, at least about 30%, at least about 40%, at least about 50%, at least about 60%, or at least about 75%, at least 80%, at least 90%, at least 95% or more than 95%.

Alternatively, the sub-lethal concentration of the known antibiotic may be determined by measuring the activity of the target proliferation-required gene product rather than by measuring growth inhibition.

Cells are contacted with a combination of each member of a panel of known antibiotics at a sub-lethal level and varying concentrations of the test antibiotic. As a control, the cells are contacted with varying concentrations of the test antibiotic alone. The $IC_{50}$ of the test antibiotic in the presence and absence of the known antibiotic is determined. If the $IC_{50}$s in the presence and absence of the known drug are substantially similar, then the test drug and the known drug act on different pathways. If the $IC_{50}$s are substantially different, then the test drug and the known drug act on the same pathway.

Similar methods may be performed using known antibiotics which act on a gene product homologous to the *Candida albicans* sequences described herein. The homologous gene product may be from animal fugal pathogens such as *Aspergillus fumigatus, Aspergillus niger, Aspergillus flavis, Candida tropicalis, Candida parapsilopsis, Candida*

*krusei, Cryptococcus neoformans, Coccidioides immitis, Exophalia dermatiditis, Fusarium oxysporum, Histoplasma capsulatum, Phneumocystis carinii, Trichosporon beigelii, Rhizopus arrhizus, Mucor rouxii, Rhizomucor pusillus,* or *Absidia corymbigera,* or the plant fungal pathogens, such as *Botrytis cinerea, Erysiphe graminis, Magnaporthe grisea, Puccinia recodita, Septoria triticii, Tilletia controversa, Ustilago maydis,* or any species falling within the genera of any of the above species. In some embodiments, the gene products are from an organism other than *Saccharomyces cerevisae.*

Another embodiment of the present invention is a method for identifying a candidate compound for use as an antibiotic in which the activity of target proteins or nucleic acids involved in pathways required for fungal proliferation, virulence or pathogenicity is reduced by contacting cells with a sub-lethal concentration of a known antibiotic which acts against the target protein or nucleic acid. The method is similar to those described above for identifying candidate compounds for use as antibiotics except that rather than reducing the activity or level of a gene product required for proliferation, virulence or pathogenicity using GRACE strains which express a rate limiting level of the gene product, the activity or level of the gene product is reduced using a sublethal level of a known antibiotic which acts against the proliferation required gene product.

The growth inhibition from the sub-lethal concentration of the known antibiotic may be at least about 5%, at least about 8%, at least about 10%, at least about 20%, at least about 30%, at least about 40%, at least about 50%, at least about 60%, or at least about 75%, or more.

Alternatively, the sub-lethal concentration of the known antibiotic may be determined by measuring the activity of the target proliferation-required gene product rather than by measuring growth inhibition.

In order to characterize test compounds of interest, cells are contacted with a panel of known antibiotics at a sub-lethal level and one or more concentrations of the test compound. As a control, the cells are contacted with the same concentrations of the test compound alone. The $IC_{50}$ of the test compound in the presence and absence of the known antibiotic is determined. If the $IC_{50}$ of the test compound is substantially different in the presence and absence of the known drug then the test compound is a good candidate for use as an antibiotic. As discussed above, once a candidate compound is identified using the above methods its structure may be optimized using standard techniques such as combinatorial chemistry.

Similar methods may be performed using known antibiotics which act on a gene product homologous to the *Candida albicans* sequences described herein. The homolgous gene product may be from animal fugal pathogens such as *Aspergillus fumigatus, Aspergillus niger, Aspergillus flavis, Candida tropicalis, Candida parapsilopsis, Candida krusei, Cryptococcus neoformans, Coccidioides immitis, Exophalia dermatiditis, Fusarium oxysporum, Histoplasma capsulatum, Phneumocystis carinii, Trichosporon beigelii, Rhizopus arrhizus, Mucor rouxii, Rhizomucor pusillus,* or *Absidia corymbigera,* or the plant fungal pathogens, such as *Botrytis cinerea, Erysiphe graminis, Magnaporthe grisea, Puccinia recodita, Septoria triticii, Tilletia controversa, Ustilago maydis,* or any species falling within the genera of any of the above species. In some embodiments, the gene products are from an organism other than *Saccharomyces cerevisae.*

An exemplary target gene product is encoded by CaTBF1. A number of features make this *C. albicans* gene product a valuable drug target. First, the protein encoded by CaTBF1 is compatible with in vitro high throughput screening of compounds that inhibit its activity. Modulated expression of this gene product in whole cell assays could be performed in parallel with in vitro assays to broaden the spectrum of possible inhibitory compounds identified. In addition, demonstration of the predicted physical interaction between CaTbf1p and chromosomal telomerases could be used to develop two-hybrid assays for drug screening purposes. Finally, because CaTBF1 is a fungal specific gene, its nucleotide sequence could serve in designing PCR-based diagnostic tools for fungal infection.

Other validated drug targets included in the GRACE-derived strain collection that represent preferred drug targets include the products encoded by the following *C. albicans* genes: CaRHO1, CaERG8, CaAUR1, and CaCHO1, as well as those encoded by SEQ ID NOs.:1–62. The ability to manipulate these genes using GRACE methods of the present invention will improve drug screening practices now in use that are designed to identify inhibitors of these critical gene products.

In another embodiment of the present invention, all potential, drug targets of a pathogen could be screened simultaneously against a library of compounds using, for example a 96 well microtiter plate format, where growth, measured by optical density or pellet size after centrifugation, may be determined for each well. A genomic approach to drug screening eliminates reliance upon potentially arbitrary and artificial criteria used in evaluating which target to screen and instead allows all potential targets to be screened. This approach not only offers the possibility of identifying specific compounds which inhibit a preferred process (e.g. cell wall biosynthetic gene products) but also the possibility of identifying all fungicidal compounds within that library and linking them to their cognate cellular targets.

In still another embodiment of the present invention, GRACE strains could be screened to identify synthetic lethal mutations, and thereby uncover a potentially novel class of drug targets of significant therapeutic value. For example two separate genes may encode homologous proteins that participate in a common and essential cellular function, where the essential nature of this function will only become apparent upon inactivation of both family members. Accordingly, examination of the null phenotype of each gene separately would not reveal the essential nature of the combined gene products, and consequently, this potential drug target would not be identified. Provided the gene products are highly homologous to one another, compounds found to inhibit one family member are likely to inhibit the other and are therefore predicted to approximate the synthetic growth inhibition demonstrated genetically. In other cases however, synthetic lethality may uncover seemingly unrelated (and often nonessential) processes, which when combined produce a synergistic growth impairment (cell death). For example, although disruption of the *S. cerevisiae* gene RVS161 does not present any discernable vegetative growth phenotype in yeast carrying this single mutation, at least 9 other genes are known to display a synthetic lethal effect when combined with inactivation of RVS161. These genes participate in processes ranging from cytoskeletal assembly and endocytosis, to signal transduction and lipid metabolism and identifies multiple avenues to pursuing a combination drug target strategy. A directed approach to uncovering synthetic lethal interactions with essential and nonessential drug targets is now performed where a GRACE strain or heterozygote strain is identified as displaying an enhanced sensitivity to the tested compound, not because it expresses a reduced level of activity for the drug target, but because its mutation is synthetically lethal in combination with inhibition of a second drug target. Discerning whether the compound specifically inhibits the drug target in the sensitized GRACE strain or heterozygote strain or a second target may be achieved by screening the entire GRACE or heterozygote strain sets for additional mutant strains displaying equal or greater sensitivity to the compound, followed by genetic characterization of a double mutant strain demonstrating synthetic lethality between the two mutations.

5.5.2.2 Screening for Non-antifungal Therapeutic Agents with GRACE Strains

The biochemical similarity existing between pathogenic fungi and the mammalian hosts they infect limits the range of clinically useful antimycotic compounds. However, this similarity can be exploited using a GRACE strain collection to facilitate the discovery of therapeutics that are not used as antimycotics, but are useful for treatment a wide-range of diseases, such as cancer, inflammation, etc.

In this embodiment of the invention, fungal genes that are homologous to disease-causing genes in an animal or plant, are selected and GRACE strains of this set of genes are used for identification of compounds that display potent and specific bioactivity towards the products of these genes, and therefore have potential medicinal value for the treatment of diseases. Essential and non-essential genes and the corresponding GRACE strains carrying modified allelic pairs of such genes are useful in this embodiment of the invention. It has been predicted that as many as 40% of the genes found within the *C. albicans* genome share human functional homologs. It has also been predicted that as many as 1% of human genes are involved in human diseases and therefore may serve as potential drug targets. Accordingly, many genes within the GRACE strain collection are homologs to disease-causing human genes and compounds that specifically inactivate individual members of this gene set may in fact have alternative therapeutic value. The invention provides a pluralities of GRACE strains in which the modified alleles are fungal genes that share sequence, structural and/or functional similarities to genes that are associated with one or more diseases of the animal or plant.

For example, much of the signal transduction machinery that promotes cell cycle progression and is often perturbed in a variety of cancers is conserved in fungi. Many of these genes encode for cyclins, cyclin-dependent kinases (CDK), CDK inhibitors, phosphatases, and transcription factors that are both structurally and functionally related. As a result, compounds found to display specificity towards any of these functional classes of proteins could be evaluated by secondary screens to test for potential anticancer activity. However, cytotoxic compounds identified in this way need not act on cancer causing targets to display therapeutic potential. For example the taxol family of anti-cancer compounds, which hold promise as therapeutics for breast and ovarian cancers, bind tubulin and promote microtubule assembly, thereby disrupting normal microtubule dynamics. Yeast tubulin displays similar sensitivity to taxol, suggesting that additional compounds affecting other fundamental cellular processes shared between yeast and man could similarly be identified and assessed for antitumor activity.

The phenomenon of pathogenesis extends far beyond the taxonomic borders of microbes and ultimately reflects the underlying physiology. In many ways, the phenomenon of cancer is analogous to the process of pathogenesis by an opportunistic pathogen such as *C. albicans*. Both are non-infectious diseases caused by either the body's own cells, or microbes from its natural fauna. These cells grow in a manner unchecked by the immune system and in both cases disease manifests itself by colonization of vital organs and eventual tissue damage resulting in death. Effective drug-based treatment is also elusive for both diseases primarily because the causative agent in both cases is highly related to the host.

In fact, a number of successful therapeutic drugs affecting processes unrelated to cancer have also been discovered through anti-fungal drug screening programs. One clinically-important class of compounds includes the immunosuppressant molecules rapamycin, cyclosporin A, and FK506, which inhibit conserved signal transduction components. Cyclosporin A and FK506, form distinct drug-prolyl isomerase complexes (CyPA- Cyclosporin A and FKBP12-FK506 respectively) which bind and inactivate the regulatory subunit of the calcium and calmodulin-dependent phosphatase, calcineurin. Rapamycin also complexes with FKBP12, but this drug-protein complex also binds to the TOR family of phosphatidylinositol kinases to inhibit translation and cell cycle progression. In each case, both the mechanism of drug action, and the drug targets themselves are highly conserved from yeast to humans.

The identification of *C. albicans* drug targets, and grouping the targets into essential-gene, fungal-specific, and pathogen-specific target sets provide the basis for the development of whole-cell screens for compounds that interact with and inhibit individual members of any of these targets. Therefore, similar analyses can be used to identify other sets of GRACE strains having modified allelic pairs of genes encoding drug targets with other specific common functions or attributes. For example, GRACE strain subsets can be established which comprise gene targets that are highly homologous to human genes, or gene targets that display a common biochemical function, enzymatic activity, or that are involved in carbon compound catabolism, biosynthesis, transport of molecules (transporter activity), cellular localization, signal transduction cascades, cell cycle control, cell adhesion, transcription, translation, DNA replication, etc.

5.5.2.3 Target Gene Dosage-based Whole Cell Assays

Experiments involving modulating the expression levels of the encoding gene to reveal phenotypes from which gene function may be inferred can be carried out in a pathogenic diploid fungus, such as *Candida albicans*, using the strains and methods of the present intention. The principle of drug-target-level variation in drug screening involves modulating the expression level of a drug target to identify specific drug resistance or drug sensitivity phenotypes, thereby linking a drug target to a particular compound. Often, these phenotypes are indicative of the target gene encoding the bona fide drug target of this compound. In examples where this is not the case, the candidate target gene may nonetheless provide important insight into the true target gene that is functioning either in a pathway or process related to that inhibited by the compound (e.g. producing synthetic phenotype), or instead functioning as a drug resistance mechanism associated with the identified compound.

Variation of the expression levels of the target protein is also incorporated within both drug screening and drug target identification procedures. The total, cellular expression level of a gene product in a diploid organism is modified by disrupting one allele of the gene encoding that product, thereby reducing its functional activity in half, creating a "haploinsufficient" phenotype. A heterozygous *S. cerevisiae* strain collection has been used in such a haploinsufficiency screen to link drug-based resistance and hypersensitive phenotypes to heterozygous drug targets. Nonessential genes are screened directly using a haploid deletion strain collection against a compound library for specific phenotypes or "chemotypes." However, this procedure cannot be used in a haploid organism where the target gene is an essential one.

The expression level of a given gene product is also elevated by cloning the gene into a plasmid vector that is maintained at multiple copies in the cell. Overexpression of the encoding gene is also achieved by fusing the corresponding open reading frame of the gene product to a more powerful promoter carried on a multicopy plasmid. Using these strategies, a number of overexpression screens have been successfully employed in S. cerevisiae to discover novel compounds that interact with characterized drug targets as well as to identify the protein targets bound by existing therapeutic compounds.

The GRACE strain collection replaces the surrogate use of S. cerevisiae in whole cell drug screening by providing a dramatic range in gene expression levels for drug targets directly within the pathogen (FIG. 5). In one embodiment of the invention, this is achieved using the C. albicans-adapted tetracycline promoter system to construct GRACE strains. Northern Blot analysis of 30 different GRACE strains grown under nonrepressing conditions (i.e. no tetracycline) reveals that 83% of conditionally expressed genes tested maintain an overexpression level greater than or equal to 3 fold of wild type, and 60% of all genes examined express greater than or equal to 5 times that of the wild type, C. albicans strain used for GRACE strain construction. As each GRACE strain is in fact heterozygous, this expression range is presumably doubled if compared against their respective heterozygote strain. For most GRACE strains then, this represents an elevated expression level rivaling that typically achieved in S. cerevisiae using standard 2μ-based multicopy plasmids, and an absolute level of constitutive expression comparable to that provided by the CaACT1 promoter. Therefore, the GRACE strain collections of the invention are not only useful in target validation under repressing conditions, but are also useful as a collection of strains overexpressing these same validated drug targets under, nonrepressing conditions for whole cell assay development and drug screening.

Variation in the level of expression of a target gene product in a GRACE strain is also used to explore resistance to antimycotic compounds. Resistance to existing antifungal therapeutic agents reflects both the limited number of antifungal drugs available and the alarming dependence and reliance clinicians have in prescribing them. For example, dependence on azole-based compounds such as fluconazole for the treatment of fungal infections, has dramatically undermined the clinical therapeutic value for this compound. The GRACE strain collection is used to combat fluconazole resistance by identifying gene products that interact with the cellular target of fluconazole. Such products are used to identify drug targets which, when inactivated in concert with fluconazole, provide a synergistic effect and thereby overcome resistance to fluconazole seen when this compound is used alone. This is accomplished, for example, by using the GRACE strain collection to overexpress genes that enhance drug resistance. Such genes include novel or known plasma membrane exporters including ATP-binding cassette (ABC) transporters and multidrug resistance (MDR) efflux pumps, pleiotropic drug resistance (PDR) transcription factors, and protein kinases and phosphatases. Alternatively, genes specifically displaying a differential drug sensitivity are identified by screening GRACE strains expressing reduced levels (either by haploinsufficiency or threshold expression via the tetracycline promoter) individual members of the target set. Identifying such genes provides important clues to drug resistance mechanisms that could be targeted for drug-based inactivation to enhance the efficacy of existing antifungal therapeutics.

In another aspect of the present invention, overexpression of the target gene for whole cell assay purposes is supported with promoters other than the tetracycline promoter system. (see Section 5.3.1) For example, the CaPGK1 promoter is used to overexpress C. albicans drug targets genes. In S. cerevisiae, the PGK1 promoter is known to provide strong constitutive expression in the presence of glucose. See, Guthrie, C., and G. R. Fink. 1991. Guide to yeast genetics and molecular biology. Methods Enzymol. 194:373–398. A preliminary analysis of five C. albicans genes placed under the control of the CaPGK1 promoter (CaKRE9, CaERG11, CaALG7, CaTUB1 and CaAUR1) revealed dramatic overexpression versus wild type as judged by Northern blot analysis. The level of overexpression achieved for all genes exceeds that obtained by the tetracycline promoter by 3–4 fold. Moreover, CaAUR1, which was not overexpressed significantly when constitutively expressed using the tetracycline promoter, was overexpressed 5-fold relative to wild type CaAUR1 expression levels, suggesting that the CaPGK1 promoter is useful in overexpressing genes normally not overexpressed by the tetracycline promoter.

In another aspect of the present invention, intermediate expression levels of individual drug targets within the GRACE strain collection may are engineered to provide strains tailored for the development of unique whole cell assays. In this embodiment of the invention, GRACE strains are grown in a medium containing a tetracycline concentration determined to provide only a partial repression of transcription. Under these conditions, it is possible to maintain an expression level between that of the constitutively expressed overproducing strain and that of wild type strain, as well as levels of expression lower than that of the wild-type strain. That is, it is possible to titrate the level of expression to the minimum required for cell viability. By repressing gene expression to this critical state, novel phenotypes, resembling those produced by a partial loss of function mutation (i.e. phenocopies of hypomorphic mutants) may be produced and offer additional target expression levels applicable for whole cell assay development and drug screening. Repressing expression of the remaining allele of an essential gene to the threshold level required for viability, therefore will provide a strain with enhanced sensitivity toward compounds active against this essential gene product.

In order to demonstrate the utility of target level expression in whole cell assays for drug screening, both a CaHIS3 heterozygote strain and a tetracycline promoter-regulated CaHIS3 GRACE strain were compared against a wild type (diploid) CaHIS3 strain for sensitivity towards the 3-aminotriazole (3-AT) (Example 6.3). The data derived from these experiments clearly indicate that distinct levels of target gene products synthesized within the pathogen could be directly applied in whole cell assay based drug screens to identify novel antifungal compounds active against novel drug targets validated using the GRACE method.

5.5.2.4 Uses of Tagged Strains

In still another aspect of the present invention, unique oligonucleotide sequence tags or "bar codes" are incorporated into individual mutant strains included within a heterozygous strain collection of validated targets. The presence of these sequence tags enables an alternative whole cell assay approach to drug screening. Multiple target strains may be screened simultaneously in a mixed population (rather than separately) to identify phenotypes between a particular drug target and its inhibitory agent.

Large-scale parallel analyses are performed using mixed populations of the entire bar coded heterozygous essential strain collection target set and comparing the relative representation of individual strains within a mixed population prior to and after growth in the presence of a compound. Drug-dependent depletion or overrepresentation of a unique bar-coded strain is determined by PCR-amplifying and fluorescently labeling all bar codes within the mixed population and hybridizing the resulting PCR products to an array of complementary oligonucleotides. Differential representation between bar coded strains indicates gene-specific hypersensitivity or resistance and suggests the corresponding gene product may represent the molecular target of the compound tested.

In one specific embodiment, the mutant strains are GRACE strains, and each of the GRACE strains of the set comprises a unique molecular tag which, generally, is incorporated within the cassette used to replace the first allele of the gene pair to be modified. Each molecular tag is flanked by primer sequences which are common to all members of the set being tested. Growth is carried out in repressive and non-repressive media, in the presence and absence of the compound to be tested. The relative growth of each strain is assessed by carrying out simultaneous PCR amplification of the entire collection of embedded sequence tags.

In one non-limiting aspect of the present invention, the PCR amplification is performed in an asymmetric manner with fluorescent primers and the resulting single stranded nucleic acid product hybridized to an oligonucleotide array fixed to a surface and comprises the entire corresponding set of complementary sequences. Analysis of the level of each fluorescent molecular tag sequence is then determined to estimate the relative amount of growth of GRACE strain of the set, in those media, in the presence and absence of the compound tested.

Therefore, for each GRACE strain of the set tested, there could be, in one non-limiting example of this method, four values for the level of the corresponding molecular tag found within the surviving population. They would correspond to cell growth under repressing and non-repressing conditions, both in the presence and absence of the compound being tested. Comparison of growth in the presence and absence of the test compound provides a value or "indicator" for each set of growth media; that is, an indicator derived under repressing and non-repressing conditions. Again, comparison of the two indicator values will reveal if the test compound is active against the gene product expressed by the modified allelic gene pair carried by that specific member of the GRACE set tested.

In still another aspect of the present invention, each potential drug target gene in this heterozygous tagged or bar-coded collection, may be overexpressed by subsequently introducing either the Tet promoter or another strong, constitutively expressed promoter (e.g. CaACT1, CaADH1 and CaPGK1) upstream of the remaining non-disrupted allele. These constructions allow a further increase in the dosage of the encoded target gene product of individual essential genes to be used in mixed-population drug susceptibility studies. Although overexpression may itself disrupt the normal growth rate of numerous to members of the population, reliable comparisons could still be made between mock and drug-treated mixed cultures to identify compound-specific growth differences.

In *S. cerevisiae*, the molecular drug targets of several well-characterized compounds including 3-amino-triazol, benomyl, tunicamycin and fluconazole were identified by a similar approach. In that study, bar-coded strains bearing heterozygous mutations in HIS3, TUB1, ALG7, and ERG11, (i.e. the respective drug targets to the compounds listed above) displayed significantly greater sensitivity when challenged with their respective compound than other heterozygote bar-coded strains when grown together in a mixed population.

In another aspect of the present invention, screens for antifungal compounds can be carried out using complex mixtures of compounds that comprise at least one compound active against the target strain. Tagging or bar-coding the GRACE strain collection facilitates a number of large scale analyses necessary to identify gene sets as well as evaluate and ultimately evaluate individual targets within particular gene sets. For example, mixed-population drug screening using a bar-coded GRACE strain collection effectively functions as a comprehensive whole cell assay. Minimal amounts of a complex compound library are sufficient to identify compounds that act on individual essential target genes within the collection. This is done without the need to array the collection. Also, strong predictions as to the 'richness' of any particular compound library could be made before committing to it in drug screening. It becomes possible then to assess whether, for example, a carbohydrate-based chemical library possesses greater fungicidal activity than a natural product or synthetic compound library. Particularly potent compounds within any complex library of molecules can be immediately identified and evaluated according to the priority of targets and assays available for drug screening. Alternatively, the invention provides applying this information to developing "tailored" screens, in which only those targets which were demonstrated to be inactivated in mixed population experiments by a particular compound library would be included in subsequent array-formatted screens.

Traditionally, drug discovery programs have relied on an individual or a limited set of validated drug targets. The preceding examples emphasize that such an approach is no longer necessary and that high throughput target evaluation and drug screening are now possible. However, a directed approach based on selecting individual targets may still be preferred depending on the expertise, interest, strategy, or budget of a drug discovery program.

5.5.3 Target Evaluation in an Animal Model System.

Currently, validation of an essential drug target is demonstrated by examining the effect of gene inactivation under standard laboratory conditions. Putative drug target genes deemed nonessential under standard laboratory conditions may be examined within an animal model, for example, by testing the pathogenicity of a strain homozygous for a deletion in the target gene versus wild type. However, essential drug targets are precluded from animal model studies. Therefore, the most desirable drug targets are omitted from the most pertinent conditions to their target evaluation.

In an embodiment of the invention, conditional expression, provided by the GRACE essential strain collection, overcomes this longstanding limitation to target validation within a host environment. Animal studies can be performed using mice inoculated with GRACE essential strains and examining the effect of gene inactivation by conditional expression. In a preferred embodiment of the invention, the effect on mice injected with a lethal inoculum of a GRACE essential strain could be determined depending on whether the mice were provided with an appropriate concentration of tetracycline to inactivate expression of a drug target gene. The lack of expression of a gene demonstrated to be essential under laboratory conditions can thus be correlated with prevention of a terminal *C. albicans* infection. In this type of experiment, only mice "treated" with tetracycline-supplemented water, are predicted to survive infection because inactivation of the target gene has killed the GRACE strain pathogen within the host.

In yet another embodiment of the invention, conditional expression could be achieved using a temperature-responsive promoter to regulate expression of the target gene or a temperature sensitive allele of a particular drug target, such that the genie is functional at 30° C. but inactivated within the normal body temperature of the mouse.

In the same manner as described above for essential genes, it is equally feasible to demonstrate whether nonessential genes comprising the GRACE strain collection are required for pathogenicity in a mouse model system. Included in this set are multiple genes whose null phenotype results in a reduced growth rate and may attenuate the virulence of the pathogen. Many mutants demonstrating a slow growth phenotype may represent hypomorphic mutations in otherwise essential genes (as demonstrated by alternative methods) which are simply not completely inactivated by the conditional expression method used to construct the GRACE strain. One important use of such strains is to assess whether any given essential gene doubly functions in the process of virulence. Essential genes that display substantially reduced virulence and growth rate when only partially, inactivated represent "multifactorial" drug targets for which even minimally inhibitory high specificity compounds would display therapeutic value. Collectively, all GRACE strains that fail to cause fungal infection in mice under conditions of gene inactivation by tetracycline (or alternative gene inactivation means) define a subset of genes that are required for pathogenicity, i.e., GRACE pathogenicity subset. More defined subsets of pathogenicity genes, for example those genes required for particular steps in pathogenesis (e.g. adherence or invasion) may be determined by applying the GRACE pathogenicity subset of strains to in vitro assays which measure the corresponding process. For example, examining GRACE pathogenicity strains in a buccal adhesion or macrophage assay by conditional expression of individual genes would identify those pathogenicity factors required for adherence or cell invasion respectively.

The GRACE strain collection or a desired subset thereof is also well suited for evaluating acquired resistance/suppression or distinguishing between fungicidal/fungistatic phenotypes for an inactivated drug target within an animal model system. In this embodiment of the invention, GRACE strains repressed for expression of different essential drug target genes would be inoculated into mice raised on tetracycline-supplemented water. Each of the GRACE strains would then be compared according to the frequency of death associated with the different mice populations they infected. It is expected that the majority of infected mice will remain healthy due to fungal cell death caused by tetracycline-dependent inactivation of the essential gene in the GRACE strain. However, a GRACE strain harboring a drug target more likely to develop extragenic suppressors because it is a fungistatic target rather than fungicidal one, or suppressed by an alternative physiological process active within a host environment, can be identified by the higher incidence of lethal infections detected in mice infected with this particular strain. By this method, it is possible to evaluate/rank the likelihood that individual drug target genes may develop resistance within the host environment.

5.5.4 Rational Design of Binding Compounds

Compounds identified via assays such as those described herein can be useful, for example, for inhibiting the growth of the infectious agent and/or ameliorating the symptoms of an infection. Compounds can include, but are not limited to, other cellular proteins. Binding compounds can also include, but are not limited to, peptides such as, for example, soluble peptides, comprising, for example, extracellular portions of target gene product transmembrane receptors, and members of random peptide libraries (see, e.g., Lam et al., 1991, *Nature* 354:82–84; Houghten et al., 1991, *Nature* 354:84–86) made of D- and/or L-configuration amino acids, rationally-designed antipeptide peptides, (see e.g., Hurby et al., Application of Synthetic Peptides: Antisense Peptides," In *Synthetic Peptides, A User's Guide*, W.H. Freeman, NY (1992), pp. 289–307), antibodies (including, but not limited to polyclonal, monoclonal, human, humanized, anti-idiotypic, chimeric or single chain antibodies, and FAb, F(ab')$_2$ and FAb expression library fragments, and epitope-binding fragments thereof), and small organic or inorganic molecules. In the case of receptor-type target molecules, such compounds can include organic molecules (e.g., peptidomimetics) that bind to the ECD and either mimic the activity triggered by the natural ligand (i.e., agonists); as well as peptides, antibodies or fragments thereof, and other organic compounds that mimic the ECD (or a portion thereof) and bind to a "neutralize" natural ligand.

Computer modeling and searching technologies permit identification of compounds, or the improvement of already identified compounds, that can modulate target gene expression or activity. Having identified such a compound or composition, the active sites or regions are preferably identified. In the case of compounds affecting receptor molecules, such active sites might typically be ligand binding sites, such as the interaction domains of ligand with receptor itself. The active site is identified using methods known in the art including, for example, from the amino acid sequences of peptides, from the nucleotide sequences of nucleic acids, or from study of complexes of the relevant compound or composition with its natural ligand. In the latter case, chemical or X-ray crystallographic methods are used to find the active site by finding where on the factor the complexed ligand is found.

The three-dimensional geometric structure of the active site is then preferably determined. This is done by known methods, including X-ray crystallography, which determines a complete molecular structure. Solid or liquid phase NMR is also used to determine certain intra-molecular distances within the active site and/or in the ligand binding complex. Other experimental methods of structure determination known to those of skill in the art, are also used to obtain partial or complete geometric structures. The geometric structures are measured with a complexed ligand, natural or artificial, which increases the accuracy of the active site structure determined. Methods of computer based numerical modeling are used to complete the structure (e.g., in embodiments wherein an incomplete or insufficiently accurate structure is determined) or to improve its accuracy.

Finally, having determined the structure of the active site, either experimentally, by modeling, or by a combination, candidate modulating compounds are identified by searching databases containing compounds along with information on their molecular structure. Such a search seeks compounds having structures that match the determined active site structure and that interact with the groups defining the active site. Such a search can be manual, but is preferably computer assisted. These compounds found in from this search are potential target or pathway gene product modulating compounds.

Alternatively, these methods are used to identify improved modulating compounds from an already known modulating compound or ligand. The composition of the known compound is modified and the structural effects of modification are determined using the experimental and computer modeling methods described above applied to the new composition. The altered structure is then compared to the active site structure of the compound to determine if an improved fit or interaction results. In this manner systematic variations in composition, such as by varying side groups, are quickly evaluated to obtain modified modulating compounds or ligands of improved specificity or activity.

Further experimental and computer modeling methods useful to identify modulating compounds based upon identification of the active sites of target or pathway gene or gene products and related transduction and transcription factors are apparent to those of skill in the art.

There are a number of articles that review the art of computer modeling of drugs that interact with specific proteins, including the following: Rotivinen et al., 1988, *Acta Pharmaceutical Fennica* 97:159–166; Ripka, (Jun. 16, 1988), *New Scientist* 54–57; McKinaly and Rossmann, 1989, *Annu. Rev. Pharmacol. Toxiciol.* 29:111–122; Perry and Davies, *OSAR: Quantitative Structure-Activity Relationships in Drug Design* pp. 189–193 (Alan R. Liss, Inc. 1989); Lewis and Dean, 1989 *Proc. R. Soc. Lond.* 236:125–140 and 1–162; and, with respect to a model receptor for nucleic acid components, Askew et al., 1989, *J. Am. Chem. Soc.* 111:1082–1090.

Although generally described above with reference to design and generation of compounds which could alter binding, one could also screen libraries of known compounds, including natural products or synthetic chemicals, as well as other biologically active materials, including proteins, for compounds which are inhibitors or activators.

5.6 Transcriptional Profiling
5.6.1 Analysis of Gene Expression

Gene expression profiling techniques are important tools for the identification of suitable biochemical targets, as well as for the determination of the mode of action of known compounds. Completion of the *C. albicans* genome sequence and development of nucleic acid microarrays incorporating this information, will enable genome-wide gene expression analyses to be carried out with this diploid pathogenic fungus. Therefore, the present invention provides methods for obtaining the transcriptional response profiles for both essential and virulence/pathogenicity genes of *Candida albicans*. Conditional expression of essential genes serves to delineate, for example, regulatory interactions valuable for the design of drug screening programs focused upon *C. albicans*.

In an embodiment of the present invention, the GRACE strain collection is used for the analysis of expression of essential genes within this pathogen. One particularly powerful application of such a strain collection involves the construction of a comprehensive transcriptional profile database for the entire essential gene set or a desired subset of essential genes within a pathogen. Such a database is used to compare the response profile characteristic of lead antimycotic compounds with the profile obtained with new anti-fungal compounds to distinguish those with similar from those with distinct modes of action. Matching (or even partially overlapping) the transcriptional response profiles determined after treatment of the strain with the lead compound with that obtained with a particular essential target gene under repressing conditions, is used to identity the target and possible mode of action of the drug.

Gene expression analysis of essential genes also permits the biological function and regulation of those genes to be examined within the pathogen, and this information is incorporated within a drug screening program. For example, transcriptional profiling of essential drug targets in *C. albicans* permits the identification of novel drug targets which participate in the same cellular process or pathway uncovered for the existing drug target and which could not otherwise be identified without direct experimentation within the pathogen. These include genes not only unique to the pathogen but also broad-range gene classes possessing a distinct function or subject to different regulation in the pathogen. Furthermore, pathogen-specific pathways may be uncovered and exploited for the first time.

In another aspect of the present invention, the gene expression profile of GRACE-derived strains under nonrepressing or induced conditions is established to evaluate the overexpression response profile for one or more drug targets. For example, overexpression of genes functioning in signal transduction pathways often display unregulated activation of the pathway under such conditions. Moreover, several signaling pathways have been demonstrated to function in the pathogenesis process. Transcriptional response profiles generated by overexpressing *C. albicans* GRACE strains provide information concerning the set of genes regulated by such pathways; any of which may potentially serve an essential role in pathogenesis and therefore representing promising drug targets. Furthermore, analysis of the expression profile may reveal one or more genes whose expression is critical to the subsequent expression of an entire regulatory cascade. Accordingly, these genes are particularly important targets for drug discovery and mutants carrying the corresponding modified allelic pair of genes form the basis of a mechanism-of-action based screening assays. Presently such an approach is not possible. Current drug discovery practices result in an exceedingly large number of "candidate" compounds and little understanding of their mode of action. A transcriptional response database comprising both gene shut-off and overexpression profiles generated using the GRACE strain collection offers a solution to this drug discovery bottleneck by 1) determining the transcriptional response or profile resulting from an antifungal's inhibition of a wild type strain, and 2) comparing this response to the transcriptional profiles resulting from inactivation or overexpression of drug targets comprising the GRACE strain collection.

Matching or significantly correlating transcriptional profiles resulting from both genetic alteration of a drug target and chemical/compound inhibition of wild type cells provides evidence linking the compound to its cellular drug target and suggests its mechanism of action.

Accordingly, the invention provides a method for evaluating a compound against a target gene product encoded by a nucleotide sequence comprising one of SEQ ID NO: 1 to 61, said method comprising the steps of (a) contacting wild type diploid fungal cells or control cells with the compound and generating a first transcription profile; (b) determining the transcription profile of mutant diploid fungal cells, such as a GRACE strain, which have been cultured under conditions wherein the second allele of the target gene is substantially underexpressed, not expressed or overexpressed and generating a second transcription profile for the cultured cells; and comparing the first transcription profile with the second transcription profile to identify similarities in the profiles. For comparisons, similarities of profiles can be expressed as an indicator value, and the higher the indicator value, the more desirable is the compound.

5.6.2 Identification of Secondary Targets

Methods are described herein for the identification of secondary targets. "Secondary target," as used herein, refers to a gene whose gene product exhibits the ability to interact with target gene products involved in the growth and/or survival of an organism (i.e., target essential gene products), under a set of defined conditions, or in the pathogenic mechanism of the organism, (i.e., target virulence gene products) during infection of a host.

Any method suitable for detecting protein-protein interactions can be employed for identifying secondary target gene products by identifying interactions between gene products and target gene products. Such known gene products can be cellular or extracellular proteins. Those gene products which interact with such known gene products represent secondary target gene products and the genes which encode them represent secondary targets.

Among the traditional methods employed are co-immunoprecipitation, crosslinking and co-purification through gradients or chromatographic columns. Utilizing procedures such as these allows for the identification of secondary target gene products. Once identified, a secondary target gene product is used, in conjunction with standard techniques, to identify its corresponding secondary target. For example, at least a portion of the amino acid sequence of the secondary target gene product is ascertained using techniques well known to those of skill in the art, such as via the Edman degradation technique (see, e.g., Creighton, 1983, "Proteins: Structures and Molecular Principles," W.H. Freeman & Co., N.Y., pp.34–49). The amino acid sequence obtained can be used as a guide for the generation of oligonucleotide mixtures that can be used to screen for secondary target gene sequences. Screening can be accomplished, for example, by standard hybridization or PCR techniques. Techniques for the generation of oligonucleotide mixtures and for screening are well-known. (See, e.g., Ausubel, supra., and PCR Protocols: A Guide to Methods and Applications, 1990, Innis, M. et al., eds. Academic Press, Inc., New York).

Additionally, methods are employed which result in the simultaneous identification of secondary targets which encode proteins interacting with a protein involved in the growth and/or survival of an organism under a set of defined conditions, or in the pathogenic mechanism of the organism during infection of a host. These methods include, for example, probing expression libraries with labeled primary target gene protein known or suggested to be involved in or critical to these mechanisms, using this protein in a manner similar to the well known technique of antibody probing of λgt11 phage libraries.

One method which detects protein interactions in vivo, the two-hybrid system, is described in detail for illustration purposes only and not by way of limitation. One version of this system has been described (Chien et al., 1991, Proc. Natl. Acad. Sci. USA, 88:9578–9582) and is commercially available from Clontech (Palo Alto, Calif.).

Briefly, utilizing such a system, plasmids are constructed that encode two hybrid proteins: one consists of the DNA-binding domain of a transcription activator protein fused to a known protein, in this case, a protein known to be involved in growth of the organism, or in pathogenicity, and the other consists of the activator protein's activation domain fused to an unknown protein that is encoded by a cDNA which has been recombined into this plasmid as part of a cDNA library. The plasmids are transformed into a strain of the yeast *S. cerevisiae* that contains a reporter gene (e.g., lacZ) whose regulatory region contains the transcription activator's binding sites. Either hybrid protein alone cannot activate transcription of the reporter gene, the DNA-binding domain hybrid cannot because it does not provide activation function, and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology is used to screen activation domain libraries for proteins that interact with a known "bait" gene products. By way of example, and not by way of limitation, target essential gene products and target virulence gene products are used as the bait gene products. Total genomic or cDNA sequences encoding the target essential gene product, target virulence gene product, or portions thereof, are fused to the DNA encoding an activation domain. This library and a plasmid encoding a hybrid of the bait gene product fused to the DNA-binding domain are cotransformed into a yeast reporter strain, and the resulting transformants are screened for those that express the reporter gene. For example, and not by way of limitation, the bait gene is cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait gene product are to be detected is made using methods routinely practiced in the art. According to the particular system described herein, for example, the cDNA fragments are inserted into a vector such that they are translationally fused to the activation domain of GAL4. This library is co-transformed along with the bait gene-GAL4 fusion plasmid into a yeast strain which contains a lacZ gene driven by a promoter which contains GAL4 activation sequence. A cDNA encoded protein, fused to GAL4 activation domain, that interacts with bait gene product reconstitutes an active GAL4 protein and thereby drive expression of the lacZ gene. Colonies which express lacZ are detected by their blue color in the presence of X-gal. The cDNA can then be purified from these strains, and used to produce and isolate the bait gene-interacting protein using techniques routinely practiced in the art.

Once a secondary target has been identified and isolated, it is further characterized and used in drug discovery by the methods of the invention.

5.6.3 Use of Gene Expression Arrays

To carry out profiling, gene expression arrays and microarrays can be employed. Gene expression arrays are high density arrays of DNA samples deposited at specific locations on a glass surface, silicon, nylon membrane, or the like. Such arrays are used by researchers to quantify relative gene expression under different conditions. An example of this technology is found in U.S. Pat. No. 5,807,522, which is hereby incorporated by reference.

It is possible to study the expression of substantially all of the genes in the genome of a particular microbial organism using a single array. For example, the arrays may consist of 12×24 cm nylon filters containing PCR products corresponding to ORFs from *Candida albicans*. 10 ngs of each PCR product are spotted every 1.5 mm on the filter. Single stranded labeled cDNAs are prepared for hybridization to the array (no second strand synthesis or amplification step is done) and placed in contact with the filter. Thus the labeled cDNAs are of "antisense" orientation. Quantitative analysis is done using a phosphorimager.

Hybridization of cDNA made from a sample of total cell mRNA to such an array followed by detection of binding by one or more of various techniques known to those in the art provides a signal at each location on the array to which cDNA hybridized. The intensity of the hybridization signal obtained at each location in the array thus reflects the amount of mRNA for that specific gene that was present in the sample. Comparing the results obtained for mRNA isolated from cells grown under different conditions thus allows for a comparison of the relative amount of expression of each individual gene during growth under the different conditions.

Gene expression arrays are used to analyze the total mRNA expression pattern at various time points after reduction in the level or activity of a gene product required for fungal proliferation, virulence or pathogenicity. Reduction of the level or activity of the gene product is accomplished by growing a GRACE strain under conditions in which the product of the nucleic acid linked to the regulatable promoter is rate limiting for fungal growth, survival, proliferation, virulence or pathogenicity or by contacting the cells with an agent which reduces the level or activity of the target gene product. Analysis of the expression pattern indicated by hybridization to the array provides information on other genes whose expression is influenced by reduction in the level or activity of the gene product. For example, levels of other mRNAs may be observed to increase, decrease or stay the same following reduction in the level or activity of the gene product required for growth, survival, proliferation, virulence or pathogenicity. Thus, the mRNA expression pattern observed following reduction in the level or activity of a gene product required for growth, survival, proliferation, virulence or pathogenicity identifies other nucleic acids required for growth, survival, proliferation, virulence or pathogenicity. In addition, the mRNA expression patterns observed when the fungi are exposed to candidate drug compounds or known antibiotics are compared to those observed when the level or activity of a gene product required for fungal growth, survival, proliferation, virulence or pathogenicity is reduced. If the mRNA expression pattern observed with the candidate drug compound is similar to that observed when the level of the gene product is reduced, the drug compound is a promising therapeutic candidate. Thus, the assay is useful in assisting in the selection of promising candidate drug compounds for use in drug development.

In cases where the source of nucleic acid deposited on the array and the source of the nucleic acid being hybridized to the array are from two different microorganisms, gene expression identify homologous genes in the two microorganisms.

5.7 Proteomics Assays

In another embodiment of the present invention, and in much the same way that the GRACE strain collection enables transcriptional profiling within a pathogen, a GRACE strain collection provides an invaluable resource for the analysis of the expressed protein complement of a genome. By evaluating the overall protein expression by members of a GRACE strain collection under repressing and non-repressing growth conditions, a correlation between the pattern of protein expression of a cell can be made with the non-expression or the level of expression of an essential gene. Accordingly, the invention provides a pattern of expression of a set of proteins in a GRACE strain as determined by methods well known in the art for establishing a protein expression pattern, such as two-dimensional gel electrophoresis. A pluralities of protein expression patterns will be generated for a GRACE strain when the strain is cultured under different conditions and different levels of expression of one of the modified allele.

In yet another embodiment, defined genetic mutations can be constructed to create strains exhibiting protein expression profiles comparable to those observed upon treatment of the strain with a previously uncharacterized compound. In this way, it is possible to distinguish between antimycotic compounds that act on multiple targets in a complicated manner from other potential lead compounds that act on unique fungal-specific targets and whose mode of action can be determined.

Evaluation of the full complement of proteins expressed within a cell depends upon definitive identification of all protein species detectable on two-dimensional polyacrylamide gels or by other separation techniques. However, a significant fraction of these proteins are of lower abundance and fall below the threshold level required for positive identification by peptide sequencing or mass spectrometry. Nevertheless, these "orphan" proteins are detectable using an analysis of protein expression by individual GRACE strains. Conditional expression of low abundance gene products facilitates their positive identification by comparing protein profiles of GRACE strains under repressing versus nonrepressing or overexpression conditions. In some cases, a more complex protein profile results because of changes of steady state levels for multiple proteins, which is caused indirectly by manipulating the low abundance gene in question. Overexpression of individual targets within the GRACE strain collection can also directly aid orphan protein identification by providing sufficient material for peptide sequencing or mass spectrometry.

In various embodiments, the present invention provides a method of quantitative analysis of the expressed protein complement of a diploid pathogenic fungal cell: a first protein expression profile is developed for a control diploid pathogenic fungus, which has two, unmodified alleles for the target gene. Mutants of the control strain, in which one allele of the target gene is inactivated, for example, in a GRACE strain, by insertion by or replacement with a disruption cassette, is generated. The other allele is modified such that expression of that second allele is under the control of a heterologous regulated promoter. A second protein expression profile is developed for this mutant fungus, under conditions where the second allele is substantially overexpressed as compared to the expression of the two alleles of the gene in the control strain. Similarly, if desired, a third protein expression profile is developed, under conditions where the second allele is substantially underexpressed as compared to the expression of the two alleles of the gene in the control strain. The first protein expression profile is then compared with the second expression profile, and if applicable, a third protein expression profile to identify an expressed protein detected at a higher level in the second profile, and if applicable, at a lower level in the third profile, as compared to the level in first profile.

Accordingly, the invention provides a method for evaluating a compound against a target gene product encoded by a nucleotide sequence comprising one of SEQ ID NO: 1 to 61, said method comprising the steps of (a) contacting wild type diploid fungal cells or control cells with the compound and generating a first protein expression profile; (b) determining the protein expression profile of mutant diploid fungal cells, such as a GRACE strain, which have been cultured under conditions wherein the second allele of the target gene is substantially underexpressed, not expressed or overexpressed and generating a second protein expression profile for the cultured cells; and comparing the first protein expression profile with the second protein expression profile to identify similarities in the profiles. For comparisons, similarities of profiles can be expressed as an indicator value; and the higher the indicator value, the more desirable is the compound.

5.8 Pharmaceutical Compositions and Uses thereof

Compounds including nucleic acid molecules that are identified by the methods of the invention as described herein can be administered to a subject at therapeutically effective doses to treat or prevent infections by a pathogenic organism, such as *Candida albicans*. Depending on the target, the compounds may also be useful for treatment of a non-infectious disease in a subject, such as but not limited to, cancer. A therapeutically effective dose refers to that amount of a compound (including nucleic acid molecules) sufficient to result in a healthful benefit in the treated subject. Typically, but not so limited, the compounds act by reducing the activity or level of a gene product encoded by a nucleic acid comprising a sequence selected from the group consisting of SEQ ID NO: 1 to 62. The subject to be treated can be a plant, a vertebrate, a mammal, an avian, or a human. These compounds can also be used for preventing or containing contamination of an object by *Candida albicans*, or used for preventing or inhibiting formation on a surface of a biofilm comprising *Candida albicans*. Biofilm comprising *C. albicans* are found on surfaces of medical devices, such as but not limited to surgical tools, implanted devices, catheters and stents.

5.8.1 Effective Dose

Toxicity and therapeutic efficacy of compounds can be determined by standard pharmaceutical procedures in cell cultures or experimental animal's, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/D_{50}$. Compounds which exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography. A useful dosage can range from 0.001 mg/kg body weight to 10 mg/kg body weight.

5.8.2 Formulations and Use

Pharmaceutical compositions for use in accordance with the present invention can be formulated in conventional manner using one or more physiologically acceptable carriers or excipients.

Thus, the compounds and their physiologically acceptable salts and solvents can be formulated for administration by inhalation or insufflation (either through the mouth or the nose) or oral, buccal, parenteral or rectal administration.

For oral administration, the pharmaceutical compositions can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

Preparations for oral administration can be suitably formulated to give controlled release of the active compound.

For buccal administration the compositions can take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g. gelatin for use in an inhaler or insufflator can be formulated containing a powder mix of the compound and a suitable powder base such as lactose or starch.

The compounds can be formulated for parenteral administration (i.e., intravenous or intramuscular) by injection, via, for example, bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

The compounds can also be formulated in rectal compositions such as suppositories or retention enemas, e.g., containing conventional suppository bases such as cocoa butter or other glycerides.

In addition to the formulations described previously, the compounds can also be formulated as a depot preparation.

Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

6. EXAMPLES

6.1 Construction of a GRACE Strain Containing Modified Alleles of CaKRE9

Oligonucleotide primers for PCR amplification of the SAT selectable marker used in Step 1 (i.e. gene replacement) contain 25 nucleotides complementary to the SAT disruption cassette in pRC18-ASP, and 65 nucleotides homologous to regions flanking the CaKRE9 open reading frame. FIG. 2 illustrates the 2.2 kb cakre9Δ::SAT disruption fragment produced after PCR amplification and resulting gene replacement of the first wild type CaKRE9 allele via homologous recombination following transformation. PCR conditions were as follows: 5–50 ng pRC18-ASP, 100 pmol of each primer; 200 μM dNTPs, 10 mM Tris-pH 8.3, 1.5 mM MgCl2, 50 mM KCl, 1 unit Taq DNA polymerase (Gibco). PCR amplification times were: 5 min 94° C., 1 min 54° C., 2 min 72° C., for 1 cycle; 45 sec 94° C., 45 sec 54° C., 2 min 72° C., for 3.0 cycles. Transformation was performed using the lithium acetate method adapted for *C. albicans*, by Braun and Johnson, (Braun, B. R., and A. D. Johnson (1997), Control of filament formation in *Candida albicans* by the transcriptional repressor TUP1, Science 277:105–109), with minor modifications, including shorter incubation times at 30° C. and 42° C. (1 hr and 5 min respectively) and a greater amount of material transformed (50 μg of ethanol-precipitated cakre9Δ::SAT PCR product). Transformed cells were spread onto YPD plates and incubated overnight at 30° C., providing a preincubation period for expression of SAT prior to replica plating onto YPD medium containing streptothricin (400 μg/ml). Streptothricin-resistant colonies were detected after 36 hr and cakre9Δ::SAT/CaKRE9 heterozygotes identified by PCR analysis using suitable primers which amplify both CaKRE9 and cakre9Δ::SAT alleles.

Oligonucleotide primers for PCR amplification of the conditional promoter used in Step 2 (i.e. promoter replacement) contain 25 nucleotides complementary to the CaHIS3-marked tetracycline regulated promoter cassette in pBSK-HT4 and 65 nucleotides of homologous sequence corresponding to promoter regions −270 to −205, relative to the point of transcription initiation, and nucleotides 1–65 of the CaKRE9 open reading frame. The resulting 2.2 kb PCR product was transformed into the cakre9Δ::SAT/CaKRE9 heterozygous strain produced in step 1, and His+ transformants selected on YNB agar. Bonafide CaKRE9 GRACE strains containing both a cakre9Δ::SAT allele and CaHIS3-Tet-CaKRE9 allele were determined by PCR analysis. Typically, 2 independent GRACE strains are constructed and evaluated to provide a reliable determination of the terminal phenotype of any given drug target. Terminal phenotype is that phenotype caused by the absence of the gene product of an essential gene

6.2 Phenotype Determination of the CaKRE9 Grace Strain

The terminal phenotype of the resulting GRACE strains was evaluated in three independent methods. In the first, rapid determination of the CaKRE9 GRACE strain terminal phenotype was achieved by streaking approximately 1.0× $10^6$ cells onto both a YNB plate and YNB plate containing 100 μg/ml tetracycline and comparing growth rate after 48 hr at room temperature. For essential genes, such as CaKRE9, no significant growth is detected in the presence of tetracycline. In the second approach, the essential nature of a gene may be determined by streaking CaKRE9 GRACE cells onto a casamino acid plate containing 625 μg/ml 5-fluroorotic acid (5FOA) and 100 μg/ml uridine to select for ura cells which have excised (via recombination between CaLEU2 sequence duplications created during targeted integration) the transactivator gene that is normally required for expression of the tetracycline promoter-regulated target gene. Again, whereas nonessential GRACE strains demonstrate robust growth under such conditions, essential GRACE strains fail to grow. Quantitative evaluation of the terminal phenotype associated with an essential GRACE strain is performed using $2 \times 10^3$ cells/ml of overnight culture inoculated into 5.0 ml YNB either lacking or supplemented with 100 μg/ml tetracycline and measuring optical density (O.D.$_{600}$) after 24 and 48 hr incubation at 30° C. Typically, for essential GRACE strains, no significant increase in optical density is detected after 48 hrs. Discrimination between cell death (cidal) and growth inhibitory (static) terminal phenotypes for a demonstrated essential gene is achieved by determining the percentage of viable cells (as judged by the number of colony forming units (CFU) from an equivalent of $2 \times 10^3$ washed cells at T=0) from the above tetracycline-treated cultures after 24 and 48 hours of incubation. Essential GRACE strains producing a cidal terminal phenotype are those which display a reduction in percent viable cells (i.e. $<2 \times 10^3$ CFU) following incubation under repressing conditions.

6.3 Target Level Variation in Whole Cell Assays

In order to demonstrate the utility of target level expression in whole cell assays for drug screening, both a CaHIS3 heterozygote strain and a tetracycline promoter-regulated CaHIS3 GRACE strain were compared against a wild type (diploid) CaHIS3 strain for sensitivity towards the 3-aminotriazole (3-AT) (FIG. 6). 3-AT is a competitive inhibitor of the enzyme encoded by CaHIS3, imidazoleglycerol phosphate dehydratase, and together serve as a model for a drug and drug target respectively. Overexpression, achieved by the constitutive expression level of CaHIS3 maintained by the tetracycline promoter, confers 3-AT resistance at concentrations sufficient to completely inhibit growth of both wild type and CaHIS3 heterozygote strains (FIG. 6A). The phenotype observed is consistent with that expected in light of the predicted 7.5 fold overexpression of CaHIS3 determined by Northern bolt analysis (see FIG. 5). A heterozygous CaHIS3 strain demonstrates enhanced sensitivity (i.e. haploinsufficient phenotype) to an intermediate 3-AT concentration unable to effect either wild type or tetracycline promoter-based overproducing CaHIS3 strains noticeably (FIG. 6B). A third CaHIS3 expression level evaluated for differential sensitivity to 3-AT was produced by partial repression of the GRACE CaHIS3 strain using a threshold concentration of tetracycline 0.1% that normally is used to achieve complete shut-off.

This level of CaHIS3 expression represents the minimum expression level required for viability and as predicted, demonstrates an enhanced drug sensitivity relative the heterozygous CaHIS3 strain at an intermediate 3-AT concentration (FIG. 6C). Similarly, GRACE strain-specific drug resistance and sensitivity phenotypes to fluconazole and tunicamycin have been demonstrated by increasing and decreasing the level of expression of their respective known drug targets, CaERG11 and CaALG7. Together these results demonstrate that three different levels of expression are achieved using the C. albicans GRACE strain collection, and that they exhibit the predicted drug sensitivity phenotypes between known drugs and their known drug target. Moreover, these experiments clearly indicate how distinct levels of target gene products synthesized within the pathogen could be directly applied in whole cell assay based drug screens to identify novel antifungal compounds against those novel drug targets validated using the GRACE method.

6.4 Identification of a Target Pathway

A target pathway is a genetic or biochemical pathway wherein one or more of the components of the pathway (e.g., enzymes, signaling molecules, etc) is a drug target as determined by the methods of the invention.

6.4.1. Preparation of Stocks of GRACE Strains for Assay

To provide a consistent source of cells to screen, frozen stocks of host GRACE strains are prepared using standard microbiological techniques. For example, a single clone of the microorganism can be isolated by streaking out a sample of the original stock onto an agar plate containing nutrients for cell growth and an antibiotic for which the GRACE strain contains a gene which confers resistance. After overnight growth an isolated colony is picked from the plate with a sterile needle and transferred to an appropriate liquid growth medium containing the antibiotic to which the GRACE strain is resistant. The cells are incubated under appropriate growth conditions to yield a culture in exponential growth. Cells are frozen using standard techniques.

6.4.2. Growth of GRACE Strains for Use in the Assay

Prior to performing an assay, a stock vial is removed from the freezer, rapidly thawed and a loop of culture is streaked out on an agar plate containing nutrients for cell growth and an antibiotic for which the GRACE strain contains a gene which confers resistance. After overnight growth, randomly chosen, isolated colonies are transferred from the plate (sterile inoculum loop) to a sterile tube containing medium containing the antibiotic to which the GRACE strain contains a gene which confers resistance. After vigorous mixing to form a homogeneous cell suspension, the optical density of the suspension is measured and if necessary an aliquot of the suspension is diluted into a second tube of medium plus antibiotic. The culture is then incubated until the cells reach an optical density suitable for use in the assay.

6.4.3. Selection of Medium to be Used in Assay

Two-fold dilution series of the inducer or repressor for the regulatable promoter which is linked to the gene required for the fungal proliferation, virulence or pathogenicity of the GRACE strain are generated in culture medium containing the appropriate antibiotic for which the GRACE strain contains a gene which confers resistance. Several medium are tested side by side and three to four wells are used to evaluate the effects of the inducer or repressor at each concentration in each media. Equal volumes of test media-inducer or repressor and GRACE cells are added to the wells of a 384 well microtiter plate and mixed. The cells are prepared as described above and diluted in the appropriate medium containing the test antibiotic immediately prior to addition to the microtiter plate wells. For a control, cells are also added to several wells of each medium that do not contain inducer or repressor. Cell growth is monitored continuously by incubation by monitoring the optical density of the wells. The percent inhibition of growth produced by each concentration of inducer or repressor is calculated by comparing the rates of logarithmic growth against that exhibited by cells growing in medium without inducer or repressor. The medium yielding greatest sensitivity to inducer or repressor is selected for use in the assays described below.

6.4.4. Measurement of Test Antibiotic Sensitivity in GRACE Strains in which the Level of the Target Gene Product is not Rate Limiting Two-fold dilution series of antibiotics of known mechanism of action are generated in the culture medium selected for further assay development that has been supplemented with the antibiotic used to maintain the GRACE strain. A panel of test antibiotics known to act on different pathways is tested side by side with three to four wells being used to evaluate the effect of a test antibiotic on cell growth at each concentration. Equal volumes of test antibiotic and cells are added to the wells of a 384 well microtiter plate and mixed. Cells are prepared as described above using the medium selected for assay development supplemented with the antibiotic required to maintain the GRACE strain and are diluted in identical medium immediately prior to addition to the microtiter plate wells. For a control, cells are also added to several wells that lack antibiotic, but contain the solvent used to dissolve the antibiotics. Cell growth is monitored continuously by incubation in a microtiter plate reader monitoring the optical density of the wells. The percent inhibition of growth produced by each concentration of antibiotic is calculated by comparing the rates of logarithmic growth against that exhibited by cells growing in medium without antibiotic. A plot of percent inhibition against log [antibiotic concentration] allows extrapolation of an $IC_{50}$ value for each antibiotic.

6.4.5. Measurement of Test Antibiotic Sensitivity in the GRACE Strains in which the Level of the Target Gene Product is Rate Limiting The culture medium selected for use in the assay is supplemented with inducer or repressor at concentrations shown to inhibit cell growth by a desired amount as described above, as well as the antibiotic used to maintain the GRACE strain. Two fold dilution series of the panel of test antibiotics used above are generated in each of these media. Several antibiotics are tested side by side in each medium with three to four wells being used to evaluate the effects of an antibiotic on cell growth at each concentration. Equal volumes of test antibiotic and cells are added to the wells of a 384 well microtiter plate and mixed. Cells are prepared as described above using the medium selected for use in the assay supplemented with the antibiotic required to maintain the GRACE strain. The cells are diluted 1:100 into two aliquots of identical medium containing concentrations of inducer that have been shown to inhibit cell growth by the desired amount and incubated under appropriate growth conditions. Immediately prior to addition to the microtiter plate wells, the cultures are adjusted to an appropriate optical density by dilution into warm sterile medium supplemented with identical concentrations of the inducer and antibiotic used to maintain the GRACE strain. For a control, cells are also added to several wells that contain solvent used to dissolve test antibiotics but which contain no antibiotic. Cell growth is monitored continuously by incubation under suitable growth conditions in a microtiter plate reader monitoring the optical density of the wells. The percent inhibition of growth produced by each concentration of antibiotic is calculated by comparing the rates of logarithmic growth against that exhibited by cells growing in medium without antibiotic. A plot of percent inhibition against log [antibiotic concentration] allows extrapolation of an $IC_{50}$ value for each antibiotic.

6.4.6. Determining the Specificity of the Test Antibiotics

A comparison of the $IC_{50}$s generated by antibiotics of known mechanism of action under conditions in which the level of the gene product required for fungal proliferation, virulence or pathogenicity is rate limiting or is not rate limiting allows the pathway in which a gene product required for fungal proliferation, virulence or pathogenicity lies to be identified. If cells expressing a rate limiting level of a gene product required for fungal proliferation, virulence or pathogenicity are selectively sensitive to an antibiotic acting via a particular pathway, then the gene product encoded by the gene linked to the regulatable promoter in the GRACE strain is involved in the pathway on which the antibiotic acts.

6.4.7. Identification of Pathway in which a Test Antibiotic Acts

As discussed above, the cell-based assay may also be used to determine the pathway against which a test antibiotic acts. In such an analysis, the pathways against in which the gene under the control of the regulatable promoter in each member of a panel of GRACE strains lies is identified as described above. A panel of cells, each containing a regulatable promoter which directs transcription of a proliferation, virulence or pathogenicity-required nucleic acid which lies in a known biological pathway required for fungal proliferation, virulence or pathogenicity, is contacted with a test antibiotic for which it is desired to determine the pathway on which it acts under conditions in which the gene product of the nucleic acid is rate limiting or is not rate limiting. If heightened sensitivity is observed in cells in which the gene product is rate limiting for a gene product which lies in a particular pathway but not in cells expressing rate limiting levels of gene products which lie in other pathways, then the test antibiotic acts against the pathway for which heightened sensitivity was observed.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various references are cited herein, the disclosures of which are incorporated by reference in their entireties.

What is claimed is:

1. A method for constructing a strain of diploid fungal cells in which both alleles of a gene are modified, the method comprising the steps of:
   (a) modifying a first allele of a gene in diploid fungal cells by recombination using a gene disruption cassette comprising a first nucleotide sequence encoding a first expressible selectable marker, thereby providing heterozygous diploid fungal cells in which the first allele of the gene is inactivated; and
   (b) modifying the second allele of the gene in the diploid fungal cells by recombination using a promoter replacement fragment comprising a second nucleotide sequence encoding a second expressible selectable marker and a heterologous promoter, such that expression of the second allele of the gene is regulated by the heterologous promoter
      wherein at least one of the first and the second expressible selectable marker is a drug-resistance marker,
      thereby constructing a strain of diploid fungal cells in which both alleles of a gene are modified.

2. A method of assembling a collection of diploid fungal cells each of which comprises modified alleles of a different gene, the method comprising the steps of:
   (a) modifying a first allele of a first gene in diploid fungal cells by recombination using a gene disruption cassette comprising a first nucleotide sequence encoding a first expressible selectable marker, thereby providing heterozygous diploid fungal cells in which the first allele of the gene is inactivated;
   (b) modifying a second allele of the first gene in the heterozygous diploid fungal cells by recombination using a promoter replacement fragment comprising a second nucleotide sequence encoding a second expressible selectable maker and a heterologous promoter, such that expression of the second allele of the gene is regulated by the heterologous promoter, wherein at least one of the first and the second expressible selectable marker is a drug-resistance selectable marker, thereby providing a first strain of diploid fungal cells comprising a modified allelic pair of the first gene; and
   (c) repeating steps (a) and (b) a plurality of times, wherein a different gene is modified with each repetition, thereby providing the collection of diploid fungal cells each comprising the modified alleles of a different gene.

3. The method of claim 1, wherein the diploid fungal cells are cells of fungal species selected from the group consisting of *Aspergillus fumigatus, Aspergillus niger, Aspergillus flavis, Candida albicans, Candida tropicalis, Candida parapsilopsis, Candida krusei, Cryptococcus neoformans, Coccidioides immitis, Exophalia dermatiditis, Fusarium oxysporum, Histoplasma capsulatum, Phneumocystis carinii, Trichosporon beigelii, Rhizopus arrhizus, Mucor rouxii, Rhizomucor pusillus, Absidia corymbigera, Botrytis cinerea, Erysiphe graminis, Magnaporthe grisea, Puccinia recodita, Septoria triticii, Tilletia controversa,* and *Ustilago maydis.*

4. The method of claim 1, wherein the diploid fungal cells are cells of Candida.

5. The method of claim 1, wherein the first and/or second expressible selectable marker is selected from the group consisting of CaHIS3, CaSAT1, CaBSR1, CaURA3, CaLEU2, CaTRP1, and combinations thereof.

6. The method of claim 1 or 2, wherein the method further comprises
   (c) introducing a nucleotide sequence encoding a transactivation fusion protein that is expressible in the diploid fungal cell, said transactivation fusion protein comprising a DNA binding domain and a transcription activation domain; and
wherein the heterologous promoter in the promoter replacement fragment comprises at least one copy of a nucleotide sequence which is bound by the DNA binding domain of the transactivation fusion protein, such that binding of the transactivation fusion protein increases transcription from the heterologous promoter.

7. The method of claim 1 or 2, wherein the first selectable marker in the gene disruption cassette is disposed between a first region and a second region, wherein the first region and the second region hybridize separately to non-contiguous regions of the first allele of the gene in the diploid fungal cells.

8. The method of claim 7, wherein the first selectable marker is selected from the group consisting of CaSAT1, CaBSR1, CaURA3, CaHIS3, CaLEU2, CaTRP1, and combinations thereof.

9. The method of claim 7, wherein the second selectable marker is selected from the group consisting of CaSAT1, CaBSR1, CaURA3, CaHIS3, CaLEU2, CaTRP1, and combinations thereof.

10. A method for constructing a strain of diploid fungal cells in which both alleles of a gene are modified, the method comprising the steps of:
(a) providing diploid fungal cells wherein a first allele of the gene is inactivated; and
(b) modifying a second allele of the gene in the diploid fungal cells by recombination using a promoter replacement fragment comprising a second nucleotide sequence encoding an expressible drug-resistance selectable marker and a heterologous promoter, such that expression of the second allele of the gene is regulated by the heterologous promoter, thereby constructing a strain of diploid fungal cells in which both alleles of a gene are modified.

11. A method for constructing a strain of diploid fungal cell in which both alleles of a gene are modified, the method comprising the steps of:
(a) providing diploid fungal cells wherein expression of a first allele of the gene is regulated by a heterologous promoter; and
(b) inactivating a second allele of the gene in the diploid fungal cells by recombination using a gene disruption cassette comprising a nucleotide sequence encoding an expressible drug-resistance selectable marker, thereby constructing a strain of diploid fungal cells in which both alleles of a gene are modified.

12. A strain of diploid fungal cells comprising modified alleles of a gene, wherein the first allele of the gene is inactivated by recombination using a gene disruption cassette comprising a nucleotide sequence encoding a first expressible selectable marker the second allele of the gene is modified by recombination using a promoter replacement fragment comprising a second nucleotide sequence encoding a second expressible selectable marker and a heterologous promoter such that expression of the second allele of the gene is regulated by the heterologous promoter that is operably linked to the coding region of the second allele of the gene; wherein the first modified allele of the gene in the strain is linked with the first expressible selectable marker and the second modified allele of the gene in the strain is linked with the second expressible selectable marker; and wherein at least one expressible selectable marker in the strain is a drug-resistance selectable marker.

13. A strain of diploid fungal cells according to claim 12, wherein the diploid fungal cells are cells of fungal species selected from the group consisting of *Aspergillus fumigatus, Aspergillus niger, Aspergillus flavis, Candida albicans, Candida tropicalis, Candida parapsilopsis, Candida krusei, Cryptococcus neoformans, Coccidioides immitis, Exophalia dermatiditis, Fusarium oxysporum, Histoplasma capsulatum, Phneumocystis carinii, Trichosporon beigelii, Rhizopus arrhizus, Mucor rouxii, Rhizomucor pusillus, Absidia corymbigera, Botrytis cinerea, Erysiphe graminis, Magnaporthe grisea, Puccinia recodita, Septoria triticii, Tilletia controversa,* and *Ustilago maydis.*

14. A strain of diploid fungal cells according to claim 12, wherein the diploid fungal cells are cells of Candida.

15. The diploid fungal cells of claim 12 further comprising a nucleotide sequence encoding a transactivation fusion protein that is expressible in the diploid fungal cell, said transactivation fusion protein comprising a DNA binding domain and a transcription activation domain; and wherein the heterologous promoter in the promoter replacement fragment comprises at least one copy of a nucleotide sequence which is bound by the DNA binding domain of the transactivation fusion protein, such that binding of the transactivation fusion protein increases transcription from the heterologous promoter.

16. The strain of diploid fungal cells of claim 12 or 15, wherein the gene is a gene essential for the growth and/or survival of the cells.

17. The strain of diploid fungal cells of claim 12 or 15, wherein the gene is a gene that contributes to the virulence and/or pathogenicity of the fungal cells against a host organism.

18. A strain of diploid fungal cells according to claim 17, wherein the diploid fungal cells are cells of fungal species selected from the group consisting of *Aspergillus fumigatus, Aspergillus niger, Aspergillus flavis, Candida albicans, Candida tropicalis, Candida parapsilopsis, Candida krusei, Cryptococcus neoformans, Coccidioides immitis, Exophalia dermatiditis, Fusarium oxysporum, Histoplasma capsulatum, Phneumocystis carinii, Trichosporon beigelii, Rhizopus arrhizus, Mucor rouxii, Rhizomucor pusillus, Absidia corymbigera, Botrytis cinerea, Erysiphe graminis, Magnaporthe grisea, Puccinia recodita, Septoria triticii, Tilletia controversa,* and *Ustilago maydis.*

19. A strain of diploid fungal cells according to claim 17, wherein the diploid fungal cells are cells of Candida.

20. A collection of diploid fungal strains of claim 12 each comprising the modified alleles of a different gene, wherein each gene is essential for the growth and/or survival of the cells.

21. The collection of diploid fungal strains of claim 20, wherein substantially all of the essential genes in the genome of the fungus are modified and present in the collection.

22. A collection of diploid fungal strains of claim 12 each strain comprising the modified alleles of a different gene, wherein each gene contributes to the virulence and/or pathogenicity of the cells to a host organism.

23. The collection of diploid fungal strains of claim 22, wherein substantially all of the genes in the genome of the diploid fungus that contribute to the virulence and/or pathogenicity of the fungal cells against a host organism are modified and present in the collection.

24. A collection of diploid fungal strains of claim 12 wherein each strain comprises modified alleles of a different gene, and wherein substantially all the different genes in the genome of the fungus are modified and represented in the collection.

25. The collection of diploid fungal strains according to claim 24, wherein the diploid fungal cells are cells of fungal species selected from the group consisting of *Aspergillus fumigatus, Aspergillus niger, Aspergillus flavis, Candida albicans, Candida tropicalis, Candida parapsilopsis, Candida krusei, Cryptococcus neoformans, Coccidioides immitis, Exophalia dermatiditis, Fusarium oxysporun, His-*

*toplasma capsulatum, Phneumocystis carinii, Trichosporon beigelii, Rhizopus arrhizus, Mucor rouxii, Rhizomucor pusillus, Absidia corymbigera, Botrytis cinerea, Erysiphe graminis, Magnaporthe grisea, Puccinia recodita, Septoria triticii, Tilletia controversa*, and *Ustilago maydis*.

26. The collection of diploid fungal strains according to claim 24, wherein the diploid fungal cells are cells of Candida.

27. The collection of diploid fungal strains of claim 24, wherein the essential genes present in the collection all share a characteristic selected from the group consisting of: similar biological activity, similar intracellular localization, structural homology, sequence homology, cidal terminal phenotype, static terminal phenotype, sequence homology to human genes, and exclusivity with respect to the organism.

28. The collection of claim 24, 20, 22, or 27 wherein the cells of each strain further comprise a molecular tag of about 20 nucleotides, the sequence of which is unique to each strain.

29. The collection of claim 28, wherein the molecular tag is disposed within the gene disruption cassette.

* * * * *

SEQUENCE LISTING

<160> NUMBER OF SEQ ID NOS: 490

<210> SEQ ID NO 1
<211> LENGTH: 660
<212> TYPE: DNA
<213> ORGANISM: Candida albicans

<400> SEQUENCE: 1

```
atggatatcg aaactgccgc ttgcttttca atagcattta tagccacacc gatcctcata      60
gtattggtaa gattgctatt cattcttcca tcattaagac ttccaacctc cgtaaagaaa     120
aagaaaaagc tcattcagga atgccaactt tcaatcttgc ttggttcagg tggccatact     180
ggggagatga tgagaattat atctaaactt gacatgggaa aagtttctcg tacatggata     240
tacacttcgg gcgacaatgc gtccttagca aaggcacagg attatgaaag gaaatcgggt     300
acatccctgc agtacatacc aatcccaaga gcacggacag tgggccaatc atatatactg     360
agcattccaa ccaccatata ctcattcttg ttttctgcaa ttgcgatgct caaacacaga     420
ccagcagtga tacttttgaa cggcccaggt acttgtgttc ccgtggcata cattttgttt     480
ctctataaac tccttggatt atgcaataca aagataattt atattgaaag tttagctaga     540
gtgaacaagt tgagtctcag tggattacta ttattaccga tcagcgatcg atttattgtc     600
cagtgggaaa gtttatatca acagtatagc cgtgtcgagt attatggtat attgatatag     660
```

<210> SEQ ID NO 2
<211> LENGTH: 504
<212> TYPE: DNA
<213> ORGANISM: Candida albicans

<400> SEQUENCE: 2

```
atgggaacca acaacaaaac tgtcactaat aagtcaaaca agagaatcca agggaaacga      60
catatcaaac atagtcccaa cttgactccc tttaatgaaa cacaaaatgc ttcgaatttt     120
ttaatcaaat catcaactcc ttatatatca gctatcaaac aaattaccaa gaaattgaat     180
aaattctcca aatcaaagaa tagtcacacg ataaataaat ttcaaaatga acaatacaag     240
```

```
acgatcaaat atatagccgt caaaggtatg ggtaaaacaa ttgaaaaagt ggcgagtatt    300
ggtactcatt tccaaaagga ttataaagtt gatgtgttga cagggtctac tacagtgtta    360
gatgagtttg caccaattga atcaaaccaa gagcctgata atgagaacaa gagtgatgat    420
gatgacgacg acgacgacga aactatatat aagaaacgta ctgtgagttc tatagagatt    480
agaatatgga taaaacgaga ttaa                                            504
```

<210> SEQ ID NO 3
<211> LENGTH: 1485
<212> TYPE: DNA
<213> ORGANISM: Candida albicans

<400> SEQUENCE: 3

```
atgctagcaa ggcttttgaa acttgcaata gtagttgcag caatagcggc aatcacaccc     60
aataacccaa tacgtacact gatttcattt ggtgtatag gttacgtggc aaccttactg    120 gtataccga aagttagccc aagttttgtc aagatcgggc tcaagggaa agatttatct    180 aaaccaccac cggtgtcaga aatacccgaa acaatggggc tagtggcgtc aactacatat    240
atgtttctta tgtttggtct tatcccattt attttttca aataccttgt ttcttttgga    300
tcaatgtcta acgacgaggt gataactaaa aattacttgt ctcaatatca atcgcttgcc    360
gacaacaggt tattccccca caataagttg gcagaatact tgagtgcctt gttgtgttta    420
cagagtacca cattgttggg attactagac gacttgtttg atatcaggtg gcgtcacaag    480 ttttttcttac ctgcagttgc atcattgccc ttattgattg tatactacgt cgactttagt    540
gtaacttcag tcgtgatccc caagtttgtc actgaattcc ctggaggcta cgttctaatt    600
aatactataa attttttttat aaagtatagt aaccatttgg tcacaagtat cactgggctt    660
tcatttagaa ctttacaaac agactatgtt gttcctgaca gttcaccaaa gttgattgat    720
ttgggaattt tctactacgt atacatgtcg gctatttcaa ttttctcacc gaattcaatc    780
aatattcttg caggcgttaa cggtttggag gttggacaat cattagtttt agcagccata    840 ttttaatta atgatttctg ctatctttttt tcaccgggaa tatcacaagc agctcatgat    900
tcacacatgt tttctgttgt atttataatt ccttttgtcg gagtgtcatt ggctttattg    960
caatacaact ggtccctgc aagagtattt gttggtgata cgtattgtta tttcagtggc   1020
atggtatttg ctattgttgg tattataggt catttttcca aaactctttt gatatttttg   1080
ttacctcaaa taatcaattt tgtgtattca gttcctcagt tgtttcacat cttgccctgt   1140
ccaagacaca gattacccag atttagtatt gaggatggtt tgatgcatcc cagttttgca   1200
gaattaaaga aagcaagccg tctaaacttg gcgattttag aaactctcag ttttttcaag   1260
ctcataaaag tggaaagggg ttccaaactg aatcagattt ttagattttc caatatgacc   1320
ataatcaatc ttacgttggt gtgggtagga cctttacgag aagaccaatt atgtatatct   1380
attttggtcg ttcaatttgt tattggcgtg acaatgatag ttgttagaca taccattgga   1440
ccatggttat ttggatacga taatttatca tggggtgtaa aataa                   1485
```

<210> SEQ ID NO 4
<211> LENGTH: 843
<212> TYPE: DNA
<213> ORGANISM: Candida albicans

<400> SEQUENCE: 4

```
atggcaccta cagaaataaa agggttttat gtgttgcctc tcaagttaac aggtaccaaa     60
tcaatacatt acatatactt taagaaacat gaactgaaag gcactgccaa tgataacaga    120
```

```
tcattattta tttgcaactt gccaatatcc acagacttgt ctactatcaa aaaattttt    180 cagaaagtag ccataggatc tacaatagaa ctgtttataa actcactttt gactgattat    240
cctgaagaca tatggattaa tttaaccaaa ctaacatcgg acttggattt ggtcgacgct    300
gttgatgaac aagcaagcaa gttacctaaa actgtggta ttgtggcatt tatagataag    360
gcctctttca cactagcctt taactcattg aaaaagttat catctagcct tactgagtgt    420
gaatggccaa tacaacagtt cacatcaaat tattatttga acaatatca gaagcagata    480 ctagacccaa atagcttaac agaagaagtc tcccaagcgt taatagattt tgacaaagca    540
gaacaacagt caattgaaga attacaactg caaagaaatt tggttgatga agatgggttc    600
actttggtgg tcggtagtca cagaaaaacc aaagcgggta ttttgggcaa acagaaatta    660
gcatcaaccg ttggagttgt gaaagctcaa tccaagatga agagtaagga aaaacaagac    720
ttttatagat ttcaattgag gcaacgaaag aaggaagaaa tgaatgagtt gttgaataag    780
ttcaaattgg atcaagaaaa ggtcagaatg atgaaggaaa agaaaagatt tagaccttat    840
tag                                                                 843

<210> SEQ ID NO 5
<211> LENGTH: 1116
<212> TYPE: DNA
<213> ORGANISM: Candida albicans

<400> SEQUENCE: 5
atgacggata cacaaccaag gaaaatacgt aaagtgtcta ctcaagagca aattgaagat     60
tatgaaaaac ttcgtcaaag aatcaaaaat catttcaaag atgcccttaa aggtaaagga    120
tcatctatgc tgttgcatta tattgatgaa ataaccgaat tatataaaag agttcaatca    180
caaaaagtta agatacaag agttcattta gaagattctg aagttttcaa agaagcatcg    240
gattttgctg ccttgaatgc acgtaatata gttttcgatg attcgggaat tgctcttgat    300
gataaagaat ttttcaaatg tttaagaaga tttgctgtta ctgatcctag tcttttaagt    360
cgtaatgata taggagataa tgatggcaat aatagtaacg atgaggatga cgtagatgat    420
gatgatctgg atgaagaaga agaagctatt actgatgaat acacattcaa taaaacaaat    480 tggttaaaaac ttgggattct ttatcatcaa gttagtaaaa aatccatact ggtagatttt    540
ttaaatggac ccttaaaagc agaaaagagg aaaatagttc gagcaagaaa tgttgatgat    600
actaaaggta gcgggatggc gaaaactgct cgacaagttc aagctagtga tatttctggt    660
aatcaagaac aaaatactgc caacatggtt aaatcagttt atcaaacata tattgaaaaa    720
tatgatggta atggtgttaa tttattaaa tttttatata acccctagatc atttggtcaa    780 agtgtggaga atttattta caccagtttc ctcgttaaag atggtcgatt gaaattatat    840
gtgaataatg acgggatgcc ttgtattcaa agagtgagta gtgatgaaat cagagaggct    900
caattggaaa gcaataaaat ttttgctagt catcatattg ctagttttaa ttacaaagca    960 tggaagaat atactcaatt atataacata agagaagcat ttttgggaca tcgtgatgaa   1020
cctgaagacc aaatgccacc tgaagatata attgattata atgacgagga acctataccg   1080
tcatctcaaa gaagggatct gaattcatcg gattaa                             1116

<210> SEQ ID NO 6
<211> LENGTH: 1695
<212> TYPE: DNA
<213> ORGANISM: Candida albicans
```

-continued

```
<400> SEQUENCE: 6
atggctagaa gaaatagaaa taaaactgtg aatgaagaag agattgaact tgatgaagtt      60
gactcattta atgccaatag agaaaagata ttattagatg aagctggaga atatggacgt     120
gatgatcaat cggaggaaga tgattctgaa gaggaagtca tgcaggtaga agaagatagt     180
gaggatgacg aagaagatca agaagacgaa gaagaggagg aggaggagga agaaggggaa     240
gaagaagaag aagaggagga aaaaggatgg ggaggaagac agaattatta tggaggagat     300
gatctaagtg atgatgaaga tgctaaacaa atgacagaag aagcattgag acaacagaag     360
aaacatttac aagaattagc aatggatgat tatttggatg atgagatgat ggaagattgg     420
cagaaaaagg ctgattcata tgacaataaa gacacactgt catcaaccca gcagcagcaa     480
caacaacaac ttatcattga aagcaatagt tctattgcga atttggaaga tagtgataaa     540
ttgaaattac ttcaacaatc attccctgaa tttattccat tattaaaaga attgaacagt     600
ttgaaagtta aattagaaga tttacaaaaa ttagaggata aaaacaaatg catagagaca     660
aagattgtag cattatcagc atatttggga gctatatcgt catattttgc catatttgtt     720
gataatttga acaatgaaga atcgtttgta tcgatgaaag ataatccaat catggaaact     780
atattgagtt ctagagagat ttggagacaa gcaaatgaat tacctgatga tattaaattg     840
gatgatgtta aagtacatgt ttccgatgtt gtttcttcta gtgatattga tgacgaagac     900
aattttgttg acgccaaaga agaacaatct gaagatgaag agatatcaga agaagaagtt     960
tctcaagacg aagacgaaga tcaatcagat gatcttgaca ttgatgctaa ttcagaaaga    1020
attatcaagc atgttttcca aaaacacggt gatgatttca cagaagctga tatcgaagat    1080
attgatatgg aggataaaca acgtcgtaaa aagacattaa gattctacac ttccaaaatt    1140
gataaagctg cagctaaaaa agaccaatca tattctggtg atatagatgt tccatataaa    1200
gaaagattgt ttgaaagaca acagcgtcta cttgaagaag caagaaaacg aggattacaa    1260
aaacaagatg atgaaaatat atcggataat gacaatgaca atgacggtgt caatgatgat    1320
gaaggatttg aacaaggtga tgattattac gaatcaataa acaacataa attaaataag    1380 aaacaatcca gaaaatcagc tcatgaagct gcggttaaag ctgctaagga aggtaaattg    1440
gcagaattac aagaagctgt tggtcaagat ggtaaaagag caattaatta tcaaattctt    1500
aagaacaaag gtcttacgcc tcacagaaag aaggaatata gaaactccag agtcaaaaag    1560
agaaaacaat acgaaaaggc acaaaagaaa cttaaatctg ttagacaagt ctatgatgct    1620
aataatagag gtccatatga aggtgaaaag acaggtatca gaaagggtt atcaaaatca    1680 gttaaattgg tgtaa                                                      1695

<210> SEQ ID NO 7
<211> LENGTH: 1521
<212> TYPE: DNA
<213> ORGANISM: Candida albicans

<400> SEQUENCE: 7
atgtcgaaag tggaagagca tgagagtgtg aataacctaa agaggaaatt ccccctcgttg     60 gcaaaaccca gacagccgtt gaaagagacg aattctaaca tcccatcacc acataagcgt    120
gctaaaatag aatccccaag taacaacaa tcaacgcaac aacctcaaca gcaaccacaa    180
ccacaaccac aacccaaacc acaacaagaa aaggctactc acaagccaaa gaaatcatca    240
catcagctga aaaataatga caagcttgct ggggatgaaa tgcacgaatg caacagtct    300 tggagaagaa ttatgaagag ttcaattgtt tactttgaag gagaccagca actgctagaa    360
```

-continued

```
tatagaaaag cacataaact attgagacta gttgggtgca aagtgactcc tttttatgac      420
aacaatgtaa ctataattat ttctaaacgt ccgtacgaca gtaagacaga atattctccg      480
catgacattt tcagcaacgt aagcaaagcg agtatcaagg tttggaacta tgataaagtg      540
tttcgttttt taaacatctc tggtattaat atccagaccg gggtagacga gcttgcggtt      600
aacacacata caattcttcc tccatcgttg accaataaca atgagaaacc cgatttatac      660
aatttgttga agaagaaaa atatatggc tcaaccgata gagatcctaa tgcaaagcgt       720
gatgatttgc attatttggg caagaactat ttatatgttt atgacttgac ccagacagta      780
cggcccattg ccattcgtga atggagtgac cattatccgg ttatgcagtt atcattggac      840
ggcaagtgtc catttataga agatcccaca gaccagaacc tggagagaaa acggcttaaa      900
cgattaagaa agttcgaagc taatcaagcg catcgtgagg ctttgagatt ggccacatat      960
aagatgatca atggcatttc aatgagtgtg catggtttca ctgccacgag caccagcaca     1020
gacaaggttg atgaagagga ggattccact gtcaaggaac ctagtgaaga tccaagattc     1080
cgtcaaccac ttaacagaaa ctcttcttgc atgcagtcaa aggcatttga ggcaatggct     1140
tctggatata atggggcatc taatgcggtt cagccctcaa tggattctaa cttgaatagt     1200
gctgctgcaa tggctggcgg gaacggttta ggtccagcat tatcacaggt tccttccaaa     1260
cagttaaata acttgaagag aaggattttg atgaagaaga aaacgacaaa cacaactgaa     1320
aagaaagata aggaacatgc ctcgggttat tgtgagaact gtcgtgttaa gtatactaat     1380
tttgatgaac atattatgac caataggcat cgcaattttg cttgtgatga tagaaatttt     1440
caagatatag atgagttaat tgctagtttg agggaaagaa aaagtttggg aaatgtcatc     1500
tcaaacggcg attatgtata g                                              1521
```

<210> SEQ ID NO 8
<211> LENGTH: 1599
<212> TYPE: DNA
<213> ORGANISM: Candida albicans

<400> SEQUENCE: 8

```
atgaaaccaa tggtgaccac actttataat ggcaagctcc cgttggcgtt ggctgaccct       60
aatgggatat tcacatggtg tccgcatttg aatttgatat ttatagccat gaacaagatg      120
tcgatctggt gttatcgaat gaatggcgag cgaatatatt ccatcaacaa caaatcgatt      180
gtcaaacata tagcgtttta ccgcgagtac ttttgtttgt cggggacaga caacttgatc      240
aagatatatg attctaataa tgggcagttg gtgaaggtgt tgccgcagga gtttgatggt      300
gttgagtttg ttgggtggaa tgggactgag tatagagtgc tggtgtcgat gccgatggtt      360
tatgacttgg ttagtgagtt ggattatttg gtggtgagcg acggcaagag gatggcgatt      420
acgtttaacc agtgttgac ggtggactgg gagtgtgaga tgagtgtgca ccagcaacta      480
aatagggact tgttcaacca agtgtatgtc gctggggata agctagttag ggtcaggttt      540
gttgtcgaca accagaagtt gtatacggag cagattatca aggtgtgtca gcttatcagt      600
ttgctagagt atggggagca gcacatacaa aagattaagg ggttggtggt accgttttg      660 ctggcgatgg accggtatat gtcgaatttg aatctgagt gtggtgattt ggcgcagtac      720
ttgtctgatc ttgttgttag taatatcatt cctgaatttt ctaaagattt ctggctaaac      780
cagtatggcg agcgtggaca caagaggatg gttaaattgg caggggtgta tgagagttgt      840
gtaaaggata cgtaccagca cttggtgagc accacagaga gggtgatttc gattgtgggg      900
```

-continued

| | |
|---|---|
| gagttgattg gtgtgtccaa atgggagcaa ggattgttgg cgacaacgga gttggaggcc | 960 |
| ttgttagacc aggcgaagct gcagctaaag ttttattata ggtttatttg ggatttgcag | 1020 |
| actgagcggc agcaggtaag tcagttttg gtatggacaa agagtattat cgatatgcta | 1080 |
| aatgatcagg agtgtgatat tgcctattcg actacagatg tgttgtgctt tatcaatggg | 1140 |
| gcacttacga agagtgtgat gctaaagtat tttgatatca aggggtacc agaaacgcca | 1200 |
| atgacgaata ttagtatgga tttgactaca attggtgagt accaccggtc gagggttgag | 1260 |
| gtggaggtgt tgcagaacat ttcattaccg tctgtctata caaacctaaa actagcccaa | 1320 |
| tgggaggagg tggtggttac ctatcaacaa ggtaacgccc ttgttattgc taatgtggat | 1380 |
| ggtgtggtgt caacggtgca agatgtgtac tcctatcaac acaggcagac cgatttggtg | 1440 |
| gcgttgacga gcaagtcgtt gttgattatt gattcgtcgt cgtgtatacc gattgcactt | 1500 |
| ccggaaacac tgttccaacc gaccaagcta attcttaacc aagagtatgg tgtgttgctc | 1560 |
| gactcaacga gacagcacta ttcaatattt aggatgtag | 1599 |

<210> SEQ ID NO 9
<211> LENGTH: 966
<212> TYPE: DNA
<213> ORGANISM: Candida albicans

<400> SEQUENCE: 9

| | |
|---|---|
| atgggtaaaa gaagagtaga tgaagaatct gattcagata ttgatgttag ttcacccgat | 60 |
| tcagaaactg aattagaaag cacgcaccac caccaccacc accaagaagg tgctactaca | 120 |
| attcaagaaa ctgttgatgt tgattttgat ttttttgatt taaatcctca aattgatttc | 180 |
| catgctacta agaatttttt aagacaatta tttggtgatg ataatggaga atttaattta | 240 |
| agtgaaatag ccgatttaat tttacgagaa aattccgtgg ggacatcaat taaaactgaa | 300 |
| ggaatggaaa gtgatccatt tgcaatttta agtgtaatta atttaactaa taatttaaat | 360 |
| gtggccgtga ttaaacaatt gattgaatat attttaaata aaaccaaatc taaaactgaa | 420 |
| ttcaatatta ttttgaaaaa attgttaacc aatcagaacg atactactag atataggaaa | 480 |
| tttaaaactg gattaataat tagtgaaaga tttataaata tgccagttga agtgattcca | 540 |
| ccaatgtata aaatgctttt acaagaaatg gaaaaagctg aagatgctca tgaaaattay | 600 |
| gaatttgatt attttttaat tatatcaaga gtttatcaat tagttgatcc agtggaaaga | 660 |
| gaagatgaag atcacgaaaa agaatccaat cgtaaaaaga gaacaagaa taagaagaag | 720 |
| aaattggcta ataatgaacc aaaaccaata gaaatggatt atttccatct tgaagatcaa | 780 |
| attttggaat yaaatactca atttaaagga atatttgaat ataataatga aaataaacaa | 840 |
| gaaacagatt caagaagagt atttactgaa tatggtattg atcctaaatt aagtttaatc | 900 |
| ttaattgata aggataattt agctaaatca gtcattgaaa tggaacaaca attcccacct | 960 |
| ccataa | 966 |

<210> SEQ ID NO 10
<211> LENGTH: 801
<212> TYPE: DNA
<213> ORGANISM: Candida albicans

<400> SEQUENCE: 10

| | |
|---|---|
| atggcaggat ttaaaaagaa tagagaaatt ttaactggag gtaagaaata tatccaacaa | 60 |
| aaacaaaaga aacatttagt tgatgaagtt gtatttgata agaatcccg tcatgaatat | 120 |
| ttaactggtt tccataaacg taaattacaa cgacagaaaa aagctcaaga atttcataaa | 180 |

```
gaacaagaac ggttagctaa aattgaagaa cgtaaacaat taaaacaaga acgtgaacga      240
gatttacaaa atcaattaca acaatttaag aaaactgctc aagaaattgc tgccataaat      300
aatgatattg gatttgatca atcagatgac aataatgaca atgataatga agaatggagt      360
ggattccaag aagatgaaga aggagaagga gaagaagtaa ctgatgaaga tgacgaagat      420
aaggaaaaac ctttgaaggg gattttacat catactgaaa tatataaaca agatccatca      480
ttatcaaata ttactaataa tggtgccata atagatgatg aaacaacagt agtggtagaa      540
tcattagata atccaaatgc tgttgatact gaagaaaaac ttcaacaatt ggctaaatta      600
aataatgtta atcttgataa atctgatcaa attttagaaa aatctattga acgagctaaa      660
aattatgctg tgatatgtgg agttgctaaa cctaatccaa tcaaacaaaa gaagaagaaa      720
ttcagatatt taacaaaagc agaacgtaga gaaaatgttc gtaaagagaa atcaaaatca      780
aaatcaaagg gcaagaagta a                                                801

<210> SEQ ID NO 11
<211> LENGTH: 999
<212> TYPE: DNA
<213> ORGANISM: Candida albicans

<400> SEQUENCE: 11
atgtcaacag tatattataa aaaactagat aaattacaat tccagattta cgacttgttc       60
agctctttgc ttcaattatc cgaagctgaa gatgaatctg tctacaaggc cagctttgat      120
gacaccgtgc aagaaattga tctgttattg attgctttca aagacctcct tagacttttta     180 cgacccaaag ataaatccaa caaattcgat acatacgaat tgaaatttca ttctttgaag      240
cacaaattgc gtgagttgca agtatttatt aatgatcaac aacaagacaa gttgcatgaa      300
tataggataa agcatttcca tctacaagat ctgcctgtgg ataccatcaa taacgaattt      360
gctcgagacc aattatttgc tgatcgttcc actaagaaga ctaagaaaga aatggaagcg      420
tctataaatc aacaaattgt cagccaaaat aaacaaataa caaatccttt gcaagcatcg      480
agacaattgt tatcagcagg tatattgcag agtgaattga acattgacaa cattgatcag      540
caaaccaagg atttatacaa gttaaatgaa ggatttatcc aattcaacga tttgttaaat      600
agatctaaga aaattgtcaa gtttattgaa agcaagata aagctgaccg tcaacgtata      660
tatttgagta tggggttctt catactttgt tgttcttggg tggtttatag aagaatttta      720
aggcgaccac ttaaaatatt cttgtggtcc tttttcaaga tctttaatat tttcaactgg      780
ttgcttggag gtggtagaag taaagggtta tctgcaagtg atatgatagt ttcatctgtg      840
attgctgcta ccacggaaat cgtcgactat gaggcaacga aaactttgtt ggataccttg      900
tcgaacgctg tggactctaa tacagcgatt gatacacttg caatggtagt ggaatctctt      960
acgacatcat caatggaaca tattgtagat gaactatag                             999

<210> SEQ ID NO 12
<211> LENGTH: 822
<212> TYPE: DNA
<213> ORGANISM: Candida albicans

<400> SEQUENCE: 12
atgacagact catcagctac cgggttctcc aagcaccaag aatcagcaat tgtatcagat       60
tcagaaggag atgcaattga ttccgaattg cacatgagtg ccaacccacc tttattgaga      120
agatcatctt cattattctc cttatcctcg aaagatgact tgccaaaacc cgattccaaa      180
```

```
gaatatttga aattcattga cgataataga catttcagta tgattagaaa cttgcacatg    240
gccgacttta tcactttatt aaatgggttt agtgggtttt attctattat ttcatgttta    300
agatacactt taactggaca aactcattac gtacaaagag cacatttttt catattgttg    360
gggttatttt tcgattttt tgatggtaga gttgcaagat taagaaataa atcatcatta    420
atgggacaag agttagattc attagctgat ttggtatcat ttggggtatc tccagcaaca    480
attgcctttg ctattggatt cagaacaact gttgatgtgt tattttttggc cttttgggtt    540 ttatgtggat taacaagatt ggctagattt aatatctccg tcaataacat tcctaaagat    600
aaacacggta atcacaata ttttgaggga ttgccaattc caacaaattt gttttgggtc    660
ggattcatgg ctttattggt gtacaaagat tggattcatg acaacttacc atttggaata    720
gttttccaag atactctgtt tgaattccat ttggtcacaa taggatttgt tttacaaggg    780
tgtgctgaaa tctcaaaatc tttaaaaatt cctaaaccat ag                      822

<210> SEQ ID NO 13
<211> LENGTH: 3528
<212> TYPE: DNA
<213> ORGANISM: Candida albicans

<400> SEQUENCE: 13
atggcaaaac ggaagttaga ggaaaatgat atttctacca ttgaagatga tgaattcaag     60
tccttttccg atcgagatga acaaatagat gaactcagca acggccatgc aaagcataga    120
gagaacaacg cacaggagag tgatgaccac agtgcaagtg aagacgacga tgatgaagac    180
gatgaggaag agggagaaaa atcagtacaa ccacctaata agaaacaaaa aaagcagctt    240
tctgcacaag atgtccaagt agccagagag acagctgaat tattcaaatc taatatattt    300
aaacttcaga ttgacgaact aatgaaagaa gtgaaagtaa agaaagctca cgaagaaaaa    360
attgagaaag tattgcaccg tttgcatgat ttgattaaac aagtgccacc tgtgaaaaat    420
ctaactttac aacaagcaga acaacatttt aatcccaaga aattagtcat cccatttcca    480
gatcccaaac caacaaaagt aaactataga ttttcttatt tgccactggg agatctttct    540
ttggttgggt cgtacggatt aaaaacagct attaaccaac cacatggaca aagtatcgaa    600
gtagcactaa ctatgcctaa agaattgttt caaccaaaag attatttaaa ttatagagca    660
ttatataaaa agtcatttta tttggcatac ttgggtgaga atttaatcca tttgtcgaaa    720
aagaataatt tgccgatcaa ggtgtcgtat caattcttca atgacgatgt attgaacccc    780
gtcttaaaaa tagagagtat ccaaactgaa atcccgaag atttgacttt tactaaaact    840
aaaattgcta ttaatttaat agtagcattc ccatttggtg tttttgactc gaaaaagcta    900
cttcctgata aaaactgtat ccgtgtgcaa tcagacaccg agactttgcc acctactcca    960
ttgtacaatt ctagcgtgtt atcacaaaca tcctacgact attatttaaa gtatttatat   1020
accaccaaaa aatcaacaga agcattcaaa gatgcatgta tgttggggaa actttggttg   1080
cagcaaagag ggttcaattc gtctctcaat aatgggggt tcggtcattt tgaatttgct   1140
attttaatga gcgcgttgtt gaatggaggt ggattaaacg gtaacaagat attgttgcat   1200
ggattttcct cataccaatt attcaaaggt accatcaagt acttggctac aatggatcta   1260 aatgagggt atttatcttt ctcgtcttta attggagaaa acattgcatc gaaatacaaa   1320
tcagatgggt ttaatgttcc taccatattc gataaaaaca ccaaattaaa catcttatgg   1380
aaaatgacca agagttctta caagagtctt caattgcaag cacaacagac tttggaatta   1440
ttgaatgacg ttgtaaaaga cagatttgac gccattttgc ttcaaaagtc tgattttgat   1500
```

```
ccgatgagat acgatattgt cttcaagtta tcagcacctg aagagttgta cgattctttt    1560
ggtccattgg aaaagatagc atacattact tttgataatt atttcaagag cagattattt    1620
gcaattttaa caaagcatt aggtgaaaga atagaactga ttgttattaa aaatgaacac    1680
ccttcaaaca catttgccat ccacaagaga aagccatcac acacaagctc aacctttgtt    1740
attggtttgc aattaaatcc agaagaatgt gacaaattag taaccaaagg tccgaataat    1800
gaagataagg atgctggtat caaattcaga tccttttggg ggaacaaagc atctttgaga    1860
agattcaaag atggatctat ccaacattgt gttgtttgga atattaaaga tcaagagcca    1920
gtggtaatga acattatcaa atatgcttta gatactcact tgcaatctga aatatcacaa    1980
catttggcat ctctgatcag ttattttgat aagaaattgc cagttccatt attgccttca    2040
gcaacaaatc aagtgatcac atctttaagc agctttactg ctttaaggaa ctcatttgaa    2100
aacttgagta aagtcttgac aaatttagag ttaccactta gtgtgaagac agttttgccc    2160
gcatcatctg gtttaagata cacgtcagta ttacagccag tgccatttgc agcatccaac    2220
cctgatttct ggaactactg tgtattacaa tttgagactt caacaagatg gccagatgaa    2280
ctaagtgcat tggagaaaac aaagacggca ttttattga aaattagcga agaattagct    2340
gaaacagaat acaattcatt tatttcaaaa gatgaatcag tacctttcaa tgaaaatata    2400
actttgttga acattttaac tccagaaggt tacggattca gaatcagagc ttttacagaa    2460
cgtgacgaat tgttatactt gagagcagta tcaaacgcag acaaacagaa agcgttagtc    2520
caagatgttt atttgaaatt caatgaaaaa tatatgggct cagtaaagca caccagatct    2580
gtaacacaac ttgcacaaca ttttcacttt tattccaccaa ctgtcagatt ttttaaacaa    2640
tggttggatt cccaattact tttgcaacat ttcagcgaag aattggtgga actcattgct    2700
ttgaaaccat tgttgaccc agctccatac tcaattcccc attctgttga aaatggattt    2760
ttacaaattt tgaatttcct agccagctgg aattggaaag aagacccatt agttcttgac    2820
ttagttaaaa gttctgctga tgatgatatc aaattaagtg ataagttaac tatacaagca    2880
catagaatca ttgagcaaaa ttttgaaaaa attagaaaaa cagacccttc aggtattaaa    2940
acacagtatt ttattggatc gaaagatgac ccttctggaa tattatggtc tcataattta    3000
actttaccaa tttctactag gctaactgca ttgtctcgag ctgccatcca gttgcttaga    3060
aaggaaggca ttactgaaac caacttggat ttgatattta ctccagcatt acaggattat    3120
gacttcacta ttaaggtcaa ggcgaataac gttactactt cttcaggtat tttaccacca    3180
aacacattta aaaacttaat tcaaccatta acttcattcc ctgatgatat aactacaaaa    3240
tacgatttgg ttcaaggtta tgttgatgaa ttgaataaaa aatttggtaa tgctattata    3300
ttttcaagta aaaagttcac aggtttatgc aagaacaatg aaaacgtcat tggtggtatt    3360
tttgttccta ccaacttgac caaaaagaaa ttcagggtca atttgggcat taacgttaaa    3420
cctttggatg ataaaggaga tgaagttata atcaacacca gctccatata cgatgaaatt    3480
gaattacttg gtggagattt aattaaagca ttcgataaac gtaaataa    3528
```

<210> SEQ ID NO 14
<211> LENGTH: 2280
<212> TYPE: DNA
<213> ORGANISM: Candida albicans

<400> SEQUENCE: 14

```
atggctaaaa aagaagagc tgctatattg cctaccaaca ttattctttt acagaatgtt    60
```

-continued

```
gtgcgtagag atcctgaatc ataccatgaa gaattcttac agcaattttc ccattatgaa      120
tctcttcgag atttgtattt aattaatccg accggtgtgg atgctaactc tacaaccgag      180
tttattgatt taataggatt tatgtcagct gtatgtaact gctatccaaa agagactgct      240
aattttccta atgaattaaa agagatatta ttaaacaacc atcgtgattt aactcccgag      300
ttacgtgaga aaattatcca atgcttgaca atgttaagaa ataaagacat tatatctgct      360
gaaatgttga tacagacaat attcccatta ttaattacta gtaatgctgg acagcaagtg      420
aagcaaatga gaaacaaat ttattccact ttgattgcat tgttgaaatc tgttaataca       480
ggcacaaaga accagaaatt gaatagatca actcaggcat tattgtttaa tttattggag      540
caaagggaca atcaagggtt atgggctact aaattgacaa gggaattatg gagaagaggt      600
atttgggatg attccagaac cgttgaaata atgactcagg ctgctttaca tccagatgtc      660
aaagttgccg tcgcaggtgc taggttcttt ttaggggctg acaaggaaag ggaagacaat      720
tttgaagaga gttcagatga agatggtttc gatatgaatg agttgagaca taaaatgcaa      780
attaataaaa agacatccaa aagaggtaag aagttggagc aagctgtaaa agccatgaaa      840
aagaagaata ttccaaaaca ttcagcaact tacttgaact tttctgccat tcatttatta      900
agagatcccc aaggctttgc ggaacaaatg tttgataatc atttgagcag taaaaattcc      960
aataaatttg atttggatca aaagattttg tttatgaatt tgatttcaag attaattggt     1020
acacataaac ttattgtgtt gggtgtatat acatttttct gaaatatct cactccaaag       1080 caaagaaatg tcactcaaat tatggctgcc gctgctcaag catcacacga tttggtacca     1140
ccagagtcaa ttcaaattgt cgtgagaaaa attgctgacg aattcgttag tgatggtgtt     1200
gctgcagaag tagcatcagc aggtataaac accattagag aaatattagc cagagcccca     1260
ttggctatcg acgctccgtt attgcaagat ttgactgaat ataagggttc aaaatctaaa     1320
gcagtgatga tggcagcaag atcattgatt tctttgtatc gtgaagtagc acccgaaatg     1380
ttgttgaaaa aagatcgtgg taaggtggct agcatagaat tgcagaaggg tgagaaaagt     1440
ggcttgcctc aatatggggt tgagaataac gttacttcaa ttccaggtat tgaattatta     1500
gctaaatgga agaaagagca aggcttagat agtagagagg acgaagaaga tgatgccaat     1560
tgggaggttg acgatgatga agatgcaagt gatatcgaag gtgattggat agatgttgaa     1620
tctgacaaag agatcaatat ttcagatagt gatgatgaca atgaagagga tgagcaagaa     1680
caagaaccag agaaaggtaa agcaaaaata ggtaaagcag aagataacga agatgaagtt     1740
tctgatttag agttgtcatc agatgacgac gatgaagata gcgaggagaa caaagatgga     1800
aaagcagttg ctgattcaga agaacctcct accaagaagc aaaagatcag aaacgaaaat     1860
gcagatatca atgccgaaca agccatgaat gagttacttt ccagcagaat attgacacca     1920
gctgatttcg ccaaattaga agaattaagg acagaagcag gtgtatcgaa gattatgggt     1980
atttcaaatg aagaagctgt tgattctact tccttggtag gtaaagtcaa atacaaacaa     2040
ttgcgagaag aaagaattgc tcatgctaaa gagggtaagg aagatcgtga gaagtttggc     2100
tctagaaaag gtaagagaga tactcctcat tctactacca ataaggaaaa ggcaagaaag     2160
aagaattttg tcatgatgat tcataaaaaa gctgttcaag gtaaacagaa actttcttta     2220
cgtgatagac aaagggtttt aagagcacat ataacgaagc aaaagaagaa agggttatag     2280
```

<210> SEQ ID NO 15
<211> LENGTH: 1587
<212> TYPE: DNA
<213> ORGANISM: Candida albicans -continued

```
<400> SEQUENCE: 15
atggctattg ttgaaactgt cattgatggc attaattatt ttttgtccct tagtgttaca      60
caacagatca gtatattatt aggggttcca tttgtttaca acttagtatg gcaatattta     120
tattcattaa gaaaagatag agctccatta gtgttttatt ggattccttg gtttggttct     180
gcagcttcat atggtcaaca accttatgaa tttttcgaat catgtcgtca aaagtatggt     240
gatgtatttt catttatgtt attagggaaa attatgacgg tttatttagg tccaaaaggt     300
catgaatttg ttttcaatgc taaattatct gatgtttctg ctgaagaagc ttataagcat     360
ttaactactc cagttttcgg taaaggggtt atttatgatt gtccaaattc tagattaatg     420
gaacaaaaaa aatttgctaa atttgctttg actactgatt catttaaaag atatgttcct     480
aagattagag aagaaatttt gaattatttt gttactgatg aaagtttcaa attgaaagaa     540
aaaactcatg gggttgccaa tgttatgaaa actcaaccag aaattactat tttcactgct     600
tcaagatctt tatttggtga tgaaatgaga agaattttg accgttcatt tgctcaacta     660
tattctgatt tagataaagg ttttacccct attaattttg ttttccctaa tttacccttta     720
cctcattatt ggagacgtga tgctgctcaa aagaaaatct ctgctactta tatgaaagaa     780
attaaactga aagagaacg tggtgatatt gatccaaatc gtgatttaat tgattcctta     840
ttgattcatt caacttataa agatggtgtg aaaatgactg atcaagaaat tgctaatctt     900
ttaattggta ttcttatggg tggtcaacat acttctgctt ctacttctgc ttggttcttg     960
ttacatttag gtgaaaaacc tcatttacaa gatgttattt atcaagaagt tgttgaattg    1020
ttgaaagaaa aaggtggtga tttgaatgat ttgacttatg aagatttaca aaaattacca    1080
tcagtcaata acactattaa ggaaactctt agaatgcata tgccattaca ttctattttt    1140
agaaaagtta ctaacccatt aagaatccct gaaccaatt atattgttcc aaaaggtcat    1200
tatgttttag tttctccagg ttatgctcat actagtgaaa gatattttga taaccctgaa    1260
gattttgatc caactagatg ggatactgct gctgccaaag ctaattctgt ttcatttaac    1320
tcttctgatg aagttgatta tgggtttggg aaagtttcta aagggtttc ttcaccttat    1380
ttaccatttg gtggtggtag acatagatgt attggggaac aatttgctta tgttcaattg    1440
ggaaccattt taactacttt tgtttataac ttaagatgga ctattgatgg ttataaagtg    1500
cctgaccctg attatagttc aatggtggtt ttacctactg aaccagcaga atcatttgg    1560
gaaaaaagag aaacttgtat gttttaa                                        1587

<210> SEQ ID NO 16
<211> LENGTH: 1302
<212> TYPE: DNA
<213> ORGANISM: Candida albicans

<400> SEQUENCE: 16
atgcctagtc atgttaccaa tgtatataac gatattgatg atggaatgct tctactgtct      60
ttgtcattaa atgagagatc aaatgataga agaggtttgg aaattgaaga ggtatacgac     120
tccagttttg atgatcctat ggatattgat gatacaggtg agttgtcgaa tcacatggat     180
atagatgata caactttga gatagatcac gtcgcaagtg ataactacgc aaataaaaga     240
gaagacgaca atgatactaa taacgaagaa gaacgtcggg aagatggggtt gttttcttta     300
ctatctccta cgttgatggg ggcaaaactt gcaatcaaaa agccattact attaatgcct     360
ccgcccactg tttcggaaca atctgattca aaaactgaaa gtgcatcttc tgttgattat     420
```

-continued

```
gaatatgaca ctagttcatt caaacccatg aaaagcaatg gattgattac acgaaaaacc 480
aatagcagta catttcagcc aagcaatata gactcgtttt tattccacag tgatggaatt 540
tcactgggtc agctgttagg tggttatcaa gatttacata gcaattatca acagccagtg 600
actatccata atcatcacca tcactattac tattacaata aagatgaatc agtaccgtcg 660
ccaccttcta acaacaattt acaatcactt gaacacgagc aaagaaattt gcagatgcaa 720
caatacaaac aacaattaga ggagcatcag ttatatttac aagagtataa acgtaacaat 780
caaatacttt taccttctcc ttggcagcat aatatatctc caatagaaag agtcccctat 840
ctattgatgt cctacttaca aatgttgata aatttcattg cttcgttata tggtgtatat 900
cttgtttatt gtttatttcg aacgataaat acagacatca aaaccaaaat agaggaacaa 960
caaacgaatt tgattatcag cattgagtcc tgtcgtcgat cgtactatca gaatggctgt 1020
gacgacaagg ataacttggt cccattattg gtatccaaat gtcaaaaatt tgagaaatgt 1080
atgaaacagg acccttacaa attaagtaac gtttccatta tgagtgctga gattattgga 1140
atgatcatca actcattaat tgaaccttta agtttaaaat tttacttgtt tatgttagca 1200
```

```
tttatattaa ttatatttgc atgcaatttt acgtttggat atattcgagc caaggcatat 1260
tatggtggta gtatgaagta tagtcttgac aaactcgatt ag 1302
```

<210> SEQ ID NO 17
<211> LENGTH: 792
<212> TYPE: DNA
<213> ORGANISM: Candida albicans

<400> SEQUENCE: 17

```
atggaatcat tagacgaaat acagtggaaa tctccagagt tcatacaaga gagagggctt 60
aataccaata atgtgttgga gtacttttct ttatcgccat tctacgaccg aacatcgaac 120
```

```
aaccaagtgt tgatgatgca atttcagtac cagcagatac aaataccacc tggtgtatca 180
ttccaccaat actttcagtc gcggttgagt gagatgaccg gaatagagtt tgttattgcg 240
tatactaaag agcctgattt ttggataatc agaaaacaaa aacgacagga cccccagaac 300
actgtgacac tacaagatta ctacataata ggagcaaatg tttaccaggc accgaggatc 360
tacgatgtgt tgtcatcgag actccttgca agcgttttgt cgataaagaa ctccactgac 420
ctattaaatg acatgacaag ctatcatatc tcagacgggg gtcattccta tatcaactcc 480
atacacggca gctcctcgaa accatcacag tcatcggctg tctcgaagcc actgtcaaca 540
aatactggaa cgaatgcaac tactaccccg atcactttga cgactccact gggtgctact 600
gtcccgagca cagtgtccaa tggaatctca accagcacag agattgccag cggagtgttt 660
gatacgttgt tgaatgatgt ggtgatgaat gatgatcact tgtacatcga tgagattcca 720
ttatatggtg agggaagcac acttgagaga cttgggttaa agggaaataa agatgcgggt 780
ttgagtctat ga 792
```

<210> SEQ ID NO 18
<211> LENGTH: 1092
<212> TYPE: DNA
<213> ORGANISM: Candida albicans

<400> SEQUENCE: 18

```
atgtcctctt ctcaagcacg aaaagctctt caagatgtaa ttcccaatta tttaggtgaa 60
tttacaccca agctactaga ttatatcaat tccttatatc aacttagttt aaggaaacaa 120
gcaatactac caaataaatc ggaaattgca cgttttcatc tatgtgctgt tgttattgtt 180
```

-continued

```
gaaaaatata aacaatctttt tgaattgccg actcctgatg tgtcaagaat accaacacaa    240
cctaaagtag cagcaaagtt actagacact tttcgtgagt tgatagaaca aatctccgca    300
gccagcacac ctgtatcaag tcccaaaaag gtgaaaccac catcccaaag tccactgaca    360
ccaacaaaga gtcgaacaag caaagagaat tgaaatcag gatcccctttt aaaacgtctt    420 cgagcagaaa tgttgcaaga agaccaggtc aatggtaact cccccgatgg ccaacttaag    480
gatgtagact ctccctttaa cccaaagaaa agaaaagaat ccaaggcagg caccccaaca    540
cataaagttt ataaatacga taagaaaacac gttctgatag cagatttat agcattctgc     600 aacactttcc ttataccagg tgatatcacc gccaagatgg tgggcacatt tttaacgcat    660
caacacaagt ttcttaaaaa aagtgattgg tcattggcct gtggtatggt ttatgcggca    720
tacattcgga taaataacag attacttgca caactggttg gcaccaagtc agagttcacg    780
aaacaattgt tacaatacca aagggaggt ttactgctag gggccatgca atcttggtgt    840
ggtataatcg aagaatggat tcaagatgaa ccatggattc aagagataga aaagacttac    900
gcttatggta gcaaaacagc tgaagaaacc agaaattctt ttgaaagaaa agcgaaaata    960
ggtgaaggct gggacctaat ggaacagttt ggggctatga ttcatggcga gacaatttcg   1020
ttatcaagtc accaagaaga gtattacaaa aactggcgta aagaggcttt agagaaatgt   1080
gaccaactat aa                                                       1092
```

<210> SEQ ID NO 19
<211> LENGTH: 2616
<212> TYPE: DNA
<213> ORGANISM: Candida albicans

<400> SEQUENCE: 19

```
atgaatacgt tttcatcccc accaaacgtg atacgagagt ataatgactc cacatatcag    60
ctgccattga attcacaatt ccaccaatca ccattcttgc agactcaatc accagactat   120
gtcagcttac gagaagaaga ggatgataat aatgataaga atctagacat catgtcatca   180
tgtatagtag attcagtaat atataaatca caaaaaattg ctggcccact attgagtcaa   240
atatccaatt tgaacattca gcaagcattg attatacgag aactactatt cacattgtta   300
ggacatgaag gtcattacat tcaatatagt aaacgttatg atccaacctc acaaatcagc   360
cgaattgaag gaccggacta aagattgca aagaacttgg atataagtct aaagttatc    420 accaagaaat tggtcaaatt tggaaagttt tacagtgggt aaaatcgtt tattcaagta    480 tttgataata acaaatttgg gaaaattgtg caaaagtttt gctctgaagt gagaaagttt   540
ttatcgagtt atcaacaagt gctaataaat gttgagcatg agttcaagtt taataagaat   600
tttaatttga atatgttgga tctgctctta catcaagaaa tatcgaatga aatgactcat   660
ttatatcaaa ttggaataga gattagtcgg ataacggaag aaagacagaa aatgtcacag   720
gcggaaatca tgggtaattt tgaaccaacg actttggcaa acacaagtat gaatgggatc   780
aattccgagc ctaatttgta ttatggcaaa tttgattgtt gtaaaggtgg actattactt    840
caagttattc aggaaagaat ggtttattat aaaggtgatc ctacatctct agattttta    900 actcaacttt tgatattgt tagttcggat tatattggga tgttgaatca gtggcttttg    960
gaaggtgtaa taaatgatcc gtttgatgag ttcatgatta gagaaaaacg agtgccagac   1020
tcctttatgg aaatatttca agtaaaagt gaatactatt ggaacgaatt gtttttaatt   1080
aaaatagatg gattactcaa tcaatttcag aattcaacca tacagtcgaa aattctcaat   1140
```

| | |
|---|---|
| acagggaaat acttgaatat attcaaacga tgcacagggt tacacaattt tgaatcatta | 1200 |
| aaagaaaaat tgacaactat aactagtttg gcagctcctg atttggaact taagattgat | 1260 |
| gagtttatc atagagcaaa caaaatgttg atgaagttgc ttttcgatgg atataatttc | 1320 |
| ccaagtgtgg tgaacatatt tcaaagatta tttcttttcg ctgattcttt tcaaatcgac | 1380 |
| aactttattg atagtacttt cagtgaattg aaacgtggga aactcaaaat ctcagtttcc | 1440 |
| agactacaaa agcaatatga tgatatattc aaagaaaaaa ttgaaaataa agttggagta | 1500 |
| cggccaagtg tatacgacgt gttgaagaaa atcagaagc tatcggtaac gtcggagtca | 1560 |
| ttgtataaag tggttgagga attaatgaaa agaacctgg attatttgat ttcagacaac | 1620 |
| aatttgcgtg ggatatttca tcgagtggcg tcgttaagag acgacctgcg acttaccata | 1680 |
| ctgagtactg ctgattctgc aactgaaaac gtgaaggatg aaccaacaat aactagtgtt | 1740 |
| gatcttacta taccgttgcc attcccatta aatttggttt tgaatcaaca attgtcatac | 1800 |
| caatatgaaa taatgtttaa attattaatt aatatcaagt ttatttcaaa atataatagt | 1860 |
| tccaattggc aagagatgaa ttattctaaa atttggacaa attcgcattt caactcgagt | 1920 |
| gtgaaaaaat ggatattgcg ttgcagagta ttgcattcga gaatttgcag ttttattcat | 1980 |
| gaacttgaaa actatatagt gcatgatgtc attgaacata attttgagga aatcaaaaat | 2040 |
| ttgattcaca ccacggctac taacttggcg acaagtgaac taggatcaga cataaatgat | 2100 |
| gaaggtgata atatattcaa tggatctttg attcgaggta catttaacaa taattcgatc | 2160 |
| tttgattcca aagttcacaa acataggaca acaacatacg tggaaggtat ttcaacagtt | 2220 |
| gaacaattaa ttcaaaaatt tctagattat tcaagtactt tgttgaatga ttcgttgctt | 2280 |
| acccgtgaag agtcgttgcg tcaattacgt aaaatgttgg acttcatttt ccatttcaat | 2340 |
| aattacattg tccaagtaaa gaaagttttg gtattgttga accatgaatt gttcaatgag | 2400 |
| tattctaagg aattccctac caagtttgaa aagccaatgg atcaagagct gatagataaa | 2460 |
| agatttgcaa acttgagtga tacttttcta atgcagtacg aaaagtttgg tgaaaatctt | 2520 |
| gttacatttt tagccaccat taaacaggtt ggtgaaagag aaaaccaagg attattggaa | 2580 |
| ttaagtaata gactagaact ttgtttccca gaatag | 2616 |

<210> SEQ ID NO 20
<211> LENGTH: 1911
<212> TYPE: DNA
<213> ORGANISM: Candida albicans

<400> SEQUENCE: 20

| | |
|---|---|
| atgtcaggac caataatttg ttcaaagttt gatcagtcgg ggaactattt ggcaaccggt | 60 |
| atggttgctc ttgattccca tcaagtcaaa gttcaatcca taacctcatc tcaagcatcg | 120 |
| ttaaatacat cattcacctt ggaaaaatca aacaaattag taaatttagc atggatccca | 180 |
| tcagattcaa tacaattgtt agctctttgt ttatccaagg gaagtatttt gatatattct | 240 |
| cctcaaacaa atgaaattgt tctggaattg attagttctg caaatgtctc aattttggat | 300 |
| ttccattact caacaactac tagaactggg tggtcttgcg atatagaagg aaacgtgtac | 360 |
| gaatgggatt tgaattctta tttgttagtt gattctttca agtcaatga atacattgaa | 420 |
| tctgttgatt cgataaatag aatatctaca gtaatgttca attctcaacc gcatttattg | 480 |
| cttggttcaa acgcagtcta ccttttcaat attaaacaaa gagaacttgt gaaaactttc | 540 |
| ccaggtcata ttcaaccagt aaactcgata acagcttaa acaacgacat gtttttaacg | 600 |
| agtgctaaag gtgaccgatt tgtcaatttg tatcaacttg ataaaactgc cacaaaggca | 660 |

-continued

| | |
|---|---|
| gtctttgtgg gtctgtcctc agtatcgagc ttatcagttt ctataaaaga cgacaagtca | 720 |
| gttttggtga ttattaatga agaaggtgat attgagattt tcaacaatcc attagcagac | 780 |
| gccaaatctc aagtttccac tcctgtaccg aaaaagaaaa gaaagcaagt tggtgtttct | 840 |
| tcaagatcat tcaatgcatc aattaaatta tctcgtccag aaccagaaat caaaagccca | 900 |
| caagatacac atttatttat caatgctgtt tccactgaag ataacttgat cacattcact | 960 |
| tggttggaaa attcaactat cccattcttt gacaccctta aatggattga tgaaaccggt | 1020 |
| tctttgcttc ttgaatcagc caaagtattg ctaaaatcta aaccaaattt aaaagtcact | 1080 |
| caacatttga ctaacggtca cgatgtggcc gcaccaaaac tttatactga agggcacacc | 1140 |
| attgtgagtg atggcagtaa tatcagagat ttggaatttc aagaccatca agaggatgaa | 1200 |
| gaggacactg aggaatcttt ggctgaaaaa ttagagcgat tggcaatgga tcaaacttca | 1260 |
| caacaaaaat caagaagaag gaaactagaa gaggcaagaa gtggtgtatc tttatcgatt | 1320 |
| gtattaaccc aatctttgaa aaataatgat caagctttat tagaaaccgt gttatcgaat | 1380 |
| cgtgatccta tcactattca aaacacaatc agtagattag acccttattc atgtgtcaca | 1440 |
| tttttggata aattgagtga aagattcaa cgtcaaccaa caagatttga tcaagtgagt | 1500 |
| ttttggctca aatggatcct tgtgattcat ggtccaacta tggcttcttt gccaaacttg | 1560 |
| agcatcaaac tatctagctt acgtgcagta ttaaataaga aagctgaaga attgccaaga | 1620 |
| ttattagaat tacaaggtag attgaaatta atggatgatt ctgctgcatt gagaaatgag | 1680 |
| tttagtgctg aagaaatagc tgaagatctt gaagaacgaa gtgatattga atacaatgaa | 1740 |
| gaaattgatg atgcaaagta tgttggggtg atcagcgacg acgaaagcat ggatgatgtg | 1800 |
| gatgactttg atgatcttga cgatgaagag aagaggaag aggaagaaga ggaagatggt | 1860 |
| attcctgatg ctgcaaattt agatgataga gaagattctg atcttgaata a | 1911 |

<210> SEQ ID NO 21
<211> LENGTH: 984
<212> TYPE: DNA
<213> ORGANISM: Candida albicans

<400> SEQUENCE: 21

| | |
|---|---|
| atgatgtcca caaattttca atggccagga accaataaga atgataatac agaagtatct | 60 |
| gttgaaacac catcaagcac agatcctcat gtccctcgct atccatttac cgcaatgtca | 120 |
| catgcgacgg caagcacaac tatgaagaaa agaaagcgag acgattttga tggcgacaag | 180 |
| tcaacaacta tcaccatgaa taccacgaca acacgtaaat acatacaatc atctttagga | 240 |
| tcttccaagt tcaagaaggc caaaacaccc aaaatcagtg ggcaaccttt gccactacct | 300 |
| agattgattg aatcattaga caaatccaat ttacaaaaac ttgtgcaaga tttaataact | 360 |
| gttcatcctg aattacaatc tacattaatt aaaatttccc ctagaccttc tattcaagat | 420 |
| tccattcaac ttttacaaga caaatttgat atgattatat ctcatttacc ttacaaatgt | 480 |
| gatgttgaaa gtgattattc atatttaaga atcaaacctc atttgcaaga atttttatca | 540 |
| tcagtgtctg atttttatttt aaattattta cccccattag aaacaaatat gacacattct | 600 |
| ttgcaatttt tacacgaaac taccaaatta gtgtataact tgcctaatt cactaatcaa | 660 |
| gaatttcaat acaccaagtc ctctgcatta gaacagattg ctaactgttg gttgattgta | 720 |
| ttaagccagg atgaagaaaa agaaggaaac actgatgtgg tgaaagttat acaagaattg | 780 |
| gaattgttag agaaattaca cgaacataat gagatatcat tcaataagtt tgaaaaagtt | 840 |

```
gttgattatt gtaaagacaa gttagaacaa catgaattaa tcatgaataa taacgaagcc      900
ggctctggtg ttacatcgtc aataagtgac ttgatcactg tggattattc taaatactct      960
atagccaata caacttctat atag                                             984

<210> SEQ ID NO 22
<211> LENGTH: 1659
<212> TYPE: DNA
<213> ORGANISM: Candida albicans

<400> SEQUENCE: 22
atgcccacaa acatacaagg agaagaagtg ataatacctc ctaaagatga agaggaaata       60
ttgttggaga aattagtatt tggagatgcc gcagggtttg aaaataactt gaaaaaatta      120
gacaacttat atgattattc agacgaggag gaagagatag atgaaaaagg tctggagaaa      180
gaatcagata ttgaagattt acaagatgaa gacctatttt ttattgatga tgggaataat      240
gaagagcata gcagtggtga tgatatggaa atagatcaat ccgaagacga agaagaaggc      300
gaagatcaag attcagataa tgcatgggag gatagcgatg atgaaaaggt taacatttcc      360
ttattaacat cagataaatt gaaaaagttg agaaaaacac cacaggattc agttatatct      420
ggcaagtcat atattattag attgagatcc caatttgaaa agatataccc aagaccacaa      480
tggatagagg atatagaaaa caacagcgat gatgagaaag acttgtcgga cgaagacaag      540
gttgacgatg aagaaggaca gtaggatca acaactgcat tattaaacat cttgtcaagt      600
actgaaaaat tcataaacac aaagcaattg aaactaattg ctgcaaataa aatatctata      660
accagattga aagatgcaaa ctataaaaga atcggtaaat cgggtatcca gaccattgac      720
ttccatccaa actatcctat tttgctaaca ggtgggtttg ataagactat tagaatttac      780
caaattgacg ggaaatcaaa aactttatc acttcatact ttttgaaaaa ctgtccaata      840
atggaagcca gcttctatcc acaattgtca ggcgatgaca ccaaaaccag caacttaata      900
tatgctagtg gtcgaagaag atatatgaat aaaatcaact tgtcaactgg ggaaatagag      960
aaaatcagtc gattatatgg gcatgagcag acacaaaagt cgtttgagta cttcaaaata     1020
agtcctcaag gtaaatacat tggattgact ggtaacaacg gatggtgtaa cttattaaat     1080
gctcaaaccg gcattgggt tcatgggttc aaaattgaag gaacaatagt cgactttgca     1140
tttgccaacg atgaatcatt tattatgatt gtaaattctg ctggtgaagt atgggagttt     1200
gctctcgaag ggaaaatcac ttccaaaacc ccaaacaaaa tcattcgcag atggtacgat     1260
gatggtggtg tcggaatcac aaagctacaa attggtggta aaaacaatcg ttgggtcgcc     1320
attggtaaca ataacgggat agtcaatatc tacgatcgat cagtatttgc tcctgaaaca     1380
acacacccaa aaccaatcaa aacagtggaa aacttaatca catcaatatc ttcgttggtt     1440
ttcaaccccg acggacaatt attatgtatt gcatcaagag ctaaacgtga tgctttgagg     1500
ttggtgcact accaagtggg ttcagtgtat agtaactggc caaccagtgg cacacctta      1560 ggtaaggtta ccagtattgc attctcgcca aataacgaga tgttggccat tgggaaccaa     1620
accggtaagg tcactttgtg gcgtttgaac cattattaa                            1659

<210> SEQ ID NO 23
<211> LENGTH: 2148
<212> TYPE: DNA
<213> ORGANISM: Candida albicans

<400> SEQUENCE: 23
atgtcattga aaccatttac ggggttatta ttctgttgca ctgggttgga atcaaccaca       60
```

-continued

```
cgacgagagg tggtagagaa gatagagacc cttgggggaa ttcattattc agatttaatg    120
acagatgtca attatcttat agtgggagat agagacactg agaaatatcg attttgcatt    180
aaatatagac ctgacattat ttttattgat gctgattcca ttttcacaat tcataaacat    240
tggataaacg gtgaagatga gaacctggac ttactacgaa tagagaaata taggttggca    300
atatttgctc aattgaatgc atgtttctca agaatagaaa tgtcaacctc tcaaattgat    360
catttagtca acacagtaaa atttcgacag cgtactaata cttcacctga gtattttcgc    420
ccgaaaaatt tattcaaatt gtttgttgat aatggtggta ttgccaaaga atctttactg    480
tgtcatcaga attttattat cacagctgat ccacgaggaa cacgatacaa caaggctctt    540
gaatggaatg tacccgcaat acatcctatt tggattgtcg atagtgtatt gagaggtgct    600
gcattagatt ggaaagatta tattttaaac aacaatccaa atgattgcta tgatcgaggg    660
tgtgatgttt ggcccgaagt tttcgattgt caggagaaac aaaaacagaa atctcaacaa    720
caacctaaaa gattagagtc tactgaacca gaagtaaaac ggaaaatcac caataataaa    780
accaatgctg atatttggaa ctcgattatg gatcatacca agaagcaaac aaagcaattg    840
attcacgaca agacctggga tgatgatgag gaggaggaag ataatgatga tgatggtgat    900
acccaaacca aaaatgaaaa gaataatcaa tacaagaata ttactacaat tcctaaagat    960
ggaaagcaaa aaccagaatt aaacggtaaa atacataatt tggatcttaa attggtgtca   1020
gaaagtaaag aaaactcacc aaatgtcctg gaaagtcaat tattttttagg gttcaactat   1080
tatacggtcg gttttgactc tcgtgagttt gacttgttat ccaaagcaat tgaaaactac   1140
ctgggagaaa tatctaatga tccaaatgac gattctatca ctcatgtggt tattcctgca   1200
aaaaagggggt atcagtcaat gctggttttg aaagtcttac ctgctgacct taagctgaga   1260
attgcaaatg ggtttgtcaa aattgttact gagttttttca ttgaaagatg tatgttttac   1320
aagaaaatta tattagatag atggggacag ccaatgaagg gattagtgcc gtctaaaaaa   1380
tcatttaaaa tttgtaccac tgggtttact ggcattgaat tattgcatat tgaaaaacta   1440
atacggtcgt ttaactttga atattgtgaa acattgtcag aacagagaga tctactaatt   1500
ctcaacgtaa atttatttaa aaaaagcttg atgaattcgc caaagttatt tcaatacaaa   1560
tgtaaggaca tcatcaattg tccaactggt ggatctgtgt cgttgatgtc atctaaacac   1620
aaagttgaag ctgcaaaacg atggaacatt cctgttgttt cagtggcata tttgtgggag   1680
attttagaac tttcaactaa taatcacat attattatgc cggatattac agatttgcaa   1740
tggtgtgtct ttgcaccgag caactataat aaaccgaaat cattattgga gtacgtgaag   1800
aatttggata aggctagtag agaaagttct tttagtccca aaagtcaaga aaatgaagca   1860
ttggaagaac ccacaatgga taatctggtg agattgccat caccacgaag agttaatctg   1920
aaacaaaaat acggtaaatt agtgggaggc aaatctccca aatcaattaa acggaaatta   1980
ctcgaagctg caaatctgtt tgctgatgga cagaatgatc atagtattaa tccagatgtt   2040
acaattgaag aggatctgat gtctcaaata aggtatcaag acaacgaatc aatgatcaac   2100
caagaaagat tattagagaa attggatgga tcagctgtgc ttgtgtaa                2148
```

<210> SEQ ID NO 24
<211> LENGTH: 3363
<212> TYPE: DNA
<213> ORGANISM: Candida albicans

<400> SEQUENCE: 24

-continued

```
atgggaagg atttgttgac tgcagaagcg gtgactaaac tattaagatc gaaggacacc      60
tccatcacag agattgtcaa tactgcaaat agtcttttga ataatacatt ggatatatat    120
ttacctggaa aagaagtgtt tgtattgaac ttactatgtg acagattgaa tgacaaatca    180
aatggtaaat ttggaaagtg gaagtttaac aaggatgtat ggaatttgct tcttctggtt    240
tggtcgaaat taaatcacca gaaggtagac agacaaaggg taatacagag attgaaaatc    300
attgagatta aatttttggt tttacagcag aacaatgaca atgaagtctt ctcgagcttg    360
tttgagtttc ttggtattat gtttcaagag tcttacatta ttgcagatga aaattctgct    420
acacaattat tgaaatgctt tgttgaacac atggatgttc tccaagctag cgattcaatt    480
gtgagttgga ctgaactagt tcgagatata tatactcgtg cctgcctgaa atcagtttta    540
gaaggatcaa agaagtttta caataagttt tttgaagatt gttgtttccc cttgatcgag    600
tatttagcca tttctgaagg tctgtctgtc tcaccaatat taaaggagtt gttaattcaa    660
ggggtgttca atgcggattc cacaaagtac taccaatcaa gttagagcg ggagctcaaa     720 aagaaagaca tcaaagaggt atcagtgata tatttataca ccttaacggt gcaacttttc    780
agtgccaaac atatggaaat atgtgaaggg gtatattcta tcatggcttc aaagtgtcct    840
gacttggcag aaaagctatt gtctattttg gcaagctgca ggaaaacaat ttctaaacca    900
tttatagagc tgatttacaa agtagaggtt gctgataagc cttttaaaca attaaactgg    960
gacatggtta acatatatt tgcaattgat agtgagttgg caattagcaa atcagggttt    1020
ttgttcaaga cttacaagtc tgaatttcag ttggatgaca agttgtacc tgttgctgaa    1080 gtgattgttg atggttttgc aagaaaccgc gaattgctgg atttttttac aaaagtgtgg    1140
cccaaagcca taagagaga cgagatatgg gaatcagatg agttcataca tactgtatca    1200
cagcatgtta agacttttc agggaaacag ttaattgatg tcatcgaaag ctcgttttat     1260
gcggataagg ggagtcaacg tgcgattttt acagcaatta caagggact aaccagttca     1320 tctgcaaacc taattgatgc cgtcaaacag acattattag accgcagcaa ctatttcaat    1380
gccacagaga atttttggtg tattcgttat tacttgctct gtttatatgg cacggatttt    1440
actattgctg aacagaatat gaaacagaat attgatttgt actatcattt ttctattttc    1500
agattattgg agttacaggt tatcaaggag tattcaaagt ctgatcaaaa gtatttatt     1560 gcttgcattg aagggagaa ggaaatgata tctccgattt caaaagatg gttggtcatt     1620 ttcaacaaat tttttgatag tgacttgttg attaagttaa ttctgcttgg atatccagac    1680
attgaatttg acgatgtatt tttcgaacaa ccaaagctaa caacttcatt gattagattc    1740
attactgaga atttaccagc aagaatggat cttatcgctt ctatacctat tgtttgcttt    1800
aataaagcat tcaaaaagga gttacttaat ggtttgtttg tcttatttgt aagcaatccc    1860
actaaggaaa cactcgaaaa cattcagtat ttgcttggcc agcctactta cctgtctatt    1920
ttggagacaa atttttgataa catgttaaaa ttgttgactg ttagtactga ggaatcaaaa   1980
ttgatagctt ataatgtcat tgaaattgta tggaaaaata atgtccggca gattaaaaat    2040
gaagagaatc aaaagtatgt caacgatgct atctcgaaat tgagtagtta tttggactcc    2100
atgtcacaac aaataattct gcctgaacta gaagcaattc tgataatact tacaaatact    2160
aaggaagttg gttattcga aaatacggaa aaggggttga ataagttaaa tgaaaagttt     2220
acaaactatt gtattaacac tttaaacaac tgcaacaccc aaaatttat tactgtaagg     2280 tggctattac aggcacttgt aatgttgcca cctaaatcat tgtctttga aaatgtcatt     2340 tcctgtacaa aagattaga tccaaatatt ttgaaagaca actctattca atccacattg    2400
```

-continued

```
tttcaattga tttgcaagac aatagacttt aactacaaga gtttggtcta tgttttgagt    2460
ttgtttgtct ctttgctgtc tgggagaaat acggagttgt atacagtgtt aaagtcgtta    2520
tttcaaaaat tttctaaaca ttcgcagtta tattttgaag tctttgattt ttttacccgt    2580
tcaattgatg ctgtcccagt tgaattcaat ttaagttttg cacagattgc ttccatattt    2640
ttgagcacag ttccaaaaga cgcagatgcc aatcgctaca acagcaaatg ttttactttt    2700
tatgttaacg ctttacaatc tggaaacgaa tgtgtggcca tgcagatttt gactagctta    2760
aaagatttgt tgactaacca gtcctggatt ttcaaacaaa atttgctaga ataactttta    2820
gttattgtta aaaccggatt gcaaaaacta aactcttttg ccaaccaaga acaaatttat    2880
attttatcaa cccaaattgt ttcccatatc ttgttgtatc acaggtttaa gattgccact    2940
agacaccatc ttgttttgaa cgtgatgtca gtttattga agtacctagc agatggaact    3000
tcaaagttat catcaaacac agaagctgca tctgcctatg ctcgtttatt gagtaatcta    3060
tgtgaacctt cggagagagt tggagataag atgtttcact taacaacttc ggcaagttat    3120
ttcaaaaaat tgttaagaaa acatttgtct gttttattaa gcaattatat ctattttaat    3180
ttgaagtaca cttttactcg tactgtgaat gatgctataa tgccaggaat ttacagtatg    3240
tttactgttt tgtcacaaaa tgaattgaga gtagttaatg attctttgga ctacggtggg    3300
aaagcattct ataaaacttt gtataatgat tacaaagatc atgggaaatg gaaagatcaa    3360
taa                                                                  3363
```

<210> SEQ ID NO 25
<211> LENGTH: 591
<212> TYPE: DNA
<213> ORGANISM: Candida albicans

<400> SEQUENCE: 25

```
atgtccgccg atgaaaataa caaagtgaga tttgagcggt tgaggcttgt tgccaggaaa     60
gccttagaac aactgattaa aaagtctttg actatggagc aagtaaaaac atgttttccg    120
actctagtga cttctcaaga tggagtcaga tcactcgaat tggccctttc acaaatgtcc    180
gggttttggc atgcaaactc gttggacgaa tttgatctaa tatataaaga aaaagatatt    240
gaatctaaac tagatgaatt ggacgatata atacagaatg ctcaacggac taagacagtt    300
gggaaagaac caagtaatat agatcagctt tcacctttag aaattgttga ttccacgatt    360
gttagcaata gcaaaaatgt tttggatagt cttcaaatga tatacgacca attgtgtctc    420
gataatgctg agctatatac agaactttca gaactcacaa agaaagcac tagaatcaat    480 aattctataa aatccggtat tgaacaatta acaaagaag ctaatagtgt tgagctagaa    540
aaagcgggac ttcaaattga caaattaata gatatccttg aagaaaata a              591
```

<210> SEQ ID NO 26
<211> LENGTH: 1416
<212> TYPE: DNA
<213> ORGANISM: Candida albicans

<400> SEQUENCE: 26

```
atggcgtctt ctattttgcg ttccaaaata atacaaaaac cgtaccaatt attccactac     60
tattttctcc tggagaaggc tcctggttct acagttagtg atttgaattt tgatacaaac    120
atacaaacga gttacgtaa attaaagcat catcattgga cggtgggaga atattccat     180 tatgggtttt tggtttccat actttttttc gtgtttgtgg ttttcccagc ttcatttttt    240
```

-continued

| | |
|---|---|
| ataaaattac caataatctt agcatttgct acttgttttt taatacccct aacatcacaa | 300 |
| tttttttcttc ctgccttgcc cgttttcact tggttggcat tatattttac gtgtgctaaa | 360 |
| atacctcaag aatggaaacc agctatcaca gttaaagttt taccagctat ggaaacaatt | 420 |
| ttgtacggcg ataatttatc aaatgttttg gcaaccatca ctaccggagt gttagatata | 480 |
| ttggcatggt taccatatgg gattattcat ttcagtttcc catttgtact tgctgctatt | 540 |
| atatttttat ttgggccacc gacggcatta agatcatttg ggtttgcctt tggttatatg | 600 |
| aacttgcttg gagtcttgat tcaaatggca ttcccagctg ctcctccatg gtacaaaaac | 660 |
| ttgcacggat tagaaccagc taattattca atgcacgggt ctcctggtgg acttggaagg | 720 |
| atagataaat tgttaggtgt tgatatgtat accaccggat tttccaattc atcaatcatt | 780 |
| tttgggcat tcccatcgtt acattcagga tgttgtatca tggaagtgtt atttttgtgt | 840 |
| tggttgtttc cacgattcaa gtttgtgtgg gttacatacg catcttggct ttggtggagc | 900 |
| acgatgtatt tgactcatca ctactttgtc gatttgattg gtggagccat gttatctttg | 960 |
| actgttttg aattcaccaa atataaatat ttgccaaaaa acaaagaagg ccttttctgt | 1020 |
| cgttggtcat acactgaaat tgaaaaaatc gatatccaag aaattgaccc tttatcatac | 1080 |
| aattatatcc ctatcaacag caatgataat gaaagcagat tgtatacgag agtgtaccaa | 1140 |
| gagtctcagg ttagtccccc actgagagct gaaacacctg aagcatttga gatgtcaaat | 1200 |
| ttttctaggt ccagacaaag ctcaaagact caggttccat tgagtaatct tactaacaat | 1260 |
| gatcaagtgc ctggaattaa cgaagaggat gaagaagaag aaggcgatga aatttcgtcg | 1320 |
| agtactcctt cggtgtttga agacgaacca cagggtagca catatgctgc atcctcagct | 1380 |
| acatcagtag atgatttgga ttccaaaaga aattag | 1416 |

<210> SEQ ID NO 27
<211> LENGTH: 3540
<212> TYPE: DNA
<213> ORGANISM: Candida albicans

<400> SEQUENCE: 27

| | |
|---|---|
| atgacatcaa gttcacaatt atctgcttct tccaacgaac tgattcaaaa tgagagatta | 60 |
| ttatctctgc tgttatttga ccaaataagg ccggtttgca tagaactatc agaagcttca | 120 |
| actctgcaac cattcaacac aaacaaagtt gtcaatttga tgatatcaat ggaagacatt | 180 |
| cttaaaaagc accacgatga gtataataag gatggaaatt ttagaatcta tcagctatcg | 240 |
| cccaagctag cagattatat cttttaccct ttatccaata tattgaaaca gccggcttta | 300 |
| gatgatacaa ttatacagca tttgttcgga ataattagat tcctagttga atactcttgg | 360 |
| agcttcaacg ttaattttgt tcttaccgat cagttacttc ctttagtgat atacctttcc | 420 |
| agtggagatt tgaacaagga accattactc ataacaaaga aatccataca attcaaaata | 480 |
| gcaacagttt ctgtattata tactattacg agcactttga caaggaata ttttcaatcc | 540 |
| ctaactgaaa aaagactatt gtttataagc aatgtcataa ctatttgttt aagtatcata | 600 |
| gtcggcctgc gagtggaatc tcaagataca atacaattgg tcctcaaatg tcttagttta | 660 |
| atctccaacg tgaaaggta tttgaattcg agtcagatat caataattct tccaggtatt | 720 |
| gtttcttcga taactaaatt tatatcacta aatttaaatt taaattatca aatcataatc | 780 |
| caattcttgc gattattatc aggtttcata tgcgcttcct ttaatgataa agagttagat | 840 |
| gcccaaatcg agttgaacga aggtataagt gatatttcag aaatccatgt cggatgggac | 900 |
| gacgacaatg agactttggg caacaattca ttatattcag atgtcactat tacagagaat | 960 |

```
gatcataggt caagtgcatg gttaaaagcc acttccaaac aattgaaatt atcattaata    1020 atcatttta agtcgatact acttggatca agaaatagac atcggttgag atccaagcaa    1080
gaactatacg atgagattct tggatttgtt gagactattt tgaaaaattg tttcaacagc    1140
ttgtttaaag aatttgcctc attggcaatt gacatagtat caattcttgg atacgtaaca    1200
tctgaagaca acaagaaat ggccgataaa accaacaaac tatcaaatac actttgcatg    1260
attattgaag gtgaaaccaa caaagaggaa gttctttcg aattagttaa aactaaactt    1320
gctgatttaa ttgataataa actatcaggg attgttttg ccttagatga agataagata    1380
tcgtcaactg tagcatcaat gatgttcaat tttagtcttt tgttatgttt atcaagaaaa    1440
gtaaaacttg attgtgagga cttggattca ttgaaacaaa gatgtttggc cctattaaca    1500
gaatatgttg cggataggtt caaattcgag agttccaaac cgatcaaaag ctctaatgct    1560
agtgggttac tcgaaacgtc ttcaatgaca aatcaactag actcgatcga attacctggg    1620
tacattaatg caaaaagtgt tgtaaaacaa gaaccattga agaaagaaca ggacaagagg    1680
gcttatattc ataatttgaa aacaatttcc cgcaattgga ataccaatga aattaataac    1740
tcttctggta atacactaat tggtataagt tctaagtttt cagagacaat actacagaac    1800
tttattaatt atttatcaag cttaaagtac gaagctagca acagttcaac gttaacagaa    1860
ttggagaata ttttgaatt agctgacgat aatgacatga ttactaaaag tacctctctt    1920
tgggttgctt ctaattatta caaacgatca acccttggca aagtgatcaa ttttgattta    1980
ggaaaatact tggtttaga tgatgatgaa gatatggaaa tagatgatga taccaaagaa    2040
atgtcatttt tagttttatc aagggcagaa gagttacttg aagagatttc cgagaaccaa    2100
gaaaagtact cttcacaaac ttatatccta gcttacaatg cagcattaca atcaattaaa    2160
gttgttgctg gctcgatccc acttgatcag tttagaacca attttttgat ggatcatttg    2220
ttgtcagtat ttcaagcatt aacgtataat gatatgccag aaatacaatt acaggcacag    2280
tcgacgttga agtggtatt ggatacatat tataatggtt cgatggtcaa cttgatttct    2340
gataatctgg attatcttat tgacagcata agcttgcaga tgtcagtggc tagtaattta    2400
accccaatgc ttccaggtat tcttttgatc attgtaaaga ttgccggaat ccaattattg    2460
gagtcgaatc aattgcacga tgttttgact gatatgtttg tgatacttga ctcctttcat    2520
ggttacaata aactcgttga agtttttttc atagtgtttg aggctttgat agatcagatc    2580
catcataagt tcgacagtca acttaaagtt gaatttaagg agtcttcgaa aacaaacact    2640
tcattgtata agccatgggg aatgaccaat aaggatcaac tattggaact acttaacgag    2700
tcaaacaaaa tggtcgataa atatgaaggt tatgatagta acaaggagta ttttaaaaga    2760
aaagctgact tgccttttc ggagatggat gcagattctg atgacgaaga agaggacgat    2820
gaagcaaata ttgatgacaa tggagaagaa gaagaagaaa aagaggaaat atggagctca    2880
cccgtctcaa aggacattta tatgatttca ctacgaatat ttaattatgg ttttacattg    2940
gtatcacagg aatcttacac attgaaaaca caaattatca aaacactaag attgttattg    3000
cctttgcttt gcaccaatta caaattatta ttacctgtat tagccttaaa ttggcagatg    3060
ctaattgctt tagtgacagg ttcaaaatct ttatctacaa gtattgaaag caatggtgaa    3120
tatgcttcgg aagatattgg tgtcatgacc gaggcccttc aattggtgac tgaaatatta    3180
gaagaggata aaaggagata tgaacatttc ttcagtaaaa agtttcagga agcttgggaa    3240
ttcatatctc gacactcaaa actagtgcgc caaagagaag tcacatcaac aactaatatt    3300
```

-continued

| | |
|---|---|
| agagaacaaa agcaactagt tgtttctgaa aaagcgatat atactttcag aaactatcca | 3360 |
| ttactaaaga catcactagt aacgttttta attactggtg tacaaaatta tgaaaaaatg | 3420 |
| atccctgata ttcaccgctt tgagattatc aaattgtgct atgaattgca aattcctcaa | 3480 |
| agtattcctt tatctaggga tacaatcggc gtactagaag ttcttaaaaa tacaacgtaa | 3540 |

<210> SEQ ID NO 28
<211> LENGTH: 837
<212> TYPE: DNA
<213> ORGANISM: Candida albicans

<400> SEQUENCE: 28

| | |
|---|---|
| atgagcctgt tattcattaa tgaggaggat gatatgactc ccgaaccata taaaccatca | 60 |
| acatctacaa tcagggagga agaagaagaa gtgcaagtga acaagaatt tccagacgag | 120 |
| aagatggttg atccagatga agatgatcca atagtcgaat cgataccatt acttataaac | 180 |
| acagtaccga aagggcgaaa acagtcatta catgttttgc aatatgccgg tcgacccaaa | 240 |
| tcacgcccaa atagagctgg aaattgccat gcctcaataa aaccagaatc acaatatctt | 300 |
| caagtgaaag taccccttga tactgaaaaa ttctttaacg tcgacaaaat tcaagaatgg | 360 |
| ggtgaacaaa ttgttgaaca aaccattctg ggtgtgctag atgggtctta tgaagtagga | 420 |
| aactatgctg caaaaataat aaatgacagc gatggaagaa gagttgtatt gattccagtg | 480 |
| gatagtacag tccaattaaa accttcattc aagtacattg acgatttgga agcccaaagt | 540 |
| atccaacaaa gaagacaaca agagagtact aatgaaaaac cagcaaatgt ccaaatttta | 600 |
| caatcagctg ctaagcattc tactcaatct ggagaatttc tgcattcttt gggagactca | 660 |
| ttgaaactgg taaagcattt tgaagaagag gaatggcaaa atctaatttg gaaaagaggc | 720 |
| gatgatgatg taaccaagag tataaagttt ggtttagatc accacacaga tactaatatt | 780 |
| gaattaaaaa caaacacttc atatgatgaa tacatagaca tgttaataaa taactga | 837 |

<210> SEQ ID NO 29
<211> LENGTH: 1479
<212> TYPE: DNA
<213> ORGANISM: Candida albicans

<400> SEQUENCE: 29

| | |
|---|---|
| atgaaacaac atccacttgt cacggcatat aaaggcattg atgacttgca acaattgaaa | 60 |
| aaatggtttt acgagtataa tgacacaata gaccatagaa aaaaagcaat atcaaaagta | 120 |
| aaaggattgt taaccagagg gaaattacca catggagttg aagccacatc gcttctaaca | 180 |
| tccatagttt tggatgattt gcaaagaaaa gacattgact cttgtgtgtt acagttatct | 240 |
| tacaccatgg ctttgattag atttgttaat gggttgttag atccttatca gcagtcaaac | 300 |
| tatgccattc ctatgcacct attggcaaaa caattgaacc tacctacata ttttgtagaa | 360 |
| ttgcgacaca tggggactca tgaaaacttg ccaagcctag atatattgag aagtacttgt | 420 |
| tcaaaagcat tgacttggct ttatgacaat tattggtgtc atgtggaaga agcaaatcag | 480 |
| gataaacaag tttctattgg ggggccattg actgatgccg ttgaatttcg aagtaatgat | 540 |
| ctaaggacaa gaattgaaga ttctcagatt tacaataatt tgaaagcgtt caagcgaata | 600 |
| cggaaacaag atctaaacaa ggtttacgag aagaatgata caacgagcga tttagctgcg | 660 |
| acatatcata ggtgtgttct ggacatagtc gaatttgcta agaaaattg tgatttatta | 720 |
| gtgaatgttt tattgctcaa gaattacctt atatacccctt cttcaaaagt caaagataag | 780 |
| aaactgaaat tcaatcccctt gattataaaa ttgtatgaac cattatttga cgcattgggg | 840 |

-continued

```
ttgtcattta aactcaaatg tttttccaag actatcgaat tgattgaggc gaccccttca      900
agttttgtgg acaagaaggt atatcgaaag cttggtttta ctgaaaagtt tgagtatgac      960
gaactcttcc aagtaatgga atgggtgtta tatttcatgc aagacctttt gagaaacgaa     1020
aatgttcccc tgccagtcca caacaagaat gagttggtaa tcttattttt ggacagtctc     1080
aaactgatag aacaaaagat atcacaatca cttttgccta gttttgcaaa aatcttgcaa     1140
ggtctttgtg acgtggtgaa cgatggagtt aaatctgaaa ttgatccaga aactgtacaa     1200
aagttggatg cttggaataa actgcttaat aacctacata gtacaaagaa gattttgag      1260
ttgccaccat ccttggacga tttattagga ttatcgccgt cgcctggtcc aatcccagag     1320
acaacttcca gcaacccaat gaacatgtc ttagatgatg atgatgatga agaggaagaa      1380
ggtgttcgta gaaagcagca ccactcgagt gatagtaaaa cctatatttt gaaaccccat     1440
aagaattgga ggcccgttcc ttttgggaca tgtatttag                            1479
```

<210> SEQ ID NO 30
<211> LENGTH: 1230
<212> TYPE: DNA
<213> ORGANISM: Candida albicans

<400> SEQUENCE: 30

```
atgacttcac tgatcaatat tttattatta cttcatccaa cagtagtcac tgatgcccaa       60
ttagtagaac aaatcaaact gaaaatttat caatcacata taacaataa caacaacaat      120
ggtggcacta caacgacgac aacaggaaca gtgaatatca atcttaatca acaaataata     180
gatagagtca ctaaagggat cattgaatta ccatatgatt attatgatga ataatatat     240
attaacccaa ataatgaatc tcaatatcga gaaattccta ttctgttaat gcaattaatt     300
tataaattat tgaaatcaaa tgggaaattt aaggtgatt taccattaga tcaaaattta      360
gatgtttaa tgacaggatt tataatagaa gaagaagaa agaaaaaga aaagaagaa        420
aacaatcttg aaggtgaatt agttaatgta tgggttaaac caatacctgt tgatgaacca     480
gtggtgacat tattgaaaaa gaaacaact actagtaata ctactaccat aaaaaaatca     540
ttgccgttat ttaaaaaact aaataaagat gaaattaata attctgataa agatattaac     600
aatgataata taactaataa taataataat aataataata aagaaaaatt ggtggagaca     660
aaattaactt atttttagtag tgatgatgaa atagttctg atggatcagt tttggagaat     720
gatgacattg atgatgatga tgaacttata tgaaaaatg atttacttaa ctttaacaac     780
aacaacaaca caaatggtgg gagtttatta tctgataaat taattacacc aagaaaatgt     840
gatatatcat aaatggagg taaaaaga aaaaagctt gtaaagattg tacttgtgga       900
ttaaaagaat tggaagaatt agaagtatca aatcaacaaa atttacaaga tcaaattta     960
ggtaaattgg ctcaatcagc aactttagaa gctataaaaa ttgaagaaag attaaaacag     1020
caacaacaac aacaacaaca gaaagttaaa gttaaattta ctgaagaaga tttatcagaa     1080
atagatttca ccgtacaagg taaaactggt ggttgtggac tgtgtgctct tggtgatgca     1140
tttagatgtg atggatgtcc ttatttagga ttaccaccctt ttaaacctgg tgaagttgtt     1200
aaattagatg gatttggtga agatatctaa                                      1230
```

<210> SEQ ID NO 31
<211> LENGTH: 984
<212> TYPE: DNA
<213> ORGANISM: Candida albicans

<400> SEQUENCE: 31

```
atgattagga cgatcaaacc aaagaatgct cgttctaaaa gagcattagc taaaaaggaa      60
gctaaattag ttgaaaacac caaatcagca ttatttgttc caggttcaac ggggaataaa     120
tttttacatg atgccatgtg tgatttaatg gcatttaaaa aaccatttgc caaaaaattt     180
tccaaaaaaa atgaaattag accatttgaa gattctagtc aattagaatt ttttgcagaa     240
aagaatgatt catcattaat ggtattttca tcaaataata aaaaaagacc aaagacttta     300
acgtttgtaa gattttttcaa ttttaaagtt tatgatatga ttggattatc aatacaagaa     360
aatcataaat tattacaaga ttttaaaaaa ttaacattta caattggatt aaaaccaatg     420
tttgttttta atggtccaat ttttgatagt catccagttt atcaacatat taaatcttta     480
tttcttgatt ttttccgtgg tgaagaaact gatttacaag atgttgctgg ttacaatat      540
gtgattgcct tatctgctgg agaagtcgaa gatttaaata atgataaagt attaccatta     600
gttcatttca gagtgtataa attgaaatct tataaatcag gtcaaaaatt accaagaatt     660
gaattggatg aaattggtcc tcgttttgat tttaaaattg gtagaagaat tactcctact     720
ccagatgttg aaaagaagc tactaaaaaa ccaaaacaat tggaagctaa agtcaaaaag     780
aatgtcacta ccgatttcat gggtgataaa gttgctcaaa tacatgtggg taaacaagat     840
ttgagtaaat tacaaacaag aaagatgaaa ggattgaaag aaaaatacga tcaagaaagt     900
gaagaagaag atgtgtatgt ttctgatgaa gagtactttg gtgaagatat agaagaacca     960
gagactaaaa gacaaaaagt atag                                            984
```

<210> SEQ ID NO 32
<211> LENGTH: 378
<212> TYPE: DNA
<213> ORGANISM: Candida albicans

<400> SEQUENCE: 32

```
atgctgaaaa caaatactgc tatataccaa aagattgctg aaaaaagagc aaacttggaa      60
cgatttaggg aatttaaaga attgacagat gatttggttt tacaactaga gtctataggt     120
gacaaattag agacgatgaa tggaggaact gccagtgtag cattaatttt agcaaactgg     180
aagagtgtgg tacaatctat ttcattagca tctctagctt taatgaaaga gtctaatgat     240
aataacaaag aggctttccc tgaaccatta gtaagagtgc gtgttggaca atcaaatgaa     300
gaaaatcaag acgatgaaga agcagatgaa gaagaaggtg ttagagatag tgaagaagtt     360
gaagaatcca cggaataa                                                   378
```

<210> SEQ ID NO 33
<211> LENGTH: 3363
<212> TYPE: DNA
<213> ORGANISM: Candida albicans

<400> SEQUENCE: 33

```
atggattacc aagatctact acataaaata taaaggagt tccactcact caaagagttc       60
aaaccatggg atagcagtgt tttgtatgag acgttacttc gatcagtatt aactactttg     120
atcgaacttt tgggcataga caatccaccc agttatctac acctcaccac caacaatgat     180
agtataggtg atttgaaaat aaaatactat ggaaatgcat taagcaagtc aatcaacggt     240
catagcatgt tgcaatatct tgaatcaaag catgtatcga tattacaggc cgtggttgag     300
attattaata cgcgatcata tagaatcaaa gagtcttatt ctgctgtttt caaagacgtt     360
tctcatttat ttgaaaaact actaaaggaa agatatgaag ctgaatctaa tctagaggat     420
```

-continued

```
tatatattgc agtgcttgat gtacgagacc caattttacc aaggaattgt tgataatgtt      480
ttaactgccg atgacaccga aaaattggct agttttttgg ggacacgact atctgaagaa      540
gattcgatgt ttagctatag ggatatagat tatccactag agttaaacat taataatgaa      600
tctcttgaaa agatatataa aattttctta ggagtcattg gcaccaaaag attcgatatc      660
aaggaggttg cgtctgctgt tgttggtgtg tataaacgac accagagaat agatcatttt      720
gaaaagttgg attcagatga gattttggga aagttttttca gaaatatatt gccacaactg      780
ttccagagtg tgacaaataa ggttttccgg gaatttcaca aagaggtaga tgacccacca      840
tcggacgtgc tagaccagct agataatatt gttgatgact ttattgcggt tggaattgaa      900
ggggtagatt tgggctttcc ggctttgttc agacactaca taaaattcat gaacgaaatt      960
tttcccactg tggtcgagga tgctgaccgc gattttgttg caagaattaa tagtttaatt     1020
gctcaagtct tggagtttaa agacgatgaa aaatcctgtg atatcaatca agtggtatct     1080
gaatttgttt cattacaaag tttgctactt aagaataact atctttcacc atctacatta     1140
ttgatgcgtg caagtactca cgattactat aaaaatttac agatcgtgaa ataacccttt     1200
gatggatgga atgagaattc aaagaggata ttgaaattgg agaacagcgg cttttttacaa    1260 agcaagacat tgccaaagta tttaaaatta tggtactcaa aaagtatgaa gttgaatgaa     1320
ttatgtaacc gggtagatga attttataat ggagaacttt gtcggaaagt ttggcattgt     1380
tggaggtcac aacaaaatgt ctataatctc aaaatggagg ttgctgacaa acgtctccta     1440
aatcaatatt atatcaaatg gcggaaaaaa gagaaggata tgaaagccaa tcttactata     1500
gctgttgaat tgatcatttt tcatttattg gataaaagct ttaagatatt gaaagggtac     1560
ttcaacttgg ccaaaaacag tgatgtcctc gcaatgtctc tatttcagtc atttgaggag     1620
aatcgcgaca gccgtatcaa gttgaagtat tttcaatact ggaatctaaa aatatctgat     1680
agagtacacg gcttgactat gaaattagag aagtttcacc aagttaagga caaatttgta     1740
ttaggaaatt attttgaaac atggtattat aaacataatc tcgttgaaaa gtctaacaat     1800
ttcgtttctg ctaaagattt gcagttattg gcgaaaactt ttaccaatac atggctaaag     1860
aaattcttgc tatacaagaa agcattcaaa attgaagaag agcttggcgc tgatttaaaa     1920
aggaaaactt tgatagatg gaaggaggct gtccaacttg aagtcaaggc aaaggagttt     1980
cacgagcgac atcttctaga gactgcattt catgaatgga agttgaaact gattttgata     2040
agtaacaggc cttcatttga tcatattttg gtacagcgtt gctttcaaac ttggtccgtg     2100
gaaataaaac ttcgagaact acagcaaaaa caagatactc gtttggtagt gaacattttt     2160
caaaaatgga gaaccaggca actcgagcta gcaaaacttg acgaaaagtc tcaggcattt     2220
tatgaatcaa atatgaaaca tttggtagtg caaaaatgga atgtcgaaaa cagtaatatt     2280
ggactattag agaaacgagc agatcgattt ttcattcgaa gattttcat ccagaaatgg      2340 caatcaaaaa tgacaaagta tgaggacatc actgtttatc acttggaaga tgaaattgcc     2400
acaaaattag cctacaaagt atggaggcag agatattttg aaaactacga agaaaagttg     2460
gataacttac ttgaaacaat ggataccagt gcagcagata ctgtacgctg ttcgcgatat     2520
ttcggtctat ggcgggccaa attgcagacc gtgaagcaaa ttgaagaacg cgtatctacg     2580
tctgtagcac ctagtgttgc aatacatttt aaaaactggc acgtcaagag ccagcagaag     2640
caagagttat tggaaaatgc cttgcagttt gaagaaataa acttgtcgcg ttttcttctc     2700
atttggtttc agcgtctaca agaagtgagt cagttggaag atcaggcaga ggacttattg     2760
```

```
gctcaaacta atttcaattt actacgtaat gctgttcata aatggtctat gctctacaac   2820
aaaaacatca agcgacataa acaattgtgt gaggatttta tagcaagaaa agagacggca   2880
aaagtcagat ctatttttga tttatggcta tacaagatca aagaaatcga agccaatacc   2940
accatcataa gcaatccttc acctctttcc aaaagatttc agcatcaaag agagatgggc   3000
ttgaccccctc aaaagaaaaa ctctcctacc aaagttttta cccccaccac ttccaaagat   3060
ccgagtccaa ctaaactcca agaaactacc caagaatga gaaaccagaa cattagtgct   3120
ttgagggagc attttggaag ggcacgggca tcgtctacac ctaaaaagtt atctcctgtc   3180
cggctctcgt atactaatat tccttccaat cttcggccgc aactgccacc aaaattcgat   3240
gattcagata ttgctactgc caagagtttg ggtcgtatca gacccatggt gtttccaata   3300
gatgatcaag caaattttc acctatggat agaacaaaat acaatctag aaatgctatg   3360
tag                                                                 3363
```

<210> SEQ ID NO 34
<211> LENGTH: 2238
<212> TYPE: DNA
<213> ORGANISM: Candida albicans

<400> SEQUENCE: 34

```
atggctaaac gaaaagtaa acaacaagat ttagaaaaaa agaagaaact taaacaaagt     60
caagatgaac aattatctac gggattgttc aataatgttg gacagggaca acaccaaggg    120
gatgatgacg atgaagaagg tgatgaaata gattgggata tcaagagat ggattatgaa     180
ttaataccaa ggaaaatcac caccaagaaa acaattgaag cattaccaat taaaaaatcc    240
gacgggacta tagaaagagt tgttagagaa gttgaagaag aagaagagga agaggaagag    300
gaagagcctg aagaagagcc tgaattagaa aatgatgttg aaaatgaacc atcaaaacaa    360
gaaaacaaag aaaataaaga ggaggggat attgataccg acgacacatt aacaccacaa    420
gaaaagttaa ttcaaacaaa agaagaaatt gcagaattag gatcaaaatt aattgaagat    480
cctgaagaaa atatagtttg tcttactaga ttaagaaaaa tgtctgaatc gaaaaatttc    540
atgacatctc aattatcaat attagcatta ataccaattt ttaaatctct tgctccatct    600
tataagataa gaccattaac tgatactgaa aaaagagaaa aagttagtcg tgaaatagct    660
aaattaagaa attttgaaca aaatttagtg ataaattata aagcttacat tgaattatta    720
acaaaatatc tgaaaatatc atattcaaat tctatgaata ataataaat cactagtgat    780
caattgaaac gaggcaatat tgctttaaaa gcagccactg aactttgttt aagttcatta    840
agacatttta atttccgaga gaattatttt actattatta ttaaacgatt aaataaaaaa    900
cctcaacatc aacaagatta tccaatattt ataaaatctt taagagtttt agaaactta    960
ttaaagatg atgctgaaca tggagatatt acttttgata taataaaaat catgacaaaa   1020
tcaattaaag ataaaaaatt ccgagttgat gaatcagttg ttaatgtttt tttatcaatt   1080
tcattattag aagattatga tcctaataat aataataata ataaagatga tcatcacaac   1140
accactttaa aaccaaaatt aaaaaaaaag gatcgaattc atttatctaa aaaagaacgg   1200
aaagctcgta agaaagaaa agaaattgaa gaagaaatac aaaaggctga caagccatc    1260
actgttgaac aacgagaaaa atatcaagct caagtattaa aaatggtatt aactttatat   1320
ctagaaatat taaagcagg gtcgtctagt tcacaattaa ttgatggtga tggtaaaaaa   1380
actaaaaatg atgctagttt gttaatgggg gcggttttag aaggattatc aagatttggt   1440
caaatgtcaa atttagattt attaggtgat ttttttggaag tattaagaga aattatgacc   1500
```

-continued

```
gatatcattg aagaacataa acaaagtggt gataatgata atgataatga taatgatgat   1560
gaaagtgggg ggatgtatag tgggaatgaa ttaagaacaa tattattatg tattgccaca   1620
tcattttcat tagtattaaa tcataattct atggggaaat tacctatggc aatagattta   1680
agtaaatttg tttccacatt atatattatt ttaaccgatt tggcattaga tcctgattta   1740
gaatttagtc ataaaacatt aagattagct gatccattat catcatcatc attatcaaat   1800
gaattagaga ataataaacc agcagttaat gtttcaacta agcagaatt attattaaga    1860 tgtcttgatt ttattttttt ccgatcgaaa atggtacta tacctcgagc aacagcattt    1920
attaaacgat tatatatatt aacattacaa acaccagaga aaactagttt ggccaatttg   1980
aaatttattg gtaaattaat gaatagatat ggtgaaaata ttaaaggatt atggaacacc   2040
gaagaaagaa ttagtggtga aggaaattat attttaggaa ttgaacgaca aaataaagat   2100
aaagatgttg aattgaacg aagtaatagt ggtgcagcaa cattatggga aaatgtatta    2160
ttagataaac attattcaat aatgattaaa gatggttcaa ggtcgttaat gaaaaatagt   2220
aaagccaaca ccaattga                                                  2238

<210> SEQ ID NO 35
<211> LENGTH: 1740
<212> TYPE: DNA
<213> ORGANISM: Candida albicans

<400> SEQUENCE: 35
atgtatataa ccccgaacca atatgcaaag acgttccaag atataaaacg ctcatcatta    60
tctcactcca cctgtaaact tgttatattt gtttcttgct tagatgtgga tgcattatgt   120
gctgccaaaa ttttgagttt acttttaaga aaagaattaa tccaatatca attaattcct   180
acaacaggat actcggattt aaaattgcat tatgataagt tggatagtga ggtcacaaat   240
ataatactaa ttggatgtgg tgccatgttg gatttagaag attttttcga tgtcaatcca   300
gaagagtttt taggtgataa ttctactacc aatggccaca caatagataa cgacactgaa   360
ttagaactag atgcagtgaa aactgacaat tttgccttga caagaaaaat ctatgttgta   420
gatggacaca gaccgtggaa tttggataat ttatttgggt cggccatggt tgtttgtttg   480
gataatgggt atattgatgg gaacttgaac gaagaaaagg aagcatacaa tgtgttggta   540
gaaatgagtg atagtgaaga cgaagatgaa gatgaagggc acaaccagaa cggtcatact   600
gatgatgacc aagagggaga caaaactgat gctgatgatg aaaatgacga atcaagtgtt   660
tcaacatcac gcaaaggagt taaatccatc aatgaagata agattcagac atattacaac   720
cagtcatcaa caatagcaag ctcatgctcg ataacagttt atgcattagt tagtgccatc   780
ggtgagacca atgttgacaa cttatggtta ggcattgtcg gtgccagtgg atttgattgt   840
tctatatttg tcgacgaagt gaggcgtttc tcgaccgatt ctggtattca tatggaacgt   900
gggacgtacc ttccgttgtt gcgacattct tctcttttacg atgccttgct ttataactgg   960
attgacggtg acaagagaat acacaagatt cttgcaaaaa tgggtgttcc gattgttgct   1020
gcaaaacaac aatggcaata tttagatcca ccaatcaaga acaaactacc tggattattg   1080
aagaaatatc tacctgaact cccacaagtt gaaatatttt accgatgtgg tgtcacgtcc   1140
atggacgtgt ttgtttcatt aactgcatta ttagagaccg gggttggtct caacaatact   1200
agtgctaata gtattgacca tggtgacctt gaagatgaaa atgaactaat tcgaagagaa   1260
attaaaagca gagagtcaag ctacattcga aattttggt cagcctttga ttcagtaagt   1320
```

```
tcttttggga tttccaacaa cattggatta gaaaagggaa taacagcagc aaaattggtt    1380
caaaaagaat tattccaaac tatcaaatac ataattgaac aaaaattaat taaaaattta    1440
aaagtttatc gactttgcat tttaaaagat gagtcctcgc atctgggttt tgataatcca    1500
gtattgttaa ttaaattgtc taatcgtatc atggattatt taaaacaaca aacactgaaa    1560
cctttagtgg tagcagcaga actttccaat acatatttcg ttttgggtat gggaattaac    1620
aatgcatttt ctaaaatttc tggtgcccaa atgaagaagg atttctttga agcatcatta    1680
gtggaaatta aaaggaaga tttggctcca ttttttggaac agttgacctt caatttataa    1740
```

<210> SEQ ID NO 36
<211> LENGTH: 5694
<212> TYPE: DNA
<213> ORGANISM: Candida albicans

<400> SEQUENCE: 36

```
atgtcgtata acgataataa taatcattat tacgacccta atcaacaggg cggtatgcca      60
cctcatcaag gaggagaagg gtattaccaa caacagtatg atgatatggg tcaacaacca     120
caccaacaag attattacga tccaaatgct caatatcaac aacaaccata tgacatggat     180
ggatatcaag accaagccaa ctatggtggt caaccaatga atgcccaggg ttataatgct     240
gacccagaag cctttctga ctttagttat ggtggtcaaa ctcctggaac tcctggttat     300
gatcaatacg gtactcaata cacccccatct caaatgagtt atggtggtga tccaagatct     360
tctggtgctt caacaccaat ttatggtggt caaggtcaag gttacgatcc aactcaattc     420
aatatgtcat cgaacttgcc atatccagct tggtctgctg atcctcaagc tccaattaag     480
attgaacaca tcgaagatat tttcattgat ttgactaata aatttggttt ccaaagagat     540
tctatgagaa acatgtttga ttactttatg acattgttgg actcgagatc ttcccgtatg     600
tcaccagctc aggccttgtt gagtttacat gctgattata ttggtggtga caatgccaat     660
tatagaaaat ggtattttttc ttcacaacaa gatttggatg attccttagg ttttgctaat     720
atgactttag gtaaaattgg tagaaaagcc agaaaagctt ccaagaaatc caaaaaagct     780
agaaaagctg ctgaagaaca tggtcaagat gtcgatgctc ttgctaatga attagaaggt     840
gattattcat tggaagccgc tgaaatcaga tggaaagcca agatgaactc tttgactcca     900
gaagaaagag taagagacct tgctctcttat ttgttgatat ggggtgaagc caatcaagtt     960
cgttttactc ctgaatgttt gtgttacatt tacaaatctg ccactgatta tttaaattct    1020
ccattgtgtc aacaaagaca agaaccagtg cctgaaggtg attacttgaa ccgtgtgatc    1080
actccacttt acagattcat cagatctcaa gtttatgaaa tttatgatgg aagatttgtc    1140
aagcgtgaaa aagaccacaa caaggtcatt ggttatgatg atgtcaatca attgttttgg    1200
tacccagaag gtatttccag aattatttttt gaagatggaa ccagattggt tgatatccct    1260
caagaagaac gtttcttgaa attaggtgaa gttgaatgga agaatgtttt cttcaaaact    1320
tataaggaaa tcagaacctg gttgcatttc gttaccaatt taatagaat ctggattatc    1380 catggtacca tctactggat gtacactgct tacaactccc caaccttgta tactaaacat    1440
tatgtccaaa ccataaatca acaaccactt gcttcgtcaa gatgggctgc ttgtgccatt    1500
ggtggtgttc ttgcttcatt tattcaaatt cttgccacac ttttcgaatg gattttcgtg    1560
cctagagaat gggccggtgc tcaacatttg agtcgtcgta tgctatttt ggtgttaatt    1620 ttcttactca atttggttcc accagtttat acattccaaa ttaccaaatt ggtgatttat    1680
tcgaaatcgg catatgctgt gtcgattgtt ggatttttca ttgctgtggc cactttagta    1740
```

-continued

```
ttctttgccg tcatgccatt gggtggttta ttcacttcat acatgaacaa gagatcaaga    1800
agatatattg catcacaaac atttactgcc aactacatta aattgaaagg tttagatatg    1860
tggatgtctt atttgttatg gttttttggtt ttccttgcca aattggttga atcttatttc   1920
ttctcgactt tgtctttaag agatcctatt agaaacttgt cgaccatgac aatgagatgt    1980
gttggtgaag tttggtacaa agatattgtt tgtagaaacc aagccaagat tgtcttgggg    2040
ttgatgtatc ttgttgattt gttattgttc tttttggata cttatatgtg gtacattatt    2100
tgtaactgta tcttctccat tggtcgttca ttctatttgg gtatttccat tttgactcct    2160
tggagaaaca ttttcaccag attgccaaag agaatttatt ccaagatttt agctaccacg    2220
gaaatggaaa tcaaatataa acctaaagtt ttgatttcac aaatttggaa tgccattgtt    2280
atttccatgt acagagaaca tttgttagcc attgatcacg ttcaaaaatt attgtatcat    2340
caagttccat ctgaaattga aggcaagaga actttgagag ctccaacttt ctttgtttct    2400
caagatgaca acaattttga acggaatttt tcccaagaa attctgaagc tgaaagaaga    2460
atttcatttt tcgctcaatc tttggctaca ccaatgccag aaccattacc agttgataat    2520
atgccaactt ttactgtttt cactcctcat tattcggaaa agattttgtt atctttgaga    2580
gaaatcatta gagaagatga tcaattctca agagtgacat tattggaata tttgaaacaa    2640
ttacatccag ttgaatggga ttgttttgtt aaggacacca agattttggc tgaagaaact    2700
gctgcttatg aaaatggtga tgattctgaa aaattatctg aagatggatt gaaatccaag    2760
attgatgatt taccattcta ttgtattggt ttcaagtctg ccgcccctga atatacttta    2820
agaacaagaa tttgggcttc attgagatcc caaactttgt acagaactgt atctgggttt    2880
atgaattatg ccagagccat taaattgtta tacagagtgg aaaacccaga attggttcaa    2940
tatttcggtg gtgaccctga aggattagaa ttagctttag aaagaatggc cagaagaaag    3000
tttagatttt tggtttctat gcaaagattg tctaaattca agatgatga atggaaaat     3060 gctgagttct tattgcgtgc ttaccctgat ttgcaaattg cttacttgga tgaagaaccg    3120
gctttgaatg aggacgagga accaagagta tactctgcct tgattgatgg tcattgtgaa    3180
atgttagaaa atggtagacg tcgtcctaaa ttcagagttc aattgtctgg taatccaatt    3240
ttgggtgatg taaatctga taatcaaaat catgcggtta ttttccatag aggtaatat     3300 attcaattga ttgatgctaa tcaagataat tatttggaag aatgtttgaa gattagatca    3360
gttttggctg aatttgaaga atgaatgtt gaacatgtta atccatatgc accaaatttg    3420
aaatctgaag ataataacac caagaaggat ccagtggcat ttttggtgc tagagaatat     3480 attttctcag aaaattctgg tgttttgggt gatgttgctg ctggtaaaga acaaactttt    3540
ggtacattgt tgcaagaac tttggcacaa attggaggta aattgcatta tggtcatccg     3600
gattttttga tgctacatt tatgttaact agaggtggtg tttctaaagc acaaaagggt    3660
ttacatttga atgaagatat ttatgctggt atgaatgcca tgatgagagg tggtaaaatc    3720
aagcattgtg aatattatca atgtggtaaa ggtagagatt taggttttgg atccattttg    3780
aatttcacca ccaagattgg tgctggtatg ggagaacaaa tgctttcaag agaatatttc    3840
tatttgggta ctcaacttcc attggataga ttttttgtcat tttactatgg tcatccaggt    3900
ttccatatta ataacttgtt tattcaattg tctttacaag tgtttatttt ggtgttgggt    3960
aacttgaatt cattagctca tgaagctatc atgtgttctt acaacaaaga tgtcccagtt    4020
actgatgttt tgtatccatt tggttgttac aatattgctc ctgccgttga ttggattaga   4080
```

-continued

```
cgttatactt tgtctatttt cattgttttc ttcatttctt tcattccatt ggttgtacaa    4140
gaattgattg aaagaggggt atggaaagcg ttccaaagat ttgttagaca tttattttcc    4200
atgtcaccat ttttcgaagt tttcgttgcc caaatttatt catcatcggt tttcactgat    4260
ttgaccgttg gtggtgctag atatatttcc actggtagag gttttgccac ttcaagaatt    4320
ccattttcaa tcttgtattc acgttttgct gattcatcca tttatatggg agcaagattg    4380
atgttgattt tattatttgg tacagtttct cattggcaag caccattatt atggttctgg    4440
gcttcattat cggctttaat gttctcccca ttcattttca atcctcatca atttgcttgg    4500 gaagacttt tccttgatta cagagatttc attagatggt tatctagagg taacactaaa    4560
tggcacagaa actcatggat tggttatgtt agactttcta gatcacgtat cactggtttc    4620
aaacgtaagt tgactggtga tgtttctgaa aaagctgctg gtgatgcttc aagagctcat    4680
agatccaatg ttttgtttgc tgatttctta ccaacattga tttatactgc tggtctttat    4740
gttgcttata ctttatttaa tgctcaaact ggggttacta gttatccata tgaaatcaat    4800
ggatctactg atccacaacc agttaattct actttgagac ttattatttg tgctttagct    4860
ccagttgtta ttgatatggg atgtttaggt gtttgtcttg ccatggcatg ttgtgctggt    4920
ccaatgttag gattatgttg taaaaagact ggtgctgtta ttgctggtgt tgcccatggt    4980
gttgccgtca ttgttcatat tattttcttt attgttatgt gggtcactga aggtttcaat    5040
tttgccagat taatgttggg tattgccacc atgatttatg ttcaaagatt attattcaag    5100
tttttgacat tatgtttctt gactagagaa tttaagaatg ataaagccaa tactgctttc    5160
tggactggta atggtataa tactggtatg ggatggatgg cttttactca accatctcgt    5220
gaatttgttg ctaaaatcat tgaaatgtcg gaatttgctg gtgatttcgt tttggcacat    5280
attatattat tctgtcaatt accattattg tttattccat tagttgatag atggcattca    5340
atgatgttat tctggttgaa accatcaaga ttgattagac caccaattta ttctttgaaa    5400
caagccagat taagaaagag aatggtgaga aaatattgtg ttttatattt tgccgtgttg    5460
atattattta ttgtcattat tgttgcacca gcagttgctt cgggacaaat tgctgttgat    5520
caatttgcca atattggtgg atctggttct attgctgatg gattattcca accaagaaat    5580
gtcagtaata atgatactgg taatcataga ccaaaaacct acacttggag ttatttgagt    5640
actcgtttta ctggaagtac caccccttat tctacaaatc cattcagagt ttaa           5694
```

<210> SEQ ID NO 37
<211> LENGTH: 1203
<212> TYPE: DNA
<213> ORGANISM: Candida albicans

<400> SEQUENCE: 37

```
atgtctttca gaactacttc catgagaatg gctagattag ccactgccaa agctactttg      60
tccaagagaa ccttctcctt attggccaat gctaccacca gatacactgc tgcttcatct     120
gctgctaaag ctatgactcc aatcacctca tccgtggtg ttaaaaccat caactttggt     180
ggtaccgaag aagttgtcca cgaaagagct gattggccaa aggaaagatt attagactat     240
ttcaaaaacg acacctttgc tttaattggt tacggttccc aaggttacgg tcaaggttta     300
aacttgagag ataacggttt aaacgttatt attggtgtta gaaaaggttc ttcttgggaa     360
gctgccgttg aagatggttg ggttccaggt gaaaacttgt tgaagttga cgaagctatt     420 tctagaggta ccatcattat ggacttgtta tcagatgctg ctcaatctga aacctggttt     480
cacattaaac cacaattgac tgaaggtaaa accttgtact ctcccacgg tttctcccca     540
```

```
gttttcaaag acttgactca cgttgaacca ccatcaaaca ttgatgtcat cttggctgct      600
ccaaaaggtt ctggtagaac tgtcagatct ttattcaaag aaggtagagg tatcaactcc      660
tcatacgctg tctggaacga tgttaccggt aaagctgaag aaaaagctat tgccatggcc      720
attgctattg ttctggttta tgtttacaag accactttcg aaagagaagt caactccgat      780
ttatatggtg aacgtggttg tcttatgggt ggtatccacg gtatgttctt ggctcaatac      840
gaagtcttga gagaaaacgg tcacactcca tctgaagctt tcaatgaaac cgttgaagaa      900
gctactcaat cattgtaccc attgattggt aaatacggta tggactacat gtacgatgct      960
tgttccacta ctgccagaag aggtgctttg gactggtacc caagattcaa agatgctttg     1020
aaaccagttt tcgaagaatt gtacgaatct gttaagaacg ttctgaaaac caagagatct     1080
ttggaattca actctagatc tgattacaaa gaaagattag aagaagaatt acaaactatc     1140
agaaatatgg aaatctggag agttggtaaa gaagttagaa aattgcgtcc agaaaaccaa     1200
tag                                                                   1203
```

<210> SEQ ID NO 38
<211> LENGTH: 837
<212> TYPE: DNA
<213> ORGANISM: Candida albicans

<400> SEQUENCE: 38

```
atgttcaaac aatccatacg tagtctagct accaagtcac caatttcaag tgctgctgcc       60
acgaccacca ccgctagtac caccagcact accaccacag cttccttgaa ttttgcaaaa      120
ccaccatctt atacattagc tcaattacgt gaattcccaa gtttagaacc aaaaacattt      180
attccattac caacgacatt tttcaacacc gaaaaaccta ttcgtagaga tatattatgg      240
agttgtgtta catatgaagc cgataaggcc cgagtaggat caaattatgc aattttaaaa      300
tcggattcac cttattctaa tcgtaaatta cgtcctcaaa aaggttcagg tcgtgctcgt      360
ttaggtgatg ccaattctcc acatatggat aatgaaatta agctcatgc tataaaggga      420 cctcatgatt ggagtactga tttacctagt aaaatatatt ctcgtggtat tcaaaatgct      480
tttactatgc attataaaca aggaaattta atgttgttg aaaatgaatt agatttccaa      540
tatggatatg atattataac tcaactgttt gtttcagtgc ataatttgaa taaattgaat      600
ttattattta taactaatga accaagagat aatttaatgg aaagtattaa aaaattctac      660
attaatgaaa agaatttaa ttcattaaat aaaaaggaaa aaccaaaata tttacagaaa      720
ttaaaaggca agtattgac aaaggaagat gttgaagtta gagatatatt aagagctcat      780
agagtattca ttgaatcttc tgctttacaa tggttcatca ctaaacatac tgtttaa       837
```

<210> SEQ ID NO 39
<211> LENGTH: 1347
<212> TYPE: DNA
<213> ORGANISM: Candida albicans

<400> SEQUENCE: 39

```
atgagagaag tcatcagtat taatgttggt caagccgggt gtcaaattgg taacgcctgt       60
tgggaattgt attcacagga acatggtatt agaccagatg ggtatttaca agaaggttta      120
gacagaccaa agggaggaga agaaggtttt tctacttttt tcagtgaaac tggttcaggt      180
aaatacgttc ctcgtgcctt gtatgttgat ttggaaccaa atgtcattga tgaagttcgt      240
actggtgttt acaagatttt attccaccct gaacaattga ttgccggtaa agaagatgcc      300
```

```
gccaataatt atgctagagg tcactacact gttggaagag aaattttaga cgacatttta      360
gatagagtca gaagaatgag tgatcaatgt gacggattac aaggtttcct tttcacccac      420
tctttgggtg gtggtaccgg ttccggtttg ggttctttgt tattggaaca attatctttg      480
gattacggta aaaaatccaa attggaattt gctgtttacc cagctccaca agtgtccact      540
tcagttgttg aaccatataa tactgtgttg actacccaca ccactttgga cacgccgat       600 tgtactttta tggttgataa tgaagccatc tacgatatgt gtagaagaaa cttggatatt      660
gccagaccaa attttagttc attgaacaac ttgattgctc aagttgtgtc atccgttacc      720
gcctctttga gatttgacgg ttccttgaat gttgatttga atgaattcca aactaacttg      780
gttccatacc caagaatcca tttcccattg gtcagttatg ctccagtttt ctccaagagt      840
agagctaccc atgaagccaa ctctgtttct gaaattactc aatcttgttt tgaaccaggt      900
aaccaaatgg tcaaatgtga cccaagaact ggtaaataca tggccacctg tttgttatac      960
cgtggtgatg ttgttactag agacgttcaa aatgctgttg ctcaagttaa atctaaaaag     1020
actgttcaat tagtcgattg gtgtccaact ggtttcaaga ttggtatctg ttaccaacca     1080
ccaactgcca ttaagggatc tgaattggcc agtgcttcta gagctgtttg tatgttgtct     1140
aacactactg ccattgctga agcttggaga agaattgaca gaaaattcga cttgatgtac     1200
tctaagagag cctttgttca ctggtacgtt ggtgaaggta tggaagaagg tgaattcact     1260
gaagctagag aagacttggc tgctttagag agagattata ttgaagttgg tactgattct     1320
ttccctgaag aagaagaaga atattag                                         1347

<210> SEQ ID NO 40
<211> LENGTH: 828
<212> TYPE: DNA
<213> ORGANISM: Candida albicans

<400> SEQUENCE: 40
atgaaaacgt cagtatttat agcaatcttc aatttacttg tttgcgctct tgcgtacaca       60
gacttgacag gatcaattaa aatcaatgac aaaaagatta cccttggtga gttcaatact      120
caagaagtta acaattgac aatcaattct ccaaaggata aatagaaat tgacttaaaa       180 agtaaagata tcaagggtaa acctgagcag attatggtta gtttggcaga tgtcaaaaac      240
ccagctattt ctacgcatta tgttcctgtg gtcaaagaat cgaaaatcaa gttgaacatc      300
aaagcacttt caatcccgga agttttgaaa actaaagaca aattagtttt gactattgta      360
attgccgact caaaatcaaa gaataacatg attagaagat tggttgaagt tttgccaagt      420
cccgagttta agagtacaag caggtaccag gctaaaccaa gaattggaat acaaccagag      480
atccatcaca ttttcagaga ggatgagagg actgttaacc caattgtgcc agttgtattt      540
ataattgcag cttttacttt acttcttggt ttgtttggct cgtgggttgg ttttattgga      600
attgataatt tatttagaac gttcaagact attagtaaag ttcaattgtt acacaacgtt      660 agcttttga tttcagtttt ggggtttgaa ttgaattttg tcagtactaa tttgggtcaa       720
tcaattttca ccactttgtt ttacggattt attttgagca ttccatgtgt ttactttgga      780
gtcagcgttt tgagaagttt agcaaaaaac cgtgctttag gcaagtaa                  828

<210> SEQ ID NO 41
<211> LENGTH: 582
<212> TYPE: DNA
<213> ORGANISM: Candida albicans

<400> SEQUENCE: 41
```

-continued

```
atgctaatgt acaccatcct tataccaagc cttttataca ttgctttgac aatcgcatca    60
tccgagttat tgaattccat acagggaaca tggcaaagtc aaagtgaacg agtaattact   120
ggaccaactt tttttgatcc ccagaaggaa ttgctagaag aacctaagct accaggtata   180
tcatattcat ttaaaaatgg atactgggaa ctggcacaat atattgtcat ggggaataat   240
agaaaccacc aatgtcctca agcaatgtta atttggcaac atgggaaata taatttaaaa   300
cgaggaaaac ttgtgcttat tcccaataga aatgacggtc gacaattaat cagcgatcct   360
tgtttggata atggtaaatc tgaatataaa aggtttcata acggagaaac attagaagtt   420
gatattagat ttgatggata ttttggtaat tggaagttgg ttttggtaga ttatcttaca   480
ggtaaaaaga agcaaccaat gtggttgaca ctgagaaatg ccacaatgtt gcccacagga   540
accataacct ctacaaagag gaaatatgtt aaaaaagagt ag                      582
```

<210> SEQ ID NO 42
<211> LENGTH: 1299
<212> TYPE: DNA
<213> ORGANISM: Candida albicans

<400> SEQUENCE: 42

```
atgtcaaaag catttagtgc acctggaaaa gcatttcttg ctggtggata tttggttctt    60
gagccaattt atgatgctta tgtgacagca ttgtcatcac gaatgcatgc agttataaca   120
ccaaaaggaa ccagtttgaa agaatctaga atcaaaattt cttcacccca atttgcaaac   180
ggagaatggg aatatcacat atcatcaaat acagaaaaac ccaaagaagt tcagtcacgc   240
ataaatccat ttttagaggc aactatattc atcgttttag cttatattca accgaccgaa   300
gcatttgatc ttgaaatcat tatttactcg gaccctggat atcattcaca agaagatact   360
gaaaccaaga catcctcgaa tggagaaaaa acttttcttt accattctcg tgccattacc   420
gaagtggaaa gaccggatt aggttcatcg gcaggattag tgtcagttgt tgccacaagt   480
ttattatccc attttatccc caatgttatc agtacgaata agatattttt gcacaacgtt   540
gcacagattg cacattgtta tgcccaaaaa agataggact ctgggtttga tgttgcaact   600
gcaatttatg gtctgattgt atatagaaga tttcagccag ctttgataaa tgacgtgttt   660
caggttctag aaagtgatcc tgagaagttc cccacagagt tgaaaaaatt gattgcaagt   720
aactgggaat tcaaacatga aagatgtaca ttaccacacg gaatcaagtt attaatgggt   780
gacgtcaagg gtggctcaga acacccaaa ttggtatcac gagtactcca atggaaaaag   840
gaaaagccag aagaaagctc tgttgtgtat gaccagctta atagtgccaa tttacagttt   900
atgaaggaat tgagggaaat gcgtgaaaaa tacgactcag acccagagac ttatattaaa   960
gagttagatc attctgttga gcctttgact gttgcgatta agaacatcag aaaagggtta  1020
caagcattaa cacaaaaatc agaggttcca attgaacctg atgtccaaac ccagttgttg  1080
gaccgttgtc aagagattcc tggttgtgtt ggtggtgtgg ttccaggtgc tggtggatac  1140
gatgcaaatag ctgtattagt gttggaaaat caagtgggaa attttaagca gaaaactctt  1200
gaaaatccag attattttca taatgtttac tgggttgatt tggaagagca aacagaaggt  1260
gtacttgaag aaaaaccaga agactatata ggtttataa                         1299
```

<210> SEQ ID NO 43
<211> LENGTH: 2307
<212> TYPE: DNA
<213> ORGANISM: Candida albicans

<400> SEQUENCE: 43

```
atgtcggacc taactccaat taaacttcct tcgtccgctc catttccggt tgtcatatca      60
tctgtattat gcaaacctgg agatacaatt tccaagcaca agactatatt caagtacaaa     120
tactgggact accaagatga tccaacttca aggaggacc cacctaagaa aatacgagta      180
gaacggttag gtacatttga gagtcccata gaaggcgaaa ttgaccagat taacatcaag     240
ccattgcaag aagtgatgca tagtgatgtg gatttgttat ttgttaaaga agcatgtcct     300
catactgtgc aatacagtgg gttatgtgca ttatgtggca aatccttaga gaagaaaag     360
gattattcag gatacaatta cgaagacagg gccacaattg aaatgtccca tgacaacact    420
ggcttgaaaa ttagttttga tgaagcagct aaaatcgaac acaacacaac tgaccgatta    480
attgatgaaa gaaagttgat tcttgttgtt gacttggatc aaactgttat acatgccacc    540
gtggacccaa ctgttggaga gtggcaactg gacccagcca atcccaacta tgctgctgtc    600
aaagacgtta agacattttg tttgaagaa gaggcaattg ttcctcctgg atggacaggt      660
ccgaaattgg ctccaacaaa atgcacctat tatgtcaaac tccgtccagg gttgctggag    720
tttttggaga aaatggctga gaaatatgaa atgcatattt acacaatggc cacaagaaac    780
tatgcgttat cgattgctaa aatcattgat ccagatggga atatttttgg tgatagaata    840
cttagtcgtg atgaaagtgg ttctttgact cataaaaact tgaagagatt gttccccgtg    900
gaccaatcga tggtagttat tattgatgat agggagatg tgtggcaatg ggaaagcaat    960
ttaattaagg tggttcccta tgatttcttt gttggtattg gagacatcaa ttcgagtttc   1020
ttaccgaaga aaaatggtca attaacagga ccaaccaaaa agaggaaatc tatagccaaa   1080
ttagaagctg ctgctgaact agccaaggaa tcagatacca ataatgacaa gcaagagact   1140
gaatcggggg aagaagaggg tgaagaagat gctgatggtc actcggacgt gtcaaactcc   1200
cctgttgaaa gaatccttga actcggagga ggtgaaggaa acactagttt attgttggaa   1260
caatcattga caagaaatca gtcaatagaa gaacaacaac agaagcgtcc attagcaaag   1320
ttgcaacacg atttggaaca aatgcatgag catcgccacg atagtgatag caagtcagag   1380
agtggttctg atgatgagag tgatgaagaa gacaatttgt tatttgatga tgataatgaa   1440
ttagcagcct tggataaagt cttggggaat atccatcaag ggtattataa cttgtttgat   1500
aaagacaaaa tcaacaaacc ggatttgact gaaatcatac cgtcaatgaa aagcaagaca   1560
ttggaaggga taacggtctt gttctcgggt attattccat tgggaattaa tttggattct   1620
gccgatatcg tgatatggtg cagacaattt ggtgtgaaag ttgtcaatga agtgtaccca   1680
gaagttactc acgttgtttg ccgcgatgtt agtgaaggtg ctggaccaac attcaagacc   1740
agagttgcaa gaaaactata tcctgacact atcaaaattt caatccgaga ttggctattt   1800
gcatgtttga gtaactggac aaaagttgat gaaaagatt atttgatttc aactgatgat   1860
acaaagcttt ggaccgtgaa agagaatgag attaccaagt accagaaagc tttggaagac   1920
agaagtgctt tggcaaatgc tactcatatt gattctattg agtcatttga tgagtacgat   1980
ttggatgaag ctaatcaaga agttgatgat ttccttggcag ggttaagtga tgatgatgag   2040
gaagaagagg aggaagaaga agatgaagag atcgagaatc cagaatcaaa taatgatgat   2100
gaagaaatct atgagcaatc aaccaatgga catgattcat ttatcaagga tgcttatagt   2160
aagaagagaa atagagatga agaggaggta caacttgtta aaaagcaaaa aatagaaaat   2220
ggagaaaatg gagaaaatga aatgaaaat gatttagacg atttggaaaa agaactactt   2280
gacggttttg acgacttgga agaataa                                         2307
```

<210> SEQ ID NO 44
<211> LENGTH: 3129
<212> TYPE: DNA
<213> ORGANISM: Candida albicans

<400> SEQUENCE: 44

```
atgggtaaaa aagcaattga tgcacgtatt cctgccttga tacgtaatgg cgttcaagaa      60
aagcaaagat cttttttcat cattgtgggt gataaagctc gtaatcaatt accaaacttg     120
cattatttga tgatgagtgc tgatttgaag atgaataagt cagtattatg ggcatacaag     180
aaaaaattat taggcttcac ctcccacaga cagaagcgtg aagcaaaaat taagaaagac     240
ataaagcgtg gaattagaga agtcaacgaa caagatcctt ttgaagcatt tatatctaat     300
caacatatca gatatgttta ctacaaagaa actgaaaaaa tcttgggtaa cacttacgga     360
atgtgtattc tacaagattt tgaagccatc acccctaatt tgttggctag aacaattgaa     420
acagtcgaag gtggtggatt agttgttatc ttgctcaaga atatgacatc attgaagcag     480
ttatatacta tgtccatgga tatacattca agatacagaa ctgaagcaca tgatgatgtt     540
gttgccagat tcaatgaaag attcttactt tctttagggt cttgcgaaaa ttgtttagtt     600
gttgatgatg aattgaatgt cttacctatt tcaggggggca acatgttaa accattgcca     660
cctaaagacg acgacgaatt gactcctaat gccaaggaat taaggagtt gaaagagagt     720
cttgctgacg tacaacctgc tgggtcatta gtgccttgt ccaaaactat aaatcaagca     780
caagcaattt tgacttttat tgatgtcatc tcagaaaaga cattgagaaa tacagtcaca     840
ttaactgcag gaagaggtcg tggtaaatct gctgctttag gtattgctat tgctgcagct     900
atttcccatg gatattccaa tattttgtt acttcaccat cacctgaaaa cttgaagaca     960
ttgtttgaat ttattttcaa aggttttgat gcattaggat ataccgaaca tatggattat    1020
gacattattc agtctactaa tccatctttc aacaaagcta ttgtcagagt tgatgttaaa    1080
agagaacaca gacaaacgat tcagtacatt tctccaaatg atagtcatgt tttaggacaa    1140
gcagaattat tgattatcga tgaagcagca gccataccac ttccaatcgt gaaaaaattg    1200
atggggccct atttgatttt tatggcttct accattaatg ggtatgaagg tactggaaga    1260
tcattatcat tgaaattgat tcaacaattg agaactcagt ccaataatgc aacaccttca    1320
gaaactaccg tggtatccag agataagaaa tccaatgaaa ttactggagc tttgactaga    1380
acattgaaag aagttgtatt ggatgagcct attagatatg caccaggcga ccctattgaa    1440
aaatggttaa ataaattgct ttgtcttgat gtttcattat ctaaaaatgc caagtttgca    1500
acaaagggca ctccacatcc atctcagtgt caacttttct atgtaaatag agatactttg    1560
ttctcctatc accctgtctc tgaagcattc ttacaaaaga tgatggcatt gtatgttgct    1620
tctcattaca aaaattcacc taatgattta caattgatga gtgatgctcc agcacatcag    1680
ttattcgtgt tgttacctcc aatagaggca ggtgataata gagtacctga cccattgtgt    1740
gttattcaat tagcattgga gggtgaaata tccaaagaaa gtgtaagaaa atcttttatct    1800
cgtggacaaa gagccggagg ggatttgata ccttggttaa tctcacaaca attccaagac    1860
gaagaatttg cctcattgtc aggtgcaaga gttgttagaa tcgctacaaa ccccgaatac    1920
tctggtatgg gttatgggtc tagagcaatg gaattattga gggactatta ctccggtaag    1980
tttaccgata tcagtgaatc caccgaattg aatgatcaca caattacaag agtcactgat    2040
agcgaattgg ccaacgcatc actaaaagat gaaattaagt tgagagacgt taagacatta    2100
```

-continued

```
cctccgttgt tattgaaatt atcagaaaaa gccccttact acttgcacta cttgggtgtc    2160
tcttatggtt tcacgtctca attacacaaa ttctggaaga aagcagggtt cactccagtt    2220
tatttgagac aaacacctaa tgaattaact ggggaacata cttcggttgt tataagtgtt    2280
ctaccaggaa gagaagataa atggttacat gaattctcga agatttccaa caaaagattt    2340
ttgagtttgt tatcatatga attcaaaaaa ttccaggctt cccaagcttt aagcattatt    2400
gaagctgcag agcaaggcga aggtgatgaa actactagtc aaaaattaac caaagaacaa    2460
ttagatctgt tgttgtctcc atttgattta aagagattgg actcgtatgc caataattta    2520
ttggattatc atgtaattgt tgatatgtta ccactaatct cccaattgtt tttttcaaaa    2580
aaaactgggc aagatatcag tttatcatca gttcaatctg ccattttatt ggctattggg    2640
ttgcagcata aagacatgga ccagatagca aagagttgaa acttaccaac gaaccaagcc    2700
atggcaatgt tgctaaaat tattcgtaaa ttctcaacct atttcagaaa agttctcagt     2760
aaagcaattg aagaaagtat gccagattta gaagatgaga atgtcgacgc catgaatggt    2820
aaggaaacgg aacaaatcga ttataaagcc attgagcaga aattgcaaga tgacttggaa    2880
gaggctggtg atgaggcaat aaaagaaatg agagaaaaac aacgtgaatt gattaatgct    2940
cttaatttag ataaatatgc tattgcagaa gatgctgaat gggatgaaaa atcaatggat    3000
aaagctacta agggaaaagg taatgttgtt agtattaaga gtgggaaaag gaaatctaaa    3060
gaaaatgcta atgatattta tgagaaagaa atgaaagcag ttaagaaatc aaagaaatca    3120
aaaaaataa                                                           3129
```

<210> SEQ ID NO 45
<211> LENGTH: 384
<212> TYPE: DNA
<213> ORGANISM: Candida albicans

<400> SEQUENCE: 45

```
atggctgcat ttgatgaaat atttgattat gtcgatagag atacttttt ccaatatttc      60 cgattgacat tagttgtttg tacttatttg attttccgta atattattc ttcatgggcc      120 attaaaaagc aaacagcaac acaattagaa caagataaaa gagaacaatc tgaaaaatct     180
gaaagagaag ctaaagaatc taagaaaaaa tttgatacta tttctaatga agctaaagaa     240
tttggttggg gtaaaaaaac tagaaataat gttaaattaa ctgaagcagt attagctgaa     300
tatagtgaac aacaaagaca agaaatcaa actagttatg atgctcaaga agatgctgat      360
attgatgatt tattagaaga ttga                                            384
```

<210> SEQ ID NO 46
<211> LENGTH: 870
<212> TYPE: DNA
<213> ORGANISM: Candida albicans

<400> SEQUENCE: 46

```
atgtcattta gaggtggtgg tggtagtggt ggtagatcaa ctcaaagaac tattcttcca     60
tttggattag attatgctga tattatatca tcaactcaag agacggaaaa accacaatta    120
ttattaccca taaatggaga tataactgaa attgaatcaa ttattgctaa acaatcaatg    180
aatttcacta aactaatgtc agaaggtcca ttttcacgg ggaatctaga tagtattgaa     240
atcaccaaaa aacgtaatca taatgatagt gaaaatgaag aagaagaaga agaagaagga    300
ggagatacag agaatactgg cgatagaaag aaaaagaaat caaagactaa tggtgatggt    360
agtagtagtg gtagtggtag tggtagtgcc agtggtgatg aatagaaag atattccgat     420
```

```
cgatataaaa aaatccaaaa aattggtaga acaattgatg aacatccata tcaaccagaa      480
tatttcccta gtgaattata ttcagtcatg ggaataacta ataaacatga taagaagaaa      540
tttttattat tatcgaaatt taaatcaaat ggaggattaa aacaaatatt atccaatgaa      600
aaattggaaa atttagatga acaatcaaaa ttaaattcaa tgaagaaaa aatgttaagt       660 atgattgata atagtgtgaa tgtcaatgat gatgataata ataatgatgg aaaacacgt       720 agtggagatg aacaagaaat tgatgaagat gatttggatg atgaatttga agatgaagat      780
gatgatgatt ataatgctga gaaatatttc gatgatggtg atgacgatga tggaggtgat      840
gatggaggtg atgatgaagc agcattttaa                                       870

<210> SEQ ID NO 47
<211> LENGTH: 1524
<212> TYPE: DNA
<213> ORGANISM: Candida albicans
<400> SEQUENCE: 47
atgttagcac tgaaaaaaaa aaggacaaga agaataaaaa ggcaaccaat ttgtgaacaa       60
attccaacct ccaatacagc attttttcttc actcttgata taccaattat gccagtgaat     120
tttttaacta gtgttgtgtt tgatgggcca gaggtgattc atattgggga ccaaattaaa      180
gaatatggac ctaccgttct tcccattcta ttaactcttg ctggagccaa gtattatttc      240
catggtgcca ccaatacgtg ggagcgagac atgcatggga aagtgtttat gattactggt      300
gggaccagtg gtattggagc tcaaatagca tatgaattgg acaacgagg agcacaacta       360 atattactta ctagaagaac caatgatcaa tgggtggctg agtatattga agatttacgt      420
gataaaacta ataatggttt gatatatgcc gaagaatgtg atttgagttc actttattca      480
atcagaaagt ttgctacaag atggcttgat aatcagccac caagaagatt agatggagtc      540
atttgttgtg ctgctgaatg tatcccacga ggaaaatcca gacaaataac tatggatgga      600
gttgaacgac aaatcggtat taattatttg gctcatttcc atttgttgac tttattgggt      660
ccatcactaa gggttcaacc tcctgataga aatgtacggg tgttgattgc aacatgttcg      720
tcgcaaaatt tgggagatgt tgatttaaac gatttattgt ggagtaacaa gaggtatcca      780
gcaactcagc catggaaggt atatggaaca tcgaaattac ttttagggtt atttgccaaa      840
gagtatcaaa gacagttgat gggatatgag cgtaaagata aggcccttg taatgttcgt       900 atcaatttaa tcaaccctgg tattgttaga acaccgtcaa caagaagatt tttgtctttg      960
ggcactgtat ggggggttgat tatctacttg attttattcc cgatctggtg gttgttttc     1020 aaaagtgctg agcaaggtgc tcaatcattt tactttgcgt tatttgctcc tattttcatg     1080
aaaatcgaag gtggtaacgt ggtacaagaa tgtaaaataa tgactaaagt tagaaaagaa     1140
tatactgatg atgacttgca acaaaaagtt ttccacaaca ctgaagaatt gatcaaacaa     1200
attgaaacaa aatcagctat tgaacgtaaa aaacatgaaa acgctaaaaa gactccagaa     1260
caaaaagcca aggaaggca agaggaattg aatagaaaga gggatttgca tattaaacca      1320
gaaactccgg aggaactaga actgaaatta aatctgttga gaaatcaaat tggtatgggg     1380
actggtattc tgtctaatga aatgccattg ttccccgatg acgaaactct caagaaggtg     1440
atcagttcca agaagaatgc tagtagtaat aatagtggtg gtctgaaatc aaataagagt     1500
caaaagaaat ctaaaaaagt atag                                            1524

<210> SEQ ID NO 48
<211> LENGTH: 993
```

```
<212> TYPE: DNA
<213> ORGANISM: Candida albicans

<400> SEQUENCE: 48
atgacagata tgtcaaacac tactactgat ggtaatgttt ctagtattgt tgttccagga      60
caatatatta gtcctactta taaattagaa aatagcaaca acgattcatc tataccagtg     120
aaatatattc ctggatcggg gacaataata tcaaatatca atatcccatc gccaaacacc     180
tcaacaaact cagttaaatc aatgccaatt atagtatcga caatattagg gaatgtatcc     240
atctcaccta ttgatcaaac cccaacatca aaaccatcca acaatgatga tatggttatc     300
gataatgagc aaactaaact ggatgaagat aaagataaag ataaatatgt taaaagttat     360
ttagtttctg tgataccaaa atctaccaaa catcaatcca ccacctccac cactactagt     420
aatcaatcag gctccaaggc aatttcagca attgcattac ctaaagaaaa tgatattgta     480
ttagttcgta ttactaaaat cactaaaatc caagcatatt gtgaaatcat atcattagat     540
accaccacca acattttacc agattcaggt cttggtaata atgggaatgg atcacatgta     600
tcaatgtcaa ttaccggaag taattctcaa cataatttca atcaaaattc aattgcttct     660
agtcaatcaa ctaatcaatc agtacaaatt tatgaattgg gagaaaattt taaagggata     720
attagaatta atgatattag atcgactgaa agagataaat taaaattaat tgattgtttt     780
aaacccggtg atattgttaa agctcaagtt atatcattag gtgatggatc taattattat     840
ttaacaacgg caaaaaatga gttaggggtt gttttcgcta aaagtgaaaa tggtgctggt     900
gatttaatgt atcctattga ttggcaaaat atgattgata ttaatagtgg ggttatagaa     960
aaacgtaaaa atgccaatcc atttttacaa taa                                 993

<210> SEQ ID NO 49
<211> LENGTH: 666
<212> TYPE: DNA
<213> ORGANISM: Candida albicans

<400> SEQUENCE: 49
atggcaggtg atctaaatct aaaaaagtct tggaatccag cattagttaa gaaccagcaa      60
aaagtttggg aagaagaaca acaaaagtta gatgaactta acgaataaaa agagagaaat     120
caggagtata aacaagaaca agaatacttg gaattactaa agctacagca tggagatcaa     180
tttcaaatta aagacttgaa caaacagcag aagctcaaaa tatccaaact aaattggatg     240
tatgatgatg taccatttga aggcaatgag aaagtggaag agaattcaag tgggtttatt     300
gaatcaaatg tagagtttac agatggcaaa tccaaagttg agaatttatt aaaaggaaat     360
catgttgtgg gcaagaagag agatggtagt ggaaccagtg atagaataaa taagataatt     420
ggggtgggga tgaccaaatc aagtaaagtc agctattccg atgatccatt actcaaaata     480
aaacagcagc aacaacaggc acaaagagtt gcccgaaaac aacatcctag tgataagcat     540
tctcatcgtt ttagacatag ttccaaaagt tcatccgata gagtgcacaa atcacatgag     600
cacgagagaa gtcgaaagca taattcctca catactcgtc acaaagatgg atcacccac      660 agataa                                                               666

<210> SEQ ID NO 50
<211> LENGTH: 2367
<212> TYPE: DNA
<213> ORGANISM: Candida albicans

<400> SEQUENCE: 50
```

```
atgttgaaaa acgataccgt tttcactaaa gatatttctt gtacggcgat aactggtaaa      60
gatgcctgga atcgrccaac accacaacca atcactatat cattatcttt cartactgat     120
ttccakaagg catcggaatt ggataatttg aaatrctcaa ttaattatgc tgttattacc     180
agaaatgtaa ctgaatttat gaaatcaaat gagcatttaa atttcaagtc attaggaaat     240
attgctcaag caattagtga tattggatta gatcaatcta gaggtggtgg atctattgtg     300
gatgtgacga taaaaagttt gaaatcagaa ataagagctg aaagtgtcga atataaaatt     360
aatagaaaca ctttgggtca acccgttcca ttagatattt tccaagttaa taaattgaga     420
ttattgacra ttattggrgt tttcacattt gaaagattac aaaaacaaat agttgatgtt     480
gatttrcaat ttaaaattgm acctaattcc aatttatatt tccatcaaat aattgctgat     540
attgtttcat acgtggaatc atctaatttc aaaactgtaa aagcattggt gtctaagatt     600
ggtcaattga catttcagaa atatgacgga gtagctgaag ttgttgctac tgtcactaaa     660
ccgaatgcat tyagtcatgt tgaaggtgtt ggagtatcat ctaccatggt caaagrcaat     720
ttcaaagata tggaaccagt taaatttgaa aacacaattg ctcaaactaa tagagcattc     780
aatttacctg ttgaaaatga gaaaactgag gattataccg gtaccacac tgcatttatt     840
gcctttggat ccaatactgg aaatcaagta gaaaatatta ccaattcatt cgaattgttg     900
caaaaatatg gaatcaccat agaagcaact tcatcattgt acatttctaa accaatgtat     960
tacttggatc aaccagattt tttcaatgga gtaattaaag tgaatttcca aaacatttca    1020
cctttccagt tgttgaaaat tctaaaagat attgaatata acatttaga aaggaaaaaa     1080
gactttgata atgggcccag atcaatagat ttggatatta tactatatga cgatttacaa    1140
ttaaataccg agaatctaat tattccacat aaatcaatgt tagaaagaac atttgtatta    1200
caaccattat gtgaagtatt gccccctgat tatattcatc ccatcagtgc agaaagtttg    1260
catagccatt tacaacaatt aataaatgat aaacctcaag agacagtaca agaatcgtct    1320
gatttattac aatttatccc agtctctaga ttgcctgtca agataatat tttgaaattt     1380
gatcaaatta atcataaatc tcctactttg attatgggta tattgaatat gactcctgat    1440
tcatttagtg atggtgggaa acattttgga aaagaactag ataatactgt gaagcaggca    1500
gagaaattag tcagtgaggg tgctacgatt attgacattg gaggagtttc cacacgccca    1560
ggaagtgttg aacccactga ggaagaagaa ttggaacgtg tgattccatt aattaaagct    1620
attcgtcaat cactgaaccc tgatttactg aaggtgttga tttcggttga tacttatcgt    1680
aggaacgttg ctgaacaaag tttacttgtg ggtgctgaca taatcaacga tatctcaatg    1740
ggcaaatatg atgaaaaaat atttgatgtg gttgctaaat acggatgtcc ttatatcatg    1800
aatcatactc gaggatcacc taaaaccatg tctaaattga ccaattatga atcaaataca    1860
aatgatgata ttatcgaata tataattgat cctaaattag gacatcaaga attggatttg    1920
tcacctgaaa tcaagaattt actcaatgga atcagtcgtg aattgagttt acaaatgttt    1980
aaagccatgg ctaaaggagt gaaaaatgg caaattattt tggatcctgg tattggattt    2040
gctaaaaatt tgaatcaaaa tttagcagtt attcgtaatg cctcgttttt taaaaaatat    2100
tctattcaaa ttaatgaacg tgttgatgat gtgacaatca acataaata tttaagttttt   2160
aatggtgctt gtgttttggt ggggacatca agaaagaagt ttttggggac attaactggt    2220
aatgaagtgc ctctggatcg agtatttggc actggtgcaa cagtgtctgc gtgtattgaa    2280
caaaacactg atattgtaag agttcatgat gttaaagaaa tgaaagatgt agtatgtata    2340
agtgatgcaa tttataaaaa tgtataa                                        2367
```

<210> SEQ ID NO 51
<211> LENGTH: 447
<212> TYPE: DNA
<213> ORGANISM: Candida albicans

<400> SEQUENCE: 51

```
atgtcagata tagatataga taatgtatta aatttagaag aagaacaata tgaattagga      60
tttaaagaag gtcaaataca aggaacaaaa gatcaatatt tagaaggaaa agaatatggt     120
tatcaaactg gatttcaacg attttttaatc attggttata ttcaagaatt aatgaaattt    180
tggttatccc atatagatca atataataac tcttcttcac ttcggaatca tttgaataat     240
ttggaaaata ttttggcaca aatttctata acgaatggag ataaagaagt tgaagattat    300
gaaaaaaata ttaaaaaggc aagaaataaa ttaagagtga tagctagtat aactaaagaa    360
acttggaaaa ttgattcatt agataatttg gtgaaagaag taggtggaac tttacaagtt    420
agtgaaaacc ccgatgatat gtggtga                                        447
```

<210> SEQ ID NO 52
<211> LENGTH: 810
<212> TYPE: DNA
<213> ORGANISM: Candida albicans

<400> SEQUENCE: 52

```
atgagacaaa agcgtgccaa ggcctataag aaacaaatga gtgtgtatgt ccacgcattc      60
aaattcagag aacctatacca aataatagta gacaatgaac tcatcaccac ttgtcaatca    120
gcatcatttg acattaataa agggtttact cgaactatcc aagcagaaaa caaacccatg    180
attactcaat gttgtatcca agcattatat gatactaaga atcaaccagc aatagatatt    240
gctaaatcat ttgaacgaag aaaatgtaat catcgtgaag ccatcgatcc tagtcaatgt    300
attgaatcaa tcgttaatat taaaggacaa aataaacatc gatatatcgt tgccagtcaa    360
gatttacaat tacgtaaaaa attgcggaaa atccctggag taccattgat ttatatgaat    420
cgatcagtga tggttatgga accgatcagt gatgttagta tcaatataa tatgaattat     480
gaatcgaaaa aattgaccgg aggattgaat gatattgaag ctgggaaatt ggaaaagcaa    540
aatgaaggtg aagatgggga tgggggatgaa ctggaagtta aaaagaagaa aagaaaagga    600
cctaaagaac caaacccatt aagtgtcaaa agaagaaaa cagataatgc aactgctgcc    660
agtactaatc aagagcagaa aaagaaacca aatagaagaa aaagacatgg caagtcaaaa    720
gcagaagaga aggaagacca agaacaggag caagtgaacg aagcaacaac taatgaagat    780
gcacaggagg caataacagc tactgaataa                                     810
```

<210> SEQ ID NO 53
<211> LENGTH: 921
<212> TYPE: DNA
<213> ORGANISM: Candida albicans

<400> SEQUENCE: 53

```
atgaccgact taacaccatt attccgtcag tgtgttgaca tcgttcagca agagtacaag      60
actcagccaa ccacagccaa acaaccttac taccttaacg acacattttat taaggagacg    120
accgcctttt tccatgtctt gaccaacttg aaccagttca tcaacgaaac caaatcaagt    180
tatctagcca taaacgatga cacgaaacta gctgggtcga ttgacgacaa aaacaagatc    240
gacgaagagt tcaattacaa ggtccagcaa atgtacaagc gattaaatca tttggagaca    300
```

| | |
|---|---:|
| tacgaaacaa agaggcagtc gttactacca aagactagcg ggtggttcag tttcctagac | 360 |
| gaatccaacg accaggacat atactttgag acattggcga atcatcgtat gcagatattg | 420 |
| cggttcctca tggagacact caaccatgta acaaacgct ttgaaaacat ccaacaaaaa | 480 |
| agattggctc gtgaacgaca actaaacttg ttaaacttcc aaaactttga agacggcgag | 540 |
| gagttggagg atgtgtttcc cacactagac caaatccagc aagtaccaga actatcccaa | 600 |
| caacaaatcc aacaacttga aacggaaaac caggaatttc tcaatatgaa aactagccaa | 660 |
| ttgaaacaag tcgaaaaagt gcagcagtca atactcgaca tcgtcaacat ccaaaacgaa | 720 |
| ttggcattta agctacaaga ccagggccaa cagatcgagt cgttgatgga ctcacatgct | 780 |
| gatgttcaaa cagaagtcca atggggaac cggacattaa gtcaggctac gaaaagaat | 840 |
| aaaagaggtg ctaatatgtt ggtcatgcta tgtatagtac taggtgtgtt attagtgttg | 900 |
| gtagactatg tatcattctg a | 921 |

<210> SEQ ID NO 54
<211> LENGTH: 579
<212> TYPE: DNA
<213> ORGANISM: Candida albicans

<400> SEQUENCE: 54

| | |
|---|---:|
| atgtcaggta taaaaatcag tttaaagaaa aagaatccaa aactaaagaa acttatagtg | 60 |
| aataattcac aacaaacaga tgaactgtca gagcagcaga agaaattgat tacatcatat | 120 |
| tctacagaag ataagactac tcataaagat gaaaccaaac caataatagt tttgaagcaa | 180 |
| ccatgtaaaa gtatgttaca gaaagaaatc gaaattgacg agaaaccaat actaccgtat | 240 |
| ggtgtaacaa cgtttgaaaa agtggagact acaaaacaat caatgatcaa aaagatcgaa | 300 |
| tcagaagatt ccgatgatga ctccagcgat gatagaaaaa tcccaataga tgaatttggt | 360 |
| gcagcatttt taagaggact tggttggcaa gaagaagagg aaaagaacaa ggatgacagc | 420 |
| aaatccacta acactcaaaa tttatctcat aggaaacatg gaatcacctt agggattgga | 480 |
| gcaaaaccta tagatgaaga aataatacaa gatttaaact ctacggaaaa aggtattcca | 540 |
| atcataaaac gacgtaaatt aaatcatata aataaataa | 579 |

<210> SEQ ID NO 55
<211> LENGTH: 2145
<212> TYPE: DNA
<213> ORGANISM: Candida albicans

<400> SEQUENCE: 55

| | |
|---|---:|
| atggctaaag catcgaaaca aacaaagaag tttcaaaata agcatttgaa acatacaata | 60 |
| gagcaacgta agaaggttca ggcacagaac aagaaaattg cttccagaaa aaagagtggt | 120 |
| agttcatcat ctgggaaag caatgccccc aaacgtgctg atggaaaagc caaggaagtc | 180 |
| tttgaagata tgtcagtaga cgactttttc ggaggtgggt ttgaagttcc taagaaaaag | 240 |
| aataagaaca agaacaagca agatacaatt gaagaaaacg aagaagaaga ctcgtcttct | 300 |
| gaagaggaag atgaagaagc aatgaaggaa aacttgaaaa aattagaggc agacgatcca | 360 |
| gaattttaca atacttgaa agataatgac atgatttat tagattttga agctgtcaat | 420 |
| cctttagatg ccataagtga tgacgagggt gatgaagatg atgacgaaga aattgaaaaa | 480 |
| gaagttccta gcgatgatga ttctgaggaa gaaccaactc taggaaaagt aaaaggatct | 540 |
| aaaattgaaa taacgaaatc gttggttaaa aaatggaatc aacaattaga taagccaacc | 600 |
| cctaagatta caagaaacat acttattgct tttaaggcag ctgtcaatat ccacaattcg | 660 |

-continued

```
gattctgaag attataagtt ttccataaca gaccctaaag catttctga attgatgtta      720
ttagttttga aaaaagttcc tatttctgtg caaaagttgg ttaaatacaa actaacact     780
caaggagtaa gaactatccc gcaaaagaat caatatgcca ctcaaattgc agctattttg    840
aaatcacatg caggttcatt catcacttta ttaaacgata tcaccaatac tgaaactgct    900
gctttaattt tggcttctat ttatgaggtg ttcccatttt atttgtcaca cagaagatta    960
ttaaaacaaa ttttgactgc cgttgtaaat gtttggtcta gttcttcaga tattgatacg   1020
caaatttcta catttgcatt tttgaacaat gtatctagag agtatcctaa atcggtcttg   1080
gaaaccgttt tgaaattaac ttactcgtct ttcttacaga attgcagaaa acaaatgtc    1140
cataccatgg cccagattaa cttttgtaaa aactcagctg tggaattgtt tggaatcaat   1200
gaaactttgg gttatcaagt tggttttgag tatgttagac aattggctat acatttacgt   1260
aacagtatca atgctacttc gaacgcaaaa gagggataca aaactatata caactggcaa   1320
tactgtcatt cattggattt ttggtccaga gttttgtctc aacattgtaa tcctgaaaaa   1380
gagttgcaaa accataaatc caagaatctc ccattgaggc aattaattta tccattagta   1440
caagttactt tgggtgctat tagattgatc cctaccgctc aatttttcc attaagattt     1500
tatttaatta gatccttgat cagattatct caatctaccg gcgtgtttat tcctttattc   1560
ccattgattt cagagatttt atcatctaca gcaatgacca aggcaccaaa agcttctact   1620
ttgcaagctg ttgatttcga acacaatatt aaagttaatc aagcatattt gggcactaga   1680
gtttaccaag atgggttatg tgagcaattt atagagttat ctggtgaatt ttttggtttg   1740
tatgcgaaga gtattgcctt cccagagttg gtgaccccag ctgtgttagc attgagaaga   1800
tttgtgaaaa aatcaaaaaa tgtaaaattc aacaaacaat tgcaacaatt gatagaaaaa   1860
ttaaatgcaa atgctgtttt cattactgga aaaagatcca atgttgagta tggaccatca   1920
aataaagcag aggtacaaca attttgagt gactttgaat gggaaaagac accttggggt    1980
caatatgtta gtgtacaaag acagttgaaa gcagaaagat taagaatctt gaaagaagcc   2040
caagaagagg aagcaaaagc acaagctgaa caaaagaaaa aagaagaaga agaggatgag   2100
caagaagatg aagatattgt aatggaggag gaagatgatg agtag                   2145
```

<210> SEQ ID NO 56
<211> LENGTH: 846
<212> TYPE: DNA
<213> ORGANISM: Candida albicans

<400> SEQUENCE: 56

```
atgtcaagag gtaaaacaat aagaccgtcg tattacgatg aagaggaatc ttcacaagat     60
gaattgagtc acactttaag taaaggccgt tcaaatattg gctcacaatc agatgatgaa    120
gaaatgtcca aaatatcatt tggtgctctt aatcgagccc aatctaaatt gaacaaacac    180
aatcaaaaac ataaaacaca ggaggacaac tataagtctt cagaagaaga gttttttcgat  240
tcaggctcag attcagatgg tccaccagag gaaacaagtt ctaaagatac taaaaagaag   300
aaaaacaaac atgctccatc agaatcctct tccaaaagac cagtttcaag gataagagat  360
atacctggat taccgtctag aaaacaacaa actttgcata ccgatattag gtttgatgct   420
gcgtatggga agctgatttt ggccaaggca agaaaagatt atgcctttttt agatgaatat  480
cgaaagcaag aaatagcgaa tatgaaagtt ttattaaaag ataaaagag tagattgaat   540
gatgatgaaa gagaagaaat caactacag ttacaatcat taaaatctcg tatggatact   600
```

-continued

```
ttgaaaaatc gtgatttgga aaataatatc ttatcaaatt ataaaaagca acaaatggaa      660
agtttcaaag aaggtaaagt gaataaacct tattttctta acgtagtga taaacgtaag      720 atattacaaa aggccaaatt tgattctatg aagcctaaac aaagagaaaa ggcaatggaa      780
aggaaaagga agaagagatt gggtaaagaa ttcagacaat tggaattcaa accaactaat      840
cgttaa                                                                846
```

<210> SEQ ID NO 57
<211> LENGTH: 2550
<212> TYPE: DNA
<213> ORGANISM: Candida albicans

<400> SEQUENCE: 57

```
atgtccgatc aattagaaaa agatatagag gaatcgatag ctaaccttga ttatcagcaa       60
aatcaagaac accatgaaac agaacaagat aaagataaag aacatcaaga cgtagagaag      120
caatccagcg aagaagaaac caaaggaatt gagcatgtta cagattcaaa tacagacgat      180
atcggcgtaa caaaactgca ggatacagaa gaagtcattg aaaattcgcc agtggaccct      240
caattgaaag aacaacagga atctacaacc aagatgctgt tgtctgaaag agatttggta      300
gatgagatag atgagctttt tactaactcc acgaaaactg tcactgaaaa taatcaacca      360
agtgaaacta acaaaagagc ctacgaatcc gtggagaccc cacaggaact aacaccaaat      420
gataaacgcc aaaaactaga tgcaaataca gaaaacctcag tgccaactga acttgaatct      480
gtaaataacc ataacgagca actgcagcct atagagccaa cccaagaaag acaaccctct      540
acaaccgaaa caacttactc catatcagta cccgtttcta ctacaaatga ggtcgaaaga      600
gcgtcttccc tgattaatga acaagaagat ctagaaatga ttgccaaaca ataccaacaa      660
gctacaaatc ttgaaataga gcgagccatg gagggtcatg gtgatggagg acaacacttt      720
tcaactcaag aaaatggtca gccttctgga tcgctgctaa tatcttccat tgttccttct      780
gattctgaat tgctcaacac caatcaggca tatgctgcat atacttcgct atcttctcaa      840
ttagaacagc atactctggc tagtgctatg ctttcttctg ccacacttc tgctttgcct       900 ttgtcgatta ttgctccagt atatttacca ccaagaattc aattgttaat aaatactttg      960
cccacattgg acaatttagc aacccagcta ttacgtacag ttgcaactag tccataccaa     1020
aaaataattg atttggcctc taacccagat acatcagcag gggctactta tagagatttg     1080
acttctttgt ttgagtttac aaaaagatta tacagtgaag atgatccatt tttaactgtt     1140
gaacatatag ctcctggtat gtggaaggaa ggagaagaaa cccctagcat tttttaaacct     1200 aaacaacaaa gtatagaatc tactttacgt aaagtcaact tggcgacatt tttggcagcc     1260
actttaggta cgatggaaat tggttctttt taccttaatg aatcgttcct agatgttttt     1320
tgtccgctga ataatttgga ccctctgaat gcattatcca atttaggagg ttatcaaaat     1380
gggttacaaa gtactgatag tcccgtaggt gcgagagtcg gaaaattgtt aaaacctcaa     1440
gccacgttgt atttagactt gaagacccaa gcgtatatct cagccattga ggctggagag     1500
agatcaaagg aagaaatttt ggaggacatt ttgcccgatg atctccatgt ttatttgatg     1560
tcaagaagga atgcaaagtt gttgagtcca acggaaactg actttgtgtg gagatgcaaa     1620
cagagaaagg agctgttatt aaattacacc gaggaaacac ctttgagtga gcaatatgat     1680
tggtttacat ttttgagaga cttgtttgat tatgtctcga agaatattgc ttatttgata     1740
tggggaaaaa tgggtaaaac aatgaaaaat agaagggaag acacacctca tactcaggaa     1800
ttgcttgata atactactgg ttctactcaa atgccaaatc agttgtcttc atcttctggt     1860
```

-continued

| | |
|---|---|
| caagcttcat cgacaccatc tgttgtagat cctaacaaaa tgttagtgtc ggagatgaga | 1920 |
| gaagcaaata ttgcagtgcc aaaaccctca caaagacggg cgtggtctcg agaagaagaa | 1980 |
| aaggctttaa ggcatgcatt agaactcaag gtccacatt gggcaacaat tctagaatta | 2040 |
| tttggtcaag gtggaaagat ttcggaagct ttgaagaata gaactcaagt gcaattaaaa | 2100 |
| gacaaggcaa gaaattggaa aaagtttttt cttagaagcg gtttggaaat tcctagttat | 2160 |
| ttgcggggtg ttacaggtgg tgtagatgat ggtaaacgga aaaggataa cgttactaag | 2220 |
| aaaactgctg ctgcacctgt tccaaatatg ctggaacaat tgcaacaaca acaacagcga | 2280 |
| caacaagaaa agcaagaaaa gcaacaacaa gaagagcaac aagcacaaca actggaaaaa | 2340 |
| caactagagc agcaacaaga gccacaacaa gagcagcaac aagagcagca acaaacagag | 2400 |
| aaacaacaag cagagcaaga gcagccagat caaccccagg aggaacaaca acaagagaaa | 2460 |
| gaacaaccgg atcagcaaca accagatcaa caacacccag atcgacaaca acaagagcag | 2520 |
| atccaacaac cagaaagtct ggataaatag | 2550 |

<210> SEQ ID NO 58
<211> LENGTH: 3294
<212> TYPE: DNA
<213> ORGANISM: Candida albicans
<220> FEATURE:
<221> NAME/KEY: misc_feature
<222> LOCATION: (1)...(3294)
<223> OTHER INFORMATION: n = A,T,C or G

<400> SEQUENCE: 58

| | |
|---|---|
| atgagtggtc ctgttacttt tgaaaagaca tttcgtagag atgccttaat cgatatagaa | 60 |
| aagaaatatc aaaaggtatg ggcagaagag aaagttttg aagttgatgc cccaactttt | 120 |
| gaagaatgtc ctattgaaga tgttgaacaa gttcaagaag cacatccaaa attctttgcc | 180 |
| actatggctt atccttacat gaatggtgtc ttgcacgccg tcatgccttt acattgtct | 240 |
| aaagttgaat ttgcaactgg gttccaaaga atgaatggta agagagcatt attcccattg | 300 |
| ggtttccatt gtacgggtat gccaattaaa gcagctgccg ataaaatcaa aagagaagtt | 360 |
| gaattgtttg gatctgattt ttctaaagct cctgctgatg acgaagatgc agaagaaagc | 420 |
| caacaaccag ctaaaaccga aactaaaaga gaagatgtca ctaaattctc ttccaaaaaa | 480 |
| tctaaggctg ctgccaaaca aggtagagcc aagttccaat atgagatcat gatgcaattg | 540 |
| ggaatcccaa gagaagaagt tgccaagttt gctaacaccg actactggtt agagttttc | 600 |
| ccaccattgt gtcaaaaaga tgtaactgct tttggggcta gagttgattg gagacgttct | 660 |
| atgatcacaa ccgatgctaa tccttattat gatgcattg ttagatggca aattaataga | 720 |
| ttgagagatg ttggtaaaat taagtttggt gaaagatata ccatttattc tgaaaaggat | 780 |
| ggccaagcat gtttggatca cgatagacaa tctggtgaag gtgttggtcc acaagaatat | 840 |
| gttggtataa aaatcagatt aactgatgta gcaccacaag cacaagaact tttcaagaaa | 900 |
| gagagtctcg atgtgaagga gaacaaagtt tacttggttg ctgcaacttt aagaccagaa | 960 |
| actatgtatg gtcaaacttg ttgttttgtg agtccaaaaa ttgattatgg tgttttgat | 1020 |
| gctggtaatg gtgactattt cattaccact gaacgtgctt tcaaaaatat gtcttccaa | 1080 |
| aacttgactc cgaaaagagg atattataaa ccacttttca ctatcaatgg taagacattg | 1140 |
| attggatctc gaattgatgc tccatatgct gtcaacaaaa acttgagagt tttgcctatg | 1200 |
| gaaacagttc ttgcaaccaa aggtactggt gtggtcactt gtgttccatc agattctcca | 1260 |

-continued

| | |
|---|---|
| gatgattttg ttaccacaag agacttggcc aataaaccag agtactatgg aattgaaaaa | 1320 |
| gactgggtac aaacagatat tgttcctatt gtccataccg aaaaatacgg tgataagtgt | 1380 |
| gctgagtttt tggttaatga tttgaagata cagtcaccaa aagattctgt gcagttggcc | 1440 |
| aacgccaagg aattggctta taaagaaggt ttttacaatg gtactatgct tattggtaaa | 1500 |
| tacaaaggtg ataaagttga agacgccaag cctaaagtca aacaagactt aattgatgaa | 1560 |
| ggtcttgctt ttgtttacaa tgaaccagaa tcccaagtta tttctagatc tggtgatgat | 1620 |
| tgttgtgtat cattggaaga tcaatggtat attgattatg gtgaagaagc ttggttgggt | 1680 |
| gaagccttag aatgtcttaa gaacatgaaa acatactcca aggaaaccag acatggtttc | 1740 |
| gaaggtgttt tagcctggat gaagaactgg gctgtcacca aaaatttgg tttgggtact | 1800 |
| aaattgcctt gggatcctca atatttggtc gaatctttgt cagattctac tgtctatatg | 1860 |
| gcttattata ctattgatcg tttcttgcat tcagattatt acggtaagaa ggcaggtaag | 1920 |
| ttcgacatta agccagagca aatgactgat gaagtatttg attacatctt tactcgtcgt | 1980 |
| gatgacgttg aaactgacat tccaaaggaa caattgaagg aaatgagaag agagtttgaa | 2040 |
| tatttttacc cattagacgt cagagtttca ggaaaagatt tgatcccaaa tcatttgaca | 2100 |
| ttcttcatct atacccatgt cgccttgttc ccaaaaagat tttggccaag aggtgttaga | 2160 |
| gccaacggac atttgttgtt gaacaatgct aagatgtcca aatcaactgg taactttatg | 2220 |
| actttagaac aaatcattga aaaattcgga gctgatgcct ctagaattgc tatggccgat | 2280 |
| gcaggtgaca ctgttgaaga tgccaacttt gacgaagcca atgctaatgc tgcaatcttg | 2340 |
| agattgacaa ctttgaaaga ttggtgtgaa gaagaagtga aaaaccaaga taagttaaga | 2400 |
| attggtgact acgattcctt ctttgatgct gcttttgaaa atgaaatgaa tgatttgatt | 2460 |
| gaaaagactt accaacaata cactttgagt aattacaaac aagcattgaa atccggattg | 2520 |
| tttgatttcc aaatcgccag agatatttat agagaaagtg taaacacaac aggaattggt | 2580 |
| atgcacaagg atcttgtttt gaaatacatt gaataccaag cattgatgtt agctccaatt | 2640 |
| gctcctcatt tgccgaata cctttacaga gaagttttag gtaaaaatgg aagtgttcaa | 2700 |
| ctagcnaagt tcccaagagc ctcaaagcct gtttccaaag ctattcttga tgctctggaa | 2760 |
| tatgtcagaa gccttaccag atctatccgt gaagcagaag gtcaagcttt gaaaaagaag | 2820 |
| aaaggaaagt ctgatgttga tgggtcaaaa ccaatcagct tgacagtttt ggtttccaac | 2880 |
| actttcccag aatggcaaga taactatatt gaacttgtca gagaattgtt tgaacaaaac | 2940 |
| aagttggacg acaataatgt tataagacaa aaggttggca aggacatgaa acgtggtatg | 3000 |
| ccatacatcc accaaattaa aactagattg gcaactgaag atgctgacac tgttttcaac | 3060 |
| agaaaattga cttttgatga aatcgataca ttgaaaaatg ttgttgaaat tgtcaagaat | 3120 |
| gccccatact ctcttaaagt tgaaaaattg gagattctta gtttcaataa cggtgaaact | 3180 |
| aaggggaaga atattattag tggtgaagac aatattgagc tcaatttcaa gggtaaaata | 3240 |
| atggaaaatg ctgtacctgg tgagcctggt atctttatta aaaatgtcga ataa | 3294 |

<210> SEQ ID NO 59
<211> LENGTH: 1563
<212> TYPE: DNA
<213> ORGANISM: Candida albicans

<400> SEQUENCE: 59

| | |
|---|---|
| atgaatgttg gatctatttt aaatgacgac ccaccatcaa gtgggaatgc gaatgggaat | 60 |
| gatgataata ccaagattat taaatcccct actgcatacc ataaaccttc tgttcatgaa | 120 |

-continued

```
cgtcattcaa taacgagcat gttgaatgac actccgtcag attcaactcc aactaaaaaa      180
ccagaaccga ctataagtcc agagtttaga aacccagca taagtctgtt aacttctcca       240
agtgttgcac ataaacctcc gccactacca ccgtcactga gtctggttgg aagtagtgag      300
cattcgagtg caagatcgtc cccggctatc acgaagagaa actcgattgc aaacattatc     360
gatgcttatg aagaaccagc tactaaaact gaaaaaagg ctgagctaaa ctcaccaaag       420
ataaaccaac tgacaccggt gccaaagctt gaggaacacg agaatgatac aaacaaagta     480
gaaaaggttg tggatagtgc acctgaacca aaaccaaaaa aggagcctca accagttttt     540
gacgaccaag acgatgactt gacaaaaatc aaaagctca agcaatctaa gaaaccacgt      600
cggtatgaaa cacctccaat ttgggcccag aggtgggttc ccccaaatag acagaaggag     660
gaaactaatg ttgatgacgg gaatgaagcc ataactagac tttctgaaaa accggtatt      720
gattatacca ctaccagaag tgttgatttg gagtgtagta ttactggtat gatacccca     780
agttcaatca cgagaaaaat agctgaatgg gtgtatgcca ttttttccaa tgttgaagaa     840
aaaagtaaaa ggaatgttga attggagttg aaatttggga aaattattga caaaagaagt     900
ggtaatagaa ttgacttgaa tgtggtgaca gaatgtattt tcactgatca ttctagtgtg     960
tttttttgaca tgcaagtgga agaggtggcc tggaaagaaa taacaaaatt cttggatgaa    1020
ttggaaaaaa gtttccaaga agggaaaaag ggaagaaaat ttaaaactct tgaatctgat    1080
aatactgaca gtttctatca attggggaga aaaggtgagc accctaagcg gattcgtgta    1140
accaaagaca acttactatc gccaccgaga ttggttgcca tacagaagga acgtgtggca    1200
gatttatata ttcacaatcc gggctcctta tttgatttga ggttatctat gtcattggaa    1260
ataccagtgc cacaggggaa cattgagtcg attattacca agaataagcc agagatggtc    1320
agggagaaga agagaatttc ttatacacat ccacctacca ttaccaaatt tgacttgact    1380
agggtcattg gtaataaaac agaagataaa tatgaggtag agttggaggc gggtgttatg    1440
gaaatatttg ctgctattga taaaatccag aaaggggtag ataatcttag attggaggaa    1500
ttaattgaag tttttttgaa caatgcaaga actctcaata atagatttgaa caagatttgc    1560
tag                                                                  1563
```

<210> SEQ ID NO 60
<211> LENGTH: 597
<212> TYPE: DNA
<213> ORGANISM: Candida albicans

<400> SEQUENCE: 60

```
atggttaacg gtccagctga acttcgtaga aaattagtca ttgtcggtga tggtgcttgt      60
ggtaagactt gtttattaat tgttttttca aaaggtactt tcccagaagt ttatgtccca    120
acagttttg aaaattacgt tgctgatgtt gaagttgatg gtagaaaagt tgaattggca    180
ttatgggata ctgctggtca agaagattat gatagattaa gaccattatc ttatccagat   240
tctaatgtta ttttgatttg ttttttcagtt gattcaccag attctttaga taacgtttta    300
gaaaaatgga tttctgaagt tttacatttc tgtcaaggtg ttccaatcat ttttagttggt    360
tgtaaatctg atttaagaga tgatcctcat actattgaag ccttgagaca caacaacaa    420
caaccagtct caacttctga aggccaacaa gttgctcaaa gaattggtgc tgctgattac   480
ttggaatgtt ctgctaaaac cggtagaggt gttagaagaa tgtttgaagc tgctactaga   540
gcttctttaa gagttaaaga aagaaggaa aagaagaaga aatgtgttgt cttgtaa       597
```

-continued

```
<210> SEQ ID NO 61
<211> LENGTH: 2127
<212> TYPE: DNA
<213> ORGANISM: Candida albicans

<400> SEQUENCE: 61
atggaagtca cttctttgcc aattaaactt cagccatcaa acattagacc catagcattt      60
cgaatattgt ctaaaaaaca tggattaaat attaatacag atgctttagc aattttaaca    120
gagaccatcg gctacaaatt tggaactgat tggaaaagtg tgagatcaca acaatttctt    180
gaagaggttg ccaaagtttg gaaatcgaa gatcggggac tatttattga tggcgatggg     240
ttaaaacaag ttttgaagga tatgaattcc aaaagcagca atgatacaaa agagctcat    300
cgaactgaca ccctagttga tatcactaat gatggtaacc aaaatcatac tcatagccac   360
caggataagc aaataagttt tgaagataaa aatatggaac atgaagaaag agatgatgta  420
ccaatcaact ggcaagatta tttcaaagtt gtatctccca ataaccaacc tactagtata  480
ttcgacaaaa caagaaaaca atttgacata gtatttaaaa ataatgatga caaggataag  540
aaagccgagc gtggcgggaa acttgagtca attgtggcag agttagtaaa aaatttgcct  600
gcatctattg aatcattcaa taatcgatac tatctcttaa gtgatcgatt atcgagaaac  660
gaaaattttc aaaaaaaatc attaatcagt ctatcagcgt taaattcttt caagaagga    720
aaaacagata gtataactgg tcatgaaatt agtttaatca aaaatatgtt gggtcgagat  780
ggtcaaaaat ttttgatatt cggtttgctc agtaaaaatg caaacgatga atacacattg  840
gaagatgaaa cagaccacat tgaattaaac ttatctcaag cttttaaatc tcaaggattg  900
ttttattgtc ccggaatgtt tctattagtg gaaggtattt attctgcaag tgggggtaat  960
tccaaccagg atcatggtta tatcggagga tgtttttatg ttagtaatat cgggcaccca 1020
ccaagtgaac gaagagagac aagcttagat gtttatggga atttggattt tttagggatg 1080
catagacaaa ttgcacctgt gacaggtgaa aaaatcacca aaatatctaa aaagtttaag 1140
agagattgg ttctaatcga aaagaccttg tataatcata acttatttt tgtgggtacc   1200
gatttatact tggatgattt caaagttttg gatgggttgc gaaagttttt ccaaaaatta 1260
gaaaattcaa ttattgaatc aatcgaggac gaagaagggc aaatggccga aggaaccaat 1320
ataccacttg ctttagtttt cacagggtca tttgtgtcaa aacctttatc agttacaaat 1380
tcatcagtga ccaacatcac caattcagaa tcatacaaga gcaattttga taatttcaca 1440
acaatcgtga gcaaataccc aaacattgta tctcgctgca aaataatatt gattccaggt 1500
aaaaatgatc cttggcaatc tacttattca ttgggatcat ctagcttaaa ctattttcct 1560
cagtcgtcta ttcaaaagt gtttatcaat cgattggaaa aattattgcc caagggaaat 1620
ttagtagttt catggaatcc cacaagaata aattacttgt cacaagagtt ggtagtattc 1680
aaagacgaat tgatgaccaa attgaaacga atgacatta ttttccctcg tgatattcaa  1740
gaacaagaag agttgattgc acaagatgac caaagaacta acgaggagag aatcaataat 1800
ttaatccaga ataaaaatac tcatttgcct tcaaaaatca acaggcaag aaaactagtg   1860
aaaccatttt tggatcaagg aaatttacaa ccattcttga agaacctaaa attaatcaac 1920
ttggcttatg attatagttt aagaattgaa ccattgccca gtgtaattat tttgaacgat 1980
tcaagtttcg acaatttga agtgacttat aatggttgca agtggttaa cattacttca   2040
gttgtcagct tgaataatag aaaattcaat tatgttgaat attatccagg aactaaaaga 2100
tttgaattta aggatttgta tttctaa                                      2127
```

<210> SEQ ID NO 62
<211> LENGTH: 3293
<212> TYPE: DNA
<213> ORGANISM: Candida albicans

<400> SEQUENCE: 62

| | | | | | |
|---|---|---|---|---|---|
| atgagtggtc | ctgttacttt | tgaaaagaca | tttcgtagag | atgccttaat | cgatatagaa | 60 |
| aagaaatatc | aaaaggtatg | ggcagaagag | aaagttttg | aagttgatgc | cccaactttt | 120 |
| gaagaatgtc | ctattgaaga | tgttaacaa | gttcaagaag | cacatccaaa | attctttgcc | 180 |
| actatggctt | atccttacat | gaatggtgtc | ttgcacgccg | tcatgcctt | acattgtct | 240 |
| aaagttgaat | ttgcaactgg | gttccaaaga | tgaatggta | agagagcatt | attcccattg | 300 |
| ggtttccatt | gtacgggtat | gccaattaaa | gcagctgccg | ataaaatcaa | aagagaagtt | 360 |
| gaattgtttg | gatctgattt | ttctaaagct | cctgctgatg | acgaagatgc | agaagaaagc | 420 |
| caacaaccag | ctaaaaccga | actaaaaga | gaagatgtca | ctaaattctc | ttccaaaaaa | 480 |
| tctaaggctg | ctgccaaaca | aggtagagcc | aagttccaat | atgagatcat | gatgcaattg | 540 |
| ggaatcccaa | gagaagaagt | tgccaagttt | gctaacaccg | actactggtt | agagttttc | 600 |
| ccaccattgt | gtcaaaaaga | tgtaactgct | tttggggcta | gagttgattg | gagacgttct | 660 |
| atgatcacaa | ccgatgctaa | tccttattat | gatgcatttg | ttagatggca | aattaataga | 720 |
| ttgagagatg | ttggtaaaat | taagtttggt | gaaagatata | ccatttattc | tgaaaaggat | 780 |
| ggccaagcat | gtttggatca | cgatagacaa | tctggtgaag | gtgttggtcc | acaagaatat | 840 |
| gttggtataa | aaatcagatt | aactgatgta | gcaccacaag | cacaagaact | tttcaagaaa | 900 |
| gagagtctcg | atgtgaagga | gaacaaagtt | tacttggttg | ctgcaacttt | aagaccagaa | 960 |
| actatgtatg | gtcaaacttg | ttgttttgtg | agtccaaaaa | ttgattatgg | tgttttgat | 1020 |
| gctggtaatg | gtgactattt | cattaccact | gaacgtgctt | tcaaaaatat | gtctttccaa | 1080 |
| aacttgactc | cgaaaagagg | atattataaa | ccacttttca | ctatcaatgg | taagacattg | 1140 |
| attggatctc | gaattgatgc | tccatatgct | gtcaacaaaa | acttgagagt | tttgcctatg | 1200 |
| gaaacagttc | ttgcaaccaa | aggtactggt | gtggtcactt | gtgttccatc | agattctcca | 1260 |
| gatgattttt | taccacaag | agacttggcc | aataaaccag | agtactatgg | aattgaaaaa | 1320 |
| gactgggtac | aaacagatat | tgttcctatt | gtccataccg | aaaaatacgg | tgataagtgt | 1380 |
| gctgagtttt | tggttaatga | tttgaagata | cagtcaccaa | aagattctgt | gcagttggcc | 1440 |
| aacgccaagg | aattggctta | taagaaggt | ttttacaatg | gtactatgct | tattggtaaa | 1500 |
| tacaaaggtg | ataagttga | agacgccaag | cctaaagtca | acaagactt | aattgatgaa | 1560 |
| ggtcttgctt | ttgtttacaa | tgaaccagaa | tcccaagtta | tttctagatc | tggtgatgat | 1620 |
| tgttgtgtat | cattggaaga | tcaatggtat | attgattatg | gtgaagaagc | ttggttgggt | 1680 |
| gaagccttag | aatgtcttaa | gaacatggaa | acatactcca | aggaaaccag | acatggtttc | 1740 |
| gaaggtgttt | tagcctggat | gaagaactgg | gctgtcacca | gaaaatttgg | tttgggtact | 1800 |
| aaattgcctt | gggatcctca | atatttggtc | gaatctttgt | cagattctac | tgtctatatg | 1860 |
| gcttattata | ctattgatcg | tttcttgcat | tcagattatt | acgtaagaa | ggcaggtaag | 1920 |
| ttcgacatta | agccagagca | aatgactgat | gaagtatttg | attacatctt | tactcgtcgt | 1980 |
| gatgacgttg | aaactgacat | tccaaaggaa | caattgaagg | aaatgagaag | agagtttgaa | 2040 |
| tatttttacc | cattagacgt | cagagtttca | ggaaaagatt | tgatcccaaa | tcatttgaca | 2100 |

-continued

```
ttcttcatct ataccoatgt cgccttgttc ccaaaaagat tttggccaag aggtgttaga      2160
gccaacggac atttgttgtt gaacaatgct aagatgtcca aatcaactgg taactttatg      2220
actttagaac aaatcattga aaaattcgga gctgatgcct ctagaattgc tatggccgat      2280
gcaggtgaca ctgttgaaga tgccaacttt gacgaagcca atgctaatgc tgcaatcttg      2340
agattgacaa ctttgaaaga ttggtgtgaa gaagaagtga aaaccaaga taagttaaga      2400 attggtgact acgattcctt ctttgatgct gcttttgaaa atgaaatgaa tgatttgatt      2460
gaaaagactt accaacaata cactttgagt aattacaaac aagcattgaa atccggattg      2520
tttgatttcc aaatcgccag agatatttat agagaaagtg taaacacaac aggaattggt      2580
atgcacaagg atcttgtttt gaaatacatt gaataccaag cattgatgtt agctccaatt      2640
gctcctcatt ttgccgaata cctttacaga gaagttttag gtaaaaatgg aagtgttcaa      2700
ctagcaagtt cccaagagcc tcaaagcctg tttccaaagc tattcttgat gctctggaat      2760
atgtcagaag ccttaccaga tctatccgtg aagcagaagg tcaagctttg aaaaagaaga      2820
aaggaaagtc tgatgttgat gggtcaaaac caatcagctt gacagttttg gtttccaaca      2880
ctttcccaga atggcaagat aactatattg aacttgtcag agaattgttt gaacaaaaca      2940
agttggacga caataatgtt ataagacaaa aggttggcaa ggacatgaaa cgtggtatgc      3000
catacatcca ccaaattaaa actagattgg caactgaaga tgctgacact gttttcaaca      3060
gaaaattgac ttttgatgaa atcgatacat tgaaaaatgt tgttgaaatt gtcaagaatg      3120
ccccatactc tcttaaagtt gaaaaattgg agattcttag tttcaataac ggtgaaacta      3180
aggggaagaa tattattagt ggtgaagaca atattgagct caatttcaag ggtaaaataa      3240
tggaaaatgc tgtacctggt gagcctggta tctttattaa aaatgtcgaa taa            3293
```

<210> SEQ ID NO 63
<211> LENGTH: 219
<212> TYPE: PRT
<213> ORGANISM: Candida albicans

<400> SEQUENCE: 63

```
Met Asp Ile Glu Thr Ala Ala Cys Phe Ser Ile Ala Phe Ile Ala Thr
 1               5                  10                  15

Pro Ile Leu Ile Val Leu Val Arg Leu Leu Phe Ile Leu Pro Ser Leu
            20                  25                  30

Arg Leu Pro Thr Ser Val Lys Lys Lys Lys Leu Ile Gln Glu Cys
        35                  40                  45

Gln Leu Ser Ile Leu Leu Gly Ser Gly Gly His Thr Gly Glu Met Met
    50                  55                  60

Arg Ile Ile Ser Lys Leu Asp Met Gly Lys Val Ser Arg Thr Trp Ile
65                  70                  75                  80

Tyr Thr Ser Gly Asp Asn Ala Ser Leu Ala Lys Ala Gln Asp Tyr Glu
                85                  90                  95

Arg Lys Ser Gly Thr Ser Ser Gln Tyr Ile Pro Ile Pro Arg Ala Arg
            100                 105                 110

Thr Val Gly Gln Ser Tyr Ile Ser Ser Ile Pro Thr Thr Ile Tyr Ser
        115                 120                 125

Phe Leu Phe Ser Ala Ile Ala Met Leu Lys His Arg Pro Ala Val Ile
    130                 135                 140

Leu Leu Asn Gly Pro Gly Thr Cys Val Pro Val Ala Tyr Ile Leu Phe
145                 150                 155                 160

Leu Tyr Lys Leu Leu Gly Leu Cys Asn Thr Lys Ile Ile Tyr Ile Glu
```

```
                    165                 170                 175
Ser Leu Ala Arg Val Asn Lys Leu Ser Leu Ser Gly Leu Leu Leu Leu
                180                 185                 190

Pro Ile Ser Asp Arg Phe Ile Val Gln Trp Glu Ser Leu Tyr Gln Gln
            195                 200                 205

Tyr Ser Arg Val Glu Tyr Tyr Gly Ile Leu Ile
        210                 215

<210> SEQ ID NO 64
<211> LENGTH: 167
<212> TYPE: PRT
<213> ORGANISM: Candida albicans

<400> SEQUENCE: 64

Met Gly Thr Asn Asn Lys Thr Val Thr Asn Lys Ser Asn Lys Arg Ile
  1               5                  10                  15

Gln Gly Lys Arg His Ile Lys His Ser Pro Asn Leu Thr Pro Phe Asn
             20                  25                  30

Glu Thr Gln Asn Ala Ser Asn Phe Leu Ile Lys Ser Ser Thr Pro Tyr
         35                  40                  45

Ile Ser Ala Ile Lys Gln Ile Thr Lys Lys Leu Asn Lys Phe Ser Lys
     50                  55                  60

Ser Lys Asn Ser His Thr Ile Asn Lys Phe Gln Asn Glu Gln Tyr Lys
 65                  70                  75                  80

Thr Ile Lys Tyr Ile Ala Val Lys Gly Met Gly Lys Thr Ile Glu Lys
                 85                  90                  95

Val Ala Ser Ile Gly Thr His Phe Gln Lys Asp Tyr Lys Val Asp Val
            100                 105                 110

Leu Thr Gly Ser Thr Thr Val Leu Asp Glu Phe Ala Pro Ile Glu Ser
        115                 120                 125

Asn Gln Glu Pro Asp Asn Glu Asn Lys Ser Asp Asp Asp Asp Asp
    130                 135                 140

Asp Asp Glu Thr Ile Tyr Lys Lys Arg Thr Val Ser Ser Ile Glu Ile
145                 150                 155                 160

Arg Ile Trp Ile Lys Arg Asp
                165

<210> SEQ ID NO 65
<211> LENGTH: 494
<212> TYPE: PRT
<213> ORGANISM: Candida albicans

<400> SEQUENCE: 65

Met Leu Ala Arg Leu Leu Lys Leu Ala Ile Val Val Ala Ala Ile Ala
  1               5                  10                  15

Ala Ile Thr Pro Asn Asn Pro Ile Arg Thr Ser Ile Ser Phe Gly Cys
             20                  25                  30

Ile Gly Tyr Val Ala Thr Leu Ser Val Ile Pro Lys Val Ser Pro Ser
         35                  40                  45

Phe Val Lys Ile Gly Leu Lys Gly Lys Asp Leu Ser Lys Pro Pro Pro
     50                  55                  60

Val Ser Glu Ile Pro Glu Thr Met Gly Leu Val Ala Ser Thr Thr Tyr
 65                  70                  75                  80

Met Phe Leu Met Phe Gly Leu Ile Pro Phe Ile Phe Lys Tyr Leu
                 85                  90                  95

Val Ser Phe Gly Ser Met Ser Asn Asp Glu Val Ile Thr Lys Asn Tyr
```

```
                   100                 105                 110
Leu Ser Gln Tyr Gln Ser Leu Ala Asp Asn Arg Leu Phe Pro His Asn
            115                 120                 125
Lys Leu Ala Glu Tyr Leu Ser Ala Leu Leu Cys Leu Gln Ser Thr Thr
            130                 135                 140
Leu Leu Gly Leu Leu Asp Asp Leu Phe Asp Ile Arg Trp Arg His Lys
145                 150                 155                 160
Phe Phe Leu Pro Ala Val Ala Ser Leu Pro Leu Leu Ile Val Tyr Tyr
                165                 170                 175
Val Asp Phe Ser Val Thr Ser Val Val Ile Pro Lys Phe Val Thr Glu
            180                 185                 190
Phe Pro Gly Gly Tyr Val Leu Ile Asn Thr Ile Asn Phe Phe Ile Lys
            195                 200                 205
Tyr Ser Asn His Leu Val Thr Ser Ile Thr Gly Leu Ser Phe Arg Thr
            210                 215                 220
Leu Gln Thr Asp Tyr Val Val Pro Asp Ser Pro Lys Leu Ile Asp
225                 230                 235                 240
Leu Gly Ile Phe Tyr Tyr Val Tyr Met Ser Ala Ile Ser Ile Phe Ser
                245                 250                 255
Pro Asn Ser Ile Asn Ile Leu Ala Gly Val Asn Gly Leu Glu Val Gly
            260                 265                 270
Gln Ser Leu Val Leu Ala Ala Ile Phe Leu Ile Asn Asp Phe Cys Tyr
            275                 280                 285
Leu Phe Ser Pro Gly Ile Ser Gln Ala Ala His Asp Ser His Met Phe
290                 295                 300
Ser Val Val Phe Ile Ile Pro Phe Val Gly Val Ser Leu Ala Leu Leu
305                 310                 315                 320
Gln Tyr Asn Trp Phe Pro Ala Arg Val Phe Val Gly Asp Thr Tyr Cys
                325                 330                 335
Tyr Phe Ser Gly Met Val Phe Ala Ile Val Gly Ile Ile Gly His Phe
                340                 345                 350
Ser Lys Thr Leu Leu Ile Phe Leu Leu Pro Gln Ile Ile Asn Phe Val
            355                 360                 365
Tyr Ser Val Pro Gln Leu Phe His Ile Leu Pro Cys Pro Arg His Arg
370                 375                 380
Leu Pro Arg Phe Ser Ile Glu Asp Gly Leu Met His Pro Ser Phe Ala
385                 390                 395                 400
Glu Leu Lys Lys Ala Ser Arg Leu Asn Leu Ala Ile Leu Glu Thr Leu
                405                 410                 415
Ser Phe Phe Lys Leu Ile Lys Val Glu Arg Gly Ser Lys Ser Asn Gln
            420                 425                 430
Ile Val Arg Phe Ser Asn Met Thr Ile Ile Asn Leu Thr Leu Val Trp
            435                 440                 445
Val Gly Pro Leu Arg Glu Asp Gln Leu Cys Ile Ser Ile Leu Val Val
            450                 455                 460
Gln Phe Val Ile Gly Val Thr Met Ile Val Arg His Thr Ile Gly
465                 470                 475                 480
Pro Trp Leu Phe Gly Tyr Asp Asn Leu Ser Trp Gly Val Lys
                485                 490

<210> SEQ ID NO 66
<211> LENGTH: 280
<212> TYPE: PRT
<213> ORGANISM: Candida albicans
```

```
<400> SEQUENCE: 66

Met Ala Pro Thr Glu Ile Lys Gly Phe Tyr Val Leu Pro Leu Lys Leu
  1               5                  10                  15

Thr Gly Thr Lys Ser Ile His Tyr Ile Tyr Phe Lys Lys His Glu Ser
             20                  25                  30

Lys Gly Thr Ala Asn Asp Asn Arg Ser Leu Phe Ile Cys Asn Leu Pro
         35                  40                  45

Ile Ser Thr Asp Leu Ser Thr Ile Lys Lys Phe Phe Gln Lys Val Ala
 50                  55                  60

Ile Gly Ser Thr Ile Glu Ser Phe Ile Asn Ser Leu Leu Thr Asp Tyr
 65                  70                  75                  80

Pro Glu Asp Ile Trp Ile Asn Leu Thr Lys Leu Thr Ser Asp Leu Asp
                 85                  90                  95

Leu Val Asp Ala Val Asp Glu Gln Ala Ser Lys Leu Pro Lys Asn Cys
                100                 105                 110

Gly Ile Val Ala Phe Ile Asp Lys Ala Ser Phe Thr Leu Ala Phe Asn
            115                 120                 125

Ser Leu Lys Lys Leu Ser Ser Leu Thr Glu Cys Glu Trp Pro Ile
    130                 135                 140

Gln Gln Phe Thr Ser Asn Tyr Tyr Leu Lys Gln Tyr Gln Lys Gln Ile
145                 150                 155                 160

Leu Asp Pro Asn Ser Leu Thr Glu Glu Val Ser Gln Ala Leu Ile Asp
                165                 170                 175

Phe Asp Lys Ala Glu Gln Gln Ser Ile Glu Glu Leu Gln Ser Gln Arg
                180                 185                 190

Asn Leu Val Asp Glu Asp Gly Phe Thr Leu Val Val Gly Ser His Arg
            195                 200                 205

Lys Thr Lys Ala Gly Ile Leu Gly Lys Gln Lys Leu Ala Ser Thr Val
    210                 215                 220

Gly Val Val Lys Ala Gln Ser Lys Met Lys Ser Lys Glu Lys Gln Asp
225                 230                 235                 240

Phe Tyr Arg Phe Gln Leu Arg Gln Arg Lys Lys Glu Glu Met Asn Glu
                245                 250                 255

Leu Leu Asn Lys Phe Lys Leu Asp Gln Glu Lys Val Arg Met Met Lys
            260                 265                 270

Glu Lys Lys Arg Phe Arg Pro Tyr
    275                 280

<210> SEQ ID NO 67
<211> LENGTH: 371
<212> TYPE: PRT
<213> ORGANISM: Candida albicans

<400> SEQUENCE: 67

Met Thr Asp Thr Gln Pro Arg Lys Ile Arg Lys Val Ser Thr Gln Glu
  1               5                  10                  15

Gln Ile Glu Asp Tyr Glu Lys Leu Arg Gln Arg Ile Lys Asn His Phe
             20                  25                  30

Lys Asp Ala Leu Lys Gly Lys Gly Ser Ser Met Ser Leu His Tyr Ile
         35                  40                  45

Asp Glu Ile Thr Glu Leu Tyr Lys Arg Val Gln Ser Gln Lys Val Lys
 50                  55                  60

Asp Thr Arg Val His Leu Glu Asp Ser Glu Val Phe Lys Glu Ala Ser
 65                  70                  75                  80
```

```
Asp Phe Ala Ala Leu Asn Ala Arg Asn Ile Val Phe Asp Asp Ser Gly
                85                  90                  95

Ile Ala Leu Asp Asp Lys Glu Phe Phe Lys Cys Leu Arg Arg Phe Ala
            100                 105                 110

Val Thr Asp Pro Ser Leu Leu Ser Arg Asn Asp Ile Gly Asp Asn Asp
            115                 120                 125

Gly Asn Asn Ser Asn Asp Glu Asp Val Asp Asp Asp Ser Asp
    130                 135                 140

Glu Glu Glu Glu Ala Ile Thr Asp Glu Tyr Thr Phe Asn Lys Thr Asn
145                 150                 155                 160

Trp Leu Lys Leu Gly Ile Leu Tyr His Gln Val Ser Lys Lys Ser Ile
                165                 170                 175

Ser Val Asp Phe Leu Asn Gly Pro Leu Lys Ala Glu Lys Arg Lys Ile
            180                 185                 190

Val Arg Ala Arg Asn Val Asp Asp Thr Lys Gly Ser Gly Met Ala Lys
            195                 200                 205

Thr Ala Arg Gln Val Gln Ala Ser Asp Ile Ser Gly Asn Gln Glu Gln
    210                 215                 220

Asn Thr Ala Asn Met Val Lys Ser Val Tyr Gln Thr Tyr Ile Glu Lys
225                 230                 235                 240

Tyr Asp Gly Asn Gly Val Asn Leu Phe Lys Phe Ile Asn Pro Arg
                245                 250                 255

Ser Phe Gly Gln Ser Val Glu Asn Leu Phe Tyr Thr Ser Phe Leu Val
            260                 265                 270

Lys Asp Gly Arg Leu Lys Leu Tyr Val Asn Asn Asp Gly Met Pro Cys
            275                 280                 285

Ile Gln Arg Val Ser Ser Asp Glu Ile Arg Glu Ala Gln Leu Glu Ser
    290                 295                 300

Asn Lys Ile Phe Ala Ser His His Ile Ala Ser Phe Asn Tyr Lys Ala
305                 310                 315                 320

Trp Lys Lys Tyr Thr Gln Leu Tyr Asn Ile Arg Glu Ala Phe Leu Gly
                325                 330                 335

His Arg Asp Glu Pro Glu Asp Gln Met Pro Pro Glu Asp Ile Ile Asp
            340                 345                 350

Tyr Asn Asp Glu Glu Pro Ile Pro Ser Ser Gln Arg Arg Asp Ser Asn
            355                 360                 365

Ser Ser Asp
    370

<210> SEQ ID NO 68
<211> LENGTH: 564
<212> TYPE: PRT
<213> ORGANISM: Candida albicans

<400> SEQUENCE: 68

Met Ala Arg Arg Asn Arg Asn Lys Thr Val Asn Glu Glu Ile Glu
  1               5                  10                  15

Leu Asp Glu Val Asp Ser Phe Asn Ala Asn Arg Glu Lys Ile Leu Leu
                20                  25                  30

Asp Glu Ala Gly Glu Tyr Gly Arg Asp Asp Gln Ser Glu Glu Asp
            35                  40                  45

Ser Glu Glu Glu Val Met Gln Val Glu Glu Asp Ser Glu Asp Asp Glu
    50                  55                  60

Glu Asp Gln Glu Asp Glu Glu Glu Glu Glu Glu Glu Glu Gly Glu
```

-continued

```
           65                  70                  75                  80
Glu Glu Glu Glu Glu Glu Lys Gly Trp Gly Arg Gln Asn Tyr
                85                  90                  95
Tyr Gly Gly Asp Asp Leu Ser Asp Glu Asp Ala Lys Gln Met Thr
                100                 105                 110
Glu Glu Ala Leu Arg Gln Gln Lys Lys His Leu Gln Glu Leu Ala Met
                115                 120                 125
Asp Asp Tyr Leu Asp Asp Glu Met Met Glu Asp Trp Gln Lys Lys Ala
                130                 135                 140
Asp Ser Tyr Asp Asn Lys Asp Thr Ser Ser Thr Gln Gln Gln
145                 150                 155                 160
Gln Gln Gln Leu Ile Ile Glu Ser Asn Ser Ser Ile Ala Asn Leu Glu
                165                 170                 175
Asp Ser Asp Lys Leu Lys Leu Leu Gln Gln Ser Phe Pro Glu Phe Ile
                180                 185                 190
Pro Leu Leu Lys Glu Leu Asn Ser Leu Lys Val Lys Leu Glu Asp Leu
                195                 200                 205
Gln Lys Leu Glu Asp Lys Asn Lys Cys Ile Glu Thr Lys Ile Val Ala
210                 215                 220
Leu Ser Ala Tyr Leu Gly Ala Ile Ser Ser Tyr Phe Ala Ile Phe Val
225                 230                 235                 240
Asp Asn Leu Asn Asn Glu Glu Ser Phe Val Ser Met Lys Asp Asn Pro
                245                 250                 255
Ile Met Glu Thr Ile Leu Ser Ser Arg Glu Ile Trp Arg Gln Ala Asn
                260                 265                 270
Glu Leu Pro Asp Asp Ile Lys Leu Asp Asp Val Lys Val His Val Ser
                275                 280                 285
Asp Val Val Ser Ser Ser Asp Ile Asp Asp Glu Asp Asn Phe Val Asp
                290                 295                 300
Ala Lys Glu Glu Gln Ser Glu Asp Glu Glu Ile Ser Glu Glu Glu Val
305                 310                 315                 320
Ser Gln Asp Glu Asp Glu Asp Gln Ser Asp Asp Leu Asp Ile Asp Ala
                325                 330                 335
Asn Ser Glu Arg Ile Ile Lys His Val Ser Lys Lys His Gly Asp Asp
                340                 345                 350
Phe Thr Glu Ala Asp Ile Glu Asp Ile Asp Met Glu Asp Lys Gln Arg
                355                 360                 365
Arg Lys Lys Thr Leu Arg Phe Tyr Thr Ser Lys Ile Asp Lys Ala Ala
                370                 375                 380
Ala Lys Lys Asp Gln Ser Tyr Ser Gly Asp Ile Asp Val Pro Tyr Lys
385                 390                 395                 400
Glu Arg Leu Phe Glu Arg Gln Gln Arg Leu Leu Glu Glu Ala Arg Lys
                405                 410                 415
Arg Gly Leu Gln Lys Gln Asp Asp Glu Asn Ile Ser Asp Asn Asp Asn
                420                 425                 430
Asp Asn Asp Gly Val Asn Asp Asp Glu Gly Phe Glu Gln Gly Asp Asp
                435                 440                 445
Tyr Tyr Glu Ser Ile Lys Gln His Lys Leu Asn Lys Lys Gln Ser Arg
                450                 455                 460
Lys Ser Ala His Glu Ala Ala Val Lys Ala Ala Lys Glu Gly Lys Leu
465                 470                 475                 480
Ala Glu Leu Gln Glu Ala Val Gly Gln Asp Gly Lys Arg Ala Ile Asn
                485                 490                 495
```

-continued

Tyr Gln Ile Leu Lys Asn Lys Gly Leu Thr Pro His Arg Lys Lys Glu
                500                 505                 510

Tyr Arg Asn Ser Arg Val Lys Lys Arg Lys Gln Tyr Glu Lys Ala Gln
            515                 520                 525

Lys Lys Leu Lys Ser Val Arg Gln Val Tyr Asp Ala Asn Asn Arg Gly
        530                 535                 540

Pro Tyr Glu Gly Glu Lys Thr Gly Ile Lys Lys Gly Leu Ser Lys Ser
545                 550                 555                 560

Val Lys Leu Val

<210> SEQ ID NO 69
<211> LENGTH: 506
<212> TYPE: PRT
<213> ORGANISM: Candida albicans

<400> SEQUENCE: 69

Met Ser Lys Val Glu Glu His Glu Ser Val Asn Asn Leu Lys Arg Lys
  1               5                  10                  15

Phe Pro Ser Leu Ala Lys Pro Arg Gln Pro Leu Lys Glu Thr Asn Ser
             20                  25                  30

Asn Ile Pro Ser Pro His Lys Arg Ala Lys Ile Glu Ser Pro Ser Lys
         35                  40                  45

Gln Gln Ser Thr Gln Gln Pro Gln Gln Pro Gln Pro Gln Pro Gln
     50                  55                  60

Pro Gln Pro Gln Gln Glu Lys Ala Thr His Lys Pro Lys Lys Ser Ser
 65                  70                  75                  80

His Gln Ser Lys Asn Asn Asp Lys Leu Ala Gly Asp Glu Met His Glu
                 85                  90                  95

Trp Gln Ser Trp Arg Arg Ile Met Lys Ser Ser Ile Val Tyr Phe
            100                 105                 110

Glu Gly Asp Gln Gln Ser Leu Glu Tyr Arg Lys Ala His Lys Leu Leu
            115                 120                 125

Arg Leu Val Gly Cys Lys Val Thr Pro Phe Tyr Asp Asn Asn Val Thr
130                 135                 140

Ile Ile Ile Ser Lys Arg Pro Tyr Asp Ser Lys Thr Glu Tyr Ser Pro
145                 150                 155                 160

His Asp Ile Phe Ser Asn Val Ser Lys Ala Ser Ile Lys Val Trp Asn
                165                 170                 175

Tyr Asp Lys Val Phe Arg Phe Leu Lys His Leu Gly Ile Asn Ile Gln
            180                 185                 190

Thr Gly Val Asp Glu Leu Ala Val Asn Thr His Thr Ile Leu Pro Pro
        195                 200                 205

Ser Leu Thr Asn Asn Asn Glu Lys Pro Asp Leu Tyr Asn Leu Leu Lys
210                 215                 220

Glu Glu Lys Ile Tyr Gly Ser Thr Asp Arg Asp Pro Asn Ala Lys Arg
225                 230                 235                 240

Asp Asp Leu His Tyr Leu Gly Lys Asn Tyr Leu Tyr Val Tyr Asp Leu
                245                 250                 255

Thr Gln Thr Val Arg Pro Ile Ala Ile Arg Glu Trp Ser Asp His Tyr
            260                 265                 270

Pro Val Met Gln Leu Ser Leu Asp Gly Lys Cys Pro Phe Ile Glu Asp
        275                 280                 285

Pro Thr Asp Gln Asn Ser Glu Arg Lys Arg Leu Lys Arg Leu Arg Lys
    290                 295                 300

-continued

```
Phe Glu Ala Asn Gln Ala His Arg Glu Ala Leu Arg Leu Ala Thr Tyr
305                 310                 315                 320

Lys Met Ile Asn Gly Ile Ser Met Ser Val His Gly Phe Thr Ala Thr
            325                 330                 335

Ser Thr Ser Thr Asp Lys Val Asp Glu Glu Asp Ser Thr Val Lys
            340                 345                 350

Glu Pro Ser Glu Asp Pro Arg Phe Arg Gln Pro Leu Asn Arg Asn Ser
            355                 360                 365

Ser Cys Met Gln Ser Lys Ala Phe Glu Ala Met Ala Ser Gly Tyr Asn
    370                 375                 380

Gly Ala Ser Asn Ala Val Gln Pro Ser Met Asp Ser Asn Leu Asn Ser
385                 390                 395                 400

Ala Ala Ala Met Ala Gly Gly Asn Gly Leu Gly Pro Ala Leu Ser Gln
            405                 410                 415

Val Pro Ser Lys Gln Leu Asn Asn Leu Lys Arg Arg Ile Leu Met Lys
            420                 425                 430

Lys Lys Thr Thr Asn Thr Thr Glu Lys Lys Asp Lys Glu His Ala Ser
            435                 440                 445

Gly Tyr Cys Glu Asn Cys Arg Val Lys Tyr Thr Asn Phe Asp Glu His
    450                 455                 460

Ile Met Thr Asn Arg His Arg Asn Phe Ala Cys Asp Asp Arg Asn Phe
465                 470                 475                 480

Gln Asp Ile Asp Glu Leu Ile Ala Ser Leu Arg Glu Arg Lys Ser Leu
            485                 490                 495

Gly Asn Val Ile Ser Asn Gly Asp Tyr Val
            500                 505

<210> SEQ ID NO 70
<211> LENGTH: 532
<212> TYPE: PRT
<213> ORGANISM: Candida albicans

<400> SEQUENCE: 70

Met Lys Pro Met Val Thr Thr Leu Tyr Asn Gly Lys Leu Pro Leu Ala
1               5                   10                  15

Leu Ala Asp Pro Asn Gly Ile Phe Thr Trp Cys Pro His Leu Asn Leu
            20                  25                  30

Ile Phe Ile Ala Met Asn Lys Met Ser Ile Trp Cys Tyr Arg Met Asn
            35                  40                  45

Gly Glu Arg Ile Tyr Ser Ile Asn Asn Lys Ser Ile Val Lys His Ile
    50                  55                  60

Ala Phe Tyr Arg Glu Tyr Phe Cys Leu Ser Gly Thr Asp Asn Leu Ile
65              70                  75                  80

Lys Ile Tyr Asp Ser Asn Asn Gly Gln Leu Val Lys Val Leu Pro Gln
            85                  90                  95

Glu Phe Asp Gly Val Glu Phe Gly Trp Asn Gly Thr Glu Tyr Arg
            100                 105                 110

Val Ser Val Ser Met Pro Met Val Tyr Asp Leu Val Ser Glu Leu Asp
            115                 120                 125

Tyr Leu Val Val Ser Asp Gly Lys Arg Met Ala Ile Thr Phe Asn Gln
    130                 135                 140

Leu Leu Thr Val Asp Trp Glu Cys Glu Met Ser Val His Gln Gln Leu
145                 150                 155                 160

Asn Arg Asp Leu Phe Asn Gln Val Tyr Val Ala Gly Asp Lys Leu Val
```

```
                     165                 170                 175
Arg Val Arg Phe Val Asp Asn Gln Lys Leu Tyr Thr Glu Gln Ile
            180                 185                 190
Ile Lys Val Cys Gln Leu Ile Ser Leu Leu Glu Tyr Gly Glu Gln His
            195                 200                 205
Ile Gln Lys Ile Lys Gly Leu Val Pro Phe Leu Ser Ala Met Asp
    210                 215                 220
Arg Tyr Met Ser Asn Leu Glu Ser Glu Cys Gly Asp Leu Ala Gln Tyr
225                 230                 235                 240
Leu Ser Asp Leu Val Ser Asn Ile Ile Pro Glu Phe Ser Lys Asp
                245                 250                 255
Phe Trp Leu Asn Gln Tyr Gly Glu Arg Gly His Lys Arg Met Val Lys
                260                 265                 270
Leu Ala Gly Val Tyr Glu Ser Cys Val Lys Asp Thr Tyr Gln His Leu
                275                 280                 285
Val Ser Thr Thr Glu Arg Val Ile Ser Ile Val Gly Glu Leu Ile Gly
    290                 295                 300
Val Ser Lys Trp Glu Gln Gly Leu Leu Ala Thr Thr Glu Leu Glu Ala
305                 310                 315                 320
Leu Leu Asp Gln Ala Lys Ser Gln Leu Lys Phe Tyr Arg Phe Ile
                325                 330                 335
Trp Asp Leu Gln Thr Glu Arg Gln Gln Val Ser Gln Phe Leu Val Trp
                340                 345                 350
Thr Lys Ser Ile Ile Asp Met Leu Asn Asp Gln Glu Cys Asp Ile Ala
            355                 360                 365
Tyr Ser Thr Thr Asp Val Leu Cys Phe Ile Asn Gly Ala Leu Thr Lys
    370                 375                 380
Ser Val Met Leu Lys Tyr Phe Asp Ile Lys Gly Val Pro Glu Thr Pro
385                 390                 395                 400
Met Thr Asn Ile Ser Met Asp Leu Thr Thr Ile Gly Glu Tyr His Arg
                405                 410                 415
Ser Arg Val Glu Val Glu Val Leu Gln Asn Ile Ser Leu Pro Ser Val
            420                 425                 430
Tyr Thr Asn Leu Lys Leu Ala Gln Trp Glu Glu Val Val Thr Tyr
        435                 440                 445
Gln Gln Gly Asn Ala Leu Val Ile Ala Asn Val Asp Gly Val Val Ser
    450                 455                 460
Thr Val Gln Asp Val Tyr Ser Tyr Gln His Arg Gln Thr Asp Leu Val
465                 470                 475                 480
Ala Leu Thr Ser Lys Ser Leu Leu Ile Ile Asp Ser Ser Cys Ile
                485                 490                 495
Pro Ile Ala Leu Pro Glu Thr Ser Phe Gln Pro Thr Lys Leu Ile Leu
            500                 505                 510
Asn Gln Glu Tyr Gly Val Leu Leu Asp Ser Thr Arg Gln His Tyr Ser
                515                 520                 525
Ile Phe Arg Met
    530

<210> SEQ ID NO 71
<211> LENGTH: 319
<212> TYPE: PRT
<213> ORGANISM: Candida albicans

<400> SEQUENCE: 71
```

```
Met Gly Lys Arg Arg Val Asp Glu Glu Ser Asp Ser Asp Ile Asp Val
 1               5                  10                  15

Ser Ser Pro Asp Ser Glu Thr Glu Leu Glu Ser Thr His His His His
            20                  25                  30

His His Gln Glu Gly Ala Thr Thr Ile Gln Glu Thr Val Asp Val Asp
        35                  40                  45

Phe Asp Phe Phe Asp Leu Asn Pro Gln Ile Asp Phe His Ala Thr Lys
 50                  55                  60

Asn Phe Leu Arg Gln Leu Phe Gly Asp Asp Asn Gly Glu Phe Asn Leu
65                  70                  75                  80

Ser Glu Ile Ala Asp Leu Ile Leu Arg Glu Asn Ser Val Gly Thr Ser
                85                  90                  95

Ile Lys Thr Glu Gly Met Glu Ser Asp Pro Phe Ala Ile Leu Ser Val
            100                 105                 110

Ile Asn Leu Thr Asn Asn Leu Asn Val Ala Val Ile Lys Gln Leu Ile
            115                 120                 125

Glu Tyr Ile Leu Asn Lys Thr Lys Ser Lys Thr Glu Phe Asn Ile Ile
            130                 135                 140

Leu Lys Lys Leu Leu Thr Asn Gln Asn Asp Thr Thr Arg Asp Arg Lys
145                 150                 155                 160

Phe Lys Thr Gly Leu Ile Ile Ser Glu Arg Phe Ile Asn Met Pro Val
                165                 170                 175

Glu Val Ile Pro Pro Met Tyr Lys Met Leu Leu Gln Glu Met Glu Lys
            180                 185                 190

Ala Glu Asp Ala His Glu Asn Glu Phe Asp Tyr Phe Leu Ile Ile Ser
            195                 200                 205

Arg Val Tyr Gln Leu Val Asp Pro Val Glu Arg Glu Asp Glu Asp His
210                 215                 220

Glu Lys Glu Ser Asn Arg Lys Lys Asn Lys Asn Lys Lys Lys Lys Lys
225                 230                 235                 240

Leu Ala Asn Asn Glu Pro Lys Pro Ile Glu Met Asp Tyr Phe His Leu
            245                 250                 255

Glu Asp Gln Ile Leu Glu Asn Thr Gln Phe Lys Gly Ile Phe Glu Tyr
            260                 265                 270

Asn Asn Glu Asn Lys Gln Glu Thr Asp Ser Arg Arg Val Phe Thr Glu
            275                 280                 285

Tyr Gly Ile Asp Pro Lys Leu Ser Leu Ile Leu Ile Asp Lys Asp Asn
            290                 295                 300

Leu Ala Lys Ser Val Ile Glu Met Glu Gln Gln Phe Pro Pro Pro
305                 310                 315

<210> SEQ ID NO 72
<211> LENGTH: 266
<212> TYPE: PRT
<213> ORGANISM: Candida albicans

<400> SEQUENCE: 72

Met Ala Gly Phe Lys Lys Asn Arg Glu Ile Leu Thr Gly Gly Lys Lys
 1               5                  10                  15

Tyr Ile Gln Gln Lys Gln Lys Lys His Leu Val Asp Glu Val Val Phe
            20                  25                  30

Asp Lys Glu Ser Arg His Glu Tyr Leu Thr Gly Phe His Lys Arg Lys
            35                  40                  45

Leu Gln Arg Gln Lys Lys Ala Gln Glu Phe His Lys Glu Gln Glu Arg
        50                  55                  60
```

-continued

```
Leu Ala Lys Ile Glu Glu Arg Lys Gln Leu Lys Gln Glu Arg Glu Arg
 65                  70                  75                  80

Asp Leu Gln Asn Gln Leu Gln Gln Phe Lys Lys Thr Ala Gln Glu Ile
                 85                  90                  95

Ala Ala Ile Asn Asn Asp Ile Gly Phe Asp Gln Ser Asp Asp Asn Asn
            100                 105                 110

Asp Asn Asp Asn Glu Glu Trp Ser Gly Phe Gln Glu Asp Glu Glu Gly
        115                 120                 125

Glu Gly Glu Glu Val Thr Asp Glu Asp Glu Asp Lys Glu Lys Pro
130                 135                 140

Leu Lys Gly Ile Leu His His Thr Glu Ile Tyr Lys Gln Asp Pro Ser
145                 150                 155                 160

Leu Ser Asn Ile Thr Asn Asn Gly Ala Ile Ile Asp Asp Glu Thr Thr
                165                 170                 175

Val Val Val Glu Ser Leu Asp Asn Pro Asn Ala Val Asp Thr Glu Glu
            180                 185                 190

Lys Leu Gln Gln Leu Ala Lys Leu Asn Asn Val Asn Leu Asp Lys Ser
        195                 200                 205

Asp Gln Ile Leu Glu Lys Ser Ile Glu Arg Ala Lys Asn Tyr Ala Val
210                 215                 220

Ile Cys Gly Val Ala Lys Pro Asn Pro Ile Lys Gln Lys Lys Lys Lys
225                 230                 235                 240

Phe Arg Tyr Leu Thr Lys Ala Glu Arg Arg Glu Asn Val Arg Lys Glu
                245                 250                 255

Lys Ser Lys Ser Lys Ser Lys Gly Lys Lys
            260                 265
```

<210> SEQ ID NO 73
<211> LENGTH: 332
<212> TYPE: PRT
<213> ORGANISM: Candida albicans

<400> SEQUENCE: 73

```
Met Ser Thr Val Tyr Tyr Lys Lys Leu Asp Lys Leu Gln Phe Gln Ile
 1               5                  10                  15

Tyr Asp Leu Phe Ser Ser Leu Leu Gln Leu Ser Glu Ala Glu Asp Glu
                20                  25                  30

Ser Val Tyr Lys Ala Ser Phe Asp Asp Thr Val Gln Glu Ile Asp Ser
            35                  40                  45

Leu Leu Ile Ala Phe Lys Asp Leu Arg Leu Leu Arg Pro Lys Asp
 50                 55                  60

Lys Ser Asn Lys Phe Asp Thr Tyr Glu Leu Lys Phe His Ser Leu Lys
 65                 70                  75                  80

His Lys Leu Arg Glu Leu Gln Val Phe Ile Asn Asp Gln Gln Gln Asp
                85                  90                  95

Lys Leu His Glu Tyr Arg Ile Lys His Phe His Leu Gln Asp Ser Pro
            100                 105                 110

Val Asp Thr Ile Asn Asn Glu Phe Ala Arg Asp Gln Leu Phe Ala Asp
        115                 120                 125

Arg Ser Thr Lys Lys Thr Lys Lys Glu Met Glu Ala Ser Ile Asn Gln
130                 135                 140

Gln Ile Val Ser Gln Asn Lys Gln Ile Thr Lys Ser Leu Gln Ala Ser
145                 150                 155                 160

Arg Gln Leu Leu Ser Ala Gly Ile Leu Gln Ser Glu Leu Asn Ile Asp
```

```
                     165                 170                 175
Asn Ile Asp Gln Gln Thr Lys Asp Leu Tyr Lys Leu Asn Glu Gly Phe
                180                 185                 190

Ile Gln Phe Asn Asp Leu Leu Asn Arg Ser Lys Lys Ile Val Lys Phe
            195                 200                 205

Ile Glu Lys Gln Asp Lys Ala Asp Arg Gln Arg Ile Tyr Leu Ser Met
        210                 215                 220

Gly Phe Phe Ile Leu Cys Cys Ser Trp Val Val Tyr Arg Arg Ile Leu
225                 230                 235                 240

Arg Arg Pro Leu Lys Ile Phe Leu Trp Ser Phe Phe Lys Ile Phe Asn
                245                 250                 255

Ile Phe Asn Trp Leu Leu Gly Gly Arg Ser Lys Gly Leu Ser Ala
            260                 265                 270

Ser Asp Met Ile Val Ser Ser Val Ile Ala Ala Thr Thr Glu Ile Val
        275                 280                 285

Asp Tyr Glu Ala Thr Lys Thr Leu Leu Asp Thr Leu Ser Asn Ala Val
    290                 295                 300

Asp Ser Asn Thr Ala Ile Asp Thr Leu Ala Met Val Val Glu Ser Leu
305                 310                 315                 320

Thr Thr Ser Ser Met Glu His Ile Val Asp Glu Leu
                325                 330

<210> SEQ ID NO 74
<211> LENGTH: 273
<212> TYPE: PRT
<213> ORGANISM: Candida albicans

<400> SEQUENCE: 74

Met Thr Asp Ser Ser Ala Thr Gly Phe Ser Lys His Gln Glu Ser Ala
1               5                   10                  15

Ile Val Ser Asp Ser Glu Gly Asp Ala Ile Asp Ser Glu Leu His Met
            20                  25                  30

Ser Ala Asn Pro Pro Leu Leu Arg Arg Ser Ser Ser Leu Phe Ser Leu
        35                  40                  45

Ser Ser Lys Asp Asp Leu Pro Lys Pro Asp Ser Lys Glu Tyr Leu Lys
    50                  55                  60

Phe Ile Asp Asp Asn Arg His Phe Ser Met Ile Arg Asn Leu His Met
65                  70                  75                  80

Ala Asp Phe Ile Thr Leu Leu Asn Gly Phe Ser Gly Phe Tyr Ser Ile
                85                  90                  95

Ile Ser Cys Leu Arg Tyr Thr Leu Thr Gly Gln Thr His Tyr Val Gln
            100                 105                 110

Arg Ala His Phe Phe Ile Leu Leu Gly Leu Phe Phe Asp Phe Phe Asp
        115                 120                 125

Gly Arg Val Ala Arg Leu Arg Asn Lys Ser Ser Leu Met Gly Gln Glu
    130                 135                 140

Leu Asp Ser Leu Ala Asp Leu Val Ser Phe Gly Val Ser Pro Ala Thr
145                 150                 155                 160

Ile Ala Phe Ala Ile Gly Phe Arg Thr Thr Val Asp Val Leu Phe Leu
                165                 170                 175

Ala Phe Trp Val Leu Cys Gly Leu Thr Arg Leu Ala Arg Phe Asn Ile
            180                 185                 190

Ser Val Asn Asn Ile Pro Lys Asp Lys His Gly Lys Ser Gln Tyr Phe
        195                 200                 205
```

```
Glu Gly Leu Pro Ile Pro Thr Asn Leu Phe Trp Val Gly Phe Met Ala
    210                 215                 220
Leu Leu Val Tyr Lys Asp Trp Ile His Asp Asn Leu Pro Phe Gly Ile
225                 230                 235                 240
Val Phe Gln Asp Thr Ser Phe Glu Phe His Leu Val Thr Ile Gly Phe
                245                 250                 255
Val Leu Gln Gly Cys Ala Glu Ile Ser Lys Ser Leu Lys Ile Pro Lys
                260                 265                 270
Pro
```

<210> SEQ ID NO 75
<211> LENGTH: 1175
<212> TYPE: PRT
<213> ORGANISM: Candida albicans

<400> SEQUENCE: 75

```
Met Ala Lys Arg Lys Leu Glu Glu Asn Asp Ile Ser Thr Ile Glu Asp
1               5                   10                  15
Asp Glu Phe Lys Ser Phe Ser Asp Arg Asp Glu Gln Ile Asp Glu Leu
                20                  25                  30
Ser Asn Gly His Ala Lys His Arg Glu Asn Asn Ala Gln Glu Ser Asp
            35                  40                  45
Asp His Ser Ala Ser Glu Asp Asp Asp Glu Asp Asp Glu Glu Glu
        50                  55                  60
Gly Glu Lys Ser Val Gln Pro Pro Asn Lys Gln Lys Lys Gln Leu
65                  70                  75                  80
Ser Ala Gln Asp Val Gln Val Ala Arg Glu Thr Ala Glu Leu Phe Lys
                85                  90                  95
Ser Asn Ile Phe Lys Leu Gln Ile Asp Glu Leu Met Lys Glu Val Lys
                100                 105                 110
Val Lys Lys Ala His Glu Glu Lys Ile Glu Lys Val Leu His Arg Leu
            115                 120                 125
His Asp Leu Ile Lys Gln Val Pro Pro Val Glu Asn Leu Thr Leu Gln
        130                 135                 140
Gln Ala Glu Gln His Phe Asn Pro Lys Lys Leu Val Ile Pro Phe Pro
145                 150                 155                 160
Asp Pro Lys Pro Thr Lys Val Asn Tyr Arg Phe Ser Tyr Leu Pro Ser
                165                 170                 175
Gly Asp Leu Ser Leu Val Gly Ser Tyr Gly Leu Lys Thr Ala Ile Asn
                180                 185                 190
Gln Pro His Gly Gln Ser Ile Glu Val Ala Leu Thr Met Pro Lys Glu
            195                 200                 205
Leu Phe Gln Pro Lys Asp Tyr Leu Asn Tyr Arg Ala Leu Tyr Lys Lys
        210                 215                 220
Ser Phe Tyr Leu Ala Tyr Leu Gly Glu Asn Leu Ile His Leu Ser Lys
225                 230                 235                 240
Lys Asn Asn Leu Pro Ile Lys Val Ser Tyr Gln Phe Asn Asp Asp
                245                 250                 255
Val Leu Asn Pro Val Leu Lys Ile Glu Ser Ile Gln Thr Glu Asn Pro
                260                 265                 270
Glu Asp Leu Thr Phe Thr Lys Thr Lys Ile Ala Ile Asn Leu Ile Val
            275                 280                 285
Ala Phe Pro Phe Gly Val Phe Asp Ser Lys Lys Leu Leu Pro Asp Lys
        290                 295                 300
```

```
Asn Cys Ile Arg Val Gln Ser Asp Thr Glu Thr Leu Pro Pro Thr Pro
305                 310                 315                 320

Leu Tyr Asn Ser Ser Val Leu Ser Gln Thr Ser Tyr Asp Tyr Tyr Leu
                325                 330                 335

Lys Tyr Leu Tyr Thr Thr Lys Lys Ser Thr Glu Ala Phe Lys Asp Ala
            340                 345                 350

Cys Met Leu Gly Lys Leu Trp Leu Gln Gln Arg Gly Phe Asn Ser Ser
        355                 360                 365

Leu Asn Asn Gly Gly Phe Gly His Phe Glu Phe Ala Ile Leu Met Ser
    370                 375                 380

Ala Leu Leu Asn Gly Gly Leu Asn Gly Asn Lys Ile Leu Leu His
385                 390                 395                 400

Gly Phe Ser Ser Tyr Gln Leu Phe Lys Gly Thr Ile Lys Tyr Leu Ala
                405                 410                 415

Thr Met Asp Leu Asn Gly Gly Tyr Leu Ser Phe Ser Ser Leu Ile Gly
            420                 425                 430

Glu Asn Ile Ala Ser Lys Tyr Lys Ser Asp Gly Phe Asn Val Pro Thr
        435                 440                 445

Ile Phe Asp Lys Asn Thr Lys Leu Asn Ile Leu Trp Lys Met Thr Lys
    450                 455                 460

Ser Ser Tyr Lys Ser Leu Gln Leu Gln Ala Gln Gln Thr Leu Glu Leu
465                 470                 475                 480

Leu Asn Asp Val Val Lys Asp Arg Phe Asp Ala Ile Leu Leu Gln Lys
                485                 490                 495

Ser Asp Phe Asp Pro Met Arg Tyr Asp Ile Val Phe Lys Leu Ser Ala
            500                 505                 510

Pro Glu Glu Leu Tyr Asp Ser Phe Gly Pro Leu Glu Lys Ile Ala Tyr
        515                 520                 525

Ile Thr Phe Asp Asn Tyr Phe Lys Ser Arg Leu Phe Ala Ile Leu Thr
    530                 535                 540

Lys Ala Leu Gly Glu Arg Ile Glu Ser Ile Val Ile Lys Asn Glu His
545                 550                 555                 560

Pro Ser Asn Thr Phe Ala Ile His Lys Arg Lys Pro Ser His Thr Ser
                565                 570                 575

Ser Thr Phe Val Ile Gly Leu Gln Leu Asn Pro Glu Glu Cys Asp Lys
            580                 585                 590

Leu Val Thr Lys Gly Pro Asn Asn Glu Asp Lys Asp Ala Gly Ile Lys
        595                 600                 605

Phe Arg Ser Phe Trp Gly Asn Lys Ala Ser Leu Arg Arg Phe Lys Asp
    610                 615                 620

Gly Ser Ile Gln His Cys Val Val Trp Asn Ile Lys Asp Gln Glu Pro
625                 630                 635                 640

Val Val Met Asn Ile Ile Lys Tyr Ala Leu Asp Thr His Leu Gln Ser
                645                 650                 655

Glu Ile Ser Gln His Leu Ala Ser Ser Ile Ser Tyr Phe Asp Lys Lys
            660                 665                 670

Leu Pro Val Pro Leu Leu Pro Ser Ala Thr Asn Gln Val Ile Thr Ser
        675                 680                 685

Leu Ser Ser Phe Thr Ala Leu Arg Asn Ser Phe Glu Asn Leu Ser Lys
    690                 695                 700

Val Leu Thr Asn Leu Glu Leu Pro Leu Ser Val Lys Thr Val Leu Pro
705                 710                 715                 720

Ala Ser Ser Gly Leu Arg Tyr Thr Ser Val Leu Gln Pro Val Pro Phe
```

```
                725                 730                 735
Ala Ala Ser Asn Pro Asp Phe Trp Asn Tyr Cys Val Leu Gln Phe Glu
            740                 745                 750

Thr Ser Thr Arg Trp Pro Asp Glu Leu Ser Ala Leu Glu Lys Thr Lys
            755                 760                 765

Thr Ala Phe Leu Leu Lys Ile Ser Glu Glu Leu Ala Glu Thr Glu Tyr
            770                 775                 780

Asn Ser Phe Ile Ser Lys Asp Glu Ser Val Pro Phe Asn Glu Asn Ile
785                 790                 795                 800

Thr Leu Leu Asn Ile Leu Thr Pro Glu Gly Tyr Gly Phe Arg Ile Arg
            805                 810                 815

Ala Phe Thr Glu Arg Asp Glu Leu Leu Tyr Leu Arg Ala Val Ser Asn
            820                 825                 830

Ala Asp Lys Gln Lys Ala Leu Val Gln Asp Val Tyr Leu Lys Phe Asn
            835                 840                 845

Glu Lys Tyr Met Gly Ser Val Lys His Thr Arg Ser Val Thr Gln Leu
            850                 855                 860

Ala Gln His Phe His Phe Tyr Ser Pro Thr Val Arg Phe Phe Lys Gln
865                 870                 875                 880

Trp Leu Asp Ser Gln Leu Leu Leu Gln His Phe Ser Glu Glu Leu Val
            885                 890                 895

Glu Leu Ile Ala Leu Lys Pro Phe Val Asp Pro Ala Pro Tyr Ser Ile
            900                 905                 910

Pro His Ser Val Glu Asn Gly Phe Leu Gln Ile Leu Asn Phe Leu Ala
            915                 920                 925

Ser Trp Asn Trp Lys Glu Asp Pro Leu Val Leu Asp Leu Val Lys Ser
            930                 935                 940

Ser Ala Asp Asp Asp Ile Lys Leu Ser Asp Lys Leu Thr Ile Gln Ala
945                 950                 955                 960

His Arg Ile Ile Glu Gln Asn Phe Glu Lys Ile Arg Lys Thr Asp Pro
            965                 970                 975

Ser Gly Ile Lys Thr Gln Tyr Phe Ile Gly Ser Lys Asp Asp Pro Ser
            980                 985                 990

Gly Ile Leu Trp Ser His Asn Leu Thr Leu Pro Ile Ser Thr Arg Leu
            995                 1000                1005

Thr Ala Leu Ser Arg Ala Ala Ile Gln Leu Leu Arg Lys Glu Gly Ile
            1010                1015                1020

Thr Glu Thr Asn Leu Asp Leu Ile Phe Thr Pro Ala Leu Gln Asp Tyr
1025                1030                1035                1040

Asp Phe Thr Ile Lys Val Lys Ala Asn Asn Val Thr Thr Ser Ser Gly
            1045                1050                1055

Ile Leu Pro Pro Asn Thr Phe Lys Asn Leu Ile Gln Pro Leu Thr Ser
            1060                1065                1070

Phe Pro Asp Asp Ile Thr Thr Lys Tyr Asp Leu Val Gln Gly Tyr Val
            1075                1080                1085

Asp Glu Leu Asn Lys Lys Phe Gly Asn Ala Ile Ile Phe Ser Ser Lys
            1090                1095                1100

Lys Phe Thr Gly Leu Cys Lys Asn Asn Glu Asn Val Ile Gly Gly Ile
1105                1110                1115                1120

Phe Val Pro Thr Asn Leu Thr Lys Lys Phe Arg Val Asn Leu Gly
            1125                1130                1135

Ile Asn Val Lys Pro Leu Asp Asp Lys Gly Asp Glu Val Ile Ile Asn
            1140                1145                1150
```

Thr Ser Ser Ile Tyr Asp Glu Ile Glu Leu Leu Gly Gly Asp Leu Ile
        1155                1160                1165

Lys Ala Phe Asp Lys Arg Lys
    1170                1175

<210> SEQ ID NO 76
<211> LENGTH: 759
<212> TYPE: PRT
<213> ORGANISM: Candida albicans

<400> SEQUENCE: 76

Met Ala Lys Lys Arg Ala Ala Ile Leu Pro Thr Asn Ile Ile Leu
1               5                   10                  15

Leu Gln Asn Val Val Arg Arg Asp Pro Glu Ser Tyr His Glu Glu Phe
                20                  25                  30

Leu Gln Gln Phe Ser His Tyr Glu Ser Leu Arg Asp Leu Tyr Leu Ile
                35                  40                  45

Asn Pro Thr Gly Val Asp Ala Asn Ser Thr Thr Glu Phe Ile Asp Leu
    50                  55                  60

Ile Gly Phe Met Ser Ala Val Cys Asn Cys Tyr Pro Lys Glu Thr Ala
65                  70                  75                  80

Asn Phe Pro Asn Glu Leu Lys Glu Ile Leu Leu Asn Asn His Arg Asp
                85                  90                  95

Leu Thr Pro Glu Leu Arg Glu Lys Ile Gln Cys Leu Thr Met Leu
                100                 105                 110

Arg Asn Lys Asp Ile Ile Ser Ala Glu Met Leu Ile Gln Thr Ile Phe
                115                 120                 125

Pro Leu Leu Ile Thr Ser Asn Ala Gly Gln Gln Val Lys Gln Met Arg
        130                 135                 140

Lys Gln Ile Tyr Ser Thr Leu Ile Ala Leu Leu Lys Ser Val Asn Thr
145                 150                 155                 160

Gly Thr Lys Asn Gln Lys Leu Asn Arg Ser Thr Gln Ala Leu Leu Phe
                165                 170                 175

Asn Leu Leu Glu Gln Arg Asp Asn Gln Gly Leu Trp Ala Thr Lys Leu
                180                 185                 190

Thr Arg Glu Leu Trp Arg Arg Gly Ile Trp Asp Asp Ser Arg Thr Val
        195                 200                 205

Glu Ile Met Thr Gln Ala Ala Leu His Pro Asp Val Lys Val Ala Val
210                 215                 220

Ala Gly Ala Arg Phe Phe Leu Gly Ala Asp Lys Glu Arg Glu Asp Asn
225                 230                 235                 240

Phe Glu Glu Ser Ser Asp Glu Asp Gly Phe Asp Met Asn Glu Leu Arg
                245                 250                 255

His Lys Met Gln Ile Asn Lys Lys Thr Ser Lys Arg Gly Lys Lys Leu
                260                 265                 270

Glu Gln Ala Val Lys Ala Met Lys Lys Asn Asn Ser Lys His Ser
        275                 280                 285

Ala Thr Tyr Leu Asn Phe Ser Ala Ile His Leu Leu Arg Asp Pro Gln
        290                 295                 300

Gly Phe Ala Glu Gln Met Phe Asp Asn His Leu Ser Ser Lys Asn Ser
305                 310                 315                 320

Asn Lys Phe Asp Leu Asp Gln Lys Ile Leu Phe Met Asn Leu Ile Ser
                325                 330                 335

Arg Leu Ile Gly Thr His Lys Leu Ile Val Leu Gly Val Tyr Thr Phe

-continued

```
            340                 345                 350
Phe Leu Lys Tyr Leu Thr Pro Lys Gln Arg Asn Val Thr Gln Ile Met
    355                 360                 365
Ala Ala Ala Gln Ala Ser His Asp Leu Val Pro Pro Glu Ser Ile
370                 375                 380
Gln Ile Val Val Arg Lys Ile Ala Asp Glu Phe Val Ser Asp Gly Val
385                 390                 395                 400
Ala Ala Glu Val Ala Ser Ala Gly Ile Asn Thr Ile Arg Glu Ile Leu
            405                 410                 415
Ala Arg Ala Pro Leu Ala Ile Asp Ala Pro Leu Leu Gln Asp Leu Thr
            420                 425                 430
Glu Tyr Lys Gly Ser Lys Ser Lys Ala Val Met Met Ala Ala Arg Ser
            435                 440                 445
Leu Ile Ser Leu Tyr Arg Glu Val Ala Pro Glu Met Leu Leu Lys Lys
450                 455                 460
Asp Arg Gly Lys Val Ala Ser Ile Glu Leu Gln Lys Gly Glu Lys Ser
465                 470                 475                 480
Gly Leu Pro Gln Tyr Gly Val Glu Asn Asn Val Thr Ser Ile Pro Gly
            485                 490                 495
Ile Glu Leu Leu Ala Lys Trp Lys Lys Glu Gln Gly Leu Asp Ser Arg
            500                 505                 510
Glu Asp Glu Glu Asp Asp Ala Asn Trp Glu Val Asp Asp Asp Glu Asp
            515                 520                 525
Ala Ser Asp Ile Glu Gly Asp Trp Ile Asp Val Glu Ser Asp Lys Glu
            530                 535                 540
Ile Asn Ile Ser Asp Ser Asp Asp Asn Glu Glu Asp Glu Gln Glu
545                 550                 555                 560
Gln Glu Pro Glu Lys Gly Lys Ala Lys Ile Gly Lys Ala Glu Asp Asn
            565                 570                 575
Glu Asp Glu Val Ser Asp Leu Glu Leu Ser Ser Asp Asp Asp Glu
            580                 585                 590
Asp Ser Glu Glu Asn Lys Asp Gly Lys Ala Val Ala Asp Ser Glu Glu
            595                 600                 605
Pro Pro Thr Lys Lys Gln Lys Ile Arg Asn Glu Asn Ala Asp Ile Asn
610                 615                 620
Ala Glu Gln Ala Met Asn Glu Leu Leu Ser Ser Arg Ile Leu Thr Pro
625                 630                 635                 640
Ala Asp Phe Ala Lys Leu Glu Glu Leu Arg Thr Glu Ala Gly Val Ser
            645                 650                 655
Lys Ile Met Gly Ile Ser Asn Glu Glu Ala Val Asp Ser Thr Ser Leu
            660                 665                 670
Val Gly Lys Val Lys Tyr Lys Gln Leu Arg Glu Glu Arg Ile Ala His
            675                 680                 685
Ala Lys Glu Gly Lys Glu Asp Arg Glu Lys Phe Gly Ser Arg Lys Gly
            690                 695                 700
Lys Arg Asp Thr Pro His Ser Thr Thr Asn Lys Glu Lys Ala Arg Lys
705                 710                 715                 720
Lys Asn Phe Val Met Met Ile His Lys Lys Ala Val Gln Gly Lys Gln
            725                 730                 735
Lys Leu Ser Leu Arg Asp Arg Gln Arg Val Leu Arg Ala His Ile Thr
            740                 745                 750
Lys Gln Lys Lys Lys Gly Leu
            755
```

<210> SEQ ID NO 77
<211> LENGTH: 528
<212> TYPE: PRT
<213> ORGANISM: Candida albicans

<400> SEQUENCE: 77

Met Ala Ile Val Glu Thr Val Ile Asp Gly Ile Asn Tyr Phe Leu Ser
1               5                   10                  15

Leu Ser Val Thr Gln Gln Ile Ser Ile Leu Gly Val Pro Phe Val
            20                  25                  30

Tyr Asn Leu Val Trp Gln Tyr Leu Tyr Ser Leu Arg Lys Asp Arg Ala
            35                  40                  45

Pro Leu Val Phe Tyr Trp Ile Pro Trp Phe Gly Ser Ala Ala Ser Tyr
50                  55                  60

Gly Gln Gln Pro Tyr Glu Phe Phe Glu Ser Cys Arg Gln Lys Tyr Gly
65                  70                  75                  80

Asp Val Phe Ser Phe Met Leu Leu Gly Lys Ile Met Thr Val Tyr Leu
                85                  90                  95

Gly Pro Lys Gly His Glu Phe Val Phe Asn Ala Lys Leu Ser Asp Val
            100                 105                 110

Ser Ala Glu Glu Ala Tyr Lys His Leu Thr Thr Pro Val Phe Gly Lys
        115                 120                 125

Gly Val Ile Tyr Asp Cys Pro Asn Ser Arg Leu Met Glu Gln Lys Lys
130                 135                 140

Phe Ala Lys Phe Ala Leu Thr Thr Asp Ser Phe Lys Arg Tyr Val Pro
145                 150                 155                 160

Lys Ile Arg Glu Glu Ile Leu Asn Tyr Phe Val Thr Asp Glu Ser Phe
                165                 170                 175

Lys Leu Lys Glu Lys Thr His Gly Val Ala Asn Val Met Lys Thr Gln
            180                 185                 190

Pro Glu Ile Thr Ile Phe Thr Ala Ser Arg Ser Leu Phe Gly Asp Glu
        195                 200                 205

Met Arg Arg Ile Phe Asp Arg Ser Phe Ala Gln Leu Tyr Ser Asp Leu
210                 215                 220

Asp Lys Gly Phe Thr Pro Ile Asn Phe Val Phe Pro Asn Leu Pro Leu
225                 230                 235                 240

Pro His Tyr Trp Arg Arg Asp Ala Ala Gln Lys Lys Ile Ser Ala Thr
                245                 250                 255

Tyr Met Lys Glu Ile Lys Ser Arg Arg Glu Arg Gly Asp Ile Asp Pro
            260                 265                 270

Asn Arg Asp Leu Ile Asp Ser Leu Leu Ile His Ser Thr Tyr Lys Asp
        275                 280                 285

Gly Val Lys Met Thr Asp Gln Glu Ile Ala Asn Leu Leu Ile Gly Ile
290                 295                 300

Leu Met Gly Gly Gln His Thr Ser Ala Ser Thr Ser Ala Trp Phe Leu
305                 310                 315                 320

Leu His Leu Gly Glu Lys Pro His Leu Gln Asp Val Ile Tyr Gln Glu
                325                 330                 335

Val Val Glu Leu Leu Lys Glu Lys Gly Gly Asp Leu Asn Asp Leu Thr
            340                 345                 350

Tyr Glu Asp Leu Gln Lys Leu Pro Ser Val Asn Asn Thr Ile Lys Glu
        355                 360                 365

Thr Leu Arg Met His Met Pro Leu His Ser Ile Phe Arg Lys Val Thr

```
            370                 375                 380
Asn Pro Leu Arg Ile Pro Glu Thr Asn Tyr Ile Val Pro Lys Gly His
385                 390                 395                 400

Tyr Val Leu Val Ser Pro Gly Tyr Ala His Thr Ser Glu Arg Tyr Phe
                405                 410                 415

Asp Asn Pro Glu Asp Phe Asp Pro Thr Arg Trp Asp Thr Ala Ala Ala
                420                 425                 430

Lys Ala Asn Ser Val Ser Phe Asn Ser Ser Asp Glu Val Asp Tyr Gly
                435                 440                 445

Phe Gly Lys Val Ser Lys Gly Val Ser Ser Pro Tyr Leu Pro Phe Gly
450                 455                 460

Gly Gly Arg His Arg Cys Ile Gly Glu Gln Phe Ala Tyr Val Gln Leu
465                 470                 475                 480

Gly Thr Ile Leu Thr Thr Phe Val Tyr Asn Leu Arg Trp Thr Ile Asp
                485                 490                 495

Gly Tyr Lys Val Pro Asp Pro Asp Tyr Ser Ser Met Val Val Leu Pro
                500                 505                 510

Thr Glu Pro Ala Glu Ile Ile Trp Glu Lys Arg Glu Thr Cys Met Phe
                515                 520                 525

<210> SEQ ID NO 78
<211> LENGTH: 433
<212> TYPE: PRT
<213> ORGANISM: Candida albicans

<400> SEQUENCE: 78

Met Pro Ser His Val Thr Asn Val Tyr Asn Asp Ile Asp Asp Gly Met
1               5                   10                  15

Leu Leu Ser Ser Leu Ser Leu Asn Glu Arg Ser Asn Asp Arg Arg Gly
                20                  25                  30

Leu Glu Ile Glu Glu Val Tyr Asp Ser Ser Phe Asp Asp Pro Met Asp
                35                  40                  45

Ile Asp Asp Thr Gly Glu Leu Ser Asn His Met Asp Ile Asp Asp Thr
50                  55                  60

Thr Phe Glu Ile Asp His Val Ala Ser Asp Asn Tyr Ala Asn Lys Arg
65                  70                  75                  80

Glu Asp Asp Asn Asp Thr Asn Asn Glu Glu Arg Arg Glu Asp Gly
                85                  90                  95

Leu Phe Ser Leu Leu Ser Pro Thr Leu Met Gly Ala Lys Leu Ala Ile
                100                 105                 110

Lys Lys Pro Leu Leu Leu Met Pro Pro Thr Val Ser Glu Gln Ser
                115                 120                 125

Asp Ser Lys Thr Glu Ser Ala Ser Ser Val Asp Tyr Glu Tyr Asp Thr
                130                 135                 140

Ser Ser Phe Lys Pro Met Lys Ser Asn Gly Leu Ile Thr Arg Lys Thr
145                 150                 155                 160

Asn Ser Ser Thr Phe Gln Pro Ser Asn Ile Asp Ser Phe Leu Phe His
                165                 170                 175

Ser Asp Gly Ile Ser Ser Gly Gln Ser Leu Gly Gly Tyr Gln Asp Leu
                180                 185                 190

His Ser Asn Tyr Gln Gln Pro Val Thr Ile His Asn His His His
                195                 200                 205

Tyr Tyr Tyr Tyr Asn Lys Asp Glu Ser Val Pro Ser Pro Ser Asn
210                 215                 220
```

```
Asn Asn Leu Gln Ser Leu Glu His Glu Gln Arg Asn Leu Gln Met Gln
225                 230                 235                 240

Gln Tyr Lys Gln Gln Leu Glu Glu His Gln Leu Tyr Leu Gln Glu Tyr
            245                 250                 255

Lys Arg Asn Asn Gln Ile Leu Leu Pro Ser Pro Trp Gln His Asn Ile
            260                 265                 270

Ser Pro Ile Glu Arg Val Pro Tyr Leu Leu Met Ser Tyr Leu Gln Met
        275                 280                 285

Leu Ile Asn Phe Ile Ala Ser Leu Tyr Gly Val Tyr Leu Val Tyr Cys
    290                 295                 300

Leu Phe Arg Thr Ile Asn Thr Asp Ile Lys Thr Lys Ile Glu Glu Gln
305                 310                 315                 320

Gln Thr Asn Leu Ile Ile Ser Ile Glu Ser Cys Arg Arg Ser Tyr Tyr
                325                 330                 335

Gln Asn Gly Cys Asp Asp Lys Asp Asn Leu Val Pro Leu Leu Val Ser
            340                 345                 350

Lys Cys Gln Lys Phe Glu Lys Cys Met Lys Gln Asp Pro Tyr Lys Leu
            355                 360                 365

Ser Asn Val Ser Ile Met Ser Ala Glu Ile Ile Gly Met Ile Ile Asn
        370                 375                 380

Ser Leu Ile Glu Pro Leu Ser Leu Lys Phe Tyr Leu Phe Met Leu Ala
385                 390                 395                 400

Phe Ile Leu Ile Ile Phe Ala Cys Asn Phe Thr Phe Gly Tyr Ile Arg
                405                 410                 415

Ala Lys Ala Tyr Tyr Gly Gly Ser Met Lys Tyr Ser Leu Asp Lys Leu
            420                 425                 430

Asp

<210> SEQ ID NO 79
<211> LENGTH: 263
<212> TYPE: PRT
<213> ORGANISM: Candida albicans

<400> SEQUENCE: 79

Met Glu Ser Leu Asp Glu Ile Gln Trp Lys Ser Pro Glu Phe Ile Gln
1               5                   10                  15

Glu Arg Gly Leu Asn Thr Asn Val Leu Glu Tyr Phe Ser Leu Ser
            20                  25                  30

Pro Phe Tyr Asp Arg Thr Ser Asn Asn Gln Val Leu Met Met Gln Phe
            35                  40                  45

Gln Tyr Gln Gln Ile Gln Ile Pro Pro Gly Val Ser Phe His Gln Tyr
        50                  55                  60

Phe Gln Ser Arg Leu Ser Glu Met Thr Gly Ile Glu Phe Val Ile Ala
65                  70                  75                  80

Tyr Thr Lys Glu Pro Asp Phe Trp Ile Ile Arg Lys Gln Lys Arg Gln
                85                  90                  95

Asp Pro Gln Asn Thr Val Thr Leu Gln Asp Tyr Tyr Ile Ile Gly Ala
            100                 105                 110

Asn Val Tyr Gln Ala Pro Arg Ile Tyr Asp Val Leu Ser Ser Arg Leu
        115                 120                 125

Leu Ala Ser Val Leu Ser Ile Lys Asn Ser Thr Asp Leu Leu Asn Asp
    130                 135                 140

Met Thr Ser Tyr His Ile Ser Asp Gly Gly His Ser Tyr Ile Asn Ser
145                 150                 155                 160
```

```
Ile His Gly Ser Ser Lys Pro Ser Gln Ser Ser Ala Val Ser Lys
                165                 170                 175

Pro Ser Ser Thr Asn Thr Gly Thr Asn Ala Thr Thr Thr Pro Ile Thr
            180                 185                 190

Leu Thr Thr Pro Ser Gly Ala Thr Val Pro Ser Thr Val Ser Asn Gly
        195                 200                 205

Ile Ser Thr Ser Thr Glu Ile Ala Ser Gly Val Phe Asp Thr Leu Leu
    210                 215                 220

Asn Asp Val Val Met Asn Asp His Leu Tyr Ile Asp Glu Ile Pro
225                 230                 235                 240

Leu Tyr Gly Glu Gly Ser Thr Leu Glu Arg Leu Gly Leu Lys Gly Asn
                245                 250                 255

Lys Asp Ala Gly Leu Ser Leu
            260

<210> SEQ ID NO 80
<211> LENGTH: 363
<212> TYPE: PRT
<213> ORGANISM: Candida albicans

<400> SEQUENCE: 80

Met Ser Ser Ser Gln Ala Arg Lys Ala Leu Gln Asp Val Ile Pro Asn
1               5                   10                  15

Tyr Leu Gly Glu Phe Thr Pro Lys Leu Leu Asp Tyr Ile Asn Ser Leu
            20                  25                  30

Tyr Gln Leu Ser Leu Arg Lys Gln Ala Ile Leu Pro Asn Lys Ser Glu
        35                  40                  45

Ile Ala Arg Phe His Leu Cys Ala Val Val Ile Glu Lys Tyr Lys
    50                  55                  60

Gln Ser Phe Glu Leu Pro Thr Pro Asp Val Ser Arg Ile Pro Thr Gln
65                  70                  75                  80

Pro Lys Val Ala Ala Lys Leu Leu Asp Thr Phe Arg Glu Leu Ile Glu
                85                  90                  95

Gln Ile Ser Ala Ala Ser Thr Pro Val Ser Ser Pro Lys Lys Val Lys
            100                 105                 110

Pro Pro Ser Gln Ser Pro Ser Thr Pro Thr Lys Ser Arg Thr Ser Lys
        115                 120                 125

Glu Asn Leu Lys Ser Gly Ser Pro Leu Lys Arg Leu Arg Ala Glu Met
130                 135                 140

Leu Gln Glu Asp Gln Val Asn Gly Asn Ser Pro Asp Gly Gln Leu Lys
145                 150                 155                 160

Asp Val Asp Ser Pro Phe Asn Pro Lys Lys Arg Lys Glu Ser Lys Ala
                165                 170                 175

Gly Thr Pro Thr His Lys Val Tyr Lys Tyr Asp Lys Lys His Val Ser
            180                 185                 190

Ile Ala Asp Phe Ile Ala Phe Cys Asn Thr Phe Leu Ile Pro Gly Asp
        195                 200                 205

Ile Thr Ala Lys Met Val Gly Thr Phe Leu Thr His Gln His Lys Phe
    210                 215                 220

Leu Lys Lys Ser Asp Trp Ser Leu Ala Cys Gly Met Val Tyr Ala Ala
225                 230                 235                 240

Tyr Ile Arg Ile Asn Asn Arg Leu Leu Ala Gln Ser Val Gly Thr Lys
                245                 250                 255

Ser Glu Phe Thr Lys Gln Leu Leu Gln Tyr Gln Lys Gly Gly Leu Ser
```

-continued

```
                    260                 265                 270
Leu Gly Ala Met Gln Ser Trp Cys Gly Ile Ile Glu Glu Trp Ile Gln
            275                 280                 285
Asp Glu Pro Trp Ile Gln Glu Ile Glu Lys Thr Tyr Ala Tyr Gly Ser
        290                 295                 300
Lys Thr Ala Glu Thr Arg Asn Ser Phe Glu Arg Lys Ala Lys Ile
305                 310                 315                 320
Gly Glu Gly Trp Asp Leu Met Glu Gln Phe Gly Ala Met Ile His Gly
                325                 330                 335
Glu Thr Ile Ser Leu Ser Ser His Gln Glu Glu Tyr Tyr Lys Asn Trp
            340                 345                 350
Arg Lys Glu Ala Leu Glu Lys Cys Asp Gln Leu
        355                 360
```

<210> SEQ ID NO 81
<211> LENGTH: 871
<212> TYPE: PRT
<213> ORGANISM: Candida albicans

<400> SEQUENCE: 81

```
Met Asn Thr Phe Ser Ser Pro Pro Asn Val Ile Arg Glu Tyr Asn Asp
  1               5                  10                  15
Ser Thr Tyr Gln Ser Pro Leu Asn Ser Gln Phe His Gln Ser Pro Phe
            20                  25                  30
Leu Gln Thr Gln Ser Pro Asp Tyr Val Ser Leu Arg Glu Glu Asp
        35                  40                  45
Asp Asn Asn Asp Lys Asn Leu Asp Ile Met Ser Ser Cys Ile Val Asp
 50                  55                  60
Ser Val Ile Tyr Lys Ser Gln Lys Ile Ala Gly Pro Leu Leu Ser Gln
 65                  70                  75                  80
Ile Ser Asn Leu Asn Ile Gln Gln Ala Leu Ile Ile Arg Glu Leu Leu
                85                  90                  95
Phe Thr Leu Leu Gly His Glu Gly His Tyr Ile Gln Tyr Ser Lys Arg
            100                 105                 110
Tyr Asp Pro Thr Ser Gln Ile Ser Arg Ile Glu Gly Pro Asp Tyr Lys
        115                 120                 125
Ile Ala Lys Asn Leu Asp Ile Ser Leu Lys Val Ile Thr Lys Lys Leu
    130                 135                 140
Val Lys Phe Gly Lys Phe Tyr Ser Gly Leu Lys Ser Phe Ile Gln Val
145                 150                 155                 160
Phe Asp Asn Asn Lys Phe Gly Lys Ile Val Gln Lys Phe Cys Ser Glu
                165                 170                 175
Val Arg Lys Phe Leu Ser Ser Tyr Gln Gln Val Leu Ile Asn Val Glu
            180                 185                 190
His Glu Phe Lys Phe Asn Lys Asn Phe Asn Leu Asn Met Leu Asp Ser
        195                 200                 205
Leu Leu His Gln Glu Ile Ser Asn Glu Met Thr His Leu Tyr Gln Ile
    210                 215                 220
Gly Ile Glu Ile Ser Arg Ile Thr Glu Glu Arg Gln Lys Met Ser Gln
225                 230                 235                 240
Ala Glu Ile Met Gly Asn Phe Glu Pro Thr Thr Leu Ala Asn Thr Ser
                245                 250                 255
Met Asn Gly Ile Asn Ser Glu Pro Asn Leu Tyr Tyr Gly Lys Phe Asp
            260                 265                 270
```

-continued

Cys Cys Lys Gly Gly Leu Leu Leu Gln Val Ile Gln Glu Arg Met Val
        275                 280                 285

Tyr Tyr Lys Gly Asp Pro Thr Ser Leu Asp Phe Leu Thr Gln Leu Phe
        290                 295                 300

Asp Ile Val Ser Ser Asp Tyr Ile Gly Met Leu Asn Gln Trp Leu Leu
305                 310                 315                 320

Glu Gly Val Ile Asn Asp Pro Phe Asp Glu Phe Met Ile Arg Glu Lys
                325                 330                 335

Arg Val Pro Asp Ser Phe Met Glu Ile Phe Gln Ser Lys Ser Glu Tyr
            340                 345                 350

Tyr Trp Asn Glu Leu Phe Leu Ile Lys Ile Asp Gly Leu Leu Asn Gln
        355                 360                 365

Phe Gln Asn Ser Thr Ile Gln Ser Lys Ile Leu Asn Thr Gly Lys Tyr
370                 375                 380

Leu Asn Ile Phe Lys Arg Cys Thr Gly Leu His Asn Phe Glu Ser Leu
385                 390                 395                 400

Lys Glu Lys Leu Thr Thr Ile Thr Ser Leu Ala Ala Pro Asp Leu Glu
                405                 410                 415

Leu Lys Ile Asp Glu Phe Tyr His Arg Ala Asn Lys Met Leu Met Lys
            420                 425                 430

Leu Leu Phe Asp Gly Tyr Asn Phe Pro Ser Val Val Asn Ile Phe Gln
        435                 440                 445

Arg Leu Phe Leu Phe Ala Asp Ser Phe Gln Ile Asp Asn Phe Ile Asp
    450                 455                 460

Ser Thr Phe Ser Glu Leu Lys Arg Gly Lys Leu Lys Ile Ser Val Ser
465                 470                 475                 480

Arg Leu Gln Lys Gln Tyr Asp Asp Ile Phe Lys Glu Lys Ile Glu Asn
                485                 490                 495

Lys Val Gly Val Arg Pro Ser Val Tyr Asp Val Leu Lys Lys Asn Gln
            500                 505                 510

Lys Leu Ser Val Thr Ser Glu Ser Leu Tyr Lys Val Val Glu Glu Leu
        515                 520                 525

Met Glu Lys Asn Ser Asp Tyr Leu Ile Ser Asp Asn Leu Arg Gly
        530                 535                 540

Ile Phe His Arg Val Ala Ser Leu Arg Asp Asp Ser Arg Leu Thr Ile
545                 550                 555                 560

Ser Ser Thr Ala Asp Ser Ala Thr Glu Asn Val Lys Asp Glu Pro Thr
                565                 570                 575

Ile Thr Ser Val Asp Leu Thr Ile Pro Leu Pro Phe Pro Leu Asn Leu
            580                 585                 590

Val Leu Asn Gln Gln Leu Ser Tyr Gln Tyr Glu Ile Met Phe Lys Leu
        595                 600                 605

Leu Ile Asn Ile Lys Phe Ile Ser Lys Tyr Asn Ser Ser Asn Trp Gln
    610                 615                 620

Glu Met Asn Tyr Ser Lys Ile Trp Thr Asn Ser His Phe Asn Ser Ser
625                 630                 635                 640

Val Lys Lys Trp Ile Leu Arg Cys Arg Val Leu His Ser Arg Ile Cys
                645                 650                 655

Ser Phe Ile His Glu Leu Glu Asn Tyr Ile Val His Asp Val Ile Glu
            660                 665                 670

His Asn Phe Glu Glu Ile Lys Asn Leu Ile His Thr Thr Ala Thr Asn
        675                 680                 685

Leu Ala Thr Ser Glu Leu Gly Ser Asp Ile Asn Asp Glu Gly Asp Asn

```
                690             695             700
Ile Phe Asn Gly Ser Leu Ile Arg Gly Thr Phe Asn Asn Ser Ile
705                     710                     720
Phe Asp Ser Lys Val His Lys His Arg Thr Thr Thr Tyr Val Glu Gly
                725                     730                 735
Ile Ser Thr Val Glu Gln Leu Ile Gln Lys Phe Leu Asp Tyr Ser Ser
                740                     745                 750
Thr Leu Leu Asn Asp Ser Leu Leu Thr Arg Glu Glu Ser Leu Arg Gln
                755                     760                 765
Leu Arg Lys Met Leu Asp Phe Ile Phe His Phe Asn Asn Tyr Ile Val
770                     775                     780
Gln Val Lys Lys Val Leu Val Leu Leu Asn His Glu Leu Phe Asn Glu
785                     790                     795                 800
Tyr Ser Lys Glu Phe Pro Thr Lys Phe Glu Lys Pro Met Asp Gln Glu
                805                     810                 815
Ser Ile Asp Lys Arg Phe Ala Asn Leu Ser Asp Thr Phe Leu Met Gln
                820                     825                 830
Tyr Glu Lys Phe Gly Glu Asn Leu Val Thr Phe Leu Ala Thr Ile Lys
                835                     840                 845
Gln Val Gly Glu Arg Glu Asn Gln Gly Leu Leu Glu Leu Ser Asn Arg
850                     855                     860
Leu Glu Leu Cys Phe Pro Glu
865                     870

<210> SEQ ID NO 82
<211> LENGTH: 636
<212> TYPE: PRT
<213> ORGANISM: Candida albicans

<400> SEQUENCE: 82

Met Ser Gly Pro Ile Ile Cys Ser Lys Phe Asp Gln Ser Gly Asn Tyr
1               5                   10                  15
Leu Ala Thr Gly Met Val Ala Leu Asp Ser His Gln Val Lys Val Gln
                20                  25                  30
Ser Ile Thr Ser Ser Gln Ala Ser Leu Asn Thr Ser Phe Thr Leu Glu
            35                  40                  45
Lys Ser Asn Lys Leu Val Asn Leu Ala Trp Ile Pro Ser Asp Ser Ile
50                  55                  60
Gln Leu Leu Ala Leu Cys Leu Ser Lys Gly Ser Ile Leu Ile Tyr Ser
65                  70                  75                  80
Pro Gln Thr Asn Glu Ile Val Ser Glu Leu Ile Ser Ser Ala Asn Val
                85                  90                  95
Ser Ile Leu Asp Phe His Tyr Ser Thr Thr Arg Thr Gly Trp Ser
            100                 105                 110
Cys Asp Ile Glu Gly Asn Val Tyr Glu Trp Asp Leu Asn Ser Tyr Leu
            115                 120                 125
Leu Val Asp Ser Phe Lys Val Asn Glu Tyr Ile Glu Ser Val Asp Ser
130                 135                 140
Ile Asn Arg Ile Ser Thr Val Met Phe Asn Ser Gln Pro His Leu Leu
145                 150                 155                 160
Leu Gly Ser Asn Ala Val Tyr Leu Phe Asn Ile Lys Gln Arg Glu Leu
                165                 170                 175
Val Lys Thr Phe Pro Gly His Ile Gln Pro Val Asn Ser Ile Thr Ala
                180                 185                 190
```

```
Leu Asn Asn Asp Met Phe Leu Thr Ser Ala Lys Gly Asp Arg Phe Val
        195                 200                 205

Asn Leu Tyr Gln Leu Asp Lys Thr Ala Thr Lys Ala Val Phe Val Gly
    210                 215                 220

Ser Ser Ser Val Ser Ser Leu Ser Val Ser Ile Lys Asp Asp Lys Ser
225                 230                 235                 240

Val Leu Val Ile Ile Asn Glu Glu Gly Asp Ile Glu Ile Phe Asn Asn
                245                 250                 255

Pro Leu Ala Asp Ala Lys Ser Gln Val Ser Thr Pro Val Pro Lys Lys
            260                 265                 270

Lys Arg Lys Gln Val Gly Val Ser Ser Arg Ser Phe Asn Ala Ser Ile
        275                 280                 285

Lys Leu Ser Arg Pro Glu Pro Glu Ile Lys Ser Pro Gln Asp Thr His
        290                 295                 300

Leu Phe Ile Asn Ala Val Ser Thr Glu Asp Asn Leu Ile Thr Phe Thr
305                 310                 315                 320

Trp Leu Glu Asn Ser Thr Ile Pro Phe Phe Asp Thr Leu Lys Trp Ile
                325                 330                 335

Asp Glu Thr Gly Ser Leu Leu Glu Ser Ala Lys Val Leu Leu Lys
            340                 345                 350

Ser Lys Pro Asn Leu Lys Val Thr Gln His Leu Thr Asn Gly His Asp
        355                 360                 365

Val Ala Ala Pro Lys Leu Tyr Thr Glu Gly His Thr Ile Val Ser Asp
    370                 375                 380

Gly Ser Asn Ile Arg Asp Leu Glu Phe Gln Asp His Gln Glu Asp Glu
385                 390                 395                 400

Glu Asp Thr Glu Glu Ser Leu Ala Glu Lys Leu Glu Arg Leu Ala Met
                405                 410                 415

Asp Gln Thr Ser Gln Gln Lys Ser Arg Arg Arg Lys Leu Glu Glu Ala
            420                 425                 430

Arg Ser Gly Val Ser Leu Ser Ile Val Leu Thr Gln Ser Leu Lys Asn
        435                 440                 445

Asn Asp Gln Ala Leu Leu Glu Thr Val Leu Ser Asn Arg Asp Pro Ile
    450                 455                 460

Thr Ile Gln Asn Thr Ile Ser Arg Leu Asp Pro Tyr Ser Cys Val Thr
465                 470                 475                 480

Phe Leu Asp Lys Leu Ser Glu Lys Ile Gln Arg Gln Pro Thr Arg Phe
                485                 490                 495

Asp Gln Val Ser Phe Trp Leu Lys Trp Ile Leu Val Ile His Gly Pro
            500                 505                 510

Thr Met Ala Ser Leu Pro Asn Leu Ser Ile Lys Leu Ser Ser Leu Arg
        515                 520                 525

Ala Val Leu Asn Lys Lys Ala Glu Glu Leu Pro Arg Leu Leu Glu Leu
    530                 535                 540

Gln Gly Arg Leu Lys Leu Met Asp Asp Ser Ala Ala Leu Arg Asn Glu
545                 550                 555                 560

Phe Ser Ala Glu Glu Ile Ala Glu Asp Leu Glu Arg Ser Asp Ile
                565                 570                 575

Glu Tyr Asn Glu Glu Ile Asp Asp Ala Lys Tyr Val Gly Val Ile Ser
            580                 585                 590

Asp Asp Glu Ser Met Asp Asp Val Asp Phe Asp Asp Leu Asp Asp
        595                 600                 605

Glu Glu Glu Glu Glu Glu Glu Glu Glu Glu Asp Gly Ile Pro Asp Ala
```

```
                        610                 615                 620
Ala Asn Leu Asp Asp Arg Glu Asp Ser Asp Leu Glu
625                 630                 635

<210> SEQ ID NO 83
<211> LENGTH: 327
<212> TYPE: PRT
<213> ORGANISM: Candida albicans

<400> SEQUENCE: 83

Met Met Ser Thr Asn Phe Gln Trp Pro Gly Thr Asn Lys Asn Asp Asn
  1               5                  10                  15

Thr Glu Val Ser Val Glu Thr Pro Ser Ser Thr Asp Pro His Val Pro
             20                  25                  30

Arg Tyr Pro Phe Thr Ala Met Ser His Ala Thr Ala Ser Thr Thr Met
         35                  40                  45

Lys Lys Arg Lys Arg Asp Asp Phe Asp Gly Asp Lys Ser Thr Thr Ile
     50                  55                  60

Thr Met Asn Thr Thr Thr Thr Arg Lys Tyr Ile Gln Ser Ser Leu Gly
 65                  70                  75                  80

Ser Ser Lys Phe Lys Lys Ala Lys Thr Pro Lys Ile Ser Gly Gln Pro
                 85                  90                  95

Leu Pro Leu Pro Arg Leu Ile Glu Ser Leu Asp Lys Ser Asn Leu Gln
            100                 105                 110

Lys Leu Val Gln Asp Leu Ile Thr Val His Pro Glu Leu Gln Ser Thr
        115                 120                 125

Leu Ile Lys Ile Ser Pro Arg Pro Ser Ile Gln Asp Ser Ile Gln Leu
    130                 135                 140

Leu Gln Asp Lys Phe Asp Met Ile Ile Ser His Leu Pro Tyr Lys Cys
145                 150                 155                 160

Asp Val Glu Ser Asp Tyr Ser Tyr Leu Arg Ile Lys Pro His Leu Gln
                165                 170                 175

Glu Phe Leu Ser Ser Val Ser Asp Phe Ile Leu Asn Tyr Leu Pro Pro
            180                 185                 190

Leu Glu Thr Asn Met Thr His Ser Leu Gln Phe Leu His Glu Thr Thr
        195                 200                 205

Lys Leu Val Tyr Asn Leu Pro Asn Phe Thr Asn Gln Glu Phe Gln Tyr
    210                 215                 220

Thr Lys Ser Ser Ala Leu Glu Gln Ile Ala Asn Cys Trp Leu Ile Val
225                 230                 235                 240

Leu Ser Gln Asp Glu Glu Lys Glu Gly Asn Thr Asp Val Val Lys Val
                245                 250                 255

Ile Gln Glu Leu Glu Leu Leu Glu Lys Leu His Glu His Asn Glu Ile
            260                 265                 270

Ser Phe Asn Lys Phe Glu Lys Val Val Asp Tyr Cys Lys Asp Lys Leu
        275                 280                 285

Glu Gln His Glu Leu Ile Met Asn Asn Asn Glu Ala Gly Ser Gly Val
    290                 295                 300

Thr Ser Ser Ile Ser Asp Leu Ile Thr Val Asp Tyr Ser Lys Tyr Ser
305                 310                 315                 320

Ile Ala Asn Thr Thr Ser Ile
                325

<210> SEQ ID NO 84
<211> LENGTH: 552
```

<212> TYPE: PRT
<213> ORGANISM: Candida albicans

<400> SEQUENCE: 84

```
Met Pro Thr Asn Ile Gln Gly Glu Val Ile Ile Pro Pro Lys Asp
 1               5                  10                  15

Glu Glu Glu Ile Leu Leu Glu Lys Leu Val Phe Gly Asp Ala Ala Gly
             20                  25                  30

Phe Glu Asn Asn Leu Lys Lys Leu Asp Asn Leu Tyr Asp Tyr Ser Asp
             35                  40                  45

Glu Glu Glu Glu Ile Asp Glu Lys Gly Ser Glu Lys Glu Ser Asp Ile
 50                  55                  60

Glu Asp Leu Gln Asp Glu Asp Leu Phe Phe Ile Asp Asp Gly Asn Asn
 65                  70                  75                  80

Glu Glu His Ser Ser Gly Asp Asp Met Glu Ile Asp Gln Ser Glu Asp
                 85                  90                  95

Glu Glu Glu Gly Glu Asp Gln Asp Ser Asp Asn Ala Trp Glu Asp Ser
            100                 105                 110

Asp Asp Glu Lys Val Asn Ile Ser Leu Leu Thr Ser Asp Lys Leu Lys
            115                 120                 125

Lys Leu Arg Lys Thr Pro Gln Asp Ser Val Ile Ser Gly Lys Ser Tyr
130                 135                 140

Ile Ile Arg Leu Arg Ser Gln Phe Glu Lys Ile Tyr Pro Arg Pro Gln
145                 150                 155                 160

Trp Ile Glu Asp Ile Glu Asn Asn Ser Asp Asp Glu Lys Asp Leu Ser
                165                 170                 175

Asp Glu Asp Lys Val Asp Asp Glu Glu Gly Gln Val Gly Ser Thr Thr
            180                 185                 190

Ala Leu Leu Asn Ile Leu Ser Ser Thr Glu Lys Phe Ile Asn Thr Lys
            195                 200                 205

Gln Leu Lys Leu Ile Ala Ala Asn Lys Ile Ser Ile Thr Arg Leu Lys
        210                 215                 220

Asp Ala Asn Tyr Lys Arg Ile Gly Lys Ser Gly Ile Gln Thr Ile Asp
225                 230                 235                 240

Phe His Pro Asn Tyr Pro Ile Leu Leu Thr Gly Gly Phe Asp Lys Thr
                245                 250                 255

Ile Arg Ile Tyr Gln Ile Asp Gly Lys Ser Asn Asn Phe Ile Thr Ser
            260                 265                 270

Tyr Phe Leu Lys Asn Cys Pro Ile Met Glu Ala Ser Phe Tyr Pro Gln
        275                 280                 285

Leu Ser Gly Asp Asp Thr Lys Thr Ser Asn Leu Ile Tyr Ala Ser Gly
    290                 295                 300

Arg Arg Arg Tyr Met Asn Lys Ile Asn Leu Ser Thr Gly Glu Ile Glu
305                 310                 315                 320

Lys Ile Ser Arg Leu Tyr Gly His Glu Gln Thr Gln Lys Ser Phe Glu
                325                 330                 335

Tyr Phe Lys Ile Ser Pro Gln Gly Lys Tyr Ile Gly Leu Thr Gly Asn
            340                 345                 350

Asn Gly Trp Cys Asn Leu Leu Asn Ala Gln Thr Gly His Trp Val His
        355                 360                 365

Gly Phe Lys Ile Glu Gly Thr Ile Val Asp Phe Ala Phe Ala Asn Asp
    370                 375                 380

Glu Ser Phe Ile Met Ile Val Asn Ser Ala Gly Glu Val Trp Glu Phe
385                 390                 395                 400
```

```
Ala Leu Glu Gly Lys Ile Thr Ser Lys Thr Pro Asn Lys Ile Ile Arg
                405                 410                 415

Arg Trp Tyr Asp Asp Gly Val Gly Ile Thr Lys Leu Gln Ile Gly
            420                 425             430

Gly Lys Asn Asn Arg Trp Val Ala Ile Gly Asn Asn Gly Ile Val
            435                 440             445

Asn Ile Tyr Asp Arg Ser Val Phe Ala Pro Glu Thr Thr His Pro Lys
        450                 455                 460

Pro Ile Lys Thr Val Glu Asn Leu Ile Thr Ser Ile Ser Ser Leu Val
465             470                 475                 480

Phe Asn Pro Asp Gly Gln Leu Leu Cys Ile Ala Ser Arg Ala Lys Arg
                485                 490                 495

Asp Ala Leu Arg Leu Val His Leu Pro Ser Gly Ser Val Tyr Ser Asn
            500                 505                 510

Trp Pro Thr Ser Gly Thr Pro Leu Gly Lys Val Thr Ser Ile Ala Phe
            515                 520                 525

Ser Pro Asn Asn Glu Met Leu Ala Ile Gly Asn Gln Thr Gly Lys Val
        530                 535                 540

Thr Leu Trp Arg Leu Asn His Tyr
545                 550

<210> SEQ ID NO 85
<211> LENGTH: 715
<212> TYPE: PRT
<213> ORGANISM: Candida albicans

<400> SEQUENCE: 85

Met Ser Leu Lys Pro Phe Thr Gly Leu Leu Phe Cys Cys Thr Gly Leu
 1               5                  10                  15

Glu Ser Thr Thr Arg Arg Glu Val Val Glu Lys Ile Glu Thr Leu Gly
            20                  25                  30

Gly Ile His Tyr Ser Asp Leu Met Thr Asp Val Asn Tyr Leu Ile Val
            35                  40                  45

Gly Asp Arg Asp Thr Glu Lys Tyr Arg Phe Cys Ile Lys Tyr Arg Pro
    50                  55                  60

Asp Ile Ile Phe Ile Asp Ala Asp Ser Ile Phe Thr Ile His Lys His
65                  70                  75                  80

Trp Ile Asn Gly Glu Asp Glu Asn Ser Asp Leu Leu Arg Ile Glu Lys
                85                  90                  95

Tyr Arg Leu Ala Ile Phe Ala Gln Leu Asn Ala Cys Phe Ser Arg Ile
            100                 105                 110

Glu Met Ser Thr Ser Gln Ile Asp His Leu Val Asn Thr Val Lys Phe
            115                 120                 125

Arg Gln Arg Thr Asn Thr Ser Pro Glu Tyr Phe Arg Pro Lys Asn Leu
130                 135                 140

Phe Lys Leu Phe Val Asp Asn Gly Gly Ile Ala Lys Glu Ser Leu Ser
145                 150                 155                 160

Cys His Gln Asn Phe Ile Ile Thr Ala Asp Pro Arg Gly Thr Arg Tyr
                165                 170                 175

Asn Lys Ala Leu Glu Trp Asn Val Pro Ala Ile His Pro Ile Trp Ile
            180                 185                 190

Val Asp Ser Val Leu Arg Gly Ala Ala Leu Asp Trp Lys Asp Tyr Ile
            195                 200                 205

Leu Asn Asn Asn Pro Asn Asp Cys Tyr Asp Arg Gly Cys Asp Val Trp
```

-continued

```
              210                 215                 220
Pro Glu Val Phe Asp Cys Gln Glu Lys Gln Lys Gln Lys Ser Gln Gln
225                 230                 235                 240

Gln Pro Lys Arg Leu Glu Ser Thr Glu Pro Glu Val Lys Arg Lys Ile
                245                 250                 255

Thr Asn Asn Lys Thr Asn Ala Asp Ile Trp Asn Ser Ile Met Asp His
                260                 265                 270

Thr Lys Lys Gln Thr Lys Gln Leu Ile His Asp Lys Thr Trp Asp Asp
                275                 280                 285

Asp Glu Glu Glu Asp Asn Asp Asp Gly Asp Thr Gln Thr Lys
290                 295                 300

Asn Glu Lys Asn Asn Gln Tyr Lys Asn Ile Thr Thr Ile Pro Lys Asp
305                 310                 315                 320

Gly Lys Gln Lys Pro Glu Leu Asn Gly Lys Ile His Asn Leu Asp Leu
                325                 330                 335

Lys Leu Val Ser Glu Ser Lys Glu Asn Ser Pro Asn Val Ser Glu Ser
                340                 345                 350

Gln Leu Phe Leu Gly Phe Asn Tyr Tyr Thr Val Gly Phe Asp Ser Arg
                355                 360                 365

Glu Phe Asp Leu Leu Ser Lys Ala Ile Glu Asn Tyr Ser Gly Glu Ile
                370                 375                 380

Ser Asn Asp Pro Asn Asp Asp Ser Ile Thr His Val Val Ile Pro Ala
385                 390                 395                 400

Lys Lys Gly Tyr Gln Ser Met Ser Val Leu Lys Val Leu Pro Ala Asp
                405                 410                 415

Leu Lys Ser Arg Ile Ala Asn Gly Phe Val Lys Ile Val Thr Glu Phe
                420                 425                 430

Phe Ile Glu Arg Cys Met Phe Tyr Lys Lys Ile Ile Leu Asp Arg Trp
                435                 440                 445

Gly Gln Pro Met Lys Gly Leu Val Pro Ser Lys Lys Ser Phe Lys Ile
450                 455                 460

Cys Thr Thr Gly Phe Thr Gly Ile Glu Leu Leu His Ile Glu Lys Leu
465                 470                 475                 480

Ile Arg Ser Phe Asn Phe Glu Tyr Cys Glu Thr Leu Ser Glu Gln Arg
                485                 490                 495

Asp Leu Leu Ile Leu Asn Val Asn Leu Phe Lys Lys Ser Leu Met Asn
                500                 505                 510

Ser Pro Lys Leu Phe Gln Tyr Lys Cys Lys Asp Ile Ile Asn Cys Pro
                515                 520                 525

Thr Gly Gly Ser Val Ser Leu Met Ser Ser Lys His Lys Val Glu Ala
                530                 535                 540

Ala Lys Arg Trp Asn Ile Pro Val Val Ser Val Ala Tyr Leu Trp Glu
545                 550                 555                 560

Ile Leu Glu Leu Ser Thr Asn Lys Ser His Ile Met Pro Asp Ile
                565                 570                 575

Thr Asp Leu Gln Trp Cys Val Phe Ala Pro Ser Asn Tyr Asn Lys Pro
                580                 585                 590

Lys Ser Leu Leu Glu Tyr Val Lys Asn Leu Asp Lys Ala Ser Arg Glu
                595                 600                 605

Ser Ser Phe Ser Pro Lys Ser Gln Glu Asn Glu Ala Leu Glu Glu Pro
                610                 615                 620

Thr Met Asp Asn Ser Val Arg Leu Pro Ser Pro Arg Arg Val Asn Ser
625                 630                 635                 640
```

-continued

```
Lys Gln Lys Tyr Gly Lys Leu Val Gly Gly Lys Ser Pro Lys Ser Ile
                645                 650                 655
Lys Arg Lys Leu Leu Glu Ala Ala Asn Ser Phe Ala Asp Gly Gln Asn
            660                 665                 670
Asp His Ser Ile Asn Pro Asp Val Thr Ile Glu Asp Ser Met Ser
        675                 680                 685
Gln Ile Arg Tyr Gln Asp Asn Glu Ser Met Ile Asn Gln Glu Arg Leu
    690                 695                 700
Leu Glu Lys Leu Asp Gly Ser Ala Val Leu Val
705                 710                 715

<210> SEQ ID NO 86
<211> LENGTH: 1120
<212> TYPE: PRT
<213> ORGANISM: Candida albicans

<400> SEQUENCE: 86

Met Gly Lys Asp Leu Leu Thr Ala Glu Ala Val Thr Lys Leu Leu Arg
 1               5                  10                  15
Ser Lys Asp Thr Ser Ile Thr Glu Ile Val Asn Thr Ala Asn Ser Leu
             20                  25                  30
Leu Asn Asn Thr Leu Asp Ile Tyr Leu Pro Gly Lys Glu Val Phe Val
         35                  40                  45
Leu Asn Leu Leu Cys Asp Arg Leu Asn Asp Lys Ser Asn Gly Lys Phe
     50                  55                  60
Gly Lys Trp Lys Phe Asn Lys Asp Val Trp Asn Leu Leu Ser Val
65                  70                  75                  80
Trp Ser Lys Leu Asn His Gln Lys Val Asp Arg Gln Arg Val Ile Gln
                 85                  90                  95
Arg Leu Lys Ile Ile Glu Ile Ile Ile Leu Val Leu Gln Gln Asn Asn
            100                 105                 110
Asp Asn Glu Val Phe Ser Ser Leu Phe Glu Phe Leu Gly Ile Met Phe
        115                 120                 125
Gln Glu Ser Tyr Ile Ile Ala Asp Glu Asn Ser Ala Thr Gln Leu Leu
    130                 135                 140
Lys Cys Phe Val Glu His Met Asp Val Leu Gln Ala Ser Asp Ser Ile
145                 150                 155                 160
Val Ser Trp Thr Glu Leu Val Arg Asp Ile Tyr Thr Arg Ala Cys Ser
                165                 170                 175
Lys Ile Ser Leu Glu Gly Ser Lys Lys Phe Tyr Asn Lys Phe Phe Glu
            180                 185                 190
Asp Cys Cys Phe Pro Leu Ile Glu Tyr Leu Ala Ile Ser Glu Gly Ser
        195                 200                 205
Ser Val Ser Pro Ile Leu Lys Glu Leu Leu Ile Gln Gly Val Phe Asn
    210                 215                 220
Ala Asp Ser Thr Lys Tyr Tyr Gln Ser Ser Leu Glu Arg Glu Leu Lys
225                 230                 235                 240
Lys Lys Asp Ile Lys Glu Val Ser Val Ile Tyr Leu Tyr Thr Leu Thr
                245                 250                 255
Val Gln Leu Phe Ser Ala Lys His Met Glu Ile Cys Glu Gly Val Tyr
            260                 265                 270
Ser Ile Met Ala Ser Lys Cys Pro Asp Leu Ala Glu Lys Leu Leu Ser
        275                 280                 285
Ile Leu Ala Ser Cys Arg Lys Thr Ile Ser Lys Pro Phe Ile Glu Ser
```

-continued

```
                290                 295                 300
Ile Tyr Lys Val Glu Val Ala Asp Lys Pro Phe Lys Gln Leu Asn Trp
305                 310                 315                 320

Asp Met Val Lys His Ile Phe Ala Ile Asp Ser Glu Leu Ala Ile Ser
                325                 330                 335

Lys Ser Gly Phe Leu Phe Lys Thr Tyr Lys Ser Glu Phe Gln Leu Asp
                340                 345                 350

Asp Lys Val Val Pro Val Ala Glu Val Ile Val Asp Gly Phe Ala Arg
                355                 360                 365

Asn Arg Glu Leu Ser Asp Phe Phe Thr Lys Val Trp Pro Lys Ala Ile
370                 375                 380

Lys Arg Asp Glu Ile Trp Glu Ser Asp Glu Phe Ile His Thr Val Ser
385                 390                 395                 400

Gln His Val Lys Thr Phe Ser Gly Lys Gln Leu Ile Asp Val Ile Glu
                405                 410                 415

Ser Ser Phe Tyr Ala Asp Lys Gly Ser Gln Arg Ala Ile Phe Thr Ala
                420                 425                 430

Ile Thr Lys Gly Leu Thr Ser Ser Ala Asn Leu Ile Asp Ala Val
                435                 440                 445

Lys Gln Thr Leu Leu Asp Arg Ser Asn Tyr Phe Asn Ala Thr Glu Asn
                450                 455                 460

Phe Trp Cys Ile Arg Tyr Tyr Leu Leu Cys Leu Tyr Gly Thr Asp Phe
465                 470                 475                 480

Thr Ile Ala Glu Gln Asn Met Lys Gln Asn Ile Asp Leu Tyr Tyr His
                485                 490                 495

Phe Ser Ile Phe Arg Leu Leu Glu Leu Gln Val Ile Lys Glu Tyr Ser
                500                 505                 510

Lys Ser Asp Gln Lys Tyr Phe Ile Ala Cys Ile Glu Gly Glu Lys Glu
                515                 520                 525

Met Ile Ser Pro Ile Phe Lys Arg Trp Leu Val Ile Phe Asn Lys Phe
530                 535                 540

Phe Asp Ser Asp Leu Leu Ile Lys Leu Ile Ser Leu Gly Tyr Pro Asp
545                 550                 555                 560

Ile Glu Phe Asp Val Phe Phe Glu Gln Pro Lys Leu Thr Ser
                565                 570                 575

Leu Ile Arg Phe Ile Thr Glu Asn Leu Pro Ala Arg Met Asp Leu Ile
                580                 585                 590

Ala Ser Ile Pro Ile Val Cys Phe Asn Lys Ala Phe Lys Lys Glu Leu
                595                 600                 605

Leu Asn Gly Leu Phe Val Leu Phe Val Ser Asn Pro Thr Lys Glu Thr
610                 615                 620

Leu Glu Asn Ile Gln Tyr Leu Leu Gly Gln Pro Thr Tyr Ser Ser Ile
625                 630                 635                 640

Leu Glu Thr Asn Phe Asp Asn Met Leu Lys Leu Leu Thr Val Ser Thr
                645                 650                 655

Glu Glu Ser Lys Leu Ile Ala Tyr Asn Val Ile Glu Ile Val Trp Lys
                660                 665                 670

Asn Asn Val Arg Gln Ile Lys Asn Glu Glu Asn Gln Lys Tyr Val Asn
                675                 680                 685

Asp Ala Ile Ser Lys Leu Ser Ser Tyr Leu Asp Ser Met Ser Gln Gln
                690                 695                 700

Ile Ile Ser Pro Glu Leu Glu Ala Ile Ser Ile Ile Leu Thr Asn Thr
705                 710                 715                 720
```

-continued

```
Lys Glu Val Gly Leu Phe Glu Asn Thr Glu Lys Gly Leu Asn Lys Leu
                725                 730                 735

Asn Glu Lys Phe Thr Asn Tyr Cys Ile Asn Thr Leu Asn Asn Cys Asn
            740                 745                 750

Thr Gln Asn Phe Ile Thr Val Arg Trp Leu Leu Gln Ala Leu Val Met
        755                 760                 765

Leu Pro Pro Lys Ser Leu Ser Phe Glu Asn Val Ile Ser Cys Thr Lys
    770                 775                 780

Arg Leu Asp Pro Asn Ile Leu Lys Asp Asn Ser Ile Gln Ser Thr Leu
785                 790                 795                 800

Phe Gln Leu Ile Cys Lys Thr Ile Asp Phe Asn Tyr Lys Ser Leu Val
                805                 810                 815

Tyr Val Leu Ser Leu Phe Val Ser Leu Ser Ser Gly Arg Asn Thr Glu
            820                 825                 830

Leu Tyr Thr Val Leu Lys Ser Leu Phe Gln Lys Phe Ser Lys His Ser
        835                 840                 845

Gln Leu Tyr Phe Glu Val Phe Asp Phe Phe Thr Arg Ser Ile Asp Ala
    850                 855                 860

Val Pro Val Glu Phe Asn Leu Ser Phe Ala Gln Ile Ala Ser Ile Phe
865                 870                 875                 880

Leu Ser Thr Val Pro Lys Asp Ala Asp Ala Asn Arg Tyr Asn Ser Lys
                885                 890                 895

Cys Phe Thr Phe Tyr Val Asn Ala Leu Gln Ser Gly Asn Glu Cys Val
            900                 905                 910

Ala Met Gln Ile Leu Thr Ser Leu Lys Asp Leu Leu Thr Asn Gln Ser
        915                 920                 925

Trp Ile Phe Lys Gln Asn Leu Leu Glu Ile Thr Leu Val Ile Val Lys
    930                 935                 940

Thr Gly Leu Gln Lys Leu Asn Ser Phe Ala Asn Gln Glu Gln Ile Tyr
945                 950                 955                 960

Ile Leu Ser Thr Gln Ile Val Ser His Ile Leu Leu Tyr His Arg Phe
                965                 970                 975

Lys Ile Ala Thr Arg His His Leu Val Leu Asn Val Met Ser Ser Leu
            980                 985                 990

Leu Lys Tyr Leu Ala Asp Gly Thr Ser Lys Leu Ser Ser Asn Thr Glu
        995                 1000                1005

Ala Ala Ser Ala Tyr Ala Arg Leu Leu Ser Asn Leu Cys Glu Pro Ser
    1010                1015                1020

Glu Arg Val Gly Asp Lys Met Phe His Leu Thr Thr Ser Ala Ser Tyr
1025                1030                1035                1040

Phe Lys Lys Leu Leu Arg Lys His Leu Ser Val Leu Leu Ser Asn Tyr
                1045                1050                1055

Ile Tyr Phe Asn Leu Lys Tyr Thr Phe Thr Arg Thr Val Asn Asp Ala
            1060                1065                1070

Ile Met Pro Gly Ile Tyr Ser Met Phe Thr Val Leu Ser Gln Asn Glu
        1075                1080                1085

Leu Arg Val Val Asn Asp Ser Leu Asp Tyr Gly Gly Lys Ala Phe Tyr
    1090                1095                1100

Lys Thr Leu Tyr Asn Asp Tyr Lys Asp His Gly Lys Trp Lys Asp Gln
1105                1110                1115                1120
```

<210> SEQ ID NO 87
<211> LENGTH: 196

```
<212> TYPE: PRT
<213> ORGANISM: Candida albicans

<400> SEQUENCE: 87

Met Ser Ala Asp Glu Asn Asn Lys Val Arg Phe Glu Arg Leu Arg Leu
 1               5                  10                  15

Val Ala Arg Lys Ala Leu Glu Gln Ser Ile Lys Lys Ser Leu Thr Met
            20                  25                  30

Glu Gln Val Lys Thr Cys Phe Pro Thr Leu Val Thr Ser Gln Asp Gly
        35                  40                  45

Val Arg Ser Leu Glu Leu Ala Leu Ser Gln Met Ser Gly Phe Trp His
50                  55                  60

Ala Asn Ser Leu Asp Glu Phe Asp Leu Ile Tyr Lys Glu Lys Asp Ile
65                  70                  75                  80

Glu Ser Lys Leu Asp Glu Leu Asp Asp Ile Ile Gln Asn Ala Gln Arg
                85                  90                  95

Thr Lys Asp Ser Gly Lys Glu Pro Ser Asn Ile Asp Gln Leu Ser Pro
            100                 105                 110

Leu Glu Ile Val Asp Ser Thr Ile Val Ser Asn Ser Lys Asn Val Leu
        115                 120                 125

Asp Ser Leu Gln Met Ile Tyr Asp Gln Leu Cys Leu Asp Asn Ala Glu
130                 135                 140

Leu Tyr Thr Glu Leu Ser Glu Leu Thr Lys Glu Ser Thr Arg Ile Asn
145                 150                 155                 160

Asn Ser Ile Lys Ser Gly Ile Glu Gln Leu Asn Lys Glu Ala Asn Ser
                165                 170                 175

Val Glu Leu Glu Lys Ala Gly Leu Gln Ile Asp Lys Leu Ile Asp Ile
            180                 185                 190

Leu Glu Glu Lys
        195

<210> SEQ ID NO 88
<211> LENGTH: 471
<212> TYPE: PRT
<213> ORGANISM: Candida albicans

<400> SEQUENCE: 88

Met Ala Ser Ser Ile Leu Arg Ser Lys Ile Ile Gln Lys Pro Tyr Gln
 1               5                  10                  15

Leu Phe His Tyr Tyr Phe Leu Ser Glu Lys Ala Pro Gly Ser Thr Val
            20                  25                  30

Ser Asp Leu Asn Phe Asp Thr Asn Ile Gln Thr Ser Leu Arg Lys Leu
        35                  40                  45

Lys His His His Trp Thr Val Gly Glu Ile Phe His Tyr Gly Phe Leu
50                  55                  60

Val Ser Ile Leu Phe Phe Val Phe Val Phe Pro Ala Ser Phe Ile Phe
65                  70                  75                  80

Ile Lys Leu Pro Ile Ile Leu Ala Phe Ala Thr Cys Phe Leu Ile Pro
                85                  90                  95

Leu Thr Ser Gln Phe Phe Leu Pro Ala Leu Pro Val Phe Thr Trp Leu
            100                 105                 110

Ala Leu Tyr Phe Thr Cys Ala Lys Ile Pro Gln Glu Trp Lys Pro Ala
        115                 120                 125

Ile Thr Val Lys Val Leu Pro Ala Met Glu Thr Ile Leu Tyr Gly Asp
130                 135                 140
```

```
Asn Leu Ser Asn Val Leu Ala Thr Ile Thr Thr Gly Val Leu Asp Ile
145                 150                 155                 160

Leu Ala Trp Leu Pro Tyr Gly Ile Ile His Phe Ser Phe Pro Phe Val
                165                 170                 175

Leu Ala Ala Ile Ile Phe Leu Phe Gly Pro Pro Thr Ala Leu Arg Ser
            180                 185                 190

Phe Gly Phe Ala Phe Gly Tyr Met Asn Leu Leu Gly Val Leu Ile Gln
        195                 200                 205

Met Ala Phe Pro Ala Ala Pro Pro Trp Tyr Lys Asn Leu His Gly Leu
    210                 215                 220

Glu Pro Ala Asn Tyr Ser Met His Gly Ser Pro Gly Gly Leu Gly Arg
225                 230                 235                 240

Ile Asp Lys Leu Leu Gly Val Asp Met Tyr Thr Thr Gly Phe Ser Asn
                245                 250                 255

Ser Ser Ile Ile Phe Gly Ala Phe Pro Ser Leu His Ser Gly Cys Cys
            260                 265                 270

Ile Met Glu Val Leu Phe Leu Cys Trp Leu Phe Pro Arg Phe Lys Phe
        275                 280                 285

Val Trp Val Thr Tyr Ala Ser Trp Leu Trp Ser Thr Met Tyr Leu
    290                 295                 300

Thr His His Tyr Phe Val Asp Leu Ile Gly Gly Ala Met Leu Ser Leu
305                 310                 315                 320

Thr Val Phe Glu Phe Thr Lys Tyr Lys Tyr Leu Pro Lys Asn Lys Glu
                325                 330                 335

Gly Leu Phe Cys Arg Trp Ser Tyr Thr Glu Ile Glu Lys Ile Asp Ile
            340                 345                 350

Gln Glu Ile Asp Pro Leu Ser Tyr Asn Tyr Ile Pro Ile Asn Ser Asn
        355                 360                 365

Asp Asn Glu Ser Arg Leu Tyr Thr Arg Val Tyr Gln Glu Ser Gln Val
370                 375                 380

Ser Pro Pro Ser Arg Ala Glu Thr Pro Glu Ala Phe Glu Met Ser Asn
385                 390                 395                 400

Phe Ser Arg Ser Arg Gln Ser Ser Lys Thr Gln Val Pro Leu Ser Asn
                405                 410                 415

Leu Thr Asn Asn Asp Gln Val Pro Gly Ile Asn Glu Glu Asp Glu Glu
            420                 425                 430

Glu Glu Gly Asp Glu Ile Ser Ser Thr Pro Ser Val Phe Glu Asp
        435                 440                 445

Glu Pro Gln Gly Ser Thr Tyr Ala Ala Ser Ser Ala Thr Ser Val Asp
    450                 455                 460

Asp Leu Asp Ser Lys Arg Asn
465                 470

<210> SEQ ID NO 89
<211> LENGTH: 1179
<212> TYPE: PRT
<213> ORGANISM: Candida albicans

<400> SEQUENCE: 89

Met Thr Ser Ser Ser Gln Leu Ser Ala Ser Ser Asn Glu Ser Ile Gln
1               5                   10                  15

Asn Glu Arg Leu Leu Ser Ser Ser Leu Phe Asp Gln Ile Arg Pro Val
            20                  25                  30

Cys Ile Glu Leu Ser Glu Ala Ser Thr Ser Gln Pro Phe Asn Thr Asn
        35                  40                  45
```

```
Lys Val Val Asn Leu Met Ile Ser Met Glu Asp Ile Leu Lys Lys His
 50                  55                  60

His Asp Glu Tyr Asn Lys Asp Gly Asn Phe Arg Ile Tyr Gln Leu Ser
 65                  70                  75                  80

Pro Lys Leu Ala Asp Tyr Ile Phe Tyr Pro Leu Ser Asn Ile Leu Lys
                 85                  90                  95

Gln Pro Ala Leu Asp Asp Thr Ile Ile Gln His Leu Phe Gly Ile Ile
            100                 105                 110

Arg Phe Leu Val Glu Tyr Ser Trp Ser Phe Asn Val Asn Phe Val Leu
            115                 120                 125

Thr Asp Gln Leu Leu Pro Leu Val Ile Tyr Leu Ser Ser Gly Asp Leu
            130                 135                 140

Asn Lys Glu Pro Leu Leu Ile Thr Lys Lys Ser Ile Gln Phe Lys Ile
145                 150                 155                 160

Ala Thr Val Ser Val Leu Tyr Thr Ile Thr Ser Thr Leu Asn Lys Glu
                165                 170                 175

Tyr Phe Gln Ser Leu Thr Glu Lys Arg Leu Leu Phe Ile Ser Asn Val
            180                 185                 190

Ile Thr Ile Cys Leu Ser Ile Ile Val Gly Ser Arg Val Glu Ser Gln
            195                 200                 205

Asp Thr Ile Gln Leu Val Leu Lys Cys Leu Ser Leu Ile Ser Asn Val
            210                 215                 220

Lys Arg Tyr Leu Asn Ser Ser Gln Ile Ser Ile Leu Pro Gly Ile
225                 230                 235                 240

Val Ser Ser Ile Thr Lys Phe Ile Ser Leu Asn Leu Asn Leu Asn Tyr
                245                 250                 255

Gln Ile Ile Ile Gln Phe Leu Arg Leu Leu Ser Gly Phe Ile Cys Ala
            260                 265                 270

Ser Phe Asn Asp Lys Glu Leu Asp Ala Gln Ile Glu Leu Asn Glu Gly
            275                 280                 285

Ile Ser Asp Ile Ser Glu Ile His Val Gly Trp Asp Asp Asn Glu
            290                 295                 300

Thr Leu Gly Asn Asn Ser Leu Tyr Ser Asp Val Thr Ile Thr Glu Asn
305                 310                 315                 320

Asp His Arg Ser Ser Ala Trp Leu Lys Ala Thr Ser Lys Gln Leu Lys
                325                 330                 335

Leu Ser Leu Ile Ile Ile Phe Lys Ser Ile Leu Leu Gly Ser Arg Asn
            340                 345                 350

Arg His Arg Leu Arg Ser Lys Gln Glu Leu Tyr Asp Glu Ile Leu Gly
            355                 360                 365

Phe Val Glu Thr Ile Leu Lys Asn Cys Phe Asn Ser Leu Phe Lys Glu
            370                 375                 380

Phe Ala Ser Leu Ala Ile Asp Ile Val Ser Ile Leu Gly Tyr Val Thr
385                 390                 395                 400

Ser Glu Asp Asn Lys Glu Met Ala Asp Lys Thr Asn Lys Leu Ser Asn
                405                 410                 415

Thr Leu Cys Met Ile Ile Glu Gly Glu Thr Asn Lys Glu Val Leu
            420                 425                 430

Phe Glu Leu Val Lys Thr Lys Leu Ala Asp Leu Ile Asp Asn Lys Leu
            435                 440                 445

Ser Gly Ile Val Phe Ala Leu Asp Glu Asp Lys Ile Ser Ser Thr Val
450                 455                 460
```

```
Ala Ser Met Met Phe Asn Phe Ser Leu Leu Leu Cys Leu Ser Arg Lys
465                 470                 475                 480

Val Lys Leu Asp Cys Glu Asp Leu Asp Ser Leu Lys Gln Arg Cys Leu
                485                 490                 495

Ala Leu Leu Thr Glu Tyr Val Ala Asp Arg Phe Lys Phe Glu Ser Ser
                500                 505                 510

Lys Pro Ile Lys Ser Ser Asn Ala Ser Gly Leu Leu Glu Thr Ser Ser
            515                 520                 525

Met Thr Asn Gln Leu Asp Ser Ile Glu Leu Pro Gly Tyr Ile Asn Ala
        530                 535                 540

Lys Ser Val Val Lys Gln Glu Pro Leu Lys Lys Glu Gln Asp Lys Arg
545                 550                 555                 560

Ala Tyr Ile His Asn Leu Lys Thr Ile Ser Arg Asn Trp Asn Thr Asn
                565                 570                 575

Glu Ile Asn Asn Ser Ser Gly Asn Thr Leu Ile Gly Ile Ser Ser Lys
                580                 585                 590

Phe Ser Glu Thr Ile Leu Gln Asn Phe Ile Asn Tyr Leu Ser Ser Leu
            595                 600                 605

Lys Tyr Glu Ala Ser Asn Ser Ser Thr Leu Thr Glu Leu Glu Asn Ile
        610                 615                 620

Phe Glu Leu Ala Asp Asp Asn Asp Met Ile Thr Lys Ser Thr Ser Leu
625                 630                 635                 640

Trp Val Ala Ser Asn Tyr Tyr Lys Arg Ser Thr Leu Gly Lys Val Ile
                645                 650                 655

Asn Phe Asp Leu Gly Lys Tyr Leu Val Leu Asp Asp Glu Asp Met
            660                 665                 670

Glu Ile Asp Asp Asp Thr Lys Glu Met Ser Phe Leu Val Leu Ser Arg
            675                 680                 685

Ala Glu Glu Leu Leu Glu Glu Ile Ser Glu Asn Gln Glu Lys Tyr Ser
        690                 695                 700

Ser Gln Thr Tyr Ile Leu Ala Tyr Asn Ala Ala Leu Gln Ser Ile Lys
705                 710                 715                 720

Val Val Ala Gly Ser Ile Pro Leu Asp Gln Phe Arg Thr Asn Phe Leu
                725                 730                 735

Met Asp His Leu Leu Ser Val Phe Gln Ala Leu Thr Tyr Asn Asp Met
                740                 745                 750

Pro Glu Ile Gln Leu Gln Ala Gln Ser Thr Leu Lys Val Val Leu Asp
            755                 760                 765

Thr Tyr Tyr Asn Gly Ser Met Val Asn Leu Ile Ser Asp Asn Ser Asp
        770                 775                 780

Tyr Leu Ile Asp Ser Ile Ser Leu Gln Met Ser Val Ala Ser Asn Leu
785                 790                 795                 800

Thr Pro Met Leu Pro Gly Ile Leu Leu Ile Val Lys Ile Ala Gly
                805                 810                 815

Ile Gln Leu Leu Glu Ser Asn Gln Leu His Asp Val Leu Thr Asp Met
            820                 825                 830

Phe Val Ile Leu Asp Ser Phe His Gly Tyr Asn Lys Leu Val Glu Ser
            835                 840                 845

Phe Phe Ile Val Phe Glu Ala Leu Ile Asp Gln Ile His His Lys Phe
        850                 855                 860

Asp Ser Gln Leu Lys Val Glu Phe Lys Glu Ser Ser Lys Thr Asn Thr
865                 870                 875                 880

Ser Leu Tyr Lys Pro Trp Gly Met Thr Asn Lys Asp Gln Leu Leu Glu
```

-continued

```
                885                 890                 895
Leu Leu Asn Glu Ser Asn Lys Met Val Asp Lys Tyr Glu Gly Tyr Asp
            900                 905                 910
Ser Asn Lys Glu Tyr Phe Lys Arg Lys Ala Asp Leu Pro Phe Ser Glu
        915                 920                 925
Met Asp Ala Asp Ser Asp Glu Glu Glu Asp Glu Ala Asn Ile
    930                 935                 940
Asp Asp Asn Gly Glu Glu Glu Glu Lys Glu Ile Trp Ser Ser
945                 950                 955                 960
Pro Val Ser Lys Asp Ile Tyr Met Ile Ser Leu Arg Ile Phe Asn Tyr
                965                 970                 975
Gly Phe Thr Leu Val Ser Gln Glu Ser Tyr Thr Leu Lys Thr Gln Ile
            980                 985                 990
Ile Lys Thr Leu Arg Leu Leu Leu Pro Leu Leu Cys Thr Asn Tyr Lys
        995                 1000                1005
Leu Leu Leu Pro Val Leu Ala Leu Asn Trp Gln Met Leu Ile Ala Leu
    1010                1015                1020
Val Thr Gly Ser Lys Ser Leu Ser Thr Ser Ile Glu Ser Asn Gly Glu
1025                1030                1035                1040
Tyr Ala Ser Glu Asp Ile Gly Val Met Thr Glu Ala Leu Gln Leu Val
                1045                1050                1055
Thr Glu Ile Leu Glu Glu Asp Lys Arg Arg Tyr Glu His Phe Phe Ser
            1060                1065                1070
Lys Lys Phe Gln Glu Ala Trp Glu Phe Ile Ser Arg His Ser Lys Leu
        1075                1080                1085
Val Arg Gln Arg Glu Val Thr Ser Thr Thr Asn Ile Arg Glu Gln Lys
    1090                1095                1100
Gln Leu Val Val Ser Glu Lys Ala Ile Tyr Thr Phe Arg Asn Tyr Pro
1105                1110                1115                1120
Leu Leu Lys Thr Ser Leu Val Thr Phe Leu Ile Thr Gly Val Gln Asn
                1125                1130                1135
Tyr Glu Lys Met Ile Pro Asp Ile His Arg Phe Glu Ile Ile Lys Leu
            1140                1145                1150
Cys Tyr Glu Leu Gln Ile Pro Gln Ser Ile Pro Leu Ser Arg Asp Thr
        1155                1160                1165
Ile Gly Val Leu Glu Val Leu Lys Asn Thr Thr
    1170                1175

<210> SEQ ID NO 90
<211> LENGTH: 278
<212> TYPE: PRT
<213> ORGANISM: Candida albicans

<400> SEQUENCE: 90

Met Ser Ser Leu Phe Ile Asn Glu Glu Asp Met Thr Pro Glu Pro
  1               5                  10                  15

Tyr Lys Pro Ser Thr Ser Thr Ile Arg Glu Glu Glu Glu Val Gln
             20                  25                  30

Val Lys Gln Glu Phe Pro Asp Glu Lys Met Val Asp Pro Asp Glu Asp
         35                  40                  45

Asp Pro Ile Val Glu Ser Ile Pro Leu Leu Ile Asn Thr Val Pro Glu
     50                  55                  60

Arg Ala Lys Gln Ser Leu His Val Leu Gln Tyr Ala Gly Arg Pro Lys
 65                  70                  75                  80
```

-continued

```
Ser Arg Pro Asn Arg Ala Gly Asn Cys His Ala Ser Ile Lys Pro Glu
            85                  90                  95

Ser Gln Tyr Leu Gln Val Lys Val Pro Leu Asp Thr Glu Lys Phe Phe
           100                 105                 110

Asn Val Asp Lys Ile Gln Glu Trp Gly Glu Gln Ile Val Glu Gln Thr
           115                 120                 125

Ile Ser Gly Val Leu Asp Gly Ser Tyr Glu Val Gly Asn Tyr Ala Ala
       130                 135                 140

Lys Ile Ile Asn Asp Ser Asp Gly Arg Arg Val Val Leu Ile Pro Val
145                 150                 155                 160

Asp Ser Thr Val Gln Leu Lys Pro Ser Phe Lys Tyr Ile Asp Asp Leu
               165                 170                 175

Glu Ala Gln Ser Ile Gln Gln Arg Arg Gln Gln Glu Ser Thr Asn Glu
           180                 185                 190

Lys Pro Ala Asn Val Gln Ile Leu Gln Ser Ala Ala Lys His Ser Thr
       195                 200                 205

Gln Ser Gly Glu Phe Ser His Ser Leu Gly Asp Ser Leu Lys Ser Val
   210                 215                 220

Lys His Phe Glu Glu Glu Trp Gln Asn Leu Ile Trp Lys Arg Gly
225                 230                 235                 240

Asp Asp Asp Val Thr Lys Ser Ile Lys Phe Gly Leu Asp His His Thr
               245                 250                 255

Asp Thr Asn Ile Glu Leu Lys Thr Asn Thr Ser Tyr Asp Glu Tyr Ile
           260                 265                 270

Asp Met Leu Ile Asn Asn
       275

<210> SEQ ID NO 91
<211> LENGTH: 492
<212> TYPE: PRT
<213> ORGANISM: Candida albicans

<400> SEQUENCE: 91

Met Lys Gln His Pro Leu Val Thr Ala Tyr Lys Gly Ile Asp Asp Leu
 1               5                  10                  15

Gln Gln Leu Lys Lys Trp Phe Glu Tyr Asn Asp Thr Ile Asp His
            20                  25                  30

Arg Lys Lys Ala Ile Ser Lys Val Lys Gly Leu Leu Thr Arg Gly Lys
         35                  40                  45

Leu Pro His Gly Val Glu Ala Thr Ser Leu Leu Thr Ser Ile Val Leu
     50                  55                  60

Asp Asp Leu Gln Arg Lys Asp Ile Asp Ser Cys Val Leu Gln Leu Ser
 65                  70                  75                  80

Tyr Thr Met Ala Leu Ile Arg Phe Val Asn Gly Leu Leu Asp Pro Tyr
                85                  90                  95

Gln Gln Ser Asn Tyr Ala Ile Pro Met His Leu Leu Ala Lys Gln Leu
           100                 105                 110

Asn Leu Pro Thr Tyr Phe Val Glu Leu Arg His Met Gly Thr His Glu
       115                 120                 125

Asn Leu Pro Ser Leu Asp Ile Leu Arg Ser Thr Cys Ser Lys Ala Leu
   130                 135                 140

Thr Trp Leu Tyr Asp Asn Tyr Trp Cys His Val Glu Glu Ala Asn Gln
145                 150                 155                 160

Asp Lys Gln Val Ser Ile Gly Gly Pro Leu Thr Asp Ala Val Glu Phe
```

```
                    165                 170                 175
Arg Ser Asn Asp Leu Arg Thr Arg Ile Glu Asp Ser Gln Ile Tyr Asn
            180                 185                 190
Asn Leu Lys Ala Phe Lys Arg Ile Arg Lys Gln Asp Leu Asn Lys Val
        195                 200                 205
Tyr Glu Lys Asn Asp Thr Thr Ser Asp Leu Ala Ala Thr Tyr His Arg
    210                 215                 220
Cys Val Ser Asp Ile Val Glu Phe Ala Lys Glu Asn Cys Asp Leu Leu
225                 230                 235                 240
Val Asn Val Leu Leu Lys Asn Tyr Leu Ile Tyr Pro Ser Ser Lys
            245                 250                 255
Val Lys Asp Lys Lys Ser Lys Phe Asn Pro Leu Ile Ile Lys Leu Tyr
        260                 265                 270
Glu Pro Leu Phe Asp Ala Leu Gly Leu Ser Phe Lys Leu Lys Cys Phe
    275                 280                 285
Ser Lys Thr Ile Glu Leu Ile Glu Ala Thr Pro Ser Ser Phe Val Asp
    290                 295                 300
Lys Lys Val Tyr Arg Lys Leu Gly Phe Thr Glu Lys Phe Glu Tyr Asp
305                 310                 315                 320
Glu Leu Phe Gln Val Met Glu Trp Val Leu Tyr Phe Met Gln Asp Leu
            325                 330                 335
Leu Arg Asn Glu Asn Val Pro Ser Pro Val His Asn Lys Asn Glu Leu
            340                 345                 350
Val Ile Leu Phe Leu Asp Ser Leu Lys Ser Ile Glu Gln Lys Ile Ser
        355                 360                 365
Gln Ser Leu Leu Pro Ser Phe Ala Lys Ile Leu Gln Gly Leu Cys Asp
    370                 375                 380
Val Val Asn Asp Gly Val Lys Ser Glu Ile Asp Pro Glu Thr Val Gln
385                 390                 395                 400
Lys Leu Asp Ala Trp Asn Lys Ser Leu Asn Asn Leu His Ser Thr Lys
            405                 410                 415
Lys Ile Phe Glu Leu Pro Pro Ser Leu Asp Asp Leu Leu Gly Leu Ser
            420                 425                 430
Pro Ser Pro Gly Pro Ile Pro Glu Thr Thr Ser Ser Asn Pro Met Lys
        435                 440                 445
His Val Leu Asp Asp Asp Asp Glu Glu Glu Gly Val Arg Arg
    450                 455                 460
Lys Gln His His Ser Ser Asp Ser Lys Thr Tyr Ile Leu Lys Pro His
465                 470                 475                 480
Lys Asn Trp Arg Pro Val Pro Phe Gly Thr Cys Ile
            485                 490

<210> SEQ ID NO 92
<211> LENGTH: 409
<212> TYPE: PRT
<213> ORGANISM: Candida albicans

<400> SEQUENCE: 92

Met Thr Ser Ser Ile Asn Ile Leu Leu Leu His Pro Thr Val Val
1               5                   10                  15

Thr Asp Ala Gln Leu Val Glu Gln Ile Lys Ser Lys Ile Tyr Gln Ser
            20                  25                  30

His Asn Asn Asn Asn Asn Asn Gly Gly Thr Thr Thr Thr Thr
        35                  40                  45
```

```
Gly Thr Val Asn Ile Asn Leu Asn Gln Gln Ile Ile Asp Arg Val Thr
 50                  55                  60

Lys Gly Ile Ile Glu Leu Pro Tyr Asp Tyr Asp Glu Ile Ile Tyr
 65                  70                  75                  80

Ile Asn Pro Asn Asn Glu Ser Gln Tyr Arg Glu Ile Pro Ile Ser Leu
                 85                  90                  95

Met Gln Leu Ile Tyr Lys Leu Leu Lys Ser Asn Gly Lys Phe Lys Gly
            100                 105                 110

Asp Leu Pro Leu Asp Gln Asn Leu Asp Val Leu Met Thr Gly Phe Ile
        115                 120                 125

Ile Glu Glu Glu Lys Glu Lys Glu Lys Glu Asn Asn Leu Glu
    130                 135                 140

Gly Glu Leu Val Asn Val Trp Val Lys Pro Ile Pro Val Asp Glu Pro
145                 150                 155                 160

Val Val Thr Leu Leu Lys Lys Thr Thr Ser Asn Thr Thr Thr
                165                 170                 175

Ile Lys Lys Ser Leu Pro Leu Phe Lys Lys Leu Asn Lys Asp Glu Ile
                180                 185                 190

Asn Asn Ser Asp Lys Asp Ile Asn Asn Asp Asn Ile Thr Asn Asn
                195                 200                 205

Asn Asn Asn Asn Asn Lys Arg Lys Leu Val Glu Thr Lys Leu Thr Tyr
    210                 215                 220

Phe Ser Ser Asp Asp Glu Asn Ser Ser Asp Gly Ser Val Leu Glu Asn
225                 230                 235                 240

Asp Asp Ile Asp Asp Asp Glu Leu Ile Asp Glu Asn Asp Leu Leu
            245                 250                 255

Asn Phe Asn Asn Asn Asn Thr Asn Gly Gly Ser Leu Leu Ser Asp
            260                 265                 270

Lys Leu Ile Thr Pro Arg Lys Cys Asp Ile Ser Leu Asn Gly Gly Lys
            275                 280                 285

Lys Arg Lys Lys Ala Cys Lys Asp Cys Thr Cys Gly Leu Lys Glu Leu
            290                 295                 300

Glu Glu Leu Glu Val Ser Asn Gln Gln Asn Leu Gln Asp Gln Ile Leu
305                 310                 315                 320

Gly Lys Leu Ala Gln Ser Ala Thr Leu Glu Ala Ile Lys Ile Glu Glu
            325                 330                 335

Arg Leu Lys Gln Gln Gln Gln Gln Gln Lys Val Lys Val Lys
            340                 345                 350

Phe Thr Glu Glu Asp Leu Ser Glu Ile Asp Phe Thr Val Gln Gly Lys
            355                 360                 365

Thr Gly Gly Cys Gly Ser Cys Ala Leu Gly Asp Ala Phe Arg Cys Asp
            370                 375                 380

Gly Cys Pro Tyr Leu Gly Leu Pro Pro Phe Lys Pro Gly Glu Val Val
385                 390                 395                 400

Lys Leu Asp Gly Phe Gly Glu Asp Ile
            405

<210> SEQ ID NO 93
<211> LENGTH: 327
<212> TYPE: PRT
<213> ORGANISM: Candida albicans

<400> SEQUENCE: 93

Met Ile Arg Thr Ile Lys Pro Lys Asn Ala Arg Ser Lys Arg Ala Leu
 1               5                  10                  15
```

-continued

```
Ala Lys Lys Glu Ala Lys Leu Val Glu Asn Thr Lys Ser Ala Leu Phe
             20                  25                  30

Val Pro Gly Ser Thr Gly Asn Lys Phe Leu His Asp Ala Met Cys Asp
         35                  40                  45

Leu Met Ala Phe Lys Lys Pro Phe Ala Lys Phe Ser Lys Lys Asn
     50                  55                  60

Glu Ile Arg Pro Phe Glu Asp Ser Ser Gln Leu Glu Phe Phe Ala Glu
 65                  70                  75                  80

Lys Asn Asp Ser Ser Leu Met Val Phe Ser Asn Asn Lys Lys Arg
                 85                  90                  95

Pro Lys Thr Leu Thr Phe Val Arg Phe Phe Asn Phe Lys Val Tyr Asp
             100                 105                 110

Met Ile Gly Leu Ser Ile Gln Glu Asn His Lys Leu Leu Gln Asp Phe
             115                 120                 125

Lys Lys Leu Thr Phe Thr Ile Gly Leu Lys Pro Met Phe Val Phe Asn
         130                 135                 140

Gly Pro Ile Phe Asp Ser His Pro Val Tyr Gln His Ile Lys Ser Leu
145                 150                 155                 160

Phe Leu Asp Phe Phe Arg Gly Glu Glu Thr Asp Leu Gln Asp Val Ala
                 165                 170                 175

Gly Leu Gln Tyr Val Ile Ala Leu Ser Ala Gly Glu Val Glu Asp Leu
             180                 185                 190

Asn Asn Asp Lys Val Leu Pro Leu Val His Phe Arg Val Tyr Lys Leu
         195                 200                 205

Lys Ser Tyr Lys Ser Gly Gln Lys Leu Pro Arg Ile Glu Leu Asp Glu
     210                 215                 220

Ile Gly Pro Arg Phe Asp Phe Lys Ile Gly Arg Arg Ile Thr Pro Thr
225                 230                 235                 240

Pro Asp Val Glu Lys Glu Ala Thr Lys Lys Pro Lys Gln Leu Glu Ala
                 245                 250                 255

Lys Val Lys Lys Asn Val Thr Thr Asp Phe Met Gly Asp Lys Val Ala
             260                 265                 270

Gln Ile His Val Gly Lys Gln Asp Leu Ser Lys Leu Gln Thr Arg Lys
         275                 280                 285

Met Lys Gly Leu Lys Glu Lys Tyr Asp Gln Glu Ser Glu Glu Glu Asp
     290                 295                 300

Val Tyr Val Ser Asp Glu Glu Tyr Phe Gly Glu Asp Ile Glu Glu Pro
305                 310                 315                 320

Glu Thr Lys Arg Gln Lys Val
                 325

<210> SEQ ID NO 94
<211> LENGTH: 125
<212> TYPE: PRT
<213> ORGANISM: Candida albicans

<400> SEQUENCE: 94

Met Ser Lys Thr Asn Thr Ala Ile Tyr Gln Lys Ile Ala Glu Lys Arg
  1               5                  10                  15

Ala Asn Leu Glu Arg Phe Arg Glu Phe Lys Glu Leu Thr Asp Asp Leu
             20                  25                  30

Val Leu Gln Leu Glu Ser Ile Gly Asp Lys Leu Glu Thr Met Asn Gly
         35                  40                  45

Gly Thr Ala Ser Val Ala Leu Ile Leu Ala Asn Trp Lys Ser Val Val
```

```
                    50                  55                  60
Gln Ser Ile Ser Leu Ala Ser Leu Ala Leu Met Lys Glu Ser Asn Asp
 65                  70                  75                  80

Asn Asn Lys Glu Ala Phe Pro Glu Pro Leu Val Arg Val Arg Val Gly
                 85                  90                  95

Gln Ser Asn Glu Glu Asn Gln Asp Asp Glu Glu Ala Asp Glu Glu Glu
                100                 105                 110

Gly Val Arg Asp Ser Glu Glu Val Glu Glu Ser Thr Glu
            115                 120                 125

<210> SEQ ID NO 95
<211> LENGTH: 1120
<212> TYPE: PRT
<213> ORGANISM: Candida albicans

<400> SEQUENCE: 95

Met Asp Tyr Gln Asp Leu Leu His Lys Ile Ile Lys Glu Phe His Ser
  1               5                  10                  15

Leu Lys Glu Phe Lys Pro Trp Asp Ser Ser Val Leu Tyr Glu Thr Leu
                 20                  25                  30

Leu Arg Ser Val Leu Thr Thr Leu Ile Glu Leu Leu Gly Ile Asp Asn
             35                  40                  45

Pro Pro Ser Tyr Leu His Leu Thr Thr Asn Asn Asp Ser Ile Gly Asp
         50                  55                  60

Leu Lys Ile Lys Tyr Tyr Gly Asn Ala Leu Ser Lys Ser Ile Asn Gly
 65                  70                  75                  80

His Ser Met Leu Gln Tyr Leu Glu Ser Lys His Val Ser Ile Leu Gln
                 85                  90                  95

Ala Val Val Glu Ile Ile Asn Thr Arg Ser Tyr Arg Ile Lys Glu Ser
                100                 105                 110

Tyr Ser Ala Val Phe Lys Asp Val Ser His Leu Phe Glu Lys Leu Leu
            115                 120                 125

Lys Glu Arg Tyr Glu Ala Glu Ser Asn Leu Glu Asp Tyr Ile Leu Gln
130                 135                 140

Cys Leu Met Tyr Glu Thr Gln Phe Tyr Gln Gly Ile Val Asp Asn Val
145                 150                 155                 160

Leu Thr Ala Asp Asp Thr Glu Lys Leu Ala Ser Phe Leu Gly Thr Arg
                165                 170                 175

Leu Ser Glu Glu Asp Ser Met Phe Ser Tyr Arg Asp Ile Asp Tyr Pro
            180                 185                 190

Leu Glu Leu Asn Ile Asn Asn Glu Ser Leu Glu Lys Ile Tyr Lys Ile
        195                 200                 205

Phe Leu Gly Val Ile Gly Thr Lys Arg Phe Asp Ile Lys Glu Val Ala
210                 215                 220

Ser Ala Val Val Gly Val Tyr Lys Arg His Gln Arg Ile Asp His Phe
225                 230                 235                 240

Glu Lys Leu Asp Ser Asp Glu Ile Leu Gly Lys Phe Arg Asn Ile
                245                 250                 255

Leu Pro Gln Ser Phe Gln Ser Val Thr Asn Lys Val Phe Arg Glu Phe
            260                 265                 270

His Lys Glu Val Asp Asp Pro Pro Ser Asp Val Leu Asp Gln Leu Asp
        275                 280                 285

Asn Ile Val Asp Asp Phe Ile Ala Val Gly Ile Glu Gly Val Asp Leu
    290                 295                 300
```

-continued

```
Gly Phe Pro Ala Leu Phe Arg His Tyr Ile Lys Phe Met Asn Glu Ile
305                 310                 315                 320

Phe Pro Thr Val Val Glu Asp Ala Asp Arg Asp Phe Val Ala Arg Ile
            325                 330                 335

Asn Ser Leu Ile Ala Gln Val Leu Glu Phe Lys Asp Asp Glu Lys Ser
        340                 345                 350

Cys Asp Ile Asn Gln Val Val Ser Glu Phe Val Ser Leu Gln Ser Leu
    355                 360                 365

Leu Leu Lys Asn Asn Tyr Leu Ser Pro Ser Thr Leu Leu Met Arg Ala
370                 375                 380

Ser Thr His Asp Tyr Tyr Lys Asn Leu Gln Ile Val Lys Ile Thr Phe
385                 390                 395                 400

Asp Gly Trp Asn Glu Asn Ser Lys Arg Ile Leu Lys Leu Glu Asn Ser
            405                 410                 415

Gly Phe Leu Gln Ser Lys Thr Leu Pro Lys Tyr Leu Lys Leu Trp Tyr
        420                 425                 430

Ser Lys Ser Met Lys Leu Asn Glu Leu Cys Asn Arg Val Asp Glu Phe
    435                 440                 445

Tyr Asn Gly Glu Leu Cys Arg Lys Val Trp His Cys Trp Arg Ser Gln
450                 455                 460

Gln Asn Val Tyr Asn Leu Lys Met Glu Val Ala Asp Lys Arg Leu Leu
465                 470                 475                 480

Asn Gln Tyr Tyr Ile Lys Trp Arg Lys Lys Glu Lys Asp Met Lys Ala
            485                 490                 495

Asn Leu Thr Ile Ala Val Glu Phe Asp His Phe His Leu Leu Asp Lys
        500                 505                 510

Ser Phe Lys Ile Leu Lys Gly Tyr Phe Asn Leu Ala Lys Asn Ser Asp
    515                 520                 525

Val Leu Ala Met Ser Leu Phe Gln Ser Phe Glu Glu Asn Arg Asp Ser
530                 535                 540

Arg Ile Lys Leu Lys Tyr Phe Gln Tyr Trp Asn Leu Lys Ile Ser Asp
545                 550                 555                 560

Arg Val His Gly Leu Thr Met Lys Leu Glu Lys Phe His Gln Val Lys
            565                 570                 575

Asp Lys Phe Val Leu Gly Asn Tyr Phe Glu Thr Trp Tyr Tyr Lys His
        580                 585                 590

Asn Leu Val Glu Lys Ser Asn Asn Phe Val Ser Ala Lys Asp Leu Gln
    595                 600                 605

Leu Leu Ala Lys Thr Phe Thr Asn Thr Trp Leu Lys Lys Phe Leu Leu
610                 615                 620

Tyr Lys Lys Ala Phe Lys Ile Glu Glu Leu Gly Ala Asp Leu Lys
625                 630                 635                 640

Arg Lys Thr Phe Asp Arg Trp Lys Glu Ala Val Gln Leu Glu Val Lys
            645                 650                 655

Ala Lys Glu Phe His Glu Arg His Leu Leu Glu Thr Ala Phe His Glu
        660                 665                 670

Trp Lys Leu Lys Ser Ile Leu Ile Ser Asn Arg Ala Ser Phe Asp His
    675                 680                 685

Ile Leu Val Gln Arg Cys Phe Gln Thr Trp Ser Val Glu Ile Lys Leu
690                 695                 700

Arg Glu Leu Gln Gln Lys Gln Asp Thr Arg Leu Val Val Asn Ile Phe
705                 710                 715                 720

Gln Lys Trp Arg Thr Arg Gln Leu Glu Leu Ala Lys Leu Asp Glu Lys
```

```
                        725                 730                 735
Ser Gln Ala Phe Tyr Glu Ser Asn Met Lys His Leu Val Val Gln Lys
            740                 745                 750
Trp Asn Val Glu Asn Ser Asn Ile Gly Leu Leu Glu Lys Arg Ala Asp
            755                 760                 765
Arg Phe Phe Ile Arg Arg Phe Phe Ile Gln Lys Trp Gln Ser Lys Met
            770                 775                 780
Thr Lys Tyr Glu Asp Ile Thr Val Tyr His Leu Glu Asp Glu Ile Ala
785                 790                 795                 800
Thr Lys Leu Ala Tyr Lys Val Trp Arg Gln Arg Tyr Phe Glu Asn Tyr
                805                 810                 815
Glu Glu Lys Leu Asp Asn Leu Leu Glu Thr Met Asp Thr Ser Ala Ala
            820                 825                 830
Asp Thr Val Arg Cys Ser Arg Tyr Phe Gly Leu Trp Arg Ala Lys Leu
            835                 840                 845
Gln Thr Val Lys Gln Ile Glu Arg Val Ser Thr Ser Val Ala Pro
            850                 855                 860
Ser Val Ala Ile His Phe Lys Asn Trp His Val Lys Ser Gln Gln Lys
865                 870                 875                 880
Gln Glu Leu Leu Glu Asn Ala Leu Gln Phe Glu Ile Asn Leu Ser
                885                 890                 895
Arg Phe Leu Leu Ile Trp Phe Gln Arg Leu Gln Glu Val Ser Gln Leu
            900                 905                 910
Glu Asp Gln Ala Glu Asp Leu Leu Ala Gln Thr Asn Phe Asn Leu Leu
            915                 920                 925
Arg Asn Ala Val His Lys Trp Ser Met Leu Tyr Asn Lys Asn Ile Lys
            930                 935                 940
Arg His Lys Gln Leu Cys Glu Asp Phe Ile Ala Arg Lys Glu Thr Ala
945                 950                 955                 960
Lys Val Arg Ser Ile Phe Asp Leu Trp Leu Tyr Lys Ile Lys Glu Ile
                965                 970                 975
Glu Ala Asn Thr Thr Ile Ile Ser Asn Pro Ser Pro Leu Ser Lys Arg
            980                 985                 990
Phe Gln His Gln Arg Glu Met Gly Leu Thr Pro Gln Lys Lys Asn Ser
            995                 1000                1005
Pro Thr Lys Val Phe Thr Pro Thr Thr Ser Lys Asp Pro Ser Pro Thr
            1010                1015                1020
Lys Leu Gln Glu Thr Thr Gln Arg Met Arg Asn Gln Asn Ile Ser Ala
1025                1030                1035                1040
Leu Arg Glu His Phe Gly Arg Ala Arg Ala Ser Ser Thr Pro Lys Lys
                1045                1050                1055
Leu Ser Pro Val Arg Leu Ser Tyr Thr Asn Ile Pro Ser Asn Leu Arg
            1060                1065                1070
Pro Gln Ser Pro Pro Lys Phe Asp Asp Ser Asp Ile Ala Thr Ala Lys
            1075                1080                1085
Ser Leu Gly Arg Ile Arg Pro Met Val Phe Pro Ile Asp Asp Gln Ala
            1090                1095                1100
Asn Phe Ser Pro Met Asp Arg Thr Lys Leu Gln Ser Arg Asn Ala Met
1105                1110                1115                1120

<210> SEQ ID NO 96
<211> LENGTH: 745
<212> TYPE: PRT
<213> ORGANISM: Candida albicans
```

<400> SEQUENCE: 96

```
Met Ala Lys Arg Lys Ser Lys Gln Gln Asp Leu Glu Lys Lys Lys
  1               5                  10                  15
Leu Lys Gln Ser Gln Asp Glu Gln Leu Ser Thr Gly Leu Phe Asn Asn
             20                  25                  30
Val Gly Gln Gly Gln His Gln Gly Asp Asp Asp Glu Glu Gly Asp
             35                  40                  45
Glu Ile Asp Trp Asp Asn Gln Glu Met Asp Tyr Glu Leu Ile Pro Arg
     50                  55                  60
Lys Ile Thr Thr Lys Lys Thr Ile Glu Ala Leu Pro Ile Lys Lys Ser
 65                  70                  75                  80
Asp Gly Thr Ile Glu Arg Val Val Arg Glu Val Glu Glu Glu Glu
                 85                  90                  95
Glu Glu Glu Glu Glu Glu Pro Glu Glu Pro Glu Leu Glu Asn Asp
                100                 105                 110
Val Glu Asn Glu Pro Ser Lys Gln Glu Asn Lys Glu Asn Lys Glu Glu
            115                 120                 125
Gly Asp Ile Asp Thr Asp Thr Leu Thr Pro Gln Glu Lys Leu Ile
    130                 135                 140
Gln Thr Lys Glu Glu Ile Ala Glu Leu Gly Ser Lys Leu Ile Glu Asp
145                 150                 155                 160
Pro Glu Glu Asn Ile Val Cys Leu Thr Arg Leu Arg Lys Met Ser Glu
                165                 170                 175
Ser Lys Asn Phe Met Thr Ser Gln Leu Ser Ile Leu Ala Leu Ile Pro
            180                 185                 190
Ile Phe Lys Ser Leu Ala Pro Ser Tyr Lys Ile Arg Pro Leu Thr Asp
        195                 200                 205
Thr Glu Lys Arg Glu Lys Val Ser Arg Glu Ile Ala Lys Leu Arg Asn
    210                 215                 220
Phe Glu Gln Asn Leu Val Ile Asn Tyr Lys Ala Tyr Ile Glu Leu Leu
225                 230                 235                 240
Thr Lys Tyr Ser Lys Ile Ser Tyr Ser Asn Ser Met Asn Asn Asn Lys
                245                 250                 255
Ile Thr Ser Asp Gln Leu Lys Arg Gly Asn Ile Ala Leu Lys Ala Ala
            260                 265                 270
Thr Glu Leu Cys Leu Ser Ser Leu Arg His Phe Asn Phe Arg Glu Glu
        275                 280                 285
Leu Phe Thr Ile Ile Ile Lys Arg Leu Asn Lys Lys Pro Gln His Gln
    290                 295                 300
Gln Asp Tyr Pro Ile Phe Ile Lys Ser Leu Arg Val Leu Glu Thr Leu
305                 310                 315                 320
Leu Lys Asp Asp Ala Glu His Gly Asp Ile Thr Phe Asp Ile Lys
                325                 330                 335
Ile Met Thr Lys Ser Ile Lys Asp Lys Lys Phe Arg Val Asp Glu Ser
            340                 345                 350
Val Val Asn Val Phe Leu Ser Ile Ser Leu Leu Glu Asp Tyr Asp Pro
        355                 360                 365
Asn Asn Asn Asn Asn Lys Asp Asp His His Asn Thr Thr Leu Lys
    370                 375                 380
Pro Lys Leu Lys Lys Asp Arg Ile His Leu Ser Lys Lys Glu Arg
385                 390                 395                 400
Lys Ala Arg Lys Glu Arg Lys Glu Ile Glu Glu Glu Ile Gln Lys Ala
```

-continued

```
                405                 410                 415
Glu Gln Ala Ile Thr Val Glu Gln Arg Glu Lys Tyr Gln Ala Gln Val
            420                 425                 430
Leu Lys Met Val Leu Thr Leu Tyr Leu Glu Ile Leu Lys Ala Gly Ser
        435                 440                 445
Ser Ser Ser Gln Leu Ile Asp Gly Asp Gly Lys Lys Thr Lys Asn Asp
    450                 455                 460
Ala Ser Leu Leu Met Gly Ala Val Leu Glu Gly Leu Ser Arg Phe Gly
465                 470                 475                 480
Gln Met Ser Asn Leu Asp Leu Leu Gly Asp Phe Leu Glu Val Leu Arg
                485                 490                 495
Glu Ile Met Thr Asp Ile Ile Glu Glu His Lys Gln Ser Gly Asp Asn
            500                 505                 510
Asp Asn Asp Asn Asp Asn Asp Glu Ser Gly Gly Met Tyr Ser Gly
        515                 520                 525
Asn Glu Leu Arg Thr Ile Leu Leu Cys Ile Ala Thr Ser Phe Ser Leu
    530                 535                 540
Val Leu Asn His Asn Ser Met Gly Lys Leu Pro Met Ala Ile Asp Leu
545                 550                 555                 560
Ser Lys Phe Val Ser Thr Leu Tyr Ile Ile Leu Thr Asp Leu Ala Leu
                565                 570                 575
Asp Pro Asp Leu Glu Phe Ser His Lys Thr Leu Arg Leu Ala Asp Pro
            580                 585                 590
Leu Ser Ser Ser Ser Leu Ser Asn Glu Leu Glu Asn Asn Lys Pro Ala
        595                 600                 605
Val Asn Val Ser Thr Lys Ala Glu Leu Leu Arg Cys Leu Asp Phe
    610                 615                 620
Ile Phe Phe Arg Ser Lys Asn Gly Thr Ile Pro Arg Ala Thr Ala Phe
625                 630                 635                 640
Ile Lys Arg Leu Tyr Ile Leu Thr Leu Gln Thr Pro Glu Lys Thr Ser
                645                 650                 655
Leu Ala Asn Leu Lys Phe Ile Gly Lys Leu Met Asn Arg Tyr Gly Glu
            660                 665                 670
Asn Ile Lys Gly Leu Trp Asn Thr Glu Glu Arg Ile Ser Gly Glu Gly
        675                 680                 685
Asn Tyr Ile Leu Gly Ile Glu Arg Gln Asn Lys Asp Lys Asp Val Glu
    690                 695                 700
Leu Glu Arg Ser Asn Ser Gly Ala Ala Thr Leu Trp Glu Asn Val Leu
705                 710                 715                 720
Leu Asp Lys His Tyr Ser Ile Met Ile Lys Asp Gly Ser Arg Ser Leu
                725                 730                 735
Met Lys Asn Ser Lys Ala Asn Thr Asn
            740                 745
```

<210> SEQ ID NO 97
<211> LENGTH: 579
<212> TYPE: PRT
<213> ORGANISM: Candida albicans

<400> SEQUENCE: 97

```
Met Tyr Ile Thr Pro Asn Gln Tyr Ala Lys Thr Phe Gln Asp Ile Lys
  1               5                  10                  15
Arg Ser Ser Leu Ser His Ser Thr Cys Lys Leu Val Ile Phe Val Ser
             20                  25                  30
```

```
Cys Leu Asp Val Asp Ala Leu Cys Ala Ala Lys Ile Leu Ser Leu Leu
        35                  40                  45

Leu Arg Lys Glu Leu Ile Gln Tyr Gln Leu Ile Pro Thr Thr Gly Tyr
    50                  55                  60

Ser Asp Leu Lys Leu His Tyr Asp Lys Leu Asp Ser Glu Val Thr Asn
65                  70                  75                  80

Ile Ile Leu Ile Gly Cys Gly Ala Met Leu Asp Leu Glu Gly Phe Phe
                85                  90                  95

Asp Val Asn Pro Glu Glu Phe Leu Gly Asp Asn Ser Thr Thr Asn Gly
            100                 105                 110

His Thr Ile Asp Asn Asp Thr Glu Leu Glu Leu Asp Ala Val Lys Thr
        115                 120                 125

Asp Asn Phe Ala Leu Thr Arg Lys Ile Tyr Val Val Asp Gly His Arg
    130                 135                 140

Pro Trp Asn Leu Asp Asn Leu Phe Gly Ser Ala Met Val Val Cys Leu
145                 150                 155                 160

Asp Asn Gly Tyr Ile Asp Gly Asn Leu Asn Glu Lys Glu Ala Tyr
                165                 170                 175

Asn Val Leu Val Glu Met Ser Asp Ser Glu Asp Glu Asp Glu Asp Glu
            180                 185                 190

Gly His Asn Gln Asn Gly His Thr Asp Asp Gln Glu Gly Asp Lys
                195                 200                 205

Thr Asp Ala Asp Asp Glu Asn Asp Glu Ser Ser Val Ser Thr Ser Arg
        210                 215                 220

Lys Gly Val Lys Ser Ile Asn Glu Asp Lys Ile Gln Thr Tyr Tyr Asn
225                 230                 235                 240

Gln Ser Ser Thr Ile Ala Ser Ser Cys Ser Ile Thr Val Tyr Ala Leu
                245                 250                 255

Val Ser Ala Ile Gly Glu Thr Asn Val Asp Asn Leu Trp Leu Gly Ile
            260                 265                 270

Val Gly Ala Ser Gly Phe Asp Cys Ser Ile Phe Val Asp Glu Val Arg
        275                 280                 285

Arg Phe Ser Thr Asp Ser Gly Ile His Met Glu Arg Gly Thr Tyr Leu
    290                 295                 300

Pro Leu Leu Arg His Ser Ser Leu Tyr Asp Ala Leu Leu Tyr Asn Trp
305                 310                 315                 320

Ile Asp Gly Asp Lys Arg Ile His Lys Ile Leu Ala Lys Met Gly Val
                325                 330                 335

Pro Ile Val Ala Ala Lys Gln Gln Trp Gln Tyr Leu Asp Pro Pro Ile
            340                 345                 350

Lys Asn Lys Leu Pro Gly Leu Leu Lys Lys Tyr Leu Pro Glu Leu Pro
        355                 360                 365

Gln Val Glu Ile Phe Tyr Arg Cys Gly Val Thr Ser Met Asp Val Phe
    370                 375                 380

Val Ser Leu Thr Ala Leu Leu Glu Thr Gly Val Gly Leu Asn Asn Thr
385                 390                 395                 400

Ser Ala Asn Ser Ile Asp His Gly Asp Leu Asp Glu Asn Glu Leu
                405                 410                 415

Ile Arg Arg Glu Ile Lys Ser Arg Glu Ser Ser Tyr Ile Arg Asn Phe
            420                 425                 430

Trp Ser Ala Phe Asp Ser Val Ser Ser Phe Gly Ile Ser Asn Asn Ile
        435                 440                 445

Gly Leu Glu Lys Gly Ile Thr Ala Ala Lys Leu Val Gln Lys Glu Leu
```

-continued

```
            450                 455                 460
Phe Gln Thr Ile Lys Tyr Ile Ile Glu Gln Lys Leu Ile Lys Asn Leu
465                 470                 475                 480

Lys Val Tyr Arg Leu Cys Ile Leu Lys Asp Glu Ser Ser His Ser Gly
                485                 490                 495

Phe Asp Asn Pro Val Leu Ile Lys Leu Ser Asn Arg Ile Met Asp
                500                 505                 510

Tyr Leu Lys Gln Gln Thr Ser Lys Pro Leu Val Val Ala Ala Glu Leu
            515                 520                 525

Ser Asn Thr Tyr Phe Val Leu Gly Met Gly Ile Asn Asn Ala Phe Ser
530                 535                 540

Lys Ile Ser Gly Ala Gln Met Lys Lys Asp Phe Phe Glu Ala Ser Leu
545                 550                 555                 560

Val Glu Ile Lys Lys Glu Asp Leu Ala Pro Phe Leu Glu Gln Leu Thr
                565                 570                 575

Phe Asn Leu

<210> SEQ ID NO 98
<211> LENGTH: 1897
<212> TYPE: PRT
<213> ORGANISM: Candida albicans

<400> SEQUENCE: 98

Met Ser Tyr Asn Asp Asn Asn His Tyr Tyr Asp Pro Asn Gln Gln
1                 5                  10                  15

Gly Gly Met Pro Pro His Gln Gly Gly Glu Gly Tyr Tyr Gln Gln Gln
                20                  25                  30

Tyr Asp Asp Met Gly Gln Gln Pro His Gln Gln Asp Tyr Tyr Asp Pro
            35                  40                  45

Asn Ala Gln Tyr Gln Gln Gln Pro Tyr Asp Met Asp Gly Tyr Gln Asp
        50                  55                  60

Gln Ala Asn Tyr Gly Gly Gln Pro Met Asn Ala Gln Gly Tyr Asn Ala
65                  70                  75                  80

Asp Pro Glu Ala Phe Ser Asp Phe Ser Tyr Gly Gly Gln Thr Pro Gly
                85                  90                  95

Thr Pro Gly Tyr Asp Gln Tyr Gly Thr Gln Tyr Thr Pro Ser Gln Met
                100                 105                 110

Ser Tyr Gly Gly Asp Pro Arg Ser Gly Ala Ser Thr Pro Ile Tyr
            115                 120                 125

Gly Gly Gln Gly Gln Gly Tyr Asp Pro Thr Gln Phe Asn Met Ser Ser
130                 135                 140

Asn Leu Pro Tyr Pro Ala Trp Ser Ala Asp Pro Gln Ala Pro Ile Lys
145                 150                 155                 160

Ile Glu His Ile Glu Asp Ile Phe Ile Asp Leu Thr Asn Lys Phe Gly
                165                 170                 175

Phe Gln Arg Asp Ser Met Arg Asn Met Phe Asp Tyr Phe Met Thr Leu
            180                 185                 190

Leu Asp Ser Arg Ser Ser Arg Met Ser Pro Ala Gln Ala Leu Leu Ser
        195                 200                 205

Leu His Ala Asp Tyr Ile Gly Gly Asp Asn Ala Asn Tyr Arg Lys Trp
    210                 215                 220

Tyr Phe Ser Ser Gln Gln Asp Leu Asp Asp Ser Leu Gly Phe Ala Asn
225                 230                 235                 240

Met Thr Leu Gly Lys Ile Gly Arg Lys Ala Arg Lys Ala Ser Lys Lys
```

-continued

```
                        245                 250                 255
Ser Lys Lys Ala Arg Lys Ala Ala Glu Glu His Gly Gln Asp Val Asp
                260                 265                 270
Ala Leu Ala Asn Glu Leu Glu Gly Asp Tyr Ser Leu Glu Ala Ala Glu
            275                 280                 285
Ile Arg Trp Lys Ala Lys Met Asn Ser Leu Thr Pro Glu Glu Arg Val
        290                 295                 300
Arg Asp Leu Ala Leu Tyr Leu Leu Ile Trp Gly Glu Ala Asn Gln Val
305                 310                 315                 320
Arg Phe Thr Pro Glu Cys Leu Cys Tyr Ile Tyr Lys Ser Ala Thr Asp
                325                 330                 335
Tyr Leu Asn Ser Pro Leu Cys Gln Gln Arg Gln Glu Pro Val Pro Glu
                340                 345                 350
Gly Asp Tyr Leu Asn Arg Val Ile Thr Pro Leu Tyr Arg Phe Ile Arg
            355                 360                 365
Ser Gln Val Tyr Glu Ile Tyr Asp Gly Arg Phe Val Lys Arg Glu Lys
        370                 375                 380
Asp His Asn Lys Val Ile Gly Tyr Asp Asp Val Asn Gln Leu Phe Trp
385                 390                 395                 400
Tyr Pro Glu Gly Ile Ser Arg Ile Ile Phe Glu Asp Gly Thr Arg Leu
                405                 410                 415
Val Asp Ile Pro Gln Glu Arg Phe Leu Lys Leu Gly Glu Val Glu
                420                 425                 430
Trp Lys Asn Val Phe Phe Lys Thr Tyr Lys Glu Ile Arg Thr Trp Leu
            435                 440                 445
His Phe Val Thr Asn Phe Asn Arg Ile Trp Ile Ile His Gly Thr Ile
        450                 455                 460
Tyr Trp Met Tyr Thr Ala Tyr Asn Ser Pro Thr Leu Tyr Thr Lys His
465                 470                 475                 480
Tyr Val Gln Thr Ile Asn Gln Gln Pro Leu Ala Ser Ser Arg Trp Ala
                485                 490                 495
Ala Cys Ala Ile Gly Gly Val Leu Ala Ser Phe Ile Gln Ile Leu Ala
            500                 505                 510
Thr Leu Phe Glu Trp Ile Phe Val Pro Arg Glu Trp Ala Gly Ala Gln
        515                 520                 525
His Leu Ser Arg Arg Met Leu Phe Leu Val Leu Ile Phe Leu Leu Asn
    530                 535                 540
Leu Val Pro Pro Val Tyr Thr Phe Gln Ile Thr Lys Leu Val Ile Tyr
545                 550                 555                 560
Ser Lys Ser Ala Tyr Ala Val Ser Ile Val Gly Phe Phe Ile Ala Val
                565                 570                 575
Ala Thr Leu Val Phe Phe Ala Val Met Pro Leu Gly Gly Leu Phe Thr
            580                 585                 590
Ser Tyr Met Asn Lys Arg Ser Arg Tyr Ile Ala Ser Gln Thr Phe
        595                 600                 605
Thr Ala Asn Tyr Ile Lys Leu Lys Gly Leu Asp Met Trp Met Ser Tyr
    610                 615                 620
Leu Leu Trp Phe Leu Val Phe Leu Ala Lys Leu Val Glu Ser Tyr Phe
625                 630                 635                 640
Phe Ser Thr Leu Ser Leu Arg Asp Pro Ile Arg Asn Leu Ser Thr Met
                645                 650                 655
Thr Met Arg Cys Val Gly Glu Val Trp Tyr Lys Asp Ile Val Cys Arg
            660                 665                 670
```

```
Asn Gln Ala Lys Ile Val Leu Gly Leu Met Tyr Leu Val Asp Leu Leu
            675                 680                 685

Leu Phe Phe Leu Asp Thr Tyr Met Trp Tyr Ile Ile Cys Asn Cys Ile
        690                 695                 700

Phe Ser Ile Gly Arg Ser Phe Tyr Leu Gly Ile Ser Ile Leu Thr Pro
705                 710                 715                 720

Trp Arg Asn Ile Phe Thr Arg Leu Pro Lys Arg Ile Tyr Ser Lys Ile
                725                 730                 735

Leu Ala Thr Thr Glu Met Glu Ile Lys Tyr Lys Pro Lys Val Leu Ile
            740                 745                 750

Ser Gln Ile Trp Asn Ala Ile Val Ile Ser Met Tyr Arg Glu His Leu
        755                 760                 765

Leu Ala Ile Asp His Val Gln Lys Leu Leu Tyr His Gln Val Pro Ser
        770                 775                 780

Glu Ile Glu Gly Lys Arg Thr Leu Arg Ala Pro Thr Phe Phe Val Ser
785                 790                 795                 800

Gln Asp Asp Asn Asn Phe Glu Thr Glu Phe Phe Pro Arg Asn Ser Glu
                805                 810                 815

Ala Glu Arg Arg Ile Ser Phe Phe Ala Gln Ser Leu Ala Thr Pro Met
            820                 825                 830

Pro Glu Pro Leu Pro Val Asp Asn Met Pro Thr Phe Thr Val Phe Thr
        835                 840                 845

Pro His Tyr Ser Glu Lys Ile Leu Leu Ser Leu Arg Glu Ile Ile Arg
        850                 855                 860

Glu Asp Asp Gln Phe Ser Arg Val Thr Leu Leu Glu Tyr Leu Lys Gln
865                 870                 875                 880

Leu His Pro Val Glu Trp Asp Cys Phe Val Lys Asp Thr Lys Ile Leu
                885                 890                 895

Ala Glu Glu Thr Ala Ala Tyr Glu Asn Gly Asp Asp Ser Glu Lys Leu
            900                 905                 910

Ser Glu Asp Gly Leu Lys Ser Lys Ile Asp Asp Leu Pro Phe Tyr Cys
        915                 920                 925

Ile Gly Phe Lys Ser Ala Ala Pro Glu Tyr Thr Leu Arg Thr Arg Ile
        930                 935                 940

Trp Ala Ser Leu Arg Ser Gln Thr Leu Tyr Arg Thr Val Ser Gly Phe
945                 950                 955                 960

Met Asn Tyr Ala Arg Ala Ile Lys Leu Leu Tyr Arg Val Glu Asn Pro
                965                 970                 975

Glu Leu Val Gln Tyr Phe Gly Gly Asp Pro Glu Gly Leu Glu Leu Ala
            980                 985                 990

Leu Glu Arg Met Ala Arg Arg Lys Phe Arg Phe Leu Val Ser Met Gln
        995                 1000                1005

Arg Leu Ser Lys Phe Lys Asp Asp Glu Met Glu Asn Ala Glu Phe Leu
        1010                1015                1020

Leu Arg Ala Tyr Pro Asp Leu Gln Ile Ala Tyr Leu Asp Glu Pro
1025                1030                1035                1040

Ala Leu Asn Glu Asp Glu Pro Arg Val Tyr Ser Ala Leu Ile Asp
            1045                1050                1055

Gly His Cys Glu Met Leu Glu Asn Gly Arg Arg Pro Lys Phe Arg
            1060                1065                1070

Val Gln Leu Ser Gly Asn Pro Ile Leu Gly Asp Gly Lys Ser Asp Asn
        1075                1080                1085
```

```
Gln Asn His Ala Val Ile Phe His Arg Gly Glu Tyr Ile Gln Leu Ile
    1090                1095                1100

Asp Ala Asn Gln Asp Asn Tyr Leu Glu Glu Cys Leu Lys Ile Arg Ser
1105                1110                1115                1120

Val Leu Ala Glu Phe Glu Glu Met Asn Val Glu His Val Asn Pro Tyr
                1125                1130                1135

Ala Pro Asn Leu Lys Ser Glu Asp Asn Thr Lys Lys Asp Pro Val
            1140                1145                1150

Ala Phe Leu Gly Ala Arg Glu Tyr Ile Phe Ser Glu Asn Ser Gly Val
            1155                1160                1165

Leu Gly Asp Val Ala Ala Gly Lys Glu Gln Thr Phe Gly Thr Leu Phe
        1170                1175                1180

Ala Arg Thr Leu Ala Gln Ile Gly Gly Lys Leu His Tyr Gly His Pro
1185                1190                1195                1200

Asp Phe Leu Asn Ala Thr Phe Met Leu Thr Arg Gly Gly Val Ser Lys
                1205                1210                1215

Ala Gln Lys Gly Leu His Leu Asn Glu Asp Ile Tyr Ala Gly Met Asn
            1220                1225                1230

Ala Met Met Arg Gly Gly Lys Ile Lys His Cys Glu Tyr Tyr Gln Cys
        1235                1240                1245

Gly Lys Gly Arg Asp Leu Gly Phe Gly Ser Ile Leu Asn Phe Thr Thr
1250                1255                1260

Lys Ile Gly Ala Gly Met Gly Glu Gln Met Leu Ser Arg Glu Tyr Phe
1265                1270                1275                1280

Tyr Leu Gly Thr Gln Leu Pro Leu Asp Arg Phe Leu Ser Phe Tyr Tyr
                1285                1290                1295

Gly His Pro Gly Phe His Ile Asn Asn Leu Phe Ile Gln Leu Ser Leu
            1300                1305                1310

Gln Val Phe Ile Leu Val Leu Gly Asn Leu Asn Ser Leu Ala His Glu
        1315                1320                1325

Ala Ile Met Cys Ser Tyr Asn Lys Asp Val Pro Val Thr Asp Val Leu
    1330                1335                1340

Tyr Pro Phe Gly Cys Tyr Asn Ile Ala Pro Ala Val Asp Trp Ile Arg
1345                1350                1355                1360

Arg Tyr Thr Leu Ser Ile Phe Ile Val Phe Phe Ile Ser Phe Ile Pro
                1365                1370                1375

Leu Val Val Gln Glu Leu Ile Glu Arg Gly Val Trp Lys Ala Phe Gln
            1380                1385                1390

Arg Phe Val Arg His Phe Ile Ser Met Ser Pro Phe Phe Glu Val Phe
        1395                1400                1405

Val Ala Gln Ile Tyr Ser Ser Ser Val Phe Thr Asp Leu Thr Val Gly
    1410                1415                1420

Gly Ala Arg Tyr Ile Ser Thr Gly Arg Gly Phe Ala Thr Ser Arg Ile
1425                1430                1435                1440

Pro Phe Ser Ile Leu Tyr Ser Arg Phe Ala Asp Ser Ser Ile Tyr Met
                1445                1450                1455

Gly Ala Arg Leu Met Leu Ile Leu Leu Phe Gly Thr Val Ser His Trp
            1460                1465                1470

Gln Ala Pro Leu Leu Trp Phe Trp Ala Ser Leu Ser Ala Leu Met Phe
        1475                1480                1485

Ser Pro Phe Ile Phe Asn Pro His Gln Phe Ala Trp Glu Asp Phe Phe
    1490                1495                1500

Leu Asp Tyr Arg Asp Phe Ile Arg Trp Leu Ser Arg Gly Asn Thr Lys
```

-continued

```
              1505                1510                1515                1520

Trp His Arg Asn Ser Trp Ile Gly Tyr Val Arg Leu Ser Arg Ser Arg
                1525                1530                1535

Ile Thr Gly Phe Lys Arg Lys Leu Thr Gly Asp Val Ser Glu Lys Ala
                1540                1545                1550

Ala Gly Asp Ala Ser Arg Ala His Arg Ser Asn Val Leu Phe Ala Asp
                1555                1560                1565

Phe Leu Pro Thr Leu Ile Tyr Thr Ala Gly Leu Tyr Val Ala Tyr Thr
                1570                1575                1580

Phe Ile Asn Ala Gln Thr Gly Val Thr Ser Tyr Pro Tyr Glu Ile Asn
1585                1590                1595                1600

Gly Ser Thr Asp Pro Gln Pro Val Asn Ser Thr Leu Arg Leu Ile Ile
                1605                1610                1615

Cys Ala Leu Ala Pro Val Val Ile Asp Met Gly Cys Leu Gly Val Cys
                1620                1625                1630

Leu Ala Met Ala Cys Cys Ala Gly Pro Met Leu Gly Leu Cys Cys Lys
                1635                1640                1645

Lys Thr Gly Ala Val Ile Ala Gly Val Ala His Gly Val Ala Ile
                1650                1655                1660

Val His Ile Ile Phe Phe Ile Val Met Trp Val Thr Glu Gly Phe Asn
1665                1670                1675                1680

Phe Ala Arg Leu Met Leu Gly Ile Ala Thr Met Ile Tyr Val Gln Arg
                1685                1690                1695

Leu Leu Phe Lys Phe Leu Thr Leu Cys Phe Leu Thr Arg Glu Phe Lys
                1700                1705                1710

Asn Asp Lys Ala Asn Thr Ala Phe Trp Thr Gly Lys Trp Tyr Asn Thr
                1715                1720                1725

Gly Met Gly Trp Met Ala Phe Thr Gln Pro Ser Arg Glu Phe Val Ala
                1730                1735                1740

Lys Ile Ile Glu Met Ser Glu Phe Ala Gly Asp Phe Val Leu Ala His
1745                1750                1755                1760

Ile Ile Leu Phe Cys Gln Leu Pro Leu Leu Phe Ile Pro Leu Val Asp
                1765                1770                1775

Arg Trp His Ser Met Met Leu Phe Trp Leu Lys Pro Ser Arg Leu Ile
                1780                1785                1790

Arg Pro Pro Ile Tyr Ser Leu Lys Gln Ala Arg Leu Arg Lys Arg Met
                1795                1800                1805

Val Arg Lys Tyr Cys Val Leu Tyr Phe Ala Val Leu Ile Leu Phe Ile
                1810                1815                1820

Val Ile Ile Val Ala Pro Ala Val Ala Ser Gly Gln Ile Ala Val Asp
1825                1830                1835                1840

Gln Phe Ala Asn Ile Gly Gly Ser Gly Ser Ile Ala Asp Gly Leu Phe
                1845                1850                1855

Gln Pro Arg Asn Val Ser Asn Asp Thr Gly Asn His Arg Pro Lys
                1860                1865                1870

Thr Tyr Thr Trp Ser Tyr Leu Ser Thr Arg Phe Thr Gly Ser Thr Thr
                1875                1880                1885

Pro Tyr Ser Thr Asn Pro Phe Arg Val
                1890                1895

<210> SEQ ID NO 99
<211> LENGTH: 400
<212> TYPE: PRT
<213> ORGANISM: Candida albicans
```

<400> SEQUENCE: 99

```
Met Ser Phe Arg Thr Thr Ser Met Arg Met Ala Arg Leu Ala Thr Ala
 1               5                  10                  15

Lys Ala Thr Leu Ser Lys Arg Thr Phe Ser Leu Leu Ala Asn Ala Thr
             20                  25                  30

Thr Arg Tyr Thr Ala Ala Ser Ser Ala Ala Lys Ala Met Thr Pro Ile
         35                  40                  45

Thr Ser Ile Arg Gly Val Lys Thr Ile Asn Phe Gly Gly Thr Glu Glu
 50                  55                  60

Val Val His Glu Arg Ala Asp Trp Pro Lys Glu Arg Leu Leu Asp Tyr
65                  70                  75                  80

Phe Lys Asn Asp Thr Phe Ala Leu Ile Gly Tyr Gly Ser Gln Gly Tyr
                 85                  90                  95

Gly Gln Gly Leu Asn Leu Arg Asp Asn Gly Leu Asn Val Ile Ile Gly
            100                 105                 110

Val Arg Lys Gly Ser Ser Trp Glu Ala Ala Val Glu Asp Gly Trp Val
        115                 120                 125

Pro Gly Glu Asn Leu Phe Glu Val Asp Glu Ala Ile Ser Arg Gly Thr
    130                 135                 140

Ile Ile Met Asp Leu Leu Ser Asp Ala Ala Gln Ser Glu Thr Trp Phe
145                 150                 155                 160

His Ile Lys Pro Gln Leu Thr Glu Gly Lys Thr Leu Tyr Phe Ser His
                165                 170                 175

Gly Phe Ser Pro Val Phe Lys Asp Leu Thr His Val Glu Pro Pro Ser
            180                 185                 190

Asn Ile Asp Val Ile Leu Ala Ala Pro Lys Gly Ser Gly Arg Thr Val
        195                 200                 205

Arg Ser Leu Phe Lys Glu Gly Arg Gly Ile Asn Ser Ser Tyr Ala Val
    210                 215                 220

Trp Asn Asp Val Thr Gly Lys Ala Glu Glu Lys Ala Ile Ala Met Ala
225                 230                 235                 240

Ile Ala Ile Gly Ser Gly Tyr Val Tyr Lys Thr Thr Phe Glu Arg Glu
                245                 250                 255

Val Asn Ser Asp Leu Tyr Gly Glu Arg Gly Cys Leu Met Gly Gly Ile
            260                 265                 270

His Gly Met Phe Leu Ala Gln Tyr Glu Val Leu Arg Glu Asn Gly His
        275                 280                 285

Thr Pro Ser Glu Ala Phe Asn Glu Thr Val Glu Glu Ala Thr Gln Ser
    290                 295                 300

Leu Tyr Pro Leu Ile Gly Lys Tyr Gly Met Asp Tyr Met Tyr Asp Ala
305                 310                 315                 320

Cys Ser Thr Thr Ala Arg Arg Gly Ala Leu Asp Trp Tyr Pro Arg Phe
                325                 330                 335

Lys Asp Ala Leu Lys Pro Val Phe Glu Glu Leu Tyr Glu Ser Val Lys
            340                 345                 350

Asn Gly Ser Glu Thr Lys Arg Ser Leu Glu Phe Asn Ser Arg Ser Asp
        355                 360                 365

Tyr Lys Glu Arg Leu Glu Glu Leu Gln Thr Ile Arg Asn Met Glu
    370                 375                 380

Ile Trp Arg Val Gly Lys Glu Val Arg Lys Leu Arg Pro Glu Asn Gln
385                 390                 395                 400
```

<210> SEQ ID NO 100
<211> LENGTH: 278
<212> TYPE: PRT
<213> ORGANISM: Candida albicans

<400> SEQUENCE: 100

Met Phe Lys Gln Ser Ile Arg Ser Leu Ala Thr Lys Ser Pro Ile Ser
1               5                   10                  15

Ser Ala Ala Thr Thr Thr Thr Ala Ser Thr Thr Ser Thr Thr Thr
            20                  25                  30

Thr Ala Ser Leu Asn Phe Ala Lys Pro Pro Ser Tyr Thr Leu Ala Gln
        35                  40                  45

Leu Arg Glu Phe Pro Ser Leu Glu Pro Lys Thr Phe Ile Pro Leu Pro
    50                  55                  60

Thr Thr Phe Phe Asn Thr Glu Lys Pro Ile Arg Arg Asp Ile Leu Trp
65                  70                  75                  80

Ser Cys Val Thr Tyr Glu Ala Asp Lys Ala Arg Val Gly Ser Asn Tyr
                85                  90                  95

Ala Ile Leu Lys Ser Asp Ser Pro Tyr Ser Asn Arg Lys Leu Arg Pro
            100                 105                 110

Gln Lys Gly Ser Gly Arg Ala Arg Leu Gly Asp Ala Asn Ser Pro His
        115                 120                 125

Met Asp Asn Glu Ile Lys Ala His Ala Ile Lys Gly Pro His Asp Trp
130                 135                 140

Ser Thr Asp Leu Pro Ser Lys Ile Tyr Ser Arg Gly Ile Gln Asn Ala
145                 150                 155                 160

Phe Thr Met His Tyr Lys Gln Gly Asn Leu Asn Val Val Glu Asn Glu
                165                 170                 175

Leu Asp Phe Gln Tyr Gly Tyr Asp Ile Ile Thr Gln Ser Phe Val Ser
            180                 185                 190

Val His Asn Leu Asn Lys Leu Asn Leu Phe Ile Thr Asn Glu Pro
        195                 200                 205

Arg Asp Asn Leu Met Glu Ser Ile Lys Lys Phe Tyr Ile Asn Glu Lys
210                 215                 220

Glu Phe Asn Ser Leu Asn Lys Lys Glu Lys Pro Lys Tyr Leu Gln Lys
225                 230                 235                 240

Leu Lys Gly Lys Val Leu Thr Lys Glu Asp Val Glu Val Arg Asp Ile
                245                 250                 255

Leu Arg Ala His Arg Val Phe Ile Glu Ser Ser Ala Leu Gln Trp Phe
            260                 265                 270

Ile Thr Lys His Thr Val
        275

<210> SEQ ID NO 101
<211> LENGTH: 448
<212> TYPE: PRT
<213> ORGANISM: Candida albicans

<400> SEQUENCE: 101

Met Arg Glu Val Ile Ser Ile Asn Val Gly Gln Ala Gly Cys Gln Ile
1               5                   10                  15

Gly Asn Ala Cys Trp Glu Leu Tyr Ser Gln Glu His Gly Ile Arg Pro
            20                  25                  30

Asp Gly Tyr Leu Gln Glu Gly Leu Asp Arg Pro Lys Gly Gly Glu Glu
        35                  40                  45

Gly Phe Ser Thr Phe Phe Ser Glu Thr Gly Ser Gly Lys Tyr Val Pro

```
                50                  55                  60
Arg Ala Leu Tyr Val Asp Leu Glu Pro Asn Val Ile Asp Glu Val Arg
 65                  70                  75                  80

Thr Gly Val Tyr Lys Asp Leu Phe His Pro Glu Gln Leu Ile Ala Gly
                 85                  90                  95

Lys Glu Asp Ala Ala Asn Asn Tyr Ala Arg Gly His Tyr Thr Val Gly
                100                 105                 110

Arg Glu Ile Leu Asp Asp Ile Leu Asp Arg Val Arg Met Ser Asp
                115                 120                 125

Gln Cys Asp Gly Leu Gln Gly Phe Leu Phe Thr His Ser Leu Gly Gly
130                 135                 140

Gly Thr Gly Ser Gly Leu Gly Ser Leu Leu Glu Gln Leu Ser Leu
145                 150                 155                 160

Asp Tyr Gly Lys Lys Ser Lys Leu Glu Phe Ala Val Tyr Pro Ala Pro
                165                 170                 175

Gln Val Ser Thr Ser Val Val Glu Pro Tyr Asn Thr Val Leu Thr Thr
                180                 185                 190

His Thr Thr Leu Glu His Ala Asp Cys Thr Phe Met Val Asp Asn Glu
                195                 200                 205

Ala Ile Tyr Asp Met Cys Arg Arg Asn Leu Asp Ile Ala Arg Pro Asn
210                 215                 220

Phe Ser Ser Leu Asn Asn Leu Ile Ala Gln Val Ser Ser Val Thr
225                 230                 235                 240

Ala Ser Leu Arg Phe Asp Gly Ser Leu Asn Val Asp Leu Asn Glu Phe
                245                 250                 255

Gln Thr Asn Leu Val Pro Tyr Pro Arg Ile His Phe Pro Leu Val Ser
                260                 265                 270

Tyr Ala Pro Val Phe Ser Lys Ser Arg Ala Thr His Glu Ala Asn Ser
                275                 280                 285

Val Ser Glu Ile Thr Gln Ser Cys Phe Glu Pro Gly Asn Gln Met Val
                290                 295                 300

Lys Cys Asp Pro Arg Thr Gly Lys Tyr Met Ala Thr Cys Leu Leu Tyr
305                 310                 315                 320

Arg Gly Asp Val Val Thr Arg Asp Val Gln Asn Ala Val Ala Gln Val
                325                 330                 335

Lys Ser Lys Lys Thr Val Gln Leu Val Asp Trp Cys Pro Thr Gly Phe
                340                 345                 350

Lys Ile Gly Ile Cys Tyr Gln Pro Pro Thr Ala Ile Lys Gly Ser Glu
                355                 360                 365

Leu Ala Ser Ala Ser Arg Ala Val Cys Met Leu Ser Asn Thr Thr Ala
370                 375                 380

Ile Ala Glu Ala Trp Arg Arg Ile Asp Arg Lys Phe Asp Leu Met Tyr
385                 390                 395                 400

Ser Lys Arg Ala Phe Val His Trp Tyr Val Gly Gly Met Glu Glu
                405                 410                 415

Gly Glu Phe Thr Glu Ala Arg Glu Asp Leu Ala Ala Leu Glu Arg Asp
                420                 425                 430

Tyr Ile Glu Val Gly Thr Asp Ser Phe Pro Glu Glu Glu Glu Tyr
                435                 440                 445

<210> SEQ ID NO 102
<211> LENGTH: 275
<212> TYPE: PRT
<213> ORGANISM: Candida albicans
```

```
<400> SEQUENCE: 102

Met Lys Thr Ser Val Phe Ile Ala Ile Phe Asn Leu Leu Val Cys Ala
 1               5                  10                  15

Leu Ala Tyr Thr Asp Leu Thr Gly Ser Ile Lys Ile Asn Asp Lys Lys
             20                  25                  30

Ile Thr Leu Gly Glu Phe Asn Thr Gln Glu Val Lys Gln Leu Thr Ile
         35                  40                  45

Asn Ser Pro Lys Asp Ile Ile Glu Ile Asp Leu Lys Ser Lys Asp Ile
     50                  55                  60

Lys Gly Lys Pro Glu Gln Ile Met Val Ser Leu Ala Asp Val Lys Asn
 65                  70                  75                  80

Pro Ala Ile Ser Thr His Tyr Val Pro Val Lys Glu Ser Lys Ile
             85                  90                  95

Lys Leu Asn Ile Lys Ala Leu Ser Ile Pro Glu Val Leu Lys Thr Lys
            100                 105                 110

Asp Lys Leu Val Leu Thr Ile Val Ala Asp Ser Lys Ser Lys Asn
            115                 120                 125

Asn Met Ile Arg Arg Leu Val Glu Val Leu Pro Ser Pro Glu Phe Lys
        130                 135                 140

Ser Thr Ser Arg Tyr Gln Ala Lys Pro Arg Ile Gly Ile Gln Pro Glu
145                 150                 155                 160

Ile His His Ile Phe Arg Glu Asp Glu Arg Thr Val Asn Pro Ile Val
                165                 170                 175

Pro Val Val Phe Ile Ile Ala Ala Phe Thr Leu Leu Leu Gly Leu Phe
            180                 185                 190

Gly Ser Trp Val Gly Phe Ile Gly Ile Asp Asn Leu Phe Arg Thr Phe
        195                 200                 205

Lys Thr Ile Ser Lys Val Gln Leu Leu His Asn Val Ser Phe Leu Ile
    210                 215                 220

Ser Val Leu Gly Phe Glu Leu Asn Phe Val Lys Tyr Tyr Leu Gly Gln
225                 230                 235                 240

Ser Ile Phe Thr Thr Leu Phe Tyr Gly Phe Ile Leu Ser Ile Pro Cys
                245                 250                 255

Val Tyr Phe Gly Val Ser Val Leu Arg Ser Leu Ala Lys Asn Arg Ala
            260                 265                 270

Leu Gly Lys
        275

<210> SEQ ID NO 103
<211> LENGTH: 193
<212> TYPE: PRT
<213> ORGANISM: Candida albicans

<400> SEQUENCE: 103

Met Leu Met Tyr Thr Ile Leu Ile Pro Ser Leu Leu Tyr Ile Ala Leu
 1               5                  10                  15

Thr Ile Ala Ser Ser Glu Leu Leu Asn Ser Ile Gln Gly Thr Trp Gln
             20                  25                  30

Ser Gln Ser Glu Arg Val Ile Thr Gly Pro Thr Phe Phe Asp Pro Gln
         35                  40                  45

Lys Glu Leu Leu Glu Glu Pro Lys Leu Pro Gly Ile Ser Tyr Ser Phe
     50                  55                  60

Lys Asn Gly Tyr Trp Glu Ser Ala Gln Tyr Ile Val Met Gly Asn Asn
 65                  70                  75                  80
```

```
Arg Asn His Gln Cys Pro Gln Ala Met Leu Ile Trp Gln His Gly Lys
                85                  90                  95

Tyr Asn Leu Lys Arg Gly Lys Leu Val Leu Ile Pro Asn Arg Asn Asp
            100                 105                 110

Gly Arg Gln Leu Ile Ser Asp Pro Cys Leu Asp Asn Gly Lys Ser Glu
        115                 120                 125

Tyr Lys Arg Phe His Asn Gly Glu Thr Leu Glu Val Asp Ile Arg Phe
    130                 135                 140

Asp Gly Tyr Phe Gly Asn Trp Lys Leu Val Leu Val Asp Tyr Leu Thr
145                 150                 155                 160

Gly Lys Lys Lys Gln Pro Met Trp Leu Thr Ser Arg Asn Ala Thr Met
                165                 170                 175

Leu Pro Thr Gly Thr Ile Thr Ser Thr Lys Arg Lys Tyr Val Lys Lys
            180                 185                 190

Glu

<210> SEQ ID NO 104
<211> LENGTH: 432
<212> TYPE: PRT
<213> ORGANISM: Candida albicans

<400> SEQUENCE: 104

Met Ser Lys Ala Phe Ser Ala Pro Gly Lys Ala Phe Leu Ala Gly Gly
  1               5                  10                  15

Tyr Leu Val Leu Glu Pro Ile Tyr Asp Ala Tyr Val Thr Ala Leu Ser
             20                  25                  30

Ser Arg Met His Ala Val Ile Thr Pro Lys Gly Thr Ser Leu Lys Glu
         35                  40                  45

Ser Arg Ile Lys Ile Ser Ser Pro Gln Phe Ala Asn Gly Glu Trp Glu
     50                  55                  60

Tyr His Ile Ser Ser Asn Thr Glu Lys Pro Lys Glu Val Gln Ser Arg
 65                  70                  75                  80

Ile Asn Pro Phe Leu Glu Ala Thr Ile Phe Ile Val Leu Ala Tyr Ile
                 85                  90                  95

Gln Pro Thr Glu Ala Phe Asp Leu Glu Ile Ile Ile Tyr Ser Asp Pro
            100                 105                 110

Gly Tyr His Ser Gln Glu Asp Thr Glu Thr Lys Thr Ser Ser Asn Gly
        115                 120                 125

Glu Lys Thr Phe Leu Tyr His Ser Arg Ala Ile Thr Glu Val Glu Lys
    130                 135                 140

Thr Gly Leu Gly Ser Ser Ala Gly Leu Val Ser Val Ala Thr Ser Ser
145                 150                 155                 160

Leu Leu Ser His Phe Ile Pro Asn Val Ile Ser Thr Asn Lys Asp Ile
                165                 170                 175

Leu His Asn Val Ala Gln Ile Ala His Cys Tyr Ala Gln Lys Lys Ile
            180                 185                 190

Gly Ser Gly Phe Asp Val Ala Thr Ala Ile Tyr Gly Ser Ile Val Tyr
        195                 200                 205

Arg Arg Phe Gln Pro Ala Leu Ile Asn Asp Val Phe Gln Val Leu Glu
    210                 215                 220

Ser Asp Pro Glu Lys Phe Pro Thr Glu Leu Lys Lys Leu Ile Ala Ser
225                 230                 235                 240

Asn Trp Glu Phe Lys His Glu Arg Cys Thr Leu Pro His Gly Ile Lys
                245                 250                 255
```

-continued

```
Leu Leu Met Gly Asp Val Lys Gly Gly Ser Glu Thr Pro Lys Leu Val
            260                 265                 270

Ser Arg Val Leu Gln Trp Lys Lys Glu Lys Pro Glu Glu Ser Ser Val
            275                 280                 285

Val Tyr Asp Gln Leu Asn Ser Ala Asn Leu Gln Phe Met Lys Glu Leu
            290                 295                 300

Arg Glu Met Arg Glu Lys Tyr Asp Ser Asp Pro Glu Thr Tyr Ile Lys
305                 310                 315                 320

Glu Leu Asp His Ser Val Glu Pro Leu Thr Val Ala Ile Lys Asn Ile
                325                 330                 335

Arg Lys Gly Leu Gln Ala Leu Thr Gln Lys Ser Glu Val Pro Ile Glu
            340                 345                 350

Pro Asp Val Gln Thr Gln Leu Leu Asp Arg Cys Gln Glu Ile Pro Gly
            355                 360                 365

Cys Val Gly Gly Val Val Pro Gly Ala Gly Tyr Asp Ala Ile Ala
    370                 375                 380

Val Leu Val Leu Glu Asn Gln Val Gly Asn Phe Lys Gln Lys Thr Leu
385                 390                 395                 400

Glu Asn Pro Asp Tyr Phe His Asn Val Tyr Trp Val Asp Leu Glu Glu
                405                 410                 415

Gln Thr Glu Gly Val Leu Glu Gly Lys Pro Glu Asp Tyr Ile Gly Leu
            420                 425                 430

<210> SEQ ID NO 105
<211> LENGTH: 768
<212> TYPE: PRT
<213> ORGANISM: Candida albicans

<400> SEQUENCE: 105

Met Ser Asp Leu Thr Pro Ile Lys Leu Pro Ser Ser Ala Pro Phe Pro
1               5                   10                  15

Val Val Ile Ser Ser Val Leu Cys Lys Pro Gly Asp Thr Ile Ser Lys
            20                  25                  30

His Lys Thr Ile Phe Lys Tyr Lys Tyr Trp Asp Tyr Gln Asp Asp Pro
        35                  40                  45

Thr Ser Lys Glu Asp Pro Pro Lys Lys Ile Arg Val Glu Arg Leu Gly
50                  55                  60

Thr Phe Glu Ser Pro Ile Glu Gly Glu Ile Asp Gln Ile Asn Ile Lys
65                  70                  75                  80

Pro Leu Gln Glu Val Met His Ser Asp Val Asp Leu Leu Phe Val Lys
                85                  90                  95

Glu Ala Cys Pro His Thr Val Gln Tyr Ser Gly Leu Cys Ala Leu Cys
            100                 105                 110

Gly Lys Ser Leu Glu Glu Glu Lys Asp Tyr Ser Gly Tyr Asn Tyr Glu
        115                 120                 125

Asp Arg Ala Thr Ile Glu Met Ser His Asp Asn Thr Gly Leu Lys Ile
    130                 135                 140

Ser Phe Asp Glu Ala Ala Lys Ile Glu His Asn Thr Thr Asp Arg Leu
145                 150                 155                 160

Ile Asp Glu Arg Lys Leu Ile Leu Val Asp Leu Asp Gln Thr Val
                165                 170                 175

Ile His Ala Thr Val Asp Pro Thr Val Gly Glu Trp Gln Ser Asp Pro
            180                 185                 190

Ala Asn Pro Asn Tyr Ala Ala Val Lys Asp Val Lys Thr Phe Cys Leu
```

-continued

```
                195                 200                 205
Glu Glu Glu Ala Ile Val Pro Pro Gly Trp Thr Gly Pro Lys Leu Ala
    210                 215                 220
Pro Thr Lys Cys Thr Tyr Tyr Val Lys Leu Arg Pro Gly Leu Ser Glu
225                 230                 235                 240
Phe Leu Glu Lys Met Ala Glu Lys Tyr Glu Met His Ile Tyr Thr Met
                245                 250                 255
Ala Thr Arg Asn Tyr Ala Leu Ser Ile Ala Lys Ile Ile Asp Pro Asp
                260                 265                 270
Gly Lys Tyr Phe Gly Asp Arg Ile Leu Ser Arg Asp Glu Ser Gly Ser
                275                 280                 285
Leu Thr His Lys Asn Leu Lys Arg Leu Phe Pro Val Asp Gln Ser Met
        290                 295                 300
Val Val Ile Ile Asp Asp Arg Gly Asp Val Trp Gln Trp Glu Ser Asn
305                 310                 315                 320
Leu Ile Lys Val Val Pro Tyr Asp Phe Phe Val Gly Ile Gly Asp Ile
                325                 330                 335
Asn Ser Ser Phe Leu Pro Lys Lys Asn Gly Gln Leu Thr Gly Pro Thr
                340                 345                 350
Lys Lys Arg Lys Ser Ile Ala Lys Leu Glu Ala Ala Glu Leu Ala
                355                 360                 365
Lys Glu Ser Asp Thr Asn Asn Asp Lys Gln Glu Thr Glu Ser Gly Glu
    370                 375                 380
Glu Glu Gly Glu Glu Asp Ala Asp Gly His Ser Asp Val Ser Asn Ser
385                 390                 395                 400
Pro Val Glu Arg Ile Leu Glu Leu Gly Gly Gly Glu Gly Asn Thr Ser
                405                 410                 415
Leu Leu Leu Glu Gln Ser Leu Thr Arg Asn Gln Ser Ile Glu Glu Gln
                420                 425                 430
Gln Gln Lys Arg Pro Leu Ala Lys Leu Gln His Asp Leu Glu Gln Met
                435                 440                 445
His Glu His Arg His Asp Ser Asp Ser Lys Ser Glu Ser Gly Ser Asp
    450                 455                 460
Asp Glu Ser Asp Glu Glu Asp Asn Leu Phe Asp Asp Asn Glu
465                 470                 475                 480
Leu Ala Ala Leu Asp Lys Val Leu Gly Asn Ile His Gln Gly Tyr Tyr
                485                 490                 495
Asn Leu Phe Asp Lys Asp Lys Ile Asn Lys Pro Asp Leu Thr Glu Ile
                500                 505                 510
Ile Pro Ser Met Lys Ser Lys Thr Leu Glu Gly Ile Thr Val Leu Phe
                515                 520                 525
Ser Gly Ile Ile Pro Leu Gly Ile Asn Leu Asp Ser Ala Asp Ile Val
    530                 535                 540
Ile Trp Cys Arg Gln Phe Gly Val Lys Val Val Asn Glu Val Tyr Pro
545                 550                 555                 560
Glu Val Thr His Val Val Cys Arg Asp Val Ser Glu Gly Ala Gly Pro
                565                 570                 575
Thr Phe Lys Thr Arg Val Ala Arg Lys Leu Tyr Pro Asp Thr Ile Lys
                580                 585                 590
Ile Val Asn Pro Asp Trp Leu Phe Ala Cys Leu Ser Asn Trp Thr Lys
                595                 600                 605
Val Asp Glu Lys Asp Tyr Leu Ile Ser Thr Asp Thr Lys Leu Trp
    610                 615                 620
```

```
Thr Val Lys Glu Asn Glu Ile Thr Lys Tyr Gln Lys Ala Leu Glu Asp
625                 630                 635                 640

Arg Ser Ala Leu Ala Asn Ala Thr His Ile Asp Ser Ile Glu Ser Phe
            645                 650                 655

Asp Glu Tyr Asp Leu Asp Glu Ala Asn Gln Glu Val Asp Asp Phe Leu
            660                 665                 670

Ala Gly Leu Ser Asp Asp Glu Glu Glu Glu Glu Glu Glu Glu Glu Asp
            675                 680                 685

Glu Glu Ile Glu Asn Pro Glu Ser Asn Asn Asp Asp Glu Glu Ile Tyr
            690                 695                 700

Glu Gln Ser Thr Asn Gly His Asp Ser Phe Ile Lys Asp Ala Tyr Ser
705                 710                 715                 720

Lys Lys Arg Asn Arg Asp Glu Glu Glu Val Gln Leu Val Lys Lys Gln
                725                 730                 735

Lys Ile Glu Asn Gly Glu Asn Gly Glu Asn Glu Asn Glu Asn Asp Leu
            740                 745                 750

Asp Asp Leu Glu Lys Glu Leu Leu Asp Gly Phe Asp Asp Leu Glu Glu
            755                 760                 765

<210> SEQ ID NO 106
<211> LENGTH: 1042
<212> TYPE: PRT
<213> ORGANISM: Candida albicans

<400> SEQUENCE: 106

Met Gly Lys Lys Ala Ile Asp Ala Arg Ile Pro Ala Leu Ile Arg Asn
1               5                   10                  15

Gly Val Gln Glu Lys Gln Arg Ser Phe Phe Ile Ile Val Gly Asp Lys
            20                  25                  30

Ala Arg Asn Gln Leu Pro Asn Leu His Tyr Leu Met Met Ser Ala Asp
        35                  40                  45

Leu Lys Met Asn Lys Ser Val Leu Trp Ala Tyr Lys Lys Lys Leu Leu
50                  55                  60

Gly Phe Thr Ser His Arg Gln Lys Arg Glu Ala Lys Ile Lys Lys Asp
65                  70                  75                  80

Ile Lys Arg Gly Ile Arg Glu Val Asn Glu Gln Asp Pro Phe Glu Ala
                85                  90                  95

Phe Ile Ser Asn Gln His Ile Arg Tyr Val Tyr Lys Glu Thr Glu
            100                 105                 110

Lys Ile Leu Gly Asn Thr Tyr Gly Met Cys Ile Leu Gln Asp Phe Glu
        115                 120                 125

Ala Ile Thr Pro Asn Leu Leu Ala Arg Thr Ile Glu Thr Val Glu Gly
    130                 135                 140

Gly Gly Leu Val Val Ile Leu Leu Lys Asn Met Thr Ser Leu Lys Gln
145                 150                 155                 160

Leu Tyr Thr Met Ser Met Asp Ile His Ser Arg Tyr Arg Thr Glu Ala
                165                 170                 175

His Asp Asp Val Val Ala Arg Phe Asn Glu Arg Phe Leu Leu Ser Leu
            180                 185                 190

Gly Ser Cys Glu Asn Cys Leu Val Val Asp Asp Glu Leu Asn Val Leu
        195                 200                 205

Pro Ile Ser Gly Gly Lys His Val Lys Pro Leu Pro Pro Lys Asp Asp
    210                 215                 220

Asp Glu Leu Thr Pro Asn Ala Lys Glu Leu Lys Glu Leu Lys Glu Ser
```

-continued

```
            225                 230                 235                 240
Leu Ala Asp Val Gln Pro Ala Gly Ser Leu Val Ala Leu Ser Lys Thr
                245                 250                 255
Ile Asn Gln Ala Gln Ala Ile Leu Thr Phe Ile Asp Val Ile Ser Glu
                260                 265                 270
Lys Thr Leu Arg Asn Thr Val Thr Leu Thr Ala Gly Arg Gly Arg Gly
                275                 280                 285
Lys Ser Ala Ala Leu Gly Ile Ala Ile Ala Ala Ala Ile Ser His Gly
                290                 295                 300
Tyr Ser Asn Ile Phe Val Thr Ser Pro Ser Pro Glu Asn Leu Lys Thr
305                 310                 315                 320
Leu Phe Glu Phe Ile Phe Lys Gly Phe Asp Ala Leu Gly Tyr Thr Glu
                325                 330                 335
His Met Asp Tyr Asp Ile Ile Gln Ser Thr Asn Pro Ser Phe Asn Lys
                340                 345                 350
Ala Ile Val Arg Val Asp Val Lys Arg Glu His Arg Gln Thr Ile Gln
                355                 360                 365
Tyr Ile Ser Pro Asn Asp Ser His Val Leu Gly Gln Ala Glu Leu Leu
370                 375                 380
Ile Ile Asp Glu Ala Ala Ala Ile Pro Leu Pro Ile Val Lys Lys Leu
385                 390                 395                 400
Met Gly Pro Tyr Leu Ile Phe Met Ala Ser Thr Ile Asn Gly Tyr Glu
                405                 410                 415
Gly Thr Gly Arg Ser Leu Ser Leu Lys Leu Ile Gln Gln Leu Arg Thr
                420                 425                 430
Gln Ser Asn Asn Ala Thr Pro Ser Glu Thr Thr Val Val Ser Arg Asp
                435                 440                 445
Lys Lys Ser Asn Glu Ile Thr Gly Ala Leu Thr Arg Thr Leu Lys Glu
                450                 455                 460
Val Val Leu Asp Glu Pro Ile Arg Tyr Ala Pro Gly Asp Pro Ile Glu
465                 470                 475                 480
Lys Trp Leu Asn Lys Leu Leu Cys Leu Asp Val Ser Leu Ser Lys Asn
                485                 490                 495
Ala Lys Phe Ala Thr Lys Gly Thr Pro His Pro Ser Gln Cys Gln Leu
                500                 505                 510
Phe Tyr Val Asn Arg Asp Thr Leu Phe Ser Tyr His Pro Val Ser Glu
                515                 520                 525
Ala Phe Leu Gln Lys Met Met Ala Leu Tyr Val Ala Ser His Tyr Lys
                530                 535                 540
Asn Ser Pro Asn Asp Leu Gln Leu Met Ser Asp Ala Pro Ala His Gln
545                 550                 555                 560
Leu Phe Val Leu Leu Pro Pro Ile Glu Ala Gly Asp Asn Arg Val Pro
                565                 570                 575
Asp Pro Leu Cys Val Ile Gln Leu Ala Leu Glu Gly Glu Ile Ser Lys
                580                 585                 590
Glu Ser Val Arg Lys Ser Leu Ser Arg Gly Gln Arg Ala Gly Gly Asp
                595                 600                 605
Leu Ile Pro Trp Leu Ile Ser Gln Gln Phe Gln Asp Glu Glu Phe Ala
                610                 615                 620
Ser Leu Ser Gly Ala Arg Val Val Arg Ile Ala Thr Asn Pro Glu Tyr
625                 630                 635                 640
Ser Gly Met Gly Tyr Gly Ser Arg Ala Met Glu Leu Leu Arg Asp Tyr
                645                 650                 655
```

-continued

Tyr Ser Gly Lys Phe Thr Asp Ile Ser Glu Ser Thr Glu Leu Asn Asp
            660                 665                 670

His Thr Ile Thr Arg Val Thr Asp Ser Glu Leu Ala Asn Ala Ser Leu
            675                 680                 685

Lys Asp Glu Ile Lys Leu Arg Asp Val Lys Thr Leu Pro Pro Leu Leu
            690                 695                 700

Leu Lys Leu Ser Glu Lys Ala Pro Tyr Tyr Leu His Tyr Leu Gly Val
705                 710                 715                 720

Ser Tyr Gly Phe Thr Ser Gln Leu His Lys Phe Trp Lys Lys Ala Gly
            725                 730                 735

Phe Thr Pro Val Tyr Leu Arg Gln Thr Pro Asn Glu Leu Thr Gly Glu
            740                 745                 750

His Thr Ser Val Val Ile Ser Val Leu Pro Gly Arg Glu Asp Lys Trp
            755                 760                 765

Leu His Glu Phe Ser Lys Asp Phe His Lys Arg Phe Leu Ser Leu Leu
            770                 775                 780

Ser Tyr Glu Phe Lys Lys Phe Gln Ala Ser Gln Ala Leu Ser Ile Ile
785                 790                 795                 800

Glu Ala Ala Glu Gln Gly Gly Asp Glu Thr Thr Ser Gln Lys Leu
            805                 810                 815

Thr Lys Glu Gln Leu Asp Ser Leu Leu Ser Pro Phe Asp Leu Lys Arg
            820                 825                 830

Leu Asp Ser Tyr Ala Asn Asn Leu Leu Asp Tyr His Val Ile Val Asp
            835                 840                 845

Met Leu Pro Leu Ile Ser Gln Leu Phe Phe Ser Lys Lys Thr Gly Gln
            850                 855                 860

Asp Ile Ser Leu Ser Ser Val Gln Ser Ala Ile Leu Leu Ala Ile Gly
865                 870                 875                 880

Leu Gln His Lys Asp Met Asp Gln Ile Ala Lys Glu Leu Asn Leu Pro
            885                 890                 895

Thr Asn Gln Ala Met Ala Met Phe Ala Lys Ile Ile Arg Lys Phe Ser
            900                 905                 910

Thr Tyr Phe Arg Lys Val Leu Ser Lys Ala Ile Glu Glu Ser Met Pro
            915                 920                 925

Asp Leu Glu Asp Glu Asn Val Asp Ala Met Asn Gly Lys Glu Thr Glu
            930                 935                 940

Gln Ile Asp Tyr Lys Ala Ile Glu Gln Lys Leu Gln Asp Asp Leu Glu
945                 950                 955                 960

Glu Ala Gly Asp Glu Ala Ile Lys Glu Met Arg Glu Lys Gln Arg Glu
            965                 970                 975

Leu Ile Asn Ala Leu Asn Leu Asp Lys Tyr Ala Ile Ala Glu Asp Ala
            980                 985                 990

Glu Trp Asp Glu Lys Ser Met Asp Lys Ala Thr Lys Gly Lys Gly Asn
            995                 1000                1005

Val Val Ser Ile Lys Ser Gly Lys Arg Lys Ser Lys Glu Asn Ala Asn
            1010                1015                1020

Asp Ile Tyr Glu Lys Glu Met Lys Ala Val Lys Lys Ser Lys Lys Ser
1025                1030                1035                1040

Lys Lys

<210> SEQ ID NO 107
<211> LENGTH: 127
<212> TYPE: PRT

<213> ORGANISM: Candida albicans

<400> SEQUENCE: 107

```
Met Ala Ala Phe Asp Glu Ile Phe Asp Tyr Val Asp Arg Asp Thr Phe
 1               5                  10                  15

Phe Gln Tyr Phe Arg Leu Thr Leu Val Val Cys Thr Tyr Leu Ile Phe
                20                  25                  30

Arg Lys Tyr Tyr Ser Ser Trp Ala Ile Lys Lys Gln Thr Ala Thr Gln
            35                  40                  45

Leu Glu Gln Asp Lys Arg Glu Gln Ser Glu Lys Ser Glu Arg Glu Ala
        50                  55                  60

Lys Glu Ser Lys Glu Lys Phe Asp Thr Ile Ser Asn Glu Ala Lys Glu
65                  70                  75                  80

Phe Gly Trp Gly Lys Lys Thr Arg Asn Asn Val Lys Leu Thr Glu Ala
                85                  90                  95

Val Leu Ala Glu Tyr Ser Glu Gln Gln Arg Gln Arg Asn Gln Thr Ser
               100                 105                 110

Tyr Asp Ala Gln Glu Asp Ala Asp Ile Asp Asp Leu Leu Glu Asp
           115                 120                 125
```

<210> SEQ ID NO 108
<211> LENGTH: 289
<212> TYPE: PRT
<213> ORGANISM: Candida albicans

<400> SEQUENCE: 108

```
Met Ser Phe Arg Gly Gly Gly Ser Gly Arg Ser Thr Gln Arg
 1               5                  10                  15

Thr Ile Leu Pro Phe Gly Leu Asp Tyr Ala Asp Ile Ile Ser Ser Thr
                20                  25                  30

Gln Glu Thr Glu Lys Pro Gln Leu Leu Leu Pro Ile Asn Gly Asp Ile
            35                  40                  45

Thr Glu Ile Glu Ser Ile Ile Ala Lys Gln Ser Met Asn Phe Thr Lys
        50                  55                  60

Leu Met Ser Glu Gly Pro Phe Phe Thr Gly Asn Leu Asp Ser Ile Glu
65                  70                  75                  80

Ile Thr Lys Lys Arg Asn His Asn Asp Ser Glu Asn Glu Glu Glu
                85                  90                  95

Glu Glu Glu Gly Gly Asp Thr Glu Asn Thr Gly Asp Arg Lys Lys Lys
               100                 105                 110

Lys Ser Lys Thr Asn Gly Asp Gly Ser Ser Gly Ser Gly Ser Gly
           115                 120                 125

Ser Ala Ser Gly Asp Gly Ile Glu Arg Tyr Ser Asp Arg Tyr Lys Lys
       130                 135                 140

Ile Gln Lys Ile Gly Arg Thr Ile Asp Glu His Pro Tyr Gln Pro Glu
145                 150                 155                 160

Tyr Phe Pro Ser Glu Leu Tyr Ser Val Met Gly Ile Thr Asn Lys His
                165                 170                 175

Asp Lys Lys Lys Phe Leu Leu Leu Ser Lys Phe Lys Ser Asn Gly Gly
           180                 185                 190

Leu Lys Gln Ile Leu Ser Asn Glu Lys Leu Glu Asn Leu Asp Glu Gln
       195                 200                 205

Ser Lys Leu Asn Ser Met Lys Glu Lys Met Leu Ser Met Ile Asp Asn
   210                 215                 220

Ser Val Asn Val Asn Asp Asp Asp Asn Asn Asn Asp Gly Lys Thr Arg
```

```
              225                 230                 235                 240
Ser Gly Asp Glu Gln Glu Ile Asp Glu Asp Leu Asp Asp Glu Phe
            245                 250                 255
Glu Asp Glu Asp Asp Asp Tyr Asn Ala Glu Lys Tyr Phe Asp Asp
            260                 265                 270
Gly Asp Asp Asp Gly Gly Asp Asp Gly Gly Asp Asp Glu Ala Ala
            275                 280                 285
Phe

<210> SEQ ID NO 109
<211> LENGTH: 507
<212> TYPE: PRT
<213> ORGANISM: Candida albicans

<400> SEQUENCE: 109

Met Leu Ala Ser Lys Lys Arg Thr Arg Ile Lys Arg Gln Pro
1               5                   10                  15
Ile Cys Glu Gln Ile Pro Thr Ser Asn Thr Ala Phe Phe Thr Leu
            20                  25                  30
Asp Ile Pro Ile Met Pro Val Asn Phe Leu Thr Ser Val Phe Asp
            35                  40                  45
Gly Pro Glu Val Ile Pro Tyr Trp Asp Gln Ile Lys Glu Tyr Gly Pro
50                  55                  60
Thr Val Leu Pro Ile Leu Leu Thr Leu Ala Gly Ala Lys Tyr Tyr Phe
65                  70                  75                  80
His Gly Ala Thr Asn Thr Trp Glu Arg Asp Met His Gly Lys Val Phe
                85                  90                  95
Met Ile Thr Gly Gly Thr Ser Gly Ile Gly Ala Gln Ile Ala Tyr Glu
            100                 105                 110
Leu Gly Gln Arg Gly Ala Gln Leu Ile Leu Leu Thr Arg Arg Thr Asn
            115                 120                 125
Asp Gln Trp Val Ala Glu Tyr Ile Glu Asp Leu Arg Asp Lys Thr Asn
            130                 135                 140
Asn Gly Leu Ile Tyr Ala Glu Glu Cys Asp Leu Ser Ser Leu Tyr Ser
145                 150                 155                 160
Ile Arg Lys Phe Ala Thr Arg Trp Leu Asp Asn Gln Pro Pro Arg Arg
                165                 170                 175
Leu Asp Gly Val Ile Cys Cys Ala Ala Glu Cys Ile Pro Arg Gly Lys
            180                 185                 190
Ser Arg Gln Ile Thr Met Asp Gly Val Glu Arg Gln Ile Gly Ile Asn
            195                 200                 205
Tyr Leu Ala His Phe His Leu Leu Thr Leu Leu Gly Pro Ser Leu Arg
            210                 215                 220
Val Gln Pro Pro Asp Arg Asn Val Arg Val Leu Ile Ala Thr Cys Ser
225                 230                 235                 240
Ser Gln Asn Leu Gly Asp Val Asp Leu Asn Asp Leu Leu Trp Ser Asn
                245                 250                 255
Lys Arg Tyr Pro Ala Thr Gln Pro Trp Lys Val Tyr Gly Thr Ser Lys
            260                 265                 270
Leu Leu Leu Gly Leu Phe Ala Lys Glu Tyr Gln Arg Gln Leu Met Gly
            275                 280                 285
Tyr Glu Arg Lys Asp Lys Ala Pro Cys Asn Val Arg Ile Asn Leu Ile
            290                 295                 300
Asn Pro Gly Ile Val Arg Thr Pro Ser Thr Arg Arg Phe Leu Ser Leu
```

```
305                 310                 315                 320
Gly Thr Val Trp Gly Leu Ile Ile Tyr Leu Ile Leu Phe Pro Ile Trp
                325                 330                 335

Trp Leu Phe Phe Lys Ser Ala Glu Gln Gly Ala Gln Ser Phe Tyr Phe
            340                 345                 350

Ala Leu Phe Ala Pro Ile Phe Met Lys Ile Glu Gly Gly Asn Val Val
            355                 360                 365

Gln Glu Cys Lys Ile Met Thr Lys Val Arg Lys Glu Tyr Thr Asp Asp
        370                 375                 380

Asp Leu Gln Gln Lys Val Phe His Asn Thr Glu Glu Leu Ile Lys Gln
385                 390                 395                 400

Ile Glu Thr Lys Ser Ala Ile Glu Arg Lys Lys His Glu Asn Ala Lys
                405                 410                 415

Lys Thr Pro Glu Gln Lys Ala Lys Glu Arg Gln Glu Glu Leu Asn Arg
            420                 425                 430

Lys Arg Asp Leu His Ile Lys Pro Glu Thr Pro Glu Glu Leu Glu Ser
        435                 440                 445

Lys Leu Asn Ser Leu Arg Asn Gln Ile Gly Met Gly Thr Gly Ile Ser
450                 455                 460

Ser Asn Glu Met Pro Leu Phe Pro Asp Asp Glu Thr Leu Lys Lys Val
465                 470                 475                 480

Ile Ser Ser Lys Lys Asn Ala Ser Ser Asn Ser Gly Gly Ser Lys
                485                 490                 495

Ser Asn Lys Ser Gln Lys Ser Lys Lys Val
            500                 505

<210> SEQ ID NO 110
<211> LENGTH: 330
<212> TYPE: PRT
<213> ORGANISM: Candida albicans

<400> SEQUENCE: 110

Met Thr Asp Met Ser Asn Thr Thr Asp Gly Asn Val Ser Ile
1               5                   10                  15

Val Val Pro Gly Gln Tyr Ile Ser Pro Thr Tyr Lys Leu Glu Asn Ser
                20                  25                  30

Asn Asn Asp Ser Ser Ile Pro Val Lys Tyr Ile Pro Gly Ser Gly Thr
            35                  40                  45

Ile Ile Ser Asn Ile Asn Ile Pro Ser Pro Asn Thr Ser Thr Asn Ser
        50                  55                  60

Val Lys Ser Met Pro Ile Val Ser Thr Ile Leu Gly Asn Val Ser
65                  70                  75                  80

Ile Ser Pro Ile Asp Gln Thr Pro Thr Ser Lys Pro Ser Asn Asn Asp
                85                  90                  95

Asp Met Val Ile Asp Asn Glu Gln Thr Lys Ser Asp Glu Asp Lys Asp
            100                 105                 110

Lys Asp Lys Tyr Val Lys Ser Tyr Leu Val Ser Val Ile Pro Lys Ser
        115                 120                 125

Thr Lys His Gln Ser Thr Thr Ser Thr Thr Ser Asn Gln Ser Gly
130                 135                 140

Ser Lys Ala Ile Ser Ala Ile Ala Leu Pro Lys Glu Asn Asp Ile Val
145                 150                 155                 160

Leu Val Arg Ile Thr Lys Ile Thr Lys Ile Gln Ala Tyr Cys Glu Ile
                165                 170                 175
```

-continued

```
Ile Ser Leu Asp Thr Thr Asn Ile Leu Pro Asp Ser Gly Leu Gly
            180                 185                 190

Asn Asn Gly Asn Gly Ser His Val Ser Met Ser Ile Thr Gly Ser Asn
        195                 200                 205

Ser Gln His Asn Phe Asn Gln Asn Ser Ile Ala Ser Ser Gln Ser Thr
    210                 215                 220

Asn Gln Ser Val Gln Ile Tyr Glu Leu Gly Glu Asn Phe Lys Gly Ile
225                 230                 235                 240

Ile Arg Ile Asn Asp Ile Arg Ser Thr Glu Arg Asp Lys Leu Lys Leu
                245                 250                 255

Ile Asp Cys Phe Lys Pro Gly Asp Ile Val Lys Ala Gln Val Ile Ser
            260                 265                 270

Leu Gly Asp Gly Ser Asn Tyr Tyr Leu Thr Thr Ala Lys Asn Glu Leu
        275                 280                 285

Gly Val Val Phe Ala Lys Ser Glu Asn Gly Ala Gly Asp Leu Met Tyr
    290                 295                 300

Pro Ile Asp Trp Gln Asn Met Ile Asp Ile Asn Ser Gly Val Ile Glu
305                 310                 315                 320

Lys Arg Lys Asn Ala Asn Pro Phe Leu Gln
                325                 330

<210> SEQ ID NO 111
<211> LENGTH: 221
<212> TYPE: PRT
<213> ORGANISM: Candida albicans

<400> SEQUENCE: 111

Met Ala Gly Asp Leu Asn Leu Lys Lys Ser Trp Asn Pro Ala Leu Val
1               5                   10                  15

Lys Asn Gln Gln Lys Val Trp Glu Glu Gln Gln Lys Leu Asp Glu
            20                  25                  30

Leu Lys Arg Ile Lys Glu Arg Asn Gln Glu Tyr Lys Gln Glu Gln Glu
        35                  40                  45

Tyr Leu Glu Leu Leu Lys Leu Gln His Gly Asp Gln Phe Gln Ile Lys
    50                  55                  60

Asp Leu Asn Lys Gln Gln Lys Leu Lys Ile Ser Lys Leu Asn Trp Met
65                  70                  75                  80

Tyr Asp Asp Val Pro Phe Glu Gly Asn Glu Lys Val Glu Glu Asn Ser
                85                  90                  95

Ser Gly Phe Ile Glu Ser Asn Val Glu Phe Thr Asp Gly Lys Ser Lys
            100                 105                 110

Val Glu Asn Leu Leu Lys Gly Asn His Val Val Gly Lys Lys Arg Asp
        115                 120                 125

Gly Ser Gly Thr Ser Asp Arg Ile Asn Lys Ile Ile Gly Val Gly Met
    130                 135                 140

Thr Lys Ser Ser Lys Val Ser Tyr Ser Asp Asp Pro Leu Leu Lys Ile
145                 150                 155                 160

Lys Gln Gln Gln Gln Gln Ala Gln Arg Val Ala Arg Lys Gln His Pro
                165                 170                 175

Ser Asp Lys His Ser His Arg Phe Arg His Ser Ser Lys Ser Ser Ser
            180                 185                 190

Asp Arg Val His Lys Ser His Glu His Glu Arg Ser Arg Lys His Asn
        195                 200                 205

Ser Ser His Thr Arg His Lys Asp Gly Ser Pro His Arg
    210                 215                 220
```

<210> SEQ ID NO 112
<211> LENGTH: 778
<212> TYPE: PRT
<213> ORGANISM: Candida albicans

<400> SEQUENCE: 112

```
Met Leu Lys Asn Asp Thr Val Phe Thr Lys Asp Ile Ser Cys Thr Ala
 1               5                  10                  15

Ile Thr Gly Lys Asp Ala Trp Asn Pro Thr Pro Gln Pro Ile Thr Ile
             20                  25                  30

Ser Leu Ser Phe Thr Asp Phe Lys Ala Ser Glu Leu Asp Asn Leu Lys
         35                  40                  45

Ser Ile Asn Tyr Ala Val Ile Thr Arg Asn Val Thr Glu Phe Met Lys
     50                  55                  60

Ser Asn Glu His Leu Asn Phe Lys Ser Leu Gly Asn Ile Ala Gln Ala
 65                  70                  75                  80

Ile Ser Asp Ile Gly Leu Asp Gln Ser Arg Gly Gly Ser Ile Val
                 85                  90                  95

Asp Val Thr Ile Lys Ser Leu Lys Ser Glu Ile Arg Ala Glu Ser Val
                100                 105                 110

Glu Tyr Lys Ile Asn Arg Asn Thr Leu Gly Gln Pro Val Pro Leu Asp
            115                 120                 125

Ile Phe Gln Val Asn Lys Leu Arg Leu Leu Ile Ile Val Phe Thr Phe
        130                 135                 140

Glu Arg Leu Gln Lys Gln Ile Val Asp Val Asp Gln Phe Lys Ile Pro
145                 150                 155                 160

Asn Ser Asn Leu Tyr Phe His Gln Ile Ile Ala Asp Ile Val Ser Tyr
                165                 170                 175

Val Glu Ser Ser Asn Phe Lys Thr Val Glu Ala Leu Val Ser Lys Ile
            180                 185                 190

Gly Gln Leu Thr Phe Gln Lys Tyr Asp Gly Val Ala Glu Val Val Ala
        195                 200                 205

Thr Val Thr Lys Pro Asn Ala Ser His Val Glu Gly Val Gly Val Ser
    210                 215                 220

Ser Thr Met Val Lys Asn Phe Lys Asp Met Glu Pro Val Lys Phe Glu
225                 230                 235                 240

Asn Thr Ile Ala Gln Thr Asn Arg Ala Phe Asn Leu Pro Val Glu Asn
                245                 250                 255

Glu Lys Thr Glu Asp Tyr Thr Gly Tyr His Thr Ala Phe Ile Ala Phe
            260                 265                 270

Gly Ser Asn Thr Gly Asn Gln Val Glu Asn Ile Thr Asn Ser Phe Glu
        275                 280                 285

Leu Leu Gln Lys Tyr Gly Ile Thr Ile Glu Ala Thr Ser Ser Leu Tyr
    290                 295                 300

Ile Ser Lys Pro Met Tyr Tyr Leu Asp Gln Pro Asp Phe Phe Asn Gly
305                 310                 315                 320

Val Ile Lys Val Asn Phe Gln Asn Ile Ser Pro Phe Gln Leu Leu Lys
                325                 330                 335

Ile Leu Lys Asp Ile Glu Tyr Lys His Leu Glu Arg Lys Lys Asp Phe
            340                 345                 350

Asp Asn Gly Pro Arg Ser Ile Asp Leu Asp Ile Ile Leu Tyr Asp Asp
        355                 360                 365

Leu Gln Leu Asn Thr Glu Asn Leu Ile Ile Pro His Lys Ser Met Leu
```

```
            370                 375                 380
Glu Arg Thr Phe Val Leu Gln Pro Leu Cys Glu Val Leu Pro Pro Asp
385                 390                 395                 400
Tyr Ile His Pro Ile Ser Ala Glu Ser Leu His Ser His Leu Gln Gln
                405                 410                 415
Leu Ile Asn Asp Lys Pro Gln Glu Thr Val Gln Glu Ser Ser Asp Leu
            420                 425                 430
Leu Gln Phe Ile Pro Val Ser Arg Leu Pro Val Lys Asp Asn Ile Leu
        435                 440                 445
Lys Phe Asp Gln Ile Asn His Lys Ser Pro Thr Leu Ile Met Gly Ile
450                 455                 460
Leu Asn Met Thr Pro Asp Ser Phe Ser Asp Gly Gly Lys His Phe Gly
465                 470                 475                 480
Lys Glu Leu Asp Asn Thr Val Lys Gln Ala Glu Lys Leu Val Ser Glu
                485                 490                 495
Gly Ala Thr Ile Ile Asp Ile Gly Gly Val Ser Thr Arg Pro Gly Ser
            500                 505                 510
Val Glu Pro Thr Glu Glu Glu Leu Glu Arg Val Ile Pro Leu Ile
        515                 520                 525
Lys Ala Ile Arg Gln Ser Ser Asn Pro Asp Leu Ser Lys Val Leu Ile
530                 535                 540
Ser Val Asp Thr Tyr Arg Arg Asn Val Ala Glu Gln Ser Leu Leu Val
545                 550                 555                 560
Gly Ala Asp Ile Ile Asn Asp Ile Ser Met Gly Lys Tyr Asp Glu Lys
                565                 570                 575
Ile Phe Asp Val Val Ala Lys Tyr Gly Cys Pro Tyr Ile Met Asn His
            580                 585                 590
Thr Arg Gly Ser Pro Lys Thr Met Ser Lys Leu Thr Asn Tyr Glu Ser
        595                 600                 605
Asn Thr Asn Asp Asp Ile Ile Glu Tyr Ile Ile Asp Pro Lys Leu Gly
610                 615                 620
His Gln Glu Leu Asp Leu Ser Pro Glu Ile Lys Asn Leu Leu Asn Gly
625                 630                 635                 640
Ile Ser Arg Glu Leu Ser Leu Gln Met Phe Lys Ala Met Ala Lys Gly
                645                 650                 655
Val Lys Lys Trp Gln Ile Ile Leu Asp Pro Gly Ile Gly Phe Ala Lys
            660                 665                 670
Asn Leu Asn Gln Asn Leu Ala Val Ile Arg Asn Ala Ser Phe Phe Lys
        675                 680                 685
Lys Tyr Ser Ile Gln Ile Asn Glu Arg Val Asp Asp Val Thr Ile Lys
690                 695                 700
His Lys Tyr Leu Ser Phe Asn Gly Ala Cys Val Leu Val Gly Thr Ser
705                 710                 715                 720
Arg Lys Lys Phe Leu Gly Thr Leu Thr Gly Asn Glu Val Pro Ser Asp
                725                 730                 735
Arg Val Phe Gly Thr Gly Ala Thr Val Ser Ala Cys Ile Glu Gln Asn
            740                 745                 750
Thr Asp Ile Val Arg Val His Asp Val Lys Glu Met Lys Asp Val Val
        755                 760                 765
Cys Ile Ser Asp Ala Ile Tyr Lys Asn Val
770                 775

<210> SEQ ID NO 113
```

```
<211> LENGTH: 148
<212> TYPE: PRT
<213> ORGANISM: Candida albicans

<400> SEQUENCE: 113

Met Ser Asp Ile Asp Ile Asp Asn Val Leu Asn Leu Glu Glu Glu Gln
 1               5                  10                  15

Tyr Glu Leu Gly Phe Lys Glu Gly Gln Ile Gln Gly Thr Lys Asp Gln
            20                  25                  30

Tyr Leu Glu Gly Lys Glu Tyr Gly Tyr Gln Thr Gly Phe Gln Arg Phe
        35                  40                  45

Leu Ile Ile Gly Tyr Ile Gln Glu Leu Met Lys Phe Trp Leu Ser His
    50                  55                  60

Ile Asp Gln Tyr Asn Asn Ser Ser Leu Arg Asn His Leu Asn Asn
65                  70                  75                  80

Leu Glu Asn Ile Leu Ala Gln Ile Ser Ile Thr Asn Gly Asp Lys Glu
                85                  90                  95

Val Glu Asp Tyr Glu Lys Asn Ile Lys Lys Ala Arg Asn Lys Leu Arg
            100                 105                 110

Val Ile Ala Ser Ile Thr Lys Glu Thr Trp Lys Ile Asp Ser Leu Asp
        115                 120                 125

Asn Leu Val Lys Glu Val Gly Gly Thr Leu Gln Val Ser Glu Asn Pro
    130                 135                 140

Asp Asp Met Trp
145

<210> SEQ ID NO 114
<211> LENGTH: 269
<212> TYPE: PRT
<213> ORGANISM: Candida albicans

<400> SEQUENCE: 114

Met Arg Gln Lys Arg Ala Lys Ala Tyr Lys Lys Gln Met Ser Val Tyr
 1               5                  10                  15

Val His Ala Phe Lys Phe Arg Glu Pro Tyr Gln Ile Ile Val Asp Asn
            20                  25                  30

Glu Leu Ile Thr Thr Cys Gln Ser Ala Ser Phe Asp Ile Asn Lys Gly
        35                  40                  45

Phe Thr Arg Thr Ile Gln Ala Glu Asn Lys Pro Met Ile Thr Gln Cys
    50                  55                  60

Cys Ile Gln Ala Leu Tyr Asp Thr Lys Asn Gln Pro Ala Ile Asp Ile
65                  70                  75                  80

Ala Lys Ser Phe Glu Arg Arg Lys Cys Asn His Arg Glu Ala Ile Asp
                85                  90                  95

Pro Ser Gln Cys Ile Glu Ser Ile Val Asn Ile Lys Gly Gln Asn Lys
            100                 105                 110

His Arg Tyr Ile Val Ala Ser Gln Asp Leu Gln Leu Arg Lys Lys Leu
        115                 120                 125

Arg Lys Ile Pro Gly Val Pro Leu Ile Tyr Met Asn Arg Ser Val Met
    130                 135                 140

Val Met Glu Pro Ile Ser Asp Val Ser Asn Gln Tyr Asn Met Asn Tyr
145                 150                 155                 160

Glu Ser Lys Lys Leu Thr Gly Gly Leu Asn Asp Ile Glu Ala Gly Lys
                165                 170                 175

Leu Glu Lys Gln Asn Glu Gly Glu Asp Gly Asp Gly Asp Glu Ser Glu
            180                 185                 190
```

```
Val Lys Lys Lys Arg Lys Gly Pro Lys Glu Pro Asn Pro Leu Ser
            195                 200                 205

Val Lys Lys Lys Thr Asp Asn Ala Thr Ala Ser Thr Asn Gln
            210                 215                 220

Glu Gln Lys Lys Lys Pro Asn Arg Arg Lys Arg His Gly Lys Ser Lys
225                 230                 235                 240

Ala Glu Glu Lys Glu Asp Gln Glu Gln Glu Gln Val Asn Glu Ala Thr
                245                 250                 255

Thr Asn Glu Asp Ala Gln Glu Ala Ile Thr Ala Thr Glu
            260                 265

<210> SEQ ID NO 115
<211> LENGTH: 306
<212> TYPE: PRT
<213> ORGANISM: Candida albicans

<400> SEQUENCE: 115

Met Thr Asp Leu Thr Pro Leu Phe Arg Gln Cys Val Asp Ile Val Gln
  1               5                  10                  15

Gln Glu Tyr Lys Thr Gln Pro Thr Thr Ala Lys Gln Pro Tyr Tyr Leu
             20                  25                  30

Asn Asp Thr Phe Ile Lys Glu Thr Thr Ala Phe Phe His Val Leu Thr
         35                  40                  45

Asn Leu Asn Gln Phe Ile Asn Glu Thr Lys Ser Ser Tyr Leu Ala Ile
     50                  55                  60

Asn Asp Asp Thr Lys Leu Ala Gly Ser Ile Asp Asp Lys Asn Lys Ile
 65                  70                  75                  80

Asp Glu Glu Phe Asn Tyr Lys Val Gln Gln Met Tyr Lys Arg Leu Asn
                 85                  90                  95

His Leu Glu Thr Tyr Glu Thr Lys Arg Gln Ser Leu Leu Pro Lys Thr
            100                 105                 110

Ser Gly Trp Phe Ser Phe Leu Asp Glu Ser Asn Asp Gln Asp Ile Tyr
            115                 120                 125

Phe Glu Thr Leu Ala Asn His Arg Met Gln Ile Leu Arg Phe Leu Met
            130                 135                 140

Glu Thr Leu Asn His Val Asn Lys Arg Phe Glu Asn Ile Gln Gln Lys
145                 150                 155                 160

Arg Leu Ala Arg Glu Arg Gln Leu Asn Leu Leu Asn Phe Gln Asn Phe
                165                 170                 175

Glu Asp Gly Glu Glu Leu Glu Asp Val Phe Pro Thr Leu Asp Gln Ile
            180                 185                 190

Gln Gln Val Pro Glu Leu Ser Gln Gln Ile Gln Gln Leu Glu Thr
            195                 200                 205

Glu Asn Gln Glu Phe Leu Asn Met Lys Thr Ser Gln Leu Lys Gln Val
            210                 215                 220

Glu Lys Val Gln Gln Ser Ile Leu Asp Ile Val Asn Ile Gln Asn Glu
225                 230                 235                 240

Leu Ala Phe Lys Leu Gln Asp Gln Gly Gln Gln Ile Glu Ser Leu Met
                245                 250                 255

Asp Ser His Ala Asp Val Gln Thr Glu Val Gln Met Gly Asn Arg Thr
            260                 265                 270

Leu Ser Gln Ala Thr Lys Lys Asn Lys Arg Gly Ala Asn Met Leu Val
            275                 280                 285

Met Leu Cys Ile Val Leu Gly Val Leu Leu Val Leu Val Asp Tyr Val
```

-continued

```
            290                 295                 300
Ser Phe
305

<210> SEQ ID NO 116
<211> LENGTH: 192
<212> TYPE: PRT
<213> ORGANISM: Candida albicans

<400> SEQUENCE: 116

Met Ser Gly Ile Lys Ile Ser Leu Lys Lys Asn Pro Lys Leu Lys
  1               5                  10                  15

Lys Leu Ile Val Asn Asn Ser Gln Gln Thr Asp Glu Ser Ser Glu Gln
             20                  25                  30

Gln Lys Lys Leu Ile Thr Ser Tyr Ser Thr Glu Asp Lys Thr Thr His
         35                  40                  45

Lys Asp Glu Thr Lys Pro Ile Ile Val Leu Lys Gln Pro Cys Lys Ser
     50                  55                  60

Met Leu Gln Lys Glu Ile Glu Ile Asp Glu Lys Pro Ile Leu Pro Tyr
 65                  70                  75                  80

Gly Val Thr Thr Phe Glu Lys Val Glu Thr Thr Lys Gln Ser Met Ile
                 85                  90                  95

Lys Lys Ile Glu Ser Glu Asp Ser Asp Asp Ser Ser Asp Asp Arg
            100                 105                 110

Lys Ile Pro Ile Asp Glu Phe Gly Ala Ala Phe Leu Arg Gly Leu Gly
        115                 120                 125

Trp Gln Glu Glu Glu Glu Lys Asn Lys Asp Asp Ser Lys Ser Thr Asn
    130                 135                 140

Thr Gln Asn Leu Ser His Arg Lys His Gly Ile Thr Leu Gly Ile Gly
145                 150                 155                 160

Ala Lys Pro Ile Asp Glu Glu Ile Ile Gln Asp Leu Asn Ser Thr Glu
                165                 170                 175

Lys Gly Ile Pro Ile Ile Lys Arg Arg Lys Leu Asn His Ile Asn Lys
            180                 185                 190

<210> SEQ ID NO 117
<211> LENGTH: 714
<212> TYPE: PRT
<213> ORGANISM: Candida albicans

<400> SEQUENCE: 117

Met Ala Lys Ala Ser Lys Gln Thr Lys Lys Phe Gln Asn Lys His Leu
  1               5                  10                  15

Lys His Thr Ile Glu Gln Arg Lys Lys Val Gln Ala Gln Asn Lys Lys
             20                  25                  30

Ile Ala Ser Arg Lys Lys Ser Gly Ser Ser Ser Gly Glu Ser Asn
         35                  40                  45

Ala Pro Lys Arg Ala Asp Gly Lys Ala Lys Glu Val Phe Glu Asp Met
     50                  55                  60

Ser Val Asp Asp Phe Gly Gly Gly Phe Glu Val Pro Lys Glu Lys
 65                  70                  75                  80

Asn Lys Asn Lys Asn Lys Gln Asp Thr Ile Glu Glu Asn Glu Glu Glu
                 85                  90                  95

Asp Ser Ser Ser Glu Glu Glu Asp Glu Glu Ala Met Lys Glu Asn Leu
            100                 105                 110

Lys Lys Leu Glu Ala Asp Asp Pro Glu Phe Tyr Lys Tyr Leu Lys Asp
```

```
            115                 120                 125
Asn Asp Asn Asp Leu Leu Asp Phe Glu Ala Val Asn Pro Leu Asp Ala
            130                 135                 140
Ile Ser Asp Asp Glu Gly Asp Glu Asp Asp Glu Glu Ile Glu Lys
145                 150                 155                 160
Glu Val Pro Ser Asp Asp Ser Glu Glu Pro Thr Leu Gly Lys
                    165                 170                 175
Val Lys Gly Ser Lys Ile Glu Ile Thr Lys Ser Leu Val Lys Lys Trp
                180                 185                 190
Asn Gln Gln Leu Asp Lys Pro Thr Pro Lys Ile Thr Arg Asn Ile Leu
            195                 200                 205
Ile Ala Phe Lys Ala Ala Val Asn Ile His Asn Ser Asp Ser Glu Asp
        210                 215                 220
Tyr Lys Phe Ser Ile Thr Asp Pro Lys Ala Phe Ser Glu Leu Met Leu
225                 230                 235                 240
Leu Val Leu Lys Lys Val Pro Ile Ser Val Gln Lys Leu Val Lys Tyr
                245                 250                 255
Lys Thr Asn Thr Gln Gly Val Arg Thr Ile Pro Gln Lys Asn Gln Tyr
            260                 265                 270
Ala Thr Gln Ile Ala Ala Ile Leu Lys Ser His Ala Gly Ser Phe Ile
        275                 280                 285
Thr Leu Leu Asn Asp Ile Thr Asn Thr Glu Thr Ala Ala Leu Ile Leu
    290                 295                 300
Ala Ser Ile Tyr Glu Val Phe Pro Phe Tyr Leu Ser His Arg Arg Leu
305                 310                 315                 320
Leu Lys Gln Ile Leu Thr Ala Val Val Asn Val Trp Ser Ser Ser Ser
                325                 330                 335
Asp Ile Asp Thr Gln Ile Ser Thr Phe Ala Phe Leu Asn Asn Val Ser
            340                 345                 350
Arg Glu Tyr Pro Lys Ser Val Leu Glu Thr Val Leu Lys Leu Thr Tyr
        355                 360                 365
Ser Ser Phe Leu Gln Asn Cys Arg Lys Thr Asn Val His Thr Met Ala
    370                 375                 380
Gln Ile Asn Phe Cys Lys Asn Ser Ala Val Glu Leu Phe Gly Ile Asn
385                 390                 395                 400
Glu Thr Leu Gly Tyr Gln Val Gly Phe Glu Tyr Val Arg Gln Leu Ala
                405                 410                 415
Ile His Leu Arg Asn Ser Ile Asn Ala Thr Ser Asn Ala Lys Glu Gly
            420                 425                 430
Tyr Lys Thr Ile Tyr Asn Trp Gln Tyr Cys His Ser Leu Asp Phe Trp
        435                 440                 445
Ser Arg Val Leu Ser Gln His Cys Asn Pro Glu Lys Glu Leu Gln Asn
    450                 455                 460
His Lys Ser Lys Glu Ser Pro Leu Arg Gln Leu Ile Tyr Pro Leu Val
465                 470                 475                 480
Gln Val Thr Leu Gly Ala Ile Arg Leu Ile Pro Thr Ala Gln Phe Phe
                485                 490                 495
Pro Leu Arg Phe Tyr Leu Ile Arg Ser Leu Ile Arg Leu Ser Gln Ser
            500                 505                 510
Thr Gly Val Phe Ile Pro Leu Phe Pro Leu Ile Ser Glu Ile Leu Ser
        515                 520                 525
Ser Thr Ala Met Thr Lys Ala Pro Lys Ala Ser Thr Leu Gln Ala Val
    530                 535                 540
```

```
Asp Phe Glu His Asn Ile Lys Val Asn Gln Ala Tyr Leu Gly Thr Arg
545                 550                 555                 560

Val Tyr Gln Asp Gly Leu Cys Glu Gln Phe Ile Glu Leu Ser Gly Glu
            565                 570                 575

Phe Phe Gly Leu Tyr Ala Lys Ser Ile Ala Phe Pro Glu Leu Val Thr
            580                 585                 590

Pro Ala Val Leu Ala Leu Arg Arg Phe Val Lys Lys Ser Lys Asn Val
            595                 600                 605

Lys Phe Asn Lys Gln Leu Gln Gln Leu Ile Glu Lys Leu Asn Ala Asn
        610                 615                 620

Ala Val Phe Ile Thr Gly Lys Arg Ser Asn Val Glu Tyr Gly Pro Ser
625                 630                 635                 640

Asn Lys Ala Glu Val Gln Gln Phe Leu Ser Asp Phe Glu Trp Glu Lys
            645                 650                 655

Thr Pro Leu Gly Gln Tyr Val Ser Val Gln Arg Gln Leu Lys Ala Glu
            660                 665                 670

Arg Leu Arg Ile Leu Lys Glu Ala Gln Glu Glu Ala Lys Ala Gln
        675                 680                 685

Ala Glu Gln Lys Lys Glu Glu Glu Asp Glu Gln Glu Asp Glu
690                 695                 700

Asp Ile Val Met Glu Glu Asp Asp Glu
705                 710

<210> SEQ ID NO 118
<211> LENGTH: 281
<212> TYPE: PRT
<213> ORGANISM: Candida albicans

<400> SEQUENCE: 118

Met Ser Arg Gly Lys Thr Ile Arg Pro Ser Tyr Tyr Asp Glu Glu Glu
1               5                   10                  15

Ser Ser Gln Asp Glu Leu Ser His Thr Leu Ser Lys Gly Arg Ser Asn
            20                  25                  30

Ile Gly Ser Gln Ser Asp Asp Glu Met Ser Lys Ile Ser Phe Gly
        35                  40                  45

Ala Leu Asn Arg Ala Gln Ser Lys Leu Asn Lys His Asn Gln Lys His
50                  55                  60

Lys Thr Gln Glu Asp Asn Tyr Lys Ser Ser Glu Glu Glu Phe Phe Asp
65                  70                  75                  80

Ser Gly Ser Asp Ser Asp Gly Pro Pro Glu Glu Thr Ser Ser Lys Asp
            85                  90                  95

Thr Lys Lys Lys Lys Asn Lys His Ala Pro Ser Glu Ser Ser Lys
            100                 105                 110

Arg Pro Val Ser Arg Ile Arg Asp Ile Pro Gly Leu Pro Ser Arg Lys
        115                 120                 125

Gln Gln Thr Leu His Thr Asp Ile Arg Phe Asp Ala Ala Tyr Gly Lys
        130                 135                 140

Ala Asp Leu Ala Lys Ala Arg Lys Asp Tyr Ala Phe Leu Asp Glu Tyr
145                 150                 155                 160

Arg Lys Gln Glu Ile Ala Asn Met Glu Ser Leu Leu Lys Asp Lys Lys
                165                 170                 175

Ser Arg Leu Asn Asp Asp Glu Arg Glu Glu Ile Lys Leu Gln Leu Gln
            180                 185                 190

Ser Leu Lys Ser Arg Met Asp Thr Leu Lys Asn Arg Asp Leu Glu Asn
```

-continued

```
            195                 200                 205
Asn Ile Leu Ser Asn Tyr Lys Lys Gln Gln Met Glu Ser Phe Lys Glu
    210                 215                 220

Gly Lys Val Asn Lys Pro Tyr Phe Leu Lys Arg Ser Asp Lys Arg Lys
225                 230                 235                 240

Ile Leu Gln Lys Ala Lys Phe Asp Ser Met Lys Pro Lys Gln Arg Glu
                245                 250                 255

Lys Ala Met Glu Arg Lys Arg Lys Lys Arg Leu Gly Lys Glu Phe Arg
                260                 265                 270

Gln Leu Glu Phe Lys Pro Thr Asn Arg
            275                 280

<210> SEQ ID NO 119
<211> LENGTH: 849
<212> TYPE: PRT
<213> ORGANISM: Candida albicans

<400> SEQUENCE: 119

Met Ser Asp Gln Leu Glu Lys Asp Ile Glu Glu Ser Ile Ala Asn Leu
  1               5                  10                  15

Asp Tyr Gln Gln Asn Gln Glu His His Glu Thr Glu Gln Asp Lys Asp
                 20                  25                  30

Lys Glu His Gln Asp Val Glu Lys Gln Ser Ser Glu Glu Thr Lys
             35                  40                  45

Gly Ile Glu His Val Thr Asp Ser Asn Thr Asp Asp Ile Gly Val Thr
         50                  55                  60

Lys Ser Gln Asp Thr Glu Glu Val Ile Glu Asn Ser Pro Val Asp Pro
 65                  70                  75                  80

Gln Leu Lys Glu Gln Gln Glu Ser Thr Thr Lys Met Ser Leu Ser Glu
                 85                  90                  95

Arg Asp Leu Val Asp Glu Ile Asp Glu Leu Phe Thr Asn Ser Thr Lys
                100                 105                 110

Thr Val Thr Glu Asn Asn Gln Pro Ser Glu Thr Asn Lys Arg Ala Tyr
            115                 120                 125

Glu Ser Val Glu Thr Pro Gln Glu Leu Thr Pro Asn Asp Lys Arg Gln
        130                 135                 140

Lys Leu Asp Ala Asn Thr Glu Thr Ser Val Pro Thr Glu Leu Glu Ser
145                 150                 155                 160

Val Asn Asn His Asn Glu Gln Ser Gln Pro Ile Glu Pro Thr Gln Glu
                165                 170                 175

Arg Gln Pro Ser Thr Thr Glu Thr Thr Tyr Ser Ile Ser Val Pro Val
            180                 185                 190

Ser Thr Thr Asn Glu Val Glu Arg Ala Ser Ser Ile Asn Glu Gln
        195                 200                 205

Glu Asp Leu Glu Met Ile Ala Lys Gln Tyr Gln Gln Ala Thr Asn Leu
    210                 215                 220

Glu Ile Glu Arg Ala Met Glu Gly His Gly Asp Gly Gln His Phe
225                 230                 235                 240

Ser Thr Gln Glu Asn Gly Gln Pro Gly Ser Ser Leu Ile Ser Ser
                245                 250                 255

Ile Val Pro Ser Asp Ser Glu Leu Leu Asn Thr Asn Gln Ala Tyr Ala
            260                 265                 270

Ala Tyr Thr Ser Leu Ser Ser Gln Leu Glu Gln His Thr Ser Ala Ser
        275                 280                 285
```

```
Ala Met Leu Ser Ser Ala Thr Leu Ser Ala Leu Pro Leu Ser Ile Ile
    290                 295                 300

Ala Pro Val Tyr Leu Pro Arg Ile Gln Leu Leu Ile Asn Thr Leu
305                 310                 315                 320

Pro Thr Leu Asp Asn Leu Ala Thr Gln Leu Leu Arg Thr Val Ala Thr
                325                 330                 335

Ser Pro Tyr Gln Lys Ile Ile Asp Leu Ala Ser Asn Pro Asp Thr Ser
            340                 345                 350

Ala Gly Ala Thr Tyr Arg Asp Leu Thr Ser Leu Phe Glu Phe Thr Lys
        355                 360                 365

Arg Leu Tyr Ser Glu Asp Asp Pro Phe Leu Thr Val Glu His Ile Ala
    370                 375                 380

Pro Gly Met Trp Lys Glu Gly Glu Thr Pro Ser Ile Phe Lys Pro
385                 390                 395                 400

Lys Gln Gln Ser Ile Glu Ser Thr Leu Arg Lys Val Asn Leu Ala Thr
                405                 410                 415

Phe Leu Ala Ala Thr Leu Gly Thr Met Glu Ile Gly Phe Phe Tyr Leu
            420                 425                 430

Asn Glu Ser Phe Leu Asp Val Phe Cys Pro Ser Asn Asn Leu Asp Pro
        435                 440                 445

Ser Asn Ala Leu Ser Asn Leu Gly Gly Tyr Gln Asn Gly Leu Gln Ser
    450                 455                 460

Thr Asp Ser Pro Val Gly Ala Arg Val Gly Lys Leu Leu Lys Pro Gln
465                 470                 475                 480

Ala Thr Leu Tyr Leu Asp Leu Lys Thr Gln Ala Tyr Ile Ser Ala Ile
                485                 490                 495

Glu Ala Gly Glu Arg Ser Lys Glu Glu Ile Leu Glu Asp Ile Leu Pro
            500                 505                 510

Asp Asp Leu His Val Tyr Leu Met Ser Arg Arg Asn Ala Lys Leu Leu
        515                 520                 525

Ser Pro Thr Glu Thr Asp Phe Val Trp Arg Cys Lys Gln Arg Lys Glu
    530                 535                 540

Ser Leu Leu Asn Tyr Thr Glu Glu Thr Pro Leu Ser Glu Gln Tyr Asp
545                 550                 555                 560

Trp Phe Thr Phe Leu Arg Asp Leu Phe Asp Tyr Val Ser Lys Asn Ile
                565                 570                 575

Ala Tyr Leu Ile Trp Gly Lys Met Gly Lys Thr Met Lys Asn Arg Arg
            580                 585                 590

Glu Asp Thr Pro His Thr Gln Glu Leu Leu Asp Asn Thr Thr Gly Ser
        595                 600                 605

Thr Gln Met Pro Asn Gln Leu Ser Ser Ser Gly Gln Ala Ser Ser
    610                 615                 620

Thr Pro Ser Val Val Asp Pro Asn Lys Met Leu Val Ser Glu Met Arg
625                 630                 635                 640

Glu Ala Asn Ile Ala Val Pro Lys Pro Ser Gln Arg Arg Ala Trp Ser
                645                 650                 655

Arg Glu Glu Lys Ala Leu Arg His Ala Leu Glu Leu Lys Gly Pro
            660                 665                 670

His Trp Ala Thr Ile Leu Glu Leu Phe Gln Gly Gly Lys Ile Ser
        675                 680                 685

Glu Ala Leu Lys Asn Arg Thr Gln Val Gln Leu Lys Asp Lys Ala Arg
    690                 695                 700

Asn Trp Lys Lys Phe Phe Leu Arg Ser Gly Leu Glu Ile Pro Ser Tyr
```

-continued

```
                705                 710                 715                 720
Leu Arg Gly Val Thr Gly Val Asp Asp Gly Lys Arg Lys Asp
                    725                 730                 735
Asn Val Thr Lys Lys Thr Ala Ala Pro Val Pro Asn Met Ser Glu
                    740                 745                 750
Gln Leu Gln Gln Gln Gln Arg Gln Gln Lys Gln Glu Lys Gln
                    755                 760                 765
Gln Gln Glu Glu Gln Ala Gln Ser Glu Lys Gln Leu Glu Gln
                    770                 775                 780
Gln Gln Glu Pro Gln Gln Glu Gln Gln Glu Gln Gln Thr Glu
785                 790                 795                 800
Lys Gln Gln Ala Glu Gln Glu Gln Pro Asp Gln Pro Gln Glu Gln
                    805                 810                 815
Gln Gln Glu Lys Glu Gln Pro Asp Gln Gln Pro Asp Gln Gln His
                    820                 825                 830
Pro Asp Arg Gln Gln Gln Glu Gln Ile Gln Gln Pro Glu Ser Ser Asp
                    835                 840                 845
Lys

<210> SEQ ID NO 120
<211> LENGTH: 1096
<212> TYPE: PRT
<213> ORGANISM: Candida albicans

<400> SEQUENCE: 120

Met Ser Gly Pro Val Thr Phe Glu Lys Thr Phe Arg Arg Asp Ala Leu
1               5                   10                  15
Ile Asp Ile Glu Lys Lys Tyr Gln Lys Val Trp Ala Glu Glu Lys Val
                20                  25                  30
Phe Glu Val Asp Ala Pro Thr Phe Glu Glu Cys Pro Ile Glu Asp Val
                35                  40                  45
Glu Gln Val Gln Glu Ala His Pro Lys Phe Phe Ala Thr Met Ala Tyr
            50                  55                  60
Pro Tyr Met Asn Gly Val Leu His Ala Gly His Ala Phe Thr Leu Ser
65                  70                  75                  80
Lys Val Glu Phe Ala Thr Gly Phe Gln Arg Met Asn Gly Lys Arg Ala
                85                  90                  95
Leu Phe Pro Leu Gly Phe His Cys Thr Gly Met Pro Ile Lys Ala Ala
                100                 105                 110
Ala Asp Lys Ile Lys Arg Glu Val Glu Leu Phe Gly Ser Asp Phe Ser
            115                 120                 125
Lys Ala Pro Ala Asp Asp Glu Ala Glu Ser Gln Gln Pro Ala
        130                 135                 140
Lys Thr Glu Thr Lys Arg Glu Asp Val Thr Lys Phe Ser Ser Lys
145                 150                 155                 160
Ser Lys Ala Ala Ala Lys Gln Gly Arg Ala Lys Phe Gln Tyr Glu Ile
                165                 170                 175
Met Met Gln Leu Gly Ile Pro Arg Glu Val Ala Lys Phe Ala Asn
                180                 185                 190
Thr Asp Tyr Trp Leu Glu Phe Pro Pro Leu Cys Gln Lys Asp Val
            195                 200                 205
Thr Ala Phe Gly Ala Arg Val Asp Trp Arg Arg Ser Met Ile Thr Thr
        210                 215                 220
Asp Ala Asn Pro Tyr Tyr Asp Ala Phe Val Arg Trp Gln Ile Asn Arg
```

-continued

```
            225                 230                 235                 240
Leu Arg Asp Val Gly Lys Ile Lys Phe Gly Glu Arg Tyr Thr Ile Tyr
                245                 250                 255

Ser Glu Lys Asp Gly Gln Ala Cys Leu Asp His Asp Arg Gln Ser Gly
                260                 265                 270

Glu Gly Val Gly Pro Gln Glu Tyr Val Gly Ile Lys Ile Arg Leu Thr
                275                 280                 285

Asp Val Ala Pro Gln Ala Gln Glu Leu Phe Lys Lys Glu Ser Leu Asp
                290                 295                 300

Val Lys Glu Asn Lys Val Tyr Leu Val Ala Ala Thr Leu Arg Pro Glu
305                 310                 315                 320

Thr Met Tyr Gly Gln Thr Cys Cys Phe Val Ser Pro Lys Ile Asp Tyr
                325                 330                 335

Gly Val Phe Asp Ala Gly Asn Gly Asp Tyr Phe Ile Thr Thr Glu Arg
                340                 345                 350

Ala Phe Lys Asn Met Ser Phe Gln Asn Leu Thr Pro Lys Arg Gly Tyr
                355                 360                 365

Tyr Lys Pro Leu Phe Thr Ile Asn Gly Lys Thr Leu Ile Gly Ser Arg
                370                 375                 380

Ile Asp Ala Pro Tyr Ala Val Asn Lys Asn Leu Arg Val Leu Pro Met
385                 390                 395                 400

Glu Thr Val Leu Ala Thr Lys Gly Thr Gly Val Val Thr Cys Val Pro
                405                 410                 415

Ser Asp Ser Pro Asp Asp Phe Val Thr Thr Arg Asp Leu Ala Asn Lys
                420                 425                 430

Pro Glu Tyr Tyr Gly Ile Glu Lys Asp Trp Val Gln Thr Asp Ile Val
                435                 440                 445

Pro Ile Val His Thr Glu Lys Tyr Gly Asp Lys Cys Ala Glu Phe Leu
450                 455                 460

Val Asn Asp Leu Lys Ile Gln Ser Pro Lys Asp Ser Val Gln Leu Ala
465                 470                 475                 480

Asn Ala Lys Glu Leu Ala Tyr Lys Glu Gly Phe Tyr Asn Gly Thr Met
                485                 490                 495

Leu Ile Gly Lys Tyr Lys Gly Asp Lys Val Glu Asp Ala Lys Pro Lys
                500                 505                 510

Val Lys Gln Asp Leu Ile Asp Glu Gly Leu Ala Phe Val Tyr Asn Glu
                515                 520                 525

Pro Glu Ser Gln Val Ile Ser Arg Ser Gly Asp Cys Cys Val Ser
                530                 535                 540

Leu Glu Asp Gln Trp Tyr Ile Asp Tyr Gly Glu Glu Ala Trp Leu Gly
545                 550                 555                 560

Glu Ala Leu Glu Cys Leu Lys Asn Met Glu Thr Tyr Ser Lys Glu Thr
                565                 570                 575

Arg His Gly Phe Glu Gly Val Leu Ala Trp Met Lys Asn Trp Ala Val
                580                 585                 590

Thr Arg Lys Phe Gly Leu Gly Thr Lys Leu Pro Trp Asp Pro Gln Tyr
                595                 600                 605

Leu Val Glu Ser Leu Ser Asp Ser Thr Val Tyr Met Ala Tyr Tyr Thr
                610                 615                 620

Ile Asp Arg Phe Leu His Ser Asp Tyr Tyr Gly Lys Lys Ala Gly Lys
625                 630                 635                 640

Phe Asp Ile Lys Pro Glu Gln Met Thr Asp Glu Val Phe Asp Tyr Ile
                645                 650                 655
```

-continued

```
Phe Thr Arg Arg Asp Asp Val Glu Thr Asp Ile Pro Lys Glu Gln Leu
            660                 665                 670

Lys Glu Met Arg Arg Glu Phe Glu Tyr Phe Tyr Pro Leu Asp Val Arg
            675                 680                 685

Val Ser Gly Lys Asp Leu Ile Pro Asn His Leu Thr Phe Phe Ile Tyr
            690                 695                 700

Thr His Val Ala Leu Phe Pro Lys Arg Phe Trp Pro Arg Gly Val Arg
705                 710                 715                 720

Ala Asn Gly His Leu Leu Leu Asn Asn Ala Lys Met Ser Lys Ser Thr
                725                 730                 735

Gly Asn Phe Met Thr Leu Glu Gln Ile Ile Glu Lys Phe Gly Ala Asp
            740                 745                 750

Ala Ser Arg Ile Ala Met Ala Asp Ala Gly Asp Thr Val Glu Asp Ala
            755                 760                 765

Asn Phe Asp Glu Ala Asn Ala Asn Ala Ala Ile Leu Arg Leu Thr Thr
            770                 775                 780

Leu Lys Asp Trp Cys Glu Glu Val Lys Asn Gln Asp Lys Leu Arg
785                 790                 795                 800

Ile Gly Asp Tyr Asp Ser Phe Phe Asp Ala Ala Phe Glu Asn Glu Met
            805                 810                 815

Asn Asp Leu Ile Glu Lys Thr Tyr Gln Gln Tyr Thr Leu Ser Asn Tyr
            820                 825                 830

Lys Gln Ala Leu Lys Ser Gly Leu Phe Asp Phe Gln Ile Ala Arg Asp
            835                 840                 845

Ile Tyr Arg Glu Ser Val Asn Thr Thr Gly Ile Gly Met His Lys Asp
            850                 855                 860

Leu Val Leu Lys Tyr Ile Glu Tyr Gln Ala Leu Met Leu Ala Pro Ile
865                 870                 875                 880

Ala Pro His Phe Ala Glu Tyr Leu Tyr Arg Glu Val Leu Gly Lys Asn
                885                 890                 895

Gly Ser Val Gln Leu Lys Phe Pro Arg Ala Ser Lys Pro Val Ser Lys
            900                 905                 910

Ala Ile Leu Asp Ala Ser Glu Tyr Val Arg Ser Leu Thr Arg Ser Ile
            915                 920                 925

Arg Glu Ala Glu Gly Gln Ala Leu Lys Lys Lys Gly Lys Ser Asp
            930                 935                 940

Val Asp Gly Ser Lys Pro Ile Ser Leu Thr Val Leu Val Ser Asn Thr
945                 950                 955                 960

Phe Pro Glu Trp Gln Asp Asn Tyr Ile Glu Leu Val Arg Glu Leu Phe
                965                 970                 975

Glu Gln Asn Lys Leu Asp Asp Asn Val Ile Arg Gln Lys Val Gly
            980                 985                 990

Lys Asp Met Lys Arg Gly Met Pro Tyr Ile His Gln Ile Lys Thr Arg
            995                1000                1005

Leu Ala Thr Glu Asp Ala Asp Thr Val Phe Asn Arg Lys Leu Thr Phe
        1010                1015                1020

Asp Glu Ile Asp Thr Leu Lys Asn Val Val Glu Ile Val Lys Asn Ala
1025                1030                1035                1040

Pro Tyr Ser Leu Lys Val Glu Lys Leu Glu Ile Leu Ser Phe Asn Asn
                1045                1050                1055

Gly Glu Thr Lys Gly Lys Asn Ile Ile Ser Gly Glu Asp Asn Ile Glu
            1060                1065                1070
```

```
Leu Asn Phe Lys Gly Lys Ile Met Glu Asn Ala Val Pro Gly Glu Pro
        1075                1080                1085

Gly Ile Phe Ile Lys Asn Val Glu
        1090                1095

<210> SEQ ID NO 121
<211> LENGTH: 520
<212> TYPE: PRT
<213> ORGANISM: Candida albicans

<400> SEQUENCE: 121

Met Asn Val Gly Ser Ile Leu Asn Asp Asp Pro Pro Ser Ser Gly Asn
 1               5                  10                  15

Ala Asn Gly Asn Asp Asp Asn Thr Lys Ile Ile Lys Ser Pro Thr Ala
            20                  25                  30

Tyr His Lys Pro Ser Val His Glu Arg His Ser Ile Thr Ser Met Leu
        35                  40                  45

Asn Asp Thr Pro Ser Asp Ser Thr Pro Thr Lys Lys Pro Glu Pro Thr
    50                  55                  60

Ile Ser Pro Glu Phe Arg Lys Pro Ser Ile Ser Ser Leu Thr Ser Pro
65                  70                  75                  80

Ser Val Ala His Lys Pro Pro Leu Pro Pro Ser Ser Ser Val
                85                  90                  95

Gly Ser Ser Glu His Ser Ser Ala Arg Ser Ser Pro Ala Ile Thr Lys
                100                 105                 110

Arg Asn Ser Ile Ala Asn Ile Ile Asp Ala Tyr Glu Glu Pro Ala Thr
            115                 120                 125

Lys Thr Glu Lys Lys Ala Glu Leu Asn Ser Pro Lys Ile Asn Gln Ser
130                 135                 140

Thr Pro Val Pro Lys Leu Glu Glu His Glu Asn Asp Thr Asn Lys Val
145                 150                 155                 160

Glu Lys Val Val Asp Ser Ala Pro Glu Pro Lys Pro Lys Lys Glu Pro
                165                 170                 175

Gln Pro Val Phe Asp Asp Gln Asp Asp Leu Thr Lys Ile Lys Lys
                180                 185                 190

Leu Lys Gln Ser Lys Lys Pro Arg Arg Tyr Glu Thr Pro Pro Ile Trp
            195                 200                 205

Ala Gln Arg Trp Val Pro Pro Asn Arg Gln Lys Glu Glu Thr Asn Val
210                 215                 220

Asp Asp Gly Asn Glu Ala Ile Thr Arg Leu Ser Glu Lys Pro Val Phe
225                 230                 235                 240

Asp Tyr Thr Thr Thr Arg Ser Val Asp Leu Glu Cys Ser Ile Thr Gly
                245                 250                 255

Met Ile Pro Pro Ser Ser Ile Thr Arg Lys Ile Ala Glu Trp Val Tyr
                260                 265                 270

Ala Asn Phe Ser Asn Val Glu Glu Lys Ser Lys Arg Asn Val Glu Leu
            275                 280                 285

Glu Leu Lys Phe Gly Lys Ile Ile Asp Lys Arg Ser Gly Asn Arg Ile
        290                 295                 300

Asp Leu Asn Val Val Thr Glu Cys Ile Phe Thr Asp His Ser Ser Val
305                 310                 315                 320

Phe Phe Asp Met Gln Val Glu Val Ala Trp Lys Glu Ile Thr Lys
                325                 330                 335

Phe Leu Asp Glu Leu Glu Lys Ser Phe Gln Gly Lys Lys Gly Arg
            340                 345                 350
```

-continued

```
Lys Phe Lys Thr Leu Glu Ser Asp Asn Thr Asp Ser Phe Tyr Gln Leu
            355                 360                 365

Gly Arg Lys Gly Glu His Pro Lys Arg Ile Arg Val Thr Lys Asp Asn
        370                 375                 380

Leu Leu Ser Pro Pro Arg Leu Val Ala Ile Gln Lys Glu Arg Val Ala
385                 390                 395                 400

Asp Leu Tyr Ile His Asn Pro Gly Ser Leu Phe Asp Leu Arg Leu Ser
                405                 410                 415

Met Ser Leu Glu Ile Pro Val Pro Gln Gly Asn Ile Glu Ser Ile Ile
            420                 425                 430

Thr Lys Asn Lys Pro Glu Met Val Arg Glu Lys Lys Arg Ile Ser Tyr
        435                 440                 445

Thr His Pro Pro Thr Ile Thr Lys Phe Asp Leu Thr Arg Val Ile Gly
    450                 455                 460

Asn Lys Thr Glu Asp Lys Tyr Glu Val Glu Leu Glu Ala Gly Val Met
465                 470                 475                 480

Glu Ile Phe Ala Ala Ile Asp Lys Ile Gln Lys Gly Val Asp Asn Leu
                485                 490                 495

Arg Leu Glu Glu Leu Ile Glu Val Phe Leu Asn Asn Ala Arg Thr Leu
            500                 505                 510

Asn Asn Arg Leu Asn Lys Ile Cys
        515                 520

<210> SEQ ID NO 122
<211> LENGTH: 198
<212> TYPE: PRT
<213> ORGANISM: Candida albicans

<400> SEQUENCE: 122

Met Val Asn Gly Pro Ala Glu Leu Arg Arg Lys Leu Val Ile Val Gly
  1               5                  10                  15

Asp Gly Ala Cys Gly Lys Thr Cys Leu Leu Ile Val Phe Ser Lys Gly
             20                  25                  30

Thr Phe Pro Glu Val Tyr Val Pro Thr Val Phe Glu Asn Tyr Val Ala
         35                  40                  45

Asp Val Glu Val Asp Gly Arg Lys Val Glu Leu Ala Leu Trp Asp Thr
 50                  55                  60

Ala Gly Gln Glu Asp Tyr Asp Arg Leu Arg Pro Leu Ser Tyr Pro Asp
 65                  70                  75                  80

Ser Asn Val Ile Leu Ile Cys Phe Ser Val Asp Ser Pro Asp Ser Leu
                 85                  90                  95

Asp Asn Val Leu Glu Lys Trp Ile Ser Glu Val Leu His Phe Cys Gln
            100                 105                 110

Gly Val Pro Ile Ile Leu Val Gly Cys Lys Ser Asp Leu Arg Asp Asp
        115                 120                 125

Pro His Thr Ile Glu Ala Leu Arg Gln Gln Gln Gln Pro Val Ser
    130                 135                 140

Thr Ser Glu Gly Gln Gln Val Ala Gln Arg Ile Gly Ala Ala Asp Tyr
145                 150                 155                 160

Leu Glu Cys Ser Ala Lys Thr Gly Arg Gly Val Arg Glu Val Phe Glu
                165                 170                 175

Ala Ala Thr Arg Ala Ser Leu Arg Val Lys Glu Lys Lys Glu Lys Lys
            180                 185                 190

Lys Lys Cys Val Val Leu
```

-continued

195

<210> SEQ ID NO 123
<211> LENGTH: 708
<212> TYPE: PRT
<213> ORGANISM: Candida albicans

<400> SEQUENCE: 123

Met Glu Val Thr Ser Leu Pro Ile Lys Leu Gln Pro Ser Asn Ile Arg
 1               5                  10                  15

Pro Ile Ala Phe Arg Ile Leu Ser Lys Lys His Gly Leu Asn Ile Asn
            20                  25                  30

Thr Asp Ala Leu Ala Ile Leu Thr Glu Thr Ile Gly Tyr Lys Phe Gly
        35                  40                  45

Thr Asp Trp Lys Ser Val Arg Ser Gln Gln Phe Leu Glu Glu Val Ala
    50                  55                  60

Lys Val Trp Lys Ile Glu Asp Arg Gly Leu Phe Ile Asp Gly Asp Gly
65                  70                  75                  80

Leu Lys Gln Val Leu Lys Asp Met Asn Ser Lys Ser Ser Asn Asp Thr
                85                  90                  95

Lys Arg Ala His Arg Thr Asp Thr Leu Val Asp Ile Thr Asn Asp Gly
            100                 105                 110

Asn Gln Asn His Thr His Ser His Gln Asp Lys Gln Ile Ser Phe Glu
        115                 120                 125

Asp Lys Asn Met Glu His Glu Glu Arg Asp Asp Val Pro Ile Asn Trp
    130                 135                 140

Gln Asp Tyr Phe Lys Val Val Ser Pro Asn Asn Gln Pro Thr Ser Ile
145                 150                 155                 160

Phe Asp Lys Thr Arg Lys Gln Phe Asp Ile Val Phe Lys Asn Asn Asp
                165                 170                 175

Asp Lys Asp Lys Lys Ala Glu Arg Gly Gly Lys Leu Glu Ser Ile Val
            180                 185                 190

Ala Glu Leu Val Lys Asn Leu Pro Ala Ser Ile Glu Ser Phe Asn Asn
        195                 200                 205

Arg Tyr Tyr Leu Leu Ser Asp Arg Leu Ser Arg Asn Glu Asn Phe Gln
    210                 215                 220

Lys Lys Ser Leu Ile Ser Leu Ser Ala Leu Asn Ser Phe Lys Glu Gly
225                 230                 235                 240

Lys Thr Asp Ser Ile Thr Gly His Glu Ile Ser Leu Ile Lys Asn Met
                245                 250                 255

Leu Gly Arg Asp Gly Gln Lys Phe Leu Ile Phe Gly Leu Leu Ser Lys
            260                 265                 270

Asn Ala Asn Asp Glu Tyr Thr Leu Glu Asp Glu Thr Asp His Ile Glu
        275                 280                 285

Leu Asn Leu Ser Gln Ala Phe Lys Ser Gln Gly Leu Phe Tyr Cys Pro
    290                 295                 300

Gly Met Phe Leu Leu Val Glu Gly Ile Tyr Ser Ala Ser Gly Gly Asn
305                 310                 315                 320

Ser Asn Gln Asp His Gly Tyr Ile Gly Gly Cys Phe Tyr Val Ser Asn
                325                 330                 335

Ile Gly His Pro Pro Ser Glu Arg Arg Glu Thr Ser Leu Asp Val Tyr
            340                 345                 350

Gly Asn Leu Asp Phe Leu Gly Met His Arg Gln Ile Ala Pro Val Thr
        355                 360                 365

-continued

```
Gly Glu Lys Ile Thr Lys Ile Ser Lys Lys Phe Lys Lys Arg Leu Val
    370                 375                 380

Leu Ile Glu Lys Thr Leu Tyr Asn His Lys Leu Ile Phe Val Gly Thr
385                 390                 395                 400

Asp Leu Tyr Leu Asp Asp Phe Lys Val Leu Asp Gly Leu Arg Lys Phe
                405                 410                 415

Phe Gln Lys Leu Glu Asn Ser Ile Ile Glu Ser Ile Glu Asp Glu Glu
            420                 425                 430

Gly Gln Met Ala Glu Gly Thr Asn Ile Pro Leu Ala Leu Val Phe Thr
        435                 440                 445

Gly Ser Phe Val Ser Lys Pro Leu Ser Val Thr Asn Ser Ser Val Thr
    450                 455                 460

Asn Ile Thr Asn Ser Glu Ser Tyr Lys Ser Asn Phe Asp Asn Phe Thr
465                 470                 475                 480

Thr Ile Val Ser Lys Tyr Pro Asn Ile Val Ser Arg Cys Lys Ile Ile
                485                 490                 495

Leu Ile Pro Gly Lys Asn Asp Pro Trp Gln Ser Thr Tyr Ser Leu Gly
            500                 505                 510

Ser Ser Ser Leu Asn Tyr Phe Pro Gln Ser Ser Ile Pro Lys Val Phe
        515                 520                 525

Ile Asn Arg Leu Glu Lys Leu Leu Pro Lys Gly Asn Leu Val Val Ser
    530                 535                 540

Trp Asn Pro Thr Arg Ile Asn Tyr Leu Ser Gln Glu Leu Val Val Phe
545                 550                 555                 560

Lys Asp Glu Leu Met Thr Lys Leu Lys Arg Asn Asp Ile Ile Phe Pro
                565                 570                 575

Arg Asp Ile Gln Glu Gln Glu Leu Ile Ala Gln Asp Asp Gln Arg
            580                 585                 590

Thr Asn Glu Glu Arg Ile Asn Asn Leu Ile Gln Asn Lys Asn Thr His
        595                 600                 605

Leu Pro Ser Lys Ile Lys Gln Ala Arg Lys Leu Val Lys Thr Ile Leu
    610                 615                 620

Asp Gln Gly Asn Leu Gln Pro Phe Leu Lys Asn Leu Lys Leu Ile Asn
625                 630                 635                 640

Leu Ala Tyr Asp Tyr Ser Leu Arg Ile Glu Pro Leu Pro Ser Val Ile
                645                 650                 655

Ile Leu Asn Asp Ser Ser Phe Asp Asn Phe Glu Val Thr Tyr Asn Gly
            660                 665                 670

Cys Lys Val Val Asn Ile Thr Ser Val Val Ser Leu Asn Asn Arg Lys
        675                 680                 685

Phe Asn Tyr Val Glu Tyr Pro Gly Thr Lys Arg Phe Glu Phe Lys
    690                 695                 700

Asp Leu Tyr Phe
705

<210> SEQ ID NO 124
<211> LENGTH: 86
<212> TYPE: DNA
<213> ORGANISM: Artificial Sequence
<220> FEATURE:
<223> OTHER INFORMATION: DNA primer

<400> SEQUENCE: 124
ctctctttta tattctcgtc aataaaatcg ctcactcgaa aaccctaaaa aaaagcagac    60
aaccccgctc tagaactagt ggatcc                                        86
```

<210> SEQ ID NO 125
<211> LENGTH: 83
<212> TYPE: DNA
<213> ORGANISM: Artificial Sequence
<220> FEATURE:
<223> OTHER INFORMATION: DNA primer

<400> SEQUENCE: 125
agaaaaaaaa gtaacccaca atgagatgaa ctaaaccaac atcaatcaac cattacacac     60
caatccgctc tagaactagt gga     83

<210> SEQ ID NO 126
<211> LENGTH: 83
<212> TYPE: DNA
<213> ORGANISM: Artificial Sequence
<220> FEATURE:
<223> OTHER INFORMATION: DNA primer

<400> SEQUENCE: 126
ttctattttt cagattgact atcctttaac cttctaatca tttacatctt caagaactaa     60
gttcccgctc tagaactagt gga     83

<210> SEQ ID NO 127
<211> LENGTH: 83
<212> TYPE: DNA
<213> ORGANISM: Artificial Sequence
<220> FEATURE:
<223> OTHER INFORMATION: DNA primer

<400> SEQUENCE: 127
ctcttcctca tctataaatc tctaatcatc tcgagtagat actgttaatc tataacttca     60
ctatacgctc tagaactagt gga     83

<210> SEQ ID NO 128
<211> LENGTH: 86
<212> TYPE: DNA
<213> ORGANISM: Artificial Sequence
<220> FEATURE:
<223> OTHER INFORMATION: DNA primer

<400> SEQUENCE: 128
aaaatataca ttcaaaatcc ctaaaatcac ttcatacttc aacaacaaca ataataaata     60
ccattcgctc tagaactagt ggatcc     86

<210> SEQ ID NO 129
<211> LENGTH: 86
<212> TYPE: DNA
<213> ORGANISM: Artificial Sequence
<220> FEATURE:
<223> OTHER INFORMATION: DNA primer

<400> SEQUENCE: 129
ttttcttata atgagatgag atttgatttg atacatcgaa ttctacaata attatacaac     60
caactcgctc tagaactagt ggatcc     86

<210> SEQ ID NO 130
<211> LENGTH: 76
<212> TYPE: DNA
<213> ORGANISM: Artificial Sequence
<220> FEATURE:
<223> OTHER INFORMATION: DNA primer -continued

```
<400> SEQUENCE: 130
ttgaaacagg acctaagtat aataaagttg attaactaat caccatcaaa caggacgctc      60
tagaactagt ggatcc                                                     76

<210> SEQ ID NO 131
<211> LENGTH: 76
<212> TYPE: DNA
<213> ORGANISM: Artificial Sequence
<220> FEATURE:
<223> OTHER INFORMATION: DNA primer

<400> SEQUENCE: 131
cgtcaaaaaa aaaaaatttt tctaggttag acgattgagt tgtgattacg taattcgctc      60
tagaactagt ggatcc                                                     76

<210> SEQ ID NO 132
<211> LENGTH: 86
<212> TYPE: DNA
<213> ORGANISM: Artificial Sequence
<220> FEATURE:
<223> OTHER INFORMATION: DNA primer

<400> SEQUENCE: 132
caccaaaaaa tttttgatat tgatcaatca cttctttctt cattgtgtaa aaactactag      60
ccgaccgctc tagaactagt ggatcc                                          86

<210> SEQ ID NO 133
<211> LENGTH: 76
<212> TYPE: DNA
<213> ORGANISM: Artificial Sequence
<220> FEATURE:
<223> OTHER INFORMATION: DNA primer

<400> SEQUENCE: 133
taacacccat agcaatacac caataccgtt gattttgaac taaacttatt ccatacgctc      60
tagaactagt ggatcc                                                     76

<210> SEQ ID NO 134
<211> LENGTH: 86
<212> TYPE: DNA
<213> ORGANISM: Artificial Sequence
<220> FEATURE:
<223> OTHER INFORMATION: DNA primer

<400> SEQUENCE: 134
aaaaaaatgt aggtgttcac caagtgttaa cacatactac ttttccattc tctacagctt      60
ctaaacgctc tagaactagt ggatcc                                          86

<210> SEQ ID NO 135
<211> LENGTH: 86
<212> TYPE: DNA
<213> ORGANISM: Artificial Sequence
<220> FEATURE:
<223> OTHER INFORMATION: DNA primer

<400> SEQUENCE: 135
cttaaacttc ctcctcacat tcagctcttc ttccactttt cttactccac acatacacac      60
ctattcgctc tagaactagt ggatcc                                          86

<210> SEQ ID NO 136
<211> LENGTH: 86
```

<212> TYPE: DNA
<213> ORGANISM: Artificial Sequence
<220> FEATURE:
<223> OTHER INFORMATION: DNA primer

<400> SEQUENCE: 136 tggtatttttt cttaagaaag gataattagc atagtaaagg tcattctact atactcatat    60
aaaatcgctc tagaactagt ggatcc    86

<210> SEQ ID NO 137
<211> LENGTH: 83
<212> TYPE: DNA
<213> ORGANISM: Artificial Sequence
<220> FEATURE:
<223> OTHER INFORMATION: DNA primer

<400> SEQUENCE: 137
gcttgtattg caaaggaagc tttataaatt acttttgata atctaatatc ctagagttta    60
caacgcgctc tagaactagt gga    83

<210> SEQ ID NO 138
<211> LENGTH: 83
<212> TYPE: DNA
<213> ORGANISM: Artificial Sequence
<220> FEATURE:
<223> OTHER INFORMATION: DNA primer

<400> SEQUENCE: 138
cgttatactt tccatattac ttgtcttctt tttattatat ataagtttt cttttcaaga    60 agatccgctc tagaactagt gga    83

<210> SEQ ID NO 139
<211> LENGTH: 86
<212> TYPE: DNA
<213> ORGANISM: Artificial Sequence
<220> FEATURE:
<223> OTHER INFORMATION: DNA primer

<400> SEQUENCE: 139
caaaggtaat ttcattacta ttgtcgtttt ttaggttttc acttacaatt aatggtctat    60
tcttacgctc tagaactagt ggatcc    86

<210> SEQ ID NO 140
<211> LENGTH: 83
<212> TYPE: DNA
<213> ORGANISM: Artificial Sequence
<220> FEATURE:
<223> OTHER INFORMATION: DNA primer

<400> SEQUENCE: 140
aaaatagagc aacaaaaaag caacacccac agtatagata tatagttacc ctcaacaata    60
gacaacgctc tagaactagt gga    83

<210> SEQ ID NO 141
<211> LENGTH: 86
<212> TYPE: DNA
<213> ORGANISM: Artificial Sequence
<220> FEATURE:
<223> OTHER INFORMATION: DNA primer

<400> SEQUENCE: 141 tactttttt tttttcaaat ttttcaatta cgacatcgag tattcacccc aaggtctcag    60

```
tacaacgctc tagaactagt ggatcc                                            86

<210> SEQ ID NO 142
<211> LENGTH: 76
<212> TYPE: DNA
<213> ORGANISM: Artificial Sequence
<220> FEATURE:
<223> OTHER INFORMATION: DNA primer

<400> SEQUENCE: 142
ctaaactaat cacacaacag cttcaacttt aatcttacca atcaactgta caaatcgctc       60
tagaactagt ggatcc                                                      76

<210> SEQ ID NO 143
<211> LENGTH: 86
<212> TYPE: DNA
<213> ORGANISM: Artificial Sequence
<220> FEATURE:
<223> OTHER INFORMATION: DNA primer

<400> SEQUENCE: 143
ctttcttaaa gaagcttctc ttttttttat tgtcatttac cataacacac cccttcctaa      60
ggatacgctc tagaactagt ggatcc                                            86

<210> SEQ ID NO 144
<211> LENGTH: 86
<212> TYPE: DNA
<213> ORGANISM: Artificial Sequence
<220> FEATURE:
<223> OTHER INFORMATION: DNA primer

<400> SEQUENCE: 144
cttttaactt tttcacatat tataaaagat tagacagttt ctcaagcata tatccctcac      60
agaaccgctc tagaactagt ggatcc                                            86

<210> SEQ ID NO 145
<211> LENGTH: 83
<212> TYPE: DNA
<213> ORGANISM: Artificial Sequence
<220> FEATURE:
<223> OTHER INFORMATION: DNA primer

<400> SEQUENCE: 145
tgaaattttt ttttttcac ataaaaaagt atctcctaca tctttccgta ctacactcat       60
cagcccgctc tagaactagt gga                                               83

<210> SEQ ID NO 146
<211> LENGTH: 86
<212> TYPE: DNA
<213> ORGANISM: Artificial Sequence
<220> FEATURE:
<223> OTHER INFORMATION: DNA primer

<400> SEQUENCE: 146
ttttaactat tcattttttt agtacataat tacaatttat tgtgagtccc cattttacta     60
aggtccgctc tagaactagt ggatcc                                            86

<210> SEQ ID NO 147
<211> LENGTH: 86
<212> TYPE: DNA
<213> ORGANISM: Artificial Sequence
<220> FEATURE:
<223> OTHER INFORMATION: DNA primer
```

<400> SEQUENCE: 147
ccatccatat atatctacca ctatcaagat ccctatatct tgttgataca cacttttttgg    60 ttaaacgctc tagaactagt ggatcc    86

<210> SEQ ID NO 148
<211> LENGTH: 76
<212> TYPE: DNA
<213> ORGANISM: Artificial Sequence
<220> FEATURE:
<223> OTHER INFORMATION: DNA primer

<400> SEQUENCE: 148
tttttatcat taaaatcata tccctcccct ctcaaaaaca actatatatc taatccgctc    60
tagaactagt ggatcc    76

<210> SEQ ID NO 149
<211> LENGTH: 86
<212> TYPE: DNA
<213> ORGANISM: Artificial Sequence
<220> FEATURE:
<223> OTHER INFORMATION: DNA primer

<400> SEQUENCE: 149
atttagcaaa cataatccgt gttttacata tattattcac ccaatatcat aacaaaaaca    60
aactgcgctc tagaactagt ggatcc    86

<210> SEQ ID NO 150
<211> LENGTH: 86
<212> TYPE: DNA
<213> ORGANISM: Artificial Sequence
<220> FEATURE:
<223> OTHER INFORMATION: DNA primer

<400> SEQUENCE: 150
ggaaatcatt aataaaacat gcttctaggg ttgttctaaa gtgaaaaacc acgacaaaca    60
cgtcgcgctc tagaactagt ggatcc    86

<210> SEQ ID NO 151
<211> LENGTH: 76
<212> TYPE: DNA
<213> ORGANISM: Artificial Sequence
<220> FEATURE:
<223> OTHER INFORMATION: DNA primer

<400> SEQUENCE: 151
ttggaagaac tcctttcctt ttctatagtc attactcgaa gcgaaataca taattcgctc    60
tagaactagt ggatcc    76

<210> SEQ ID NO 152
<211> LENGTH: 86
<212> TYPE: DNA
<213> ORGANISM: Artificial Sequence
<220> FEATURE:
<223> OTHER INFORMATION: DNA primer

<400> SEQUENCE: 152
gaaaaaaaaa acttttttgac agtacgtcta acagattatt gtgatgaact aatcccacat    60
atttccgctc tagaactagt ggatcc    86

<210> SEQ ID NO 153

<211> LENGTH: 76
<212> TYPE: DNA
<213> ORGANISM: Artificial Sequence
<220> FEATURE:
<223> OTHER INFORMATION: DNA primer

<400> SEQUENCE: 153
ttatttatta aattaatcct taataattca agcatttcta gacacacaca aatcacgctc    60
tagaactagt ggatcc    76

<210> SEQ ID NO 154
<211> LENGTH: 83
<212> TYPE: DNA
<213> ORGANISM: Artificial Sequence
<220> FEATURE:
<223> OTHER INFORMATION: DNA primer

<400> SEQUENCE: 154
aaatttcaaa attctctgac acccactctt tatcttatta aactcaatac actcccatat    60
cacaacgctc tagaactagt gga    83

<210> SEQ ID NO 155
<211> LENGTH: 76
<212> TYPE: DNA
<213> ORGANISM: Artificial Sequence
<220> FEATURE:
<223> OTHER INFORMATION: DNA primer

<400> SEQUENCE: 155
aaaataaatc actctaatca tttcattcat caatacccac cacaaaacct ttcaacgctc    60
tagaactagt ggatcc    76

<210> SEQ ID NO 156
<211> LENGTH: 83
<212> TYPE: DNA
<213> ORGANISM: Artificial Sequence
<220> FEATURE:
<223> OTHER INFORMATION: DNA primer

<400> SEQUENCE: 156
agaaattgaa acaatcggaa aacaacaata tcaaactgat gcccaataac actgtatgta    60
cctagcgctc tagaactagt gga    83

<210> SEQ ID NO 157
<211> LENGTH: 83
<212> TYPE: DNA
<213> ORGANISM: Artificial Sequence
<220> FEATURE:
<223> OTHER INFORMATION: DNA primer

<400> SEQUENCE: 157 aattttcaa tattcaaaaa ctacacttat tcattaatca atcatcaacc attaaactat    60
ttgtccgctc tagaactagt gga    83

<210> SEQ ID NO 158
<211> LENGTH: 83
<212> TYPE: DNA
<213> ORGANISM: Artificial Sequence
<220> FEATURE:
<223> OTHER INFORMATION: DNA primer

<400> SEQUENCE: 158
aatttgaaat tttacaacaa acaacaacat tcaacgttca ccaccaccca ccactagtaa    60

```
acacacgctc tagaactagt gga                                           83

<210> SEQ ID NO 159
<211> LENGTH: 83
<212> TYPE: DNA
<213> ORGANISM: Artificial Sequence
<220> FEATURE:
<223> OTHER INFORMATION: DNA primer

<400> SEQUENCE: 159
ccccccttct tttttttaa atattaaaaa ccaacaccca actgatatac taacttatct    60
tttttcgctc tagaactagt gga                                           83

<210> SEQ ID NO 160
<211> LENGTH: 83
<212> TYPE: DNA
<213> ORGANISM: Artificial Sequence
<220> FEATURE:
<223> OTHER INFORMATION: DNA primer

<400> SEQUENCE: 160 cttttttct ttatcaacaa taagaaagaa ttactcaatt ccgtaatatt tattctacat    60
taacacgctc tagaactagt gga                                           83

<210> SEQ ID NO 161
<211> LENGTH: 86
<212> TYPE: DNA
<213> ORGANISM: Artificial Sequence
<220> FEATURE:
<223> OTHER INFORMATION: DNA primer

<400> SEQUENCE: 161
caacaaacga tctatttaaa ggatactcta agaaatcgag gggtgttcaa ccatagctca    60
taatccgctc tagaactagt ggatcc                                        86

<210> SEQ ID NO 162
<211> LENGTH: 83
<212> TYPE: DNA
<213> ORGANISM: Artificial Sequence
<220> FEATURE:
<223> OTHER INFORMATION: DNA primer

<400> SEQUENCE: 162
ttcttctacc cttttttca atagaaacaa ctacacatat ttttatcgat aatataattc    60
aaaaacgctc tagaactagt gga                                           83

<210> SEQ ID NO 163
<211> LENGTH: 76
<212> TYPE: DNA
<213> ORGANISM: Artificial Sequence
<220> FEATURE:
<223> OTHER INFORMATION: DNA primer

<400> SEQUENCE: 163
acttgaaagg taacttgaga ctaaccaatc atagtaacga tacattcgag tcaatcgctc    60
tagaactagt ggatcc                                                   76

<210> SEQ ID NO 164
<211> LENGTH: 86
<212> TYPE: DNA
<213> ORGANISM: Artificial Sequence
<220> FEATURE:
```

<223> OTHER INFORMATION: DNA primer

<400> SEQUENCE: 164
tggaaatgga tgcaaatgag attttctact attcttttac catgtttctt tgttatggat    60
cgtgccgctc tagaactagt ggatcc    86

<210> SEQ ID NO 165
<211> LENGTH: 86
<212> TYPE: DNA
<213> ORGANISM: Artificial Sequence
<220> FEATURE:
<223> OTHER INFORMATION: DNA primer

<400> SEQUENCE: 165
agattccaac ttcagaatat tcattcagat ctgaacattt cttttctcc gatcatcaat    60 tggcacgctc tagaactagt ggatcc    86

<210> SEQ ID NO 166
<211> LENGTH: 76
<212> TYPE: DNA
<213> ORGANISM: Artificial Sequence
<220> FEATURE:
<223> OTHER INFORMATION: DNA primer

<400> SEQUENCE: 166
taaatataaa aatccattat tctactgttt ttcagctttg cattgctatt tactccgctc    60
tagaactagt ggatcc    76

<210> SEQ ID NO 167
<211> LENGTH: 83
<212> TYPE: DNA
<213> ORGANISM: Artificial Sequence
<220> FEATURE:
<223> OTHER INFORMATION: DNA primer

<400> SEQUENCE: 167
acttcaactt gcttttcttt tttaaatcct cagttgtaca ttaatcagat tgttcacatt    60
aaatccgctc tagaactagt gga    83

<210> SEQ ID NO 168
<211> LENGTH: 76
<212> TYPE: DNA
<213> ORGANISM: Artificial Sequence
<220> FEATURE:
<223> OTHER INFORMATION: DNA primer

<400> SEQUENCE: 168
acaacaacaa caacaacatc aacttctaaa gcattatact actctttcct tcacgcgctc    60
tagaactagt ggatcc    76

<210> SEQ ID NO 169
<211> LENGTH: 86
<212> TYPE: DNA
<213> ORGANISM: Artificial Sequence
<220> FEATURE:
<223> OTHER INFORMATION: DNA primer

<400> SEQUENCE: 169
cctcaaaaca gtataacctt tgcctccttt ctatcctctt tataattcat taaataatta    60
caccccgctc tagaactagt ggatcc    86

<210> SEQ ID NO 170
<211> LENGTH: 76
<212> TYPE: DNA
<213> ORGANISM: Artificial Sequence
<220> FEATURE:
<223> OTHER INFORMATION: DNA primer

<400> SEQUENCE: 170
tgaacaaatt cccacctcca atacagcatt tttcttcact cttgatatac caattcgctc    60
tagaactagt ggatcc                                                   76

<210> SEQ ID NO 171
<211> LENGTH: 83
<212> TYPE: DNA
<213> ORGANISM: Artificial Sequence
<220> FEATURE:
<223> OTHER INFORMATION: DNA primer

<400> SEQUENCE: 171
ccacccattc attctttctt tttgaaggtg cttgcagcta agtttaataa cagacgtatt    60
ctaatcgctc tagaactagt gga                                           83

<210> SEQ ID NO 172
<211> LENGTH: 76
<212> TYPE: DNA
<213> ORGANISM: Artificial Sequence
<220> FEATURE:
<223> OTHER INFORMATION: DNA primer

<400> SEQUENCE: 172
atcacaaaca ctttcctaaa ttaatccagc gttaattatc tcaatataat caactcgctc    60
tagaactagt ggatcc                                                   76

<210> SEQ ID NO 173
<211> LENGTH: 86
<212> TYPE: DNA
<213> ORGANISM: Artificial Sequence
<220> FEATURE:
<223> OTHER INFORMATION: DNA primer

<400> SEQUENCE: 173
tcaagtcggc gattaacccg acaataaata aacaatttcg aaaagcattc cattattcta    60
tcactcgctc tagaactagt ggatcc                                        86

<210> SEQ ID NO 174
<211> LENGTH: 76
<212> TYPE: DNA
<213> ORGANISM: Artificial Sequence
<220> FEATURE:
<223> OTHER INFORMATION: DNA primer

<400> SEQUENCE: 174
ttccttactt tgaacaactt ccctctcctc ctcgtctccc ccctcaccaa cagcccgctc    60
tagaactagt ggatcc                                                   76

<210> SEQ ID NO 175
<211> LENGTH: 86
<212> TYPE: DNA
<213> ORGANISM: Artificial Sequence
<220> FEATURE:
<223> OTHER INFORMATION: DNA primer

<400> SEQUENCE: 175

```
tcacataaaa ccacattaac attctttatt cttcatttca taactaatca cccacatatt    60
ccatccgctc tagaactagt ggatcc                                         86

<210> SEQ ID NO 176
<211> LENGTH: 76
<212> TYPE: DNA
<213> ORGANISM: Artificial Sequence
<220> FEATURE:
<223> OTHER INFORMATION: DNA primer

<400> SEQUENCE: 176
taaatagtgt gtgcagcaac aaaaaattag aaaaaaaaga caactcactt cttcacgctc    60
tagaactagt ggatcc                                                    76

<210> SEQ ID NO 177
<211> LENGTH: 86
<212> TYPE: DNA
<213> ORGANISM: Artificial Sequence
<220> FEATURE:
<223> OTHER INFORMATION: DNA primer

<400> SEQUENCE: 177
gagcacacaa aaaaaaaaac accacccagt atcgaaccaa cattgtttcc ccaaccccca    60
ttcttcgctc tagaactagt ggatcc                                         86

<210> SEQ ID NO 178
<211> LENGTH: 76
<212> TYPE: DNA
<213> ORGANISM: Artificial Sequence
<220> FEATURE:
<223> OTHER INFORMATION: DNA primer

<400> SEQUENCE: 178
tgagaatttt ttaagaaatt taatctgcta ataactcttt tctacacaag gaacccgctc    60
tagaactagt ggatcc                                                    76

<210> SEQ ID NO 179
<211> LENGTH: 76
<212> TYPE: DNA
<213> ORGANISM: Artificial Sequence
<220> FEATURE:
<223> OTHER INFORMATION: DNA primer

<400> SEQUENCE: 179
tttgtatttc tattttgcaa gttctacttt taatatcatt tgatcaagac catctcgctc    60
tagaactagt ggatcc                                                    76

<210> SEQ ID NO 180
<211> LENGTH: 86
<212> TYPE: DNA
<213> ORGANISM: Artificial Sequence
<220> FEATURE:
<223> OTHER INFORMATION: DNA primer

<400> SEQUENCE: 180
gggaaactat aaacaaagag ttcagatgag gtaatagttt caaggagaag attagttaaa    60
aaatacgctc tagaactagt ggatcc                                         86

<210> SEQ ID NO 181
<211> LENGTH: 83
<212> TYPE: DNA
<213> ORGANISM: Artificial Sequence
```

```
<220> FEATURE:
<223> OTHER INFORMATION: DNA primer

<400> SEQUENCE: 181
tttttcactt cttgagtcat tcttgtaacc ataatccact tttgtttcca acgaactata      60
aaatccgctc tagaactagt gga                                              83

<210> SEQ ID NO 182
<211> LENGTH: 83
<212> TYPE: DNA
<213> ORGANISM: Artificial Sequence
<220> FEATURE:
<223> OTHER INFORMATION: DNA primer

<400> SEQUENCE: 182
tctccaaaaa tgtcagaact agcttgttga tgggcaaccg ttgacttgtt tatggccata      60
ctgcacgctc tagaactagt gga                                              83

<210> SEQ ID NO 183
<211> LENGTH: 83
<212> TYPE: DNA
<213> ORGANISM: Artificial Sequence
<220> FEATURE:
<223> OTHER INFORMATION: DNA primer

<400> SEQUENCE: 183
tccctcccct ccctcttcc cctttaata atacatctat caaatataac atataaactt        60
acatacgctc tagaactagt gga                                              83

<210> SEQ ID NO 184
<211> LENGTH: 83
<212> TYPE: DNA
<213> ORGANISM: Artificial Sequence
<220> FEATURE:
<223> OTHER INFORMATION: DNA primer

<400> SEQUENCE: 184
aagacgcgtt gttttacctt ctttcaacat cttttagcaa caccacccat tcaataacct     60
tcaatcgctc tagaactagt gga                                              83

<210> SEQ ID NO 185
<211> LENGTH: 86
<212> TYPE: DNA
<213> ORGANISM: Artificial Sequence
<220> FEATURE:
<223> OTHER INFORMATION: DNA primer

<400> SEQUENCE: 185
ctctatatca ataccata atactcgaca cggctatact gttgatataa actttcccac        60
tggacccctc gaggtcgacg gtatcg                                           86

<210> SEQ ID NO 186
<211> LENGTH: 83
<212> TYPE: DNA
<213> ORGANISM: Artificial Sequence
<220> FEATURE:
<223> OTHER INFORMATION: DNA primer

<400> SEQUENCE: 186
attatcgtaa cattaaattt atacatcaga tatttataat tacacttctt aaataaaata    60
ttcagtcgag gtcgacggta tcg                                              83
```

<210> SEQ ID NO 187
<211> LENGTH: 83
<212> TYPE: DNA
<213> ORGANISM: Artificial Sequence
<220> FEATURE:
<223> OTHER INFORMATION: DNA primer

<400> SEQUENCE: 187
ctacgatgta tatacataca aaagctgtac attaatactg atagaacatt taagttatag    60
gttcatcgag gtcgacggta tcg    83

<210> SEQ ID NO 188
<211> LENGTH: 83
<212> TYPE: DNA
<213> ORGANISM: Artificial Sequence
<220> FEATURE:
<223> OTHER INFORMATION: DNA primer

<400> SEQUENCE: 188
ttcaaggtat ttgcatttta gtttttgcta cttctataac attacaaatt atatacaact    60
atttgtcgag gtcgacggta tcg    83

<210> SEQ ID NO 189
<211> LENGTH: 86
<212> TYPE: DNA
<213> ORGANISM: Artificial Sequence
<220> FEATURE:
<223> OTHER INFORMATION: DNA primer

<400> SEQUENCE: 189
tttgtaaata ttaaatagta cacacacaca caattcttgt atataatacg aacaaacagt    60
aatagccctc gaggtcgacg gtatcg    86

<210> SEQ ID NO 190
<211> LENGTH: 86
<212> TYPE: DNA
<213> ORGANISM: Artificial Sequence
<220> FEATURE:
<223> OTHER INFORMATION: DNA primer

<400> SEQUENCE: 190
tatatatata tataaatatt tacaaagtga atcttggata aatatcatac actatcttta    60
ctcttccctc gaggtcgacg gtatcg    86

<210> SEQ ID NO 191
<211> LENGTH: 76
<212> TYPE: DNA
<213> ORGANISM: Artificial Sequence
<220> FEATURE:
<223> OTHER INFORMATION: DNA primer

<400> SEQUENCE: 191
ggtttgtcac attacacgca ctacactaaa tttatattag ataaaacgaa acattccctc    60
gaggtcgacg gtatcg    76

<210> SEQ ID NO 192
<211> LENGTH: 76
<212> TYPE: DNA
<213> ORGANISM: Artificial Sequence
<220> FEATURE:
<223> OTHER INFORMATION: DNA primer

<400> SEQUENCE: 192
cttcgccgat cctcaaacaa tacttggcta gacagttcta cttagaagac ggaaaccctc    60
gaggtcgacg gtatcg                                                   76

<210> SEQ ID NO 193
<211> LENGTH: 86
<212> TYPE: DNA
<213> ORGANISM: Artificial Sequence
<220> FEATURE:
<223> OTHER INFORMATION: DNA primer

<400> SEQUENCE: 193
catcatcatc attgtaaatc tatttctttt tatggaggtg ggaattgttg ttccatttca    60
atgacccctc gaggtcgacg gtatcg                                        86

<210> SEQ ID NO 194
<211> LENGTH: 76
<212> TYPE: DNA
<213> ORGANISM: Artificial Sequence
<220> FEATURE:
<223> OTHER INFORMATION: DNA primer

<400> SEQUENCE: 194
aaataataca attaacttta taacaatata taaatctata ttatcaaaca actacccctc    60
gaggtcgacg gtatcg                                                   76

<210> SEQ ID NO 195
<211> LENGTH: 86
<212> TYPE: DNA
<213> ORGANISM: Artificial Sequence
<220> FEATURE:
<223> OTHER INFORMATION: DNA primer

<400> SEQUENCE: 195
tagaaactcc ataggatgta taaaaaaaaa cacgtatcga attcttatta ctttgtttat    60
aaaacccctc gaggtcgacg gtatcg                                        86

<210> SEQ ID NO 196
<211> LENGTH: 86
<212> TYPE: DNA
<213> ORGANISM: Artificial Sequence
<220> FEATURE:
<223> OTHER INFORMATION: DNA primer

<400> SEQUENCE: 196
taatcgactc ctacagcgtc tgataatacc aaaaaaagag aaaaggattc tattttagaa    60
tcatcccctc gaggtcgacg gtatcg                                        86

<210> SEQ ID NO 197
<211> LENGTH: 86
<212> TYPE: DNA
<213> ORGANISM: Artificial Sequence
<220> FEATURE:
<223> OTHER INFORMATION: DNA primer

<400> SEQUENCE: 197
acaacaacac atctaagggt tgtagttatt ctttacttgt ttgtatcttg tgagattact    60 tcaaccccctc gaggtcgacg gtatcg                                       86

<210> SEQ ID NO 198
<211> LENGTH: 83
<212> TYPE: DNA

<213> ORGANISM: Artificial Sequence
<220> FEATURE:
<223> OTHER INFORMATION: DNA primer

<400> SEQUENCE: 198

```
tttttatctc tatatgtaaa gtgtataaaa aaaagaaata caaacctaaa aaacttatat      60
gtagatcgag gtcgacggta tcg                                             83
```

<210> SEQ ID NO 199
<211> LENGTH: 83
<212> TYPE: DNA
<213> ORGANISM: Artificial Sequence
<220> FEATURE:
<223> OTHER INFORMATION: DNA primer

<400> SEQUENCE: 199

```
gtatatgtgt taatccaact aagtaacaaa atgaaaacaa tctgaacact gaatcgaaag      60
aaagttcgag gtcgacggta tcg                                             83
```

<210> SEQ ID NO 200
<211> LENGTH: 86
<212> TYPE: DNA
<213> ORGANISM: Artificial Sequence
<220> FEATURE:
<223> OTHER INFORMATION: DNA primer

<400> SEQUENCE: 200

```
catactgaat tgccaccta cacgaagtga taccaatggc tgtcgtattc tggacaactt       60
taaacccctc gaggtcgacg gtatcg                                          86
```

<210> SEQ ID NO 201
<211> LENGTH: 83
<212> TYPE: DNA
<213> ORGANISM: Artificial Sequence
<220> FEATURE:
<223> OTHER INFORMATION: DNA primer

<400> SEQUENCE: 201

```
aaatacacgt atccgtacat ttatatgtat ataggtac attttacctc aatagtatag        60
ccagttcgag gtcgacggta tcg                                             83
```

<210> SEQ ID NO 202
<211> LENGTH: 86
<212> TYPE: DNA
<213> ORGANISM: Artificial Sequence
<220> FEATURE:
<223> OTHER INFORMATION: DNA primer

<400> SEQUENCE: 202

```
aaatcataaa ctagtcctta acaaatctaa tagtctatgc attactaatt atttatctcc      60
atgtcccctc gaggtcgacg gtatcg                                          86
```

<210> SEQ ID NO 203
<211> LENGTH: 76
<212> TYPE: DNA
<213> ORGANISM: Artificial Sequence
<220> FEATURE:
<223> OTHER INFORMATION: DNA primer

<400> SEQUENCE: 203

```
aaatgtaagt catttataaa aaaaaaaata caaactttct ttgttttttaa aaaccccctc    60 gaggtcgacg gtatcg                                                     76
```

<210> SEQ ID NO 204
<211> LENGTH: 86
<212> TYPE: DNA
<213> ORGANISM: Artificial Sequence
<220> FEATURE:
<223> OTHER INFORMATION: DNA primer

<400> SEQUENCE: 204
taataggatt tatttttata ttaatatgag gtatatttac tatctataaa ggaaaaaaaa    60 atccccctc gaggtcgacg gtatcg    86

<210> SEQ ID NO 205
<211> LENGTH: 86
<212> TYPE: DNA
<213> ORGANISM: Artificial Sequence
<220> FEATURE:
<223> OTHER INFORMATION: DNA primer

<400> SEQUENCE: 205
tatgaaataa agtgggtttc taaattagat ataacgataa taagtgttgt gtattctttt    60
ttgcaccctc gaggtcgacg gtatcg    86

<210> SEQ ID NO 206
<211> LENGTH: 83
<212> TYPE: DNA
<213> ORGANISM: Artificial Sequence
<220> FEATURE:
<223> OTHER INFORMATION: DNA primer

<400> SEQUENCE: 206
aaatggtaat ttgtagggtt ttacatattc aatctagaca taacatttat taattgtttc    60
ctctatcgag gtcgacggta tcg    83

<210> SEQ ID NO 207
<211> LENGTH: 86
<212> TYPE: DNA
<213> ORGANISM: Artificial Sequence
<220> FEATURE:
<223> OTHER INFORMATION: DNA primer

<400> SEQUENCE: 207
agctgatcca tccaatttct ctaataatct ttcttggttg atcattgatt cgttgtcttg    60
ataccccctc gaggtcgacg gtatcg    86

<210> SEQ ID NO 208
<211> LENGTH: 86
<212> TYPE: DNA
<213> ORGANISM: Artificial Sequence
<220> FEATURE:
<223> OTHER INFORMATION: DNA primer

<400> SEQUENCE: 208
gaatattggt aaaatactac ataatgatgc aaatagatat ttatagagac aacaacgaca    60 acgaccctc gaggtcgacg gtatcg    86

<210> SEQ ID NO 209
<211> LENGTH: 76
<212> TYPE: DNA
<213> ORGANISM: Artificial Sequence
<220> FEATURE:
<223> OTHER INFORMATION: DNA primer

```
<400> SEQUENCE: 209
taaatcatgt acatatatta ttattttgca ttactaatct attactattt tacatccctc    60
gaggtcgacg gtatcg                                                    76

<210> SEQ ID NO 210
<211> LENGTH: 86
<212> TYPE: DNA
<213> ORGANISM: Artificial Sequence
<220> FEATURE:
<223> OTHER INFORMATION: DNA primer

<400> SEQUENCE: 210
gatagtgtag gtattgaaca taaaatcatt aattaggagg aaataaagaa attaatagaa    60
actgcccctc gaggtcgacg gtatcg                                         86

<210> SEQ ID NO 211
<211> LENGTH: 86
<212> TYPE: DNA
<213> ORGANISM: Artificial Sequence
<220> FEATURE:
<223> OTHER INFORMATION: DNA primer

<400> SEQUENCE: 211
aggtcaggtc ttacgttgta tttttaagaa cttctagtac gccgattgta tccctagata    60
aaggaccctc gaggtcgacg gtatcg                                         86

<210> SEQ ID NO 212
<211> LENGTH: 76
<212> TYPE: DNA
<213> ORGANISM: Artificial Sequence
<220> FEATURE:
<223> OTHER INFORMATION: DNA primer

<400> SEQUENCE: 212
ataaatctat attatagtta taaaacctcc aaaaaattgt acatcttcct atgtcccctc    60
gaggtcgacg gtatcg                                                    76

<210> SEQ ID NO 213
<211> LENGTH: 86
<212> TYPE: DNA
<213> ORGANISM: Artificial Sequence
<220> FEATURE:
<223> OTHER INFORMATION: DNA primer

<400> SEQUENCE: 213
aagagagaaa caacttctta catcatactt attaataagt catatataca ttataccagc    60
atctaccctc gaggtcgacg gtatcg                                         86

<210> SEQ ID NO 214
<211> LENGTH: 76
<212> TYPE: DNA
<213> ORGANISM: Artificial Sequence
<220> FEATURE:
<223> OTHER INFORMATION: DNA primer

<400> SEQUENCE: 214
aaaaaaagta tggttaaaaa ggaaaaaaaa taagctatca tcatcttctt cttaaccctc    60
gaggtcgacg gtatcg                                                    76

<210> SEQ ID NO 215
<211> LENGTH: 83
```

```
<212> TYPE: DNA
<213> ORGANISM: Artificial Sequence
<220> FEATURE:
<223> OTHER INFORMATION: DNA primer

<400> SEQUENCE: 215
tggtgtaaat gagaaatcct tttgcattac tactatctac tcattagtat acttatatga    60
tgacctcgag gtcgacggta tcg                                           83

<210> SEQ ID NO 216
<211> LENGTH: 76
<212> TYPE: DNA
<213> ORGANISM: Artificial Sequence
<220> FEATURE:
<223> OTHER INFORMATION: DNA primer

<400> SEQUENCE: 216
agagttatta tatgtacaca ttttttttaa tataaacatg tagcaatata ctttacccctc   60 gaggtcgacg gtatcg                                                   76

<210> SEQ ID NO 217
<211> LENGTH: 83
<212> TYPE: DNA
<213> ORGANISM: Artificial Sequence
<220> FEATURE:
<223> OTHER INFORMATION: DNA primer

<400> SEQUENCE: 217
ggaaattcga caagatgtaa acgagcagat agacaagttt gaaagtgctg tattataata    60
aataatcgag gtcgacggta tcg                                           83

<210> SEQ ID NO 218
<211> LENGTH: 83
<212> TYPE: DNA
<213> ORGANISM: Artificial Sequence
<220> FEATURE:
<223> OTHER INFORMATION: DNA primer

<400> SEQUENCE: 218
tttagtatta agtaaatatc tctttctctc tctctctcta tatatatata tatatgtatc    60
tttgatcgag gtcgacggta tcg                                           83

<210> SEQ ID NO 219
<211> LENGTH: 83
<212> TYPE: DNA
<213> ORGANISM: Artificial Sequence
<220> FEATURE:
<223> OTHER INFORMATION: DNA primer

<400> SEQUENCE: 219
atattattac aaaaattatg gtttgaatgc aatatagtag tatatttttc tttcgctttc    60
tttcctcgag gtcgacggta tcg                                           83

<210> SEQ ID NO 220
<211> LENGTH: 83
<212> TYPE: DNA
<213> ORGANISM: Artificial Sequence
<220> FEATURE:
<223> OTHER INFORMATION: DNA primer

<400> SEQUENCE: 220
aatggatttg tagaataagg ggtggtactt ccagtaaaac gagtactcaa ataactccaa    60
```

```
gtgtatcgag gtcgacggta tcg                                           83

<210> SEQ ID NO 221
<211> LENGTH: 83
<212> TYPE: DNA
<213> ORGANISM: Artificial Sequence
<220> FEATURE:
<223> OTHER INFORMATION: DNA primer

<400> SEQUENCE: 221
cataattttt tatatttga ttgaaagaaa atcttgaaaa agttttataa tccccctcaag   60 ttaactcgag gtcgacggta tcg                                           83

<210> SEQ ID NO 222
<211> LENGTH: 86
<212> TYPE: DNA
<213> ORGANISM: Artificial Sequence
<220> FEATURE:
<223> OTHER INFORMATION: DNA primer

<400> SEQUENCE: 222
acatgtatta acaaattata taatgacata aaacatttta catctgctag ttcttaaact   60
taaacccctc gaggtcgacg gtatcg                                        86

<210> SEQ ID NO 223
<211> LENGTH: 83
<212> TYPE: DNA
<213> ORGANISM: Artificial Sequence
<220> FEATURE:
<223> OTHER INFORMATION: DNA primer

<400> SEQUENCE: 223
agacctttgt aattaaaaaa atttaaacat tagcaacaaa gtaagaacac gatcaaccat   60
actactcgag gtcgacggta tcg                                           83

<210> SEQ ID NO 224
<211> LENGTH: 76
<212> TYPE: DNA
<213> ORGANISM: Artificial Sequence
<220> FEATURE:
<223> OTHER INFORMATION: DNA primer

<400> SEQUENCE: 224
gatgtttcta tttaatgatt tatagaataa ggatatagcg tgttattgca caagcccctc   60
gaggtcgacg gtatcg                                                   76

<210> SEQ ID NO 225
<211> LENGTH: 86
<212> TYPE: DNA
<213> ORGANISM: Artificial Sequence
<220> FEATURE:
<223> OTHER INFORMATION: DNA primer

<400> SEQUENCE: 225
tccacaaatg tcaaatacat atatttgcac ctaccaatta gagggatctt gaattaataa   60 cttaccccctc gaggtcgacg gtatcg                                       86

<210> SEQ ID NO 226
<211> LENGTH: 86
<212> TYPE: DNA
<213> ORGANISM: Artificial Sequence
<220> FEATURE:
<223> OTHER INFORMATION: DNA primer
```

<400> SEQUENCE: 226
atatgttaaa acgggtagca gaaaatctaa tcgaaatcac cttgtagaca tatcctagtg    60
atattccctc gaggtcgacg gtatcg    86

<210> SEQ ID NO 227
<211> LENGTH: 76
<212> TYPE: DNA
<213> ORGANISM: Artificial Sequence
<220> FEATURE:
<223> OTHER INFORMATION: DNA primer

<400> SEQUENCE: 227
gtaacatgtc tcaatttagt ttggcatttg aatcgactaa ttcacccat ttcatccctc    60 gaggtcgacg gtatcg    76

<210> SEQ ID NO 228
<211> LENGTH: 83
<212> TYPE: DNA
<213> ORGANISM: Artificial Sequence
<220> FEATURE:
<223> OTHER INFORMATION: DNA primer

<400> SEQUENCE: 228
gatagagcta aaaacgttta taacaaatta ataatatttg actaaactaa cttcctattc    60
acctttcgag gtcgacggta tcg    83

<210> SEQ ID NO 229
<211> LENGTH: 76
<212> TYPE: DNA
<213> ORGANISM: Artificial Sequence
<220> FEATURE:
<223> OTHER INFORMATION: DNA primer

<400> SEQUENCE: 229
aatactcata tatatgta tgtatatata tatattacat aaccattcac cccaaccctc    60
gaggtcgacg gtatcg    76

<210> SEQ ID NO 230
<211> LENGTH: 86
<212> TYPE: DNA
<213> ORGANISM: Artificial Sequence
<220> FEATURE:
<223> OTHER INFORMATION: DNA primer

<400> SEQUENCE: 230 gaggggtat ttcactccat atttgctcta ttatttgtaa ttcttgctat ttattatcca    60
tggtcccctc gaggtcgacg gtatcg    86

<210> SEQ ID NO 231
<211> LENGTH: 76
<212> TYPE: DNA
<213> ORGANISM: Artificial Sequence
<220> FEATURE:
<223> OTHER INFORMATION: DNA primer

<400> SEQUENCE: 231
ttcagttcta gttcctctgg agtttctggt ttaatatgca aatccctctt tctatccctc    60
gaggtcgacg gtatcg    76

<210> SEQ ID NO 232

```
<211> LENGTH: 83
<212> TYPE: DNA
<213> ORGANISM: Artificial Sequence
<220> FEATURE:
<223> OTHER INFORMATION: DNA primer

<400> SEQUENCE: 232 accccccatat atatttagca tcaatttttta taaatgtata ttagatcctt attccactca    60
cttattcgag gtcgacggta tcg                                             83

<210> SEQ ID NO 233
<211> LENGTH: 76
<212> TYPE: DNA
<213> ORGANISM: Artificial Sequence
<220> FEATURE:
<223> OTHER INFORMATION: DNA primer

<400> SEQUENCE: 233
taaaaataag taaattataa atgctaatcg tttattatgc agctattcaa ccaagccctc      60
gaggtcgacg gtatcg                                                     76

<210> SEQ ID NO 234
<211> LENGTH: 86
<212> TYPE: DNA
<213> ORGANISM: Artificial Sequence
<220> FEATURE:
<223> OTHER INFORMATION: DNA primer

<400> SEQUENCE: 234
cgttgggaaa cgtaacagct cccgataaag aaaaagattc cttttttgata tttttttttaa   60 tctatccctc gaggtcgacg gtatcg                                          86

<210> SEQ ID NO 235
<211> LENGTH: 76
<212> TYPE: DNA
<213> ORGANISM: Artificial Sequence
<220> FEATURE:
<223> OTHER INFORMATION: DNA primer

<400> SEQUENCE: 235
tgaattggcc ccatatgata tgttttccta tttcttcata tcatctaatt attgcccctc      60
gaggtcgacg gtatcg                                                     76

<210> SEQ ID NO 236
<211> LENGTH: 86
<212> TYPE: DNA
<213> ORGANISM: Artificial Sequence
<220> FEATURE:
<223> OTHER INFORMATION: DNA primer

<400> SEQUENCE: 236
tgtagtacta ttgatattat agcattaaaa ttttcttcct tttttgtcaa atgtatctgt      60
agtatccctc gaggtcgacg gtatcg                                          86

<210> SEQ ID NO 237
<211> LENGTH: 76
<212> TYPE: DNA
<213> ORGANISM: Artificial Sequence
<220> FEATURE:
<223> OTHER INFORMATION: DNA primer

<400> SEQUENCE: 237
aatcgttata agaagagagg gtacaactat tggcgcaggt acggttattg attttccctc      60
```

```
gaggtcgacg gtatcg                                              76

<210> SEQ ID NO 238
<211> LENGTH: 86
<212> TYPE: DNA
<213> ORGANISM: Artificial Sequence
<220> FEATURE:
<223> OTHER INFORMATION: DNA primer

<400> SEQUENCE: 238
gaacttgtac atatattaca tacacaaatt acggtttatt gtgcattatt ttatctattg    60
atttaccctc gaggtcgacg gtatcg                                        86

<210> SEQ ID NO 239
<211> LENGTH: 76
<212> TYPE: DNA
<213> ORGANISM: Artificial Sequence
<220> FEATURE:
<223> OTHER INFORMATION: DNA primer

<400> SEQUENCE: 239
atgtaatatt attatcgtgt attaacacaa ctgtaaatta tttgttaaat ctaaaccctc    60
gaggtcgacg gtatcg                                                   76

<210> SEQ ID NO 240
<211> LENGTH: 76
<212> TYPE: DNA
<213> ORGANISM: Artificial Sequence
<220> FEATURE:
<223> OTHER INFORMATION: DNA primer

<400> SEQUENCE: 240
attccaattg tctgaattct tactccaatc tctgcttcct tttccttccc attgcccctc    60
gaggtcgacg gtatcg                                                   76

<210> SEQ ID NO 241
<211> LENGTH: 86
<212> TYPE: DNA
<213> ORGANISM: Artificial Sequence
<220> FEATURE:
<223> OTHER INFORMATION: DNA primer

<400> SEQUENCE: 241
aagatagatt aattaacaat acaaatataa tgctacatgg aaataaatag taaatataaa    60
aactcccctc gaggtcgacg gtatcg                                        86

<210> SEQ ID NO 242
<211> LENGTH: 83
<212> TYPE: DNA
<213> ORGANISM: Artificial Sequence
<220> FEATURE:
<223> OTHER INFORMATION: DNA primer

<400> SEQUENCE: 242
catagtatta ttgatatctc taaacaaaaa gttatgtatt aaaagcaacc taaacaagac    60
tctattcgag gtcgacggta tcg                                           83

<210> SEQ ID NO 243
<211> LENGTH: 83
<212> TYPE: DNA
<213> ORGANISM: Artificial Sequence
<220> FEATURE:
```

<223> OTHER INFORMATION: DNA primer

<400> SEQUENCE: 243
taaagactga ttctaggatt acaaatgata cactacatta catcataaca ggtcaggaag    60
tcctgtcgag gtcgacggta tcg    83

<210> SEQ ID NO 244
<211> LENGTH: 83
<212> TYPE: DNA
<213> ORGANISM: Artificial Sequence
<220> FEATURE:
<223> OTHER INFORMATION: DNA primer

<400> SEQUENCE: 244
aactcataag agggcttcag gtttctttct attctgactt tgccttttgt tgtatttgct    60
tgacttcgag gtcgacggta tcg    83

<210> SEQ ID NO 245
<211> LENGTH: 83
<212> TYPE: DNA
<213> ORGANISM: Artificial Sequence
<220> FEATURE:
<223> OTHER INFORMATION: DNA primer

<400> SEQUENCE: 245
ggtattcacg ataactgcta gaatgaccta cttcttaata caaattactt tctagtatta    60
actattcgag gtcgacggta tcg    83

<210> SEQ ID NO 246
<211> LENGTH: 87
<212> TYPE: DNA
<213> ORGANISM: Artificial Sequence
<220> FEATURE:
<223> OTHER INFORMATION: DNA primer

<400> SEQUENCE: 246
ttctcttaaa aatgacttat atttaatata cacttgcaaa actgttagta taacgctact    60
caaagagtgt gattatgtaa gcaggcg    87

<210> SEQ ID NO 247
<211> LENGTH: 83
<212> TYPE: DNA
<213> ORGANISM: Artificial Sequence
<220> FEATURE:
<223> OTHER INFORMATION: DNA primer

<400> SEQUENCE: 247
tgttttcatt catcgaacgc gtgggccaaa aaaaaaacaa tcgattattt agactggtac    60
aaatatgatt atgtaagcag gcg    83

<210> SEQ ID NO 248
<211> LENGTH: 72
<212> TYPE: DNA
<213> ORGANISM: Artificial Sequence
<220> FEATURE:
<223> OTHER INFORMATION: DNA primer

<400> SEQUENCE: 248
tcaccacgag tactcatctt gtatttcttt aaatcggtca ataattactt agtgtgatta    60
tgtaagcagg cg    72

<210> SEQ ID NO 249
<211> LENGTH: 83
<212> TYPE: DNA
<213> ORGANISM: Artificial Sequence
<220> FEATURE:
<223> OTHER INFORMATION: DNA primer

<400> SEQUENCE: 249
tgtattgtgg gcgtgtctgt gcgtctgtgt gtgtgtacca ctgtcatttt ctttctttcg      60
gttgatgatt atgtaagcag gcg                                              83

<210> SEQ ID NO 250
<211> LENGTH: 87
<212> TYPE: DNA
<213> ORGANISM: Artificial Sequence
<220> FEATURE:
<223> OTHER INFORMATION: DNA primer

<400> SEQUENCE: 250
ttttgaattg cgaagaatac gtgtagtaat atggatctta ttttaagtag ggtataactg      60
attcaagtgt gattatgtaa gcaggcg                                          87

<210> SEQ ID NO 251
<211> LENGTH: 87
<212> TYPE: DNA
<213> ORGANISM: Artificial Sequence
<220> FEATURE:
<223> OTHER INFORMATION: DNA primer

<400> SEQUENCE: 251
cgatccagaa gatgaagatg aagatactgg ctttctagga tttaatgatt ccaatcgatt      60
agacaagtgt gattatgtaa gcaggcg                                          87

<210> SEQ ID NO 252
<211> LENGTH: 77
<212> TYPE: DNA
<213> ORGANISM: Artificial Sequence
<220> FEATURE:
<223> OTHER INFORMATION: DNA primer

<400> SEQUENCE: 252
taccaaatac ggaagaaagt cagtttcagt gtttactttt tcatgtacat agttgagtgt      60
gattatgtaa gcaggcg                                                     77

<210> SEQ ID NO 253
<211> LENGTH: 77
<212> TYPE: DNA
<213> ORGANISM: Artificial Sequence
<220> FEATURE:
<223> OTHER INFORMATION: DNA primer

<400> SEQUENCE: 253
atctacctga accactctcg ccaattatca tgatggagaa gttgattgat ttcttagtgt      60
gattatgtaa gcaggcg                                                     77

<210> SEQ ID NO 254
<211> LENGTH: 87
<212> TYPE: DNA
<213> ORGANISM: Artificial Sequence
<220> FEATURE:
<223> OTHER INFORMATION: DNA primer

<400> SEQUENCE: 254

```
atgacagaat tgttgaaat gatccagcaa atgttttcac tttttaaat ggtggtcgct      60 cattaagtgt gattatgtaa gcaggcg                                        87

<210> SEQ ID NO 255
<211> LENGTH: 77
<212> TYPE: DNA
<213> ORGANISM: Artificial Sequence
<220> FEATURE:
<223> OTHER INFORMATION: DNA primer

<400> SEQUENCE: 255
caggttaggg atttgggctg aatgtattt taatagttgt tcaactggct aggatagtgt    60
gattatgtaa gcaggcg                                                   77

<210> SEQ ID NO 256
<211> LENGTH: 87
<212> TYPE: DNA
<213> ORGANISM: Artificial Sequence
<220> FEATURE:
<223> OTHER INFORMATION: DNA primer

<400> SEQUENCE: 256
ttagacaaat tacttttatt gtttctttca ttacttgtcg gcagcattct aatgttgtct    60
agagaagtgt gattatgtaa gcaggcg                                        87

<210> SEQ ID NO 257
<211> LENGTH: 87
<212> TYPE: DNA
<213> ORGANISM: Artificial Sequence
<220> FEATURE:
<223> OTHER INFORMATION: DNA primer

<400> SEQUENCE: 257
aaattgaagc acaaatttca caaatgtcat tttcgttcct tgccatttca tttcaaagca    60
atcaaagtgt gattatgtaa gcaggcg                                        87

<210> SEQ ID NO 258
<211> LENGTH: 87
<212> TYPE: DNA
<213> ORGANISM: Artificial Sequence
<220> FEATURE:
<223> OTHER INFORMATION: DNA primer

<400> SEQUENCE: 258
tagaacagcc aattctgtta ttattttttt ttgtgagtgt gtgtgtcgtc gtgcataatt    60
tcattagtgt gattatgtaa gcaggcg                                        87

<210> SEQ ID NO 259
<211> LENGTH: 83
<212> TYPE: DNA
<213> ORGANISM: Artificial Sequence
<220> FEATURE:
<223> OTHER INFORMATION: DNA primer

<400> SEQUENCE: 259
ttattataga tttggtgttt aaaaattagt aatatagtac tttaacttat atttggtttt    60
ctttatgatt atgtaagcag gcg                                            83

<210> SEQ ID NO 260
<211> LENGTH: 72
<212> TYPE: DNA
<213> ORGANISM: Artificial Sequence
```

```
<220> FEATURE:
<223> OTHER INFORMATION: DNA primer

<400> SEQUENCE: 260
atatcgtacc cgattatgtc gtatattctt ttttcaatgt caatttgaga agtgtgatta      60
tgtaagcagg cg                                                          72

<210> SEQ ID NO 261
<211> LENGTH: 87
<212> TYPE: DNA
<213> ORGANISM: Artificial Sequence
<220> FEATURE:
<223> OTHER INFORMATION: DNA primer

<400> SEQUENCE: 261
tataattaat gtatacaatt aaggtttatt aatataaaaa aattatatta aacaggttac      60
aaaaaagtgt gattatgtaa gcaggcg                                          87

<210> SEQ ID NO 262
<211> LENGTH: 83
<212> TYPE: DNA
<213> ORGANISM: Artificial Sequence
<220> FEATURE:
<223> OTHER INFORMATION: DNA primer

<400> SEQUENCE: 262
atcagattga ccagatgacc aaaaagaacg aattctccaa aggtgacgag gaaagggtag      60
caagatgatt atgtaagcag gcg                                              83

<210> SEQ ID NO 263
<211> LENGTH: 87
<212> TYPE: DNA
<213> ORGANISM: Artificial Sequence
<220> FEATURE:
<223> OTHER INFORMATION: DNA primer

<400> SEQUENCE: 263
tacaatacaa ttgaaaatga tgaaaaccga gaaagtagtg cgaattgcaa caaaacttca      60
ggactagtgt gattatgtaa gcaggcg                                          87

<210> SEQ ID NO 264
<211> LENGTH: 77
<212> TYPE: DNA
<213> ORGANISM: Artificial Sequence
<220> FEATURE:
<223> OTHER INFORMATION: DNA primer

<400> SEQUENCE: 264
ggatgatgat gttagcaatg atattgatga ggattctgag tggttaagtt gatagagtgt      60
gattatgtaa gcaggcg                                                     77

<210> SEQ ID NO 265
<211> LENGTH: 87
<212> TYPE: DNA
<213> ORGANISM: Artificial Sequence
<220> FEATURE:
<223> OTHER INFORMATION: DNA primer

<400> SEQUENCE: 265
taatatttca atatcgaaag acatggaagt gcatgaacct gaagtaaaga agtttaatac      60
atgagagtgt gattatgtaa gcaggcg                                          87
```

```
<210> SEQ ID NO 266
<211> LENGTH: 87
<212> TYPE: DNA
<213> ORGANISM: Artificial Sequence
<220> FEATURE:
<223> OTHER INFORMATION: DNA primer

<400> SEQUENCE: 266
tttatacact tcatttggac ttaactttta aaatatatcc atcaatcaac aacttattta      60
caaatagtgt gattatgtaa gcaggcg                                         87

<210> SEQ ID NO 267
<211> LENGTH: 83
<212> TYPE: DNA
<213> ORGANISM: Artificial Sequence
<220> FEATURE:
<223> OTHER INFORMATION: DNA primer

<400> SEQUENCE: 267
cacaatttgg atttaaaaga ttttaaaaag tattttatca gttttatcaa caaaatgaaa      60
agtggtgatt atgtaagcag gcg                                             83

<210> SEQ ID NO 268
<211> LENGTH: 87
<212> TYPE: DNA
<213> ORGANISM: Artificial Sequence
<220> FEATURE:
<223> OTHER INFORMATION: DNA primer

<400> SEQUENCE: 268
acagacttga attagtatta gaaactagaa ccacagcatc tttaaaatca acttatttgc      60
atcgaagtgt gattatgtaa gcaggcg                                         87

<210> SEQ ID NO 269
<211> LENGTH: 87
<212> TYPE: DNA
<213> ORGANISM: Artificial Sequence
<220> FEATURE:
<223> OTHER INFORMATION: DNA primer

<400> SEQUENCE: 269
aaagacaaga ttgaaacttt gttgatctaa gtagtaaatg caattcaaac tattatttgt      60
atataagtgt gattatgtaa gcaggcg                                         87

<210> SEQ ID NO 270
<211> LENGTH: 77
<212> TYPE: DNA
<213> ORGANISM: Artificial Sequence
<220> FEATURE:
<223> OTHER INFORMATION: DNA primer

<400> SEQUENCE: 270
agtctgattc ttccttcaaa aaagaaaggg aaaagcaagt gaatttgatt gcataagtgt      60
gattatgtaa gcaggcg                                                    77

<210> SEQ ID NO 271
<211> LENGTH: 87
<212> TYPE: DNA
<213> ORGANISM: Artificial Sequence
<220> FEATURE:
<223> OTHER INFORMATION: DNA primer

<400> SEQUENCE: 271
```

```
tctcttctca tattcccatt ttgtataaaa cttcttacaa gtccacttag acaaccaacc    60
agcctagtgt gattatgtaa gcaggcg                                        87

<210> SEQ ID NO 272
<211> LENGTH: 87
<212> TYPE: DNA
<213> ORGANISM: Artificial Sequence
<220> FEATURE:
<223> OTHER INFORMATION: DNA primer

<400> SEQUENCE: 272
cttattattt gttcttgttt ataattatta aggaagaaag agtttaaaat attctggtga    60
aaattagtgt gattatgtaa gcaggcg                                        87

<210> SEQ ID NO 273
<211> LENGTH: 77
<212> TYPE: DNA
<213> ORGANISM: Artificial Sequence
<220> FEATURE:
<223> OTHER INFORMATION: DNA primer

<400> SEQUENCE: 273
atacgtttcc ttaatgtcaa aatcagccat tctagattag ttatgagttg ggagtagtgt    60
gattatgtaa gcaggcg                                                   77

<210> SEQ ID NO 274
<211> LENGTH: 87
<212> TYPE: DNA
<213> ORGANISM: Artificial Sequence
<220> FEATURE:
<223> OTHER INFORMATION: DNA primer

<400> SEQUENCE: 274
ttctaacaac tatagctgca agtattgttg agcgtttaat attgtgttta aatgaattgg    60
atgtgagtgt gattatgtaa gcaggcg                                        87

<210> SEQ ID NO 275
<211> LENGTH: 77
<212> TYPE: DNA
<213> ORGANISM: Artificial Sequence
<220> FEATURE:
<223> OTHER INFORMATION: DNA primer

<400> SEQUENCE: 275
tctgaccaat tcgattacta atctttcaca ctcactcact ccctcactca tttccagtgt    60
gattatgtaa gcaggcg                                                   77

<210> SEQ ID NO 276
<211> LENGTH: 83
<212> TYPE: DNA
<213> ORGANISM: Artificial Sequence
<220> FEATURE:
<223> OTHER INFORMATION: DNA primer

<400> SEQUENCE: 276
tcatcaacca cttttattat tggcatcata ggtcaaacgt taatactatg ttgctctttc    60 tttttttgatt atgtaagcag gcg                                           83

<210> SEQ ID NO 277
<211> LENGTH: 77
<212> TYPE: DNA
```

```
<213> ORGANISM: Artificial Sequence
<220> FEATURE:
<223> OTHER INFORMATION: DNA primer

<400> SEQUENCE: 277
tcgtcttgcc ccctatcac taatggggat ttccgatctc cttgccatat tttgaagtgt    60
gattatgtaa gcaggcg                                                  77

<210> SEQ ID NO 278
<211> LENGTH: 83
<212> TYPE: DNA
<213> ORGANISM: Artificial Sequence
<220> FEATURE:
<223> OTHER INFORMATION: DNA primer

<400> SEQUENCE: 278
ttgataagca ctggaaaaat ggaaagaggt attaacacag gaggattct agataaacgg    60 tttcgtgatt atgtaagcag gcg                                           83

<210> SEQ ID NO 279
<211> LENGTH: 83
<212> TYPE: DNA
<213> ORGANISM: Artificial Sequence
<220> FEATURE:
<223> OTHER INFORMATION: DNA primer

<400> SEQUENCE: 279
attgtaatat gatttgatgg ggaaaataga aattcaactt tcgtagtagt tggttggttg    60
gttagtgatt atgtaagcag gcg                                           83

<210> SEQ ID NO 280
<211> LENGTH: 83
<212> TYPE: DNA
<213> ORGANISM: Artificial Sequence
<220> FEATURE:
<223> OTHER INFORMATION: DNA primer

<400> SEQUENCE: 280
caaaatagca tatcgaacat agattcaagt atgttgctat ccccaacaat actttccatt    60
atctttgatt atgtaagcag gcg                                           83

<210> SEQ ID NO 281
<211> LENGTH: 77
<212> TYPE: DNA
<213> ORGANISM: Artificial Sequence
<220> FEATURE:
<223> OTHER INFORMATION: DNA primer

<400> SEQUENCE: 281
ctacgtttca catatactat tatttcaatt tcccatcatt gcaacaacaa acgaaagtgt    60
gattatgtaa gcaggcg                                                  77

<210> SEQ ID NO 282
<211> LENGTH: 83
<212> TYPE: DNA
<213> ORGANISM: Artificial Sequence
<220> FEATURE:
<223> OTHER INFORMATION: DNA primer

<400> SEQUENCE: 282
agggcctgca tcgcgcaacg cttatgtaca ggattttatg aatcattgaa tgaaaatttt    60
tcaattgatt atgtaagcag gcg                                           83
```

<210> SEQ ID NO 283
<211> LENGTH: 87
<212> TYPE: DNA
<213> ORGANISM: Artificial Sequence
<220> FEATURE:
<223> OTHER INFORMATION: DNA primer

<400> SEQUENCE: 283
tttcggtaca gtggagatta gagatcttgt agatttatat aacgaataat agtttgattt    60
ttattagtgt gattatgtaa gcaggcg    87

<210> SEQ ID NO 284
<211> LENGTH: 72
<212> TYPE: DNA
<213> ORGANISM: Artificial Sequence
<220> FEATURE:
<223> OTHER INFORMATION: DNA primer

<400> SEQUENCE: 284
aattgtatat gattacacga ccatacaaaa attttgcgaa ttgagattct agtgtgatta    60
tgtaagcagg cg    72

<210> SEQ ID NO 285
<211> LENGTH: 77
<212> TYPE: DNA
<213> ORGANISM: Artificial Sequence
<220> FEATURE:
<223> OTHER INFORMATION: DNA primer

<400> SEQUENCE: 285
ggattaatat tcacctagga gtcatatttt gcagcaccta gtatcaaggg atgttagtgt    60
gattatgtaa gcaggcg    77

<210> SEQ ID NO 286
<211> LENGTH: 87
<212> TYPE: DNA
<213> ORGANISM: Artificial Sequence
<220> FEATURE:
<223> OTHER INFORMATION: DNA primer

<400> SEQUENCE: 286
taacttggat ttttcttatt tcaactttt tttagcattt gaatctttat atatatatat    60
atcgtagtgt gattatgtaa gcaggcg    87

<210> SEQ ID NO 287
<211> LENGTH: 87
<212> TYPE: DNA
<213> ORGANISM: Artificial Sequence
<220> FEATURE:
<223> OTHER INFORMATION: DNA primer

<400> SEQUENCE: 287
ttgtaaattc tttaattcag tttccgccat agctatatgt gtaacttgtt tattaactag    60
gcttgagtgt gattatgtaa gcaggcg    87

<210> SEQ ID NO 288
<211> LENGTH: 77
<212> TYPE: DNA
<213> ORGANISM: Artificial Sequence
<220> FEATURE:
<223> OTHER INFORMATION: DNA primer -continued

```
<400> SEQUENCE: 288
aagagaaaaa ttaagccaag aagaatgaaa aaagtacaaa aactgtttga ctactagtgt    60
gattatgtaa gcaggcg                                                  77

<210> SEQ ID NO 289
<211> LENGTH: 83
<212> TYPE: DNA
<213> ORGANISM: Artificial Sequence
<220> FEATURE:
<223> OTHER INFORMATION: DNA primer

<400> SEQUENCE: 289 ttgtattta tgaacaaaag tggtagcact tggagaactt tttaatagag tgagatctgc     60
gcttatgatt atgtaagcag gcg                                           83

<210> SEQ ID NO 290
<211> LENGTH: 77
<212> TYPE: DNA
<213> ORGANISM: Artificial Sequence
<220> FEATURE:
<223> OTHER INFORMATION: DNA primer

<400> SEQUENCE: 290 gatttttta atagccgacg tgaataaaag agctaagtga ttatagagta tcggtagtgt     60
gattatgtaa gcaggcg                                                  77

<210> SEQ ID NO 291
<211> LENGTH: 87
<212> TYPE: DNA
<213> ORGANISM: Artificial Sequence
<220> FEATURE:
<223> OTHER INFORMATION: DNA primer

<400> SEQUENCE: 291
gtagttaaac aatatatatt gcactaacac caaaacagta caatttttt ttttcctttc     60 taaagagtgt gattatgtaa gcaggcg                                       87

<210> SEQ ID NO 292
<211> LENGTH: 77
<212> TYPE: DNA
<213> ORGANISM: Artificial Sequence
<220> FEATURE:
<223> OTHER INFORMATION: DNA primer

<400> SEQUENCE: 292
tcagctggat caccttgagc tatgtaaaat actacttcat ccatgtttgt gaattagtgt    60
gattatgtaa gcaggcg                                                  77

<210> SEQ ID NO 293
<211> LENGTH: 83
<212> TYPE: DNA
<213> ORGANISM: Artificial Sequence
<220> FEATURE:
<223> OTHER INFORMATION: DNA primer

<400> SEQUENCE: 293
tcatattctt ttaatgttat tgttggtggt gttgtatcgt tgatatattt tggaagaaat    60
gattgtgatt atgtaagcag gcg                                           83

<210> SEQ ID NO 294
<211> LENGTH: 77
```

```
<212> TYPE: DNA
<213> ORGANISM: Artificial Sequence
<220> FEATURE:
<223> OTHER INFORMATION: DNA primer

<400> SEQUENCE: 294
agctgtggct ataagaactg taaccagtgt tttgatttca gagtgatttc tactgagtgt    60
gattatgtaa gcaggcg                                                   77

<210> SEQ ID NO 295
<211> LENGTH: 87
<212> TYPE: DNA
<213> ORGANISM: Artificial Sequence
<220> FEATURE:
<223> OTHER INFORMATION: DNA primer

<400> SEQUENCE: 295
ttggttccaa gagggaaaa aaacaattga ctcaaatagt tttttaaatc gttccaactt     60
tttagagtgt gattatgtaa gcaggcg                                        87

<210> SEQ ID NO 296
<211> LENGTH: 77
<212> TYPE: DNA
<213> ORGANISM: Artificial Sequence
<220> FEATURE:
<223> OTHER INFORMATION: DNA primer

<400> SEQUENCE: 296 ctccccttttt ccttcttcta ctgctattat tcacagtgga ttcaccaaca ttactagtgt   60
gattatgtaa gcaggcg                                                   77

<210> SEQ ID NO 297
<211> LENGTH: 87
<212> TYPE: DNA
<213> ORGANISM: Artificial Sequence
<220> FEATURE:
<223> OTHER INFORMATION: DNA primer

<400> SEQUENCE: 297
tgaggttcta tgaacataaa gtggtttgta agttcaacta ataagttggg cgctcacaca    60
gaatgagtgt gattatgtaa gcaggcg                                        87

<210> SEQ ID NO 298
<211> LENGTH: 77
<212> TYPE: DNA
<213> ORGANISM: Artificial Sequence
<220> FEATURE:
<223> OTHER INFORMATION: DNA primer

<400> SEQUENCE: 298
gctcccgagt acgtggtcta cgtaaacttt tcacccgatg agaaaaagct ctacaagtgt    60
gattatgtaa gcaggcg                                                   77

<210> SEQ ID NO 299
<211> LENGTH: 87
<212> TYPE: DNA
<213> ORGANISM: Artificial Sequence
<220> FEATURE:
<223> OTHER INFORMATION: DNA primer

<400> SEQUENCE: 299
ctcaccgctt aggttcacat gtaataggtt acaaaactag agcatatacc agcgttctat    60
```

-continued gtgtgagtgt gattatgtaa gcaggcg    87

<210> SEQ ID NO 300
<211> LENGTH: 77
<212> TYPE: DNA
<213> ORGANISM: Artificial Sequence
<220> FEATURE:
<223> OTHER INFORMATION: DNA primer

<400> SEQUENCE: 300
taagctatac tactggctac aaaatgcatt cagaggaaat tttgacgaat taaacagtgt    60
gattatgtaa gcaggcg    77

<210> SEQ ID NO 301
<211> LENGTH: 77
<212> TYPE: DNA
<213> ORGANISM: Artificial Sequence
<220> FEATURE:
<223> OTHER INFORMATION: DNA primer

<400> SEQUENCE: 301
cagaagagga ttaatacact taaattatac cgatataaaa ctctctacaa ttgggagtgt    60
gattatgtaa gcaggcg    77

<210> SEQ ID NO 302
<211> LENGTH: 87
<212> TYPE: DNA
<213> ORGANISM: Artificial Sequence
<220> FEATURE:
<223> OTHER INFORMATION: DNA primer

<400> SEQUENCE: 302
ggctctggta taccataatc attagcgcat cactctttga tcattcatta tttggtcttt    60
taatgagtgt gattatgtaa gcaggcg    87

<210> SEQ ID NO 303
<211> LENGTH: 72
<212> TYPE: DNA
<213> ORGANISM: Artificial Sequence
<220> FEATURE:
<223> OTHER INFORMATION: DNA primer

<400> SEQUENCE: 303
ttagtgatta gtcacttaac gaccctaaat agttttgaaa cctcccgtaa agtgtgatta    60
tgtaagcagg cg    72

<210> SEQ ID NO 304
<211> LENGTH: 72
<212> TYPE: DNA
<213> ORGANISM: Artificial Sequence
<220> FEATURE:
<223> OTHER INFORMATION: DNA primer

<400> SEQUENCE: 304
cgagacctac aaatacaact tttgaacttg tcacaatcat cgcattcttt agtgtgatta    60
tgtaagcagg cg    72

<210> SEQ ID NO 305
<211> LENGTH: 72
<212> TYPE: DNA
<213> ORGANISM: Artificial Sequence
<220> FEATURE:
<223> OTHER INFORMATION: DNA primer

```
<400> SEQUENCE: 305
aacttttttc tctctcacac tctcaaaatt tcttccaaca acaaaccttt agtgtgatta      60
tgtaagcagg cg                                                         72

<210> SEQ ID NO 306
<211> LENGTH: 83
<212> TYPE: DNA
<213> ORGANISM: Artificial Sequence
<220> FEATURE:
<223> OTHER INFORMATION: DNA primer

<400> SEQUENCE: 306
tattgtttaa aaagcaaatc aataccttcc agataaatcg gtattctcta taactgatta    60
tatggtgatt atgtaagcag gcg                                             83

<210> SEQ ID NO 307
<211> LENGTH: 90
<212> TYPE: DNA
<213> ORGANISM: Artificial Sequence
<220> FEATURE:
<223> OTHER INFORMATION: DNA primer

<400> SEQUENCE: 307
aatactatga ggatcggtgt ggctataaat gctattgaaa agcaagcggc agtttcgata    60
tccatcgaat tgatccggta atttagtgtg                                      90

<210> SEQ ID NO 308
<211> LENGTH: 83
<212> TYPE: DNA
<213> ORGANISM: Artificial Sequence
<220> FEATURE:
<223> OTHER INFORMATION: DNA primer

<400> SEQUENCE: 308
atatgtcgtt tcccttggat tctcttgttt gacttattag tgacagtttt gttgttggtt    60
cccatatccg gtaatttagt gtg                                             83

<210> SEQ ID NO 309
<211> LENGTH: 75
<212> TYPE: DNA
<213> ORGANISM: Artificial Sequence
<220> FEATURE:
<223> OTHER INFORMATION: DNA primer

<400> SEQUENCE: 309
gccgctattg ctgcaactac tattgcaagt ttcaaaagcc ttgctagcat cgaattgatc    60
cggtaattta gtgtg                                                      75

<210> SEQ ID NO 310
<211> LENGTH: 83
<212> TYPE: DNA
<213> ORGANISM: Artificial Sequence
<220> FEATURE:
<223> OTHER INFORMATION: DNA primer

<400> SEQUENCE: 310
attgatttgg tacctgttaa cttgagaggc aacacataaa acccttttat ttctgtaggt    60
gccatatccg gtaatttagt gtg                                             83

<210> SEQ ID NO 311
```

```
<211> LENGTH: 90
<212> TYPE: DNA
<213> ORGANISM: Artificial Sequence
<220> FEATURE:
<223> OTHER INFORMATION: DNA primer

<400> SEQUENCE: 311
tcataatctt caatttgctc ttgagtagac actttacgta ttttccttgg ttgtgtatcc    60
gtcatcgaat tgatccggta atttagtgtg                                    90

<210> SEQ ID NO 312
<211> LENGTH: 90
<212> TYPE: DNA
<213> ORGANISM: Artificial Sequence
<220> FEATURE:
<223> OTHER INFORMATION: DNA primer

<400> SEQUENCE: 312
gagtcaactt catcaagttc aatctcttct tcattcacag ttttatttct atttcttcta    60
gccatcgaat tgatccggta atttagtgtg                                    90

<210> SEQ ID NO 313
<211> LENGTH: 80
<212> TYPE: DNA
<213> ORGANISM: Artificial Sequence
<220> FEATURE:
<223> OTHER INFORMATION: DNA primer

<400> SEQUENCE: 313
aggggaattt cctctttagg ttattcacac tctcatgctc ttccactttc gacatcgaat    60
tgatccggta atttagtgtg                                               80

<210> SEQ ID NO 314
<211> LENGTH: 80
<212> TYPE: DNA
<213> ORGANISM: Artificial Sequence
<220> FEATURE:
<223> OTHER INFORMATION: DNA primer

<400> SEQUENCE: 314
cagccaacgc aacgggagc ttgccattat aaagtgtggt caccattggt ttcatcgaat     60
tgatccggta atttagtgtg                                               80

<210> SEQ ID NO 315
<211> LENGTH: 90
<212> TYPE: DNA
<213> ORGANISM: Artificial Sequence
<220> FEATURE:
<223> OTHER INFORMATION: DNA primer

<400> SEQUENCE: 315
tctgaatcgg gtgaactaac atcaatatct gaatcagatt cttcatctac tcttctttta    60
cccatcgaat tgatccggta atttagtgtg                                    90

<210> SEQ ID NO 316
<211> LENGTH: 80
<212> TYPE: DNA
<213> ORGANISM: Artificial Sequence
<220> FEATURE:
<223> OTHER INFORMATION: DNA primer

<400> SEQUENCE: 316
ggatatattt cttacctcca gttaaaattt ctctattctt tttaaatcct gccatcgaat    60
```

```
-continued tgatccggta atttagtgtg                                              80

<210> SEQ ID NO 317
<211> LENGTH: 90
<212> TYPE: DNA
<213> ORGANISM: Artificial Sequence
<220> FEATURE:
<223> OTHER INFORMATION: DNA primer

<400> SEQUENCE: 317
gagctgaaca agtcgtaaat ctggaattgt aatttatcta gttttttata atatactgtt   60
gacatcgaat tgatccggta atttagtgtg                                   90

<210> SEQ ID NO 318
<211> LENGTH: 90
<212> TYPE: DNA
<213> ORGANISM: Artificial Sequence
<220> FEATURE:
<223> OTHER INFORMATION: DNA primer

<400> SEQUENCE: 318
tctgaatctg atacaattgc tgattcttgg tgcttggaga acccggtagc tgatgagtct   60
gtcatcgaat tgatccggta atttagtgtg                                   90

<210> SEQ ID NO 319
<211> LENGTH: 90
<212> TYPE: DNA
<213> ORGANISM: Artificial Sequence
<220> FEATURE:
<223> OTHER INFORMATION: DNA primer

<400> SEQUENCE: 319
aaggacttga attcatcatc ttcaatggta gaaatatcat tttcctctaa cttccgtttt   60
gccatcgaat tgatccggta atttagtgtg                                   90

<210> SEQ ID NO 320
<211> LENGTH: 83
<212> TYPE: DNA
<213> ORGANISM: Artificial Sequence
<220> FEATURE:
<223> OTHER INFORMATION: DNA primer

<400> SEQUENCE: 320
cgcacaacat tctgtaaaag aataatgttg gtaggcaata tagcagctct tcttttttta   60
gccatatccg gtaatttagt gtg                                          83

<210> SEQ ID NO 321
<211> LENGTH: 75
<212> TYPE: DNA
<213> ORGANISM: Artificial Sequence
<220> FEATURE:
<223> OTHER INFORMATION: DNA primer

<400> SEQUENCE: 321
agggacaaaa aataattaat gccatcaatg acagtttcaa caatagccat cgaattgatc   60
cggtaattta gtgtg                                                   75

<210> SEQ ID NO 322
<211> LENGTH: 90
<212> TYPE: DNA
<213> ORGANISM: Artificial Sequence
<220> FEATURE:
```

```
<223> OTHER INFORMATION: DNA primer

<400> SEQUENCE: 322
gacaaagaca gtagaagcat tccatcatca atatcgttat atacattggt aacatgacta    60
ggcatcgaat tgatccggta atttagtgtg                                    90

<210> SEQ ID NO 323
<211> LENGTH: 83
<212> TYPE: DNA
<213> ORGANISM: Artificial Sequence
<220> FEATURE:
<223> OTHER INFORMATION: DNA primer

<400> SEQUENCE: 323
gtattaagcc ctctctcttg tatgaactct ggagatttcc actgtatttc gtctaatgat    60
tccatatccg gtaatttagt gtg                                           83

<210> SEQ ID NO 324
<211> LENGTH: 90
<212> TYPE: DNA
<213> ORGANISM: Artificial Sequence
<220> FEATURE:
<223> OTHER INFORMATION: DNA primer

<400> SEQUENCE: 324
gtaaattcac ctaaataatt gggaattaca tcttgaagag cttttcgtgc ttgagaagag    60
gacatcgaat tgatccggta atttagtgtg                                    90

<210> SEQ ID NO 325
<211> LENGTH: 80
<212> TYPE: DNA
<213> ORGANISM: Artificial Sequence
<220> FEATURE:
<223> OTHER INFORMATION: DNA primer

<400> SEQUENCE: 325
atgtggagtc attatactct cgtatcacgt ttggtgggga tgaaaacgta ttcatcgaat    60
tgatccggta atttagtgtg                                               80

<210> SEQ ID NO 326
<211> LENGTH: 90
<212> TYPE: DNA
<213> ORGANISM: Artificial Sequence
<220> FEATURE:
<223> OTHER INFORMATION: DNA primer

<400> SEQUENCE: 326
accataccgg ttgccaaata gttccccgac tgatcaaact ttgaacaaat tattggtcct    60
gacatcgaat tgatccggta atttagtgtg                                    90

<210> SEQ ID NO 327
<211> LENGTH: 90
<212> TYPE: DNA
<213> ORGANISM: Artificial Sequence
<220> FEATURE:
<223> OTHER INFORMATION: DNA primer

<400> SEQUENCE: 327
tcaacagata cttctgtatt atcattctta ttggttcctg gccattgaaa atttgtggac    60
atcatcgaat tgatccggta atttagtgtg                                    90
```

<210> SEQ ID NO 328
<211> LENGTH: 83
<212> TYPE: DNA
<213> ORGANISM: Artificial Sequence
<220> FEATURE:
<223> OTHER INFORMATION: DNA primer

<400> SEQUENCE: 328
aacaatattt cctcttcatc tttaggaggt attatcactt cttctccttg tatgtttgtg     60
ggcatatccg gtaatttagt gtg                                             83

<210> SEQ ID NO 329
<211> LENGTH: 90
<212> TYPE: DNA
<213> ORGANISM: Artificial Sequence
<220> FEATURE:
<223> OTHER INFORMATION: DNA primer

<400> SEQUENCE: 329
cgtcgtgtgg ttgattccaa cccagtgcaa cagaataata accccgtaaa tggtttcaat     60
gacatcgaat tgatccggta atttagtgtg                                      90

<210> SEQ ID NO 330
<211> LENGTH: 90
<212> TYPE: DNA
<213> ORGANISM: Artificial Sequence
<220> FEATURE:
<223> OTHER INFORMATION: DNA primer

<400> SEQUENCE: 330
atggaggtgt ccttcgatct taatagttta gtcaccgctt ctgcagtcaa caaatccttc     60
cccatcgaat tgatccggta atttagtgtg                                      90

<210> SEQ ID NO 331
<211> LENGTH: 80
<212> TYPE: DNA
<213> ORGANISM: Artificial Sequence
<220> FEATURE:
<223> OTHER INFORMATION: DNA primer

<400> SEQUENCE: 331
tggcaacaag cctcaaccgc tcaaatctca ctttgttatt ttcatcggcg gacatcgaat     60
tgatccggta atttagtgtg                                                 80

<210> SEQ ID NO 332
<211> LENGTH: 90
<212> TYPE: DNA
<213> ORGANISM: Artificial Sequence
<220> FEATURE:
<223> OTHER INFORMATION: DNA primer

<400> SEQUENCE: 332
aaatagtagt ggaataattg gtacggtttt tgtattattt tggaacgcaa aatagaagac     60
gccatcgaat tgatccggta atttagtgtg                                      90

<210> SEQ ID NO 333
<211> LENGTH: 90
<212> TYPE: DNA
<213> ORGANISM: Artificial Sequence
<220> FEATURE:
<223> OTHER INFORMATION: DNA primer

<400> SEQUENCE: 333

```
gataataatc tctcattttg aatcagttcg ttggaagaag cagataattg tgaacttgat    60
gtcatcgaat tgatccggta atttagtgtg                                    90
```

<210> SEQ ID NO 334
<211> LENGTH: 80
<212> TYPE: DNA
<213> ORGANISM: Artificial Sequence
<220> FEATURE:
<223> OTHER INFORMATION: DNA primer

<400> SEQUENCE: 334

```
gtttatatgg ttcgggagtc atatcatcct cctcattaat gaataacagg ctcatcgaat    60
tgatccggta atttagtgtg                                               80
```

<210> SEQ ID NO 335
<211> LENGTH: 90
<212> TYPE: DNA
<213> ORGANISM: Artificial Sequence
<220> FEATURE:
<223> OTHER INFORMATION: DNA primer

<400> SEQUENCE: 335

```
cattttttca attgttgcaa gtcatcaatg cctttatatg ccgtgacaag tggatgttgt    60
ttcatcgaat tgatccggta atttagtgtg                                    90
```

<210> SEQ ID NO 336
<211> LENGTH: 80
<212> TYPE: DNA
<213> ORGANISM: Artificial Sequence
<220> FEATURE:
<223> OTHER INFORMATION: DNA primer

<400> SEQUENCE: 336

```
catcagtgac tactgttgga tgaagtaata ataaaatatt gatcagtgaa gtcatcgaat    60
tgatccggta atttagtgtg                                               80
```

<210> SEQ ID NO 337
<211> LENGTH: 83
<212> TYPE: DNA
<213> ORGANISM: Artificial Sequence
<220> FEATURE:
<223> OTHER INFORMATION: DNA primer

<400> SEQUENCE: 337

```
ttagcttcct ttttagctaa tgctctttta gaacgagcat tctttggttt gatcgtccta    60
atcatatccg gtaatttagt gtg                                           83
```

<210> SEQ ID NO 338
<211> LENGTH: 80
<212> TYPE: DNA
<213> ORGANISM: Artificial Sequence
<220> FEATURE:
<223> OTHER INFORMATION: DNA primer

<400> SEQUENCE: 338

```
agtttgctct tttttcagca atcttttggt atatagcagt atttgttttc agcatcgaat    60
tgatccggta atttagtgtg                                               80
```

<210> SEQ ID NO 339
<211> LENGTH: 83
<212> TYPE: DNA
<213> ORGANISM: Artificial Sequence

```
<220> FEATURE:
<223> OTHER INFORMATION: DNA primer

<400> SEQUENCE: 339
ggtttgaact ctttgagtga gtggaactcc tttattattt tatgtagtag atcttggtaa      60
tccatatccg gtaatttagt gtg                                              83

<210> SEQ ID NO 340
<211> LENGTH: 83
<212> TYPE: DNA
<213> ORGANISM: Artificial Sequence
<220> FEATURE:
<223> OTHER INFORMATION: DNA primer

<400> SEQUENCE: 340
tcttgacttt gtttaagttt cttctttttt tctaaatctt gttgtttact ttttcgttta      60
gccatatccg gtaatttagt gtg                                              83

<210> SEQ ID NO 341
<211> LENGTH: 83
<212> TYPE: DNA
<213> ORGANISM: Artificial Sequence
<220> FEATURE:
<223> OTHER INFORMATION: DNA primer

<400> SEQUENCE: 341
tgagataatg atgagcgttt tatatcttgg aacgtctttg catattggtt cggggttata      60
tacatatccg gtaatttagt gtg                                              83

<210> SEQ ID NO 342
<211> LENGTH: 80
<212> TYPE: DNA
<213> ORGANISM: Artificial Sequence
<220> FEATURE:
<223> OTHER INFORMATION: DNA primer

<400> SEQUENCE: 342
taccgccctg ttgattaggg tcgtaataat gattattatt atcgttatac gacatcgaat      60
tgatccggta atttagtgtg                                                  80

<210> SEQ ID NO 343
<211> LENGTH: 83
<212> TYPE: DNA
<213> ORGANISM: Artificial Sequence
<220> FEATURE:
<223> OTHER INFORMATION: DNA primer

<400> SEQUENCE: 343
ttggacaaag tagctttggc agtggctaat ctagccattc tcatggaagt agttctgaaa      60
gacatatccg gtaatttagt gtg                                              83

<210> SEQ ID NO 344
<211> LENGTH: 90
<212> TYPE: DNA
<213> ORGANISM: Artificial Sequence
<220> FEATURE:
<223> OTHER INFORMATION: DNA primer

<400> SEQUENCE: 344
gtcgtggcag cagcacttga aattggtgac ttggtagcta gactacgtat ggattgtttg      60
aacatcgaat tgatccggta atttagtgtg                                       90
```

<210> SEQ ID NO 345
<211> LENGTH: 75
<212> TYPE: DNA
<213> ORGANISM: Artificial Sequence
<220> FEATURE:
<223> OTHER INFORMATION: DNA primer

<400> SEQUENCE: 345
acggtaaaca atcactaaga cataccatta atactgatga cttctctcat cgaattgatc    60
cggtaattta gtgtg                                                    75

<210> SEQ ID NO 346
<211> LENGTH: 80
<212> TYPE: DNA
<213> ORGANISM: Artificial Sequence
<220> FEATURE:
<223> OTHER INFORMATION: DNA primer

<400> SEQUENCE: 346
acgcaagagc gcaaacaagt aaattgaaga ttgctataaa tactgacgtt ttcatcgaat    60
tgatccggta atttagtgtg                                               80

<210> SEQ ID NO 347
<211> LENGTH: 90
<212> TYPE: DNA
<213> ORGANISM: Artificial Sequence
<220> FEATURE:
<223> OTHER INFORMATION: DNA primer

<400> SEQUENCE: 347
tcggatgatg cgattgtcaa agcaatgtat aaaaggcttg gtataaggat ggtgtacatt    60
agcatcgaat tgatccggta atttagtgtg                                    90

<210> SEQ ID NO 348
<211> LENGTH: 90
<212> TYPE: DNA
<213> ORGANISM: Artificial Sequence
<220> FEATURE:
<223> OTHER INFORMATION: DNA primer

<400> SEQUENCE: 348
ggctcaagaa ccaaatatcc accagcaaga aatgcttttc caggtgcact aaatgctttt    60
gacatcgaat tgatccggta atttagtgtg                                    90

<210> SEQ ID NO 349
<211> LENGTH: 80
<212> TYPE: DNA
<213> ORGANISM: Artificial Sequence
<220> FEATURE:
<223> OTHER INFORMATION: DNA primer

<400> SEQUENCE: 349
tgacaaccgg aaatggagcg gacgaaggaa gtttaattgg agttaggtcc gacatcgaat    60
tgatccggta atttagtgtg                                               80

<210> SEQ ID NO 350
<211> LENGTH: 83
<212> TYPE: DNA
<213> ORGANISM: Artificial Sequence
<220> FEATURE:
<223> OTHER INFORMATION: DNA primer

<400> SEQUENCE: 350

```
tgcttttctt gaacgccatt acgtatcaag gcaggaatac gtgcatcaat tgctttttta    60
cccatatccg gtaatttagt gtg                                            83
```

```
<210> SEQ ID NO 351
<211> LENGTH: 80
<212> TYPE: DNA
<213> ORGANISM: Artificial Sequence
<220> FEATURE:
<223> OTHER INFORMATION: DNA primer

<400> SEQUENCE: 351
attggaaaaa agtatctcta tcgacataat caaatatttc atcaaatgca gccatcgaat    60
tgatccggta atttagtgtg                                                80
```

```
<210> SEQ ID NO 352
<211> LENGTH: 90
<212> TYPE: DNA
<213> ORGANISM: Artificial Sequence
<220> FEATURE:
<223> OTHER INFORMATION: DNA primer

<400> SEQUENCE: 352
ccaaatggaa gaatagttct ttgagttgat ctaccaccac taccaccacc acctctaaat    60
gacatcgaat tgatccggta atttagtgtg                                     90
```

```
<210> SEQ ID NO 353
<211> LENGTH: 80
<212> TYPE: DNA
<213> ORGANISM: Artificial Sequence
<220> FEATURE:
<223> OTHER INFORMATION: DNA primer

<400> SEQUENCE: 353
atggaatcac ctctggccca tcaaacacaa cactagttaa aaaattcact ggcatcgaat    60
tgatccggta atttagtgtg                                                80
```

```
<210> SEQ ID NO 354
<211> LENGTH: 83
<212> TYPE: DNA
<213> ORGANISM: Artificial Sequence
<220> FEATURE:
<223> OTHER INFORMATION: DNA primer

<400> SEQUENCE: 354
tattgtcctg gaacaacaat actagaaaca ttaccatcag tagtagtgtt tgacatatct    60
gtcatatccg gtaatttagt gtg                                            83
```

```
<210> SEQ ID NO 355
<211> LENGTH: 80
<212> TYPE: DNA
<213> ORGANISM: Artificial Sequence
<220> FEATURE:
<223> OTHER INFORMATION: DNA primer

<400> SEQUENCE: 355
ggttcttaac taatgctgga ttccaagact ttttagatt tagatcacct gccatcgaat     60
tgatccggta atttagtgtg                                                80
```

```
<210> SEQ ID NO 356
<211> LENGTH: 90
<212> TYPE: DNA
```

<213> ORGANISM: Artificial Sequence
<220> FEATURE:
<223> OTHER INFORMATION: DNA primer

<400> SEQUENCE: 356

```
gcatctttac cagttatcgc cgtacaagaa atatctttag tgaaaacggt atcgttttc      60 aacatcgaat tgatccggta atttagtgtg                                      90
```

<210> SEQ ID NO 357
<211> LENGTH: 80
<212> TYPE: DNA
<213> ORGANISM: Artificial Sequence
<220> FEATURE:
<223> OTHER INFORMATION: DNA primer

<400> SEQUENCE: 357

```
attcatattg ttcttcttct aaatttaata cattatctat atctatatct gacatcgaat      60
tgatccggta atttagtgtg                                                 80
```

<210> SEQ ID NO 358
<211> LENGTH: 90
<212> TYPE: DNA
<213> ORGANISM: Artificial Sequence
<220> FEATURE:
<223> OTHER INFORMATION: DNA primer

<400> SEQUENCE: 358

```
aatttgaatg cgtggacata cacactcatt tgtttcttat aggccttggc acgcttttgt      60
ctcatcgaat tgatccggta atttagtgtg                                      90
```

<210> SEQ ID NO 359
<211> LENGTH: 80
<212> TYPE: DNA
<213> ORGANISM: Artificial Sequence
<220> FEATURE:
<223> OTHER INFORMATION: DNA primer

<400> SEQUENCE: 359

```
actcttgctg aacgatgtca acacactgac ggaataatgg tgttaagtcg gtcatcgaat      60
tgatccggta atttagtgtg                                                 80
```

<210> SEQ ID NO 360
<211> LENGTH: 90
<212> TYPE: DNA
<213> ORGANISM: Artificial Sequence
<220> FEATURE:
<223> OTHER INFORMATION: DNA primer

<400> SEQUENCE: 360

```
ttattcacta taagtttctt tagttttgga ttcttttttct ttaaactgat ttttataccct    60 gacatcgaat tgatccggta atttagtgtg                                      90
```

<210> SEQ ID NO 361
<211> LENGTH: 80
<212> TYPE: DNA
<213> ORGANISM: Artificial Sequence
<220> FEATURE:
<223> OTHER INFORMATION: DNA primer

<400> SEQUENCE: 361

```
tatgtttcaa atgcttattt tgaaacttct ttgtttgttt cgatgcttta gccatcgaat      60
tgatccggta atttagtgtg                                                 80
```

<210> SEQ ID NO 362
<211> LENGTH: 80
<212> TYPE: DNA
<213> ORGANISM: Artificial Sequence
<220> FEATURE:
<223> OTHER INFORMATION: DNA primer

<400> SEQUENCE: 362
gtgaagattc ctcttcatcg taatacgacg gtcttattgt tttacctctt gacatcgaat    60
tgatccggta atttagtgtg                                                80

<210> SEQ ID NO 363
<211> LENGTH: 90
<212> TYPE: DNA
<213> ORGANISM: Artificial Sequence
<220> FEATURE:
<223> OTHER INFORMATION: DNA primer

<400> SEQUENCE: 363
tgattttgct gataatcaag gttagctatc gattcctcta tatcttttc taattgatcg     60 gacatcgaat tgatccggta atttagtgtg                                     90

<210> SEQ ID NO 364
<211> LENGTH: 75
<212> TYPE: DNA
<213> ORGANISM: Artificial Sequence
<220> FEATURE:
<223> OTHER INFORMATION: DNA primer

<400> SEQUENCE: 364
attaaggcat ctctacgaaa tgtcttttca aaagtaacag gaccactcat cgaattgatc    60
cggtaattta gtgtg                                                     75

<210> SEQ ID NO 365
<211> LENGTH: 75
<212> TYPE: DNA
<213> ORGANISM: Artificial Sequence
<220> FEATURE:
<223> OTHER INFORMATION: DNA primer

<400> SEQUENCE: 365
gcattcccac ttgatggtgg gtcgtcattt aaaatagatc caacattcat cgaattgatc    60
cggtaattta gtgtg                                                     75

<210> SEQ ID NO 366
<211> LENGTH: 75
<212> TYPE: DNA
<213> ORGANISM: Artificial Sequence
<220> FEATURE:
<223> OTHER INFORMATION: DNA primer

<400> SEQUENCE: 366
tcaccgacaa tgactaattt tctacgaagt tcagctggac cgttaaccat cgaattgatc    60
cggtaattta gtgtg                                                     75

<210> SEQ ID NO 367
<211> LENGTH: 83
<212> TYPE: DNA
<213> ORGANISM: Artificial Sequence
<220> FEATURE:
<223> OTHER INFORMATION: DNA primer

```
<400> SEQUENCE: 367
attcgaaatg ctatgggtct aatgtttgat ggctgaagtt taattggcaa agaagtgact    60
tccatatccg gtaatttagt gtg                                            83

<210> SEQ ID NO 368
<211> LENGTH: 22
<212> TYPE: DNA
<213> ORGANISM: Artificial Sequence
<220> FEATURE:
<223> OTHER INFORMATION: DNA primer

<400> SEQUENCE: 368
cctgtttgat catcttgatt cg                                             22

<210> SEQ ID NO 369
<211> LENGTH: 26
<212> TYPE: DNA
<213> ORGANISM: Artificial Sequence
<220> FEATURE:
<223> OTHER INFORMATION: DNA primer

<400> SEQUENCE: 369
tgaattgaaa aatgaaaaca gcttcg                                         26

<210> SEQ ID NO 370
<211> LENGTH: 25
<212> TYPE: DNA
<213> ORGANISM: Artificial Sequence
<220> FEATURE:
<223> OTHER INFORMATION: DNA primer

<400> SEQUENCE: 370
ccagtgaaaa tccacgtgta gatgg                                          25

<210> SEQ ID NO 371
<211> LENGTH: 26
<212> TYPE: DNA
<213> ORGANISM: Artificial Sequence
<220> FEATURE:
<223> OTHER INFORMATION: DNA primer

<400> SEQUENCE: 371
ttgtcctttt cccacttcta tcaatg                                         26

<210> SEQ ID NO 372
<211> LENGTH: 22
<212> TYPE: DNA
<213> ORGANISM: Artificial Sequence
<220> FEATURE:
<223> OTHER INFORMATION: DNA primer

<400> SEQUENCE: 372
atttccttta acgcgtttgc tg                                             22

<210> SEQ ID NO 373
<211> LENGTH: 22
<212> TYPE: DNA
<213> ORGANISM: Artificial Sequence
<220> FEATURE:
<223> OTHER INFORMATION: DNA primer

<400> SEQUENCE: 373
gtgttaagta ggagtgggat gg                                             22
```

```
<210> SEQ ID NO 374
<211> LENGTH: 27
<212> TYPE: DNA
<213> ORGANISM: Artificial Sequence
<220> FEATURE:
<223> OTHER INFORMATION: DNA primer

<400> SEQUENCE: 374
tgggtattat aggccttgtt tgtcaga                                27

<210> SEQ ID NO 375
<211> LENGTH: 21
<212> TYPE: DNA
<213> ORGANISM: Artificial Sequence
<220> FEATURE:
<223> OTHER INFORMATION: DNA primer

<400> SEQUENCE: 375
acctgaacca ctctcgccaa t                                     21

<210> SEQ ID NO 376
<211> LENGTH: 22
<212> TYPE: DNA
<213> ORGANISM: Artificial Sequence
<220> FEATURE:
<223> OTHER INFORMATION: DNA primer

<400> SEQUENCE: 376
gttgccgttt caattgttta gc                                    22

<210> SEQ ID NO 377
<211> LENGTH: 24
<212> TYPE: DNA
<213> ORGANISM: Artificial Sequence
<220> FEATURE:
<223> OTHER INFORMATION: DNA primer

<400> SEQUENCE: 377
tgttctccat ttttggtggt gatt                                  24

<210> SEQ ID NO 378
<211> LENGTH: 22
<212> TYPE: DNA
<213> ORGANISM: Artificial Sequence
<220> FEATURE:
<223> OTHER INFORMATION: DNA primer

<400> SEQUENCE: 378
tatatcacca gccccgttag ac                                    22

<210> SEQ ID NO 379
<211> LENGTH: 22
<212> TYPE: DNA
<213> ORGANISM: Artificial Sequence
<220> FEATURE:
<223> OTHER INFORMATION: DNA primer

<400> SEQUENCE: 379
ccttgccatt tcatttcaaa gc                                    22

<210> SEQ ID NO 380
<211> LENGTH: 22
<212> TYPE: DNA
<213> ORGANISM: Artificial Sequence
<220> FEATURE:
<223> OTHER INFORMATION: DNA primer
```

```
<400> SEQUENCE: 380
cgagagagta tttggaaagt cg                                          22

<210> SEQ ID NO 381
<211> LENGTH: 21
<212> TYPE: DNA
<213> ORGANISM: Artificial Sequence
<220> FEATURE:
<223> OTHER INFORMATION: DNA primer

<400> SEQUENCE: 381
cagctgccga tagtgcaaag a                                           21

<210> SEQ ID NO 382
<211> LENGTH: 22
<212> TYPE: DNA
<213> ORGANISM: Artificial Sequence
<220> FEATURE:
<223> OTHER INFORMATION: DNA primer

<400> SEQUENCE: 382
tttgagaaca gccacacgac aa                                          22

<210> SEQ ID NO 383
<211> LENGTH: 22
<212> TYPE: DNA
<213> ORGANISM: Artificial Sequence
<220> FEATURE:
<223> OTHER INFORMATION: DNA primer

<400> SEQUENCE: 383
ggagccattc cattcaatag tg                                          22

<210> SEQ ID NO 384
<211> LENGTH: 22
<212> TYPE: DNA
<213> ORGANISM: Artificial Sequence
<220> FEATURE:
<223> OTHER INFORMATION: DNA primer

<400> SEQUENCE: 384
cgcgaatacc aggagttctt cc                                          22

<210> SEQ ID NO 385
<211> LENGTH: 22
<212> TYPE: DNA
<213> ORGANISM: Artificial Sequence
<220> FEATURE:
<223> OTHER INFORMATION: DNA primer

<400> SEQUENCE: 385
tatgagacaa ctgggaagaa gt                                          22

<210> SEQ ID NO 386
<211> LENGTH: 22
<212> TYPE: DNA
<213> ORGANISM: Artificial Sequence
<220> FEATURE:
<223> OTHER INFORMATION: DNA primer

<400> SEQUENCE: 386
tgctcgaaga tttgtcgttg ga                                          22

<210> SEQ ID NO 387
<211> LENGTH: 22
```

```
<212> TYPE: DNA
<213> ORGANISM: Artificial Sequence
<220> FEATURE:
<223> OTHER INFORMATION: DNA primer

<400> SEQUENCE: 387
cgagctgttc aaaactggtt ag                                              22

<210> SEQ ID NO 388
<211> LENGTH: 22
<212> TYPE: DNA
<213> ORGANISM: Artificial Sequence
<220> FEATURE:
<223> OTHER INFORMATION: DNA primer

<400> SEQUENCE: 388
caagtggtag caaaaaccaa gc                                              22

<210> SEQ ID NO 389
<211> LENGTH: 27
<212> TYPE: DNA
<213> ORGANISM: Artificial Sequence
<220> FEATURE:
<223> OTHER INFORMATION: DNA primer

<400> SEQUENCE: 389
cgattaattg ctcaagaaat tgccata                                         27

<210> SEQ ID NO 390
<211> LENGTH: 22
<212> TYPE: DNA
<213> ORGANISM: Artificial Sequence
<220> FEATURE:
<223> OTHER INFORMATION: DNA primer

<400> SEQUENCE: 390
tacagagaca ttcaaacgcg tc                                              22

<210> SEQ ID NO 391
<211> LENGTH: 22
<212> TYPE: DNA
<213> ORGANISM: Artificial Sequence
<220> FEATURE:
<223> OTHER INFORMATION: DNA primer

<400> SEQUENCE: 391
ttgcactgtc tggtgtgagt tg                                              22

<210> SEQ ID NO 392
<211> LENGTH: 21
<212> TYPE: DNA
<213> ORGANISM: Artificial Sequence
<220> FEATURE:
<223> OTHER INFORMATION: DNA primer

<400> SEQUENCE: 392
tcatggaagc ggaagaacct g                                               21

<210> SEQ ID NO 393
<211> LENGTH: 22
<212> TYPE: DNA
<213> ORGANISM: Artificial Sequence
<220> FEATURE:
<223> OTHER INFORMATION: DNA primer

<400> SEQUENCE: 393
```
atcaggcgac tacaccagaa cc                                         22

<210> SEQ ID NO 394
<211> LENGTH: 22
<212> TYPE: DNA
<213> ORGANISM: Artificial Sequence
<220> FEATURE:
<223> OTHER INFORMATION: DNA primer

<400> SEQUENCE: 394
gttacttaca acttcatggg gc                                         22

<210> SEQ ID NO 395
<211> LENGTH: 20
<212> TYPE: DNA
<213> ORGANISM: Artificial Sequence
<220> FEATURE:
<223> OTHER INFORMATION: DNA primer

<400> SEQUENCE: 395
tgccgcgata ggcatagtca                                            20

<210> SEQ ID NO 396
<211> LENGTH: 22
<212> TYPE: DNA
<213> ORGANISM: Artificial Sequence
<220> FEATURE:
<223> OTHER INFORMATION: DNA primer

<400> SEQUENCE: 396
ggtggtggtg gcagaaatag ga                                         22

<210> SEQ ID NO 397
<211> LENGTH: 20
<212> TYPE: DNA
<213> ORGANISM: Artificial Sequence
<220> FEATURE:
<223> OTHER INFORMATION: DNA primer

<400> SEQUENCE: 397
cggaggagga ggaggaggag                                            20

<210> SEQ ID NO 398
<211> LENGTH: 21
<212> TYPE: DNA
<213> ORGANISM: Artificial Sequence
<220> FEATURE:
<223> OTHER INFORMATION: DNA primer

<400> SEQUENCE: 398
cctccttgta actccggttc g                                          21

<210> SEQ ID NO 399
<211> LENGTH: 25
<212> TYPE: DNA
<213> ORGANISM: Artificial Sequence
<220> FEATURE:
<223> OTHER INFORMATION: DNA primer

<400> SEQUENCE: 399
tgatgaagaa gaacttgggg gtaga                                      25

<210> SEQ ID NO 400
<211> LENGTH: 21
<212> TYPE: DNA
<213> ORGANISM: Artificial Sequence

```
<220> FEATURE:
<223> OTHER INFORMATION: DNA primer

<400> SEQUENCE: 400
cgttatcgat gccttccttc g                                              21

<210> SEQ ID NO 401
<211> LENGTH: 24
<212> TYPE: DNA
<213> ORGANISM: Artificial Sequence
<220> FEATURE:
<223> OTHER INFORMATION: DNA primer

<400> SEQUENCE: 401
gggttccaga ggttatcatg tgtg                                           24

<210> SEQ ID NO 402
<211> LENGTH: 21
<212> TYPE: DNA
<213> ORGANISM: Artificial Sequence
<220> FEATURE:
<223> OTHER INFORMATION: DNA primer

<400> SEQUENCE: 402
ttgatgggtc cgagatcaag c                                              21

<210> SEQ ID NO 403
<211> LENGTH: 26
<212> TYPE: DNA
<213> ORGANISM: Artificial Sequence
<220> FEATURE:
<223> OTHER INFORMATION: DNA primer

<400> SEQUENCE: 403
ggtcagattc acatttccag atctca                                         26

<210> SEQ ID NO 404
<211> LENGTH: 20
<212> TYPE: DNA
<213> ORGANISM: Artificial Sequence
<220> FEATURE:
<223> OTHER INFORMATION: DNA primer

<400> SEQUENCE: 404
tcccttttcc gctgatccat                                                20

<210> SEQ ID NO 405
<211> LENGTH: 22
<212> TYPE: DNA
<213> ORGANISM: Artificial Sequence
<220> FEATURE:
<223> OTHER INFORMATION: DNA primer

<400> SEQUENCE: 405
gatgagttta taattggcag cg                                             22

<210> SEQ ID NO 406
<211> LENGTH: 25
<212> TYPE: DNA
<213> ORGANISM: Artificial Sequence
<220> FEATURE:
<223> OTHER INFORMATION: DNA primer

<400> SEQUENCE: 406
tcgagtgaat gttaggggag agaga                                          25
```

-continued

<210> SEQ ID NO 407
<211> LENGTH: 22
<212> TYPE: DNA
<213> ORGANISM: Artificial Sequence
<220> FEATURE:
<223> OTHER INFORMATION: DNA primer

<400> SEQUENCE: 407
gtggaggaca atgctcttga gg                                          22

<210> SEQ ID NO 408
<211> LENGTH: 22
<212> TYPE: DNA
<213> ORGANISM: Artificial Sequence
<220> FEATURE:
<223> OTHER INFORMATION: DNA primer

<400> SEQUENCE: 408
ttatccaaac accttttcct gg                                          22

<210> SEQ ID NO 409
<211> LENGTH: 22
<212> TYPE: DNA
<213> ORGANISM: Artificial Sequence
<220> FEATURE:
<223> OTHER INFORMATION: DNA primer

<400> SEQUENCE: 409
ttaattcagt ttccgccata gc                                          22

<210> SEQ ID NO 410
<211> LENGTH: 21
<212> TYPE: DNA
<213> ORGANISM: Artificial Sequence
<220> FEATURE:
<223> OTHER INFORMATION: DNA primer

<400> SEQUENCE: 410
tggaacattg ccgaaactga a                                           21

<210> SEQ ID NO 411
<211> LENGTH: 30
<212> TYPE: DNA
<213> ORGANISM: Artificial Sequence
<220> FEATURE:
<223> OTHER INFORMATION: DNA primer

<400> SEQUENCE: 411
aggtatgata tttgacgttg tttattttgc                                  30

<210> SEQ ID NO 412
<211> LENGTH: 23
<212> TYPE: DNA
<213> ORGANISM: Artificial Sequence
<220> FEATURE:
<223> OTHER INFORMATION: DNA primer

<400> SEQUENCE: 412
tccatttgct gatgatgatg atg                                         23

<210> SEQ ID NO 413
<211> LENGTH: 22
<212> TYPE: DNA
<213> ORGANISM: Artificial Sequence
<220> FEATURE:
<223> OTHER INFORMATION: DNA primer

<400> SEQUENCE: 413
cctttctaaa gaatcccatc gc                                                    22

<210> SEQ ID NO 414
<211> LENGTH: 21
<212> TYPE: DNA
<213> ORGANISM: Artificial Sequence
<220> FEATURE:
<223> OTHER INFORMATION: DNA primer

<400> SEQUENCE: 414
ccggaccaat accagttacc g                                                     21

<210> SEQ ID NO 415
<211> LENGTH: 23
<212> TYPE: DNA
<213> ORGANISM: Artificial Sequence
<220> FEATURE:
<223> OTHER INFORMATION: DNA primer

<400> SEQUENCE: 415
caagtagttg aagcccacga tgc                                                   23

<210> SEQ ID NO 416
<211> LENGTH: 27
<212> TYPE: DNA
<213> ORGANISM: Artificial Sequence
<220> FEATURE:
<223> OTHER INFORMATION: DNA primer

<400> SEQUENCE: 416
tttgaaagga actatcggat tattggt                                               27

<210> SEQ ID NO 417
<211> LENGTH: 22
<212> TYPE: DNA
<213> ORGANISM: Artificial Sequence
<220> FEATURE:
<223> OTHER INFORMATION: DNA primer

<400> SEQUENCE: 417
ccaggaagaa tttgatgcta cc                                                    22

<210> SEQ ID NO 418
<211> LENGTH: 23
<212> TYPE: DNA
<213> ORGANISM: Artificial Sequence
<220> FEATURE:
<223> OTHER INFORMATION: DNA primer

<400> SEQUENCE: 418
tcctcctcca gttgttgttg ttg                                                   23

<210> SEQ ID NO 419
<211> LENGTH: 22
<212> TYPE: DNA
<213> ORGANISM: Artificial Sequence
<220> FEATURE:
<223> OTHER INFORMATION: DNA primer

<400> SEQUENCE: 419
gatgaaacac aaaacgcaag gc                                                    22

<210> SEQ ID NO 420

```
<211> LENGTH: 20
<212> TYPE: DNA
<213> ORGANISM: Artificial Sequence
<220> FEATURE:
<223> OTHER INFORMATION: DNA primer

<400> SEQUENCE: 420
tgccccagga acattgattg                                               20

<210> SEQ ID NO 421
<211> LENGTH: 22
<212> TYPE: DNA
<213> ORGANISM: Artificial Sequence
<220> FEATURE:
<223> OTHER INFORMATION: DNA primer

<400> SEQUENCE: 421
ggtagtgctc aaaagtcatt gc                                            22

<210> SEQ ID NO 422
<211> LENGTH: 24
<212> TYPE: DNA
<213> ORGANISM: Artificial Sequence
<220> FEATURE:
<223> OTHER INFORMATION: DNA primer

<400> SEQUENCE: 422
catggcactg gtgatgacaa tgta                                          24

<210> SEQ ID NO 423
<211> LENGTH: 23
<212> TYPE: DNA
<213> ORGANISM: Artificial Sequence
<220> FEATURE:
<223> OTHER INFORMATION: DNA primer

<400> SEQUENCE: 423
tccgggtaaa ccaagaagtc aga                                           23

<210> SEQ ID NO 424
<211> LENGTH: 22
<212> TYPE: DNA
<213> ORGANISM: Artificial Sequence
<220> FEATURE:
<223> OTHER INFORMATION: DNA primer

<400> SEQUENCE: 424
atatattctg ctgagcgcat tc                                            22

<210> SEQ ID NO 425
<211> LENGTH: 24
<212> TYPE: DNA
<213> ORGANISM: Artificial Sequence
<220> FEATURE:
<223> OTHER INFORMATION: DNA primer

<400> SEQUENCE: 425
tgattcccac cacagttaga cgaa                                          24

<210> SEQ ID NO 426
<211> LENGTH: 21
<212> TYPE: DNA
<213> ORGANISM: Artificial Sequence
<220> FEATURE:
<223> OTHER INFORMATION: DNA primer

<400> SEQUENCE: 426
```
tcgtcagatg cagcacacgt t                                              21

<210> SEQ ID NO 427
<211> LENGTH: 20
<212> TYPE: DNA
<213> ORGANISM: Artificial Sequence
<220> FEATURE:
<223> OTHER INFORMATION: DNA primer

<400> SEQUENCE: 427
ttcccagcca aacaccaaaa                                                20

<210> SEQ ID NO 428
<211> LENGTH: 24
<212> TYPE: DNA
<213> ORGANISM: Artificial Sequence
<220> FEATURE:
<223> OTHER INFORMATION: DNA primer

<400> SEQUENCE: 428
aagcaccacc aaatctacac caaa                                           24

<210> SEQ ID NO 429
<211> LENGTH: 22
<212> TYPE: DNA
<213> ORGANISM: Artificial Sequence
<220> FEATURE:
<223> OTHER INFORMATION: DNA primer

<400> SEQUENCE: 429
tcttgggatt ggtatgtact gc                                             22

<210> SEQ ID NO 430
<211> LENGTH: 27
<212> TYPE: DNA
<213> ORGANISM: Artificial Sequence
<220> FEATURE:
<223> OTHER INFORMATION: DNA primer

<400> SEQUENCE: 430
tcgtgtgact attctttgat ttggaga                                        27

<210> SEQ ID NO 431
<211> LENGTH: 20
<212> TYPE: DNA
<213> ORGANISM: Artificial Sequence
<220> FEATURE:
<223> OTHER INFORMATION: DNA primer

<400> SEQUENCE: 431
ttgacgccac tagccccatt                                                20

<210> SEQ ID NO 432
<211> LENGTH: 21
<212> TYPE: DNA
<213> ORGANISM: Artificial Sequence
<220> FEATURE:
<223> OTHER INFORMATION: DNA primer

<400> SEQUENCE: 432
cgaccaaatc caagtccgat g                                              21

<210> SEQ ID NO 433
<211> LENGTH: 22
<212> TYPE: DNA

-continued

<213> ORGANISM: Artificial Sequence
<220> FEATURE:
<223> OTHER INFORMATION: DNA primer

<400> SEQUENCE: 433
ccagatcatc atcatctacg tc                                              22

<210> SEQ ID NO 434
<211> LENGTH: 22
<212> TYPE: DNA
<213> ORGANISM: Artificial Sequence
<220> FEATURE:
<223> OTHER INFORMATION: DNA primer

<400> SEQUENCE: 434
gctgggttga tgacagtgtg tc                                              22

<210> SEQ ID NO 435
<211> LENGTH: 21
<212> TYPE: DNA
<213> ORGANISM: Artificial Sequence
<220> FEATURE:
<223> OTHER INFORMATION: DNA primer

<400> SEQUENCE: 435
tggttgtggt tgtggttgtg g                                               21

<210> SEQ ID NO 436
<211> LENGTH: 20
<212> TYPE: DNA
<213> ORGANISM: Artificial Sequence
<220> FEATURE:
<223> OTHER INFORMATION: DNA primer

<400> SEQUENCE: 436
actcctgcgg caacaccttc                                                 20

<210> SEQ ID NO 437
<211> LENGTH: 22
<212> TYPE: DNA
<213> ORGANISM: Artificial Sequence
<220> FEATURE:
<223> OTHER INFORMATION: DNA primer

<400> SEQUENCE: 437
ggatcacttt ccattccttc ag                                              22

<210> SEQ ID NO 438
<211> LENGTH: 21
<212> TYPE: DNA
<213> ORGANISM: Artificial Sequence
<220> FEATURE:
<223> OTHER INFORMATION: DNA primer

<400> SEQUENCE: 438
tggcagcaat ttcttgagca g                                               21

<210> SEQ ID NO 439
<211> LENGTH: 22
<212> TYPE: DNA
<213> ORGANISM: Artificial Sequence
<220> FEATURE:
<223> OTHER INFORMATION: DNA primer

<400> SEQUENCE: 439
ggaacgatca gcaaataatt gg                                              22

<210> SEQ ID NO 440
<211> LENGTH: 22
<212> TYPE: DNA
<213> ORGANISM: Artificial Sequence
<220> FEATURE:
<223> OTHER INFORMATION: DNA primer

<400> SEQUENCE: 440
ggcaattgtt gctggagata cc     22

<210> SEQ ID NO 441
<211> LENGTH: 22
<212> TYPE: DNA
<213> ORGANISM: Artificial Sequence
<220> FEATURE:
<223> OTHER INFORMATION: DNA primer

<400> SEQUENCE: 441
gtccatgtgg ttggttaata gc     22

<210> SEQ ID NO 442
<211> LENGTH: 26
<212> TYPE: DNA
<213> ORGANISM: Artificial Sequence
<220> FEATURE:
<223> OTHER INFORMATION: DNA primer

<400> SEQUENCE: 442
aaactcggtt gtagagttag catcca     26

<210> SEQ ID NO 443
<211> LENGTH: 25
<212> TYPE: DNA
<213> ORGANISM: Artificial Sequence
<220> FEATURE:
<223> OTHER INFORMATION: DNA primer

<400> SEQUENCE: 443 cctttggac ctaaataaac cgtca     25

<210> SEQ ID NO 444
<211> LENGTH: 22
<212> TYPE: DNA
<213> ORGANISM: Artificial Sequence
<220> FEATURE:
<223> OTHER INFORMATION: DNA primer

<400> SEQUENCE: 444
gtcactggct gttgataatt gc     22

<210> SEQ ID NO 445
<211> LENGTH: 21
<212> TYPE: DNA
<213> ORGANISM: Artificial Sequence
<220> FEATURE:
<223> OTHER INFORMATION: DNA primer

<400> SEQUENCE: 445
ctcactcaac cgcgactgaa a     21

<210> SEQ ID NO 446
<211> LENGTH: 22
<212> TYPE: DNA
<213> ORGANISM: Artificial Sequence
<220> FEATURE:

<223> OTHER INFORMATION: DNA primer

<400> SEQUENCE: 446
ctttatgtgt tggggtgcct gc                22

<210> SEQ ID NO 447
<211> LENGTH: 21
<212> TYPE: DNA
<213> ORGANISM: Artificial Sequence
<220> FEATURE:
<223> OTHER INFORMATION: DNA primer

<400> SEQUENCE: 447
tgactcaata gtgggccagc a                 21

<210> SEQ ID NO 448
<211> LENGTH: 22
<212> TYPE: DNA
<213> ORGANISM: Artificial Sequence
<220> FEATURE:
<223> OTHER INFORMATION: DNA primer

<400> SEQUENCE: 448
tacacgtttc cttctatatc gc                22

<210> SEQ ID NO 449
<211> LENGTH: 22
<212> TYPE: DNA
<213> ORGANISM: Artificial Sequence
<220> FEATURE:
<223> OTHER INFORMATION: DNA primer

<400> SEQUENCE: 449
tctaggtagt ggcaaaggtt gc                22

<210> SEQ ID NO 450
<211> LENGTH: 27
<212> TYPE: DNA
<213> ORGANISM: Artificial Sequence
<220> FEATURE:
<223> OTHER INFORMATION: DNA primer

<400> SEQUENCE: 450
tctgattctt tctccagacc tttttca           27

<210> SEQ ID NO 451
<211> LENGTH: 22
<212> TYPE: DNA
<213> ORGANISM: Artificial Sequence
<220> FEATURE:
<223> OTHER INFORMATION: DNA primer

<400> SEQUENCE: 451
tatctgttcc tcgtggatca gc                22

<210> SEQ ID NO 452
<211> LENGTH: 22
<212> TYPE: DNA
<213> ORGANISM: Artificial Sequence
<220> FEATURE:
<223> OTHER INFORMATION: DNA primer

<400> SEQUENCE: 452
tggtagtact ttgtggaatc cg                22

<210> SEQ ID NO 453
<211> LENGTH: 20
<212> TYPE: DNA
<213> ORGANISM: Artificial Sequence
<220> FEATURE:
<223> OTHER INFORMATION: DNA primer

<400> SEQUENCE: 453
catgccaaaa cccggacatt                    20

<210> SEQ ID NO 454
<211> LENGTH: 22
<212> TYPE: DNA
<213> ORGANISM: Artificial Sequence
<220> FEATURE:
<223> OTHER INFORMATION: DNA primer

<400> SEQUENCE: 454
acccgtgcat tgaataatta gc                 22

<210> SEQ ID NO 455
<211> LENGTH: 22
<212> TYPE: DNA
<213> ORGANISM: Artificial Sequence
<220> FEATURE:
<223> OTHER INFORMATION: DNA primer

<400> SEQUENCE: 455
ttccttgttc aaatctccac tg                 22

<210> SEQ ID NO 456
<211> LENGTH: 21
<212> TYPE: DNA
<213> ORGANISM: Artificial Sequence
<220> FEATURE:
<223> OTHER INFORMATION: DNA primer

<400> SEQUENCE: 456
tgactgtttc gccctttctg g                  21

<210> SEQ ID NO 457
<211> LENGTH: 22
<212> TYPE: DNA
<213> ORGANISM: Artificial Sequence
<220> FEATURE:
<223> OTHER INFORMATION: DNA primer

<400> SEQUENCE: 457
ccttgtttag atcttgtttc cg                 22

<210> SEQ ID NO 458
<211> LENGTH: 25
<212> TYPE: DNA
<213> ORGANISM: Artificial Sequence
<220> FEATURE:
<223> OTHER INFORMATION: DNA primer

<400> SEQUENCE: 458
ccactggttc atcaacaggt attgg              25

<210> SEQ ID NO 459
<211> LENGTH: 26
<212> TYPE: DNA
<213> ORGANISM: Artificial Sequence
<220> FEATURE:
<223> OTHER INFORMATION: DNA primer

<400> SEQUENCE: 459
attggaccat taaaaacaaa cattgg                              26

<210> SEQ ID NO 460
<211> LENGTH: 23
<212> TYPE: DNA
<213> ORGANISM: Artificial Sequence
<220> FEATURE:
<223> OTHER INFORMATION: DNA primer

<400> SEQUENCE: 460
catttgattg tccaacacgc act                                 23

<210> SEQ ID NO 461
<211> LENGTH: 24
<212> TYPE: DNA
<213> ORGANISM: Artificial Sequence
<220> FEATURE:
<223> OTHER INFORMATION: DNA primer

<400> SEQUENCE: 461
tcattgttgg tggtgaggtg taga                                24

<210> SEQ ID NO 462
<211> LENGTH: 22
<212> TYPE: DNA
<213> ORGANISM: Artificial Sequence
<220> FEATURE:
<223> OTHER INFORMATION: DNA primer

<400> SEQUENCE: 462
tcttggtggt gattttcctt gg                                  22

<210> SEQ ID NO 463
<211> LENGTH: 20
<212> TYPE: DNA
<213> ORGANISM: Artificial Sequence
<220> FEATURE:
<223> OTHER INFORMATION: DNA primer

<400> SEQUENCE: 463
tccaacatgg caccacatcc                                     20

<210> SEQ ID NO 464
<211> LENGTH: 20
<212> TYPE: DNA
<213> ORGANISM: Artificial Sequence
<220> FEATURE:
<223> OTHER INFORMATION: DNA primer

<400> SEQUENCE: 464
ccctgggcat tcattggttg                                     20

<210> SEQ ID NO 465
<211> LENGTH: 21
<212> TYPE: DNA
<213> ORGANISM: Artificial Sequence
<220> FEATURE:
<223> OTHER INFORMATION: DNA primer

<400> SEQUENCE: 465
gccaatcagc tctttcgtgg a                                   21

<210> SEQ ID NO 466
<211> LENGTH: 22

```
<212> TYPE: DNA
<213> ORGANISM: Artificial Sequence
<220> FEATURE:
<223> OTHER INFORMATION: DNA primer

<400> SEQUENCE: 466
tgatcctact cgggccttat cg                                          22

<210> SEQ ID NO 467
<211> LENGTH: 22
<212> TYPE: DNA
<213> ORGANISM: Artificial Sequence
<220> FEATURE:
<223> OTHER INFORMATION: DNA primer

<400> SEQUENCE: 467
aacatacaag gcacgaggaa cg                                          22

<210> SEQ ID NO 468
<211> LENGTH: 25
<212> TYPE: DNA
<213> ORGANISM: Artificial Sequence
<220> FEATURE:
<223> OTHER INFORMATION: DNA primer

<400> SEQUENCE: 468
tgccaaacta accataatct gctca                                       25

<210> SEQ ID NO 469
<211> LENGTH: 22
<212> TYPE: DNA
<213> ORGANISM: Artificial Sequence
<220> FEATURE:
<223> OTHER INFORMATION: DNA primer

<400> SEQUENCE: 469
atcgatagac ggaacggaac ag                                          22

<210> SEQ ID NO 470
<211> LENGTH: 22
<212> TYPE: DNA
<213> ORGANISM: Artificial Sequence
<220> FEATURE:
<223> OTHER INFORMATION: DNA primer

<400> SEQUENCE: 470
tggcaacaac tgacactaat cc                                          22

<210> SEQ ID NO 471
<211> LENGTH: 22
<212> TYPE: DNA
<213> ORGANISM: Artificial Sequence
<220> FEATURE:
<223> OTHER INFORMATION: DNA primer

<400> SEQUENCE: 471
tcgccttcta tgggactctc aa                                          22

<210> SEQ ID NO 472
<211> LENGTH: 21
<212> TYPE: DNA
<213> ORGANISM: Artificial Sequence
<220> FEATURE:
<223> OTHER INFORMATION: DNA primer

<400> SEQUENCE: 472
```

-continued cgcttctgtc tgtgggaggt g    21

<210> SEQ ID NO 473
<211> LENGTH: 24
<212> TYPE: DNA
<213> ORGANISM: Artificial Sequence
<220> FEATURE:
<223> OTHER INFORMATION: DNA primer

<400> SEQUENCE: 473 cccccaaccaa attctttagc ttca    24

<210> SEQ ID NO 474
<211> LENGTH: 22
<212> TYPE: DNA
<213> ORGANISM: Artificial Sequence
<220> FEATURE:
<223> OTHER INFORMATION: DNA primer

<400> SEQUENCE: 474
tttcttgttc atctccacta cg    22

<210> SEQ ID NO 475
<211> LENGTH: 21
<212> TYPE: DNA
<213> ORGANISM: Artificial Sequence
<220> FEATURE:
<223> OTHER INFORMATION: DNA primer

<400> SEQUENCE: 475
tgtgctcctc gttgtcccaa t    21

<210> SEQ ID NO 476
<211> LENGTH: 20
<212> TYPE: DNA
<213> ORGANISM: Artificial Sequence
<220> FEATURE:
<223> OTHER INFORMATION: DNA primer

<400> SEQUENCE: 476
gttgaggtgt ttggcgatgg    20

<210> SEQ ID NO 477
<211> LENGTH: 24
<212> TYPE: DNA
<213> ORGANISM: Artificial Sequence
<220> FEATURE:
<223> OTHER INFORMATION: DNA primer

<400> SEQUENCE: 477
ttttgagctt ctgctgtttg ttca    24

<210> SEQ ID NO 478
<211> LENGTH: 22
<212> TYPE: DNA
<213> ORGANISM: Artificial Sequence
<220> FEATURE:
<223> OTHER INFORMATION: DNA primer

<400> SEQUENCE: 478
tatctaatgg aacgggttga cc    22

<210> SEQ ID NO 479
<211> LENGTH: 25
<212> TYPE: DNA
<213> ORGANISM: Artificial Sequence

```
<220> FEATURE:
<223> OTHER INFORMATION: DNA primer

<400> SEQUENCE: 479
tcaaatgatt ccgaagtgaa gaaga                                              25

<210> SEQ ID NO 480
<211> LENGTH: 22
<212> TYPE: DNA
<213> ORGANISM: Artificial Sequence
<220> FEATURE:
<223> OTHER INFORMATION: DNA primer

<400> SEQUENCE: 480
cccatcttca ccttcatttt gc                                                 22

<210> SEQ ID NO 481
<211> LENGTH: 22
<212> TYPE: DNA
<213> ORGANISM: Artificial Sequence
<220> FEATURE:
<223> OTHER INFORMATION: DNA primer

<400> SEQUENCE: 481
cgacccagct agtttcgtgt ca                                                 22

<210> SEQ ID NO 482
<211> LENGTH: 22
<212> TYPE: DNA
<213> ORGANISM: Artificial Sequence
<220> FEATURE:
<223> OTHER INFORMATION: DNA primer

<400> SEQUENCE: 482
cgaatttggt gagagatgat gc                                                 22

<210> SEQ ID NO 483
<211> LENGTH: 21
<212> TYPE: DNA
<213> ORGANISM: Artificial Sequence
<220> FEATURE:
<223> OTHER INFORMATION: DNA primer

<400> SEQUENCE: 483
tggcttttcc atcagcacgt t                                                  21

<210> SEQ ID NO 484
<211> LENGTH: 23
<212> TYPE: DNA
<213> ORGANISM: Artificial Sequence
<220> FEATURE:
<223> OTHER INFORMATION: DNA primer

<400> SEQUENCE: 484
ggaccatctg aatctgagcc tga                                                23

<210> SEQ ID NO 485
<211> LENGTH: 22
<212> TYPE: DNA
<213> ORGANISM: Artificial Sequence
<220> FEATURE:
<223> OTHER INFORMATION: DNA primer

<400> SEQUENCE: 485
tagcttgttg gtattgtttg gc                                                 22
```

```
<210> SEQ ID NO 486
<211> LENGTH: 20
<212> TYPE: DNA
<213> ORGANISM: Artificial Sequence
<220> FEATURE:
<223> OTHER INFORMATION: DNA primer

<400> SEQUENCE: 486
ggcgtgcaag acaccattca                                              20

<210> SEQ ID NO 487
<211> LENGTH: 20
<212> TYPE: DNA
<213> ORGANISM: Artificial Sequence
<220> FEATURE:
<223> OTHER INFORMATION: DNA primer

<400> SEQUENCE: 487
tggcggaggt ttatgtgcaa                                              20

<210> SEQ ID NO 488
<211> LENGTH: 22
<212> TYPE: DNA
<213> ORGANISM: Artificial Sequence
<220> FEATURE:
<223> OTHER INFORMATION: DNA primer

<400> SEQUENCE: 488
tgagcaactt gttggccttc ag                                           22

<210> SEQ ID NO 489
<211> LENGTH: 20
<212> TYPE: DNA
<213> ORGANISM: Artificial Sequence
<220> FEATURE:
<223> OTHER INFORMATION: DNA primer

<400> SEQUENCE: 489
ccccgatctt cgattttcca                                              20

<210> SEQ ID NO 490
<211> LENGTH: 1561
<212> TYPE: DNA
<213> ORGANISM: Candida albicans

<400> SEQUENCE: 490
atgagagaag tcatcagtat taatggtatg tcttagtgat tgtttaccgt ttcaaaatcg    60
ccatcagttt ttttttttggg gatggattga aaacactaag atccggtttt tttggttgtc   120
ttgatttcaa agtttgatcc aagcttcatt agtaagcagc cataacaatc catcttaaac   180
gcgtcgattt tgattgaat caatcaaaga attctgttca tactaacgcc attgtatagt     240
tggtcaagcc gggtgtcaaa ttggtaacgc ctgttgggaa ttgtattcac aggaacatgg    300
tattagacca gatgggtatt tacaagaagg tttagacaga ccaaagggag gagaagaagg    360
tttttctact tttttcagtg aaactggttc aggtaaatac gttcctcgtg ccttgtatgt    420
tgatttggaa ccaaatgtca ttgatgaagt tcgtactggt gtttacaaag atttattcca    480
ccctgaacaa ttgattgccg gtaaagaaga tgccgccaat aattatgcta gaggtcacta    540
cactgttgga agagaaattt tagacgacat tttagataga gtcagaagaa tgagtgatca    600
atgtgacgga ttcaaaggtt tcctttcac ccactctttg ggtggtggta ccggttccgg     660
tttgggttct ttgttattgg aacaattatc tttggattac ggtaaaaaat ccaaattgga    720
```

```
                                                           -continued atttgctgtt  tacccagctc  cacaagtgtc  cacttcagtt  gttgaaccat  ataatactgt    780
gttgactacc  cacaccactt  tggaacacgc  cgattgtact  tttatggttg  ataatgaagc    840
catctacgat  atgtgtagaa  gaaacttgga  tattgccaga  ccaaatttta  gttcattgaa    900
caacttgatt  gctcaagttg  tgtcatccgt  taccgcctct  ttgagatttg  acggttcctt    960
gaatgttgat  ttgaatgaat  tccaaactaa  cttggttcca  tacccaagaa  tccatttccc   1020
attggtcagt  tatgctccag  ttttctccaa  gagtagagct  acccatgaag  ccaactctgt   1080
ttctgaaatt  actcaatctt  gttttgaacc  aggtaaccaa  atggtcaaat  gtgacccaag   1140
aactggtaaa  tacatggcca  cctgtttgtt  ataccgtggt  gatgttgtta  ctagagacgt   1200
tcaaaatgct  gttgctcaag  ttaaatctaa  aaagactgtt  caattagtcg  attggtgtcc   1260
aactggtttc  aagattggta  tctgttacca  accaccaact  gccattaagg  gatctgaatt   1320
ggccagtgct  tctagagctg  tttgtatgtt  gtctaacact  actgccattg  ctgaagcttg   1380
gagaagaatt  gacagaaaat  tcgacttgat  gtactctaag  agagcctttg  ttcactggta   1440
cgttggtgaa  ggtatggaag  aaggtgaatt  cactgaagct  agagaagact  tggctgcttt   1500
agagagagat  tatattgaag  ttggtactga  ttctttccct  gaagaagaag  aagaatatta   1560
g                                                                       1561
```